US010136856B2

(12) United States Patent
Tzvieli et al.

(10) Patent No.: US 10,136,856 B2
(45) Date of Patent: Nov. 27, 2018

(54) WEARABLE RESPIRATION MEASUREMENTS SYSTEM

(71) Applicant: Facense Ltd., Kiryat Tivon (IL)

(72) Inventors: Arie Tzvieli, Berkeley, CA (US); Gil Thieberger, Kiryat Tivon (IL); Ari M Frank, Haif (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 15/635,178

(22) Filed: Jun. 27, 2017

(65) Prior Publication Data

US 2017/0367651 A1 Dec. 28, 2017

Related U.S. Application Data

(60) Provisional application No. 62/354,833, filed on Jun. 27, 2016, provisional application No. 62/372,063, filed on Aug. 8, 2016.

(51) Int. Cl.
*A61B 5/00* (2006.01)
*A61B 5/01* (2006.01)
(Continued)

(52) U.S. Cl.
CPC .......... *A61B 5/6803* (2013.01); *A61B 5/0075* (2013.01); *A61B 5/0077* (2013.01);
(Continued)

(58) Field of Classification Search
CPC ..... A61B 5/015; A61B 5/0878; A61B 5/1118; A61B 5/6801; A61B 5/6847;
(Continued)

(56) References Cited

U.S. PATENT DOCUMENTS 5,143,086 A 9/1992 Duret et al.
5,664,578 A 9/1997 Boczan
(Continued)

FOREIGN PATENT DOCUMENTS

EP 2233071 A1 9/2013
WO WO2016025323 2/2016

OTHER PUBLICATIONS

Written opinion of the international searching authority, PCT/IB2017/056066, dated Jan. 29, 2018.
(Continued)

*Primary Examiner* — David Porta
*Assistant Examiner* — Faye Boosalis
(74) *Attorney, Agent, or Firm* — Active Knowledge Ltd.

(57) ABSTRACT

A wearable system configured to collect thermal measurements related to respiration. The system includes a frame configured to be worn on a user's head, and at least one non-contact thermal camera (e.g., thermopile or microbolometer based sensor). The thermal camera is small and lightweight, physically coupled to the frame, located close to the user's face, does not occlude any of the user's mouth and nostrils, and is configured to take thermal measurements of: a portion of the right side of the user's upper lip, a portion of the left side of the user's upper lip, and a portion of the user's mouth. The thermal measurements are forwarded to a computer that calculates breathing related parameters, such as breathing rate, an extent to which the breathing was done through the mouth, an extent to which the breathing was done through the nostrils, and ratio between exhaling and inhaling durations.

21 Claims, 41 Drawing Sheets

(51) Int. Cl.
| | |
|---|---|
| *A61B 5/08* | (2006.01) |
| *A61B 5/087* | (2006.01) |
| *A61B 7/00* | (2006.01) |
| *A61B 5/16* | (2006.01) |
| *A61B 5/091* | (2006.01) |
| *A61M 21/02* | (2006.01) |
| *A61B 5/0205* | (2006.01) |
| *A61B 5/11* | (2006.01) |
| *A61M 21/00* | (2006.01) |

(52) U.S. Cl.
CPC ............ *A61B 5/015* (2013.01); *A61B 5/0816* (2013.01); *A61B 5/0823* (2013.01); *A61B 5/0878* (2013.01); *A61B 5/091* (2013.01); *A61B 5/165* (2013.01); *A61B 5/486* (2013.01); *A61B 5/7267* (2013.01); *A61B 5/7275* (2013.01); *A61B 5/7282* (2013.01); *A61B 5/746* (2013.01); *A61B 5/7475* (2013.01); *A61B 7/003* (2013.01); *A61M 21/02* (2013.01); *A61B 5/02055* (2013.01); *A61B 5/1118* (2013.01); *A61B 2503/12* (2013.01); *A61B 2562/0204* (2013.01); *A61B 2562/0233* (2013.01); *A61B 2562/0271* (2013.01); *A61B 2562/046* (2013.01); *A61B 2576/00* (2013.01); *A61M 2021/0088* (2013.01); *A61M 2205/507* (2013.01); *A61M 2230/42* (2013.01); *A61M 2230/50* (2013.01); *A61M 2230/63* (2013.01); *A61M 2230/65* (2013.01)

(58) Field of Classification Search
CPC ..... A61B 5/0077; A61B 5/0075; A61B 5/165; A61B 5/6803; A61B 5/7282; A61B 5/746; A61B 2503/12; A61B 2562/0233; A61B 2562/0271; A61B 2562/046; A61B 5/0816; A61B 5/0823; A61B 5/091; A61B 5/486
See application file for complete search history.

(56) References Cited

U.S. PATENT DOCUMENTS

| | | | |
|---|---|---|---|
| 6,121,953 | A | 9/2000 | Walker |
| 6,286,958 | B1 | 9/2001 | Koest et al. |
| 6,771,423 | B2 | 8/2004 | Geist |
| 6,837,615 | B2 | 1/2005 | Newman |
| 6,996,256 | B2 | 2/2006 | Pavlidis |
| 7,027,621 | B1 | 4/2006 | Prokoski |
| 7,135,980 | B2 | 11/2006 | Moore et al. |
| 7,138,905 | B2 | 11/2006 | Pavlidis et al. |
| 8,149,273 | B2 | 4/2012 | Liu et al. |
| 8,289,443 | B2 | 10/2012 | MacKenzie |
| 8,334,872 | B2 | 12/2012 | Epps et al. |
| 8,360,986 | B2 | 1/2013 | Farag et al. |
| 8,573,866 | B2 | 11/2013 | Bond et al. |
| 8,585,588 | B2 | 11/2013 | Kovarik et al. |
| 8,723,790 | B1 | 5/2014 | Schaefer |
| 8,768,438 | B2 | 7/2014 | Mestha et al. |
| 8,786,698 | B2 | 7/2014 | Chen et al. |
| 8,855,384 | B2 | 10/2014 | Kyal et al. |
| 8,964,298 | B2 | 2/2015 | Haddick et al. |
| 9,019,174 | B2 | 4/2015 | Jerauld |
| 9,020,185 | B2 | 4/2015 | Mestha et al. |
| 9,194,749 | B2 | 11/2015 | Pompei |
| 9,211,069 | B2 | 12/2015 | Larsen et al. |
| 9,410,854 | B2 | 8/2016 | Padiy |
| 9,569,734 | B2 | 2/2017 | Thieberger et al. |
| 2002/0080094 | A1 | 6/2002 | Biocca et al. |
| 2005/0083248 | A1 | 4/2005 | Biocca et al. |
| 2005/0271117 | A1 | 12/2005 | Grassi et al. |
| 2007/0047768 | A1 | 3/2007 | Gordon et al. |
| 2007/0248238 | A1 | 10/2007 | Abreu |
| 2007/0265507 | A1 | 11/2007 | de Lemos |
| 2008/0260212 | A1 | 10/2008 | Moskal et al. |
| 2009/0221888 | A1 | 9/2009 | Wijesiriwardana |
| 2009/0237564 | A1 | 9/2009 | Kikinis et al. |
| 2010/0191124 | A1 | 7/2010 | Prokoski |
| 2010/0280334 | A1 | 11/2010 | Carlson et al. |
| 2012/0062719 | A1 | 3/2012 | Debevec et al. |
| 2012/0105473 | A1 | 5/2012 | Bar-Zeev et al. |
| 2012/0197093 | A1 | 8/2012 | LeBoeuf et al. |
| 2012/0327194 | A1 | 12/2012 | Shiratori et al. |
| 2013/0124039 | A1 | 5/2013 | Abreu |
| 2013/0215244 | A1 | 8/2013 | Mestha et al. |
| 2013/0241805 | A1 | 9/2013 | Gomez |
| 2013/0257709 | A1 | 10/2013 | Raffle et al. |
| 2014/0180449 | A1 | 6/2014 | Sung |
| 2014/0282911 | A1 | 9/2014 | Bare et al. |
| 2014/0347265 | A1 | 11/2014 | Aimone et al. |
| 2014/0366049 | A1 | 12/2014 | Lehtiniemi et al. |
| 2015/0087924 | A1 | 3/2015 | Li et al. |
| 2015/0126872 | A1* | 5/2015 | Dubielczyk ............ A61B 90/39 600/473 |
| 2015/0148618 | A1 | 5/2015 | Sitko et al. |
| 2015/0157255 | A1 | 6/2015 | Nduka |
| 2015/0297126 | A1 | 10/2015 | Atsumori et al. |
| 2015/0310263 | A1 | 10/2015 | Zhang et al. |
| 2015/0359443 | A1 | 12/2015 | Poh |
| 2016/0015289 | A1 | 1/2016 | Simon et al. |
| 2016/0081622 | A1 | 3/2016 | Abreu |
| 2016/0091877 | A1 | 3/2016 | Fullam et al. |
| 2016/0098592 | A1 | 4/2016 | Lee et al. |
| 2016/0100790 | A1 | 4/2016 | Cantu et al. |
| 2016/0170996 | A1 | 6/2016 | Frank et al. |
| 2016/0216760 | A1 | 7/2016 | Trutna et al. |
| 2016/0224803 | A1 | 8/2016 | Frank et al. |
| 2016/0235324 | A1 | 8/2016 | Mershin et al. |
| 2016/0270656 | A1 | 9/2016 | Samec et al. |
| 2016/0342835 | A1 | 11/2016 | Kaehler |
| 2017/0007167 | A1 | 1/2017 | Kostic et al. |
| 2017/0231490 | A1 | 8/2017 | Toth et al. |
| 2017/0235931 | A1 | 8/2017 | Publicover et al. |

OTHER PUBLICATIONS

Written opinion of the international searching authority, PCT/IB2017/056067, dated Jan. 29, 2018.

Written opinion of the international searching authority, PCT/IB2017/056069, dated Jan. 29, 2018.

Alghoul, K., Alharthi, S., Al Osman, H., & El Saddik, A. (2017). Heart Rate Variability extraction from videos signals: ICA vs. EVM comparison. IEEE Access, 5, 4711-4719.

Al-Khalidi, F. Q., Saatchi, R., Burke, D., Elphick, H., & Tan, S. (2011). Respiration rate monitoring methods: A review. Pediatric pulmonology, 46(6), 523-529.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE ras & embs International Conference on (pp. 276-280). IEEE.

Aryal, A., Ghahramani, A., & Becerik-Gerber, B. (2017). Monitoring fatigue in construction workers using physiological measurements. Automation in Construction.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Cardone, D., Pinti, P., & Merla, A. (2015). Thermal infrared imaging-based computational psychophysiology for psychometrics. Computational and mathematical methods in medicine, 2015.

Carine Collé, Re-Experience Big-Data, 3 months group project with Sanya Rai Gupta and Florian Puech, UK, London, RCA, IDE, 2014, Amoeba.

Choi, J. S., Bang, J. W., Heo, H., & Park, K. R. (2015). Evaluation of Fear Using Nonintrusive Measurement of Multimodal Sensors. Sensors, 15(7), 17507-17533.

(56) References Cited

OTHER PUBLICATIONS

Clay-Warner, J., & Robinson, D. T. (2015). Infrared thermography as a measure of emotion response. Emotion Review, 7(2), 157-162.
Cross, C. B., Skipper, J. A., & Petkie, D. (May 2013). Thermal imaging to detect physiological indicators of stress in humans. In SPIE Defense, Security, and Sensing (pp. 870501-870501). International Society for Optics and Photonics.
Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.
Fei, J., & Pavlidis, I. (2010). Thermistor at a distance: unobtrusive measurement of breathing. IEEE Transactions on Biomedical Engineering, 57(4), 988-998.
Fernández-Cuevas, I., Mains, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.
Ghahramani, A., Castro, G., Becerik-Gerber, B., & Yu, X. (2016). Infrared thermography of human face for monitoring thermoregulation performance and estimating personal thermal comfort. Building and Environment, 109, 1-11.
Hawkes, P. W. (2012). Advances in Imaging and Electron Physics (vol. 171). Academic Press. Chapter 2.
Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE vol. (vol. 7486, pp. 74860I-1).
Ioannou, S., Gallese, V., & Merla, A. (2014). Thermal infrared imaging in psychophysiology: potentialities and limits. Psychophysiology, 51(10), 951-963.
Jenkins, S. D., & Brown, R. D. H. (2014). A correlational analysis of human cognitive activity using Infrared Thermography of the supraorbital region, frontal EEG and self-report of core affective state. QIRT.
Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.
Jovanov, E., Raskovic, D., & Hormigo, R. (2001). Thermistor-based breathing sensor for circadian rhythm evaluation. Biomedical sciences instrumentation, 37, 493-498.
Joyal, C. C., & Henry, M. (2013). Long-wave infrared functional brain imaging in human: a pilot study. The open neuroimaging journal, 7(1).
Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.
Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.
Lewis, G. F., Gatto, R. G., & Porges, S. W. (2011). A novel method for extracting respiration rate and relative tidal volume from infrared thermography. Psychophysiology, 48(7), 877-887.
Merla, A. (2014). Thermal expression of intersubjectivity offers new possibilities to human—machine and technologically mediated interactions.
Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.
Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In The International Conference on Electronics and Software Science (ICESS2015) Proceedings (pp. 212-215).
Murthy, R., & Pavlidis, I. (2006). Noncontact measurement of breathing function. IEEE Engineering in Medicine and Biology Magazine, 25(3), 57-67.
Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.
Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.
Nhan, B. R., & Chau, T. (2010). Classifying affective states using thermal infrared imaging of the human face. IEEE Transactions on Biomedical Engineering, 57(4), 979-987.
Pavlidis, I., & Levine, J. (2002). Thermal image analysis for polygraph testing. IEEE Engineering in Medicine and Biology Magazine, 21(6), 56-64.
Pavlidis, I., Dowdall, J., Sun, N., Puri, C., Fei, J., & Garbey, M. (2007). Interacting with human physiology. Computer Vision and Image Understanding, 108(1), 150-170.
Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.
Rajoub, B. A., & Zwiggelaar, R. (2014). Thermal facial analysis for deception detection. IEEE transactions on information forensics and security, 9(6), 1015-1023.
Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).
Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.
Sharma, N., Dhall, A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.
Sharma, N., Dhall, A., Gedeon, T., & Goecke, R. (2014). Thermal spatio-temporal data for stress recognition. EURASIP Journal on Image and Video Processing, 2014(1), 28.
Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.
Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.
Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

\* cited by examiner

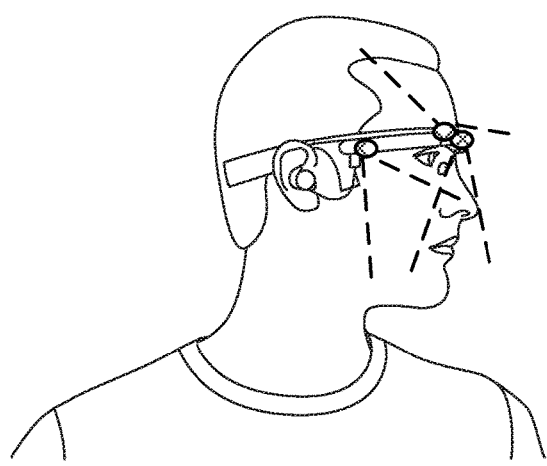
FIG. 2a  FIG. 2b
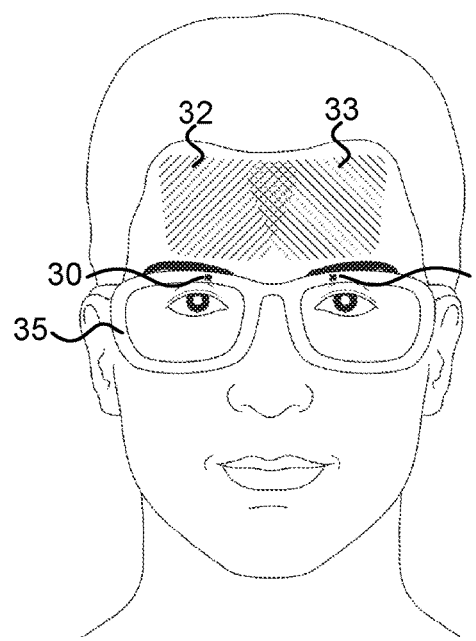
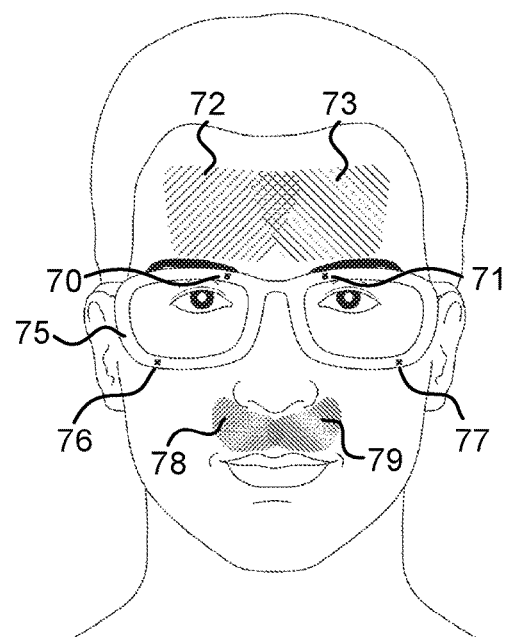
FIG. 3  FIG. 4

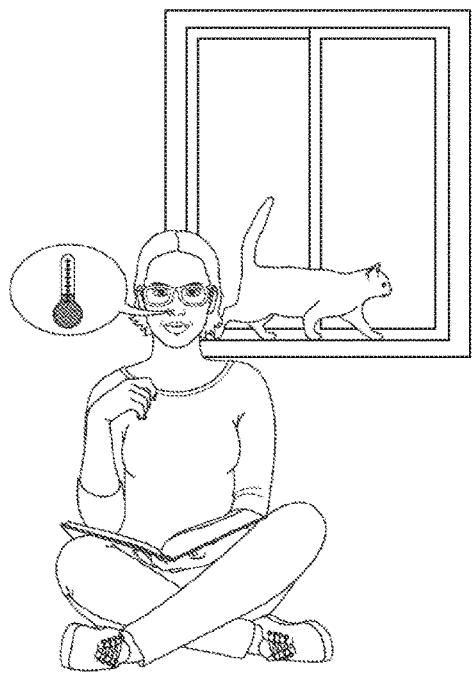
FIG. 27a    FIG. 27b
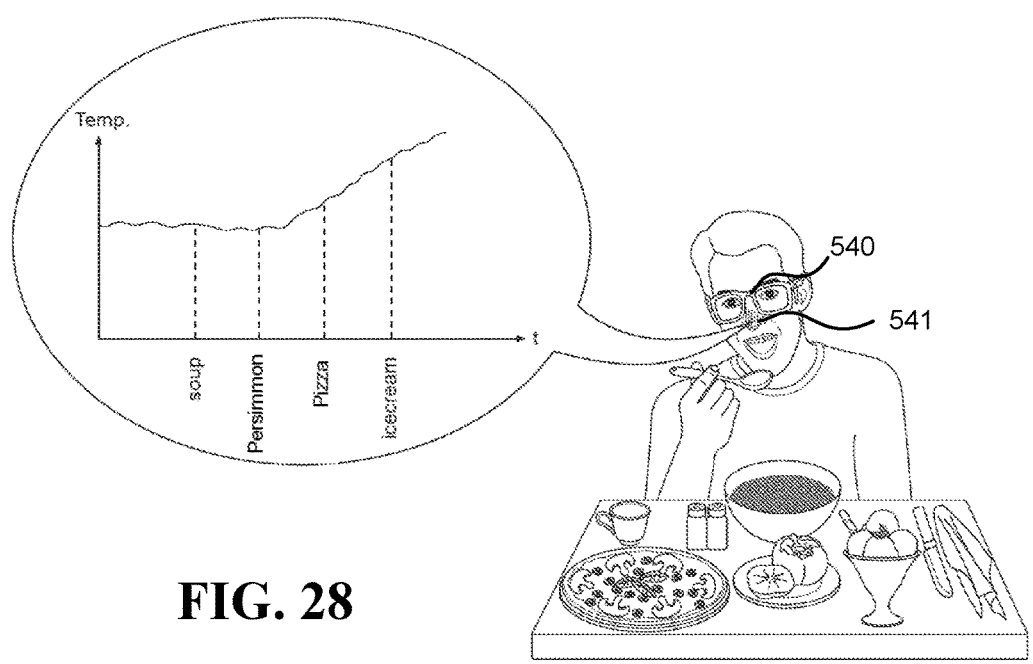
FIG. 28

WEARABLE RESPIRATION MEASUREMENTS SYSTEM

CROSS-REFERENCE TO RELATED APPLICATIONS

This Application claims priority to U.S. Provisional Patent Application No. 62/354,833, filed Jun. 27, 2017, and U.S. Provisional Patent Application No. 62/372,063, filed Aug. 8, 2017.

ACKNOWLEDGMENTS

Gil Thieberger would like to thank his holy and beloved teacher, Lama Dvora-hla, for her extraordinary teachings and manifestation of love, compassion and morality, and for her endless efforts, support, and skills in guiding him and others on their paths to freedom and ultimate happiness. Gil would also like to thank his beloved parents for raising him exactly as they did.

BACKGROUND

Many physiological responses are manifested in the temperatures and/or temperature changes at various regions of the human face. For example, measuring these temperatures and/or temperature changes may help determine the amount of stress a person is feeling or the extent of an allergic reaction the person has. In another example, measuring temperatures at regions of the face can help determine how a user feels, e.g., whether the user is nervous or calm. Thus, monitoring and analyzing such temperatures can be useful for many health-related and life-logging related applications. However, collecting such data over time when people are going through their daily activities can be very difficult. Typically, collection of such data involves utilizing thermal cameras that are bulky, expensive and need to be continually pointed at a person's face. Additionally, due to the people's movements in their day-to-day activities, collecting the required measurements often involves performing various complex image analysis procedures, such as procedures involving image registration and face tracking.

Therefore, due to the many applications they may enable, there is a need to be able to collect thermal measurements at various regions of a person's face. Preferably, the measurements are to be collected over a long period of time, while the person performs various day-to-day activities.

SUMMARY

Herein disclosed various embodiments of a wearable system configured to collect thermal measurements related to respiration. The system includes a frame configured to be worn on a user's head, and at least one non-contact thermal camera (e.g., thermopile or microbolometer based sensor). The thermal camera is small and lightweight, physically coupled to the frame, located close to the user's face, does not occlude any of the user's mouth and nostrils, and is configured to take thermal measurements of: a portion of the right side of the user's upper lip, a portion of the left side of the user's upper lip, and a portion of the user's mouth. The thermal measurements are forwarded to a computer that calculates breathing related parameters, such as breathing rate, an extent to which the breathing was done through the mouth, an extent to which the breathing was done through the nostrils, and ratio between exhaling and inhaling durations.

BRIEF DESCRIPTION OF THE DRAWINGS

The embodiments are herein described by way of example only, with reference to the accompanying drawings. No attempt is made to show structural details of the embodiments in more detail than is necessary for a fundamental understanding of the embodiments. In the drawings:

FIG. 2a and FIG. 2b illustrate various types of head-mounted systems with cameras thereon, where the dotted lines illustrate boundaries of fields of view of the cameras;

FIG. 3 illustrates an embodiment of a system configured to collect thermal measurements of the forehead useful for detecting a physiological response;

FIG. 4 illustrates an embodiment of a system configured to collect thermal measurements of the forehead and the area of the upper lip;

FIG. 27a and FIG. 27b illustrate a scenario in which a user is alerted about an expected allergic reaction;

FIG. 28 illustrates a scenario in which a trigger factor (food item) for an allergy is detected;

DETAILED DESCRIPTION

Figure 1A:
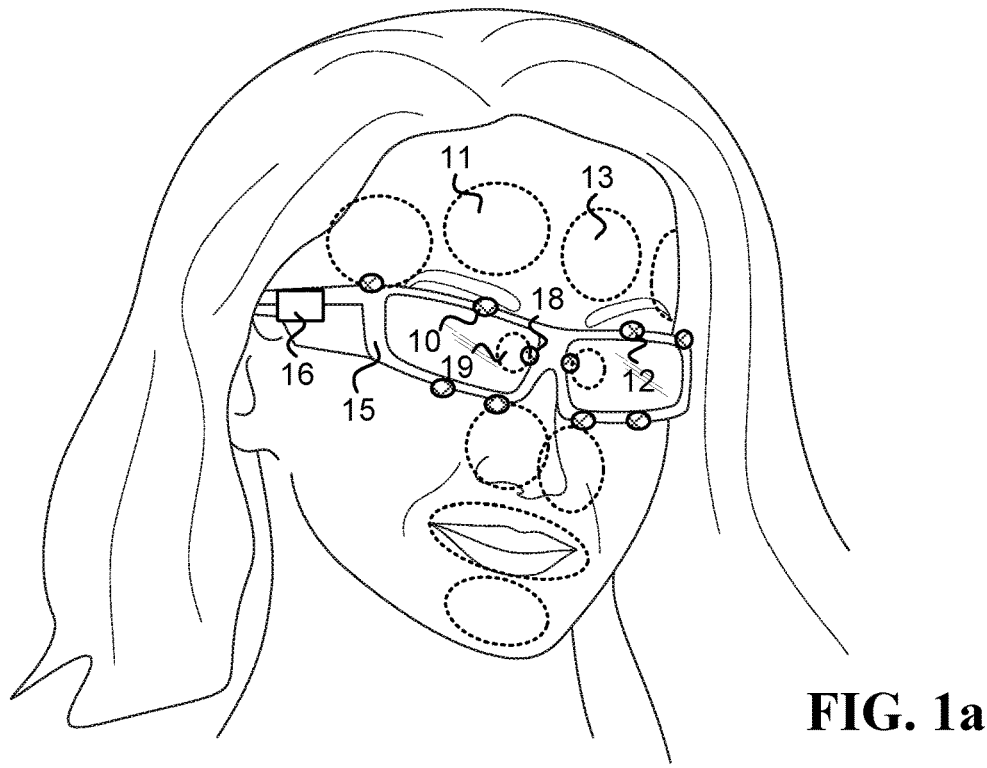
FIG. 1a and FIG. 1b illustrate various types of head-mounted systems with cameras thereon.

Some of the various head-mounted systems (HMSs) described in this disclosure, e.g., as illustrated in FIG. 1a to FIG. 4, may involve at least two thermal cameras that are physically coupled to a frame worn on a user's head. The at least two thermal cameras are used to take thermal measurements of different ROIs. Optionally, the thermal measurements taken by the at least two thermal cameras are used to detect one or more of the physiological responses mentioned in this disclosure. One embodiment of such a system, which is illustrated in FIG. 1a, includes at least a frame 15, a first thermal camera 10, and a second thermal camera 12.

The frame may be any of the frames of a head-mounted system (HMS) described in this disclosure, such as a frame of eyeglasses (e.g., as illustrated in FIG. 1a), or a frame of some other HMS, such as a hat, a helmet, and/or part of a system comprising a head-mounted display (e.g., an augmented reality system, a virtual reality system, or a mixed reality system). In FIG. 1a, the frame is denoted by the reference numeral 15, but in illustrations of other embodiments, the frame may be denoted by other reference numerals, such as a frame 35 in FIG. 3, a frame 75 in FIG. 4, or a frame 90 in FIG. 6. Various properties of the frame (and other system components) are described in more detail in Section 2.

The first thermal camera is physically coupled to the right side of the frame. Optionally, the first thermal camera is located less than 15 cm away from the user's face (herein "g" denotes centimeters). Optionally, the first thermal camera is lightweight, weighing less than 5 g (herein "g" denotes grams). The first thermal camera is configured to take thermal measurements of a first region of interest (these thermal measurements are denoted $TH_{ROI1}$). Optionally, $ROI_1$ (the first region of interest) covers a portion of the right side of the user's forehead, and the first thermal camera does not occlude $ROI_1$. In one example, the first thermal camera may be the thermal camera 10 in FIG. 1a and $ROI_1$ may be ROI 11 in that figure.

It is noted that the distance in sentences such as "a thermal camera located less than 15 cm away from the user's face" refers to the shortest possible distance between the thermal camera and the face. For example, the shortest distance between thermal camera 10 and the user's face in FIG. 1a is from the thermal camera 10 to the lower part of the right eyebrow, and not from thermal camera 10 to ROI 11.

The second thermal camera is physically coupled to the left side of the frame. Optionally, the second thermal camera is located less than 15 cm away from the user's face. Optionally, the second thermal camera is lightweight, weighing less than 5 g. The second thermal camera is configured to take thermal measurements of a second region of interest (these thermal measurements are denoted $TH_{ROI2}$). Optionally, $ROI_2$ covers a portion of the left side of the user's forehead, and the second thermal camera does not occlude $ROI_2$. In one example, the second thermal camera may be thermal camera 12 in FIG. 1a and $ROI_2$ may be ROI 13 in that figure.

In different embodiments, $ROI_1$ and $ROI_2$ may cover slightly different regions on the user's face. In one example, the right side of the user's forehead covers at least 30% of $ROI_1$, and the left side of the user's forehead covers at least 30% of $ROI_2$. In another example, the right side of the user's forehead covers at least 80% of $ROI_1$, and the left side of the user's forehead covers at least 80% of $ROI_2$. In some embodiments, the overlap between $ROI_1$ and $ROI_2$ is lower than 80% of the smallest area from among the areas of $ROI_1$ and $ROI_2$.

In different embodiments, the first and second thermal cameras may have different characteristics and/or may be located at various distances relative to the face. In one embodiment, each of the first and second thermal cameras weighs below 5 g, and is located less than 10 cm away from the face. In another embodiment, each of the first and second thermal cameras weighs below 1 g, and is located less than 5 cm away from the face. In yet another embodiment, at least one of the first and second thermal cameras is based on at least one of the following uncooled sensors: a thermopile, a microbolometer, and a pyroelectric sensor. In still another embodiment, at least at least one of the first and second thermal cameras is a focal-plane array (FPA) thermal camera.

According to the definition of a thermal camera as used in this disclosure, the first and second thermal cameras are not in physical contact with their corresponding ROIs. Additionally, as a result of being physically coupled to the frame, the thermal cameras remain pointed at their corresponding ROIs when the user's head makes angular movements. In one example, the angular movements include movements of more than 45°. In another example, the locations of the first and second cameras relative to the user's head do not change even when the user's head performs wide angular and lateral movements, where wide angular and lateral movements include angular movements of more than 60° and lateral movements of more than 1 meter.

It is to be noted that because the first and second thermal cameras are coupled to the frame, challenges faced by non-head mounted systems known in the art that acquire thermal measurements may be simplified and even eliminated with some of the embodiments described herein. Some of these challenges may involve dealing with complications caused by movements of the user, image registration, ROI alignment, tracking based on hot spots or markers, and motion compensation in the IR domain A more detailed discussion regarding the various types of thermal cameras that may be used in embodiments described in this disclosure, including properties of thermal measurements (e.g., $TH_{ROI1}$ and $TH_{ROI2}$ mentioned above), is provided in Section 1.

FIG. 3 illustrates an embodiment of a system configured to collect thermal measurements of the forehead useful for detecting a physiological response. The system includes frame 35 (which is a frame of a pair of eyeglasses) and thermal cameras 30 and 31, which here depicted as small black squares on the right and left sides of the frame, respectively. These thermal cameras are configured to take thermal measurements of ROI 32 and ROI 33, which are illustrated as patches of slanted lines on the right and left sides of the forehead, respectively.

Tough the description above involves first and second thermal cameras, in some embodiments, additional thermal cameras may be utilized to take thermal measurements that may be used to detect the physiological response (in addition to $TH_{ROI1}$ and $TH_{ROI2}$). For example, FIG. 1a and FIG. 1b each illustrate more than two thermal cameras. The characteristics of the first and second thermal cameras, and the advantages of utilizing thermal cameras physically coupled to the frame, which are set forth above, are applicable to additional thermal cameras that are utilized in various embodiments.

In one embodiment, in addition to the first and second thermal cameras described above, the HMS may include third and fourth thermal cameras that are physically coupled to the frame and configured to take thermal measurements of third and fourth ROIs (denoted $TH_{ROI3}$ and $TH_{ROI4}$, respectively). Optionally, the third region of interest ($ROI_3$) covers an area below the user's nostrils and the fourth region of interest ($ROI_4$) covers a portion of the user's nose. In one example, an area below the nostrils refers to an area that includes portions of the upper lip, the mouth, and/or the chin. In another example, an area below the nostrils refers to an area projected in front of a user's face, which is below the height of the nostrils and intersects with the exhale streams blowing from the user's nostrils and/or mouth. Optionally, $TH_{ROI3}$ may be utilized to determine a value of respiratory parameter of the user as discussed in more detail in Section 5.

Figure 1B:
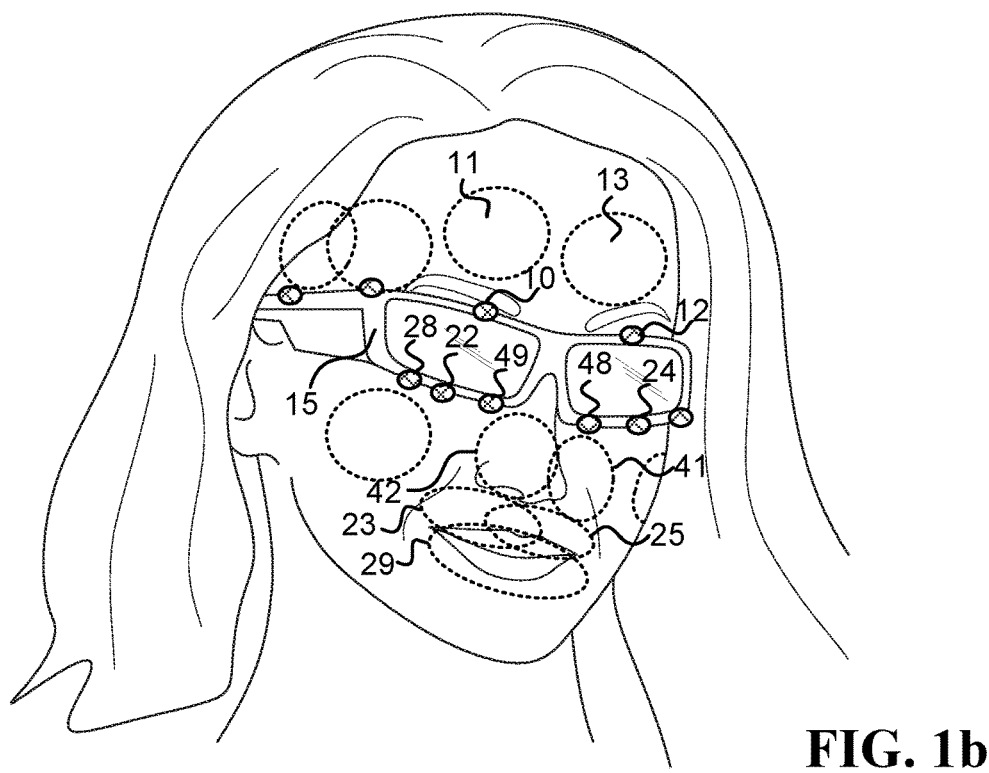

Referring to FIG. 1b, in one example, the third thermal camera may be thermal camera 22 and $ROI_3$ may include portion of the regions corresponding to reference numerals 23 and/or 29. In this example, the fourth thermal camera may be thermal camera 49, and $ROI_4$ may include a portion of the region 42.

In some embodiments, the HMS described above (e.g., illustrated in FIG. 1a or FIG. 3), is further configured to forward $TH_{ROI1}$ and $TH_{ROI2}$ to a computer that is configured to detect a physiological response based on $TH_{ROI1}$ and $TH_{ROI2}$. One example of such a computer is the computer 16 in FIG. 1a. The computer includes one or more processors and memory. Optionally, the memory stores $TH_{ROI1}$ and $TH_{ROI2}$, prior to them being forwarded to the one or more processors. Optionally, the computer may be at least one of the following: a computer belonging to a device carried by the user, a computer of a smartphone, a personal computer, a remote server (e.g., a cloud-based server), and an analog circuit. In one example, the computer is computer system 400 illustrated in FIG. 72a. In another example, the computer may be computer system 410 illustrated in FIG. 72b. Additional details regarding various types of computers and hardware components that may be utilized to detect the physiological response are given in Sections 2 and 7.

In one embodiment, the physiological response detected by the computer is indicative of an occurrence of at least one of the following: stress, an allergic reaction, mental workload, a pulse, a headache, dehydration, intoxication and a stroke. In another embodiment, the physiological response is indicative of an occurrence of at least one of the following emotional states of the user: fear, anxiety, guilt, pain, and sexual arousal.

In some embodiments, detecting the physiological response may involve utilizing baseline thermal measurement values, most of which were taken when the user was not experiencing the physiological response. Thus, detecting the physiological response may rely on observing a change to typical temperatures at the ROIs (where different users might have different typical temperatures at the ROIs). In one example, the computer is further configured to detect the physiological response based on at least one of the following values: (i) a difference between $TH_{ROI1}$ and a first baseline value determined based on a first set of previous measurements taken by the first thermal camera, and (ii) a difference between $TH_{ROI2}$ and a second baseline value determined based on a second set of previous measurements taken by the second thermal camera.

The computer may utilize $TH_{ROI1}$ and/or $TH_{ROI2}$ in various ways in order to detect the physiological response. In one example, the computer may be configured to compare one or more values derived from $TH_{ROI1}$ and/or $TH_{ROI2}$ to a certain threshold, and determine whether the threshold is reached (which is indicative of an occurrence of the physiological response). In another example, the computer may be configured to determine a similarity between a reference time series corresponding to the physiological response and $TH_{ROI1}$ and/or $TH_{ROI2}$ (or a time series derived from $TH_{ROI1}$ and/or $TH_{ROI2}$). Optionally, when a sufficiently high similarity is detected, the computer may interpret that as an indication of an occurrence of the physiological response. In yet another example, the computer may generate feature values based on $TH_{ROI1}$ and/or $TH_{ROI2}$, and utilize a machine learning-based model to calculate, based on the feature values, a value indicative of whether the physiological response occurred (and/or the extent of the physiological response). Section 4 provides a more detailed discussion regarding how the computer may detect a physiological response based on thermal measurements such as $TH_{ROI1}$ and $TH_{ROI2}$, and more details on what it means to detect a physiological response.

In one embodiment, detecting the physiological response may involve calculations involving thermal measurements received from four thermal cameras ($TH_{ROI1}$, $TH_{ROI2}$, $TH_{ROI3}$ and $TH_{ROI4}$, mentioned above). For example, the computer may be configured to: (i) generate feature values based on $TH_{ROI1}$, $TH_{ROI2}$, $TH_{ROI3}$ and $TH_{ROI4}$; and (ii) utilize a model to calculate, based on the feature values, a value indicative of the extent of the physiological response. Optionally, the model may be a personalized model for a user, such that the model is generated based on previous $TH_{ROI1}$, $TH_{ROI2}$, $TH_{ROI3}$, and $TH_{ROI4}$ of the user. Optionally, at least some of the previous $TH_{ROI1}$, $TH_{ROI2}$, $TH_{ROI3}$, and $TH_{ROI4}$ of the user were taken while the user had the physiological response. Optionally, in this embodiment, the physiological response involves the user experiencing at least one of the following: stress, mental workload, fear, sexual arousal, anxiety, pain, a headache, dehydration, intoxication, and a stroke.

Many known systems for analyzing physiological responses based on temperature measurements receive series of thermal images composed of pixels that represent temperature measurements. Measuring the temperature (T), as opposed to a temperature change ($\Delta T$), is required in order to perform image registration and run a tracker, which compensates for the movements of the user in relation to the (non-head-mounted) thermal camera and brings the images into precise alignment for analysis and comparison.

However, in various embodiments described herein, thermal cameras are physically coupled to a frame worn on a user's head (e.g., a frame of eyeglasses, a head-mounted display, or a hat). In this configuration, a thermal camera moves with the user's head when the head changes its spatial location, and thus, there may be no need for image registration and/or object tracking. As a result, it is possible to run the image processing and/or signal processing algorithms on a series of thermal measurements taken by each pixel. This increases the accuracy of the system compared to the case where a temperature change ($\Delta T$) is derived from thermal measurements taken by different pixels (after tracking and registration). Optionally, the temperature change at an ROI over time ($\Delta T_{ROI}$) is analyzed in relation to another parameter, such as the stimulus the user is exposed to, and/or other physiological measurements (such as FFG, skin conductance, pulse, breathing rate, and/or blood pressure).

Thermal measurements taken with the first and second thermal cameras may have different properties in different embodiments. In particular, due to the physical coupling of the thermal cameras to the frame, the thermal measurements may exhibit certain measurement errors for the temperature, but when processed, may result in lower errors for the temperature change (ΔT), as discussed below. The following are some examples of embodiments in which thermal measurements taken by the first and second thermal cameras (e.g., $TH_{ROI1}$ and $TH_{ROI2}$) have different accuracies.

In one example, the first and second thermal cameras measure temperature with a possible measurement error above ±1° C. and provide temperature change (ΔT) with an error below ±0.1° C. Optionally, the system includes a computer configured to estimate a physiological response based on ΔT measured by the first and second thermal cameras.

In another example, the first and second thermal cameras measure temperature with a possible measurement error above ±0.2° C. and provide temperature change (ΔT) with an error of below ±0.05° C. Optionally, the system includes a computer configured to estimate a physiological response based on ΔT measured by the first and second thermal cameras.

In yet another example, the first and second thermal cameras measure temperatures at $ROI_1$ and $ROI_2$, and the system's nominal measurement error of the temperatures at $ROI_1$ and $ROI_2$ ($ERR_{TROI}$) is at least twice the system's nominal measurement error of the temperature changes at $ROI_1$ and $ROI_2$ ($ERR_{\Delta TROI}$) when the user's head makes angular movements with an angular velocity above 0.1 rad/sec (radians per second). Optionally, the system includes a computer configured to identify affective response that causes a temperature change at $ROI_1$ and $ROI_2$, which is between $ERR_{TROI}$ and $ERR_{\Delta TROI}$.

In still another example, the first and second thermal cameras measure temperatures at $ROI_1$ and $ROI_2$, and the system's nominal measurement error of the temperatures at $ROI_1$ and $ROI_2$ ($ERR_{TROI}$) is at least five times the system's nominal measurement error of the temperature changes at $ROI_1$ and $ROI_2$ ($ERR_{\Delta TROI}$) when the user's head makes angular movements with an angular velocity above 0.5 rad/sec (radians per second). Optionally, the system includes a computer configured to identify affective response that causes a temperature change at $ROI_1$ and $ROI_2$, which is between $ERR_{TROI}$ and $ERR_{\Delta TROI}$.

Measurements of the thermal cameras may be utilized for various calculations in different embodiments. In one embodiment, the first and second thermal cameras measure temperatures at $ROI_1$ and $ROI_2$, respectively. The system, in this embodiment, may include a circuit that is configured to: receive a series of temperature measurements at $ROI_1$ ($T_{ROI1}$) and calculate temperature changes at $ROI_1$ ($\Delta T_{ROI1}$), receive a series of temperature measurements at $ROI_2$ ($T_{ROI2}$) and calculate temperature changes at $ROI_2$ ($\Delta T_{ROI2}$), and utilize $\Delta T_{ROI1}$ and $\Delta T_{ROI2}$ to identify a physiological response. Optionally, the system's nominal measurement error of $T_{ROI1}$ is at least twice the system's nominal measurement error of the temperature changes $\Delta T_{ROI1}$ when the user's head makes angular movements that involve an angular velocity that is above 0.1 rad/sec. Optionally, the system's nominal measurement error of $T_{ROI1}$ is at least five times the system's nominal measurement error of $\Delta T_{ROI1}$ when the user's head makes angular movements that involve an angular velocity that is above 0.5 rad/sec.

In one embodiment, the computer is configured to calculate $\Delta T_{ROI1}$ and $\Delta T_{ROI2}$ based on $T_{ROI1}$ and $T_{ROI2}$, and to identify the physiological response based on a difference between $\Delta T_{ROI1}$ and $\Delta T_{ROI2}$. For example, assuming the physiological response is allergic reaction, $ROI_1$ is the nasal area, and $ROI_2$ is the forehead; when both $\Delta T_{ROI1}$ and $\Delta T_{ROI2}$ increase in 1° C. then it is less probable that the cause is allergic reaction compared to a case where $\Delta T_{ROI1}$ increases in 1° C. while $\Delta T_{ROI2}$ stays essentially the same. In another example, assuming the physiological response is allergic reaction, $ROI_1$ is the right side of the nasal area, and $ROI_2$ is the left side of the nasal area; when both $\Delta T_{ROI1}$ and $\Delta T_{ROI2}$ increase in 0.5° C. then it is more probable that the cause is allergic reaction compared to a case where $\Delta T_{ROI1}$ increases in 0.5° C. while $\Delta T_{ROI2}$ stays essentially the same. In still another example, assuming the physiological response is stress, $ROI_1$ is the nose, and $ROI_2$ is the maxillary; when both $\Delta T_{ROI1}$ and $\Delta T_{ROI2}$ decrease more than 0.2° C. then it is more probable that the cause is stress compared to a case where $\Delta T_{ROI1}$ decreases more than 0.2° C. while $\Delta T_{ROI2}$ stays essentially the same.

A specific physiological response, which is a physiological signal, which may be identified utilizing first and second thermal cameras involves detection of the blood flow in the user's body. For example, in one embodiment, $ROI_1$ and $ROI_2$ may be located such that $ROI_1$ covers a portion of the right side of the frontal superficial temporal artery of the user, and $ROI_2$ covers a portion of the left side of the frontal superficial temporal artery of the user. Optionally, in this embodiment, the system is configured to forward $TH_{ROI1}$ and $TH_{ROI2}$ to a computer that is configured to identify, based on $TH_{ROI1}$ and $TH_{ROI2}$, at least one of the following: an arterial pulse, a headache, dehydration, intoxication, and a stroke.

The following is an example of how some of the embodiments described in this disclosure may be utilized to obtain values of a physiological signal that has periodic features, such as pulse or respiration. Optionally, in these embodiments, the thermal camera(s) may include multiple sensing elements, and a computer may extract temporal signals for individual pixels that measure regions inside $ROI_1$ and/or $ROI_2$, and/or extract temporal signals for pixel clusters that measure regions inside $ROI_1$ and/or $ROI_2$, depending on the movement and/or the noise level. The calculation of the physiological signal may include harmonic analysis, such as a fast Fourier transform, applied to the temperature signal and/or temperature change signal of each pixel, or pixel clusters, over time in a sliding window, which may be followed by a non-linear filter to reduce low-frequency signal leakage in the measured frequency range. In cases where some pixels may be less informative than others, a clustering procedure may be implemented to remove the outliers. Following that, the frequency peaks in the set of pixels of interest may be used to vote for the dominant frequency component, the bin with the most votes is selected as the dominant frequency, and the estimate of the physiological signal may be obtained from the median filtered results of the dominant frequency components in a small sliding window.

One example of a contact-free heart rate and respiratory rate detection through measuring changes to infrared light emitted near the superficial blood vessels or the nasal area, respectively, is described in the reference Yang, M., Liu, Q., Turner, T., & Wu, Y. (2008), "Vital sign estimation from passive thermal video", In Computer Vision and Pattern Recognition, 2008 (pp. 1-8), CVPR 2008 IEEE. Pulsating blood flow induces subtle periodic temperature changes to the skin above the superficial vessels by heat diffusion, which may be detected by thermal video to reveal the associated heart rate. The temperature modulations may be detected through pixel intensity changes in the ROI using a thermal camera, and the corresponding heart rate may be measured quantitatively by harmonic analysis of these changes on the skin area above the superficial temporal artery (in this context, "the skin area above the artery" refers to "the skin area on top of the artery").

The temperature modulation level due to blood pulsating is far less than normal skin temperature, therefore, in one embodiment, the subtle periodic changes in temperature are quantified based on differences between image frames. For example, after an optional alignment, the frame differences against a certain reference frame are calculated for every frame, based on corresponding pixels or corresponding pixel clusters. The temperature differences may look like random noise in the first several frames, but a definite pattern appears close to half of the pulse period; then the temperature differences become noisy again as approaching the pulse period. The heart rate is estimated by harmonic analysis of the skin temperature modulation above the superficial temporal artery. In one embodiment, a similar method is applied for respiration rate estimation by measuring the periodic temperature changes around the nostril area.

Figure 7:
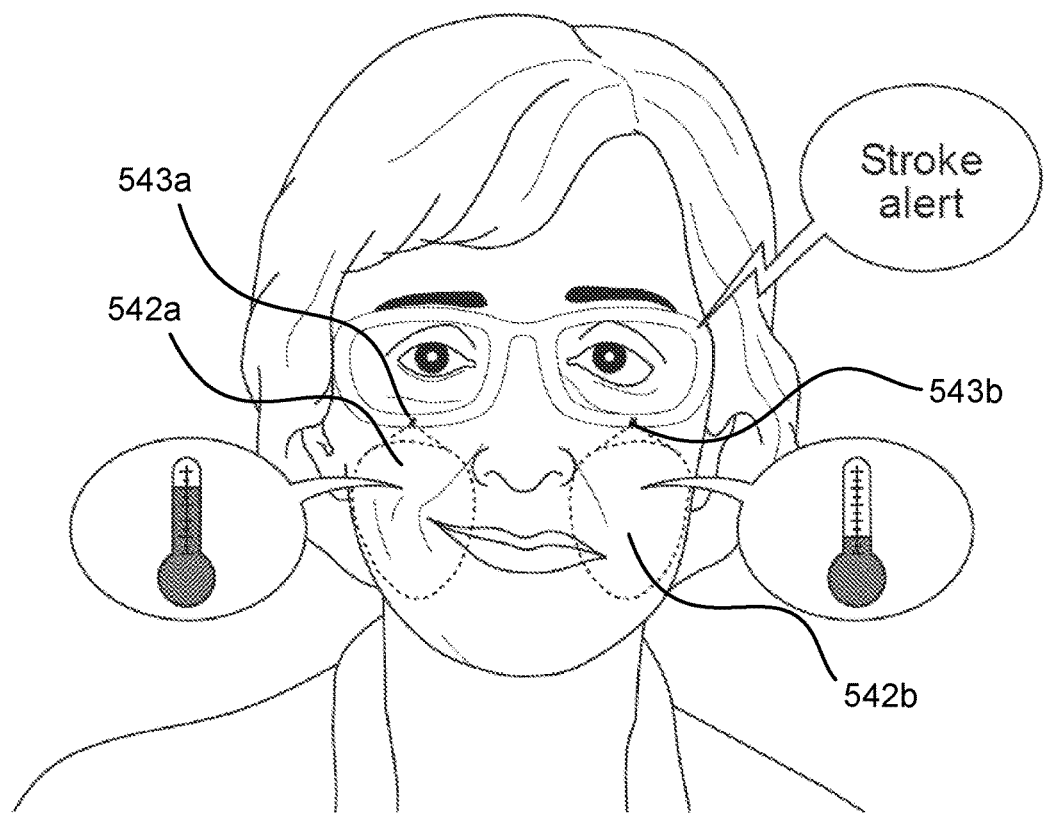
FIG. 7 illustrates a scenario in which an alert regarding a possible stroke may be issued by an embodiment of a system described herein.

In one embodiment, $ROI_1$ covers a portion of the right side of the superficial temporal artery of the user, and $ROI_2$ covers a portion of the left side of the superficial temporal artery of the user. Optionally, in this embodiment, the system is configured to forward $TH_{ROI1}$ and $TH_{ROI2}$ to a computer configured to identify, based on $TH_{ROI1}$ and $TH_{ROI2}$, at least one of the following: an arterial pulse, a headache, and a stroke. FIG. 7 in U.S. Pat. No. 8,360,986 awarded to Farag et at illustrates the right and left superficial temporal artery ROIs of one person. The locations and dimensions of the right and left superficial temporal artery ROIs may differ to some extent between different people. Due to the inherent benefits obtained from the disclosed head-mounted thermal cameras, it may be enough that $ROI_1$ and $ROI_2$ cover just a portion of the right and left superficial temporal artery ROIs. Additionally or alternatively, $ROI_1$ and $ROI_2$ may cover greater areas than the ROIs illustrated in FIG. 7 in U.S. Pat. No. 8,360,986.

FIG. 1b, FIG. 2a, and FIG. 2b illustrate various types of head-mounted systems with cameras thereon; the dotted circles and ellipses illustrate the ROIs of which the cameras take measurements. The cameras may be thermal cameras and/or visible-light cameras. In the illustrations, cameras are designated by a button like symbol (see for example thermal camera 10 in FIG. 1a). FIG. 2a and FIG. 2b illustrate a side view of various types of head-mounted systems with cameras thereon; the dotted lines illustrate the Fields Of View (FOVs) of the cameras.

As mentioned above, some of the various systems described in this disclosure, e.g., as illustrated in FIG. 1a, FIG. 1b, FIG. 4, FIG. 6, and other figures, may involve at least four thermal cameras that are used to take thermal measurements of different ROIs. Optionally, the thermal measurements taken by the at least four thermal cameras are used to detect one or more of the physiological responses mentioned in this disclosure. One embodiment of such a system includes at least a frame, and first, second, third, and fourth thermal cameras that are each physically coupled to the frame. The frame is configured to be worn on the user's head. Various properties of the frame (and other system components) are described in more detail in Section 2.

In one embodiment, each of the first, second, third and fourth thermal cameras weighs below 5 g and is located less than 15 cm away from the user's face. In another embodiment, each of the first, second, third and fourth thermal cameras weighs below 1 g, and is located less than 5 cm away from the face. In yet another embodiment, at least one of the first, second, third and fourth thermal cameras is based on at least one of the following uncooled sensors: a thermopile, a microbolometer, and a pyroelectric sensor. In still another embodiment, at least one of the first, second, third and fourth thermal cameras is a focal-plane array (FPA) thermal camera. Additional details regarding the various types of thermal cameras that may be used, including properties of thermal measurements, is provided in Section 1.

The first, second, third, and fourth thermal cameras may be located at various positions relative to the face. In one example, the first and third thermal cameras are located to the right of the vertical symmetry axis that divides the face, and the second and fourth thermal cameras are located to the left of the vertical symmetry axis. An illustration of the vertical symmetry axis is given in FIG. 71. Additionally, the third and fourth thermal cameras are located at least 1 cm below the first and second thermal cameras, respectively. Due to their different locations, and possibly different orientations, each of the thermal cameras may be configured to take thermal measurements of a different region of interest (ROI) on the user's face. In one embodiment, the first thermal camera is configured to take thermal measurements of a first region of interest ($TH_{ROI1}$), where $ROI_1$ covers a portion of the right side of the user's forehead, and the second thermal camera is configured to take thermal measurements of a second ROI ($TH_{ROI2}$), where $ROI_2$ covers a portion of the left side of the forehead. Additionally, in this embodiment, the third thermal camera is configured to take thermal measurements of a third ROI ($TH_{ROI3}$), where $ROI_3$ covers a portion of the right side of the user's upper lip, and the fourth thermal camera is configured to take thermal measurements of a fourth ROI ($TH_{ROI4}$), where $ROI_4$ covers a portion of the left side of the user's upper lip.

Optionally, the third and fourth thermal cameras are located outside the exhale streams of the mouth and nostrils.

Depending on the locations and orientations of the thermal cameras, there may be overlaps between at least some of the ROIs. In one example, the overlap between the portions of the right and left sides of the user's forehead ($P_1$ and $P_2$) is lower than 50% of the smallest area from among the areas of $P_1$ and $P_2$, and the overlap between the portions of the right and left sides of the user's upper lip ($P_3$ and $P_4$) is lower than 50% of the smallest area from among the areas of $P_3$ and $P_4$. In another example, there is no overlap between the portions of the right and left sides of the user's forehead, and there is no overlap between the portions of the right and left sides of the user's upper lip.

In some embodiments, at least some of the thermal cameras do not occlude their respective ROIs. In one example, the first and second thermal cameras do not occlude $ROI_1$ and $ROI_2$, respectively. In another example, the third and fourth thermal cameras do not occlude $ROI_3$ and $ROI_4$, respectively.

Due to their physical coupling to the frame, in one embodiment, the first, second, third and fourth thermal cameras remain pointed at their respective ROIs when the user's head makes angular movements. For example, the first, second, third and fourth thermal cameras may remain pointed at their respective ROIs when the user's head makes angular movements that exceed 0.1 rad/sec.

In one embodiment, the third and fourth thermal cameras are located outside the exhale streams of the mouth and nostrils, and the first, second, third and fourth thermal cameras are located less than 5 cm away from the face.

In some embodiments, the system described above may include one or more additional thermal cameras (in addition to the first, second, third, and fourth cameras described above). In one example, the system may include an additional thermal camera coupled to the frame, configured to take thermal measurements of a portion of the user's nose. Additionally, the system may include a sixth thermal camera physically coupled to the frame, configured to take thermal measurements of a portion of periorbital region of the face. Optionally, thermal measurements of the fifth and/or sixth thermal cameras may be utilized by a computer (as described below) to detect the physiological response (m addition to $TH_{ROI1}$, $TH_{ROI2}$, $TH_{ROI3}$, and $TH_{ROI4}$).

FIG. 1b illustrates one example of such a system that comprises a frame and at least four thermal cameras. As illustrated in the figure, the first thermal camera may be thermal camera 10, and $ROI_1$ may be ROI 11, which covers a region on the right side of the forehead. Additionally, the second thermal camera may be thermal camera 12, and $ROI_2$ may be ROI 13, which covers a region on the left side of the forehead. As illustrated in the figure, the third thermal camera may be thermal camera 22, and $ROI_3$ may be ROI 23, which covers a portion of the right side of the user's upper lip. Additionally, the fourth thermal camera may be thermal camera 24, and $ROI_4$ may be ROI 25, which covers a portion of the left side of the user's upper lip.

Another illustration of an embodiment of the system is given in FIG. 4, which illustrates an embodiment of a system configured to collect thermal measurements of the forehead and the area of the upper lip. The system includes frame 75 (which is a frame of a pair of eyeglasses) and thermal cameras 70 and 71, which are illustrated as small black squares on the right and left sides of the top of the frame, respectively. These thermal cameras are configured to take thermal measurements of ROI 72 and ROI 73, which are illustrated as patches of slanted lines on the right and left sides of the forehead, respectively. Additionally, the system includes thermal cameras 76 and 77, which are illustrated as small black squares on the right and left side of the bottom of the frame, respectively. These thermal cameras are configured to take thermal measurements of ROI 78 and ROI 79, which are illustrated as patches of slanted lines on the right and left sides of the area above the upper lip, respectively.

In some embodiments, the system described above (e.g., illustrated in FIG. 1b or FIG. 4) is further configured to forward $TH_{ROI1}$, $TH_{ROI2}$, $TH_{ROI3}$, and $TH_{ROI4}$ to a computer that is configured to detect a physiological response based on $TH_{ROI1}$, $TH_{ROI2}$, $TH_{ROI3}$, and $TH_{ROI4}$. The computer includes one or more processors and memory. Optionally, the memory stores $TH_{ROI1}$ and $TH_{ROI2}$ prior to them being forwarded to the one or more processors. Optionally, the computer may be at least one of the following: a computer belonging to a device carried by the user, a computer of a smartphone, a personal computer, a remote server (e.g., a cloud-based server), and an analog circuit. In one example, the computer is computer system 400 illustrated in FIG. 72a. In another example, the computer may be computer system 410 illustrated in FIG. 72b. Additional details regarding various types of computers and hardware components that may be utilized to detect the physiological response are given in Sections 2 and 7.

In one embodiment, the physiological response detected by the computer is indicative of an occurrence of at least one of the following: stress, an allergic reaction, an asthma attack, mental workload, a pulse, a headache, dehydration, intoxication and a stroke. In another embodiment, the physiological response is indicative of an occurrence of at least one of the following emotional states of the user: fear, anxiety, guilt, pain, and sexual arousal.

The computer may utilize $TH_{ROI1}$, $TH_{ROI2}$, $TH_{ROI3}$, and $TH_{ROI4}$ in various ways in order to detect the physiological response. In one example, the computer may be configured to compare one or more values derived from $TH_{ROI1}$, $TH_{ROI2}$, $TH_{ROI3}$, and $TH_{ROI4}$ to a certain threshold, and determine whether the threshold is reached (which is indicative of an occurrence of the physiological response). In another example, the computer may be configured to determine a similarity between a reference time series corresponding to the physiological response and $TH_{ROI1}$, $TH_{ROI2}$, $TH_{ROI3}$, and $TH_{ROI4}$ (or a time series derived from $TH_{ROI1}$, $TH_{ROI2}$, $TH_{ROI3}$, and $TH_{ROI4}$). Optionally, when a sufficiently high similarity is detected, the computer may interpret that as an indication of an occurrence of the physiological response. In another example, the computer may generate feature values based on $TH_{ROI1}$, $TH_{ROI2}$, $TH_{ROI3}$, and $TH_{ROI4}$, and utilize a machine learning-based model to calculate, based on the feature values, a value indicative of whether the physiological response occurred (and/or the extent of the physiological response).

In one embodiment, detecting the physiological response may involve calculations involving thermal measurements received from four thermal cameras ($TH_{ROI}$, $TH_{ROI2}$, $TH_{ROI3}$, and $TH_{ROI4}$, mentioned above). For example, the computer may be configured to: (i) generate feature values based on $TH_{ROI}$, $TH_{ROI2}$, $TH_{ROI3}$, and $TH_{ROI4}$; and (ii) utilize a model to calculate, based on the feature values, a value indicative of the extent of the physiological response. Optionally, the model may be a personalized model for a user, such that the model is generated based on previous $TH_{ROI}$, $TH_{ROI2}$, $TH_{ROI3}$, and $TH_{ROI4}$ of the user. Optionally, at least some of the previous $TH_{ROI}$, $TH_{ROI2}$, $TH_{ROI3}$, and $TH_{ROI4}$ of the user were taken while the user had the physiological response.

Additional details regarding detection of a physiological response based on thermal measurements such as $TH_{ROI1}$, $TH_{ROI2}$, $TH_{ROI3}$, and $TH_{ROI4}$ described above may be found in this disclosure at least in Section 4.

With many people, there is an asymmetry of blood vessels in the face. Thus, certain physiological responses may manifest differently on different sides of the face. In particular, the temperatures at different positions on the right side of the face may not be a mirror image of temperatures at the corresponding positions on the left side of the face. Thus, having two or more thermal cameras pointed at different areas of the face can, in some embodiments, help make more accurate detections of a physiological response.

With some people, for example, stress may be manifested by the cooling of an area on one side of the nose more than the symmetric area on the other side. Thus, while the average temperature change of the whole nose may be below a threshold, which is indicative of a certain stress level, the average temperature change of one of the sides of the nose may be above that threshold. Similarly, with some people, an allergic reaction may manifest by the nose heating to different extents on each side.

Thus, having two or more thermal cameras pointed at different sides of the nose, may enable a more accurate detection of physiological responses such as stress and/or an allergic reaction. Furthermore, thermal cameras that measure different sides of the face can also improve a system's robustness to thermal radiation that heats one side of the face more than the other side. Therefore, in some cases, utilizing two or more thermal cameras pointed at different regions of the face can improve the ability of the system to detect a physiological response compared to the case of utilizing just one thermal camera to measure the nose.

The following is an example of an embodiment of a head-mounted system (HMS) that is configured to take thermal measurements of the right and left sides of a user's nose. Optionally, these measurements may be useful for detecting whether the user is experiencing a physiological response such as stress and/or an allergic reaction.

In one embodiment, the HMS includes at least a frame, a first thermal camera, and a second thermal camera. The frame is configured to be worn on the user's head. Optionally, the frame may be any of the frames of an HMS described in this disclosure, such as a frame of eyeglasses (e.g., frame 84 illustrated in FIG. 5), or a frame of some other HMS, such as a hat, a helmet, and/or part of a system comprising a head-mounted display (e.g., an augmented reality system, a virtual reality system, or a mixed reality system). Various properties of the frame (and other system components) are described in more detail in Section 2.

In one embodiment, each of the first and second thermal cameras is physically coupled to the frame, and is located less than 10 cm away from the user's face. Additionally, the first and second thermal cameras are located at least 0.5 cm to the right and to the left of the vertical symmetry axis that divides the face, respectively (see for example the illustration of vertical symmetry axis 444 in FIG. 71). Optionally, each of the first and second thermal cameras weighs below 5 g. Optionally, each of the first and second thermal cameras is located less than 3 cm away from the face and weighs below 1 g. Optionally, at least one of the first and second thermal cameras is based on at least one of the following uncooled sensors: a thermopile, a microbolometer, and a pyroelectric sensor. Optionally, at least at least one of the first and second thermal cameras is a focal-plane array (FPA) thermal camera.

In one embodiment, the first thermal camera is configured to take thermal measurements of a first region of interest ($TH_{ROI1}$), where $ROI_1$ covers a portion of the right side of the nose. The second thermal camera is configured to take thermal measurements of a second region of interest ($TH_{ROI2}$), where $ROI_2$ covers a portion of the left side of the nose, and the center of $ROI_1$ is to the right of the center of $ROI_2$. Optionally, the first thermal camera does not occlude $ROI_1$ and/or the second thermal camera does not occlude $ROI_2$.

A more detailed discussion regarding the various types of thermal cameras that may be used, including properties of thermal measurements (e.g., $TH_{ROI1}$ and $TH_{ROI2}$ mentioned above), is provided in Section 1.

Figure 5:
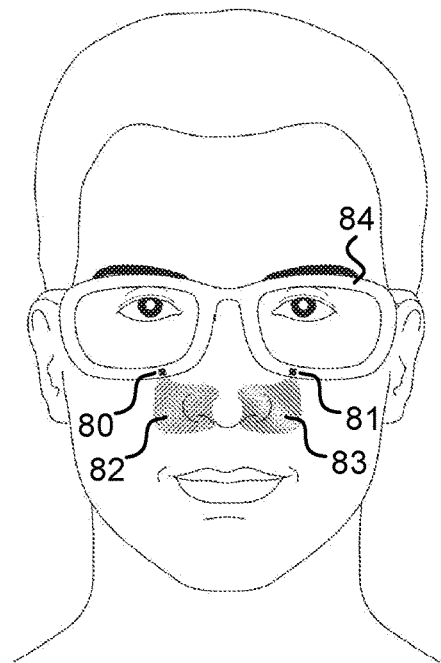
FIG. 5 illustrates an embodiment of a system configured to take thermal measurements of the right and left sides of a user's nose.

FIG. 5 illustrates an embodiment of a system that is configured to take thermal measurements of the right and left sides of a user's nose. The system includes the frame 84 (which in the figure is a frame of a pair of eyeglasses) and first and second thermal cameras denoted with reference numerals 80 and 81, respectively. The first thermal camera 80 and the second thermal camera 81 are depicted as small black squares on the right and left sides of the bottom of the frame, respectively. These thermal cameras are configured to take thermal measurements of ROI 82 and ROI 83, which are illustrated as patches of slanted lines on the right and left sides of the nose, respectively.

Depending on the locations and orientations of the first and second thermal cameras, there may be different overlaps between at least some of $ROI_1$ and $ROI_2$. In one example, the overlap between $ROI_1$ and $ROI_2$ is below 50% of the smallest area from among the areas of $ROI_1$ and $ROI_2$. In another example, there is no overlap between $ROI_1$ and $ROI_2$.

Due to their physical coupling to the frame, in one embodiment, the first and second thermal cameras remain pointed at their respective ROIs when the user's head makes angular movements. For example, the first and second thermal cameras may remain pointed at their respective ROIs when the user's head makes angular movements that exceed 0.1 rad/sec, 0.5 rad/sec, and/or 2 rad/sec.

Tough the description above involves first and second thermal cameras, in some embodiments, additional thermal cameras may be utilized to take thermal measurements that may be used to detect the physiological response (e.g., FIG. 1*a* and FIG. 1*b* each illustrate more than two thermal cameras). The characteristics of the first and second thermal cameras, and the advantages of utilizing thermal cameras physically coupled to the frame, which are set forth above, are applicable to additional thermal cameras that are utilized in various embodiments.

In one embodiment, in addition to the first and second thermal cameras described above, the HMS may include third and fourth thermal cameras that are physically coupled to the frame and configured to take thermal measurements of third and fourth ROIs (denoted $TH_{ROI3}$ and $TH_{ROI4}$, respectively). Optionally, $ROI_3$ covers an area below the user's nostrils and $ROI_4$ covers a portion of the user's forehead. In one example, an area below the nostrils refers to an area that includes portions of the upper lip, the mouth, and/or the chin. In another example, an area below the nostrils refers to an area projected in front of a user's face, which is below the height of the nostrils and intersects with the exhale streams blowing from the user's nostrils and/or mouth. Optionally, $TH_{ROI1}$ may be utilized to determine a value of respiratory parameter of the user as discussed in more detail in Section 5.

Referring to FIG. 1*b*, in one example, the third thermal may be thermal camera 22 and $ROI_3$ may include portion of the regions corresponding to reference numerals 23 and/or 29. In this example, the fourth thermal camera may be thermal camera 10, and $ROI_4$ may include a portion of ROI 11. In this example, the first and second thermal cameras may be thermal cameras 49 and 48, respectively (covering ROIs 42 and 41, respectively).

In another embodiment, the third and fourth thermal cameras may be configured to take thermal measurements of slightly different combination ROIs than the ones mentioned above. Optionally, $ROI_3$ covers a portion of a periorbital region and $ROI_4$ covers a portion of the user's forehead. Referring to FIG. 1*a*, in one example, the third thermal may be thermal camera 18 and $ROI_3$ may include portion of the region corresponding to reference numeral 19. In this example, the fourth thermal camera may be thermal camera 10, and $ROI_4$ may include a portion of ROI 11.

It is to be noted that in addition to the third and fourth thermal cameras mentioned in the examples above, in some embodiments, an HMS may include further additional thermal cameras, such as fifth and sixth thermal cameras that are the symmetric counterparts of the fourth and fifth cameras (i.e., in a similar position on the other side of the frame).

In some embodiments, the HMS described above is further configured to forward $TH_{ROI1}$ and $TH_{ROI2}$ to a computer that is configured to detect a physiological response based on $TH_{ROI1}$ and $TH_{ROI2}$. The computer includes one or more processors and memory. Optionally, the memory stores $TH_{ROI1}$ and $TH_{ROI2}$ prior to them being forwarded to the one or more processors. Optionally, the computer may be at least one of the following: a computer belonging to a device carried by the user, a computer of a smartphone, a personal computer, a remote server (e.g., a cloud-based server), and an analog circuit. In one example, the computer is computer system 400 illustrated in FIG. 72a. In another example, the computer may be computer system 410 illustrated in FIG. 72b. Additional details regarding various types of computers and hardware components that may be utilized to detect the physiological response are given in Sections 2 and 7.

In one embodiment, detecting the physiological response involves calculating a value indicative of the extent to which the user is experiencing the physiological response. In one example, the physiological response is stress felt by the user. Optionally, when the stress level exceeds a certain value, at least one of $TH_{ROI1}$ and $TH_{ROI2}$ reaches a threshold, and when the levels of stress does not exceed the certain value, both $TH_{ROI1}$ and $TH_{ROI2}$ do not reach the threshold. In another example, the physiological response is indicative of an occurrence of an allergic reaction. In still another example, the physiological response is indicative of an occurrence of at least one of the following emotional states: fear, joy, guilt, and sexual arousal.

In some embodiments, detecting the physiological response may involve utilizing baseline thermal measurement values, most of which were taken when the user was not experiencing the physiological response. Thus, detecting the physiological response may rely on observing a change to typical temperatures at the ROIs (where different users might have different typical temperatures at the ROIs). In one example, the computer is further configured to calculate the stress level of the user based on at least one of the following values: (i) a difference between $TH_{ROI1}$ and a first baseline value determined based on a first set of previous measurements taken by the first thermal camera, and (ii) a difference between $TH_{ROI2}$ and a second baseline value determined based on a second set of previous measurements taken by the second thermal camera. In this example, most of the measurements belonging to each of the first and second sets were taken while the user was not stressed.

As described in more detail elsewhere in this disclosure, the computer may utilize $TH_{ROI1}$ and/or $TH_{ROI2}$ in various ways in order to detect the physiological response. In one example, the computer may be configured to compare one or more values derived from $TH_{ROI1}$ and/or $TH_{ROI2}$ to a certain threshold, and determine whether the threshold is reached (which is indicative of an occurrence of the physiological response). In another example, the computer may be configured to determine a similarity between a reference time series corresponding to the physiological response, and $TH_{ROI1}$ and/or $TH_{ROI2}$ (or a time series derived from $TH_{ROI1}$ and/or $TH_{ROI2}$). Optionally, when a sufficiently high similarity is detected, the computer may interpret that as an indication of an occurrence of the physiological response.

In another embodiment, the computer is configured to generate feature values, and to utilize a model to calculate an extent of the physiological response based on the feature values. Optionally, at least one of the feature values are generated based on $TH_{ROI1}$ and/or $TH_{ROI2}$. Optionally, the model is generated based on samples, each sample comprising corresponding feature values generated based on corresponding measurements of a certain user taken with the first and second thermal cameras, and a label indicative of an extent of the physiological response of the certain user while the corresponding measurements were taken.

In some embodiments, at least some of the feature values may be generated based on additional data (besides $TH_{ROI1}$ and/or $TH_{ROI2}$). In one example, the computer is further configured to: (i) receive one or more values indicative of at least one of the following parameters of the user: heart rate, heart rate variability, galvanic skin response, respiratory rate, and respiratory rate variability, and (ii) to generate one or more of the feature values based on the one or more values. In another example, the computer is further configured to: (i) receive one or more values indicative of at least one of the following: whether the user touched the nose, whether the user is engaged in physical activity, and an environmental parameter, and (ii) to generate one or more of the feature values based on the one or more values.

In one embodiment, detecting the physiological response may involve calculations involving thermal measurements received from four thermal cameras ($TH_{ROI1}$, $TH_{ROI2}$, $TH_{ROI3}$, and $TH_{ROI4}$, mentioned above). For example, the computer may be configured to: (i) generate feature values based on $TH_{ROI1}$, $TH_{ROI2}$, $TH_{ROI3}$, and $TH_{ROI4}$; and (ii) utilize a model to calculate, based on the feature values, a value indicative of the extent of the physiological response. Optionally, the model may be a personalized model for a user, such that the model is generated based on previous $TH_{ROI1}$, $TH_{ROI2}$, $TH_{ROI3}$, and $TH_{ROI4}$ of the user. Optionally, at least some of the previous $TH_{ROI1}$, $TH_{ROI2}$, $TH_{ROI3}$, and $TH_{ROI4}$ of the user were taken while the user had the physiological response.

Additional details regarding detection of a physiological response based on thermal measurements such as $TH_{ROI1}$ and $TH_{ROI2}$ mentioned above may be found in this disclosure at least in Section 4.

In one embodiment, the system described above may further comprise a user interface that is configured to present the user with an alert indicative of the occurrence of the physiological response. For example, the physiological response may be indicative of a stress level, and the user interface is configured to alert the user when the stress level reaches a predetermined threshold. In another example, the physiological response may be an allergic reaction, and the user interface is configured to alert the user when an allergic reaction, which reaches a certain extent, is imminent.

The difference between the right and left sides around the nose may be used to detect asymmetric patterns that characterize the user (such as right side being a bit colder when the user reaches a certain stress level), and/or detect environmental interference (such as direct sunlight on the right side of the nose, which makes it a bit hotter than the left side of the nose). Thus, the thermal measurements may be utilized by the computer in various ways in order to detect the physiological response.

In one embodiment, the first and second thermal cameras provide to the computer measurements of temperatures at $ROI_1$ and $ROI_2$, denoted $T_{ROI1}$ and $T_{ROI2}$, respectively, and the computer is configured to: calculate a change-to-temperature-at-$ROI_1$ ($\Delta T_{ROI1}$) based on $T_{ROI1}$, calculate a change-to-temperature-at-$ROI_2$ ($\Delta T_{ROI2}$) based on $T_{ROI2}$, and to detect the physiological response based on $\Delta T_{ROI1}$ and $\Delta T_{ROI2}$. For example, $\Delta T_{ROI1}$ and/or $\Delta T_{ROI2}$ may be compared to a threshold in order to detect the physiological response (e.g., $\Delta T_{ROI1}$ and/or $\Delta T_{ROI2}$ reaching the threshold is indicative of the occurrence of the physiological response). In another example, the computer may generate one or more feature values based on $\Delta T_{ROI1}$ and/or $\Delta T_{ROI2}$, and use the one or more feature values as part of an input provided to a predictor that utilizes a machine learning based model to detect the physiological response.

In another embodiment, the first and second thermal cameras provide to the computer measurements of temperatures at $ROI_1$ and $ROI_2$, denoted $T_{ROI1}$ and $T_{ROI2}$ respectively. In this embodiment, the computer is configured to: calculate a difference between $T_{ROI1}$ and $T_{ROI2}$ at time m (denoted $\Delta T_m$), calculate a difference between $T_{ROI1}$ and $T_{ROI2}$ at time n (denoted $\Delta T_n$), and to detect the physiological response based on a difference between $\Delta T_m$ and $\Delta T_n$. For example, if the difference between $\Delta T_m$ and $\Delta T_n$ reaches a threshold (e.g., indicating heating or cooling of certain regions of the face), this may be indicative of an occurrence of the physiological response. In another example, the computer may generate one or more feature values based on $\Delta T_m$ and/or $\Delta T_n$, and use the one or more feature values as part of an input provided to a predictor that utilizes a machine learning-based model to detect the physiological response.

Due to the mostly symmetric nature of the human body, when the face undergoes temperature changes, e.g., due to external factors such as the temperature in the environment or internal factors such as an activity-related rise in body temperature, the changes to the face are generally symmetric. That is, the temperature changes at a region of interest (ROI) on the left side of the face (e.g., the left side of the forehead) are similar to the temperature changes at the symmetric ROI on the right side of the face (e.g., the right side of the forehead). However, when the temperature on the face changes in an asymmetric way, this can be indicative of various physiological responses and/or undesirable phenomena. For example, some phenomena that may be identified by detecting asymmetric thermal patterns ("thermal asymmetry") on a user's face include migraines, sinusitis, nerve damage, some types of strokes, and Bell's palsy, to name a few. Additionally, some forms of disorders such as Attention Deficit Hyperactivity Disorder (ADHD), stress, anxiety, and/or depression can also be identified based on thermal asymmetry involving various ROIs of the face.

Although it is possible to combine symmetric measurements in order to simplify the system (such as by using a single sensor with a wide field of view (FOV) that captures both the right and left areas), such a simplified system may, in some embodiments, provide results that are less accurate compared to a system configured to measure and utilize the data that reflects the asymmetric thermal behavior. Measuring and utilizing the asymmetric data also improves the robustness of the system against interferences that may cause an asymmetric effect, such as an external heat source located to the user's side, a cooling air-conditioner that blows air from the side, touching and/or wiping one side of the face, and for some people also eating and/or having a physical activity.

The following is a description of embodiments of a system that may be utilized to collect thermal measurements that may be indicative of thermal asymmetry on a user's face. These thermal measurements may be utilized in various ways in order to detect a wide array of medical conditions, as described further below. In one embodiment, a system configured to collect thermal measurements that may be indicative of thermal asymmetry on a user's face includes at least a frame, a first thermal camera, and a second thermal camera. Optionally, the system may further include a computer that may be used to process the thermal measurements, a memory configured to store the thermal measurements, a transmitter configured to transmit the thermal measurements, and/or a user interface that is configured to alert the user about various phenomena identified based on the thermal measurements.

The frame is configured to be worn on the user's head. Optionally, the frame may be any of the frames of an HMS described in this disclosure, such as a frame of eyeglasses (e.g., frame 90 illustrated in FIG. 6), or a frame of some other HMS, such as a hat, a helmet, and/or part of a system comprising a head-mounted display (e.g., an augmented reality system, a virtual reality system, or a mixed reality system). Various properties of the frame (and other system components) are described in more detail in Section 2.

The first and second thermal cameras are physically coupled to the frame and are located less than 15 cm away from the face. Optionally, each of the first and second thermal cameras weighs below 5 g. Optionally, each of the first and second thermal cameras is located less than 3 cm away from the face and weighs below 1 g. Optionally, at least one of the first and second thermal cameras is based on at least one of the following uncooled sensors: a thermopile, a microbolometer, and a pyroelectric sensor. Optionally, at least at least one of the first and second thermal cameras is a focal-plane array (FPA) thermal camera. A more detailed discussion regarding the various types of thermal cameras that may be used, including properties of thermal measurements (e.g., $TH_{ROI1}$ and $TH_{ROI2}$ mentioned above), is provided in Section 1.

The first thermal camera is configured to take thermal measurements of a first region of interest ($TH_{ROI1}$), where the first region of interest ($ROI_1$) covers a portion of the right side of the face, and the first thermal camera does not occlude $ROI_1$. The second thermal camera is configured to take thermal measurements of a second region of interest ($TH_{ROI2}$), where the second region of interest ($ROI_2$) covers a portion of the left side of the face. Additionally, the second thermal camera does not occlude $ROI_2$, the center of $ROI_1$ is to the right of the center of $ROI_2$, and the symmetric overlapping between $ROI_1$ and $ROI_2$ is above 60%. Some examples of possible locations for the first and second thermal cameras coupled to the frame and their corresponding ROIs are given in FIG. 1a and FIG. 1b. In one example, the first thermal camera is thermal camera 10 in FIG. 1a and the second thermal camera is thermal camera 12 in FIG. 1a.

Figure 71:
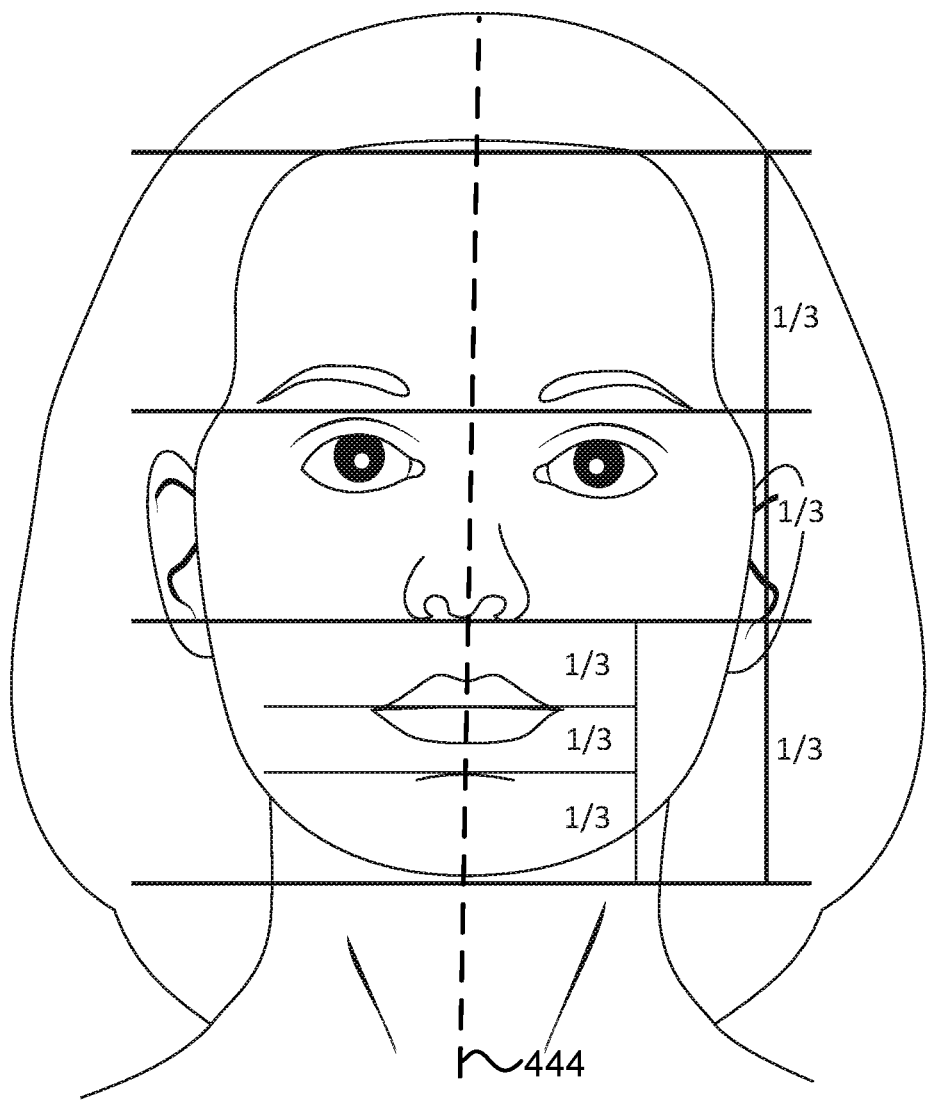

It is noted that the symmetric overlapping is considered with respect to the vertical symmetry axis that divides the face to the right and left portions, as illustrated in FIG. 71 in which the vertical symmetry axis 444 divides the face to the right and left sides. The vertical symmetry axis 444 also divides the frame to its right and left sides (not shown in the figure). The symmetric overlapping between $ROI_1$ and $ROI_2$ may be observed by comparing the overlap between $ROI_1$ and a mirror image of $ROI_2$, where the mirror image is with respect to a mirror that is perpendicular to the front of the face and whose intersection with the face is along the vertical symmetry axis 444. Depending on the application for which the thermal measurements are utilized, the ROIs may have different degrees of symmetric overlapping. For example, the symmetric overlapping between $ROI_1$ and $ROI_2$ is above 80% of the smallest area from among the areas of $ROI_1$ and $ROI_2$. In another example, the overlap between $ROI_1$ and $ROI_2$ is above 5% and below 80% of the smallest area from among the areas of $ROI_1$ and $ROI_2$.

Depending on the locations of $ROI_1$ and $ROI_2$, in different embodiments, the first and second thermal cameras may be located in specific locations on the frame and/or with respect to the face. In one example, $ROI_1$ and $ROI_2$ cover a portion of the nose and/or a portion of the mouth, and the first and second thermal cameras are located outside the exhale streams of the mouth and/or nostrils. In another example, the first and second thermal cameras are located less than at least 2 cm and/or less than at least 5 cm away from the face. Additionally, the first and second thermal cameras may be located at least 0.5 cm to the right and to the left of the vertical symmetry axis that divides the face, respectively.

In some embodiments, the system for collecting thermal measurements that may be indicative of thermal asymmetry on a user's face includes third and fourth thermal cameras. The third and fourth thermal cameras are physically coupled to the frame, and are configured to take thermal measurements of the environment to the right and to the left of the face, respectively. In these embodiments, the system further comprises a computer that is configured to utilize the thermal measurements from the third and fourth thermal cameras to identify asymmetry resulting from the environment rather than from a physiological response (which may optionally be a medical disorder). Optionally, the first, second, third and fourth thermal cameras comprise sensors that comprise at least one of the following sensors: thermopile sensors, pyroelectric sensors, and microbolometer sensors. Optionally, the environment that caused the asymmetry comprises at least one of the following: sunlight, an air-conditioner, direct wind, a heater, and an oven.

In some embodiments, the system for collecting thermal measurements that may be indicative of thermal asymmetry on a user's face includes a computer. Optionally, the computer is configured to detect a physiological response (which may be a medical disorder) based on the thermal measurements. For example, the computer may be configured to calculate a value indicative of a probability of a certain physiological response based on thermal asymmetry between the right and left sides of the face. In this example, the thermal asymmetry is determined based on a difference between $TH_{ROI1}$ and $TH_{ROI2}$. In another example, the system may be configured to detect an occurrence of a physiological response based on a difference between $TH_{ROI1}$ and $TH_{ROI2}$. In this example, the physiological response is not body temperature.

In some embodiments, the above computer may be any of the computers mentioned in this disclosure, such as at least one of the following: a computer belonging to a device carried by the user, a computer of a smartphone, a personal computer, a remote server (e.g., a cloud-based server), and an analog circuit. In one example, the computer is computer system 400 illustrated in FIG. 72a. In another example, the computer may be computer system 410 illustrated in FIG. 72b. Additional details regarding various types of computers and hardware components that may be utilized to detect the physiological response are given in Sections 2 and 7.

Herein, detecting an occurrence of a physiological response may involve one or more of the following: determining whether the user is experiencing the physiological response, and determining the extent of the physiological response (e.g., a severity of the medical disorder). In one embodiment, the computer is configured to detect an occurrence of the physiological response based on finding that the difference between $TH_{ROI1}$ and $TH_{ROI2}$, reached at least one of the following thresholds: a threshold in the time domain, a threshold in the frequency domain, an upper threshold where reaching the threshold means equal or above the threshold, and a lower threshold where reaching the threshold means equal or below the threshold. In another embodiment, the computer is configured to detect an occurrence of the physiological response by determining a similarity between a reference time series, which corresponds to the physiological response, and $TH_{ROI1}$ and/or $TH_{ROI2}$ (or a time series derived from $TH_{ROI1}$ and/or $TH_{ROI2}$). Optionally, when a sufficiently high similarity is detected, the computer may interpret that as an indication of an occurrence of the physiological response (e.g., that the user suffers from a certain medical disorder). In another embodiment, the computer may be configured to generate feature values based on $TH_{ROI1}$ and/or $TH_{ROI2}$, and utilize a machine learning-based model to calculate, based on the feature values, a value indicative of whether the physiological response occurred (e.g., whether the user suffers from the medical disorder).

In one embodiment, the detection of the physiological response utilizes a personalized model of the user. Optionally, the computer configured to: (i) generate feature values based on $TH_{ROI}$ and $TH_{ROI2}$; and (ii) utilize a model to calculate, based on the feature values, a value indicative of the extent of the physiological response. Optionally, the model is generated based on previous $TH_{ROI}$ and $TH_{ROI2}$ of the user taken while the user had the physiological response. Optionally, the physiological response involves the user experiencing at least one of the following: stress, mental workload, fear, sexual arousal, anxiety, pain, a headache, a migraine, dehydration, intoxication, and a stroke.

In different embodiments, the difference between $TH_{ROI1}$ and $TH_{ROI2}$ may be interpreted in different ways. In one embodiment, an extent of a physiological response may be proportional to the difference between $TH_{ROI1}$ and $TH_{ROI2}$ when the value of the difference is in a certain range. Optionally, when the value of the difference is outside of the range, which may be indicative of the occurrence of other phenomena (which are not the physiological response). In another embodiment, when the value of the difference between $TH_{ROI1}$ and $TH_{ROI2}$ reaches a threshold, that is indicative of an occurrence of the physiological response. In yet another embodiment, at least one feature value utilized by a predictor that predicts occurrences of the physiological response is based on the value of the difference between $TH_{ROI1}$ and $TH_{ROI2}$.

Often changes in the values of the thermal asymmetry may be indicative of a physiological response. To this end, in some embodiments, the computer is configured to calculate an output indicative of a change to thermal asymmetry on the face based on a change between thermal measurements taken at different times. Optionally, the computer is further configured to calculate extent of a physiological response based on the output. For example, given thermal measurements taken at time $t_1$ $[TH_{ROI1}, TH_{ROI2}]^{t1}$ and thermal measurement taken at time $t_2$ $[TH_{ROI1}, TH_{ROI2}]^{t2}$, the computer can calculate a value representing the change in thermal asymmetry of the face between the times $t_1$ and $t_2$. This calculation can be performed in different ways, as described below.

In one embodiment, the computer is configured to calculate the change between the thermal measurements as follows: calculate a temperature difference between $ROI_1$ and $ROI_2$ at time x ($\Delta T_x$) based on $[TH_{ROI1}, TH_{ROI2}]^{t1}$, calculate a temperature difference between $ROI_1$ and $ROI_2$ at time y ($\Delta T_y$) based on $[TH_{ROI1}, TH_{ROI2}]^{t2}$, and calculate the output indicative of the change in the thermal asymmetry on the face based on a difference between $\Delta T_x$ and $\Delta T_y$.

The embodiment described above may optionally be implemented using a differential amplifier that is configured to receive $TH_{ROI1}$ and $TH_{ROI2}$ as inputs, and output the temperature difference between $ROI_1$ and $ROI_2$. Optionally, the first and second thermal cameras in this embodiment are based on thermopile sensors. Optionally, the first and second thermal cameras in this embodiment may be based on pyroelectric sensors. In one example, pairs of thermal sensor elements are wired as opposite inputs to a differential amplifier. In this example, the thermal measurements may cancel each other and thereby remove the average temperature of the field of view from the electrical signal. This allows the thermal cameras to be less prone to provide false indications of temperature changes in the event of being exposed to brief flashes of radiation or field-wide illumination. This embodiment may also minimize common-mode interference, and as a result improve the accuracy of the thermal cameras.

In another embodiment, the computer is configured to calculate the change between the thermal measurements as follows: calculate a temperature difference between $TH_{ROI1}$ taken at times $t_1$ and $t_2$ ($\Delta TH_{ROI1}$), calculate a temperature difference between $TH_{ROI2}$ taken at times $t_1$ and $t_2$ ($\Delta TH_{ROI2}$), and then calculate the output indicative of the thermal asymmetry on the face based on a difference between $\Delta TH_{ROI1}$ and $\Delta TH_{ROI2}$.

It is noted that sentences such as "calculate a difference between X and Y" are to be interpreted as "calculate a value indicative of a difference between X and Y", which means that said calculation can be achieved by any function that is proportional to the difference between X and Y.

The computer may utilize values indicative of changes in thermal asymmetry in order to detect a physiological response in various ways. For example, the values may be compared to a threshold, which if reached, is indicative of the occurrence of the physiological response. Optionally, the threshold needs to be reached a certain number of times and/or for a certain amount time, before it is assumed that the user experienced the physiological response. In another example, time series data that comprises values indicative of changes to thermal asymmetry of the face may be compared to reference time series comprising values indicative of changes in thermal asymmetry observed with the physiological response. In still another example, values indicative of changes in thermal asymmetry may be utilized to generate feature values that are provided to a predictor that uses a machine teaming-based model to detect an occurrence of a physiological response.

Additional details regarding detection of a physiological response based on thermal measurements such as $TH_{ROI1}$ and $TH_{ROI2}$ described above may be found in this disclosure at least in Section 4.

Figure 6:
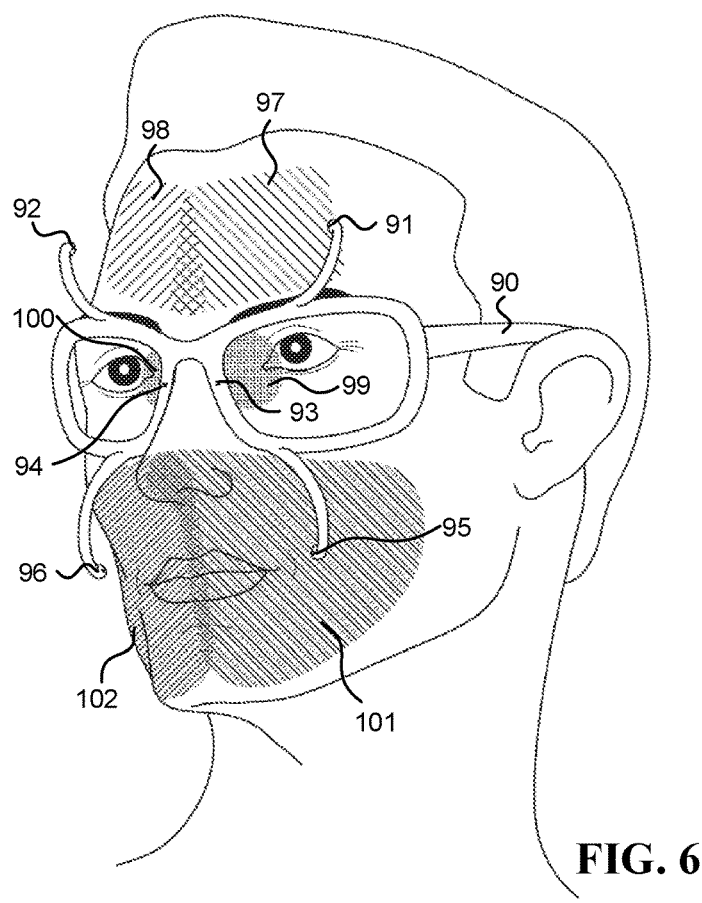
FIG. 6 illustrates an embodiment of a system configured to collect thermal measurements that may be indicative of thermal asymmetry on a user's face.

In some embodiments, the system configured to collect thermal measurements, which may be indicative of thermal asymmetry on a user's face, may involve multiple thermal cameras, which may take thermal measurements of various ROIs on the face. FIG. 6 illustrates one embodiment of such a system. The system includes a frame 90, which has six thermal cameras coupled to it (some embedded in protruding arms). Thermal cameras 91 and 92 are located on arms on the left and right sides of the top of the frame 90, respectively, and they take thermal measurements of ROI 97 (left side of the forehead) and ROI 98 (right side of the forehead), respectively. Thermal cameras 93 and 94 are located on the left and right sides of the frame 90 near the nose, respectively, and they take thermal measurements of ROI 99 (left periorbital region) and ROI 100 (right periorbital region), respectively. Thermal cameras 95 and 96 are located on arms on the left and right sides of the bottom of the frame 90, respectively, and they take thermal measurements of ROI 101 (left side of bottom half of the face) and ROI 102 (right side of bottom half of the face), respectively. It is to be noted that some (or all) of the cameras may contain multiple sensing elements.

In some embodiments, accounting for the thermal asymmetry of a user is done utilizing a model of the user. Thus, data from different users may be interpreted differently based on their (possibly different) models. For example, a first user may show an average decrease of 0.5° C. on both the right and left sides of the nose during a stressful task, while a second user may show an average decrease of 0.4° C. on the right side of the nose and 0.5° C. on the left side of the nose during a stressful task. Distinctions between different users may result from different distribution of blood vessels over the right and left sides, different shapes of their faces that cause thermal cameras on an HMS to measure slightly different locations on the users' faces, and/or having various diseases, such a unilateral sinusitis, a chronic clogged nostril, periodontitis, or Bell's palsy. For example, the second user from the previous example may have a higher facial asymmetry compared to the first user, which may cause the HMS to measure slightly different areas on the face of the second user, which may be the cause of the difference between the right and left thermal measurements. As another example, the second user may have essentially a symmetrical face, but the second user suffers from a unilateral sinusitis or a chronic clogged nostril, which causes the difference between the right and left thermal measurements. Therefore, in some cases, processing asymmetric measurements provides accuracy that cannot be achieved from measurements of just one side of the face or from averaging measurements taken around the vertical symmetry axis. For example, taking one thermal measurement of the entire nose and/or the entire forehead may provide, for some users, less information than taking two or more thermal measurements of the right and left sides of the nose, and/or the right and left sides of the forehead.

Following is a more detailed discussion of some physiological responses, some of which are considered medical disorders, which may be identified utilizing a system that collects thermal measurements that may be indicative of thermal asymmetry on a user's face.

There are various forms of sinusitis that may be detected utilizing different embodiments of the system. In one example, $ROI_1$ covers a portion of the right anterior sinus group, $ROI_2$ covers a portion of the left anterior sinus group, and the system comprises a computer configured to diagnose the user's anterior sinuses based on comparing $TH_{ROI1}$ and $TH_{ROI2}$ taken from the user during different days. Herein, the left anterior sinus group comprises the left frontal sinus, the left maxillary sinus, and the left anterior ethmoid sinus. Similarly, the right anterior sinus group comprises the right frontal sinus, the right maxillary sinus, and the right anterior ethmoid sinus.

In another example, $ROI_1$ covers a portion of the right anterior sinus group and $ROI_2$ covers a portion of the left anterior sinus group, and the system includes a computer configured to diagnose the user's anterior sinuses based on comparing $TH_{ROI1}$ and $TH_{ROI2}$ taken from the user with corresponding thermal measurements obtained from a healthy control patient who used a similar system. In yet another example, $ROI_1$ covers a portion of the right anterior sinus group and $ROI_2$ covers a portion of the left anterior sinus group. In this example, the system includes a computer configured to diagnose the user's anterior sinuses based on comparing $TH_{ROI1}$ and $TH_{ROI2}$ taken from the user with corresponding thermal measurements obtained from a patient having at least one of maxillary sinusitis and frontal sinusitis who used a similar system. In still another example, $ROI_1$ covers a portion of the user's right frontal sinus, $ROI_2$ covers a portion of the user's left frontal sinus, and the system includes a computer configured to detect a physiological response indicative of an occurrence of a unilateral frontal sinusitis. And in yet another example, $ROI_1$ covers a portion of the user's right maxillary sinus, $ROI_2$ covers a portion of the user's left maxillary sinus, and the system includes a computer configured to detect a physiological response indicative of an occurrence of a unilateral maxillary sinusitis.

Herein, sentences of the form "comparing $TH_{ROI1}$ and $TH_{ROI2}$ taken from the user during different days" should be interpreted as comparing between at least two sets of measurements of the user; with the at least two sets comprising a first set that includes thermal measurements of $ROI_1$ and $ROI_2$ taken during a first day, and a second set that includes thermal measurements of $ROI_1$ and $ROI_2$ taken during a second day, which is after the first day.

Some forms of strokes may be detected using embodiments of the system. In a first example, $ROI_1$ may cover a portion of the right superficial temporal artery and $ROI_2$ may cover a portion of the left superficial temporal artery. In a second example, each of $ROI_1$ and $ROI_2$ may cover above 20%, or above 40%, of the right and left sides of the naked facial skin between the mouth and the eyebrows, respectively. In these two examples, the system includes a computer configured to calculate a value indicative of whether the user had a stroke based on changes observed by comparing $TH_{ROI1}$ and $TH_{ROI2}$ taken from the user during different days. Optionally, if the probability that the user had a stroke reaches a certain threshold, such as at least 5%, at least 25%, or at least 50%, the user and/or a third party are alerted about this fact so the user can receive immediate medical attention, which may improve the outcome of a treatment.

FIG. 7 illustrates a scenario in which an alert regarding a possible stroke may be issued by an embodiment of a system described herein. The figure illustrates a user wearing a frame with at least two thermal cameras (543*a* and 543*b*) that measure ROIs that include portions of the user's left and right cheeks (ROIs 542*a* and 542*b* respectively). The measurements indicate that the user's left side of the face is warmer than the user's right side of the face. Based on these measurements (and possibly other data), the system may issue an alert to the user and/or other parties. It is to be noted that as the figure illustrates, the user's facial expression is also slightly distorted. In some embodiments, a visual-light camera may be used to take images of the user's face and use analysis of the images as additional information upon which it may be determined whether the user is having a stroke.

Various forms of nerve damage often cause significant thermal differences on the face. At times, the thermal differences may manifest prior to changes to the appearance of the face. Thus, thermal measurements may be utilized for early detection of nerve damage, which may improve the outcome of a treatment. For example, in one embodiment, $ROI_1$ and $ROI_2$ may each cover a portion of at least one of the following: the eyes, the nose, and mouth. In this embodiment, the system includes a computer configured to identify nerve damage based on changes observed by comparing $TH_{ROI1}$ and $TH_{ROI2}$ taken from the user during different days.

Stress and the user's affective state (e.g., the extent to which the user feels certain emotions) are examples of physiological responses that may also be detected, in some embodiments of the system. In one example, $ROI_1$ covers a portion of at least one of the supraorbital and periorbital areas on the right side of the face, and $ROI_2$ covers a portion of at least one of the supraorbital and periorbital areas on the left side of the face. In this example, the system includes a computer configured to detect, based on $TH_{ROI1}$ and $TH_{ROI2}$, a physiological response indicative of an affective state of the user (e.g., whether the user is happy, sad, excited, depressed, etc.) In another example, $ROI_1$ covers a portion of at least one of the supraorbital and periorbital areas on the right side of the face, and $ROI_2$ covers a portion of at least one of the supraorbital and periorbital areas on the left side of the face. In this example, the system includes a computer configured to detect, based on $TH_{ROI1}$ and $TH_{ROI2}$, a physiological response indicative of a stress level. Optionally, the system also includes a user interface configured to alert the user when the stress level reaches a predetermined threshold. Detecting stress may be assisted by obtaining thermal measurements of the cheeks. Thus, in one embodiment, the system also includes third and fourth thermal cameras, each of which: weighs below 5 g, is physically coupled to the frame, and is located less than 10 cm away from the face. The third and fourth thermal cameras are configured to take thermal measurements of portions of the right and left cheeks, respectively, and the computer is further configured to calculate the stress level also based on the thermal measurements of the cheeks.

Migraines may also be detected utilizing some embodiments of the system. In one embodiment, $ROI_1$ and $ROI_2$ cover the right and left portions of at least one of the following regions: right and left sides of the nose, right and left sides of the mouth, the right and left areas between the temples and orbits, the right and left frontotemporal regions, the supraorbitals of the right and left eyes, and the periorbitals of the right and left eyes. In this embodiment, the system includes a computer configured to detect an onset of a migraine headache based on $TH_{ROI1}$ and $TH_{ROI2}$. In another embodiment, the system includes a computer that is configured to detect an imminent migraine based on changes observed by comparing $TH_{ROI1}$ and $TH_{ROI2}$ taken from the user during different days.

The following are some examples from the literature that may aid selection of relevant ROIs for detecting a migraine, and which support utilization of thermal measurements for this purpose. For example, the reference Zaproudina N, Narhi M, Lipponen J A, Tarvainen M P, Karjalainen P A, Karhu J, Airaksinen O, Giniatullin R, "Nitroglycerin-induced changes in facial skin temperature: 'cold nose' as a predictor of headache?" demonstrates that the nose and the mouth are relevant ROIs to predict headache. In another example, the reference Peter D. Drummond and Dr. James W. Lance (1982), "Extracranial vascular changes and the source of pain in migraine headache" demonstrates that there are significant differences in heat loss from the temples and orbits between migrainous patients and controls, frontotemporal changes being more conspicuous in the extracranial vascular group. The reference PD Drummond and J W Lance (1984), "Facial temperature in migraine, tension-vascular and tension headache" demonstrates that thermal asymmetry in the frontotemporal regions and the orbits are possible ROIs to predict a headache. In addition, the reference Garza, Ivan, Hadi Montakhabi, Peggy Lindner, Panagiotis Tsiamyrtzis, Jerry Swanson, Leslie MacBride, Tom Krouskop, and Ioannis Pavlidis. "The Face of Migraine; Thermal Imaging Revisited (P06. 154)", Neurology 80, no. Meeting Abstracts 1 (2013): P06-154, demonstrates that each subject had a significantly higher mean supraorbital temperature in the baseline session compared to the migraine session, and in 7 out of 8 subjects the baseline session had a significantly higher mean periorbital temperature compared to the migraine session.

In one embodiment, the head-mounted system includes at least one head-mounted thermal camera pointed to the supraorbital area and/or at least one head-mounted thermal camera pointed to the periorbital region. Based on the data received from the one or more thermal cameras, the system identifies the presence of a migraine headache attack by identifying the supraorbital and/or periorbital cooling effect. Optionally, after identifying the cooling effect, and even before the patient suspects the migraine headache attack, the system may alert the patient in order to enable an early treatment of the migraine headache attack before full development.

In some embodiments, responsive to detecting the onset of the migraine headache, a user interface is configured to suggest the user to perform at least one of the following activities: drink cold water, cool the head, practice Sitali and Sitkari pranayama, and listen to brain entrainment sounds.

Additionally, in some embodiments, a relationship between the stress the user feels and migraines the user has may be studied utilizing the system. Optionally, the system includes a training module configured to receive training data comprising physiological measurements indicative of levels of stress of the user, values indicative of durations during which the user felt stressed, and values indicative of durations during which the user had a migraine. The training module is further configured to utilize a machine Teaming-based training algorithm to train the model utilizing the training data. The model may be used to predict when and/or to what extent the user will suffer from a migraine based on an input indicative of stress the user felt.

Bell's palsy is another medical disorder that may be identified based on thermal measurements. In one embodiment, the system includes a computer configured to detect Bell's palsy based on comparing $TH_{ROI1}$ and $TH_{ROI2}$ taken from the user during different days. Optionally, the system includes a visual light camera configured to take photos of the face. The computer is further configured to analyze the visual photos for asymmetry in order to improve the probability of identifying Bell's palsy. Optionally, the system suggests the user to take a medical examination when the facial thermal asymmetry reaches a threshold for more than a predetermined duration. Examples of predetermined duration are 1 minute, 5 minutes, and more than 30 minutes.

Collection of measurements indicative of thermal asymmetry on a user's face may involve, in some embodiments, thermal cameras with multiple sensing elements. An example of utilization of such thermal cameras is given in the description of the following system, which is configured to collect close range thermal measurements indicative of thermal asymmetry on a user's face. Thermal measurements obtained by the system described below may be utilized to detect various physiological responses, as discussed in more detail in the examples given above (Sinusitis, a stroke, a migraine, etc.)

In one embodiment, the system comprises at least a frame configured to be worn on the user's head, and first and second focal-plane array (FPA) thermal cameras ($CAM_1$, $CAM_2$). Optionally, the frame may be any of the frames of an HMS described in this disclosure, such as a frame of eyeglasses (e.g., frame 90 illustrated in FIG. 6), or a frame of some other HMS, such as a hat, a helmet, and/or part of a system comprising a head-mounted display (e.g., an augmented reality system, a virtual reality system, or a mixed reality system). Various properties of the frame (and other system components) are described in more detail in Section 2.

Each of $CAM_1$ and $CAM_2$ is physically coupled to the frame, is located less than 15 cm away from the face, has an angle greater than 20° between its optical axis and the Frankfort horizontal plane, and comprises optics and multiple sensing elements. Optionally, each of $CAM_1$ and $CAM_2$ weighs below 5 g. Optionally, each of $CAM_1$ and $CAM_2$ comprises at least 6 sensing elements (pixels). Alternatively or additionally, each of $CAM_1$ and $CAM_2$ comprises at least 12 sensing elements.

Figure 69:
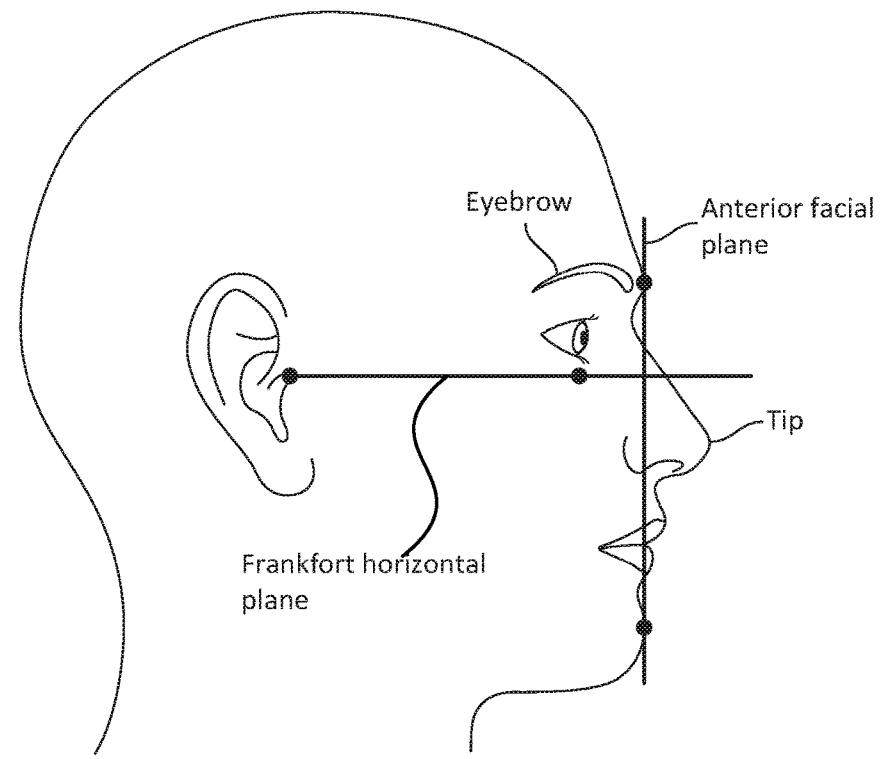
FIG. 69, FIG. 70, and FIG. 71 illustrate various facial regions and related nomenclature.

It is noted that phrases in the form of "the angle between the optical axis of a camera and the Frankfort horizontal plane is greater than 20°" refer to absolute values (which may be +20° or −20° in this example) and are not limited to just positive or negative angles, unless specifically indicated such as in a phrase having the form of "the optical axis of the camera points at least 20° below the Frankfort horizontal plane" where it is clearly indicated that the camera is pointed downwards. The Frankfort horizontal plane is illustrated in FIG. 69.

$CAM_1$ is located to the right of the vertical symmetry axis that divides the face and is configured to take thermal measurements of a first region of interest ($TH_{ROI1}$), where $ROI_1$ covers more of the right side of the face than of the left side of the face. $CAM_2$ is located to the left of the vertical symmetry axis and is configured to take thermal measurements of a second region of interest ($TH_{ROI2}$), where $ROI_2$ covers more of the left side of the face than of the right side of the face.

In some embodiments, $CAM_1$ and $CAM_2$ are located close to the face. For example, the $CAM_1$ and $CAM_2$ are located less than 5 cm and/or less than 2 cm away from the face. Additionally, $CAM_1$ and $CAM_2$ are located at least 0.5 cm to the right and to the left of the vertical symmetry axis, respectively.

It is to be noted that in some embodiments the system may be constructed in a way that none of the system components (including the frame and the thermal cameras) occludes $ROI_1$ and/or $ROI_2$. In other embodiments, the system may be constructed in a way that at least some of the system components (e.g., the frame and/or the thermal cameras) may occlude $ROI_1$ and/or $ROI_2$.

As discussed above, in some embodiments, the system may include a computer that is configured to identify a physiological response based on $TH_{ROI1}$ and $TH_{ROI2}$ In one embodiment, the computer calculates a value indicative of changes to the thermal asymmetry of the face (thermal variability), and utilizes the value to detect the physiological response. Optionally, the computer estimates, based on the thermal asymmetry, status of at least one of the following disorders: ADHD, a migraine, anger, anxiety, and depression. Herein, estimating the status of a disorder means evaluation of one or more of the following: a duration the user is affected by the disorder, a severity of the disorder, and an effectiveness of a treatment for the disorder.

Due to the angle between the optical axis of $CAM_1$ and the Frankfort horizontal plane, in some embodiments, $CAM_1$ utilizes a Scheimpflug adjustment suitable for its position relative to $ROI_1$ when the user wears the frame. Similarly, in some embodiments, $CAM_2$ also utilizes a Scheimpflug adjustment suitable for its position relative to $ROI_2$ when the user wears the frame. The Scheimpflug adjustment is discussed in more detail elsewhere in this disclosure.

For various applications, cameras such as thermal cameras or visible-light cameras may be mounted on the head. However, in some configurations, such as when an inward-facing camera is physically coupled to an eyeglasses frame with a sharp angle relative to the face, most of the face is out of focus due to the close proximity between the camera and the face. Thus, there is a need to improve the quality of the images obtained from cameras mounted in close proximity to the face.

Some aspects of this disclosure involve utilizing the Scheimpflug principle to improve quality of images of certain regions of the face, taken by cameras located close to the face and coupled to a frame worn on the face.

The Scheimpflug principle is a geometric rule that describes the orientation of the plane of focus of a camera when the lens plane is not parallel to the image plane. "Scheimpflug adjustment" refers to correction of images using the Scheimpflug principle when the orientation between the lens and image planes is greater than 2°, and this is not due to a manufacturing error. When the lens and image planes are parallel, the depth of field (DoF) extends between parallel planes on either side of the plane of focus (PoF). When the Scheimpflug principle is employed, the DoF becomes wedge shaped with the apex of the wedge at the PoF rotation axis (for a system having a rotating Scheimpflug mechanism) In usual Scheimpflug configurations, the DoF is zero at the apex, remains shallow at the edge of the lens's field of view, and increases with distance from the camera. On a plane parallel to the image plane, the DoF is equally distributed above and below the PoF. This distribution can be helpful in determining the best position for the PoF.

Figure 8A:
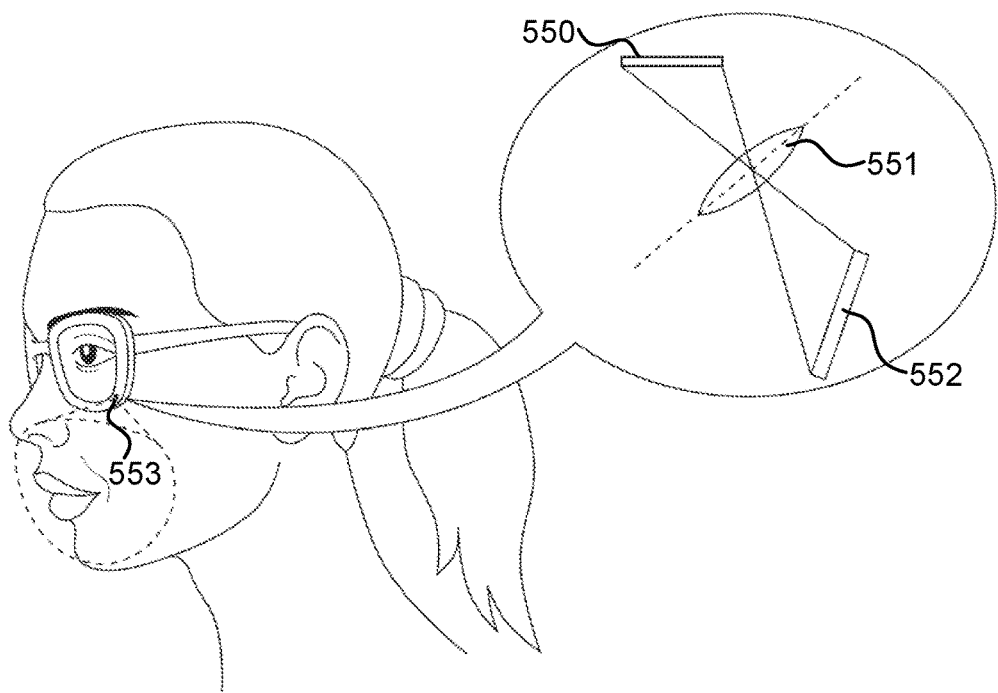
FIG. 8a is a schematic illustration of an HMS (on an eyeglasses frame) that utilizes the Scheimpflug principle to improve measurements taken by a camera.

FIG. 8a is a schematic illustration of a HMS (on an eyeglasses frame) that utilizes the Scheimpflug principle to improve the measurements taken by a camera 553. The tilt of optics 551 relative to a sensor 550 is fixed according to the expected position of the camera 553 relative to ROI 552 when the user wears the HMS. In some embodiments, the optics 551 may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the optics 551 may include one or more diffractive optical elements, and/or or a combination of one or more diffractive optical elements and one or more refractive optical elements.

It is to be noted that the Scheimpflug principle may be used for both thermal cameras and visible-light cameras. In one example, the sensor 550 is a sensor of one of the thermal cameras mentioned in Section 1. Optionally, the tilt optics 551 are optics appropriate for radiation in the IR bandwidth (e.g., optics that are effective with light having wavelengths longer than 2500 nm). In another example, the sensor 550 is a sensor of a visible-light camera, and the tilt optics are optics appropriate for light in the visible-light spectrum (e.g., 400-700 nm).

Figure 8B:
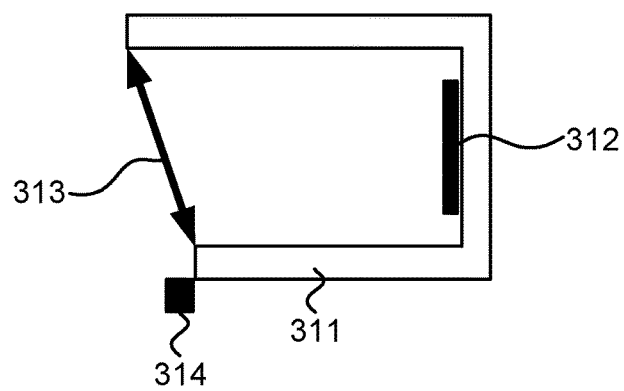
FIG. 8b illustrates a camera that utilizes the Scheimpflug principle.

Another illustration of a utilization of the Scheimpflug principle in camera that may be utilized in various embodiments described in this disclosure is given in FIG. 8b. Housing 311 mounts a sensor 312 and optics 313. The optics 313 is tilted relative to the sensor 312. The sensor 312 and optics 313 may be thermal sensor and corresponding optics (e.g., optics appropriate for wavelengths longer than 2500 nm) or a visible-light sensor and optics appropriate for or visible light (e.g., wavelengths 400-700 nm). The tilt of the optics 313 relative to the sensor 312 may be fixed according to the expected position of the camera relative to the ROI when the user wears the HMS, or may be adjusted using motor 314. Examples of references that may be relevant to some of the embodiments related to Scheimpflug principle include: (i) Depth of field for the tilted lens plane, by Leonard Evens, 2008; (ii) Addendum to focusing the view camera, by Harold M. Merklinger, World Wide Web Edition, 1993; (iii) U.S. Pat. No. 6,963,074, and (iv) US Patent Applications 20070267584 and 20070057164.

In some embodiments, a system that utilizes the Scheimpflug principle includes at least a frame and a camera. The frame is configured to be worn on the user's head. The camera weighs less than 10 g, is physically coupled to the frame, is located less than 15 cm away from the user's face, and is configured to take measurements of a region of interest (ROI) on the face. The camera includes at least a lens module and a sensor (e.g., the lens 551 and the sensor 550 illustrated in FIG. 8a). The lens module comprises one or more lenses, and the sensor comprises multiple sensing elements. Optionally, the weight of the camera is below at least one of the following weights: 5 g, 2 g, 1 g, 0.5 g, 0.3 g, and 0.1 g.

The lens module is positioned relative to the sensor such that a plane-parallel-to-the-lens-module ($P_L$) is tilted by an angle >2° relative to a plane-parallel-to-the-sensor ($P_S$), and an image obtained from the camera when the user wears the frame is sharper than an image that would be obtained from a similar camera, having essentially the same lens module and sensor, in which $P_L$ is parallel to $P_S$.

It is to be noted that for refractive optical lenses, the plane-parallel-to-the-lens-module ($P_L$) refers to a plane that is perpendicular to the optical axis of the lens module.

In one embodiment, the tilt of the $P_L$ relative to the $P_S$ is fixed. The fixed tilt is selected according to an expected orientation between the camera and the ROI when a user wears the frame. Having a fixed tilt between $P_L$ and $P_S$ may eliminate the need for an adjustable electromechanical tilting mechanism. As a result, a fixed tilt may reduce the weight and cost of the camera, while still providing a sharper image than an image that would be obtained from a similar camera in which $P_L$ is parallel to the $P_S$. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt of the $P_L$ relative to the $P_S$ according to the Scheimpflug principle based on the orientation between the camera and the ROI when the user wears the frame. In one example, the Scheimpflug adjustment is achieved using at least one brushless DC motor, such as a stepper motor (also known as a step motor) that divides rotation into a number of steps without requiring a feedback sensor. In another example, the Scheimpflug adjustment is achieved using at least one brushed DC electric motor. In still another example, the Scheimpflug adjustment is achieved using at least one piezoelectric motor, such as described in the reference Morita, T. (2003), "Miniature piezoelectric motors", Sensors and Actuators A: Physical, 103(3), 291-300. In still another example, the Scheimpflug adjustment is achieved using at least one micro-motion motor, such as described in the reference Ouyang, P. R., Tjiptoprodjo, R. C., Zhang, W. J., & Yang, G. S. (2008), "Micro-motion devices technology: The state of arts review", The International Journal of Advanced Manufacturing Technology, 38(5-6), 463-478.

The adjustable electromechanical tilting mechanism configured to change the tilt of the $P_L$ relative to the $P_S$ may include one or more of the following mechanisms: (i) a mirror that changes its angle; (ii) a device that changes the angle of the lens module relative to the sensor; and (iii) a device that changes the angle of the sensor relative to the lens module. In one embodiment, the camera, including the adjustable electromechanical tilting mechanism, weighs less than 5 g, and the adjustable electromechanical tilting mechanism is able to change the tilt of the $P_L$ relative to the $P_S$ in a limited range below 30° between the two utmost orientations between $P_L$ and $P_S$. In another embodiment, the camera, including the adjustable electromechanical tilting mechanism, weighs less than 5 g, and the adjustable electromechanical tilting mechanism is able to change the tilt of the $P_L$ relative to the $P_S$ in a limited range below 10° between the two utmost orientations between $P_L$ and $P_S$.

In some embodiments, being able to change the tilt of the $P_L$ relative to the $P_S$ in a limited range reduces at least one of the weight, cost, and size of the camera, which is advantageous for a wearable device. In one example, the camera is manufactured with a fixed predetermined tilt of the $P_L$ relative to the $P_S$, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt of the $P_L$ relative to the $P_S$ for the specific user who wears the frame and has facial dimensions that are different from the average user.

Figure 72A:
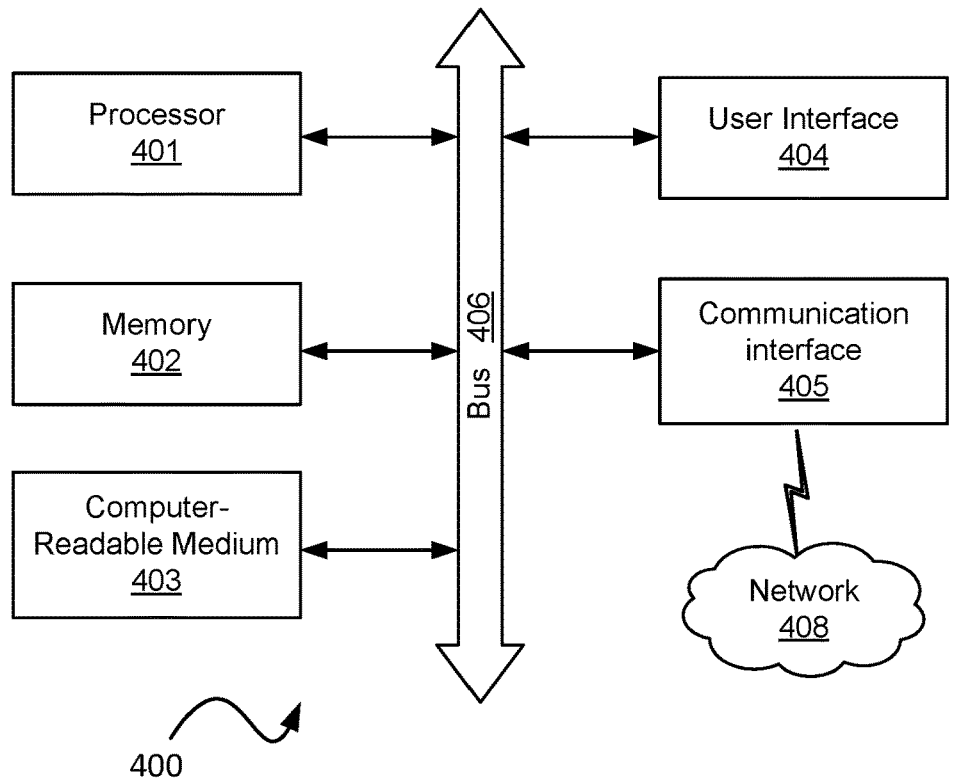
FIG. 72a and FIG. 72b are schematic illustrations of computers able to realize one or more of the embodiments discussed herein.
Figure 72B:
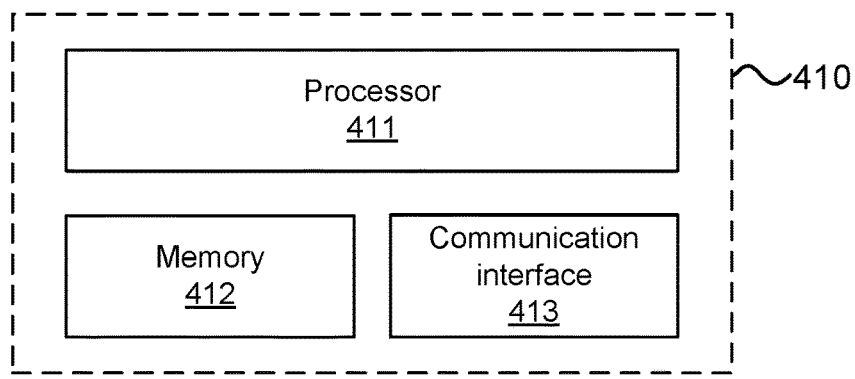

Various types of cameras may be utilized in different embodiments described herein. In one embodiment, the camera is a thermal camera configured to take thermal measurements of the ROI. The sensor of the camera, in this embodiment, is an uncooled focal plane array thermal sensor, and the angle between optical axis of the lens module and an average normal to the ROI is above 20°. Optionally, the system further comprises a computer configured to detect a physiological response based on the thermal measurements. For example, the computer may be computer system 400 or computer system 410 which are illustrated in FIG. 72a and FIG. 72b, respectively. Additional details regarding detecting the physiological response based on thermal measurements may be found in Section 4.

Many regions of the face are not planar, thus the average normal to the ROI is a normal that represents well the orientation of the ROI, such as the average of multiple normals distributed evenly over the ROI. Optionally, the computer is configured to process time series measurements of each sensing element individually in order to detect the physiological response.

In another embodiment, the camera is a visible-light camera configured to take visible-light images of the ROI. Optionally, in this embodiment, the system further includes a computer configured to generate an avatar for the user based on the visible-light images. Additionally or alternatively, the computer may detect an affective response of the user based on analyzing facial expressions extracted from the visible-light images utilizing image processing. Still additionally or alternatively, the computer may calculate, based on the visible-light images, hemoglobin concentration changes (HCC), and detect an emotional state of the user based on the HCC.

In still another embodiment, the camera is a light field camera configured to implement a predetermined blurring at a certain Scheimpflug angle, and to decode the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and is expected to become more blurred as the Scheimpflug adjustment does not fit. Additionally or alternatively, the autofocusing may use the variance of the neighborhood around each pixel as a measure of sharpness, where the Scheimpflug adjustment improves as the variance of its neighborhood increases.

In one embodiment, a system that utilizes the Scheimpflug principle includes at least a frame configured to be worn on a user's head and a camera. The camera weighs below 10 g, is physically coupled to the frame, is located less than 15 cm away from the user's face, and is configured to capture a region of interest (ROI) on the user's body. Additionally, the camera comprises a lens module and a sensor. The lens module comprises one or more lenses, and the sensor comprises multiple sensing elements. Optionally, the lens module is positioned relative to the sensor such that a plane-parallel-to-the-lens-module ($P_L$) is tilted by a fixed angle >5° relative to a plane-parallel-to-the-sensor ($P_S$). Optionally, the fixed angle is selected according to a Scheimpflug adjustment suitable for an expected orientation between the camera and the ROI when a user wears the frame. Optionally, the weight of the camera is below at least one of the following weights: 5 g, 2 g, 1 g, 0.5 g, 0.3 g, and 0.1 g.

Some advantages of the system described above include increasing the sharpness of images in some situations. In one example, the ROI comprises a region of the face, and an image of that region obtained from the camera when the user wears the frame is sharper than an image of that region that would be obtained from a similar camera (having essentially the same lens module and sensor) in which $P_L$ is parallel to $P_S$. In another example, the ROI comprises a region of the body below the face, and for a predetermined scenario, an image of that region obtained from the camera when the user wears the frame is sharper than an image of that region that would be obtained from a similar camera in which $P_L$ is parallel to $P_S$. Optionally, the predetermined scenario comprises at least one of the following scenarios: the user is standing, the user is running, and the user is sitting.

Various types of cameras may be utilized in the system described above. In one example, the camera is a thermal camera configured to take thermal measurements of the ROI, the camera's sensor is an uncooled focal plane array thermal sensor, and the angle between optical axis of the lens module and an average normal to the ROI is above 20°. Optionally, in this example, the system comprises a computer configured to detect a physiological response based on the thermal measurements.

In another example, the camera is a visible-light camera configured to take visible-light images of the ROI, and the angle between optical axis of the lens module and an average normal to the ROI is above 20°. Optionally, in this example, the system includes a computer configured to generate an avatar for the user based on the visible-light images. Additionally or alternatively, the computer may detect an affective response of the user based on analyzing facial expressions extracted from the visible-light images utilizing image processing. Still additionally or alternatively, the computer may calculate, based on the visible-light images, hemoglobin concentration changes (HCC), and detect an emotional state of the user based on the HCC.

The following is a description of different embodiments of systems, methods, and computer programs that may be utilized to detect a physiological response. The embodiments below involve detection utilizing a model (e.g., a machine learning-based model). Section 4 in this disclosure describes other approaches that may be utilized to detect a physiological response (e.g., comparing to a threshold or to a reference times series). That section also includes additional details regarding the nature of physiological responses that may be detected as well as other information that may be relevant to the embodiments described below.

Figure 9:
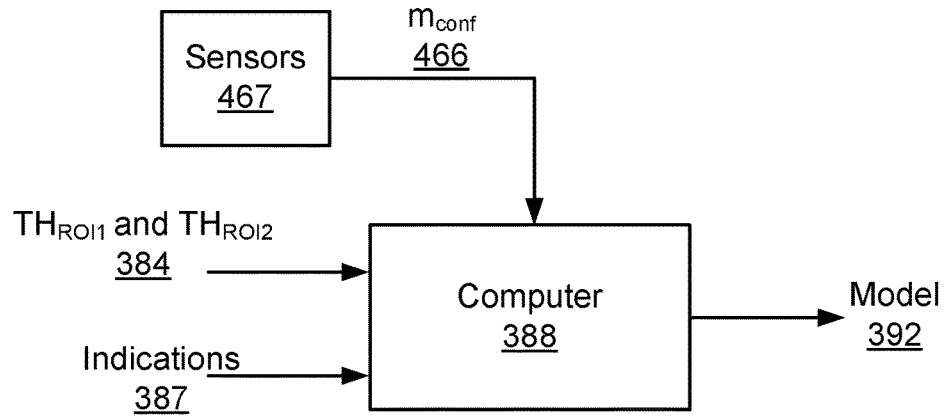
FIG. 9 illustrates an embodiment of a system configured to generate a model for detecting a physiological response based on thermal measurements of the face.

FIG. 9 illustrates an embodiment of a system configured to generate a model for detecting a physiological response based on thermal measurements of the face. The system includes head-mounted systems (HMSs) configured to be worn by users, sensors 467, and a computer 388.

Each HMS may be one of the HMSs described in this disclosure, such as HMSs illustrated in FIG. 1a, FIG. 1b, FIG. 2a, FIG. 2b, FIG. 3, FIG. 4, FIG. 5, FIG. 6, or FIG. 8a. Each HMS comprises first and second thermal cameras configured to take thermal measurements of first and second regions of interest (denoted $TH_{ROI1}$ and $TH_{ROI2}$, respectively) on the face of a user who wears the HMS. Optionally, each HMS further comprises a frame that is configured to be worn on the user's head and each of the first and second thermal cameras is physically coupled to the frame.

In different embodiments, the first and second thermal cameras may have different characteristics and/or may be located at various distances relative to the face. In one embodiment, each of the first and second thermal cameras weighs below 5 g, and is located less than 15 cm away from the face. In another embodiment, each of the first and second thermal cameras weighs below 1 g, and is located less than 5 cm away from the face. In yet another embodiment, at least one of the first and second thermal cameras is based on at least one of the following uncooled sensors: a thermopile, a microbolometer, and a pyroelectric sensor. In still another embodiment, at least at least one of the first and second thermal cameras is a focal-plane array (HA) thermal camera.

According to the definition of a thermal camera as used in this disclosure, the first and second thermal cameras are not in physical contact with their corresponding ROIs. Additionally, as a result of being physically coupled to the frame, the thermal cameras remain pointed at their corresponding ROIs when the user's head makes angular movements. In one example, the angular movements include movements of more than 45°. In another example, the locations of the first and second cameras relative to the user's head do not change even when the user's head performs wide angular and lateral movements, where wide angular and lateral movements include angular movements of more than 60° and lateral movements of more than 1 meter.

It is to be noted that because the first and second thermal cameras are coupled to the frame, challenges faced by non-head mounted systems known in the art that acquire thermal measurements may be simplified and even eliminated with some of the embodiments described herein. Some of these challenges may involve dealing with complications caused by movements of the user, image registration, ROI alignment, tracking based on hot spots or markers, and motion compensation in the IR domain.

A more detailed discussion regarding the various types of thermal cameras that may be used in embodiments described in this disclosure, including properties of thermal measurements (e.g., $TH_{ROI1}$ and $TH_{ROI2}$ mentioned above), is provided in Section 1.

The sensors 467 are configured, in one embodiment, to take additional measurements ($m_{conf}$ 466) of at least one of the following: the users, and the environment in which the users are in. The $m_{conf}$ 466 are indicative of magnitudes to which a confounding factor occurred while $TH_{ROI1}$ and $TH_{ROI2}$ were taken. Herein, a "confounding factor" may be a cause of warming and/or cooling of certain regions of the face, which is unrelated to a physiological response being detected, and as such, may be considered an artifact that can reduce the accuracy of the detection of the physiological response. Optionally, each HMS may have at least one sensor from among the sensors 467 communicatively and/or physically coupled to the HMS.

In one example, at least some of the sensors 467 may include a visible-light camera, which take images of the face. In this example, $m_{conf}$ 466 may include indications of one or more of the following: a skin inflammation on the face of a user, and touching the face of the user. Optionally, the indications are obtained by analysis of the images of the face. In another example, the $m_{conf}$ 466 may include values indicative of a magnitude of thermal radiation directed at the face of a user, measured by an outfacing thermal camera that is physically coupled to a frame worn by the user. In yet another example, the $m_{conf}$ 466 may include values indicative of a magnitude of direct airflow on the face of the user, measured by an anemometer that is physically coupled to the frame. A more extensive discussion regarding confounding factors, and how sensor measurements may be utilized to address them, is given below in the discussion regarding embodiments illustrated in FIG. 13.

The computer 388 may include any of the computers described in this disclosure. In particular, the computer 388 may be the computer 400 (illustrated in FIG. 72a) or the computer 410 (illustrated in FIG. 72b). Optionally, the computer 388 may include at least one of the following: a computer belonging to a device carried by the user, a computer of a smartphone, a personal computer, a remote server (e.g., a cloud based server), and an analog circuit.

In one embodiment, the computer 388 receives data comprising: $TH_{ROI1}$ and $TH_{ROI2}$ of the one or more users (denoted with the reference numeral 384), indications 387, and $m_{conf}$ 466. The computer 388 is configured to: generate samples based on data pertaining to the users, which comprises for each user: (i) $TH_{ROI1}$ and $TH_{ROI2}$ of the user (from among $TH_{ROI1}$ and $TH_{ROI2}$ 384); (ii) $m_{conf}$ of the user (from among $m_{conf}$ 466); and (iii) indications corresponding to different times (from among the indications 387), which are indicative of an extent of the physiological response of the user at the different times. The computer 388 is further configured to generate a model 392 based on the samples, and to provide the model 392 to be used by a system that detects the physiological response based on future $TH_{ROI1}$ and $TH_{ROI2}$, such as an embodiment of the system illustrated in FIG. 11.

It is to be noted that references to "the computer 388" should be interpreted as one or more computers. In some embodiments, multiple computers, possibly in different sites, may be employed in order to implement the functionality attributed herein to the computer 388. In one example, samples generated based on data of different users may be generated by different computers (e.g., computers belonging to devices of the users), while generating the model 392 may be done by a computer that is a server (which does not belong to any of the users).

There are various types of physiological responses for which the model 392 may be generated using an embodiment of the system illustrated in FIG. 9. The following are some examples of physiological responses and some of the ROIs at which thermal measurements, which may be relevant for the detection of the physiological responses, can be taken.

In one embodiment, the physiological response comprises an allergic reaction and $TH_{ROI1}$ and $TH_{ROI2}$ of each user from among the one or more users comprises thermal measurements of a portion of the user's nose. Additionally or alternatively, $TH_{ROI1}$ and $TH_{ROI2}$ of each user may include different regions/sides of the mouth. Some examples of possible locations for thermal cameras coupled to the frame and their corresponding ROIs are given in FIG. 1a and FIG. 1b. In one example, temperature measurements at ROIs 41, 42, 23, 25, and/or 29 may be utilized for the detection of an allergic reaction.

In another embodiment, the physiological response comprises experiencing stress and $TH_{ROI1}$ and $TH_{ROI2}$ of each user comprise at least one of the following: thermal measurements of a portion of the user's periorbital regions, and thermal measurements of a portion of the user's forehead. In one example, $TH_{ROI1}$ and $TH_{ROI2}$ of each user comprise measurements taken of at least two ROIs; the first ROI covers a portion of at least one of the supraorbital and periorbital areas on the right side of the face, and the second ROI covers a portion of at least one of the supraorbital and periorbital areas on the left side of the face.

In yet another embodiment, the physiological response comprises a respiratory parameter and $TH_{ROI1}$ and $TH_{ROI2}$ of each user comprise at least one of the following: thermal measurements of a portion of the user's nasal region, and thermal measurements of a portion of the user's upper lip. Some examples of respiratory parameters include breathing rate and the type of breathing (e.g., mouth breathing vs. nasal breathing). Additional details regarding various respiratory parameters are given in Section 5.

In still another embodiment, the physiological response comprises at least one of the following: Attention-Deficit/Hyperactivity Disorder (ADHD) symptomatic behavior, a migraine, and Obsessive-Compulsive Disorder (OCD) symptomatic behavior. Optionally, in this embodiment, $TH_{ROI1}$ and $TH_{ROI2}$ of each user comprise thermal measurements of a portion of the user's forehead.

In yet another embodiment, the physiological response comprises a manifestation of an emotional response that involves manifestation of one or more of the following emotions: fear, startle, sexual arousal, anxiety, joy, pain and guilt. Optionally, $TH_{ROI1}$ and $TH_{ROI2}$ of each user comprise at least one of the following: thermal measurements of a portion of the user's nose, thermal measurements of a portion of the user's cheeks, thermal measurements of a portion of the user's forehead, thermal measurements of a portion of the user's periorbital regions, and thermal measurements of a portion of the user's mouth.

And in still other embodiment, the physiological response may involve a medical condition such intoxication or dehydration, or a medical disorder involving one or more of the following: nerve damage, a stroke, and Bell's palsy.

An extent of a physiological response may refer to various types of values. In one embodiment, the extent is treated as a binary value indicative of whether or not the user experienced, and/or is experiencing, the physiological response (e.g., is the user having an allergic reaction or not). In another embodiment, the extent is as a numerical value indicative of the magnitude of the physiological response (e.g., on a scale from 1 to 10). In still another embodiment, the extent is a categorial value indicative of the severity of the physiological response (e.g., the categories may correspond to no stress, low-level stress, or high-level stress). In yet another embodiment, the extent of the physiological response is expressed as an expected change in temperature or as a temporal value. For example, when the physiological response is an allergic reaction, the extent of the physiological response may be expressed as the maximum change that is measured for the temperature at the nasal area. In another example, the extent of the allergic reaction may be expressed as a temporal value, such as the time it took an increase to the temperature in the nasal area to reach a certain threshold, or the expected time until the temperature at the nasal area will return to normal. In still another embodiment, the extent of the physiological response is determined based on the rate of change in temperature, such that the larger the increase for a given period of time (e.g., five minutes), the more severe the physiological response is considered. And in still another embodiment, the extent of a physiological response is a value that is indicative of the area under the curve of the temperature change at an ROI over time. When the physiological response corresponds to a physiological signal (e.g., a heart rate, a respiration rate, and an extent of frontal lobe brain activity), the extent of the physiological response may be interpreted as the value of the physiological signal.

The indications 387 may be generated in different ways, in different embodiments. In one embodiment, at least some of the indications 387 corresponding to $TH_{ROI1}$ and $TH_{ROI2}$ of a user, from among the one or more users, are generated by an external source such as an entity that observes the user, which may be a human observer or a software program. Optionally, the software program is a software agent operating on behalf of the user.

In another embodiment, at least some of the indications 387 corresponding to $TH_{ROI1}$ and $TH_{ROI2}$ of a user, from among the one or more users, may be generated by the user. In one example, the user may provide indications indicating whether he/she is experiencing a certain physiological response (and/or the extent of the physiological response) via a mobile "app" (e.g., by pressing a certain button on a screen of a smartphone). In another example, the user may provide an indication by making a comment that is interpreted by a software agent and/or a program with speech analysis capabilities.

In yet another embodiment, at least some of the indications 387 corresponding to $TH_{ROI1}$ and $TH_{ROI2}$ of a user, from among the one or more users, are determined based on analysis of behavior of the user. For example, monitoring of the behavior of the user using a camera and/or microphone may indicate that the user is suffering from an allergic reaction (e.g., by detecting coughing and/or sneezing). Optionally, monitoring the user is done by measuring additional physiological signals of the user with sensors that are not thermal cameras, such as measurements of the user's heart rate, brainwave activity, and/or other signals. Optionally, algorithms that detect the physiological response based on the additional physiological signals may be used to generate the indications.

The computer 388 is configured, in one embodiment, to receive data pertaining to one or more users. The data pertaining to each user, from among the one or more users, includes: (i) $TH_{ROI1}$ and $TH_{ROI2}$ of the user, (ii) $m_{conf}$ of the user, and (iii) indications corresponding to different times, which are indicative of an extent of the physiological response of the user at the different times. The data is utilized the computer 388 to generate samples, where each sample comprises feature values and a label. The feature values include one or more feature values generated based on $TH_{ROI1}$ and $TH_{ROI2}$ of a user taken during a certain period, and one or more feature values generated based on $m_{conf}$ of the user taken during the certain period.

The label, which is generated based on at least one of the indications 387, comprises a value that is indicative of the extent of the physiological response of the certain user, which corresponds to the certain period. Optionally, the extent of the physiological response corresponding to the certain period refers to the extent of the physiological response during the certain period (e.g., the amount of stress the user was under during the certain period). Additionally or alternatively, the extent of the physiological response corresponding to the certain period refers to the extent of the physiological response shortly after the certain period, such as up to one hour after the certain period, two hours after the certain period, or some other number of hours after the certain period that is less than a day. For example, the extent may refer to the severity of migraine or an allergic reaction up to one hour after the end of the certain period.

It is to be noted that stating that feature values are generated based on $TH_{ROI1}$ and $TH_{ROI2}$ of a user means that the feature values include at least one feature value generated based on $TH_{ROI1}$ of the user and at least one feature value generated based on $TH_{ROI2}$ of the user. Optionally, the feature values may include at least one feature value generated based on both $TH_{ROI1}$ and $TH_{ROI2}$ of the user. Additionally, a sample that is generated based on $TH_{ROI1}$ and $TH_{ROI2}$ of a user includes feature values generated based $TH_{ROI1}$ and $TH_{ROI2}$ of the user.

The term "feature values" is typically used herein to represent data comprising values on which calculations may be performed. In one exemplary embodiment, feature values may be provided to a machine learning based estimator (which may also be called a "predictor") in order to perform calculations on the data utilizing a model (e.g., in order to perform inference). In one example, feature values are data that may be represented as a vector of numerical values (e.g., integer and/or real values), with each position in the vector corresponding to a certain feature. In some examples, in vectors representing feature values of different samples, each position (dimension) in the vectors corresponds to the same feature. Thus, in these examples, different samples may be considered to include data representing the same features, but include different feature values. For example, the vectors may include measurements of temperatures at ROIs, but each sample may include different values of temperatures (at the ROIs). In another example, feature values are stored in a data structure having a predetermined section that identifies the type of data stored in the data structure. For example, the feature values may be stored in the payload of a packet, and a predefined data structure in the packet's header identifies the one or more types of data stored in the payload. Alternatively or additionally, a predefined data structure in the packet's tail may identify the one or more types of data stored in the packet's payload.

The certain period of time, during which $TH_{ROI1}$, $TH_{ROI2}$, and $m_{conf}$ used to generate each sample were taken, may be different in different embodiments. In some embodiments, each of the samples includes feature values representing a snapshot of temperatures and/or changes to temperatures at $ROI_1$ and $ROI_2$; thus, the certain period in these embodiments may be less than one second, less than five seconds, or less than one minute. In some embodiments, each of the samples may be based on $TH_{ROI1}$ and $TH_{ROI2}$ taken during a period of time sufficiently long to include multiple measurements of temperatures and/or temperature changes at each $ROI_1$ and $ROI_2$. Optionally, the certain period during which $TH_{ROI1}$ and $TH_{ROI2}$ for each of the samples were taken is at least a half of second, at least two seconds, at least five second, at least one minute, at least five minutes, at least one hour, or at least one day.

When the certain period is sufficiently long to include successive thermal measurements at the same ROIs, the feature values generated based on $TH_{ROI1}$ and $TH_{ROI2}$ taken during the certain period may include various types of features. In one embodiment, some of the feature values may represent statistics of the successive thermal measurements at the one or more ROIs (e.g., the average at an ROI during the certain period). In another embodiment, the feature values may include multiple values based on the successive measurements (e.g., a first feature value representing a temperature at an ROI during the first half of the certain period and a second feature value representing the temperature at the ROI during the second half of the certain period). In yet another embodiment, the feature values may include a feature value that represents a trend of $TH_{ROI1}$ and $TH_{ROI2}$ during the certain period. For example, the feature values may include a feature value indicative of the extent the temperature at a certain ROI, from among the one or more ROIs, changed throughout the certain period and/or a feature value indicative of the extent the average temperature at multiple ROIs changed during the certain period.

The following are some examples of feature values that may be generated for a sample based on $TH_{ROI1}$, $TH_{ROI2}$, and/or $m_{conf}$ of a user taken during a certain period.

In some embodiments, at least one of the feature values generated based on $TH_{ROI1}$ and $TH_{ROI2}$ of a user taken during the certain period include values measured by the first and/or second thermal cameras during the certain period. Optionally, the values measured by the first and/or second thermal cameras may undergo various forms of filtering and/or normalization. In one example, some feature values may be average values of certain sensors (pixels) of the first or second thermal cameras during the certain period and/or some feature values may be values measured at certain times during the certain period by the certain sensors. In another example, feature values generated based on $TH_{ROI1}$ and $TH_{ROI2}$ of the user taken during the certain period may include time series data comprising values measured by the one or more thermal cameras during the certain period.

In addition to the feature values based on $TH_{ROI1}$ and $TH_{ROI2}$ of a user, which were taken during the certain period mentioned above, in some embodiments, at least some feature values may include feature values representing a baseline of the user. For example, the feature values may include one or more features values representing values of $TH_{ROI1}$ and $TH_{ROI2}$ of the user taken before the certain period (e.g., more than five minutes before or more than one hour before). In another example, the feature values may include one or more features values representing averages of values of $TH_{ROI1}$ and $TH_{ROI2}$ of the user taken over long periods (e.g., days, weeks, and even months or more). Additionally or alternatively, in some embodiments, at least some feature values may include feature values representing a difference between $TH_{ROI1}$ and $TH_{ROI2}$ of the user taken during the certain period, and at least some of the baseline values mentioned above. Additionally or alternatively, feature values generated based on $TH_{ROI1}$ and $TH_{ROI2}$ of the user taken during the certain period may be normalized with respect to the baseline values. For example, the baseline values may be subtracted from values $TH_{ROI1}$ and $TH_{ROI2}$ of the user taken during the certain period, or using other forms of normalization (e.g., converting to z-values based on distributions learned from baseline values).

In some embodiments, at least some of the feature values generated based on $TH_{ROI1}$ and $TH_{ROI2}$ of a user taken during the certain period include processed results of $TH_{ROI1}$ and $TH_{ROI2}$, such a value of a physiological signal. In one example, the physiological signal may be a heart rate or heart rate variability. In another example, the physiological signal may be a respiratory parameter. Some examples of respiratory parameters that may be used as feature values include the following: respiration rate, respiration volume, indications of mouth vs. nasal breathing, exhale (inhale) duration, post-exhale (post-inhale) breathing pause, indication of the dominant nostril, exhale stream shape, exhale stream smoothness, and exhale stream temperature. Respiratory parameters are discussed in more detail in Section 5.

In some embodiments, one or more of the feature values of a sample may be generated based on $m_{conf}$ of the user taken during the certain period. In one example, the one or more feature values comprise a feature value that is a value obtained by a sensor from among the sensors 467, which is used to generate the $m_{conf}$ of the user. In another example, the one or more feature values comprise a feature value that is a product of analysis of the $m_{conf}$ of the user (e.g., an image analysis algorithm that detects presence of a finger touching the face, hair on the face, etc.).

In addition to $TH_{ROI1}$, $TH_{ROI2}$, and $m_{conf}$ of a user taken during the certain period, in some embodiments, additional sources of information may be utilized to generate one or more of the feature values of a sample. Optionally, these additional sources of information pertain to the user. Additionally or alternatively, the additional sources of information may pertain to the environment the user is in.

In one embodiment, the computer 388 may be further configured to receive additional measurements of the user taken during the certain period and to generate at least one of the feature values of the sample based on the additional measurements. Optionally, the additional measurements are indicative of one or more of the following signals of the user: a heart rate, heart rate variability, brainwave activity, galvanic skin response, muscle activity, and an extent of movement. Optionally, the additional measurements may be obtained utilizing one or more of the various sensors that are described in Section 4, which are not thermal cameras and/or are not among the sensors 467.

In another embodiment, the computer 388 may be further configured to receive measurements of the environment the user was in during the certain period and to generate at least one feature value of the sample based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

The samples used to generate the model 392 include, in some embodiments, samples corresponding to different extents of the physiological response. In particular, in these embodiments, the samples comprise at least first and second samples, with the first sample having a label indicative of a first extent of the physiological response and a second sample having a second label indicative of a second extent of the physiological response. Optionally, in this example, the first and second samples are generated based on $TH_{ROI1}$, $TH_{ROI2}$, and $m_{conf}$ of the same user. Herein, a sample is considered generated based on $TH_{ROI1}$, $TH_{ROI2}$, and $m_{conf}$ of a user if the sample includes one or more feature values generated based on $TH_{ROI1}$, $TH_{ROI2}$, and $m_{conf}$ of the user.

In one embodiment, in which the physiological response is a medical disorder (e.g., ADHD, Bell's palsy, a stroke, and/or nerve damage), the samples include both samples with feature values generated based on $TH_{ROI1}$, $TH_{ROI2}$, and $m_{conf}$ taken from a first user while the first user did not suffer from the medical disorder and other samples with feature values generated based on $TH_{ROI1}$, $TH_{ROI2}$, and $m_{conf}$ taken from a second user while the second user suffered from the medical disorder. Optionally, the first and second users are the same user, and the samples include both "before" and "after" samples, which may be used to identify a manifestation of the effect of the medical disorder in $TH_{ROI1}$ and $TH_{ROI2}$.

In another embodiment, in which the physiological response is transient (e.g., a migraine, an allergic reaction, stress, expression of a certain emotion, etc.), the samples include one or more samples, each with feature values generated based on $TH_{ROI1}$, $TH_{ROI2}$, and $m_{conf}$ taken while a first user being measured had the physiological response, and one or more other samples, each with feature values generated based on $TH_{ROI1}$, $TH_{ROI2}$, and $m_{conf}$ taken while a second user being measured did not have the physiological response. Optionally, the samples may include at least one sample generated based on $TH_{ROI1}$, $TH_{ROI2}$, and $m_{conf}$ taken while a certain user had the physiological response, and at least one other sample generated based on $TH_{ROI1}$, $TH_{ROI2}$, and $m_{conf}$ taken while the certain user did not have the physiological response.

In another embodiment, in which the physiological response is transient (e.g., a heart rate or a respiratory parameter), an allergic reaction, stress, expression of a certain emotion, etc.), the samples include samples reflecting various values of the physiological signal. For example, in an embodiment in which the model 392 is used to detect a breathing rate, the samples include samples that have corresponding labels indicating different breathing rates; e.g., there are at least a first sample with a first label corresponding to a first breathing rate, and a second sample with a second label corresponding to a second breathing rate, which is different from the first breathing rate.

The samples utilized to generate the model 392 may include samples taken while the one or more users were in different environments. In one example, the samples comprise first and second samples that are based on $TH_{ROI1}$, $TH_{ROI2}$, and $m_{conf}$ of a user taken during first and second periods, respectively. Optionally, different environmental conditions prevailed during the first and second periods, which involved one or more of the following differences: (i) the temperature of the environment in which the user was during the first period was at least 10° C. higher than the temperature of the environment in which the user was during the second period; (ii) the humidity level in the environment in which the user was during the first period was at least 30% higher than the humidity level in the environment in which the user was during the second period; and (iii) the user was exposed to at least one of rain, hail, and snow during the first period and the user was not exposed to any of rain, hail, and snow during the second period.

Additionally or alternatively, the samples utilized to generate the model 392 may include samples taken while the one or more users were in various situations. In one example, the samples comprise first and second samples that are based on $TH_{ROI1}$, $TH_{ROI2}$, and $m_{conf}$ of a user taken during first and second periods, respectively. Optionally, the user was in different situations during the first and second periods, which involved one or more of the following differences: (i) the user was sedentary during the first period while the user was performing at least one of the following during the second period: walking, running, and biking; and (ii) the user was indoors during the first period, while the user was outdoors during the second period.

Additionally or alternatively, the samples utilized to generate the model 392 may be based on measurements ($TH_{ROI1}$, $TH_{ROI2}$, and $m_{conf}$) taken over a long period of time, such as more than a day, more than a week, more than a month, or more than a year. Herein, samples may be considered to be generated based on measurements taken over more than a certain period (e.g., a week) if the samples include at least first and second samples, generated based on measurements taken during first and second periods of time, respectively, such that the difference between when the first period and the second period start is at least as long as the certain period. That is, the starting times first and second periods are at least the certain period apart.

The computer 388 may employ various computational approaches to generate the model 392. In one example, generating the model 392 may involve selecting, based on the samples, a threshold. Optionally, if a certain feature value reaches the threshold then the physiological response is detected (e.g., an allergic reaction). Optionally, the model 392 includes a value describing the threshold. In another example, the computer 388 is configured to utilize a machine learning based training algorithm to generate the model 392 based on the samples. Optionally, the model comprises parameters of at least one of the following models: a regression model, a neural network, a nearest neighbor model, a support vector machine, a support vector machine for regression, a naïve Bayes model, a Bayes network, and a decision tree.

In some embodiments, the computer 388 may utilize deep learning algorithms to generate the model 392. In one example, the model 392 may include parameters describing multiple hidden layers of a neural network. In one embodiment, when $TH_{ROI1}$ and $TH_{ROI2}$ include measurements of multiple pixels, such as when the one or more thermal camera include a focal-plane array (FPA), the model 392 may include a convolution neural network (CNN). In one example, a CNN may be utilized to identify certain patterns in the thermal images, such as patterns of temperatures on the forehead that may be indicative of a certain physiological response (e.g., a migraine, stress, or anger). In another example, a CNN may be utilized to detect a respiratory parameter such as the location, direction, size, and/or shape of an exhale stream from the nose or mouth. In another embodiment, detecting the physiological response may be done based on multiple, possibly successive, measurements. In one example, the physiological response may be a physiological signal such as a respiratory parameter. In another example, the physiological response may involve a progression of a state of the user (e.g., a gradual warming of the nose in an allergic reaction or the forming of a certain thermal pattern on the forehead). In such cases, detecting the physiological response may involve retaining state information that is based on previous measurements. Optionally, the model 392 may include parameters that describe an architecture that supports such a capability. In one example, the model 392 may include parameters of a recurrent neural network (RNN), which is a connectionist model that captures the dynamics of sequences of samples via cycles in the network of nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

Depending on the composition of the samples, the model 392 may be considered, in some embodiments, either a general model or a personalized model. In one embodiment, the samples comprise samples generated based on measurements of multiple users (i.e., $TH_{ROI1}$, $TH_{ROI2}$, and/or $m_{conf}$ of the multiple users). In this case, the model 392 may be considered a general model that is capable of detecting the physiological response with a variety of users who may have different manifestations of the physiological response (as it is reflected in $TH_{ROI1}$ and $TH_{ROI2}$ and/or other sensor measurements).

In other embodiments, the samples comprise samples generated based on measurements of a certain user, or a certain proportion of the samples are generated based on measurements of a certain user. For example, at least 20% of the samples are generated based on measurements of the certain user, which is larger than a proportion of the samples that are generated based on measurements of any other user. In this embodiment, the model 392 may be considered personalized for the certain user, and as such, in some cases, may be more adept at detecting the physiological response when the certain user experiences it, compared to its ability to detect the physiological response when other users experience it.

Generating a model that is personalized for the certain user may require collecting a sufficient number of training samples that are generated based on measurements of the certain user. Thus, initially detecting the physiological response with the certain user may be done utilizing a general model, which may be replaced by a personalized model for the certain user as a sufficiently large number of samples are generated based on $TH_{ROI1}$ $TH_{ROI2}$, and/or $m_{conf}$ of the certain user. Another approach involves gradually modifying a general model based on samples of the certain user. To this end, in one embodiment, generating the model 392 involves altering parameters of another model, which is generated based on $TH_{ROI1}$, $TH_{ROI2}$, and/or $m_{conf}$ of other users. For example, the computer 388 may utilize the other model as an initial model. As the samples are acquired from measurements of the certain user, the computer 388 may update parameters of an initial model based on the samples. Thus, this process may be considered personalizing a general model according to measurements of the certain user.

Providing a model to be used by a system that detects the physiological response, such as when the computer 388 provides the model 392, may involve performing different operations, in different embodiments. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model. For example, the model may be stored on a database and/or cloud based storage (e.g., an "app" store) from which the system may retrieve the model. In still another embodiment, providing the model for use by the system involves notifying the system regarding the existence of the model and/or regarding an update to the model. Optionally, this notification includes information needed in order for the system to obtain the model.

Figure 10:
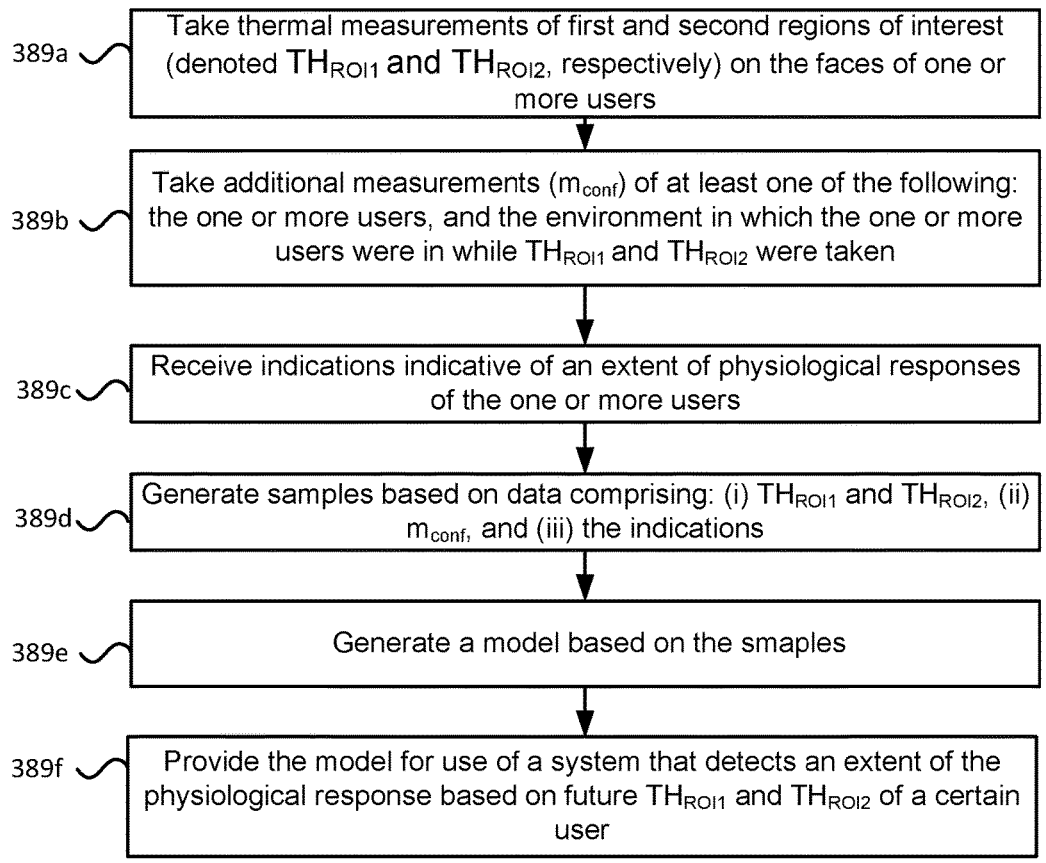
FIG. 10 illustrates an embodiment of a method for generating a model for detecting a physiological response based on thermal measurements.

FIG. 10 illustrates steps that may be performed in one embodiment of a method for generating a model for detecting a physiological response based on thermal measurements. The steps described below may be, in some embodiments, part of the steps performed by an embodiment of a system described above, which is illustrated in FIG. 9. In some embodiments, instructions for implementing an embodiment of the method described below may be stored on a computer-readable medium, which may optionally be a non transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a. Optionally, different steps of the method may be performed utilizing different systems comprising a processor and memory.

In one embodiment, a method for generating a model for detecting a physiological response based on thermal measurements includes at least the following steps:

In Step 389a, taking thermal measurements of first and second regions of interest (denoted $TH_{ROI1}$ and $TH_{ROI2}$, respectively) on the face of users. Optionally, $TH_{ROI1}$ and $TH_{ROI2}$ of each user are taken utilizing a thermal camera physically coupled to a frame of a head-mounted system (HMS) worn by the user. Optionally, each thermal camera weighs below 5 g and is located less than 15 cm away from the user's face.

In Step 389b, taking, utilizing sensors, additional measurements ($m_{conf}$) of at least one of the following: the users, and the environment the users are in. Optionally, $m_{conf}$ are indicative of magnitudes to which a confounding factor occurred while $TH_{ROI1}$ and $TH_{ROI2}$ were taken. In one example, the sensors comprise visible-light cameras, taking $m_{conf}$ comprises taking one or more images of a user's face utilizing the visible-light cameras and analyzing the one or more images to identify at least one of the following: a skin inflammation on the face of the user, and touching the face of the user. In another example, taking $m_{conf}$ comprises one or more of the following: (i) measuring, utilizing an outfacing thermal camera that is physically coupled to a frame worn by a user, a magnitude of thermal radiation directed at the face of the user, and (ii) measuring, utilizing an anemometer that is physically coupled to the frame worn by a user, a magnitude of direct airflow on the face of the user.

In Step 389c, receiving indications corresponding to different times, which are indicative of extents of the physiological response of the users during at least some of the different times.

In Step 389d, generating samples based on the data obtained in Steps 389a, 389b, and 389c. Optionally, each sample comprises feature values generated based on $TH_{ROI1}$, $TH_{ROI2}$, and/or $m_{conf}$ of a user taken during a certain period and a label indicative of an extent of the physiological response of the user corresponding to the certain period.

In Step 389e, generating a model based on the samples generated in Step 389d. Optionally, the model is the model 392. Optionally, generating the model based on the samples involves utilizing a machine learning-based training algorithm. Optionally, generating the model involves personalizing the model for a certain user by updating parameters of an initial model based on samples generated based on $TH_{ROI1}$, $TH_{ROI2}$, and/or $m_{conf}$ of the certain user, where the initial model is generated based on samples generated from $TH_{ROI1}$, $TH_{ROI2}$, and/or $m_{conf}$ of other users.

Figure 11:
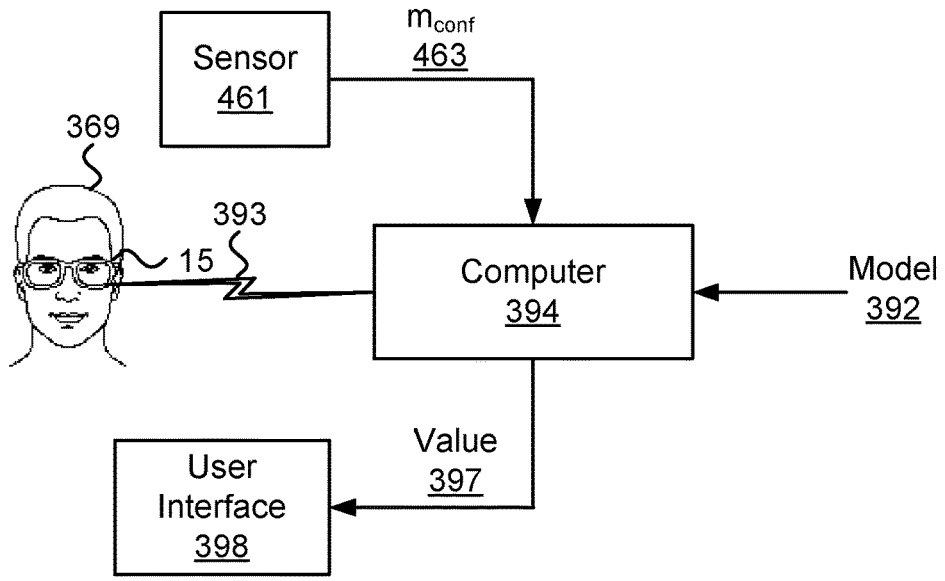
FIG. 11 illustrates an embodiment of a system configured detect a physiological response based on thermal measurements of the face.

And in Step 389f, providing the model to be used by a system that detects a physiological response based on $TH_{ROI1}$, $TH_{ROI2}$, and $m_{conf}$ such as the system illustrated in FIG. 11.

In one embodiment, generating the samples in Step 389d may optionally involve receiving additional data pertaining to a user from among the one or more users and generating one or more feature values belonging to at least one of the samples based on the additional data. Optionally, the additional data pertaining to the user comprise s additional measurements of the user that are indicative of one or more of the following signals: a heart rate of the user, heart rate variability of the user, brainwave activity of the user, galvanic skin response of the user, muscle activity of the user, and an extent of movement of the user.

Once the model 392 is generated, it may be utilized to detect a physiological response of a user 369 based on $TH_{ROI1}$ and $TH_{ROI2}$ 393, of the user 369, which are not among $TH_{ROI1}$ and $TH_{ROI2}$ 384 that were used for generating the model 392. Such utilization of the model 392 is illustrated in FIG. 11, which illustrates an embodiment of a system configured to detect a physiological response based on thermal measurements of the face. One embodiment of the illustrated system includes a frame (e.g., the frame 15), first and second thermal cameras, a sensor 461, and a computer 394.

The frame and first and second thermal cameras may belong to an HMS from among the HMSs described in this disclosure, such as HMSs illustrated in FIG. 1a, FIG. 1b, FIG. 2a, FIG. 2b, FIG. 3, FIG. 4, FIG. 5, FIG. 6, and FIG. 8a. The first and second thermal cameras are physically coupled to the frame and configured to take thermal measurements of first and second regions of interest on the face (denoted $TH_{ROI1}$ and $TH_{ROI2}$, respectively) of the user 369.

In different embodiments, the first and second thermal cameras may have different characteristics and/or may be located at various distances relative to the face. In one embodiment, each of the first and second thermal cameras weighs below 5 g, and is located less than 15 cm away from the face. In another embodiment, each of the first and second thermal cameras weighs below 1 g, and is located less than 5 cm away from the face. In yet another embodiment, at least one of the first and second thermal cameras is based on at least one of the following uncooled sensors: a thermopile, a microbolometer, and a pyroelectric sensor. In still another embodiment, at least at least one of the first and second thermal cameras is a focal-plane array (FPA) thermal camera.

According to the definition of a thermal camera as used in this disclosure, the first and second thermal cameras are not in physical contact with their corresponding ROIs. Additionally, as a result of being physically coupled to the frame, the thermal cameras remain pointed at their corresponding ROIs when the user's head makes angular movements. In one example, the angular movements include movements of more than 45°. In another example, the locations of the first and second cameras relative to the user's head do not change even when the user's head performs wide angular and lateral movements, where wide angular and lateral movements include angular movements of more than 60° and lateral movements of more than 1 meter.

It is to be noted that because the first and second thermal cameras are coupled to the frame, challenges faced by non-head mounted systems known in the art that acquire thermal measurements may be simplified and even eliminated with some of the embodiments described herein. Some of these challenges may involve dealing with complications caused by movements of the user, image registration, ROI alignment, tracking based on hot spots or markers, and motion compensation in the IR domain A more detailed discussion regarding the various types of thermal cameras that may be used in embodiments described in this disclosure, including properties of thermal measurements (e.g., $TH_{ROI1}$ and $TH_{ROI2}$ mentioned above), is provided in Section 1.

The sensor 461 is configured to take additional measurements ($m_{conf}$ 463) of at least one of the following: the user 369, and the environment in which the user 369 was in while $TH_{ROI1}$ and $TH_{ROI2}$ 393 were taken. Optionally, $m_{conf}$ 463 are indicative of a magnitude to which a confounding factor occurred while $TH_{ROI1}$ and $TH_{ROI2}$ were taken. Optionally, the sensor 461 is communicatively and/or physically coupled to the frame.

In one example, the sensor 461 includes a visible-light camera, which take images of the face. In this example, $m_{conf}$ 463 may include indications of one or more of the following: a skin inflammation on the face of the user 369, and touching the face of the user 369. Optionally, the indications are obtained by analysis of the images of the face. In another example, the $m_{conf}$ 463 may include values indicative of a magnitude of thermal radiation directed at the face of the user 369, measured by the sensor 461, which is an outfacing thermal camera that is physically coupled to the frame. In yet another example, the $m_{conf}$ 463 may include values indicative of a magnitude of direct airflow on the face of the user, measured by the sensor 461, which includes an anemometer that is physically coupled to the frame. A more extensive discussion regarding confounding factors, and how measurements of the sensor 461 may be utilized to address them, is given below in the discussion regarding embodiments illustrated in FIG. 13.

In one embodiment, the computer 394 is configured to generate feature values based on: (i) $TH_{ROI1}$ and $TH_{ROI2}$ 393, and (ii) $m_{conf}$ 463, and to utilize the model 392 to calculate, based on the feature values, a value 397, which is indicative of the extent of the physiological response. Optionally, the model 392 is generated based on previous $TH_{ROI1}$ and $TH_{ROI2}$ (and optionally $m_{conf}$) of the user 393 (e.g., the model 392 may be personalized for the user 393). Additionally or alternatively, the model 392 may be generated based on $TH_{ROI1}$ and $TH_{ROI2}$ (and optionally $m_{conf}$) of other users, who are not the user 393. Optionally, the model 392 is generated based on $TH_{ROI1}$ and $TH_{ROI2}$ (and optionally $m_{conf}$) taken over more than a week.

In one embodiment, the computer 394 is configured to generate feature values based on $TH_{ROI1}$ and $TH_{ROI2}$ 393 and $m_{conf}$ 463. $TH_{ROI1}$ and $TH_{ROI2}$ 393 are similar in their nature to $TH_{ROI1}$ and $TH_{ROI2}$ 384, which were used to generate the samples used to generate the model 392 (e.g., both sets of feature values include the same types of values, but taken at different times, and possibly involving different users). Similarly, $m_{conf}$ 463 are similar in their nature to $m_{conf}$ 466 (which were also used to generate the model 392). As such, the discussion above regarding the nature of the feature values generated based on $TH_{ROI1}$ and $TH_{ROI2}$ 384 and/or $m_{conf}$ 466 is applicable to the generation of the feature values based on $TH_{ROI1}$ and $TH_{ROI2}$ 393 and/or $m_{conf}$ 463. In particular, the feature values generated based on $TH_{ROI1}$ and $TH_{ROI2}$ 393 and/or $m_{conf}$ 463 may include various types of values. Some examples of feature values that may be generated by the computer 394 include: (i) values comprised in $TH_{ROI1}$ and $TH_{ROI2}$ 393 (optionally these values may undergo various forms of filtering and/or normalization), (ii) values comprised in $m_{conf}$ 463 (optionally these values may undergo various forms of filtering and/or normalization), (iii) baseline values, (iv) values of one or more respiratory parameters calculated based on $TH_{ROI1}$ and $TH_{ROI2}$ 393, (v) values generated based on additional measurements of the user 369 (e.g., measurements of heart rate, heart rate variability, brainwave activity, galvanic skin response, muscle activity, and amount of movement), and (vi) measurements of the environment in which the user 369 was in while $TH_{ROI1}$ and $TH_{ROI2}$ 393 were taken.

The computer 394 is configured, in one embodiment, to utilize the model 392 to calculate, based on the feature values generated based on $TH_{ROI1}$ and $TH_{ROI2}$ 393 and/or $m_{conf}$ 463, the value 397, which is indicative of the extent of the physiological response of the user 369. Optionally, the value 397 is presented to the user 369 via a user interface 398. Optionally, responsive to the value 397 indicating that the extent reaches a threshold, an alert is presented to the user 369 via the user interface 398. Optionally, the value 397 is stored (e.g., for life-logging purposes) and/or forwarded to a software agent operating on behalf of the user 369 (e.g., in order for the software agent to make a decision regarding the user 369).

As discussed in more detail above (in the discussion regarding FIG. 9), the physiological response to which the value 397 relates may involve one or of the following: an occurrence of an allergic reaction, an asthma attack, feeling stress, a respiratory parameter of the user 369, ADHD, OCD, suffering from a migraine, intoxication, dehydration, nerve damage, stroke, Bell's palsy, and expressing an emotional response (e.g., fear, startle, sexual arousal, anxiety, joy, pain and guilt).

The model 392 may include different types of parameters, in different embodiments. Following are some examples of various possibilities for the model 392 and the type of calculations that are accordingly performed by the computer 394 to generate the value 397.

In one embodiment, the model 392 comprises parameters of a decision tree. Optionally, in this embodiment, in order to calculate the value 397 the computer 394 simulates a traversal along a path in the decision tree, determining which branches to take based on the feature values. Optionally, the value 397 is obtained from a leaf node of the tree that is reached at the end of the path. Optionally, the value 397 is calculated based on values of nodes of the tree that are on the traversed path.

In another embodiment, the model 392 comprises parameters of a regression model (e.g., regression coefficients in a linear regression model or a logistic regression model). Optionally, in this embodiment, in order to calculate the value 397 the computer 394 multiplies the feature values (which may be considered a regressor) with the parameters of the regression model.

In yet another embodiment, the model 392 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, in this embodiment, in order to calculate the value 397, the computer 394 provides the feature values as inputs to the neural network, computes the values of the various activation functions and propagates values between layers, and obtains an output from the network, which is the value 397.

The user interface 398 may be utilized, in some embodiments, to present the user 369 the value 397. Additionally or alternatively, in some embodiments, the user interface 398 may be utilized to present to the user 369 an alert responsive to an indication that the extent of the physiological response of the user 369 reaches a threshold. In one embodiment, the user interface 398 may comprise a screen on which the value 397 and/or the alert may be presented (e.g., in the form of text, an image, or video). Optionally, the screen may be part of a display coupled to a frame worn by the user 369 (e.g., a screen of an augmented reality headset, a mixed reality headset, or a virtual reality headset). Additionally or alternatively, the screen may be a display of a device of the user, such as a display of a smartphone or smartwatch. In another embodiment, presenting the value 397 and/or the alert may involve an audio notification that is generated via the user interface 398. For example, the user interface 398 may include a speaker, earphones, or an earbud through which an audio signal is provided to the user 369 in order to make the user 369 aware of the magnitude of the value 397 and/or that the alert has been generated. In still another embodiment, the user interface 398 may be part of a frame worn by the user 398; presenting the user 369 with the value 397 and/or the alert may involve the frame and/or another device physically and/or communicatively coupled to the frame making noises (e.g., beeping sounds), making a visual indication (e.g., lighting of lights on the frame), and/or providing a tactile indication (e.g., by vibrating).

Figure 12:
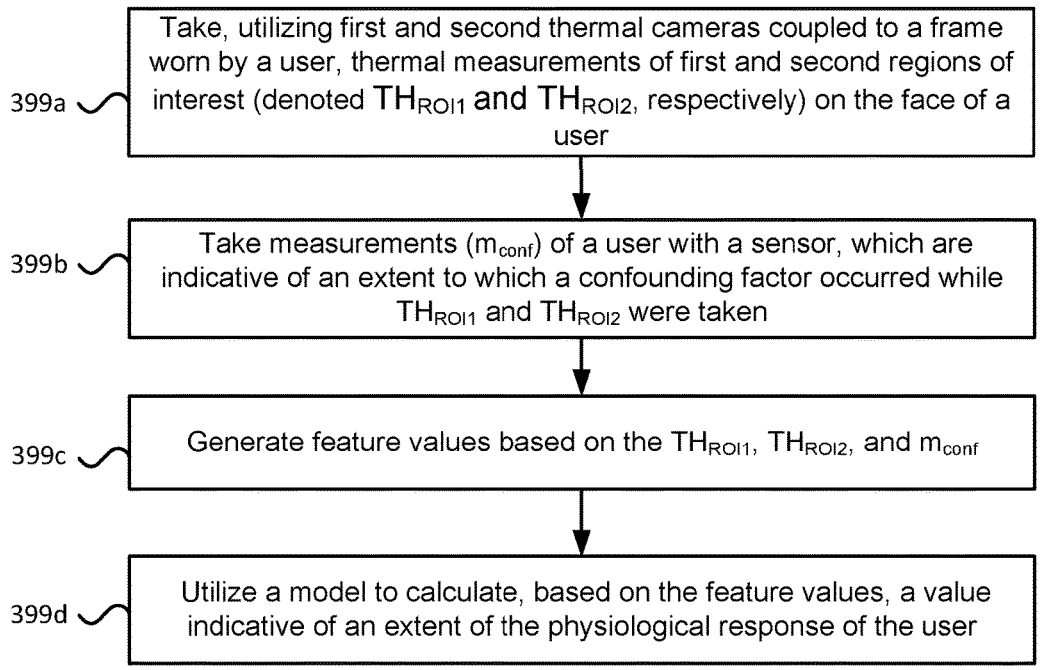
FIG. 12 illustrates an embodiment of a method for detecting a physiological response based on thermal measurements of the face.

FIG. 12 illustrates steps that may be performed in one embodiment of a method for detecting a physiological response based on thermal measurements of the face. The steps described below may be, in some embodiments, part of the steps performed by an embodiment of a system described above, which is illustrated in FIG. 11. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a or FIG. 72b. Optionally, different steps of the method may be performed utilizing different systems comprising a processor and memory.

In one embodiment, a method for detecting a physiological response based on thermal measurements of the face includes at least the following steps:

In Step 399a, taking, utilizing first and second thermal cameras that are physically coupled to a frame worn on a user's head, thermal measurements of first and second regions of interest (denoted $TH_{ROI1}$ and $TH_{ROI2}$, respectively) on the face of a user. Optionally, each thermal camera weighs below 5 g and is located less than 15 cm away from the face.

In Step 399b, utilizing a sensor, additional measurements ($m_{conf}$) of at least one of the following: the user, and the environment in which the user was in while $TH_{ROI1}$ and $TH_{ROI2}$ were taken. Optionally, $m_{conf}$ are indicative of a magnitude to which a confounding factor occurred while $TH_{ROI1}$ and $TH_{ROI2}$ were taken. In one example, the sensor comprise visible-light cameras, and taking $m_{conf}$ comprises taking one or more images of the user's face utilizing the visible-light cameras and analyzing the one or more images to identify at least one of the following: a skin inflammation on the face of the user, and touching the face of the user. In another example, taking $m_{conf}$ comprises one or more of the following: (i) measuring, utilizing an outfacing thermal camera that is physically coupled to a frame worn by the user, a magnitude of thermal radiation directed at the face of the user, and (ii) measuring, utilizing an anemometer that is physically coupled to the frame worn by a user, a magnitude of direct airflow on the face of the user.

In Step 399c, generating feature values based on data obtain in Steps 399a and 399b.

And in Step 399d, utilizing a model to calculate, based on the feature values generated in Step 399c, a value indicative of the extent of the physiological response of the user. The model used in this step is generated based on previous $TH_{ROI1}$ and $TH_{ROI2}$. Optionally, the model used in this step is the model 392.

In one embodiment, the method described above may optionally include a step involving presenting the user with the value indicative of the extent of the physiological response. For example, the value may be presented via a user interface, such as the user interface 398 mentioned above. In another embodiment, the method described above may optionally include a step involving alerting the user responsive to the extent of the physiological response of the user, which is calculated in Step 399d, reaching a threshold.

Generating the feature values in Step 399c may involve, in some embodiments, utilization of additional sources of information, which may be utilized in addition to $TH_{ROI1}$, $TH_{ROI2}$, and/or $m_{conf}$ of the user. In one embodiment, Step 399c optionally involves receiving additional measurements of the user taken during the same period $TH_{ROI1}$ and $TH_{ROI2}$ of the user 369 were taken and generating at least one of the feature values in Step 399c based on the additional measurements. Optionally the additional measurements are indicative of one or more of the following signals: a heart rate of the user, heart rate variability of the user, brainwave activity of the user, galvanic skin response of the user, muscle activity of the user, and amount of movement of the user.

In another embodiment, Step 399c optionally involves receiving measurements of the environment in which the user was in while $TH_{ROI1}$ and $TH_{ROI2}$ of the user were taken and generating at least one of the feature values in Step 399c based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

Many physiological responses can be detected by measuring physiological signals of users using wearable sensors. Being able to perform this detection while the users conduct their daily activities can have many benefits (e.g., health-related applications and affective computing applications). One region of the body that may provide indications that may be used to detect a variety of physiological responses is the human face. In particular, manifestation of many physiological responses involves temperature changes at a various regions on the face. However, when thermal measurements are collected in real world settings, as opposed to controlled laboratory settings, the thermal measurements may be affected by various factors, which may be referred to as confounding factors. While confounding factors can affect the value of the thermal measurements, they are not related to the physiological response that is being detected. Some examples of confounding factors include facial movements (e.g., eating, talking, and sneezing), facial blemishes (e.g., sores or inflammation), environmental conditions (e.g., direct sunlight or wind), and certain physical movements (e.g., touching the face or bending over). Thus, there is a need for a way to account for the effects of confounding factors when detecting a physiological response from thermal measurements of a user's face.

Collecting thermal measurements of various regions of a user's face can have many health-related (and other) applications. However, movements of the user and/or of the user's head can make acquiring this data difficult with many of the known approaches.

Some embodiments described herein utilize various combinations of thermal cameras that are physically coupled to a frame of a head-mounted system (HMS). For example, in some embodiments, taking thermal measurements of a user is done utilizing one or more thermal cameras physically coupled to a frame that is configured to be worn on the user's head. Optionally, each thermal camera weighs below 5 g and is located less than 15 cm away from the user's face.

One aspect of this disclosure involves detection of physiological responses of a user based on thermal measurements of one or more regions of interest (ROIs) on the user's face using an HMS that includes one or more thermal cameras that are physically coupled to a frame worn by the user. The term "physiological response" may cover one or more of various physiological phenomena. Some examples of physiological responses include an allergic reaction, stress, a stroke, dehydration, intoxication, and a migraine. In other examples, a physiological response may refer to a manifestation of an emotional response, such as fear, startle, sexual arousal, anxiety, joy, pain and guilt. In yet other examples, a physiological response may be medical disorder that may be detected based on thermal measurements of ROIs on the face, such as a stroke, nerve damage, sinusitis, a migraine, and Bell's palsy. And in still other examples, a physiological response may refers to vital signs such as the pulse or the breathing rate, in which case the physiological response may be referred to herein as a "physiological signal".

Another aspect of this disclosure involves accounting for the effects of a confounding factor on the thermal measurements in the process of detection of the physiological response. Optionally, accounting for the effects of the confounding factor is done utilizing additional measurements of the user and/or the environment, taken with a sensor that is not a thermal camera. Optionally, an occurrence of the confounding factor is identified utilizing the additional measurements.

In one example, the sensor is a visible-light camera physically coupled to the frame, and configured to take images of a portion of the face of the user that includes at least 25% of an ROI measured by a thermal camera. Optionally, in this example, the confounding factor comprises at least one of the following: inflammation of the skin, skin blemishes, residues on the face, making a disruptive facial movement (DFM), occlusion of the ROI (e.g., by clothing or the user's hair), and touching the face. In another example, the sensor is a microphone and the confounding factor comprises that user performing at least one of the following actions: eating, drinking, talking, coughing, and sneezing. In still another example, the sensor comprises a movement sensor configured to measure a movement of the user and the confounding factor involves the user performing at least one of the following: walking, running, exercising, bending over, and getting up from a sitting or lying position. And in yet another example, the sensor is configured to measure at least one of the following environmental parameters: a temperature of the environment, a humidity level of the environment, a noise level of the environment, air quality in the environment, a wind speed in the environment, an extent of precipitation in the environment, and an infrared radiation level in the environment.

Figure 13:
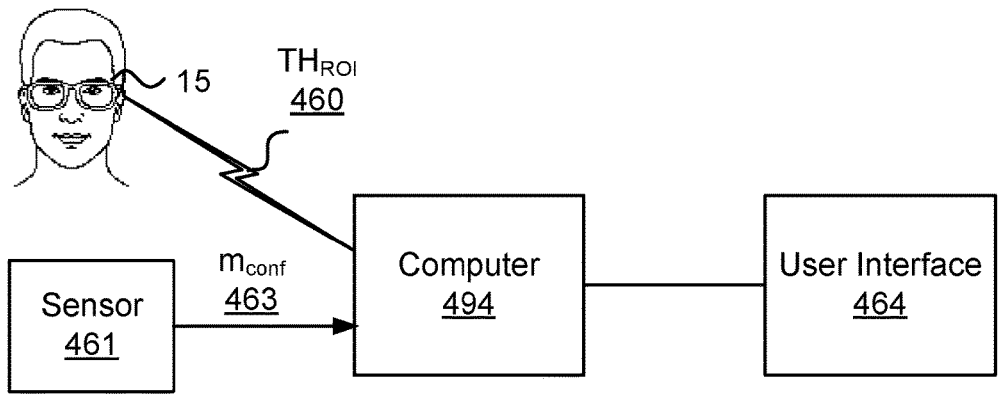
FIG. 13 illustrates an embodiment of a system configured to detect a physiological response while taking into account a confounding factor.

FIG. 13 illustrates an embodiment of a system configured to detect a physiological response while taking into account a confounding factor. The system includes a frame (e.g., the frame 15), a thermal camera, a sensor 461, and a computer 494. Optionally, the system may be implemented utilizing memory. Optionally, the memory is configured to store computer executable. Optionally, the computer 494 may be one of the processor mentioned in this disclosure such as the processor 401 (which is illustrated in FIG. 72a) or the processor 411 (which is illustrated in FIG. 72b).

The frame is configured to be worn on a user's head. The thermal camera is physically coupled to the frame, is located less than 15 cm away from the user's face, and is configured to take thermal measurements of a region of interest on the user's face ($TH_{ROI}$ 460). In the embodiment illustrated in FIG. 13, the frame is the frame 15, but in other embodiments, the frame may be one of the other frames described in this disclosure. Optionally, the thermal camera weighs below 5 g. Examples of the various types of thermal cameras that may be utilized to obtain $TH_{ROI}$ 460 are given at least in Section 1. Some examples of various systems that include a frame and one or more thermal cameras that may be utilized to take $TH_{ROI}$ 460, in some embodiments, include systems illustrated in FIG. 1a, FIG. 1b, FIG. 2a, FIG. 2b, FIG. 3, FIG. 4, FIG. 5, FIG. 6, and FIG. 8a.

It is to be noted that while the description below refers to a thermal camera that takes measurements of a Region of Interest (ROI), the teachings below may be applied to systems in which multiple thermal cameras take thermal measurements of multiple ROIs and utilize the multiple ROIs to detect the physiological response, as described in the descriptions of the embodiments of the various systems illustrated in the figures mentioned above.

In one example, the ROI covers a portion of the user's nose and a portion of the user's upper lip. In another example, the ROI covers a portion of the user's nose, and the system includes second and third thermal cameras that are physically coupled to the frame and configured to take thermal measurements of a portion of the user's forehead ($TH_{ROI2}$) and a portion of the user's periorbital regions ($TH_{ROI3}$).

The system illustrated in FIG. 13 may be utilized to detect one or more of the various physiological responses described in this disclosure. Depending on the physiological response, the thermal camera may take measurements of various ROIs in order for $TH_{ROI}$ 460 to be utilized to detect different physiological responses. The following are some examples of the ROIs and physiological responses that may be detects using the corresponding $TH_{ROI}$ 460. In one example, the ROI includes a portion of the forehead of the user and the physiological response comprises at least one of the following: stress, a migraine, and a stroke. In another example, the ROI includes a portion of the nose of the user and the physiological response is an allergic reaction. In yet another example, the physiological response is indicative of an occurrence of at least one of the following: mental workload, fear, sexual arousal, anxiety, pain, a heart pulse, a headache, dehydration, and intoxication.

The sensor 461 is configured, in one embodiment, to take additional measurements ($m_{conf}$ 463) of at least one of the following: the user, the environment in which the user is in while $TH_{ROI}$ 460 were taken. Optionally, $m_{conf}$ 463 are indicative of a magnitude to which a confounding factor occurred while $TH_{ROI}$ 460 were taken. In one embodiment, the sensor 461 is physically coupled to the frame worn on the user's head. In another embodiment, the sensor 461 is coupled to a device carried by the user, such as a smartphone, a smartwatch, and/or smart clothing (e.g., clothing embedded with sensors that can measure the user and/or the environment). In yet another embodiment, the sensor 461 may be an external sensor that is not carried by the user.

Since real world, day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may be considered an artifact that can reduce the accuracy of the detection of the physiological response. Some examples of confounding factors include disruptive facial movements (DFMs), which may include things such as making a facial expression (e.g., smiling or frowning), talking, eating, drinking, sneezing, and coughing. Other examples of confounding factors may include things that are on the user's face, which are not typically there (or do not characterize the faces of most users), which may include things like skin blemishes, piercings, stubble or other forms of facial hair, hair and/or clothing that occlude the ROI, acne, inflammation, and/or presence of various matter on the face such as makeup, body paint, snot or food leftovers. Still other examples of confounding factors include movements that may affect the heart rate, blood circulation, and/or blood distribution, such as running, jumping, and/or bending over (which can cause the face to warm). And in yet other examples, environmental phenomena such as direct sunlight, air conditioning, and/or wind may be considered confounding factors that may affect the detection of the physiological response.

Various types of sensors may be utilized, in different embodiments, in order to generate $m_{conf}$ 463. The choice of which type of sensor to utilize for the sensor 461 may depend on the type of confounding factor that is to be accounted for in the detection of the physiological response. The following are some examples of different types of sensors and examples of some of the confounding factors that may be accounted for using measurements of the sensors. It is to be noted that while a single sensor is mentioned in the examples, in some embodiments, multiple sensors may be utilized to generate $m_{conf}$ 463. Optionally, these may include multiple sensors of the same type and/or multiple sensors of different types (which may include both the sensors mentioned below and other sensors not mentioned below).

In one embodiment, the sensor 461 is a visible-light camera physically coupled to the frame worn by the user, which is configured to take images of the face of the user. Optionally, the images capture a portion of the face of the user that includes at least 25% of the ROI. In this embodiment, the confounding factor may involve at least one of the following: inflammation of the skin, skin blemishes, residues on the face, occlusion of the ROI by a foreign object, making a disruptive facial movement (DFM), and touching the face. Each of these phenomena may influence the values of $TH_{ROI}$ 460, but are not necessarily related to the physiological response that is detected based on $TH_{ROI}$ 460.

Detecting and/or accounting for one or more of the confounding factors mentioned above may involve applying image analysis techniques. In one embodiment, $m_{conf}$ 463 include images taken by the visible-light camera, which are utilized by the computer 494 (or some other processor) to generate feature values. These feature values may be various low-level features and/or high-level facial features described in this disclosure. For example, the feature values may include feature values derived using Gabor filters, local binary patterns and their derivatives, features derived using algorithms such as SIFT, SURF, and/or ORB, image keypoints, HOG descriptors and features derived using PCA or LDA. Other examples of features may include features derived from sequences of images taken at different times, such as volume local binary patterns (VLBP), cuboids, and/or optical strain based features. Additionally or alternatively, the feature values may include feature values indicative of locations and/or dimensions of facial features and/or facial landmarks, identification of action units (AUs) in sequences of images, and/or blendshape weights. Additional details regarding various image processing approaches that may be used and facial feature values that may be generated is given in Section 6. As explained in more detail further below, these feature values may be utilized in different ways. In one example, the feature values may be part of the input values utilized to detect the physiological response. In another example, the feature values may be utilized to identify an occurrence of a confounding factor, which in turn may be utilized in the detection of the physiological response.

In another embodiment, the sensor 461 is a microphone that can measure sounds made by the user and/or in the user's surroundings. Optionally, $m_{conf}$ 463 in this embodiment may be utilized to identify occurrences of a confounding factor that involve the user performing at least one of the following actions: eating, drinking, talking, coughing, and sneezing. Performing each of the actions above may influence the thermal $TH_{ROI}$ 460 and may not necessarily be related to the physiological response that is being detected.

In yet another embodiment, the sensor 461 comprises a movement sensor configured to measure a movement of the user. For example, the sensor 461 may include one or more accelerometers. Optionally, $m_{conf}$ 463 in this embodiment may be utilized to identify occurrences of a confounding factor that involves the user performing at least one of the following actions: walking, running, exercising, bending over, and getting up from a sitting or lying position. Performing the various actions above may cause the face of the user to warm without being necessarily related to the physiological response that is being detected.

In still another embodiment, the sensor 461 is configured to measure at least one of the following environmental parameters: a temperature of the environment, a humidity level of the environment, air quality in the environment, a wind speed in the environment, an extent of precipitation in the environment, and an infrared radiation level in the environment. Under some conditions, at least some of the various environmental conditions mentioned above may cause the face of the user to warm without being necessarily related to the physiological response that is being detected.

The computer 494 is configured, in one embodiment, to detect a physiological response based on $TH_{ROI}$ 460 and $m_{conf}$ 463. Following is a brief overview of different approaches that may be used to detect a physiological response (these approaches are elaborated on in Section 4).

One approach for detecting a physiological response, which may be utilized in some embodiments, involves comparing $TH_{ROI}$ 460, and/or values derived therefrom (e.g., statistics of $TH_{ROI}$ 460), to a threshold. Optionally, when the threshold is reached, this is indicative of an occurrence of the physiological response. Another approach for detecting a physiological response, which may be utilized in some embodiments, involves comparing $TH_{ROI}$ 460 to one or more reference time series that correspond to periods of time in which the physiological response occurred. Optionally, if the similarity between $TH_{ROI}$ 460 and a reference time series corresponding to a physiological response reaches a certain threshold, this is indicative of the fact that $TH_{ROI}$ 460 correspond to a period of time during which the user experienced the physiological response. Yet another approach for detecting a physiological response based on $TH_{ROI}$ 460 may involve utilization of machine learning methods. Optionally, the computer 494 is configured to detect the physiological response by generating feature values based on $TH_{ROI}$ 460 (and possibly other values such as $m_{conf}$ 463), and/or based on values derived therefrom (e.g., statistics of $TH_{ROI}$ 460 and/or $m_{conf}$ 463). The computer 494 then utilizes a machine learning based model to calculate, based on the feature values, a value that is indicative of whether, and/or to what extent, the user experienced the physiological response. Such a machine learning-based approach is discussed in more detail the description of embodiments illustrated in FIG. 11. In one example, the computer 494 may be utilized similarly to how the computer 394 is utilized, as illustrated in FIG. 11.

In one embodiment, ROI covers a portion of the user's nose, and the system includes second and third thermal cameras that are physically coupled to the frame and configured to take thermal measurements of a portion of the user's forehead ($TH_{ROI2}$) and a portion of the user's periorbital regions ($TH_{ROI3}$). In this embodiment, the computer 494 is further configured to: (i) generate feature values based on $m_{conf}$, $TH_{ROI}$, $TH_{ROI2}$, and $TH_{ROI3}$; and (ii) utilize a model (e.g., the model 392) to calculate, based on the feature values, a value indicative of the extent of the physiological response. Optionally, the model is generated based on previous $m_{conf}$, $TH_{ROI}$, $TH_{ROI2}$, and $TH_{ROI3}$ of the user taken while the user had the physiological response.

It is to be noted that when detecting the physiological response, the computer 494 may utilize, in some embodiments, various data sources in addition to $TH_{ROI}$ 460 and $m_{conf}$ 463. These data sources may include one or more of the following: (i) measurements of the environment in which the thermal measurements were taken (which are not $m_{conf}$ 463), (ii) measurements of sensors for movement or activity (e.g., radar or miniature Lidar), measurements of temperatures of other ROIs on the face or body (which, for example, may serve as a baseline and/or in order to normalize $TH_{ROI}$ 460), (iv) values that describe the user (e.g., from a user profile), (v) indication of consumptions of products by the user (e.g., indications of taking medication, smoking, alcohol, drugs, drinking cold liquids, eating a hot soup, and/or eating spicy food); and (vi) various physiological signals of the user (e.g., heart rate and/or galvanic skin response). Additional details regarding the various additional data sources described above, as well as how they may be utilized may be found in Section 4.

Considering $m_{conf}$ 463 when detecting the physiological response can lead to detections that are more accurate when confounding factors are involved. To this end, the computer 494 is configured, in some embodiments, to utilize $m_{conf}$ 463 in the detection of the physiological response. This may be done in various ways. In some embodiments, $m_{conf}$ 463 are utilized directly in the detection of the physiological response. In one example, the computer 494 is further configured to refrain from detecting the physiological response when $m_{conf}$ 463 reaches a threshold. In another example, $m_{conf}$ 463 are utilized to calculate a value indicative of the magnitude of a certain confounding factor; this value, in turn, may be utilized by the computer 494 in the detection of the physiological response.

Utilizing $m_{conf}$ 463 in the detection of the physiological response can lead to different detection behaviors as the following example illustrates. In one embodiment, the computer 494 receives two sets of measurements and performs calculations for detecting the physiological response with each set. The first set comprises first $TH_{ROI}$ and first $m_{conf}$ that are both taken during a first period by the thermal camera and sensor 461, respectively. The second set comprises second $TH_{ROI}$ and second $m_{conf}$ that are both taken during a second period by the thermal camera and sensor 461, respectively. Optionally, in this example, the first and second periods do not overlap.

The physiological response in this example may be manifested via certain warming of an ROI. For example, warming of certain portions of the forehead may indicate stress. A confounding factor in this example may be touching the forehead with one's hand (in which case the sensor 461 may be a visible-light camera) or bending over (in which case the sensor 461 may include a gyroscope and/or an accelerometer). These confounding factors can be responsible for warming of the ROI (forehead), which is not related to the physiological response (stress).

The two sets of measurements in this example have different characteristics. In particular, the second $TH_{ROI}$ indicate a greater change to temperature at the ROI compared to the change indicated by the first $TH_{ROI}$. Without additional information, this would indicate to the computer 494 that the extent of the physiological response during the second period is greater than the extent of the physiological response in the first period (e.g., the second $TH_{ROI}$ represent a greater extent of warming to the forehead than the first $TH_{ROI}$). However, in addition to the difference between the first and second $TH_{ROI}$, there is a difference in the first and second $m_{conf}$. The second $m_{conf}$ is indicative of a greater magnitude of a confounding factor than the first $m_{conf}$. For example, the second $m_{conf}$ indicates touching of the ROI, while the first $m_{conf}$ does not.

Taking into account both $TH_{ROI}$ and the $m_{conf}$ can lead to different detections than those that would have been typically performed by the computer 494 had no consideration been given to the $m_{conf}$. For example, with the first and second sets mentioned above, based on the on the first $TH_{ROI}$ and the first $m_{conf}$ the computer 494 detects the physiological response (e.g., that the user is stressed). However, based on the second $TH_{ROI}$ and the second $m_{conf}$ the computer 494 does not detect the physiological response (e.g., corresponding to a case where the user is not stressed). This is despite the fact that the second $TH_{ROI}$ represents a greater change to the temperature at the ROI, and without other information, would typically lead to a detection of at least the same extent of the physiological response as in the detection made based on the first $TH_{ROI}$ (if not a greater extent).

Optionally, in the example above, detection of the physiological response by the computer 494 corresponds to a case in which a first value representing the extent of the physiological response during the first period, as calculated by the computer 494 based on the first $TH_{ROI}$ and the first $m_{conf}$ reaches a threshold. While when the computer 494 does not detect the physiological response, this corresponds to a case in which a second value representing the extent of the physiological response during the second period, as calculated by the computer 494 based on the second $TH_{ROI}$ and the second $m_{conf}$ does not reach the threshold.

There are different ways in which the computer 494 may utilize $m_{conf}$ 463. In one embodiment, the computer 494 is configured to refrain from detecting the physiological response when $m_{conf}$ 463 reaches a certain threshold. Optionally, reaching the certain threshold is indicative of at least a certain probability that a confounding factor occurred (e.g., that the user touched the face). Optionally, reaching the certain threshold is indicative of at least a certain magnitude of a confounding factor (e.g., wind of at least a certain speed directed at the user's face). Optionally, in the example above with the two sets of measurements, the first $m_{conf}$ does not reach the certain threshold and the second $m_{conf}$ reaches the certain threshold.

In another embodiment, the computer 494 may perform different calculations based on $TH_{ROI}$ 460 based on the values of $m_{conf}$ 463. In one example, in which the computer 494 detects the physiological response based on $TH_{ROI}$ 460 reaching a threshold, the computer 494 may utilize different threshold values based on the values of $m_{conf}$ 463. For example, responsive to $m_{conf}$ 463 not reaching a certain value, a first threshold is selected, and responsive to $m_{conf}$ 463 reaching the certain value, a second threshold is selected, which is greater than the first threshold. Optionally, in the example above with the two sets of measurements, the first $m_{conf}$ do not reach the certain value, the first $TH_{ROI}$ reach the first threshold, the second $m_{conf}$ reach the certain value, and the second $TH_{ROI}$ do not reach the second threshold (which is higher than the first threshold). In a similar fashion, depending on the approach used to detect the physiological response, the computer 494 may utilize the values of $m_{conf}$ 463 to select different reference time series with which to compare $TH_{ROI}$ 460 or to select different machine learning-based models for its calculations with feature values generated based on $TH_{ROI}$ 460.

Utilizing different thresholds, reference time series, and/or machine learning-based models by the computer 494 can improve the accuracy of detections of the physiological response in some embodiments. Optionally, the different thresholds, reference time series, and/or machine learning-based models may be designed for cases in which certain confounding factors occur (e.g., persistence of certain environmental conditions or when the user conducts certain types of activities). For example, the different thresholds, reference time series, and/or machine learning-based models may be generated based on data collected while the certain confounding factors occurred.

In yet another embodiment, the computer 494 may be configured to utilize a machine learning-based model (e.g., the model 392) to calculate, based on feature values, a value indicative of the extent of the physiological response. In this embodiment, the feature values comprise at least one feature value that is based on $TH_{ROI}$ 460 and at least one feature value that is based on $m_{conf}$ 463. Thus, in this embodiment, the calculation may directly factor in effects of a confounding factor (e.g., environmental conditions).

Another way in which $m_{conf}$ 463 may be utilized, in some embodiments, is to determine based on $m_{conf}$ 463 whether, and/or to what magnitude, a confounding factor occurred, and to utilize a value indicative of the occurrence of the confounding factor in the detection of the physiological response.

In one embodiment, the computer 494 is further configured to generate one or more feature values based on $m_{conf}$ 463 and to utilize a certain model to calculate, based on the one or more feature values, a specific value indicative of the magnitude to which the confounding factor occurred while $TH_{ROI}$ 460 were taken. The computer 494 is further configured in this embodiment to utilize the specific value in the detection of the physiological response. Optionally, the certain model is a machine learning based mode generated utilizing a machine learning-based training algorithm that operates on training data comprising samples. Each sample comprises one or more feature values that are based on $m_{conf}$ taken during a certain period and a label indicative of the magnitude of the confounding factor during the certain period. Optionally, the model may include parameters for one or more of the following models: a regression model, a classifier, a neural network, a support vector machine, and a graphical model.

In another embodiment, calculation of the specific value that is indicative of a magnitude of a confounding factor may be performed remotely from the user. For example, $m_{conf}$ 463 may be transmitted to a cloud-based server, which may utilize a model such as the certain model described above, in order to calculate the specific value based on feature values generated from $m_{conf}$ 463.

The specific value mentioned above, which is indicative of the magnitude of the confounding factor, may be utilized by the computer 494 in various ways when making the detection of the physiological response. In one embodiment, the computer 494 is further configured to refrain from detecting the physiological response when the specific value reaches a certain threshold. In another embodiment, the computer 494 may perform different calculations based on $TH_{ROI}$ 460 depending on the specific value calculated based on $m_{conf}$ 463. In one example, in which the computer 494 detects the physiological response based on $TH_{ROI}$ 460 reaching a threshold, the computer 494 may utilize different threshold values based on specific value. In yet another embodiment, the computer 494 may be configured to utilize a machine learning-based model to calculate, based on feature values, a value indicative of the extent of the physiological response. In this embodiment, the feature values comprise at least one feature value that is based on $TH_{ROI}$ 460 and at least one feature value that is based on the specific value calculated based on $m_{conf}$ 463.

Since confounding factors can hinder the correct detection of the physiological response, in some embodiments, the user may be notified about the occurrence of a confounding factor (e.g., which is detected based on $m_{conf}$ 463). In one example, the notification indicates to the user that the ability to detect the physiological response is diminished due to the confounding factor or that detection of the physiological response is not possible at the time (due to the confounding factor). In another example, the notification may involve a request to eliminate or curtail the confounding factor. Optionally, the notification is generated by a software agent operating on behalf of the user.

In one embodiment, the notification is provided via a user interface 464. Optionally, the user interface 464 is part of an HMS that includes the frame that is worn on the user's head. In one example, the user interface 464 includes a display through which the user is presented a visual cue (e.g., and image or text) identifying the confounding factor and/or indicating an action the user may take to address the confounding factor. In another example, the user interface 464 includes a speaker that generates a sound effect and/or speech identifying the confounding factor and/or indicating an action the user may take to address the confounding factor. In yet another example, the user interface 464 includes a haptic feedback mechanism (e.g., a motor that causes vibrations that may be sensed by the user).

The following are some illustrations of scenarios in which the system illustrated in FIG. 13 may be utilized in the detection of the physiological response.

Figure 16A:
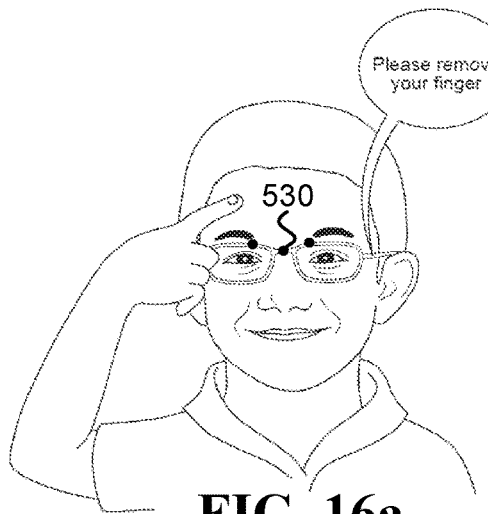
FIG. 16a illustrates a sensor that provides indications indicative of times at which a user touches an ROI that includes a portion of the forehead.
Figure 16B:
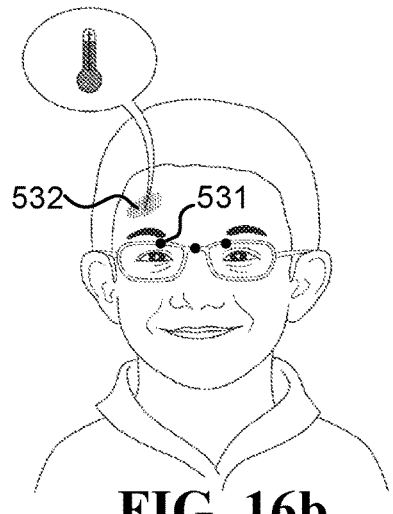
FIG. 16b illustrates a hot spot that is measured by a thermal camera as a result of touching the ROI that includes the portion of the forehead.

FIG. 16a illustrates a scenario in which a confounding factor involves touching the face. A sensor 530 that provide indications indicative of times at which the user touches an ROI on the face. As a result of the touch, the temperature at the ROI is likely to increase without relation to the physiological response that is to be detected. The figure also illustrates how the user receives a notification (e.g., via a speaker) requesting to remove the finger from the face. FIG. 16b illustrates a region 532 on the forehead in which the temperature increased because of the touch, as measured by a thermal camera 531.

Figure 15A:
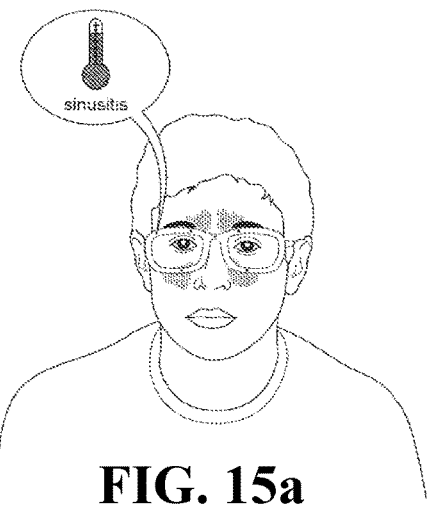
FIG. 15a illustrates heating of an ROI on the face because of sinusitis, for which the user is alerted.
Figure 15B:
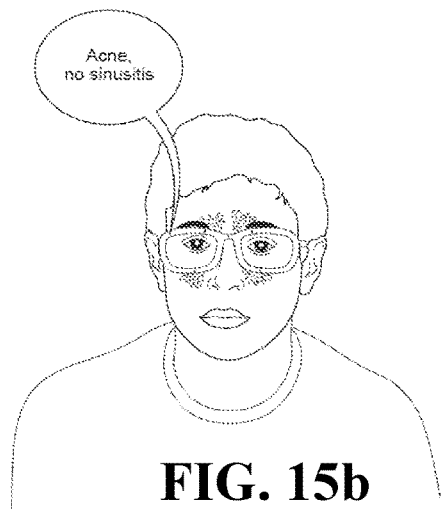
FIG. 15b illustrates heating of the same ROI because of acne, for which the user is not alerted.

Thermal measurements of ROIs near the sinuses may be utilized, in some embodiments, to detect sinusitis. Such a scenario is illustrated in FIG. 15a. However, temperatures at the same ROIs may increase due to other reasons such as skin inflammations due to acne. In such a case, a system configured to detect sinusitis may utilize a sensor such as a visible-light camera to detect the acne, and refrain from detecting sinusitis (as illustrate in FIG. 15b).

Figure 17A:
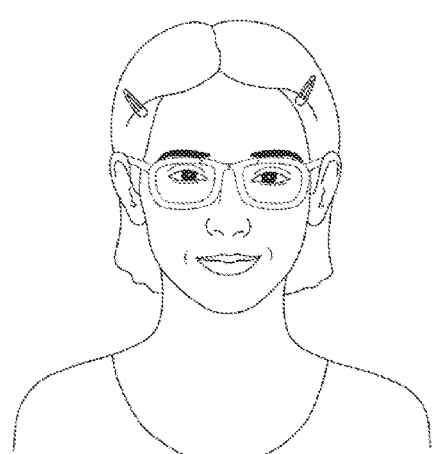
FIG. 17a illustrates a case where the user's hair does not occlude the forehead.
Figure 17B:
FIG. 17b illustrates a case where the user's hair does occlude the forehead.

Falling strands of hair may occlude certain ROIs and interfere with the detection of a physiological response. Such a scenario is illustrated in FIG. 17a and FIG. 17b. FIG. 17a illustrates a first case where the user's hair does not occlude the forehead. FIG. 17b illustrates a second case where the user's hair does occlude the forehead. This situation may be identified (e.g., using a visible-light camera coupled to the frame worn by the user) and accounted for. For example, the user may be requested to move the hair in order to enable correct measurements of the forehead.

Figure 18:
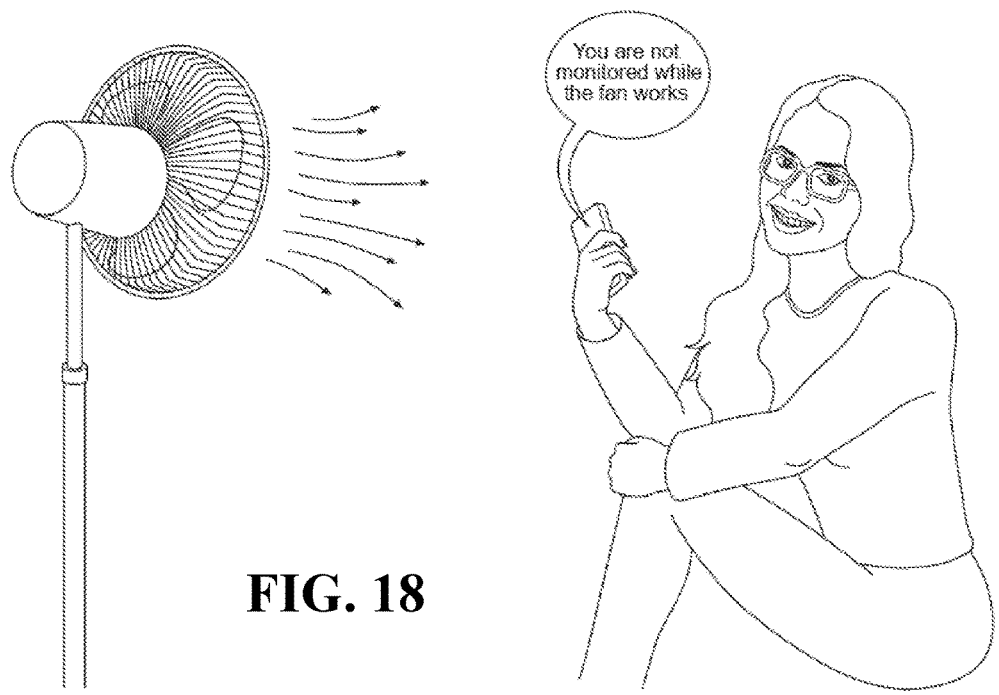
FIG. 18 illustrates indicating to a user that she is not monitored in wind above a threshold.

Direct wind blowing on a user's face can alter facial temperatures in such a way that may make it difficult to accurately detect various physiological responses. In such a case, in some embodiments, the user may be warned (e.g., via the user interface 464) that monitoring in order to detect a physiological response is suspended, as illustrated in FIG. 18.

Figure 19:
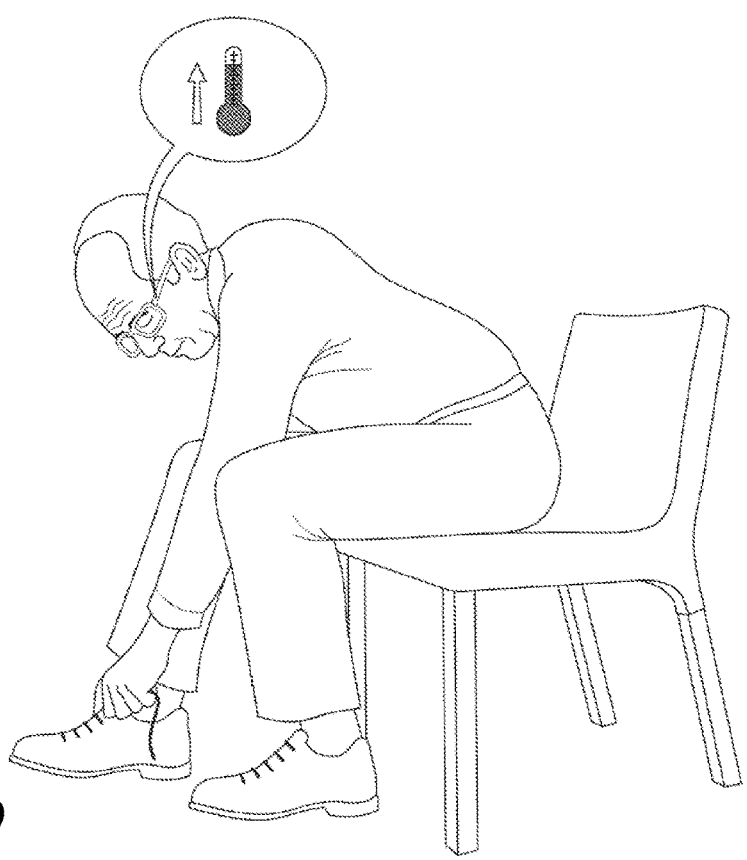
FIG. 19 illustrates an elderly person whose facial temperature increases as a result of bending the head down towards the floor.

Certain physical actions can affect a user's blood flow, and consequently lead to an increase in the user's facial temperatures, which is unrelated to the physiological response being monitored (e.g., stress). For example, when bending the head down towards the floor, like while standing forward and bending, or when lacing up shoes, the temperature of certain regions on the face may rise more than the rise in body core temperature as a result of the bending. This temporary rise in temperature is usually unrelated to the physiological response of interest, and therefore may be accounted for by the system. FIG. 19 illustrates an elderly person whose facial temperature increases as a result of bending the head down towards the floor. In this example, the a system configured to detect a physiological response can receive an indication of the user's action via a sensor (e.g., one or more gyroscopes) and consequently refrain from erroneously detecting certain physiological responses, since it identifies that the increase in temperature may result from bending over.

Figure 14:
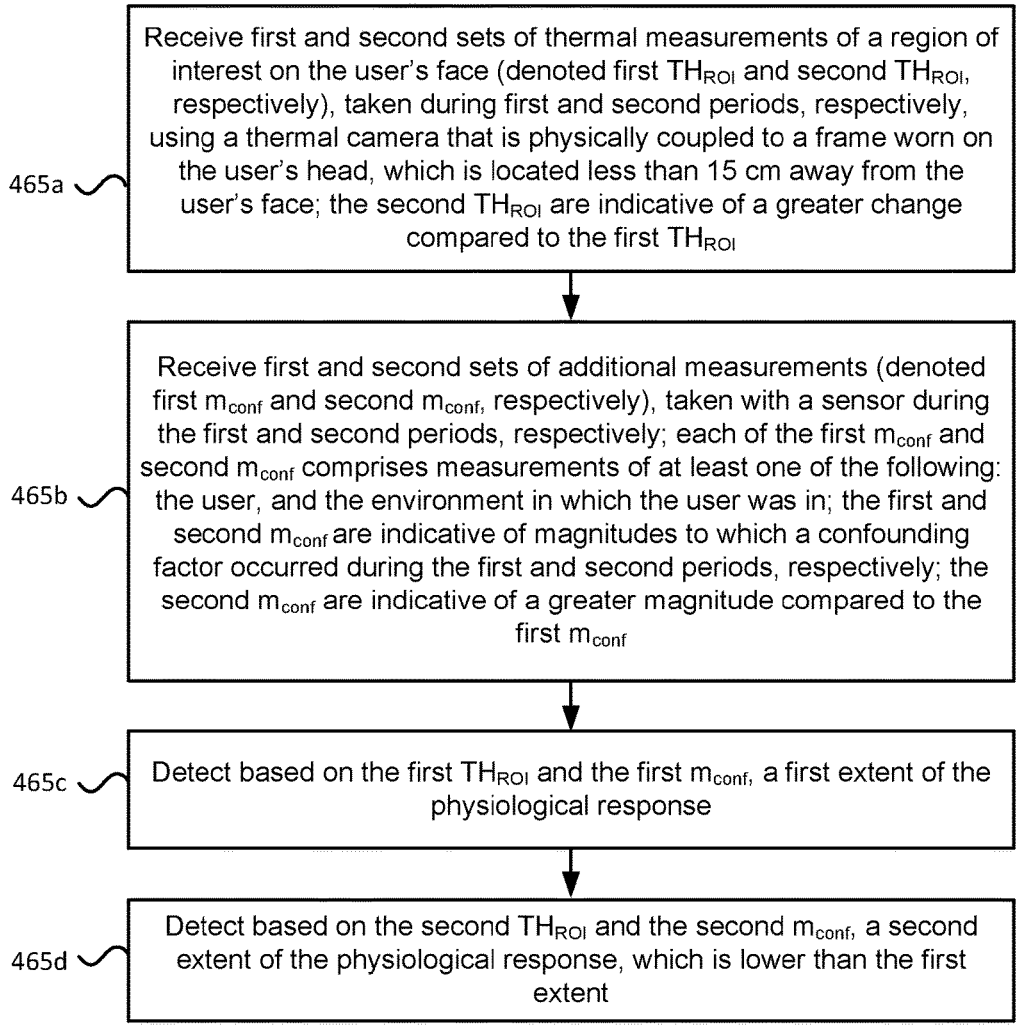
FIG. 14 illustrates an embodiment of a method for detecting a physiological response while taking into account a confounding factor.

Identifying an occurrence of a confounding factor can affect whether certain physiological responses are detected by a system such as a system illustrated in FIG. 13. Thus, depending on whether the confounding factor occurred, different operations may be involved in the detection of a physiological response using thermal measurements. This is illustrated in FIG. 14, which illustrates steps that may be performed in one embodiment of a method for detecting a physiological response (while taking into account a confounding factor). The steps described below may be, in some embodiments, part of the steps performed by an embodiment of a system described above, which is illustrated in FIG. 13. In some embodiments, instructions for implementing an embodiment of the method described below may be stored on a computer-readable medium, which may optionally be a non transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a and/or the computer illustrated in FIG. 72b. Optionally, different steps of the method may be performed utilizing different systems comprising a processor and memory.

In one embodiment, method for detecting a physiological response includes at least the following steps:

In Step 465a, receiving first and second sets of thermal measurements of a region of interest on the user's face (denoted first $TH_{ROI}$ and second $TH_{ROI}$, respectively), taken during first and second periods, respectively, using a thermal camera that is physically coupled to a frame worn on the user's head, which is located less than 15 cm away from the user's face. Optionally, the second $TH_{ROI}$ are indicative of a greater change compared to the first $TH_{ROI}$. Examples of various frames and thermal cameras that may be utilized to collect the first $TH_{ROI}$ are given in the descriptions of the system illustrated in FIG. 1a, FIG. 1b, FIG. 2a, FIG. 2b, FIG. 3, FIG. 4, FIG. 5, FIG. 6, and FIG. 8a.

In Step 465b, receiving first and second sets of additional measurements (denoted first $m_{conf}$ and second $m_{conf}$, respectively), taken with a sensor during the first and second periods, respectively; each of the first $m_{conf}$ and second $m_{conf}$ comprise measurements of at least one of the following: the user, and the environment in which the user was in; whereby the first and second $m_{conf}$ are indicative of magnitudes to which a confounding factor occurred during the first and second periods, respectively. The second $m_{conf}$ are indicative of a greater magnitude compared to the first $m_{conf}$. Optionally, the sensor is the sensor 461. In one example, the second $m_{conf}$ indicate the user was in direct sunlight during the second period, while the first $m_{conf}$ indicate the user was not in direct sunlight during the first period. In another example, the second $m_{conf}$ indicate the user touched the face for at least 10 seconds during the second period, while the first $m_{conf}$ indicate the user did not touch the face for more than a second during the first period. In yet another example, the second $m_{conf}$ indicate the user's forehead was occluded with hair that fell out of place, while the first $m_{conf}$ indicate the user's forehead was not occluded.

In Step 465c, detecting, based on the first $TH_{ROI}$ and the first $m_{conf}$, a first extent of the physiological response. Optionally, the physiological response is detected utilizing the computer 494, as described above. Optionally, detecting the physiological response in this step involves calculating a value that is indicative of the first extent. Optionally, the first extent reaches a threshold that is indicative of that the physiological response occurred during the first period (e.g., the first extent corresponds to the user having a migraine).

And in Step 465d, detecting, based on the second $TH_{ROI}$ and the second $m_{conf}$, a second extent of the physiological response, which is lower than the first extent. Optionally, the second extent does not reach the threshold reached by the first extent. Optionally, the second extent is indicative that the physiological response did not occur during the second period.

It is to be noted that while steps of the method refer to $TH_{ROI}$ being taken with a thermal camera that takes measurements of a ROI, the teachings herein may be applied to systems in which multiple thermal cameras take thermal measurements of multiple ROIs and utilize the multiple ROIs to detect the physiological response, as described in the descriptions of the embodiments of the various systems illustrated in the figures mentioned above. Similarly, while the method above refers to $m_{conf}$ as being taken with a sensor, in some embodiments, multiple sensors (of the same or different types) may be used to take $m_{conf}$.

The physiological response detected in Step 465c may involve one or more of the physiological responses mentioned in this disclosure (e.g., stress, allergic reaction, a migraine, a stroke, expression of an emotion, etc.) In one example, the ROI includes a portion of the forehead of the user and detecting the first extent of the physiological response in Step 465c comprises detecting that the user experienced at least one of the following during the first period: stress, a migraine, and a stroke. In another example, the ROI includes a portion of the nose of the user and detecting the first extent of the physiological response in Step 465c comprises detecting that the user had an allergic reaction during the first period and/or shortly thereafter (e.g., within an hour from the end of the first period).

In one embodiment, the method illustrated in FIG. 14 may optionally include a step of forwarding a first indication indicative of an occurrence of the physiological response during the first period. Optionally, the method may also include a step of refraining from forwarding a second indication indicative of an occurrence of the physiological response in the second period. Optionally, the first indication is forwarded to the user interface 464 in order to notify the user regarding the detected physiological response. Optionally, the method includes a step of forwarding the user a third notification during the second period or shortly thereafter (e.g., within a minute following the second period). The third notification may be indicative of the confounding factor and/or include a request to reduce its effect. Optionally, the third notification is presented to the user via the user interface 464.

As discussed above, various types of sensors may be utilized to take the additional measurements of the user (e.g., the first $m_{conf}$ and the second $m_{conf}$). These different sensors may be utilized to take measurements that are indicative of the magnitude of various confounding factor. The following are some non-limiting examples of confounding factors and types of sensors that may be utilized to take measurements indicative of the confounding factors. Though the examples below list pairings of certain confounding factors and sensors, in some embodiments, multiple sensors may be used to take measurements that are indicative of a certain confounding factor. Similarly, some of the sensors described below may be used to take measurements that are indicative of multiple confounding factors (and not necessarily the ones given in the examples).

In one example, the confounding factor comprises at least one of the following: inflammation of the skin, skin blemishes, residues on the face, making a disruptive facial movement (DFM), occlusion of the ROI by at least one of hair and a foreign object, and touching the face. Optionally, the method includes a step of generating the second $m_{conf}$ by taking images of the face of the user during the second period using a visible-light camera physically coupled to the frame.

In another example, the confounding factor invokes the user performing at least one of the following actions: eating, drinking, talking, coughing, and sneezing. Optionally, the method includes a step of generating the second $m_{conf}$ by collecting auditory signals during the second period utilizing a microphone.

In yet another example, the confounding factor involves the user performing at least one of the following: walking, running, exercising, bending over, and getting up from a sitting or lying position. Optionally, the method includes a step of generating the second $m_{conf}$ by measuring the user with a movement sensor during the second period.

In still another example, the method may optionally include a step of generating the second $m_{conf}$ by measuring at least one of the following environmental parameters during the second period: a temperature of the environment, a humidity level of the environment, air quality in the environment, a wind speed in the environment, an extent of precipitation in the environment, and an infrared radiation level in the environment. These measurements may be indicative of one or more environmental conditions that may be considered confounding factors.

Utilizing the first $m_{conf}$ and/or the second $m_{conf}$ for detecting the physiological response in Step 465c and/or Step 465d may involve performing various operations. In one embodiment, Step 465c may involve selecting a first threshold based on the first $m_{conf}$ and comparing the first $TH_{ROI}$ to the first threshold. Optionally, because the first $TH_{ROI}$ reached the first threshold, the first extent of the physiological response is detected. Similarly, Step 465d may involve selecting a second threshold based on the second $m_{conf}$ and comparing the second $TH_{ROI}$ to the second threshold (which is higher than the first). Optionally, because the second $TH_{ROI}$ did not reach the second threshold, the second extent of the physiological response is detected.

In another embodiment, the first and/or second $m_{conf}$ may be utilized to generate a feature value that is used, along with feature values generated based on the corresponding $TH_{ROI}$, to calculate a value indicative of the extent of the physiological response. For example, Step 465d may involve generating feature values and utilizing a machine learning-based model to calculate, based on the feature values, a value indicative of the second extent of the physiological response during the second period. Optionally, the feature values comprise at least one feature value that is based on the second $TH_{ROI}$ and at least one feature value that is based on the second $m_{conf}$.

In some embodiments, the first $m_{conf}$ and/or the second $m_{conf}$ may be utilized to identify whether a confounding factor occurred (and/or to what magnitude) during the first and/or second periods. For example, the method may optionally include the following steps: generating one or more feature values based on the second $m_{conf}$; utilizing a certain model to calculate, based on the one or more feature values, a specific value indicative of the magnitude to which the confounding factor occurred during the second period; and utilizing the specific value to detect the second extent of the physiological response. Optionally, the certain model is generated based on samples, where each sample comprises one or more feature values that are based on $m_{conf}$ taken by a sensor during a certain period, and a label indicative of the magnitude of the confounding factor during the certain period.

One application for which thermal measurements of one or more ROIs on the face may be useful is to detect an allergic reaction. In one embodiment, a system configured to determine an extent of an allergic reaction of a user includes at least a frame, a thermal camera, and a computer. Optionally, the allergic reaction involves one or more of the following reactions: allergic rhinitis, atopic dermatitis, and anaphylaxis. Herein an allergen may be any substance that causes the user to experience an allergic reaction due to the exposure of the user to the allergen (e.g., by consuming, inhaling, and/or coming into physical contact with the allergen). For example, herein, an allergic reaction may be a reaction to one or more of the following allergens: a drug, peanuts, eggs, wheat, dairy products, seafood, pollen, dust, and perfume.

Figure 20:
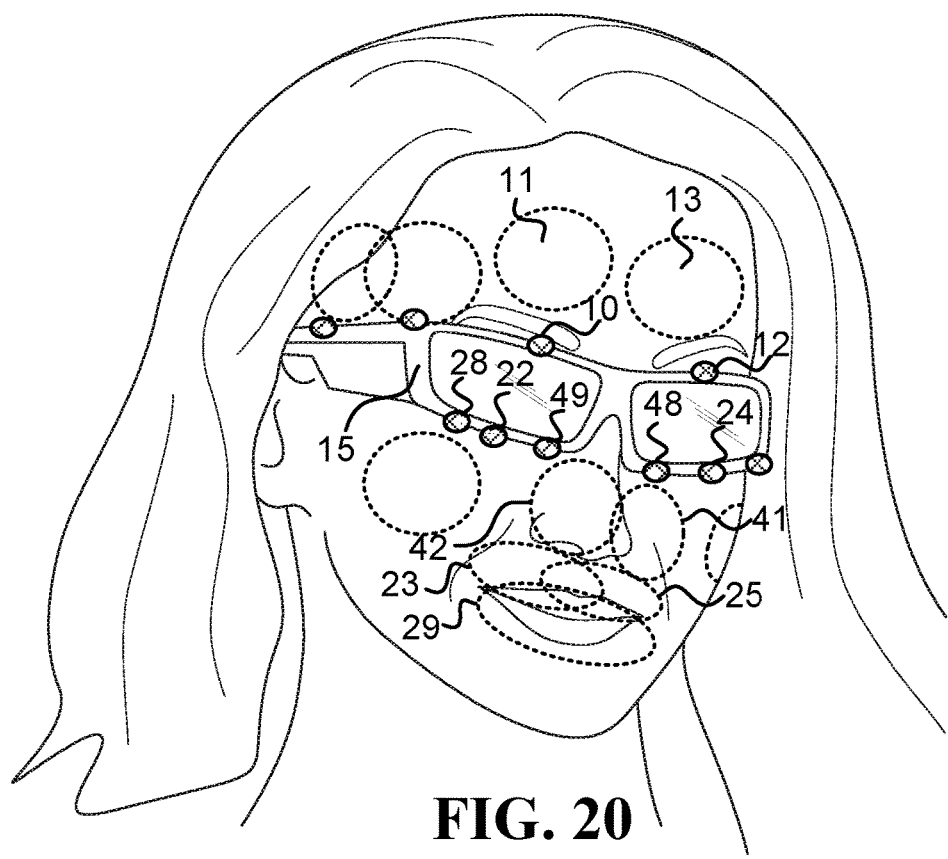
FIG. 20 illustrates a head-mounted system with cameras thereon.

The frame is configured to be worn on the user's head. Optionally, the frame may be any of the frames of an HMS described in this disclosure, such as a frame of eyeglasses or a frame of some other HMS, such as a hat, a helmet, and/or part of a system comprising a head-mounted display (e.g., an augmented reality system, a virtual reality system, or a mixed reality system). In one example, the frame may be the frame 84, which is illustrated in FIG. 5. In another example, the frame may be the frame 15, which is illustrated in FIG. 20. Various properties of the frame (and other system components) are described in more detail in Section 2.

The thermal camera is physically coupled to the frame and located less than 15 cm away from the user's face. Optionally, the thermal camera weighs less than 5 g. The thermal camera is configured to take thermal measurements of a portion of the user's nose (denoted $TH_N$), which are utilized by the computer to detect the allergic reaction.

In one embodiment, the thermal camera is based on at least one of the following uncooled sensors: a thermopile sensor, a pyroelectric sensor, and a microbolometer sensor. In another embodiment, the thermal cameras is a focal-plane array (FPA) thermal camera. In one example, the thermal camera is the thermal camera 80 or the thermal camera 81, which are illustrated in FIG. 5. In another example, the thermal camera is the thermal camera 22 or the thermal camera 24, which hare illustrated in FIG. 20.

Due to the physical coupling to the frame, the thermal camera remains pointed at the nose when the user's head makes angular movements that may involve an angular velocity that is above 0.1 rad/sec. Optionally, the thermal camera is located less than 5 cm away from the user's face and weighs below 1 g. Optionally, the thermal camera does not occlude its ROI.

A more detailed discussion regarding the various types of thermal cameras that may be used in embodiments described in this disclosure, including properties of thermal measurements (e.g., $TH_N$ mentioned above), is provided in Section 1.

It is to be noted that while some of the embodiments, such as the embodiment above, describe a single thermal camera, in some cases multiple thermal cameras may be utilized to obtain measurements of various ROIs such as different regions/sides of the nose and/or different regions/sides of the mouth and/or cheeks. One example of an embodiment of a system that is configured to take thermal measurements useful for detecting an allergic reaction (involving ROIs on the right and left sides of a user's nose) is illustrated in FIG. 5. Some examples of possible locations for one or more thermal cameras coupled to the frame and their corresponding ROIs are given in FIG. 20. For example, temperature measurements at ROIs 41, 42, 23, 25, and/or 29 may be utilized, in some embodiments, for the detection of an allergic reaction.

In one embodiment, the system configured to detect an allergic reaction of a user further includes second and third thermal cameras, each of which: weighs below 5 g, is physically coupled to the frame, and is located less than 15 cm away from the user's face. The second and third thermal cameras are located to the right and left of the vertical symmetry axis, respectively, and are configured to take thermal measurements of portions of the right and left cheeks (denoted $TH_{ch}$), respectively. Optionally, the computer is configured to detect the allergic reaction based on $TH_{CH}$ (in addition to thermal measurements of the nose, as discussed below).

An allergic reaction may cause red eyes, itchy eyes, tearing eyes, swollen eyelids, and/or burning eyes/eyelids. In some cases, a thermal camera that captures a portion of the periorbital region ($TH_{peri}$) around at least one of the eyes can detect an eye allergy symptom before the user is aware of the allergic reaction. In other cases, $TH_{peri}$ are used to assess the extent of the allergic reaction. In order to obtain $TH_{peri}$, in one embodiment, the system configured to detect an allergic reaction of a user further includes second and third thermal cameras, each of which: weighs below 5 g, is physically coupled to the frame, and is located less than 15 cm away from the user's face. The second and third thermal cameras are located to the right and left of the vertical symmetry axis, respectively, and are configured to take thermal measurements of portions of the right and left periorbital regions ($TH_{peri}$) of the eyes, respectively. Optionally, the computer is further configured to detect the allergic reaction also based on $TH_{peri}$.

Allergic reaction may also cause hives (also known as urticarial) around the mouth and/or other parts of the face. In some cases, a thermal camera that captures the area around the mouth ($TH_{lips}$) can detect itching and/or hives around the mouth before the user is aware of the allergic reaction. In other cases, $TH_{lips}$ are used to assess the extent of the allergic reaction. In one embodiment, the computer is further configured to receive thermal measurements of a portion around the lips ($TH_{lips}$), and to detect the allergic reaction also based on $TH_{lips}$. Optionally, $TH_{lips}$ are taken by the thermal camera or by a second thermal cameras that is physically coupled to the frame and is located less than 15 cm away from the user's mouth. For example, the second thermal camera may be the thermal camera 22, which takes measurements of ROI 23 and/or ROI 29, which are illustrated in FIG. 20.

The computer is configured, in one embodiment, to detect the allergic reaction based on $TH_N$ and possibly other thermal measurements such as $TH_{CH}$, $TH_{peri}$, and/or $TH_{lips}$ mentioned above. The computer includes one or more processors and memory. Optionally, the computer may be at least one of the following: a computer belonging to a device carried by the user, a computer of a smartphone, a personal computer, a remote server (e.g., a cloud-based server), and an analog circuit. In one example, the computer is computer system 400 illustrated in FIG. 72a. In another example, the computer may be computer system 410 illustrated in FIG. 72b. Additional details regarding various types of computers and hardware components that may be utilized to detect the physiological response are given in Sections 2 and 7.

In one embodiment, detecting the allergic reaction may involve one or more of the following: determining whether the user is experiencing an allergic reaction, and determining the extent of the allergic reaction. Optionally, the allergic reaction involves one or more of the following reactions: allergic rhinitis, atopic dermatitis, and anaphylaxis. Optionally, the extent of the allergic reaction may be indicative of one or more of the following: the severity of the allergic reaction, the duration of the allergic reaction (e.g., total time of the allergic reaction and/or time remaining until the allergic reaction subsides).

In some cases, changes to temperatures at regions of the face (e.g., in the nasal area) occur quickly at the initial stages of an allergic reaction. Thus, the computer may detect the allergic reaction at its initial stages even before the user is aware that allergic reaction is occurring. Thus, in some embodiments, detecting the allergic reaction involves detecting an onset of the allergic reaction, which may involve determining the time until the reaction reaches its peak severity (e.g., a rash, coughing, respiratory distress, sneezing) and/or determining the expected degree of severity (extent) of the allergic reaction.

Herein, an "onset of an allergic reaction" refers to an allergic reaction that is happening, i.e., at least some of activity of the immune system related to the allergic reaction is taking place and/or various symptoms of the allergic reaction are beginning to manifest. The activity and/or symptoms may continue to occur even beyond a point in time identified as corresponding to an onset of the allergic reaction. Additionally, in some cases, at the time an onset of an allergic reaction is identified, a user having the allergic reaction may not be aware of the allergic reaction, e.g., because the symptoms are not strong enough at the time. Thus, being notified about an onset of an allergic reaction before its full manifestation may have an advantage, in some embodiments, of allowing the user to take early action to alleviate and/or decrease the symptoms (e.g., take antihistamines) or seek medical attention, which may help to reduce to overall effects of the allergic reaction on the user.

In some allergic reactions, the nasal temperature can rise rapidly within minutes, before other more noticeable symptoms may manifest themselves (e.g., sneezing, itching, and/or respiratory problems). Thus, rising nasal temperatures may serve as an indication of an onset of the allergic reaction. The reference Clark, A. T., Mangat, J. S., Tay, S. S., King, Y., Monk, C. J., White, P. A., & Ewan, P. W. (2007), "Facial thermography is a sensitive and specific method for assessing food challenge outcome", Allergy, 62(7), 744-749, shows the fast increase in mean nasal temperature is indicative of an allergic reaction. For example, a fast increase due to an allergic reaction may correspond to an increase of more than 0.8° C. within a period of less than 30 minutes, less than 20 minutes, or even a shorter period than that. Additionally, the reference Clark, A., Mangat, J., King, Y., Islam, S., Anagnostou, K., Foley, L., & Ewan, P. (2012), "Thermographic imaging during nasal peanut challenge may be useful in the diagnosis of peanut allergy", Allergy, 67(4), 574-576, illustrates the fast response to nasal challenge, which can be used as a rapid, safe and objective clinical allergy test together with the head-mounted thermal camera. Thus, in some embodiments, the computer may detect an early rise in nasal temperature, and alert the user of a possible allergic reaction before the user is aware of the symptoms of the allergy reaction.

FIG. 27a and FIG. 27b illustrate a scenario in which a user is alerted about an expected allergic reaction. In FIG. 27a, the user's nasal temperature is normal (e.g., as measured using the system illustrated in FIG. 5). At that time, a cat, to which the user is allergic, walks past the user. FIG. 27b illustrates the situation some minutes later. The user's nasal temperature has increased, and based on thermal measurements of the nasal region, a computer, which for example may be embedded in a device carried by the user or on a cloud-based server, issues an alert to the user about the expected allergic reaction. Note that at the time the alert is issued, the user may not be aware of any symptoms of the allergic reaction. Receiving an early warning in this case may enable the user to take measures to alleviate the effects of the allergic reaction, such as taking an antihistamine medicine.

The following are some examples of ways the computer may utilize $TH_N$ in order to detect a physiological response such as an allergic reaction. Additional details regarding detection of a physiological response (including an allergic reaction) based on thermal measurements, such as $TH_N$ and optionally $TH_{CH}$, $TH_{peri}$, and/or $TH_{lips}$ may be found in this disclosure at least in Section 4.

In one embodiment, the computer is configured to compare one or more values derived from $TH_N$ to a certain threshold, and determine whether the threshold is reached (which is indicative of an occurrence of the allergic reaction). Optionally, the threshold is determined based on previous $TH_N$ of the user (e.g., the previous $TH_N$ may have been taken while the user had an allergic reaction at some previous time). Additionally or alternatively, the threshold may be determined based on $TH_N$ of other users. Optionally, different thresholds may be utilized to detect different types of allergic reactions, to detect allergic reactions to different allergens, and/or to detect different extents of an allergic reaction.

In another embodiment, the computer is configured to determine a similarity between a reference time series corresponding to the allergic reaction and $TH_N$ (or a time series derived from $TH_N$). Optionally, when a sufficiently high similarity is detected, the computer may interpret that as an indication of an occurrence of the allergic reaction. Optionally, the reference time series is generated based on previous $TH_N$ of the user (e.g., the previous $TH_N$ may have been taken while the user had an allergic reaction at some previous time). Additionally or alternatively, the reference time series may be determined based on $TH_N$ of other users. Optionally, different reference time series may be created to detect different types of allergic reactions, to detect allergic reactions to different allergens, and/or to detect different extents of an allergic reaction.

In yet another embodiment, the computer may generate feature values based on thermal measurements comprising $TH_N$ and optionally $TH_{CH}$, $TH_{peri}$, and/or $TH_{lips}$, and utilize a machine learning based model to calculate, based on the feature values, a value indicative of whether the allergic reaction occurred (and/or whether an onset of the allergic reaction is expected). Optionally, the model is generated based on previous thermal measurements of the user. For example, the previous thermal measurements may have been taken while the user had an allergic reaction at some previous time; in this case, the model may be considered a personalized model for the user. Additionally or alternatively, the model may be determined based on thermal measurements of other users (e.g., a general model). Optionally, different models may be created to detect different types of allergic reactions, to detect allergic reactions to different allergens, and/or to detect different extents of an allergic reaction.

In one example, the computer is further configured to: (i) generate feature values based on thermal measurements comprising $TH_N$ and optionally $TH_{CH}$, $TH_{peri}$, and/or $TH_{lips}$; and (ii) utilize a model to calculate, based on the feature values, a value indicative of the extent of the allergic reaction. Optionally, the model is generated based on previous thermal measurements of the user comprising $TH_N$ and optionally $TH_{CH}$, $TH_{peri}$ and/or $TH_{lips}$, which were taken while the user had an allergic reaction.

In some embodiments, detecting the allergic reaction may involve utilizing baseline $TH_N$, most of which were taken when the user did not have an allergic reaction. Thus, detecting the allergic reaction may rely on observing a change relative to typical temperatures at the ROIs. In one example, the computer is further configured to detect the allergic reaction based a difference between $TH_N$ and a baseline value determined based on a set of previous $TH_N$ of the user taken with the thermal camera. In this example, most of $TH_N$ belonging to the set were taken while the user had an allergic reaction, or within thirty minutes before or after the user had an allergic reaction.

Receiving early notice regarding an onset of an allergic reaction and/or regarding an occurrence of a mild allergic reaction, may be useful in some embodiments, since it may enable a user to take action in order to reduce the severity of the allergic reaction. For example, the user may attempt to reduce exposure to an allergen (e.g., leave an area that has a high concentration of pollen), take certain medication (e.g., antihistamines) to reduce the effects of the allergic reaction, and/or promptly seek medical attention (in anticipation of a more severe allergic reaction that is to come). However, providing such early indications may involve relaxing the conditions under which an allergic reaction is considered detected (e.g., lowering thresholds for $TH_N$). This can come at a cost of having more false positives in the detection of allergic reactions. Thus, in order to avoid excessive false positives, in some embodiments, a system may need to be judicious about when it employs more relaxed conditions for detecting an allergic reaction.

One way in which false positive allergic reaction detections may be reduced is to utilize in the detection an allergic reaction knowledge of conditions and/or times in which it is more likely that the user may experience an allergic reaction. For example, if it is known with high probability that the user was exposed to an allergen to which the user is known, or suspected, to be allergic, then more relaxed conditions for detecting the allergic reaction may be employed. Optionally, if there is no reason to believe that the user was exposed to an allergen, then the more strict conditions may be employed for detecting the allergic reaction.

In some embodiments, the computer is configured to receive an indication that is indicative of whether the user was exposed to an allergen and to utilize the indication in the process of detecting the allergic reactions. This indication may be utilized in various ways, which may depend on how the computer detects allergic reactions, as the following embodiments demonstrate.

In one embodiment, the computer compares $TH_N$ (or certain values computed based on $TH_N$) to a threshold, such that if $TH_N$ reach the threshold, this is indicative of a likely occurrence of the allergic reaction. In this embodiment, the threshold may be selected based on the indication that indicates exposure, or possible exposure, to the allergen. For example, responsive to receiving a first indication indicating that the user was exposed to the allergen, the computer selects a first threshold, and responsive to receiving a second indication indicating that the user was not exposed to the allergen, the computer selects a second threshold that is higher than the first threshold. Thus, the second threshold requires greater changes in $TH_N$ in order to detect the allergic reaction.

In another embodiment, the computer calculates a value indicative of a similarity between $TH_N$ and a reference time series comprising data indicative of temperatures at different points in time during an allergic reaction (e.g., time series of the user having the allergic reaction). When the calculated value reaches a certain threshold, this is indicative of an occurrence of the allergic reaction. In this embodiment, the certain threshold may be selected based on the indication that indicates exposure, or possible exposure, to the allergen. For example, responsive to receiving a first indication indicating that the user was exposed to the allergen, the computer selects a first certain threshold, and responsive to receiving a second indication indicating that the user was not exposed to the allergen, the computer selects a second certain threshold that corresponds to a higher extent of similarity than the first certain threshold. Thus, the second certain threshold requires greater similarity to the reference time series in order to detect the allergic reaction.

In yet another embodiment, the computer is further configured to utilize $TH_N$ to generate feature values and to utilize a model to calculate, based on the feature values, a value indicative of the extent of the allergic reaction. In this embodiment, the model is a machine learning based model that is generated based on previous thermal measurements of portions of the noses of one or more users (which may include the user and/or other users). In this embodiment, at least some of the feature values are generated based on the indication, and may describe various properties of the exposure to an allergen, such as the type of allergen, the duration of exposure, the extent of exposure (e.g., dosage), and/or the time that has elapsed since the exposure. Thus, the above factors may be taken into account by the model, which may increase the chances of detecting an allergic reaction when the features indicate sufficient exposure to certain allergens.

The indication that is indicative of exposure to the allergen may be received from various sources. In one embodiment, the indication may be self-reported by the user. For example, the user may provide information about the exposure through interaction with a device such as a smartphone or speaking with a software agent via a microphone. In another embodiment, various camera-based systems may be utilized to take images comprising the allergen or an object associated with the allergen, analyze the images, and generate the indication about the exposure based on the analysis. Such systems that monitor the environment the user is in and/or substances the user consumes are discussed in more detail below. In yet another embodiment, an external source may provide indication based on determining the location of the user. For example, the user's location may be determined based on GPS, cellphone transmissions, and/or Wi-Fi transmissions. Additionally, an external database that includes real-time data about the presence of various allergens (e.g., dust or pollen) may be queried in order to determine whether the user is likely exposed to a potential allergen.

Some of the embodiments described herein may be utilized to identify potential causes for the change (e.g., rise) of the temperature at an ROI (e.g., a portion of the nose). These causes may include inhaled allergens, food, drugs, and/or various chemicals which the user might have been exposed to (e.g., via ingestion, inhalation, and/or physical contact). In one embodiment, the computer may be further configured to identify a potential allergen by estimating the time of exposure to the allergen from data indicative of a deviation over time of mean nasal temperature from a baseline, and analyzing the substances consumed and/or exposed to by the user around that time. For example, by identifying when the nasal temperature started to rise, and taking into account the time required for the allergic reaction to be manifested via a temperature rise, a window of time can be determined during which the user was likely exposed to the allergen Examining which substances the user was exposed to during the window can yield a list of one or more potential allergens. Optionally, the system is further configured to alert the user about the one or more potential allergens. Optionally, the system is further configured to store in a database plurality of potential allergens identified based on data indicative of a deviation over time of mean nasal temperature from baseline (such as allergens identified based on deviation over time of mean nasal temperature from baseline). In some embodiments, the system includes a camera, mounted to the frame, to capture images of substances consumed by the user. Optionally, the system is further configured to show the user an image of a substance associated with the potential allergen.

There are various known systems that may be utilized to monitor what substances a user was exposed to and/or what substances a user consumed. For example, systems that may be utilized to determine what the user ate or drank are described in the patent application US 20110318717 (Personalized Food Identification and Nutrition Guidance System), in the U.S. Pat. No. 9,053,483 (Personal audio/visual system providing allergy awareness), and in the U.S. Pat. No. 9,189,021 (Wearable food nutrition feedback system). Additionally, obtaining indications of possible allergens to which the user was exposed is described in the U.S. Pat. No. 9,000,933 (Automated allergy alerts). In one embodiment, upon identifying an increase in nasal temperature, the system can identify the potential cause to be one of the substances to which the user was exposed during the preceding 20 minutes, or even during the preceding 10 minutes, or even during the preceding 5 minutes.

In some embodiments, determination of the extent of the allergic reaction may be utilized in the context of allergen challenge tests. For example, the system may be configured to receive an indication of when at least one of a non-invasive intranasal histamine and allergen challenge is performed, and to estimate effects of the histamine and/or allergen challenge in the tissues, based on an increase to nasal temperature. In one example, this involves utilizing the change in $TH_N$, induced by the histamine provocation, as a marker of the intensity of the actions of histamine in the nose. In another example, this may involve utilizing the change in $TH_N$, induced by the allergen challenge, as a marker of the intensity of the actions of the allergen in the nose. Additional examples and discussion regarding allergen challenge tests are provided in the reference Larbig, M., Stamm, H., Hohlfeld, J., & Krug, N. (2003, June), "Levocetirizine but not desloratadine inhibits histamine-induced changes of nasal temperature measured by facial thermography: a pilot study", In 22nd Congress of the European Academy of Allergy and Clinical Immunology.

Some aspects of this disclosure involve detecting a physiological response, such as an allergic reaction, based on thermal measurements of Regions Of Interest (ROIs) on a user's face. The thermal measurements are taken using one or more thermal cameras physically coupled to a frame worn on the user's head. Detecting the allergic reaction may involve utilizing the thermal measurements along with a model. In one example, the model may include a threshold and/or time series to which the measurements may be compared in order to detect the allergic reaction. In another example, the model may be a machine learning-based model, which is utilized to calculate, based on feature values generated based on the measurements, a value that is indicative of the extent of the allergic reaction.

In some embodiments, a model used to detect a physiological response such as an allergic reaction is generated based on thermal measurements of multiple users. However, in some cases, due to unique characteristics of each person's physiology, different people may exhibit different patterns of thermal measurements when measured with systems described in this disclosure. Additionally, a physiological response, such as an allergic reaction, may manifest itself differently with different individuals. For example, with different people, an allergic reaction can lead to different extents of warming in the nasal region and/or cheeks, different rates of warming of the nasal region and/or cheeks, and/or warming of slightly different regions around the nose and/or cheeks. Thus, in order to improve accuracy of models used to detect a physiological response of a certain user, in some embodiments, it may be beneficial to utilize a model generated based on thermal measurements of the certain user, which can reflect the unique characteristics of the user.

Figure 21:
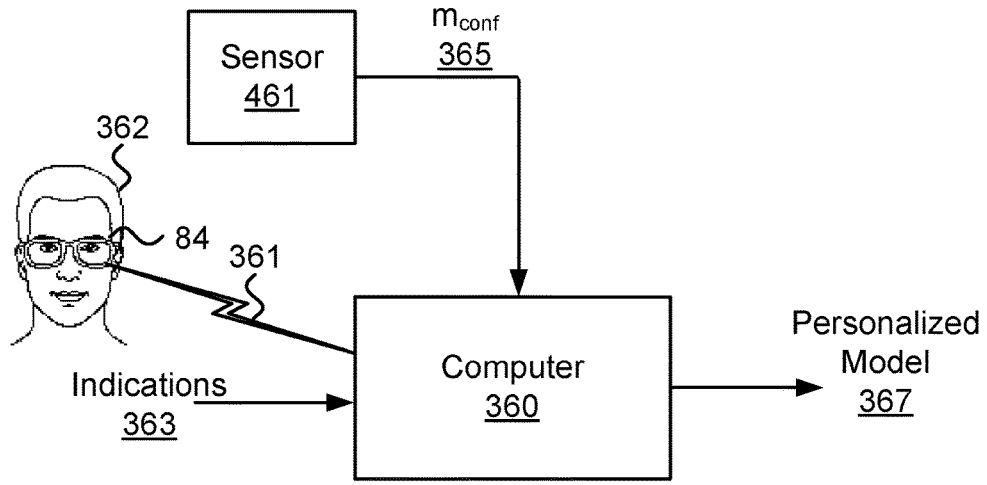
FIG. 21 illustrates an embodiment of a system configured to generate a personalized model for detecting an allergic reaction based on thermal measurements.

FIG. 21 illustrates an embodiment of a system configured to generate a personalized model for detecting an allergic reaction based on thermal measurements of the face. The system includes a frame (e.g., the frame 84), a thermal camera, and a computer 360.

The frame and thermal camera may belong to an HMS from among the HMSs described in this disclosure, such as HMSs illustrated in FIG. 5, FIG. 20, FIG. 2a, or FIG. 2b. The thermal camera is coupled to the frame, which is worn on the head of a user 362, and is configured to take thermal measurements portion of a nose ($TH_N$ 361) of the user 362. In one example, the thermal camera may be the thermal camera 80 or the thermal camera 81, which are physically coupled to the frame 84.

In different embodiments, the thermal camera may have different characteristics and/or may be located at various distances relative to the face. In one embodiment, the thermal camera weighs below 5 g and is located less than 15 cm away from the face. In another embodiment, the thermal camera weighs below 1 g, and is located less than 5 cm away from the face. In yet another embodiment, the thermal camera is based on at least one of the following uncooled sensors: a thermopile, a microbolometer, and a pyroelectric sensor. In still another embodiment, at least at least one of the first and second thermal cameras is a focal-plane array (FPA) thermal camera. A more detailed discussion regarding the various types of thermal cameras that may be used in embodiments described in this disclosure, including properties of thermal measurements (e.g., $TH_N$ 361 mentioned above), is provided in Section 1.

In one embodiment, the computer 360 is configured to generate samples based on data comprising: (i) $TH_N$ 361, and (ii) indications 363, which correspond to different times, which are indicative of whether the user 362 experienced an allergic reaction at the different times. Optionally, each sample comprises: (i) feature values based on $TH_N$ taken during a certain period (from among $TH_N$ 361), and (ii) a label, based on an indication from among the indications 363, which is indicative of whether the user 362 had an allergic reaction and/or to what extent the user 362 had the allergic reaction. Optionally, at least one of the feature values in the sample may be generated based on other sources of information such as physiological measurements of the user 362, which are not among $TH_N$ 361 of the user 362, and/or measurements of the environment in which the user 362 was in when while $TH_N$ 361 were taken. The computer 360 is further configured to generate a model 367 based on the samples, and provide the model to be used by a system that detects an allergic reaction based on $TH_N$, such as a system illustrated in FIG. 23.

The term "feature values" is typically used herein to represent data comprising values on which calculations may be performed. In one exemplary embodiment, feature values may be provided to a machine learning based estimator (which may also be called a "predictor") in order to perform calculations on the data utilizing a model (e.g., in order to perform inference). In one example, feature values are data that may be represented as a vector of numerical values (e.g., integer and/or real values), with each position in the vector corresponding to a certain feature. In some examples, in vectors representing feature values of different samples, each position (dimension) in the vectors corresponds to the same feature. Thus, in these examples, different samples may be considered to include data representing the same features, but include different feature values. For example, the vectors may include measurements of temperatures at ROIs, but each sample may include different values of temperatures (at the ROIs). In another example, feature values are stored in a data structure having a predetermined section that identifies the type of data stored in the data structure. For example, the feature values may be stored in the payload of a packet, and a predefined data structure in the packet's header identifies the one or more types of data stored in the payload. Alternatively or additionally, a predefined data structure in the packet's tail may identify the one or more types of data stored in the packet's payload.

The time frame for an indication, from among the indications 363, regarding an allergic reaction of the user 362 may vary between different embodiments. In one embodiment, an indication corresponds to a certain time and is indicative of whether the user 362 had an allergic reaction at the certain time and/or whether at the certain time there was an onset of an allergic reaction. In another embodiment, an indication corresponds to a certain period and is indicative of whether at a time that falls within the certain period, the user 362 had an allergic reaction and/or there was an onset of an allergic reaction. In yet another embodiment, an indication may be relative to a period during which certain $TH_N$ of the user 362 were taken. Optionally, the indication may be indicative of whether the user 362 had an allergic reaction at some time that falls within the certain period and/or at some time that falls within temporal proximity of the certain period. For example, if the certain period is $[t,t+\Delta]$ then the indication may indicate whether the user 362 had an allergic reaction some time during the period $[t-\delta, t+\Delta+\Delta\delta]$, where $\delta$ may be a period of time such as ten minutes, thirty minutes, one hour, two hours, or some other period of time that is shorter than twelve hours.

The indications 363 may be generated in different ways, in different embodiments. In one embodiment, at least one of the indications 363 is generated by an entity that observes the user 362, such as a human observer or a software program (e.g., a software agent operating on behalf of the user 362). In another embodiment, one or more of the indications 363 may be provided by the user 362. In one example, the user 362 may provide an indication via a mobile "app" (e.g., by pressing a certain button on a screen of a smartphone). In another example, the user 362 may provide an indication by making a comment that is interpreted by a software agent and/or a program with speech analysis capabilities. In yet another embodiment, one or more of the indications 363 are determined based on analysis of behavior of the user 362. For example, monitoring of the behavior of the user 362 using a camera and/or microphone may indicate that the user 362 is suffering from an allergic reaction (e.g., by detecting coughing and/or sneezing). And in still another embodiment, one or more of the indications 363 are determined based on physiological signals of the user 362 that are not thermal measurements of one or more ROIs on the face, such as measurements of the user's heart rate and/or brainwave activity.

The following are some examples of feature values that may be generated for the samples used to generate the model 367. Each sample comprises feature values that are based on $TH_N$ of the user 362 (from among $TH_N$ 361), which were taken during a certain period, and possibly other information sources mentioned below.

In some embodiments, at least one of the feature values generated based on $TH_N$ of the user 362 taken during the certain period include values measured by the one or more thermal cameras during the certain period. Optionally, the values measured by the one or more thermal cameras may undergo various forms of filtering and/or normalization. In one example, some feature values may be average values of certain sensors (pixels) of the one or more thermal cameras during the certain period and/or some feature values may be values measured at certain times during the certain period by the certain sensors. In another example, at least one of the feature values generated based on $TH_N$ of the user 362 may be a time series of values measured by the one or more sensors during the certain period.

In some embodiments, at least one of the feature values generated based on $TH_N$ of the user 362 taken during the certain period include a value of a respiratory parameter of the user 362 during the certain period. Optionally, this feature value may be generated based on additional thermal measurements of other ROIs (besides the nose) taken with one or more thermal cameras (which may be different from one or more thermal cameras used to take $TH_N$). For example, the additional thermal measurements may include thermal measurements of an ROI that includes the region of the user's mouth. Some examples of respiratory parameters that may be used as feature values include the following: respiration rate, respiration volume, indications of mouth vs. nasal breathing, exhale (inhale) duration, post-exhale (post-inhale) breathing pause, indication of the dominant nostril, exhale stream shape, exhale stream smoothness, and exhale stream temperature. Additional details regarding respiratory parameters may be found in Section 5.

In addition to $TH_N$ of the user 362, taken during the certain period, in some embodiments, additional sources of information may be utilized to generate one or more feature values that are included in a sample from among the samples. In one embodiment, the computer 360 may receive additional measurements of the user 362 and to generate at least one of the feature values of the sample based on the additional measurements. Optionally, the additional measurements are indicative of one or more of the following signals of the user 362: a heart rate, heart rate variability, brainwave activity, galvanic skin response, muscle activity, and an extent of movement. Optionally, the additional measurements may be obtained utilizing one or more of the various sensors that are described in this disclosure (e.g., in Section 4) which are not thermal cameras.

Some of the additional sources of information may relate to the environment the user 362 was in when at least some of $TH_N$ of the user 362 were taken. In one embodiment, the computer 360 may be further configured to receive measurements of the environment in which the user 362 was in while $TH_N$ of the user 362 were taken and to generate at least one of the feature values of a sample from among the samples based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In one embodiment, the computer 360 may be further configured to receive one or more values indicative of exposure of the user 362 to one or more allergens during a certain period while $TH_N$ of the user 362 were taken, or up to twelve hours before $TH_N$ were taken. The computer 360 may be further configured to generate at least one of the feature values of a sample (which corresponds to $TH_N$ of the user 362 that were taken during the certain period) based on the one or more values. Optionally, each of the one or more values is indicative of one or more of the following: consumption of a certain drug, consumption of a certain food item, exposure to at least a certain concentration of pollen, exposure to at least a certain concentration of dust, exposure to a certain cosmetics product, and exposure to a certain aerosol.

In one embodiment, at least some of the samples are generated based on at least some of $TH_N$ of the user 362 that were taken after the user 362 was exposed to a certain allergen and at least some $TH_N$ of the user that were taken after the user 362 was not exposed to the certain allergen. Thus, the samples in this embodiment may include some samples that correspond to exposure to the allergen and some samples that do not. Optionally, determining exposure of the user 362 to an allergen may be done utilizing analysis of images captures utilizing a camera configured to capture images of substances consumed by the user 362. Optionally, the computer 360 (and/or some other module) is further configured to utilize the images to detect the exposure of the user 362 to the one or more allergens.

In one embodiment, the computer 360 is further configured to receive measurements ($m_{conf}$ 365), which are indicative of at least one of the following confounding factors: a skin inflammation on the face of the user, touching the face of the user, a magnitude of thermal radiation directed at the face of the user, and a magnitude of direct airflow on the face of the user. Optionally, $m_{conf}$ 365 are measured utilizing the sensor 461. In one example, the sensor 461 is physically coupled to the frame worn on the user's head. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. In one embodiment, the computer 360 generates at least some of the feature values of a sample based on $m_{conf}$ 365. For example, the feature values of the sample may include values of measurements from among $m_{conf}$ 365, which were taken during the certain period during which $TH_N$ used to generate the sample were taken.

In one embodiment, the samples used to generate the model 367 include one or more samples that were generated based on $TH_N$ of the user 362 taken while the user 362 had an allergic reaction and/or when there was an onset of an allergic reaction of the user 362. Additionally, the samples include one or more samples that were generated based on $TH_N$ of the user 362, taken while the user 362 did not have an allergic reaction nor was there an onset of an allergic reaction of the user 362. Thus, the samples 365 may be utilized to generate a model that can help distinguish between cases in which $TH_N$ of the user 362 are taken while the user 362 has an allergic reaction and/or while there is an onset of an allergic reaction, and cases in which $TH_N$ of the user 362 are taken while the user 362 has no allergic reaction (and there is no onset of an allergic reaction).

The samples utilized to generate the model 367 may include samples taken while user 362 were in different environments. In one example, the samples comprise first and second samples that are based on $TH_N$ of the user 362 taken during first and second periods, respectively. Optionally, different environmental conditions prevailed during the first and second periods, which involved one or more of the following differences: (i) the temperature of the environment in which the user 362 was during the first period was at least 10° C. higher than the temperature of the environment in which the user 362 was during the second period; (ii) the humidity level in the environment in which the user 362 was during the first period was at least 30% higher than the humidity level in the environment in which the user 362 was during the second period; and (iii) the user 362 was exposed to at least one of rain, hail, and snow during the first period and the user was not exposed to any of rain, hail, and snow during the second period.

Additionally or alternatively, the samples utilized to generate the model 367 may include samples taken while the user 362 was in various situations. In one example, the samples comprise first and second samples that are based on $TH_N$ of the user 362 taken during first and second periods, respectively. Optionally, the user 362 was in different situations during the first and second periods, which involved one or more of the following differences: (i) the user 362 was sedentary during the first period while the user 362 was performing at least one of the following during the second period: walking, running, and biking; and (ii) the user 362 was indoors during the first period, while the user 362 was outdoors during the second.

Additionally or alternatively, the samples utilized to generate the model 367 may be based on $TH_N$ taken over a long period of time, such as more than a day, more than a week, more than a month, or more than a year. Herein, samples may be considered to be generated based on measurements taken over more than a certain period (e.g., a week) if the samples include at least first and second samples, generated based on measurements taken during first and second periods of time, respectively, such that the difference between when the first period and the second period start is at least as long as the certain period. That is, the starting times first and second periods are at least the certain period apart.

Generating the model 367 may involve one or more of the various computational approaches mentioned in this disclosure for generating a model used to detect a physiological response. In one example, generating the model 367 may involve selecting, based on the samples, a threshold; if a certain feature value reaches the threshold then an allergic reaction (or an onset thereof) is detected. In another example, the computer 360 is configured to utilize a machine learning based training algorithm to generate the model 367 based on the samples. Optionally, the model comprises parameters of at least one of the following models: a regression model, a model utilized by a neural network, a nearest neighbor model, a model for a support vector machine for regression, and a model of a decision tree.

In some embodiments, the computer 360 may utilize deep learning algorithms to generate the model 367. In one example, the model 367 may include parameters describing multiple hidden layers of a neural network. In one embodiment, when $TH_N$ include measurements of multiple pixels, such as when the thermal camera includes a focal-plane array (FPA), the model 367 may include a convolution neural network (CNN). In another embodiment, detecting the allergic reaction may be done based on multiple, possibly successive, measurements. For example, the allergic reaction may involve a progression of a state of the user (e.g., a gradual warming of the nose in an). In such cases, detecting the allergic reaction may involve retaining state information that is based on previous measurements. Optionally, the model 367 may include parameters that describe an architecture that supports such a capability. In one example, the model 367 may include parameters of a recurrent neural network (RNN), which is a connectionist model that captures the dynamics of sequences of samples via cycles in the network of nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, generating the model 367 involves altering parameters of another model, which is generated based on $TH_N$ of one or more other users. For example, the computer 360 may utilize the other model as an initial model. As the samples are acquired from measurements of the user 362, the computer 360 may update parameters of the initial model based on the samples. Thus, this process may be considered personalizing a general model according to measurements of the user 362.

It is to be noted that similar to embodiments of the system configured to detect an allergic reaction of a user, which is discussed further above, some embodiments of the system configured to generate a personalized model for detecting an allergic reaction may include multiple thermal cameras. Optionally, thermal measurements of the multiple thermal cameras may be utilized to generate feature values of samples similarly to how $TH_N$ 361 are utilized, as described above.

In one example, the system configured to generate a personalized model for detecting an allergic reaction may include second and third thermal cameras, each of which: weighs below 5 g, is physically coupled to the frame, and is located less than 15 cm away from the user's face. The second and third thermal cameras in this example are located to the right and left of the vertical symmetry axis, respectively, and are configured to take thermal measurements of portions of the right and left cheeks, respectively. Optionally, the computer 360 is further configured to generate the samples also based on the thermal measurements of the cheeks.

In another example, the system configured to generate a personalized model for detecting an allergic reaction may include second and third thermal cameras, each of which: weighs below 5 g, is physically coupled to the frame, and is located less than 15 cm away from the user's face. The second and third thermal cameras in this example are located to the right and left of the vertical syn lefty axis, respectively, and are configured to take thermal measurements of portions of the right and left periorbital regions, respectively. Optionally, the computer 360 is further configured to generate the samples also based on the thermal measurements of the periorbital regions.

Figure 22:
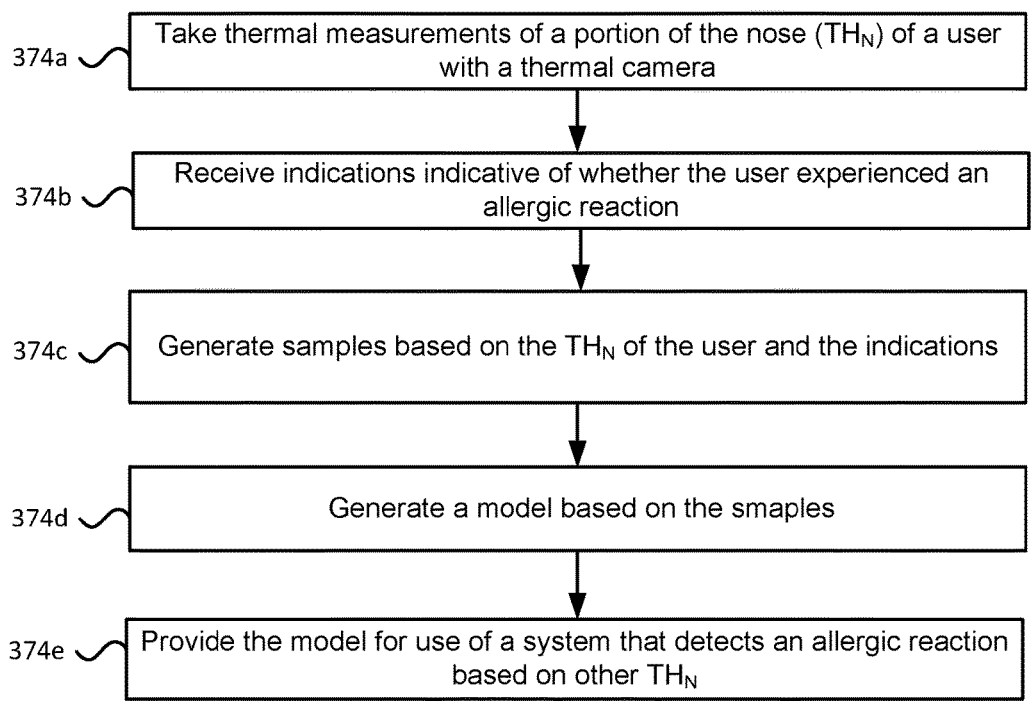
FIG. 22 illustrates an embodiment of a method for generating a personalized model for detecting an allergic reaction based on thermal measurements.

FIG. 22 illustrates steps that may be performed in one embodiment of a method for generating a personalized model for detecting an allergic reaction based on thermal measurements of the face. The steps described below may be, in some embodiments, part of the steps performed by an embodiment of a system described above, which is illustrated in FIG. 21. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a. Optionally, different steps of the method may be performed utilizing different systems comprising a processor and memory.

In one embodiment, a method for generating a personalized model for detecting an allergic reaction based on thermal measurements includes at least the following steps:

In Step 374a, taking utilizing a thermal camera physically coupled to a frame worn on a user's head, thermal measurements of a portion of the nose ($TH_N$) of the user. Optionally, $TH_N$ are taken from a distance of less than 15 cm from the user's face.

In Step 374b, receiving indications corresponding to different times, which are indicative of whether the user experienced an allergic reaction at the different times.

In Step 374c, generating samples based on $TH_N$ of the user and the indications. Optionally, each sample comprises feature values based on $TH_N$ taken during a certain period and a label indicative of whether the user had an allergic reaction at a time that is at most one hour before the start of the certain period and at most one hour after the end of the certain period.

In Step 374d, generating a model based on the samples. Optionally, generating the model based on the samples involves utilizing a machine learning-based training algorithm. Optionally, generating the model is done by updating parameters of an initial model based on the samples, where the initial model is generated based on previous samples generated from $TH_N$ of one or more other users.

Figure 23:
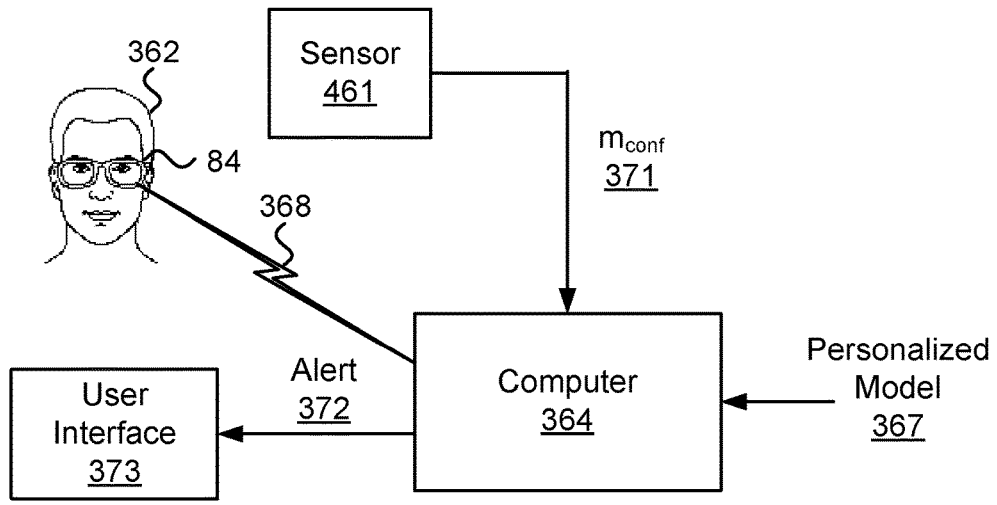
FIG. 23 illustrates an embodiment of a system configured to perform personalized detection of an allergic reaction.

And in Step 374e, providing the model to be used by a system that detects an allergic reaction based on $TH_N$, such as the system illustrated in FIG. 23.

In one embodiment, generating the samples in Step 374c may optionally involve receiving additional measurements of the user and generating at least one of the feature values of a sample from among the samples based on the additional measurements. Optionally, the additional measurements are indicative of one or more of the following signals: a heart rate of the user, heart rate variability of the user, brainwave activity of the user, galvanic skin response of the user, muscle activity of the user, and an extent of movement of the user.

In another embodiment, generating the samples in Step 374c may optionally involve receiving values comprising measurements of the environment in which the user was in while $TH_N$ of the user were taken and generating at least one of the feature values of a sample from among the samples based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In yet another embodiment, generating the samples in Step 374c may optionally involve: receiving one or more values indicative of exposure of the user to one or more allergens while $TH_N$ of the user were taken, or up to twelve hours before $TH_N$ of the user were taken. Additionally, this step may involve generating at least one of the feature values of a samples from among the samples based on the one or more values. Optionally, each of the one or more values is indicative of one or more of the following: consumption of a certain drug, consumption of a certain food item, exposure to at least a certain concentration of pollen, exposure to at least a certain concentration of dust, exposure to a certain cosmetics product, and exposure to a certain aerosol.

In one embodiment the method may optionally include steps comprising: taking measurements of the user (denoted $m_{conf}$) with a sensor, which are indicative of at least one of the following: a skin inflammation on the face of the user, touching the face of the user, a magnitude of thermal radiation directed at the face of the user, and a magnitude of direct airflow on the face of the user, and generating one or more of the samples also based on $m_{conf}$ (by generating at least one feature value belonging the one or more samples based on $m_{conf}$).

In another embodiment, the method may optionally involve obtaining and utilizing thermal measurements of additional thermal cameras. In one example, the method optionally includes steps comprising: taking thermal measurements of portions of the right and left cheeks utilizing second and third thermal cameras, respectively, and generating the samples also based on the thermal measurements of the cheeks. Optionally, the second and third thermal cameras each: weighs below 5 g, is physically coupled to the frame, and is located less than 15 cm away from the user's face. Additionally, in this example, the second and third thermal cameras are located to the right and left of the vertical symmetry axis, respectively. In another example, the method optionally includes steps comprising: taking thermal measurements of portions of the right and left periorbital regions utilizing second and third thermal cameras, respectively, and generating the samples also based on the thermal measurements of the periorbital regions. Optionally, the second and third thermal cameras each: weighs below 5 g, is physically coupled to the frame, and is located less than 15 cm away from the user's face. Optionally, the second and third thermal cameras are located to the right and left of the vertical symmetry axis, respectively.

Once the model 367 is generated, it may be utilized to detect an allergic reaction of the user 362 based on other $TH_N$ of the user 362, which are not among $TH_N$ 361 that were used for generating the model 367. Such utilization of the model 367 is illustrated in FIG. 23, which illustrates an embodiment of a system configured to perform personalized detection of an allergic reaction based on thermal measurements of the face. One embodiment of the illustrated system includes a frame (e.g., the frame 84), a thermal camera, and a computer 364.

The frame and thermal camera may belong to an HMS from among the HMSs described in this disclosure, such as HMSs illustrated in FIG. 5, FIG. 20, FIG. 2a, or FIG. 2b. The thermal camera is coupled to the frame, which is worn on the head of a user 362, and is configured to take thermal measurements portion of a nose ($TH_N$ 368) of the user 362. Optionally, $TH_N$ 368 are taken over a certain period, such as at least ten seconds, at least one minute, at least five minutes, at least twenty minutes, at least one hour, or at least three hours.

In one example, the thermal camera may be the thermal camera 80 or the thermal camera 81, which are physically coupled to the frame 84. Optionally, the frame and thermal camera are the same as the frame and thermal camera utilized to take $TH_N$ 361. Optionally, the thermal camera may have different characteristics and/or may be located at various distances relative to the face. In one embodiment, the thermal camera weighs below 5 g and is located less than 15 cm away from the face. In another embodiment, the thermal camera weighs below 1 g, and is located less than 5 cm away from the face. In yet another embodiment, the thermal camera is based on at least one of the following uncooled sensors: a thermopile, a microbolometer, and a pyroelectric sensor. In still another embodiment, at least at least one of the first and second thermal cameras is a focal-plane array (FPA) thermal camera. A more detailed discussion regarding the various types of thermal cameras that may be used in embodiments described in this disclosure, including properties of thermal measurements (e.g., $TH_N$ 368 mentioned above), is provided in Section 1.

It is to be noted $TH_N$ 368 are similar in their nature to $TH_N$ 361; $TH_N$ 368 are taken using the same hardware setup as $TH_N$ 361. However, $TH_N$ 368 are taken after $TH_N$ 361 were taken, and after the model 367 was generated. Thus, in this embodiment, $TH_N$ 368 were not utilized to generate the model 367.

In one embodiment, the computer 364 is configured to: generate feature values based on $TH_N$ 368 and utilize the model 367 to calculate, based on the feature values, a value indicative of the extent of an allergic reaction of the user 362. Optionally, the model is generated based on previous $TH_N$ of the user 362 (e.g., $TH_N$ 361), which were taken over more than a week The feature values generated based on $TH_N$ 368 are similar in their nature to the feature values generated based on $TH_N$ 361, which were discussed in more detail above. Some examples of feature values that may be generated based on $TH_N$ 368 include: (i) values comprised in $TH_N$ 368 (optionally these values may undergo various forms of filtering and/or normalization), (ii) values of one or more respiratory parameters calculated based on $TH_N$ 368, (iii) values generated based on additional measurements of the user 362 (e.g., measurements of heart rate, heart rate variability, brainwave activity, galvanic skin response, muscle activity, and an extent of movement), and (iv) measurements of the environment in which the user 362 was in while $TH_N$ 368 were taken.

In one embodiment, the computer 364 may receive one or more values indicative of exposure of the user 362 to an allergen while $TH_N$ 368 were taken, or up to twelve hours before $TH_N$ 368 were taken, and generate at least one of the feature values based on the indication. Optionally, the indication is indicative of one or more of the following: consumption of a certain drug, consumption of a certain food item, exposure to at least a certain concentration of pollen, exposure to at least a certain concentration of dust, exposure to a certain cosmetics product, and exposure to a certain aerosol. Optionally, determining exposure of the user 362 to the allergen may be done utilizing analysis of images captures utilizing a camera configured to capture images of substances consumed by the user 362. Optionally, the computer 364 is further configured to utilize the images to detect the exposure of the user 362 to the allergen.

In one embodiment, the computer 364 is configure to utilize the model 367 to calculate, based on the feature values, a value indicative of the extent of an allergic reaction of the user 362. Optionally, responsive to the value indicating that the extent reaches a threshold, the computer 364 generates an alert 372 that is presented to the user 362 via a user interface 373.

In one embodiment, the extent of the allergic reaction may be indicative of one or more of the following: the severity of the allergic reaction severity (e.g., a level of manifestation of symptoms on a scale of 1 to 10) and/or the duration of the allergic reaction (e.g., total time of the allergic reaction and/or time remaining until the allergic reaction subsides). Optionally, the extent of the allergic reaction may correspond to whether there is an onset of an allergic reaction of the user 362. Thus, the value indicative of the extent may be indicative of one or more of the following values: the time until the allergic reaction reaches its peak severity (e.g., a rash, coughing, respiratory distress, sneezing) and/or the expected degree of severity of the allergic reaction.

The model 367 may include different types of parameters, in different embodiments. Following are some examples of various possibilities for the model 367 and the type of calculations that are accordingly performed by the computer 364.

In one embodiment, the model 367 comprises parameters of a decision tree. Optionally, in this embodiment, in order to calculate the value indicative of the extent of the allergic reaction, computer 364 simulates a traversal along a path in the decision tree, determining which branches to take based on the feature values. Optionally, the value indicative of the extent is obtained from a leaf node of the tree that is reached at the end of the path. Additionally or alternatively, the value indicative of the extent is calculated based on values of nodes of the tree that are on the traversed path.

In another embodiment, the model 367 comprises parameters of a regression model (e.g., regression coefficients in a linear regression model or a logistic regression model). Optionally, in this embodiment, in order to calculate the value indicative of the extent of the allergic reaction, the computer 364 multiplies the feature values (which may be considered a regressor) with the parameters of the regression model.

In yet another embodiment, the model 367 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, in this embodiment, in order to calculate the value indicative of the extent of the allergic reaction, the computer 364 provides the feature values as inputs to the neural network, computes the values of the various activation functions and propagates values between layers, and obtains an output from the network which is the value indicative of the extent of the extent of the allergic reaction.

In one embodiment, the user interface 373 is configured to present the user 362 with the alert 372 responsive to an indication that the extent of the allergic reaction of the user 362 reaches a threshold. In one embodiment, the user interface 373 may comprise a screen on which the alert 372 may be presented (e.g., in the form of text, an image, or video). Optionally, the screen may be part of a display coupled to a frame worn by the user 362 (e.g., a screen of an augmented reality or a virtual reality headset). Additionally or alternatively, the screen may be a display of a device of the user, such as a display of a smartphone or smartwatch. In another embodiment, the alert 372 may involve and audio notification that is generated via the user interface 373. For example, the user interface 373 may include a speaker, earphones, and/or an earbud through which an audio signal is provided to the user 362 in order to make the user 362 aware of the allergic reaction (or impending allergic reaction). In still another embodiment, the user interface 373 may be part of a frame worn on the head of the user 362 and the alert 372 involves the frame and/or another device physically and/or communicatively coupled to the frame making noises (e.g., beeping sounds), making a visual indication (e.g., lighting of lights on the frame), and/or providing a tactile indication (e.g., by vibrating).

In one embodiment, the computer 364 is further configured to detect an early rise in nasal temperature of the user 362, which is detectable before the user 362 is aware of a manifestation of a symptom of the allergic reaction. Optionally, in this embodiment, the user interface 373 may present the user 362 with the alert 372 that is indicative of a possible allergic reaction, before the user 362 is aware of the symptom. In one example, For example, an early rise in nasal temperature may involve a rise of at least 0.5° C. within less than 10 minutes and/or a rise of at least 0.75° C. within less than 20 minutes.

It is to be noted that some embodiments of the system configured to perform a personalized detection an allergic reaction may include multiple thermal cameras. Optionally, thermal measurements of the multiple thermal cameras may be utilized to generate feature values similarly to how $TH_N$ 368 are utilized, as described above.

In one example, the system configured to perform personalized detection of an allergic reaction may include second and third thermal cameras, each of which: weighs below 5 g, is physically coupled to the frame, and is located less than 15 cm away from the user's face. The second and third thermal cameras in this example are located to the right and left of the vertical symmetry axis, respectively, and are configured to take thermal measurements of portions of the right and left cheeks, respectively. Optionally, the computer 364 is further configured to generate one or more feature values based on thermal measurements of portions of the right and left cheeks, which are utilized to calculate the value indicative of the extent of the allergic reaction of the user.

In another example, the system configured to perform personalized detection of an allergic reaction may include second and third thermal cameras, each of which: weighs below 5 g, is physically coupled to the frame, and is located less than 15 cm away from the user's face. The second and third thermal cameras in this example are located to the right and left of the vertical symmetry axis, respectively, and are configured to take thermal measurements of portions of the right and left periorbital regions, respectively. Optionally, the computer 364 is further configured to generate one or more feature values based on thermal measurements of the periorbital regions, which are utilized to calculate the value indicative of the extent of the allergic reaction of the user.

In one embodiment, the computer 364 is further configured to receive measurements ($m_{conf}$ 371), which are indicative of at least one of the following confounding factors: a skin inflammation on the face of the user, touching the face of the user, a magnitude of thermal radiation directed at the face of the user, and a magnitude of direct airflow on the face of the user. Optionally, $m_{conf}$ 371 are measured utilizing the sensor 461. In one example, the sensor 461 is physically coupled to the frame worn on the user's head. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. In one embodiment, the computer 364 generates at least some of feature values based on $m_{conf}$ 371 and utilizes the at least some feature values to calculate the value indicative of the extent of the allergic reaction. For example, at least some of the feature values may include values of measurements from among $m_{conf}$ 371, which were taken during the certain period during which $TH_N$ 368 were taken.

It is to be noted that since the model 367 is personalized for the user 362, when such a model is generated for different users, it may lead to different detections of allergic reactions, even when provided with similar $TH_N$ of the users. In one example, first and second models generated based on previous $TH_N$ of first and second different users, respectively. Responsive to utilizing the first model, a first value is calculated based on first feature values generated based on $TH_N$ of the first user, which is indicative of a first extent of an allergic reaction. Responsive to utilizing the second model, a second value is calculated based on second feature values generated based on $TH_N$ of the second user, which is indicative of a second extent of an allergic reaction. In this example, $TH_N$ of the first user indicate a greater temperature change at the portion of the nose of the first user compared to the change at the portion of the nose of the second user indicated by $TH_N$ of the second user. However, in this example, the first extent corresponds to a milder allergic reaction than the second extent.

Figure 24:
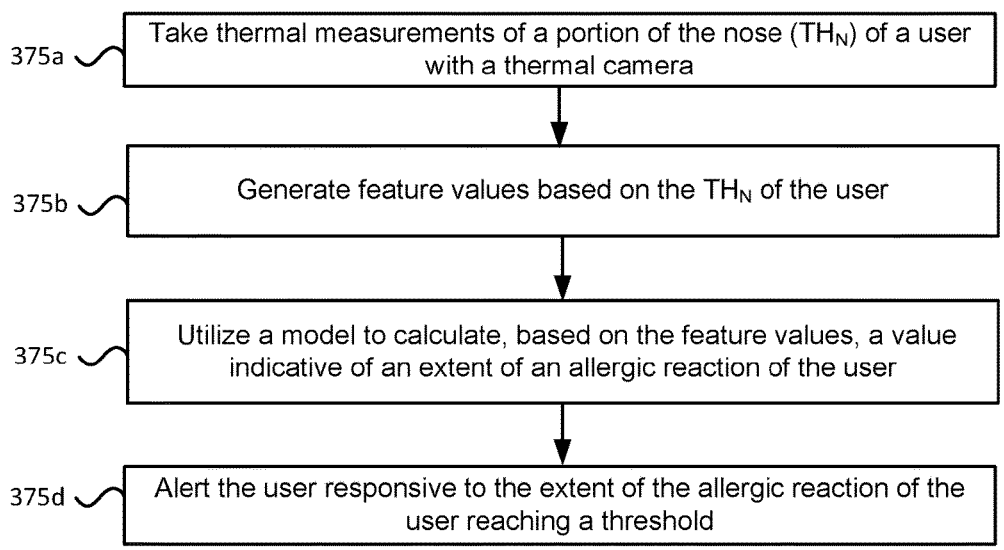
FIG. 24 illustrates an embodiment of a method for performing a personalized detection of an allergic reaction.

FIG. 24 illustrates steps that may be performed in one embodiment of a method for performing a personalized detection of an allergic reaction. The steps described below may be, in some embodiments, part of the steps performed by an embodiment of a system described above, which is illustrated in FIG. 23. In some embodiments, instructions for implementing an embodiment of the method described below may be stored on a computer-readable medium, which may optionally be a non transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a or FIG. 72b. Optionally, different steps of the method may be performed utilizing different systems comprising a processor and memory.

In one embodiment, a method for performing a personalized detection of an allergic reaction of a user includes at least the following steps:

In Step 375a, taking thermal measurements of a portion of the nose of the user ($TH_N$) utilizing a thermal camera coupled to a frame worn on the user's head. Optionally, the thermal camera weighs below 5 g. Optionally, the thermal camera is physically coupled to the frame and is located less than 15 cm away from the face. For example, the thermal camera may be one of the thermal cameras illustrated in FIG. 5. Optionally, multiple thermal cameras may be utilized to take thermal measurements of ROIs that include the nasal and/or mouth areas, such as multiple thermal cameras illustrated in FIG. 20, and FIG. 2a.

In Step 375b, generating feature values based on $TH_N$ of the user.

And in Step 375c, utilizing a model to calculate, based on the feature values, a value indicative of the extent of an allergic reaction of the user. The model used in this step is generated based on previous $TH_N$ of the user. Optionally, the model is the model 367.

In one embodiment, the method described above may optionally include a step involving alerting the user responsive to the extent of the allergic reaction of the user, which is calculated in Step 375c, reaching a threshold. Optionally, alerting the user may involve detecting an early rise in nasal temperature of the user, which is evident before the user is aware of a symptom of the allergic reaction. Responsive to a detection of the early rise in nasal temperature, the user may be alerted regarding a possible allergic reaction even before the user becomes aware of the symptom of the allergic reaction. Optionally, alerting the user is done by providing the user some form of notification via the user interface 373.

Generating the feature values in Step 375c may involve, in some embodiments, additional sources of information in Step 375b. Additional discussion regarding various sources of information which may be utilized to detect a physiological response in general, which are applicable to detecting an allergic reaction, are provided in Section 4.

In one embodiment, Step 375b optionally involves receiving additional measurements of the user taken during the same period $TH_N$ of the user were taken and generating at least one of the feature values based on the additional measurements. Optionally the additional measurements are indicative of one or more of the following signals: a heart rate of the user, heart rate variability of the user, brainwave activity of the user, galvanic skin response of the user, muscle activity of the user, and an extent of movement of the user.

In another embodiment, Step 375b optionally involves receiving measurements of the environment in which the user was in while $TH_N$ of the user were taken and generating at least one of the feature values based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In yet another embodiment, Step 375b optionally involves receiving one or more values indicative of exposure of the user to one or more allergens while $TH_N$ of the user were taken, or up to twelve hours before $TH_N$ of the user were taken. Additionally, Step 375b optionally involves generating at least one of the feature values based on the one or more values. Optionally, each of the one or more values is indicative of one or more of the following: consumption of a certain drug, consumption of a certain food item, exposure to at least a certain concentration of pollen, exposure to at least a certain concentration of dust, exposure to a certain cosmetics product, and exposure to a certain aerosol.

In one embodiment the method may optionally include steps comprising: taking measurements of the user (denoted $m_{conf}$) with a sensor, which are indicative of at least one of the following: a skin inflammation on the face of the user, touching the face of the user, a magnitude of thermal radiation directed at the face of the user, and a magnitude of direct airflow on the face of the user, generating one or more feature values based on $m_{conf}$ and utilizing the one or more feature values to calculate the value indicative of the extent of an allergic reaction of the user.

In another embodiment, the method may optionally involve obtaining and utilizing thermal measurements of additional thermal cameras. In one example, the method optionally includes steps comprising: taking thermal measurements of portions of the right and left cheeks utilizing second and third thermal cameras, respectively; generating one or more feature values based on those thermal measurements, and utilizing the one or more feature values to calculate the value indicative of the extent of an allergic reaction of the user. Optionally, the second and third thermal cameras each: weighs below 5 g, is physically coupled to the frame, and is located less than 15 cm away from the user's face. Additionally, in this example, the second and third thermal cameras are located to the right and left of the vertical symmetry axis, respectively. In another example, the method optionally includes steps comprising: taking thermal measurements of portions of the right and left periorbital regions utilizing second and third thermal cameras, respectively; generating one or more feature values based on those thermal measurements, and utilizing the one or more feature values to calculate the value indicative of the extent of an allergic reaction of the user. Optionally, the second and third thermal cameras each: weighs below 5 g, is physically coupled to the frame, and is located less than 15 cm away from the user's face. Optionally, the second and third thermal cameras are located to the right and left of the vertical symmetry axis, respectively.

Some aspects of this disclosure involve monitoring a user over time with a head-mounted system that includes one or more thermal cameras that are pointed to one or more Regions Of Interest (ROIs) on the user's face. One application for which the thermal measurements of the one or more ROIs may be useful is to detect when a user has an allergic reaction. Analysis of these detections combined with information regarding factors that affected the user at different times can reveal what factors may be trigger factors that may cause an allergic reaction for the user.

Some examples of factors that may be considered trigger factors for certain users include ingested substances such as food (e.g., eggs, dairy, or peanuts) or certain drugs and chemicals and/or compounds to which the user may be exposed (e.g., pollen, dust, a certain cosmetics product, and a certain aerosol). Additionally, a trigger factor may be an indirect factor that is correlated with allergic reactions of the user, such as being at a certain location, being in contact with a certain animal, conducting in a certain activity, and being in contact with a certain object.

Having knowledge of which factors are likely trigger factors for an allergic reaction can help the user avoid the trigger factors and/or take early measures to alleviate the effects of an allergic reaction.

Figure 25:
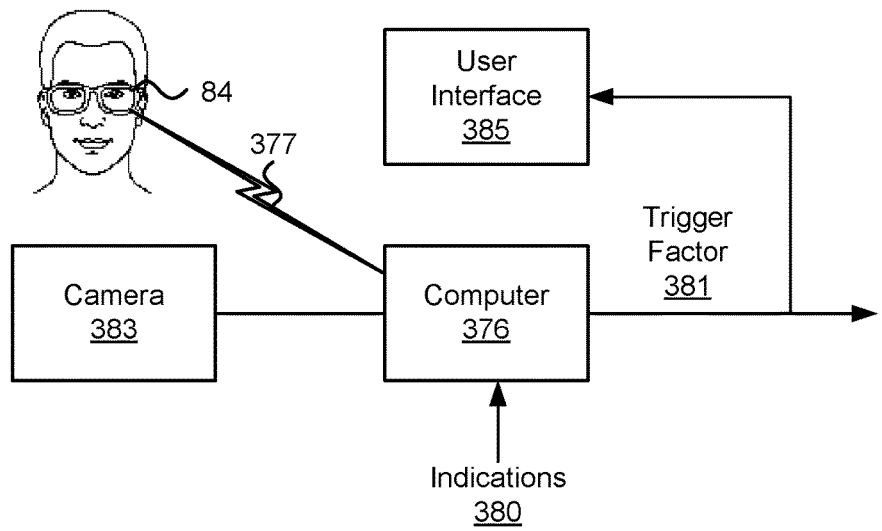
FIG. 25 illustrates an embodiment of a system configured to select a trigger factor of an allergic reaction of a user.

FIG. 25 illustrates an embodiment of a system configured to select a trigger factor of an allergic reaction of a user. The illustrated system includes at least a thermal camera and a computer 376. The system may optionally include a frame that is worn on the user's head (e.g., the frame 84 illustrated in FIG. 5), a camera 383, and/or a user interface 385.

The thermal camera is configured, in one embodiment, to take thermal measurements of a portion of the nose (denoted $TH_N$) 377 of the user. Optionally, the thermal camera may be any of the thermal cameras described herein which measure a region of interest (ROI) that includes a portion of the nose. For example, the thermal camera may be the thermal camera 80 or the thermal camera 81 illustrated in FIG. 5. In another example, the thermal camera may be a thermal camera illustrated in FIG. 20, or FIG. 2a, which measures an ROI that covers a portion of the user's nose. Optionally, the thermal camera is physically coupled to a frame worn on the user's head (e.g., the frame 84). Optionally, the frame is the frame of eyeglasses and/or the frame with a head-mounted display (e.g., a frame of a virtual reality head-mounted display or an augmented reality head-mounted display). Optionally, the thermal camera weighs below 5 g. Optionally the thermal camera is located less than 15 cm away from the user's face. A more detailed discussion regarding the various types of thermal cameras that may be used to measure $TH_N$ 377, including properties of thermal measurements, is provided in Section 1.

In one embodiment, multiple thermal cameras may be utilized to measure $TH_N$ 377. Additionally or alternatively, $TH_N$ 377 may include thermal measurements multiple ROIs on the user's nose and/or thermal measurements of additional one or more additional ROIs on other regions of the user's face.

$TH_N$ 377 are provided, in one embodiment, to the computer 376, which is configured to calculate, based on $TH_N$ 377 of the user, values that are indicative of an extent of the allergic reaction of the user at different times.

In order to calculate the values that are indicative of the extents of the allergic reaction, in one embodiment, first computer 376 may execute operations described in this disclosure that may be used to detect an extent of an allergic reaction based on $TH_N$. For example, in one embodiment, the computer 376 implements operations described above, which are attributed to the computer 364. Additionally or alternatively, the computer 376 may implement one or more of the various approaches to detecting a physiological response (of which an allergic reaction is a specific type), which are described in Section 4.

In one embodiment, the extent of the allergic reaction may be indicative of one or more of the following: the severity of the allergic reaction, the duration of the allergic reaction (e.g., total time of the allergic reaction and/or time remaining until the allergic reaction subsides). Optionally, the extent may be a binary value (e.g., indicating whether the user is having an allergic reaction or not) and/or some other categorial or numerical value that indicates a measure of severity (e.g., a level of symptoms on a scale of 1 to 10).

In one embodiment, the values that are indicative of the extents of the allergic reaction describe the extent of the allergic reaction of the user at different times. Optionally, the values indicate different periods of time during which the user had an allergic reaction. Optionally, the values indicate the severity of the allergic reaction of the user during the different periods of time.

In some embodiments, calculating the values of the extents of the allergic reaction of the user at different times may involve utilizing thermal measurements of other regions on the face, in addition to $TH_N$ 377

In one example, the system configured to select a trigger factor of an allergic reaction of the user further includes second and third thermal cameras, each of which: weighs below 5 g, is physically coupled to the frame, and is located less than 15 cm away from the user's face. Optionally, the second and third thermal cameras are located to the right and left of the vertical symmetry axis, respectively, and are configured to take thermal measurements of portions of the right and left cheeks, respectively. Optionally, the computer 376 is further configured to calculate the values indicative of an extent of allergic reaction of the user at different times based on the thermal measurements of the portions of the right and left cheeks.

In another example, the system configured to select a trigger factor of an allergic reaction of the user further includes second and third thermal cameras, each of which: weighs below 5 g, is physically coupled to the frame, and is located less than 15 cm away from the user's face; the second and third thermal cameras are located to the right and left of the vertical symmetry axis, respectively, and are configured to take thermal measurements of portions of the right and left periorbital regions, respectively; the computer is further configured to calculate the values indicative of an extent of allergic reaction of the user at different times based on the thermal measurements of the portions of the right and left periorbital regions.

The computer 376 is configured, in one embodiment, to receive indications 380 of factors that affected the user at various times. Optionally, each of the indications 380 is indicative of a time during which a certain factor, from among the factors, affected the user. Additionally, the computer 376 is further configured to select a trigger factor 381, from among the factors, based on the indications 380 and the values that are indicative of the extents of the allergic reaction.

In one embodiment, the indications 380 include a list of periods of time during which various factors affected the user. Optionally, the indications 380 are provided via a data structure and/or a queryable system that provides information for different points in time about which of the factors affected the user at the points in time. There are various types of factors that may be indicated by the indications 380. The following are some examples of types of factors that may be analyzed in some embodiments.

In one embodiment, one or more of the factors may relate to allergens in various foods, beverages, and/or other substances that may be consumed and digested by the user and may lead to an allergic reaction. For example, the indications 380 may comprise a certain indication of a factor that is indicative of the user consuming at least one of the following: a certain drug, and a certain food item (e.g., eggs, bread, or a yogurt).

In another embodiment, one or more of the factors may relate to allergens to which the user may be exposed in the environment. Optionally, an allergic reaction may occur after such an allergen is inhaled by the user and/or comes in contact with the user's skin. For example, the indications 380 may comprise a certain indication of a factor that is indicative of the user being exposed to at least one of the following: pollen, dust, a certain cosmetics product, and a certain aerosol (e.g., a certain perfume fragrance).

In yet another embodiment, one or more of the factors may indirectly relate to an allergic reaction (e.g., they may be correlated with allergic reactions of the user). For example, the indications 380 may comprise a certain indication of a factor that is indicative of at least one of the following: the user being at a certain location, the user being in contact with a certain animal, the user conducting in a certain activity, and the user being in contact with a certain object.

Herein, stating that a factor affected the user at a certain time does not imply a certain minimal extent to which the factor affected user. Rather, the term "affected" in this context should be interpreted as having the potential to have an effect on the user. In practice, many factors may not cause a noticeable or measurable effect on the user (with respect to the allergic reaction). Stating that a certain factor affected a user at a certain time implies that the factor is relevant to a certain time. For example, if the user ate an egg on a certain morning, then the egg may be considered a factor that affected the user that certain morning (even if the user is not considered allergic to the egg). However, if the user did not eat a banana that day then eating a banana is not a factor that affected the user that certain morning.

The extent of an allergic reaction may depend on quantitative aspects of the factors. For example, a person who is allergic to dairy products may not have a noticeable allergic reaction following digestion of a small amount of dairy (e.g., adding milk to a cup of coffee), but may have a noticeable allergic reaction following a consumption of a larger amount of a dairy product (e.g., drinking a large milkshake). Thus, in some embodiments, the indications 380 include values that quantify how much at least some of factors affected the user. For example, these values may corresponds to amounts of substances consumed by the user, time spent by the user in certain environments, and/or values of environmental parameters (e.g., a concentration of pollen in the air). Optionally, the indications 380 are indicative of whether certain factors reach a threshold. For example, if a factor reaches the threshold it is considered to affect the user (e.g., if the user consumes at least a certain amount of a certain food), and if it does not reach the threshold it is not considered to affect the user (e.g., when the user consumes less than the certain amount of the certain food).

The trigger factor 381 is a factor that is correlated with the occurrence of an allergic reaction of the user. Additionally, in some embodiments, the trigger factor 381 may be a factor that may b e considered a direct cause of the allergic reaction (e.g., when the trigger factor 381 is a substance to which the user's immune system has an excessive reaction). When considering how being affected by factors relates to the extent of the allergic reaction, an effect of the trigger factor 381 is higher than effects of most of the factors.

The effect of a factor may be considered a measure of how much the factor influences the extent of the allergic reaction of the user. This can range from no influence on the allergic reaction of the user to a profound influence on the extent of the allergic reaction (e.g., when the effect of the factor is to send the user into anaphylaxis shock). More specifically, in one embodiment, the effect of a factor is a value indicative of the average extent of the allergic reaction of the user at a predetermined time $t+\Delta$ after being affected by the factor at time t. Here, A corresponds to the typical time it may take the allergic reaction to occur following being affected by the factor. This time may range from a short period for certain allergic reactions (e.g., minutes), to several hours, or even twelve hours or more. In one example, certain anaphylaxis reactions may occur within minutes of exposure to an allergen. In another example, some allergic reactions may take 12 hours or more (e.g., up to 24 hours) to manifest following being affected by a trigger factor (e.g., when the factor is a certain allergen that is consumed with slowly digesting food).

In some embodiments, the effect of the trigger factor 381 is not lower than the effect of any of the other factors. And in some embodiments, the effect of the trigger factor 381 is higher than the effect observed when the trigger factor 381 does not affect the user. For example, based on the values indicative of the extents of the allergic reaction and indications 380, an average extent of the allergic reaction of the user at a time $t+\Delta$ when the user was affected by the trigger factor 381 at some time during $[t, t+\Delta]$, is greater than an average extent of the allergic reaction of the user at a time $t+\Delta$ when the user was not affected by the trigger factor at any time during $[t, t+\Delta]$.

There are various ways in which the computer 376 may select, based on the indications 380 and the values indicative of the extents of the allergic reaction, the trigger factor 381 from among the multiple factors being considered. The following are some examples of approaches the computer 376 may employ in order to analyze the indications 380 and the values indicative of the extents of the allergic reaction and select, based on the analysis, the trigger factor 381.

In some embodiments, the computer 376 performs a direct analysis of the effect of each of the factors in order to identify factors that have a large effect (meaning they are likely to trigger an allergic reaction with the user). Optionally, the effect of each factor is calculated by determining, based on the indications 380, times at which the user was affected by each factor, and observing the extent of the allergic reaction of the user at one or more times that are up to a certain period Δ later (where Δ may be a period of time up to 12 hours long or shorter, depending on the type of allergic reaction). In one example, an observed extent of the allergic reaction following being affected by a factor is the maximum extent of the allergic reaction that is observed from the time t the user was affected by a factor until the time t+Δ. In another example, the observed extent of the allergic reaction following being affected by a factor is the extent of the allergic reaction that is observed at a time t+Δ (when the user was affected by a factor at time t). Optionally, the observed extent of allergic reaction may be normalized based on a quantitative value representing how much the user was affected by the factor (e.g., the observed extent may be normalized based on a dosage of a drug taken or the amount of time spent outdoors). Optionally, the effect of each factor from among the factors is calculated based on the observed extents of the allergic reactions following being affected by the factor, as described above. In one example, the effect may be an average of the observed extents. In another example, the effect may be a value indicative of the proportion of the observed extents that reach a threshold (which may signify an allergic reaction of at least a certain severity).

Following a calculation of the effects of the factors, in one embodiment, the computer 376 selects a factor from among the factors as the trigger factor 381. Optionally, the trigger factor 381 is a factor from among the factors that has a maximal effect (i.e., there is no other factor from among the factors that has a higher effect). Optionally, the trigger factor 381 is a factor from among the factors that has an effect that reaches a threshold, while the effect of most of the factors does not reach the threshold.

In one embodiment, in order to increase confidence in the selection of the trigger factor, the trigger factor 381 is selected based on at least a certain number of times in which the user was affected by the trigger factor 381. For example, the certain number may be at least 3, at least 5, or at least 10 different times. Thus, in this embodiment, factors that did not affect the user at least the certain number of times are not considered trigger factors.

FIG. 28 illustrates how the system may be utilized to identify a trigger factor. A thermal camera 540 is coupled to a frame of eyeglasses worn by the user and takes thermal measurements of an ROI 541 that covers the user's nose, while the user eats different types of food. The dotted lines on the graph indicate when the user started eating each type of food. The nasal temperature increases shortly after starting to each the persimmon; however, it may reach a threshold indicating an allergic reaction only after some time, during which the user may have eaten other foods such as the pizza or the ice cream. Thus, in this case, the allergic reaction should likely be attributed to the fruit and not the other foods.

In some embodiments, the computer 376 is configured to generate a machine learning-based model based on the indications 380 and the values indicative of the extents of the allergic reaction, and to select the trigger factor 381 based on an analysis of the model. Optionally, the computer 376 generates samples used to train the model.

In one embodiment, the samples may correspond to different times, with each samples corresponding to a time t+Δ including feature values and a label (target value) indicative of the extent of the allergic reaction of the user at the time t+Δ (where depending on the embodiment Δ may have a value between several minutes to 12 or even 24 hours). Optionally, Δ is at least one minute. Optionally, the label of each sample is determined based on one or more of the values that are indicative of the extent of the allergic reaction at the time t+Δ or thereabouts (e.g., up to an hour before or after the time t+Δ). Optionally, the feature values are based on indications, from among the indications 380, which are indicative of the extent various factors affected the user during a period [t, t+Δ]. Optionally, some of the feature values are indicative of how long before t+Δ some of the factors affected the user. Optionally, some of the feature values are indicative of quantitative values representing to magnitude of some the factors (e.g., amounts of food items consumed, dosages of drugs taken, etc.)

Each of the samples described above may be considered to represent a snapshot of factors that affected the user during a certain period and a label that is indicative of the extent of the allergic reaction of the user following being affected by those factors. Given multiple such samples, a machine learning training algorithm can be utilized to generate a model for a predictor module that can predict the extent of the user's allergic reaction at a certain time based on feature values that describe the factors that affected the user during a certain period of time leading up to a certain time. For example, if the model is a regression model, the predictor module may perform a dot product multiplication between a vector of regression coefficients (from the model) and a vector of the feature values in order to calculate a value corresponding to the predicted extent of the allergic reaction of the user at the certain time.

When such a predictor module is capable of predicting extents of the allergic reaction of the user based on the feature values described above, this may mean that the model captures, at least to some extent, the effects of at least some of the factors on the extent of the allergic reaction of the user. Thus, extracting this information about the effects of the factors can help to select a factor that has a large effect on the user.

Generating the model based on the samples described above may involve utilizing one or more of various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

In some embodiments, the predictor module may be provided multiple inputs representing the factors that affected the user at different points of time. For example, the predictor module may be provided with a series of vectors of feature values, each representing the factors that affect the user during a period (e.g., during a minute, five minutes, thirty minutes, an hour, or six hours). In these embodiments, the predictor module may have a capability to store state information of previous inputs corresponding to earlier times when it comes to predict the extent of the allergic reaction of the user at a certain time. One example of a predictor module with such a capability is a predictor module that is based on a recurrent neural network.

The indications 380 may be received from various sources. In one embodiment, the user may provide at least some of the indications 380 (e.g., by inputting data via an app and/or providing vocal annotations that are interpreted by a speech analysis software). In other embodiments, at least some of the indications 380 are provided by analysis of one or more sources of data. Optionally, the computer 376 generates one or more of the indications 380 based on the analysis of data obtained from the one or more sources. The following are some examples of sources of data that may be utilized to identify factors that affected the user at different times.

In one embodiment, the system configured to select a trigger factor of an allergic reaction of a user may optionally include the camera 383 that is configured to capture images of the surroundings of the user. Optionally, the camera 383 may be coupled to a frame worn on the user's head. Optionally, the camera 383 may belong to a device of the user (e.g., a smartphone). Optionally, the camera 383 is not coupled to the user (e.g., a webcam or a camera that is part of CCTV system). There are various ways in which the camera 383 may be utilized to identify factors that affect the user. In one example, camera-based systems such as OrCam (http://www.orcam.com/) may be utilized to identify various objects, products, faces, and/or recognize text. In another, the images captured by the camera 383 may be utilized to determine the nutritional composition of food a user consumes. Such an approach in which images of meals are utilized to generate estimates of food intake and meal composition, is described in Noronha, et al., "Platemate: crowdsourcing nutritional analysis from food photographs", *Proceedings of the* 24*th annual ACM symposium on User interface software and technology*, ACM, 2011.

Other sensors may be used, in some embodiments, to identify factors that affect the user, in addition to, or instead of, the camera 383. Examples of such sensors include microphones, accelerometers, thermometers, pressure sensors, and/or barometers, which may be used to identify factors that may affect the user, such as identifying what the user is doing (e.g., by analyzing movement patterns) and/or under what conditions (e.g., by analyzing ambient noise, temperature, and/or pressure).

Measurements of the environment that user is in are another source of information for determining what factors affect the user at a certain time. Optionally, at least some of the measurements of the environment are performed using a device of the user that contains one or more sensors that are used to measure or record the environment. Optionally, the measurements are received from a third party (e.g., a website that provides environmental information for various locations). Optionally, these measurements may be indicative of one or more of the following: temperature, pressure, humidity, and/or particle counts for various types of chemicals or compounds (e.g. pollutants and/or allergens).

Some examples of additional sources of information that may be utilized by the computer 376 to identify factors that affect the user at different times include various IoT (Internet of Things) devices. For example, such devices may provide information when they are moved and/or utilized. Additionally or alternatively, communications of the user (e.g., email, text messages, voice conversations, and/or video conversations) may also be analyzed, in some embodiments, to provide context and/or to identify factors that affect the user. Similarly, the user's calendar and/or schedule, as well as billing information, may provide information that may be used in some embodiments to identify factors that affect the user.

There are various approaches known in the art for identifying, indexing, and/or searching for factors that may affect the user, which may be utilized in embodiments described herein. In one example, identifying factors that affect the user may be done according to the teachings described in U.S. Pat. No. 9,087,058 titled "Method and apparatus for enabling a searchable history of real-world user experiences", which describes a searchable history of real-world user experiences of a user utilizing data captured by a mobile computing device. In another example, identifying factors that affect the user may be done according to the teachings described in U.S. Pat. No. 8,762,102 titled "Methods and systems for generation and rendering interactive events having combined activity and location information", which describes identification of events based on sensor data of mobile devices.

In some embodiments, identifying factors that affect the user is done, at least in part, by a software agent operating on behalf of the user. Optionally, a software agent operating on behalf of a user may participate in the process of selecting which factors are relevant to an event and/or assigning weights to the factors. For example, the software agent may narrow down a list of possible factors provided by another program and select certain ones that best represent factors that are relevant to allergic reactions.

Knowledge of the trigger factor 381 may be utilized for various purposes. In one embodiment, the trigger factor 381 is utilized by a software agent operating on behalf of the user in order to better serve the user. For example, the software agent may ensure that food items that are ordered for the user do not include components that are known to trigger an allergic reaction (e.g., if the trigger factor 381 is a type of food). In another example, the software agent may plan routes for the user that do not include environments in which the trigger factor 381 may be present (e.g., if the trigger factor 381 is pollen).

Figure 26:
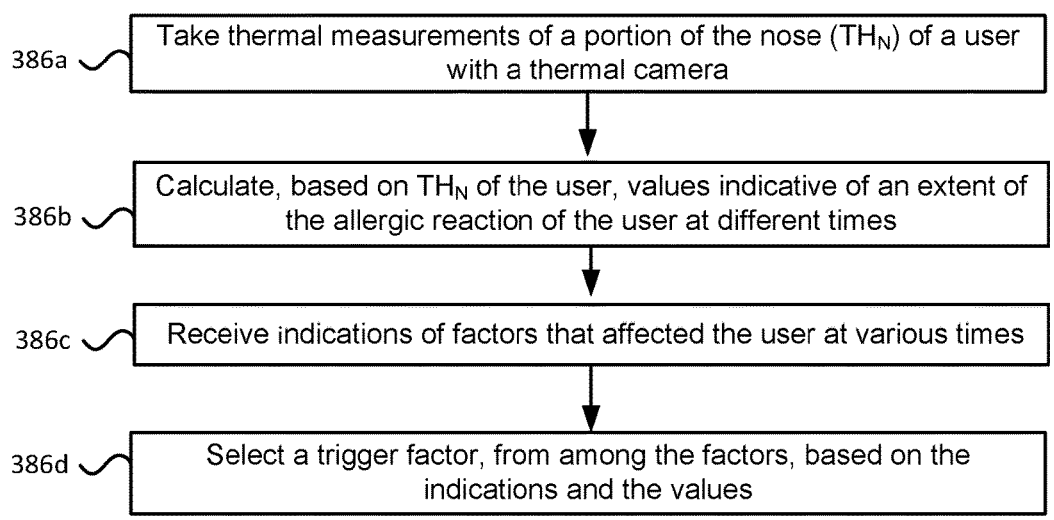
FIG. 26 illustrates an embodiment of a method for selecting a trigger factor of an allergic reaction of a user.

FIG. 26 illustrates steps that may be performed in one embodiment of a method for selecting a trigger factor of an allergic reaction of a user. In some embodiments, the steps described below may be part of the steps performed by an embodiment of a system described above, which is illustrated in FIG. 25. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72*a*. Optionally, different steps of the method may be performed utilizing different systems comprising a processor and memory.

In one embodiment, a method for selecting a trigger factor of an allergic reaction of a user includes at least the following steps:

In Step 386*a*, taking thermal measurements of a portion of the nose (denoted $TH_N$) of the user. Optionally, $TH_N$ of the user are received by the computer 376. Optionally, the thermal camera is physically coupled to a frame worn on the user's head and is located less than 15 cm away from the user's face. Optionally, the thermal camera weighs below 5 g.

In Step 386*b*, calculating, based on $TH_N$ of the user, values indicative of an extent of the allergic reaction of the user at different times. Optionally, the values are calculated by the computer 376.

In Step 386*c*, receiving indications of factors that affected the user at various times. Optionally, each indication is indicative of a time during which a certain factor, from among the factors, affected the user. Optionally, the indications are received by the computer 376. Optionally, the indications received in this step are the indications 380.

And in Step 386d, selecting the trigger factor, from among the factors, based on the indications received in Step 386c and the values calculated in Step 386b. Optionally, selecting the trigger factor is done by the computer 376. Optionally, the trigger factor selected in this step is the trigger factor 381. Optionally, the trigger factor has a higher effect than most of the factors, where the effect of a factor is the average extent of the allergic reaction of the user at a predetermined time t+Δ after being affected by the factor at time t. Optionally, Δ is at least one minute. Optionally, Δ is shorter than at least one of the following durations: twelve hours, four hours, one hour, ten minutes, and one minute.

In one embodiment, the method optionally includes a step that involves taking images of the surroundings of the user and generating at least some of the indications based on analysis of the images. Optionally, the images are taken with the camera 383 and/or the indications are generated by the computer 376.

Selecting the trigger factor in Step 386d may involve various calculation in different embodiments. Optionally, the various calculations are performed by the computer 376. In one embodiment, Step 386d involves calculating, based on the indications received in Step 386c and the values calculated in Step 386b, an effect of each of the factors, and selecting as the trigger factor a factor with a maximal calculated effect. In another embodiment, Step 386d involves generating a machine learning-based model based on the indications and values, and selecting the trigger factor based on an analysis of the model. Optionally, the model may include parameters of one or more of the following: a regression model (e.g., a regression model), a nave Bayes model, a Bayes network, a support vector machine for regression, a decision tree, and a neural network model.

In one example, the analysis of the model involves evaluating parameters of the model that correspond to the factors and selecting as the trigger factor a certain factor that has a corresponding parameter that is indicative of an effect that reaches a threshold while effects indicated in parameters corresponding to most of the factors do not reach the threshold.

In another example, the analysis of the model involves: (i) providing a predictor module with various inputs that correspond to different factors that affect the user, (ii) calculating, based on the inputs and the model, various predicted extents of an allergic reaction of the user, and (iii) determining, based on the various predicted extents of the allergic reaction of the user, effects of the factors; and (iv) selecting the trigger factor based on the effects. The trigger factor is selected such that the effect of the trigger factor reaches a threshold, while the effect of most of the factors does not reach the threshold.

Experiencing stress is generally detrimental to people's health. Reducing the amount of stress a user experiences in day-to-day life typically requires knowing when the user is stressed, for how long, and in what conditions. However, this information is often difficult to come by.

Various embodiments of systems in this disclosure may be utilized to detect a stress level of a user in an automated way based on thermal measurements of the user's face. In particular, the thermal measurements may include Regions Of Interest (ROIs) that includes portions of the periorbital regions (i.e., areas around the eyes). Some examples of systems that may be used to detect the stress level of the user are described in FIG. 29 and FIG. 6.

In one embodiment, a system configured to calculate a stress level based on thermal measurements of periorbital regions of the eyes includes at least a frame, a first thermal camera, a second thermal camera, and a computer.

The frame is configured to be worn on the user's head. Optionally, the frame may be any of the frames of Head-Mounted Systems (HMSs) described in this disclosure, such as a frame of eyeglasses (e.g., frame 15 illustrated in FIG. 29 or frame 90 illustrated in FIG. 6), or a frame of some other HMS, such as a hat, a helmet, and/or part of a system comprising a head-mounted display (e.g., an augmented reality system, a virtual reality system, or a mixed reality system). Various properties of the frame (and other system components) are described in more detail in Section 2.

Each of the first and second thermal cameras is physically coupled to the frame, and is located less than 10 cm away from the user's face (herein "cm" denotes centimeters). Optionally, the first and second thermal cameras are located at least 0.5 cm to the right and to the left of the vertical symmetry axis that divides the face, respectively (e.g., the vertical symmetry axis is illustrated in FIG. 71). Optionally, each of the first and second thermal cameras weighs below 5 g (herein "g" denotes grams). Optionally, each of the first and second thermal cameras is located less than 3 cm away from the face and weighs below 1 g. Optionally, at least one of the first and second thermal cameras is based on at least one of the following uncooled sensors: a thermopile, a microbolometer, and a pyroelectric sensor. Optionally, at least one of the first and second thermal cameras is a focal-plane array (FPA) thermal camera. In one example, the first and second thermal cameras are cameras 30 and 32 in FIG. 29, respectively. In another example, the first and second thermal cameras are cameras 94 and 93 in FIG. 6, respectively.

The first thermal camera is configured to take thermal measurements of a first region of interest ($TH_{ROI1}$), where the first region of interest ($ROI_1$) covers a portion of the periorbital region of the right eye. The second thermal camera is configured to take thermal measurements of a second region of interest ($TH_{ROI2}$), where the second region of interest ($ROI_2$) covers a portion of the periorbital region of the left eye. $TH_{ROI1}$ and $TH_{ROI2}$ may include values that are indicative of the temperature at the $ROI_1$ and $ROI_2$, respectively. Additionally or alternatively, $TH_{ROI1}$ and $TH_{ROI2}$ may include values that are indicative of the change to temperature at the $ROI_1$ and $ROI_2$, respectively. In one embodiment, the first thermal camera does not occlude $ROI_1$ and/or the second thermal camera does not occlude $ROI_2$. In one example, $ROI_1$ is the region denoted by the reference numeral 31 in FIG. 29 and $ROI_2$ is the region denoted by the reference numeral 33 in that figure. In another example, $ROI_1$ is the region denoted by the reference numeral 100 in FIG. 6 and $ROI_2$ is the region denoted by the reference numeral 99 in that figure.

Figure 30:
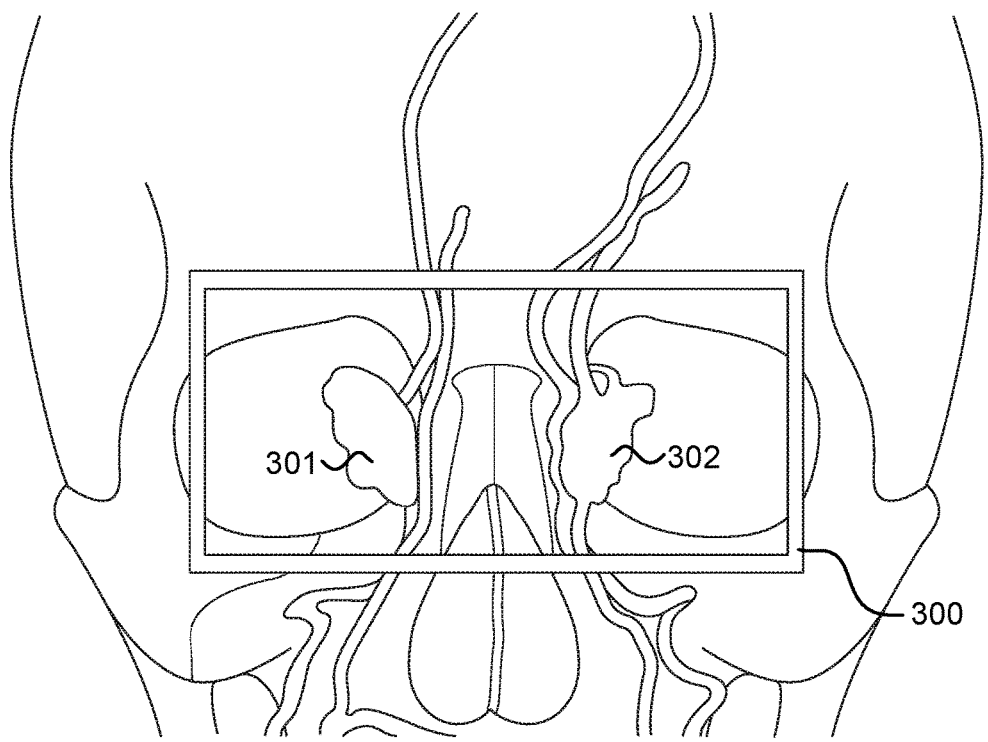
FIG. 30 illustrates the periorbital Region Of Interest (ROI)

Additional details regarding the periorbital region and/or how stress effects the temperature at the periorbital region is given in the following references. The periorbital region of the user's face is discussed, for example, in the reference Tsiamyrtzis, P., Dowdall, J., Shastri, D., Pavlidis, I. T., Frank, M. G., & Ekman, P (2007), "Imaging facial physiology for the detection of deceit", International Journal of Computer Vision, 71(2), 197-214. FIG. 30 illustrates the periorbital ROI, schematically represented by rectangle 300. Regions 301 and 302, referred to as the conduits in the eye corners, schematically represent about 10% of the hottest area within the periorbital ROI, which may be sufficient to detect the "fight or flight" reaction/response during stress (also known as fight or flight syndrome). The reference Pavlidis, I., Levine, J., & Baukol, P. (2000), "Thermal imaging for anxiety detection", In Computer Vision Beyond the Visible Spectrum: Methods and Applications, 2000. Proceedings IEEE Workshop on (pp. 104-109), also shows the periorbital region, together with the nasal area, right and left cheeks, chin area, and the neck area.

According to the definition of a thermal camera as used in this disclosure, the first and second thermal cameras are not in physical contact with their corresponding ROIs. Additionally, as a result of being physically coupled to the frame, the first and second thermal cameras remain pointed at their corresponding ROIs when the user's head makes angular movements. For example, the first and second thermal cameras may remain pointed at their respective ROIs when the user's head makes angular movements that exceed 0.1 rad/sec, 0.5 rad/sec, and/or 2 rad/sec. In another example, the locations of the first and second cameras relative to the user's head do not change even when the user's head performs wide angular and lateral movements, where wide angular and lateral movements include angular movements of more than 60° and lateral movements of more than 1 meter.

It is to be noted that because the first and second thermal cameras are coupled to the frame, challenges faced by other systems known in the art that acquire thermal measurements may be simplified and even eliminated with some of the embodiments described herein. Some of these challenges may involve dealing with complications caused by movements of the user, image registration, ROI alignment, tracking based on hot spots or markers, and motion compensation in the IR domain A more detailed discussion regarding the various types of thermal cameras that may be used, including properties of thermal measurements (e.g., $TH_{ROI1}$ and $TH_{ROI2}$ mentioned above), is provided in Section 1.

Tough the description above involves first and second thermal cameras, in some embodiments, additional thermal cameras may be utilized to take thermal measurements that may be used to detect the physiological response (in addition to $TH_{ROI1}$ and $TH_{ROI2}$). For example, FIG. 29 and FIG. 6 each illustrate more than two thermal cameras). The characteristics of the first and second thermal cameras, and the advantages of utilizing thermal cameras physically coupled to the frame, which are set forth above, are applicable to additional thermal cameras that are utilized in various embodiments.

In one embodiment, in addition to the first and second thermal cameras described above, the system configured to calculate a stress level based on thermal measurements of periorbital regions may include third and fourth thermal cameras that are physically coupled to the frame and configured to take thermal measurements of third and fourth ROIs (denoted $TH_{ROI3}$ and $TH_{ROI4}$, respectively). Optionally, the third region of interest ($ROI_3$) covers a portion of the user's forehead and the fourth region of interest ($ROI_4$) covers a portion of the user's nose.

Figure 29:
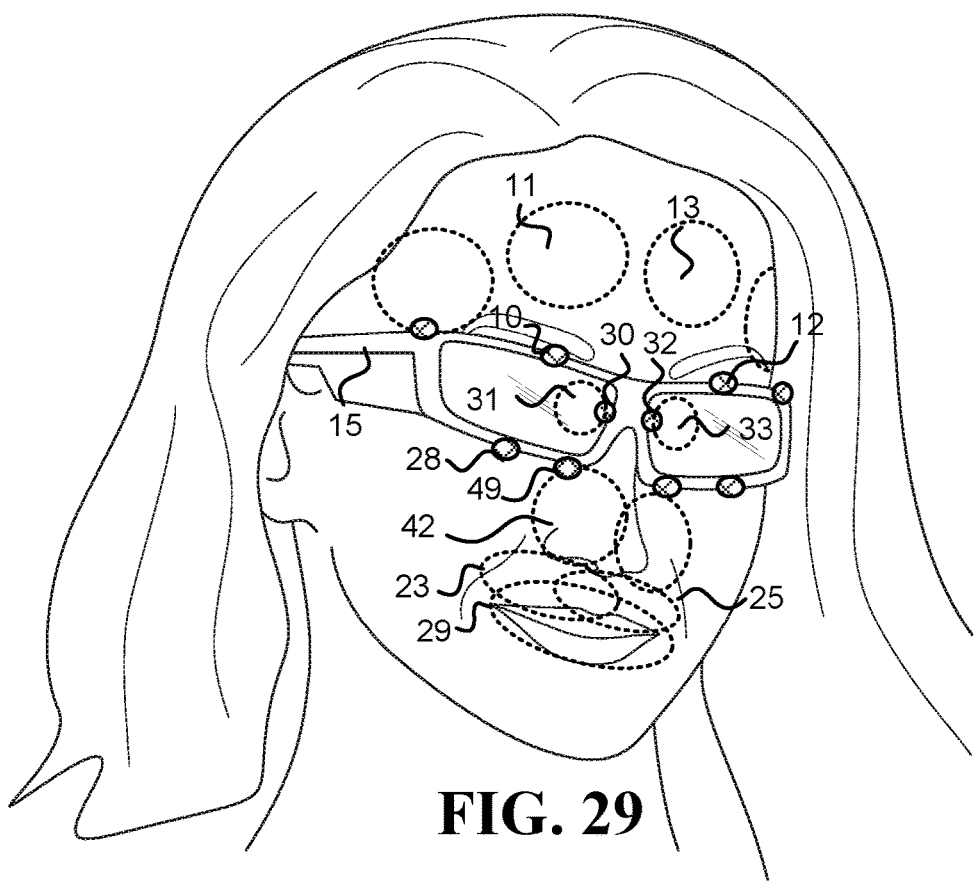
FIG. 29 illustrates an embodiment of a head-mounted system (HMS) configured to collect thermal measurements of Regions Of Interest (ROIs) on the face.

Referring to FIG. 29, in one example, the third thermal camera may be thermal camera 12 and $ROI_3$ may include portion of the region corresponding to reference numeral 13 or thermal camera 10 and $ROI_3$ may include portion of the region corresponding to reference numeral 11. In this example, the fourth thermal camera may be thermal camera 49, and $ROI_4$ may include a portion of the region 42.

In one embodiment, in addition to the first and second thermal cameras described above, the system configured to calculate a stress level based on thermal measurements of periorbital regions may include a third thermal camera that is physically coupled to the frame and configured to take thermal measurements of a third region of interest ($TH_{ROI3}$). Optionally, the third region of interest ($ROI_3$) covers an area below the nostrils. In one example, an area below the nostrils refers to an area that includes portions of the upper lip, the mouth, and/or the chin. In another example, an area below the nostrils refers to an area projected in front of a user's face, which is below the height of the nostrils and intersects with the exhale streams blowing from the user's nostrils and/or mouth. Optionally, $TH_{ROI3}$ may be utilized to determine a value of respiratory parameter of the user as discussed in more detail in Section 5.

Referring to FIG. 29, in one example, the third thermal camera may be thermal camera 49, and $ROI_3$ may include portions of the regions corresponding to reference numerals 23, 25, and/or 29.

Some embodiments of a system that is configured to calculate a stress level include one or more additional thermal cameras (beyond the first and second thermal cameras mentioned above). In one embodiment, the system configured to calculate a stress level based on thermal measurements of periorbital regions includes third and fourth thermal cameras, each of which: weighs below 5 g, is physically coupled to the frame worn on the user's head, and is located less than 10 cm away from the user's face. The third and fourth thermal cameras are configured to take thermal measurements of portions of the right and left cheeks, respectively. The computer, in this embodiment, is further configured to calculate the stress level based on the thermal measurements of the cheeks (in addition to $TH_{ROI1}$ and/or $TH_{ROI2}$). In another embodiment, the system configured to calculate a stress level based on thermal measurements of periorbital regions includes third and fourth thermal cameras, which are each physically coupled to the frame, and are located at least 1 cm to the right and to the left of the vertical symmetry axis that divides the face, respectively. The third and fourth thermal cameras are configured to take thermal measurements of portions of the right and left sides of the user's nose, respectively. The computer, in this embodiment, is further configured to calculate the stress level based on the thermal measurements of the nose (in addition to $TH_{ROI1}$ and/or $TH_{ROI2}$)

The computer is configured to calculate the stress level based on $TH_{ROI1}$ and $TH_{ROI2}$. The computer includes one or more processors and memory. Optionally, the memory stores $TH_{ROI1}$ and $TH_{ROI2}$ prior to them being forwarded to the one or more processors. Optionally, the computer may be at least one of the following: a computer belonging to a device carried by the user, a computer of a smartphone, a personal computer, a remote server (e.g., a cloud-based server), and an analog circuit. In one example, the computer is computer system 400 illustrated in FIG. 72a. In another example, the computer may be computer system 410 illustrated in FIG. 72b. Additional details regarding various types of computers and hardware components that may be utilized to detect the physiological response are given in Sections 2 and 7.

In some embodiments, when the stress level exceeds a certain value, at least one of $TH_{ROI1}$ and $TH_{ROI2}$ reaches a threshold, and when the stress level does not exceed the certain value, both $TH_{ROI1}$ and $TH_{ROI2}$ do not reach the threshold. Optionally, the stress level is proportional to the values of $TH_{ROI1}$ and $TH_{ROI2}$, such that the higher $TH_{ROI1}$ and $TH_{ROI2}$ and/or the higher the change to $TH_{ROI1}$ and $TH_{ROI2}$ (e.g., with reference to a baseline), the higher the stress level. The following is a description of various approaches that may be utilized by the computer to calculate the stress level.

In some embodiments, detecting the stress level may involve utilizing baseline thermal measurement values, most of which were taken when the user was not stressed (or the stress level of the user was below a certain threshold). Thus, detecting the stress level may rely on observing a change to typical temperatures at $ROI_1$ and/or $ROI_2$. In one example, the computer is further configured to calculate the stress level of the user based on at least one of the following values: (i) a difference between $TH_{ROI1}$ and a first baseline value determined based on a first set of previous measurements taken by the first thermal camera, and (ii) a difference between $TH_{ROI2}$ and a second baseline value determined based on a second set of previous measurements taken by the second thermal camera.

As described in more detail elsewhere in this disclosure (e.g., in Section 4), the computer may utilize $TH_{ROI4}$ and/or $TH_{ROI2}$ in various ways in order to detect the stress level of the user. In one embodiment, the computer is configured to compare one or more values derived from $TH_{ROI1}$ and/or $TH_{ROI2}$ to a threshold, and determine whether the threshold is reached. For example, the one or more values may be indicative of the minimum, maximum, and/or average of $TH_{ROI1}$ and/or $TH_{ROI2}$. Optionally, when the threshold is reached, that is indicative of at least a certain stress level of the user. Optionally, the threshold is determined based on thermal measurements of the user taken when the user experienced the certain stress level. Optionally, the threshold is determined based on thermal measurements of one or more other users taken when the one or more other users experienced the certain stress level. Optionally, the computer utilizes multiple thresholds, corresponding to different stress levels, in order to determine a range in which the stress the user is experiencing falls.

In another embodiment, the computer may be configured to determine a similarity between a reference time series corresponding to a certain stress level, and $TH_{ROI1}$ and/or $TH_{ROI2}$ (or a time series derived from $TH_{ROI1}$ and/or $TH_{ROI2}$). Optionally, when a sufficiently high similarity is detected, the computer may interpret that as an indication that the user experienced the certain stress level. Optionally, the reference time series is based on thermal measurements of the user taken when the user was in a certain stress level. Optionally, the reference time series is based on thermal measurements of one or more other users taken when the one or more other users were experiencing the certain stress level. Optionally, the computer utilizes multiple time series, corresponding to different stress levels, in order to determine in what range the stress level of the user falls.

In yet another embodiment, the computer is further configured to generate feature values, and to utilize a model to calculate the stress level based on the feature values. Optionally, at least one of the feature values are generated based on $TH_{ROI1}$ and/or $TH_{ROI2}$. Optionally, the model is generated based on samples, with each sample comprising feature values that are generated based on corresponding measurements of the user taken with the first and second thermal cameras and a label that is indicative of a stress level of the user while the corresponding measurements were taken.

In one example, the computer may utilize thermal measurements of more than two cameras to calculate the stress level. For example, the thermal measurements may include thermal measurements of the forehead, nose, and/or an area below the nostrils. Optionally, in this example, the computer is further configured to: (i) generate feature values based on $TH_{ROI1}$, $TH_{ROI2}$, and $TH_{ROI3}$ mentioned above (or $TH_{ROI1}$, $TH_{ROI2}$, $TH_{ROI3}$, and $TH_{ROI4}$) utilize a model to calculate, based on the feature values, a value indicative of the stress level of the user. Optionally, is a personalized model the model of the user, which is generated based on previous thermal measurements of the user taken while the user had at least two different stress levels according to a predetermined stress scale (e.g., a stress scale known in the art).

Calculating the stress level using the machine learning based model may involve utilization of other values besides thermal measurements. Optionally, at least some of the other values are obtained by sensors that are not the first and second thermal cameras.

In one embodiment, the computer is further configured to receive one or more values that represent a physiological signal of the user and to generate one or more of the feature values used to calculate the stress level based on the one or more values. Some examples of physiological signals that the one or more values may represent include a heart rate, heart rate variability, galvanic skin response, a respiratory rate, and respiratory rate variability. Optionally, the one or more values are obtained utilizing at least one of the following sensors: a photoplethysmogram (PPG) sensor, an electrocardiogram (ECG) sensor, an electroencephalography (EEG) sensor, a galvanic skin response (GSR) sensor, and a thermistor. Optionally, the one or more values include values that are an output of at least one of the sensors mentioned above. Additionally or alternatively, the one or more values include values obtained by processing values generated by at least one of the sensors mentioned above.

In another embodiment, the computer is further configured to receive one or more values that represent an environmental condition and/or a situation of the user that may be considered a confounding factor (e.g., a disruptive facial movement (DFM) or an atypical facial feature). The computer is also configured generate one or more of the feature values used to calculate the stress level based on these one or more values. Some examples of values that may be among the one or more values include an indication of whether the user touched at least one of the eyes, an indication of whether the user is engaged in physical activity (and possibly the type and/or extent of the physical activity). Some additional examples of values that may be among the one or more values include the temperature, humidity, IR radiation level, and a noise level. Optionally, the one or more values are obtained at least one of the following sensors: an accelerometer, a pedometer, a humidity sensor, a miniature radar, a miniature Lidar, an anemometer, an acoustic sensor, and a light meter. Optionally, the one or more values include values that are an output of at least one of the sensors mentioned above. Additionally or alternatively, the one or more values include values obtained by processing values generated by at least one of the sensors mentioned above. In one example, a sensor from among the at least one of the sensors is physically coupled to the frame. In another example, a sensor from among the at least one of the sensors is not physically coupled to the frame.

In yet another embodiment, the computer is further configured to receive one or more values that represent properties describing the user, such as information that may be in a profile of the user. The computer is also configured generate one or more of the feature values used to calculate the stress level based on these one or more values. In one example, the one or more values may include values indicative of the age of the user, the user's gender, the user's marital status, the user's occupation, and/or the user's education level. In another example, the one or more values may include information indicative of the user's health, such as indications of health conditions (e.g., high blood pressure) and/or mental health issues that the user may have.

Additional details regarding detection of a physiological response (of which stress is a certain type) based on thermal measurements such as $TH_{ROI1}$ and $TH_{ROI2}$ mentioned above may be found in this disclosure at least in Section 4.

It is to be noted that many known systems for analyzing physiological responses based on temperature measurements receive series of thermal images composed of pixels that represent temperature measurements. Measuring the temperature (T), as opposed to a temperature change ($\Delta T$), is required in order to perform image registration and run a tracker, which compensates for the movements of the user in relation to the (non-head-mounted) thermal camera and brings the images into precise alignment for analysis and comparison.

However, in various embodiments described herein, thermal cameras are physically coupled to a frame worn on a user's head (e.g., a frame of eyeglasses, a head-mounted display, or a hat). In this configuration, a thermal camera moves with the user's head when the head changes its spatial location, and thus, there may be no need for image registration and/or object tracking. As a result, it is possible to run the image processing and/or signal processing algorithms on a series of thermal measurements taken by each pixel. This increases the accuracy of the system compared to the case where a temperature change ($\Delta T$) is derived from thermal measurements taken by different pixels (after tracking and registration). Optionally, the temperature change at an ROI over time ($\Delta T_{ROI}$) is analyzed in relation to another parameter, such as the stimulus the user is exposed to, and/or other physiological measurements (such as FFG, skin conductance, pulse, breathing rate, and/or blood pressure).

Thermal measurements taken with the first and second thermal cameras may have different properties in different embodiments. In particular, due to the physical coupling of the thermal cameras to the frame, the thermal measurements may exhibit certain measurement errors for the temperature, but when processed, may result in lower errors for the temperature change ($\Delta T$), as discussed below. The following are some examples of embodiments in which thermal measurements taken by the first and second thermal cameras (e.g., $TH_{ROI1}$ and $TH_{ROI2}$) have different accuracies.

In one example, the first and second thermal cameras measure temperature with a possible measurement error above $\pm 1°$ C. and provide temperature change ($\Delta T$) with an error below $\pm 0.1°$ C. Optionally, the computer is configured to calculate a stress level based on $\Delta T$ measured by the first and second thermal cameras.

In another example, the first and second thermal cameras measure temperature with a possible measurement error above $\pm 0.2°$ C. and provide temperature change ($\Delta T$) with an error of below $\pm 0.05°$ C. Optionally, the computer is configured to calculate a stress level based on $\Delta T$ measured by the first and second thermal cameras.

In yet another example, the first and second thermal cameras measure temperatures at $ROI_1$ and $ROI_2$, and the system's nominal measurement error of the temperatures at $ROI_1$ and $ROI_2$ ($ERR_{TROI}$) is at least twice the system's nominal measurement error of the temperature changes at $ROI_1$ and $ROI_2$ ($ERR_{\Delta TROI}$) when the user's head makes angular movements with an angular velocity above 0.1 rad/sec (radians per second). Optionally, the computer is configured to identify a stress level that causes a temperature change at $ROI_1$ and $ROI_2$, which is between $ERR_{TROI}$ and $ERR_{\Delta TROI}$.

In still another example, the first and second thermal cameras measure temperatures at $ROI_1$ and $ROI_2$, and the system's nominal measurement error of the temperatures at $ROI_1$ and $ROI_2$ ($ERR_{TROI}$) is at least five times the system's nominal measurement error of the temperature changes at $ROI_1$ and $ROI_2$ ($ERR_{\Delta TROI}$) when the user's head makes angular movements with an angular velocity above 0.5 rad/sec (radians per second). Optionally, the computer is configured to calculate a value of a stress level that causes a temperature change at $ROI_1$ and $ROI_2$, which is between $ERR_{TROI}$ and $ERR_{\Delta TROI}$.

In some embodiments, the computer may receive an indication of a type of stressor, and utilize the indication to calculate the stress level. Optionally, the indication is indicative of a period and/or duration during which the user was affected by the stressor. In one example, the indication is utilized to select a certain threshold value, which is appropriate for the type of stressor, and to which $TH_{ROI1}$ and/or $TH_{ROI2}$ may be compared in order to determine whether the user is experiencing a certain stress level. Optionally, the certain threshold is determined based on thermal measurements of the user when the user reacted to a stressor of the indicated type. In another example, the indication is utilized to select a certain reference time series, which corresponds to the type of stressor, and to which $TH_{ROI1}$ and/or $TH_{ROI2}$ may be compared in order to determine whether the user is experiencing a certain stress level. Optionally, the certain time series is based on thermal measurements of the user taken when the user reacted to a stressor of the indicated type. In yet another example, the computer generates one or more feature values based on the indication, and the one or more feature values are utilized to calculate the stress level using a machine learning-based model (in addition to feature values generated based on $TH_{ROI1}$ and/or $TH_{ROI2}$). In still another example, the computer may select a window of time based on the indication, which corresponds to the expected duration of stress induced by the type of stressor indicated in the indication. In this example, in order to calculate a value indicative of the stress level of the user, the computer evaluates thermal measurements from among $TH_{ROI1}$ and/or $TH_{ROI2}$ that were taken at a time that falls in the window.

Figure 31:
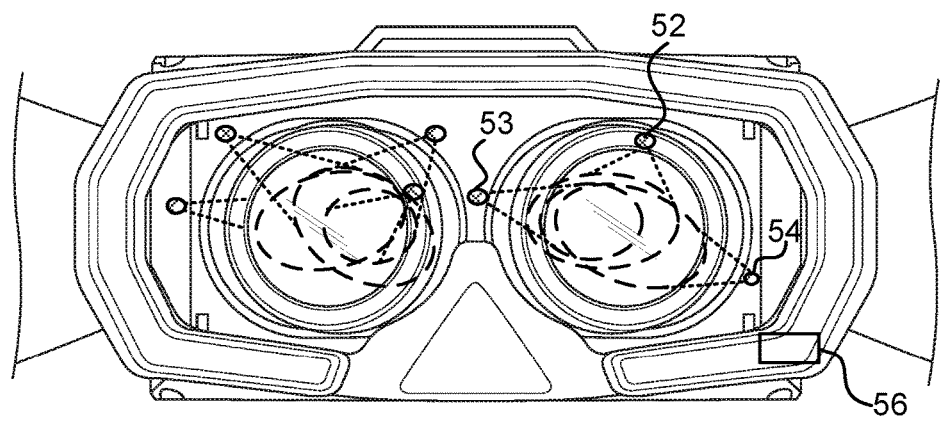
FIG. 31, FIG. 32 and FIG. 33 illustrate various potential locations to connect thermal cameras to frames of various HMSs in order to have at least some of the periorbital ROI within the field of view of one or more of the thermal cameras.

FIG. 31a illustrates one embodiment of a wearable system, such as a head-mounted system (HMS), configured to calculate a stress level of a user. The system includes a frame, thermal cameras and a computer. The frame is configured to be worn on a user's head. The thermal cameras are physically coupled to the frame, are located less than 15 cm away from an eye of the user, and take thermal measurements of regions of interest that cover portions of the periorbital regions of the eyes. Locations 52, 53, and 54 in FIG. 31 illustrate possible positions for locating tiny thermal cameras for measuring the periorbital region around the right eye. Because the thermal cameras are located close to their respective ROIs, they can be small, lightweight, and may be placed in many potential locations having line of sight to their respective ROIs. The computer 56, which may by located on the HMS, worn by the user, and/or remote such as in the cloud, is configured to calculate the stress level based on changes to temperature of the periorbital regions received from the thermal cameras.

Due to the asymmetry of blood vessels in human faces and different shapes of human faces, having at least one thermal camera pointed at the periorbital region of the right eye and at least one thermal camera pointed at the periorbital region of the left eye, may enable a more accurate detection of physiological phenomena such as stress. For example, with some people stress may be manifested by the warming of the periorbital region of the left eye more than the periorbital region of the right eye. Therefore, in some cases, measuring the periorbital regions of both eyes can enable detection of stress that is not possible when measuring only a single periorbital region.

Figure 32:
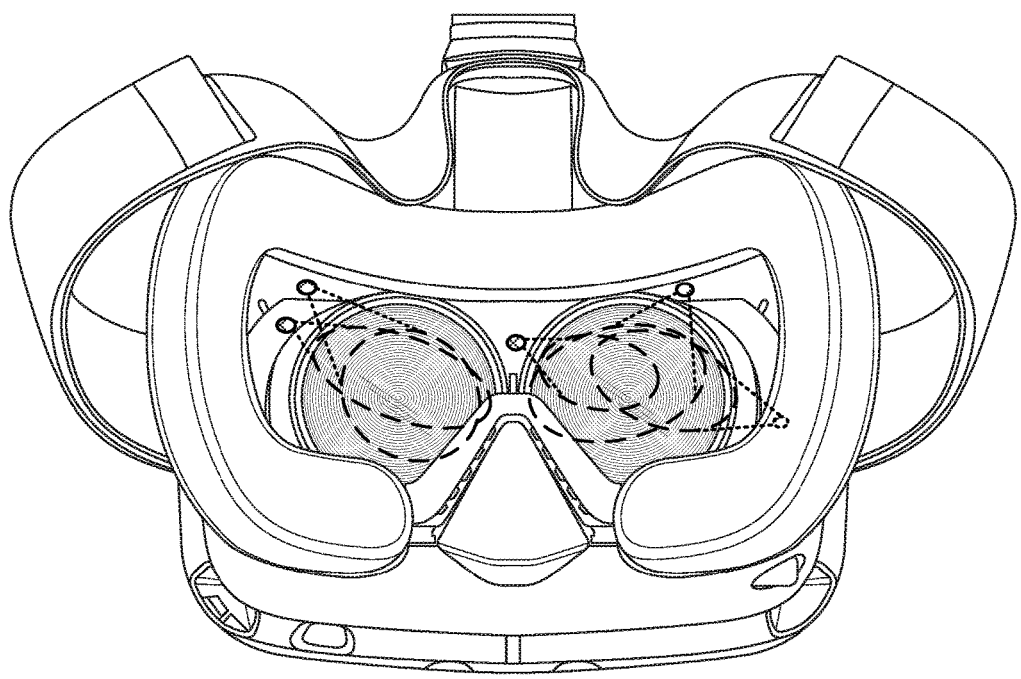
Figure 33:
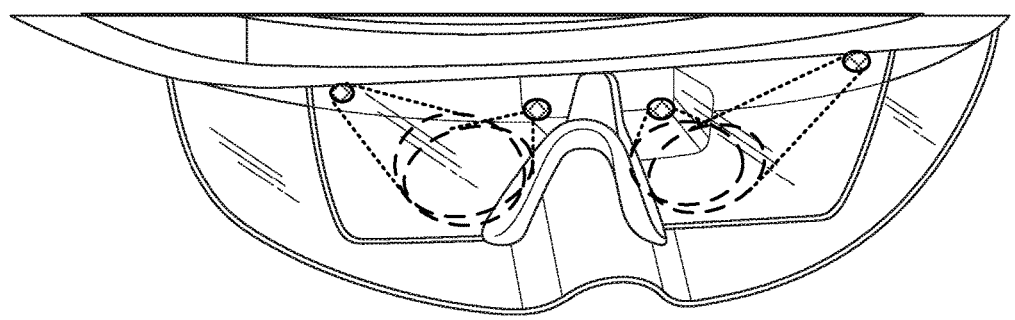

While FIG. 31 and FIG. 32 illustrate possible asymmetric positions for locating the thermal cameras to measure the periorbital regions around the right and left eyes, FIG. 33 illustrates possible symmetric positions for locating the thermal cameras to measure the periorbital regions around the eyes. In some embodiments, using thermal measurements from both symmetric and asymmetric located sensors may improve the system's adaptability to different faces having different proportions.

Due to asymmetrical placement of blood vessels in the face, the thermal emissions of the faces of many people may be asymmetric to a certain extent. That is, the pattern of thermal emission from the left side of the face may be different (possibly even noticeably different) from the pattern of thermal emission from the right side of the face. Thus, for example, the temperature changes at the periorbital regions, in response to experiencing at least a certain level of stress, may be asymmetric for some users (e.g., the region near the left eye may warm more than the region near the right eye). The fact that various embodiments described above include two (or more) thermal cameras that take measurements of ROIs covering different sides of the face (e.g., $ROI_1$ and $ROI_2$ mentioned above) can enable the computer to account for the asymmetry when calculating the stress level based on $TH_{ROI1}$ and $TH_{ROI2}$. Following are some examples of various ways the computer may account for the asymmetry when calculating the stress level based on $TH_{ROI1}$ and $TH_{ROI2}$.

In one embodiment, when comparing $TH_{ROI1}$ and $TH_{ROI2}$, the computer may utilize different thresholds for $TH_{ROI1}$ and $TH_{ROI2}$, in order to determine whether the user experienced a certain level of stress. Optionally, the different thresholds may be learned based on previous $TH_{ROI1}$ and $TH_{ROI2}$, which were measured when the user experienced the certain level of stress.

In another embodiment, the computer may utilize different reference time series to which $TH_{ROI1}$ and $TH_{ROI2}$ are compared in order to determine whether the user experienced the certain level of stress. Optionally, accounting for the asymmetric manifestation of the stress is reflected in the fact that a reference time series to which $TH_{ROI1}$ is compared is different from a reference time series to which $TH_{ROI2}$ is compared.

In yet another embodiment, when the computer utilizes a machine learning-based model to calculate a stress level based on feature values generated based on $TH_{ROI1}$ and/or $TH_{ROI2}$. Optionally, the feature values includes: (i) at least first and second feature values generated based on $TH_{ROI1}$ and $TH_{ROI2}$, respectively; and/or (ii) a third feature value indicative of the magnitude of a difference between $TH_{ROI1}$ and $TH_{ROI2}$. In this embodiment, the computer may provide different results for first and second events that involve the same average change in $TH_{ROI1}$ and $TH_{ROI2}$ but involve different extents of asymmetry between $TH_{ROI1}$ and $TH_{ROI2}$. For example, the computer may determine the user experienced a certain stress level in a first event, in which temperature changes $\Delta T_{ROI1}=0.2°$ C. and $\Delta T_{ROI2}=0.3°$ C. were measured, while it may not determine the user experienced the certain stress level in a second event, in which temperature changes $\Delta T_{ROI1}=\Delta T_{ROI2}=0.25°$ C. were measured.

In still another embodiment, the computer may utilize the fact that asymmetric temperature changes occur when the user experiences stress in order to distinguish between stress and other causes of temperature changes in the periorbital regions. For example, drinking a hot beverage may cause a symmetric warming pattern to the periorbital regions (i.e., $\Delta T_{ROI1} \approx \Delta T_{ROI2}$). Thus, if a symmetric warming pattern is observed, the computer may refrain from identifying the temperature changes as being stress-related. However, if the warming pattern is asymmetric and corresponds to temperature changes in the periorbital regions of the user when the user experiences stress, then the computer may identify the changes in the temperatures being stress-related.

Figure 34A:
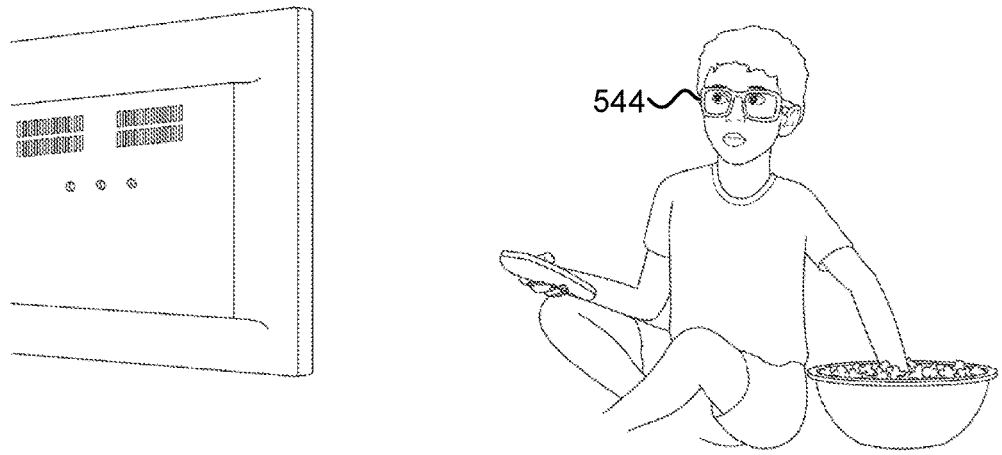
FIG. 34a and FIG. 34b illustrate a scenario in which a user's stress is detected while the user watches a movie.
Figure 34B:
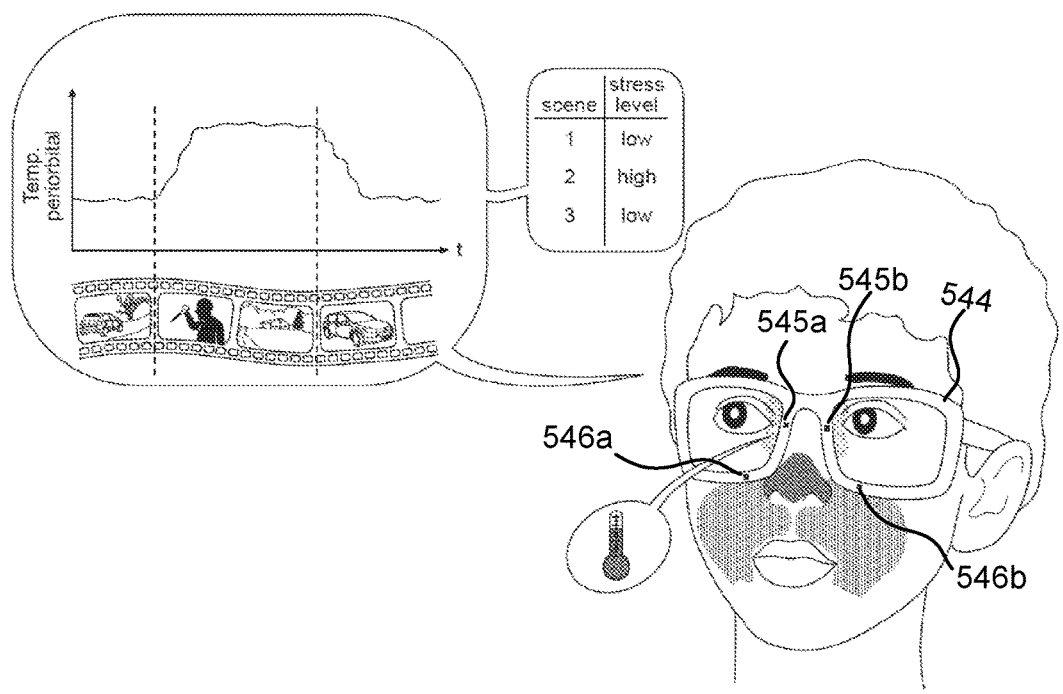

FIG. 34a and FIG. 34b illustrate a scenario in which an embodiment of a system described above may be utilized to detect a user's stress level. FIG. 34a illustrates a child watching a movie while wearing an eyeglasses frame 544 with at least four physically coupled thermal cameras (545a, 545b, 546a, and 546b which hare illustrated in FIG. 34b). FIG. 34b illustrates the thermal cameras mentioned above, which measure ROIs that include the periorbital regions, and optionally the nose and cheeks. These measurements may be used by the system to detect a stress level of the user at different times. The figure further illustrates how the system produces a graph of the stress level detected at different times while different movie scenes were viewed.

In one embodiment, the system configured to calculate a stress level based on thermal measurements of periorbital regions of the eyes includes a display that is physically coupled to the frame, and is configured to present digital content to the user. Optionally, the display does not prevent the first and second thermal cameras from measuring the periorbital regions of the right and left eyes. Optionally, the system further includes a computer configured to change the digital content presented to the user based on the calculated stress level. For example, in response to detecting an elevated stress level, the computer may display calming video (e.g., tranquil nature scenes).

In another embodiment, the system may include an eye tracking module coupled to the frame, which is configured to track the gaze of the user, and an optical see through head-mounted display configured to operate in cooperation with the following components: a visible-light camera configured to capture images of objects the user is looking at, and a computer configured to match the objects the user is looking at with the calculated stress levels.

An eye tracking module is a device for measuring eye positions and/or eye movement. The disclosed embodiments may use any type of suitable eye tracking, such as image processing of video images to extract eye positions, signal processing of reflected IR signals to extract eye positions from changes in the reflections, and/or signal processing of measurements obtained using electrooculography (FOG). In one example, an eye tracking module may utilize image processing to calculate the direction of the gaze based on tracking the center of the pupil, tracking reflections from the front of the cornea, tracking reflections from the back of the eye lens, and/or tracking image features from inside the eye, such as the retinal blood vessels, and follow these features as the eye moves.

In yet another embodiment, the system may include a display coupled to the frame and configured to present video comprising objects, and an eye tracking module coupled to the frame and configured to track the gaze of the user. Optionally, the computer is configured to utilize data generated by the eye tracking module to match the objects the user is looking at with the calculated stress levels.

It is to be noted that there may be a delay between being affected by a stressor and a manifestation of stress as a reaction. In one example, the delay between a stressful event and its manifestation on a portion of the periorbital region is less than 30 seconds, and most of the manifestation diminishes within less than five minutes after the stressful event is over. Thus, in some embodiments, this delay may be taken into account when determining what objects caused the user stress.

In one embodiment, the system further includes a user interface configured to notify the user when the stress level reaches a predetermined threshold. Optionally, the user interface utilizes at least one of the following indications to notify the user: an audio indication, visual indication, and a haptic notification (e.g., via vibrations). Optionally, the greater the change to the temperature of the periorbital regions, the higher the calculated stress level, and the indication is proportional to the stress level. Optionally, the user interface is further configured to provide the user with encouragement not to engage in certain behavior that causes stress. Some examples of behavior that may cause stress include displaying anger, screaming, denigrating others, lying, and cheating. In one example, the encouragement may include evidence based on calculated stress levels of the user, which indicates that conducting in the certain behavior increases stress. In another example, the encouragement may include reminding the user that the certain behavior is against the user's beliefs and/or the certain behavior is contrary to the user's goals, interests, and/or resolutions.

In another embodiment, the system further includes a computer and a user interface configured to suggest the user to partake in at least one of the following activities when the stress level reaches a first predetermined threshold: practice pranayama, physical exercise, listen to brainwave entrainment, and listen to positive loving statements. Optionally, the computer is further configured to suggest the user to stop the activity when the stress level gets below a second predetermined threshold.

Figure 35:
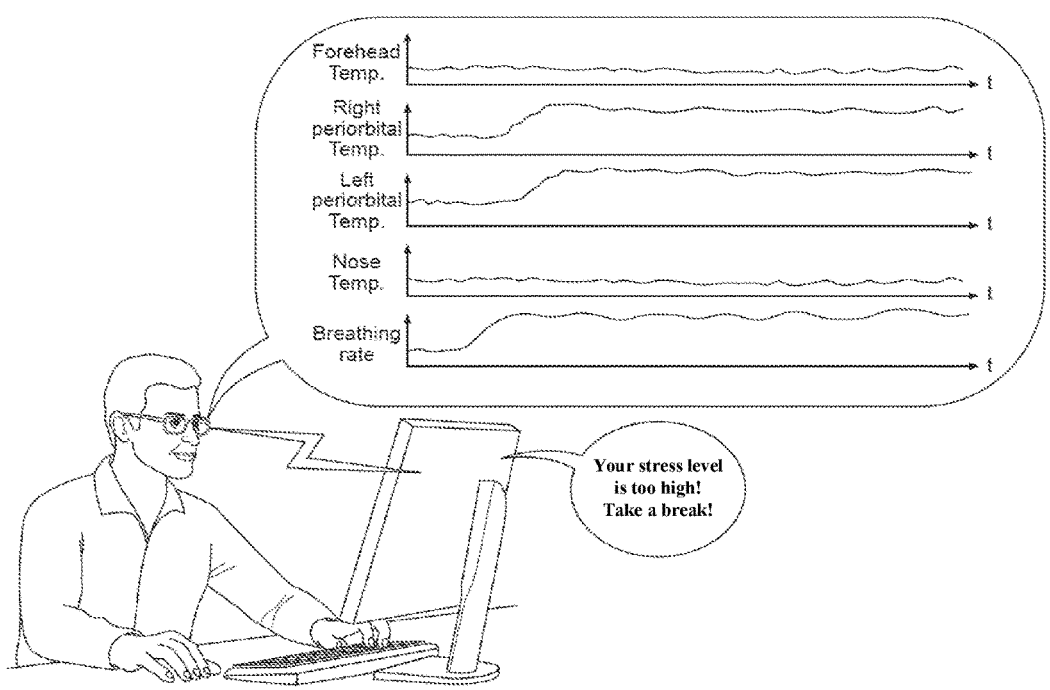
FIG. 35 illustrates a scenario in which an embodiment of a system suggests, based on a set of physiological parameters of a user, that the user to take a break in order to reduce the stress.

FIG. 35 illustrates a scenario in which an embodiment of a system described above measures a set of physiological parameters of a user. Based on the measurements, which include thermal measurements of ROIs on the face, the system suggests to the user to take a break in order to reduce the stress level of the user.

In yet another embodiment, the system further includes a display configured to show the user a video comprising objects, and a documenting module configured to store the calculated stress level associated with the viewed objects.

Figure 36:
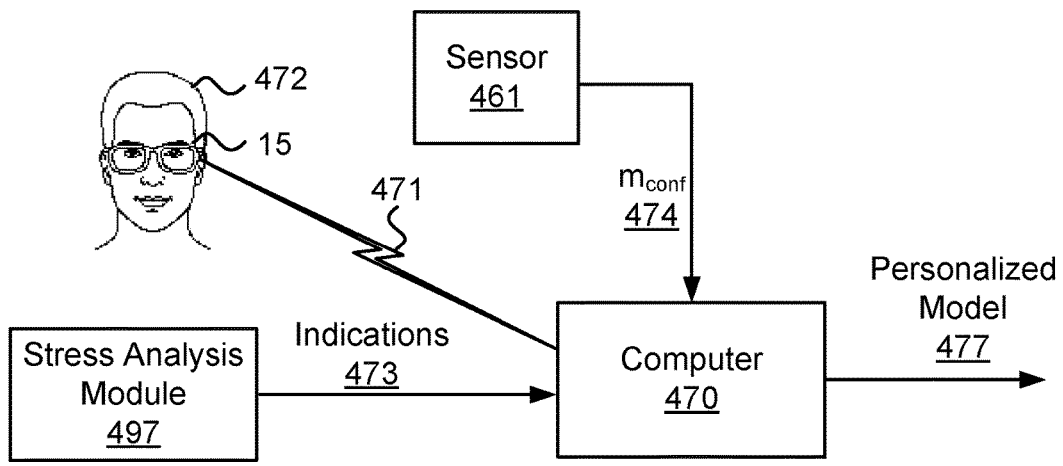
FIG. 36 illustrates an embodiment of a system configured to generate a personalized model for detecting stress based on thermal measurements.

FIG. 36 illustrates an embodiment of a system configured to generate a personalized model for detecting stress based on thermal measurements of the face. The system includes a frame (e.g., the frame 15), first and second thermal cameras, and a computer 470.

The frame and first and second thermal cameras may belong to an HMS from among the HMSs described in this disclosure, such as HMSs illustrated in FIG. 29, FIG. 6, and FIG. 8a. Optionally, each of the first and second thermal cameras is physically coupled to the frame, and is located less than 10 cm away from the user's face. Optionally, the first and second thermal cameras are located at least 0.5 cm to the right and to the left of the vertical symmetry axis that divides the face, respectively. Optionally, each of the first and second thermal cameras weighs below 5 g. Optionally, each of the first and second thermal cameras is located less than 3 cm away from the face and weighs below 1 g. Optionally, at least one of the first and second thermal cameras is based on at least one of the following uncooled sensors: a thermopile, a microbolometer, and a pyroelectric sensor. Optionally, at least one of the first and second thermal cameras is a focal-plane array (FPA) thermal camera.

The first thermal camera is configured to take thermal measurements of a first region of interest (denoted $TH_{ROI1}$), where the first region of interest ($ROI_1$) covers a portion of the periorbital region of the right eye of a user 472. The second thermal camera is configured to take thermal measurements of a second region of interest (denoted $TH_{ROI2}$), where the second region of interest ($ROI_2$) covers a portion of the periorbital region of the left eye of the user 472. In FIG. 36 $TH_{ROI1}$ and $TH_{ROI2}$ of the user 472 are referred to with the reference numeral 471. In one example, $TH_{ROI1}$ of the user 472 are measured using the thermal camera 30 and $TH_{ROI1}$, of the user 472 are measured using the thermal camera 32. In this example, the thermal camera 30 and the thermal camera 32 are physically coupled to the frame 15, which is worn by the user 472. In another example, $TH_{ROI1}$ of the user 472 are measured using the thermal camera 94 and $TH_{ROI2}$ of the user 472 are measured using the thermal camera 93. In this example, the thermal camera 94 and the thermal camera 93 are physically coupled to the frame 90, which is worn by the user 472. A more detailed discussion regarding the various types of thermal cameras that may be used to measure $TH_{ROI1}$ and $TH_{ROI2}$ 471, including properties of thermal measurements, is provided in Section 1.

In one embodiment, the computer 360 is configured to generate samples based on data comprising: (i) $TH_{ROI1}$ and $TH_{ROI2}$ 471, and (ii) indications 473 corresponding to different times, which are indicative of stress levels of the user at the different times. Optionally, each sample comprises: (i) feature values based on $TH_{ROI1}$ and $TH_{ROI2}$ (from among $TH_{ROI1}$ and $TH_{ROI2}$ 471) taken during a certain period, and (ii) a label indicative of a stress level of the user 472. Optionally, at least one of the feature values in a sample may be generated based on other sources of information such as physiological measurements of the user 472, which are not among $TH_{ROI1}$ and $TH_{ROI2}$ 471, and/or measurements of the environment in which the user 472 was in when while $TH_{ROI1}$ and $TH_{ROI2}$ 471 were taken. Optionally, the stress levels indicated in the indications 473 correspond to levels of a known stress level scale. The computer 470 is further configured to generate a model 477 based on the samples, and to provide the model 477 to be used by a system that detects stress based on $TH_{ROI1}$ and $TH_{ROI2}$, such as an embodiment of the system illustrated in FIG. 38.

The term "feature values" is typically used herein to represent data comprising values on which calculations may be performed. In one exemplary embodiment, feature values may be provided to a machine learning based estimator (which may also be called a "predictor") in order to perform calculations on the data utilizing a model (e.g., in order to perform inference). In one example, feature values are data that may be represented as a vector of numerical values (e.g., integer and/or real values), with each position in the vector corresponding to a certain feature. In some examples, in vectors representing feature values of different samples, each position (dimension) in the vectors corresponds to the same feature. Thus, in these examples, different samples may be considered to include data representing the same features, but include different feature values. For example, the vectors may include measurements of temperatures at ROIs, but each sample may include different values of temperatures (at the ROIs). In another example, feature values are stored in a data structure having a predetermined section that identifies the type of data stored in the data structure. For example, the feature values may be stored in the payload of a packet, and a predefined data structure in the packet's header identifies the one or more types of data stored in the payload. Alternatively or additionally, a predefined data structure in the packet's tail may identify the one or more types of data stored in the packet's payload.

The time frame for an indication, from among the indications 473, regarding a stress level of the user 472 may vary between different embodiments. In one embodiment, an indication corresponds to a certain time and is indicative of a stress level of the user 472 at the certain time. In another embodiment, an indication corresponds to a certain period and is indicative of whether at a time that falls within the certain period, the stress level of the user 472 reached a certain value. In yet another embodiment, an indication may be relative to a period during which certain $TH_{ROI1}$ and $TH_{ROI2}$ of the user 472 were taken. Optionally, the indication may be indicative of the stress level of the user 472 at some time that falls within the certain period and/or at some time that falls within temporal proximity of the certain period. For example, if the certain period is [t,t+Δ] then the indication may indicate a stress level of the user 472 at some time during the period [t−δ,t+Δ+δ], where δ may be a period of time such as ten seconds, thirty second, one minute, five minutes, thirty minutes, or some other period of time that is shorter than one hour.

The indications 473 may be generated in different ways, in different embodiments. In one embodiment, at least one of the indications 473 is generated by an entity that observes the user 472, such as a human observer or a software program (e.g., a software agent operating on behalf of the user 472). In another embodiment, one or more of the indications 473 may be provided by the user 472. In one example, the user 472 may provide an indication via a mobile "app" (e.g., by pressing a certain button on a screen of a smartphone). In another example, the user 472 may provide an indication by making a comment that is interpreted by a software agent and/or a program with speech analysis capabilities. In yet another embodiment, one or more of the indications 473 are determined based on analysis of behavior of the user 472. For example, monitoring of the behavior of the user 472 using a camera and/or microphone may indicate that the user 472 is experiencing a certain stress level. And in still another embodiment, one or more of the indications 473 are determined based on physiological signals of the user 472 that are not thermal measurements of one or more ROIs on the face, such as measurements of the user's heart rate and/or brainwave activity.

In one embodiment, the system illustrated in FIG. 36 optionally includes a stress analysis module 497 that is configured to receive descriptions of events corresponding to when at least some of $TH_{ROI1}$ and $TH_{ROI2}$ 471 were taken, and to generate one or more of the indications 473 based on analysis the descriptions. Optionally, the stress analysis module 497 is implemented by the computer 470. Alternatively, it may be implemented using some other computer. Optionally, all of the indications 473 are generated by the stress analysis module 497. Optionally, the stress analysis module 497 may be a module of a software agent operating on behalf of the user 472. The descriptions received by the stress analysis module 497 may include various forms of information. In one example, the descriptions include content of a communication of the user 472, and the stress analysis module 497 utilizes semantic analysis in order to determine whether the communication is indicative a stressful event for the user 472 (e.g., the communication is indicative of something going wrong at work). Optionally, the stress analysis module 497 utilizes a machine learning-based model to calculate based on features derived from the communication, a predicted stress level for the user 472. In another example, the stress analysis module 497 receives images of an event, such as images taken by a visible-light camera coupled to the frame worn by the user 472 and pointed away from the user 472. In this example, the stress analysis module 497 may utilize image analysis to determine whether the event corresponds to a stressful event. Optionally, the stress analysis module 497 utilizes a machine learning-based model to calculate based on features derived from the images, a predicted stress level for the user 472.

The following are some examples of feature values that may be generated for the samples used to generate the model 477. Each sample comprises feature values that are based on $TH_{ROI1}$ and $TH_{ROI2}$ of the user 472 (from among $TH_{ROI1}$ and $TH_{ROI2}$ 471), which were taken during a certain period, and possibly other information sources mentioned below.

In some embodiments, at least one of the feature values generated based on $TH_{ROI1}$ and $TH_{ROI2}$, of the user 472 taken during the certain period include values measured by the first and/or second thermal cameras during the certain period. Optionally, the values measured by the first and/or second thermal cameras may undergo various forms of filtering and/or normalization. In one example, some feature values may be average values of certain sensors (pixels) of the first and/or second thermal cameras during the certain period and/or some feature values may be values measured at certain times during the certain period by the certain sensors. In another example, at least one of the feature values generated based on the first and/or second of the user 472 taken during the certain period may be a time series of values measured by the one or more sensors during the certain period.

In some embodiments, at least one of the feature values generated based on $TH_{ROI1}$ and $TH_{ROI2}$, 471 of the user 472 taken during the certain period include a value of a respiratory parameter of the user 472 during the certain period. Optionally, this feature value may be generated based on additional thermal measurements of other ROIs taken with one or more thermal cameras (which may be different from one or more thermal cameras used to measure $TH_{ROI1}$ and $TH_{ROI2}$ 471). For example, the additional thermal measurements may include thermal measurements of an ROI that includes the nasal and/or mouth regions of the user 472. Some examples of respiratory parameters that may be used as feature values include the following: respiration rate, respiration volume, indications of mouth vs. nasal breathing, exhale (inhale) duration, post-exhale (post-inhale) breathing pause, indication of the dominant nostril, exhale stream shape, exhale stream smoothness, and exhale stream temperature. Additional details regarding respiratory parameters may be found in Section 5.

In addition to $TH_{ROI1}$ and $TH_{ROI2}$ 471 of the user 472, taken during the certain period, in some embodiments, additional sources of information may be utilized to generate one or more feature values that are included in a sample. In one embodiment, the computer 470 may be further configured to receive additional measurements of the user 472 and to generate at least one of the feature values of the sample based on the additional measurements. Optionally, the additional measurements are indicative of one or more of the following signals of the user 472: a heart rate, heart rate variability, brainwave activity, galvanic skin response, muscle activity, and an extent of movement. Optionally, the additional measurements may be obtained utilizing one or more of the various sensors that are described in this disclosure (e.g., in Section 4) which are not thermal cameras.

In one embodiment, the computer 470 may be further configured to receive measurements of the environment in which the user 472 was in while $TH_{ROI1}$ and $TH_{ROI2}$ of the user 472 were taken and to generate at least one of the feature values of a sample based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In one embodiment, the computer 470 is further configured to receive measurements ($m_{conf}$ 474), which are indicative of at least one of the following confounding factors: a skin inflammation on the face of the user, touching the face of the user, a magnitude of thermal radiation directed at the face of the user, and a magnitude of direct airflow on the face of the user. Optionally, $m_{conf}$ 474 are measured utilizing the sensor 461. In one example, the sensor 461 is physically coupled to the frame worn on the user's head. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. In one embodiment, the computer 470 generates at least some of the feature values of a sample based on $m_{conf}$ 474. For example, the feature values of the sample may include values of measurements from among $m_{conf}$ 474, which were taken during the certain period during which $TH_{ROI1}$ and $TH_{ROI2}$ used to generate the sample were taken.

In some embodiments, the samples used to generate the model 477 include samples that were generated based on $TH_{ROI1}$ and $TH_{ROI2}$ of the user 472 taken while the user 472 had different stress levels. In one embodiment, one or more samples that were generated based on $TH_{ROI1}$ and $TH_{ROI2}$ of the user 472 taken while a stress level of the user 472 reached a threshold. Optionally, the stress level is evaluated using one or more known stress level scales. Optionally, a user whose stress level reaches the threshold is considered "stressed". Additionally, in this embodiment, the samples include one or more samples that were generated based $TH_{ROI1}$ and $TH_{ROI2}$ of the user 472, which were taken while a stress level of the user 472 did not reach the threshold. Optionally, a user whose stress level does not reach the threshold is not considered "stressed". Thus, the samples may be utilized to generate a model that can help distinguish between cases in which $TH_{ROI1}$ and $TH_{ROI2}$ of the user 472 are taken while the user 472 is stressed (and/or the user 472 has a certain stress level), and cases in which $TH_{ROI1}$ and $TH_{ROI2}$ of the user 472 are taken while the user 472 is not stressed (and/or the user 472 does not have a certain stress level).

The samples used to generate the model 477 may include samples taken while user 472 was in different environments. In one example, the samples comprise first and second samples that are based on $TH_{ROI1}$ and $TH_{ROI2}$ of the user 472 taken during first and second periods, respectively. Optionally, different environmental conditions prevailed during the first and second periods, which involved one or more of the following differences: (i) the temperature of the environment in which the user 472 was during the first period was at least 10° C. higher than the temperature of the environment in which the user 472 was during the second period; (ii) the humidity level in the environment in which the user 472 was during the first period was at least 30% higher than the humidity level in the environment in which the user 472 was during the second period; and (iii) the user 472 was exposed to at least one of rain, hail, and snow during the first period and the user was not exposed to any of min, hail, and snow during the second period.

Additionally or alternatively, the samples utilized to generate the model 477 may include samples taken while the user 472 was in various situations. In one example, the samples comprise first and second samples that are based on $TH_{ROI1}$ and $TH_{ROI2}$ of the user 472 taken during first and second periods, respectively. Optionally, the user 472 was in different situations during the first and second periods, which involved one or more of the following differences: (i) the user 472 was sedentary during the first period while the user 472 was performing at least one of the following during the second period: walking, conning, and biking; and (ii) the user 472 was indoors during the first period, while the user 472 was outdoors during the second.

Additionally or alternatively, the samples utilized to generate the model 477 may be based on $TH_{ROI1}$ and $TH_{ROI2}$ taken over a long period of time, such as more than a day, more than a week, more than a month, or more than a year. Herein, samples may be considered to be generated based on measurements taken over more than a certain period (e.g., a week) if the samples include at least first and second samples, generated based on measurements taken during first and second periods of time, respectively, such that the difference between when the first period and the second period start is at least as long as the certain period. That is, the starting times first and second periods are at least the certain period apart.

Generating the model 477 may involve one or more of the various computational approaches mentioned in this disclosure for generating a model used to detect a physiological response. In one example, generating the model 477 may involve selecting, based on the samples, a threshold; if a certain feature value reaches the threshold then a certain level of stress of the user is detected. In another example, the computer 470 is configured to utilize a machine learning-based training algorithm to generate the model 477 based on the samples. Optionally, the model comprises parameters of at least one of the following models: a regression model, a model utilized by a neural network, a nearest neighbor model, a model for a support vector machine for regression, and a model of a decision tree.

In some embodiments, the computer 470 may utilize deep learning algorithms to generate the model 477. In one example, the model 477 may include parameters describing multiple hidden layers of a neural network. In one embodiment, when $TH_{ROI1}$ and $TH_{ROI2}$ include measurements of multiple pixels, such as when the thermal camera includes a focal-plane array (FPA), the model 477 may include a convolution neural network (CNN). In one example, a CNN may be utilized to identify certain patterns in the thermal images, such as patterns of temperatures on the forehead that may be indicative of a certain physiological response (e.g., a migraine, stress, or anger). In another embodiment, detecting the stress level may be done based on multiple, possibly successive, measurements. For example, stress may involve a progression of a state of the user (e.g., a gradual warming of certain areas of the forehead). In such cases, detecting the stress level may involve retaining state information that is based on previous measurements. Optionally, the model 477 may include parameters that describe an architecture that supports such a capability. In one example, the model 477 may include parameters of a recurrent neural network (RNN), which is a connectionist model that captures the dynamics of sequences of samples via cycles in the network of nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, generating the model 477 involves altering parameters of another model, which is generated based on $TH_{ROI1}$ and $TH_{ROI2}$ of one or more other users. For example, the computer 470 may utilize the other model as an initial model. As the samples are acquired from measurements of the user 472, the computer 470 may update parameters of the initial model based on the samples. Thus, this process may be considered personalizing a general model according to measurements of the user 472.

It is to be noted that similar to embodiments of the system configured to detect the stress level user, which is discussed further above, some embodiments of the system configured to generate a personalized model for detecting stress may include multiple thermal cameras. Optionally, thermal measurements of the multiple thermal cameras may be utilized to generate feature values of samples similarly to how $TH_{ROI1}$ and $TH_{ROI2}$ 471 are utilized, as described above.

In one example, the system configured to generate a personalized model for detecting stress may include third and fourth thermal cameras, which are physically coupled to the frame and configured to take thermal measurements of third and fourth ROIs (denoted $TH_{ROI3}$ and $TH_{ROI4}$, respectively). Optionally, the third region of interest ($ROI_3$) covers a portion of the user's forehead and the fourth region of interest ($ROI_4$) covers a portion of the user's nose.

In another example, the system configured to generate a personalized model for detecting stress may include a third thermal camera that is physically coupled to the frame and configured to take thermal measurements of a third region of interest ($TH_{ROI3}$). Optionally, the third region of interest ($ROI_3$) covers an area below the nostrils. Optionally, $TH_{ROI3}$ may be utilized to determine a value of respiratory parameter of the user as discussed in more detail in Section 5.

Figure 37:
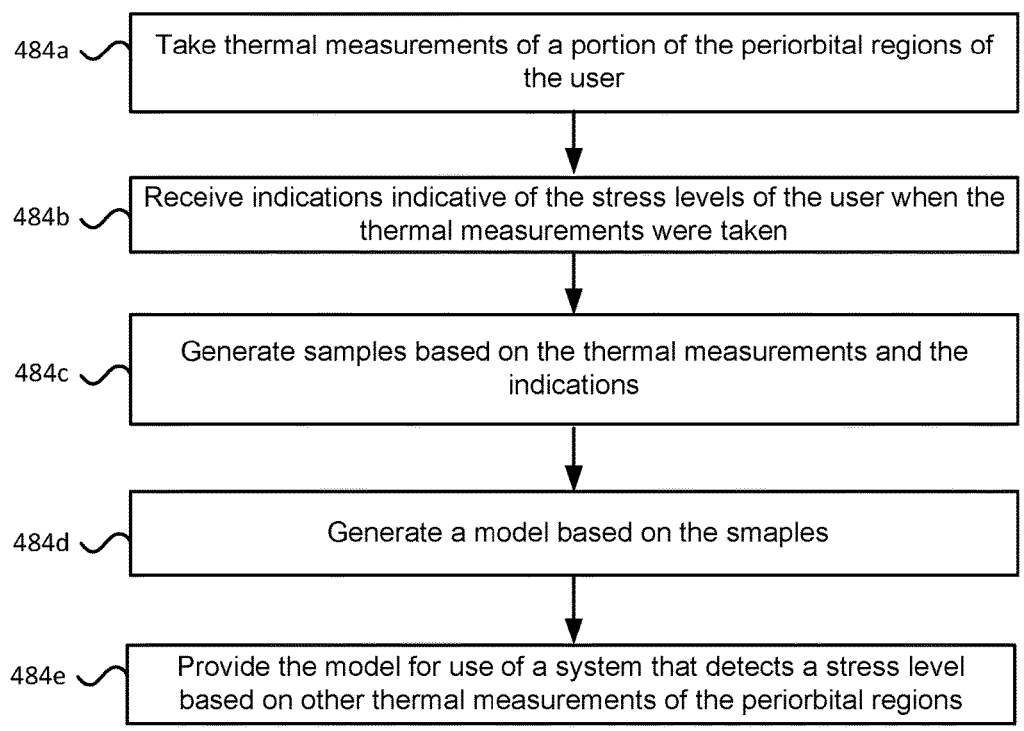
FIG. 37 illustrates an embodiment of a method for generating a personalized model for detecting stress based on thermal measurements.

FIG. 37 illustrates steps that may be performed in one embodiment of a method for generating a personalized model for detecting stress based on thermal measurements of the periorbital regions. The steps described below may be, in some embodiments, part of the steps performed by an embodiment of a system described above, which is illustrated in FIG. 36. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a. Optionally, different steps of the method may be performed utilizing different systems comprising a processor and memory.

In one embodiment, a method for generating a personalized model for detecting stress based on thermal measurements of the periorbital regions includes at least the following steps:

In Step 484a, taking utilizing a first thermal camera, thermal measurements of a first region of interest ($TH_{ROI1}$), where the first region of interest ($ROI_1$) covers a portion of the periorbital region of the right eye of a user, and taking, utilizing a second thermal camera, thermal measurements of a second region of interest ($TH_{ROI2}$), where the second region of interest ($ROI_2$) covers a portion of the periorbital region of the left eye of the user. Optionally, each of the first and second thermal cameras is physically coupled to a frame worn by the user, and is located less than 10 cm away from the user's face. Optionally, the first and second thermal cameras are located at least 0.5 cm to the right and to the left of the vertical symmetry axis that divides the face, respectively. Optionally, each of the first and second thermal cameras weighs below 5 g.

In Step 484b, receiving indications corresponding to different times, which are indicative of stress levels of the user at the different times.

In Step 484c, generating samples based on $TH_{ROI1}$ and $TH_{ROI2}$ of the user and the indications. Each sample comprises feature values based on at least one of $TH_{ROI1}$ and $TH_{ROI2}$, which were taken during a certain period and a label indicative of a stress level of the user at a time that is at most one hour before the start of the certain period and at most one hour after the end of the certain period. Optionally, the label is indicative of a stress level of the user during the certain period.

In Step 484d, generating a model based on the samples. Optionally, generating the model based on the samples involves utilizing a machine learning-based training algorithm. Optionally, generating the model is done by updating parameters of an initial model based on the samples, where the initial model is generated based on previous samples generated from $TH_{ROI1}$ and $TH_{ROI2}$ of one or more other users.

Figure 38:
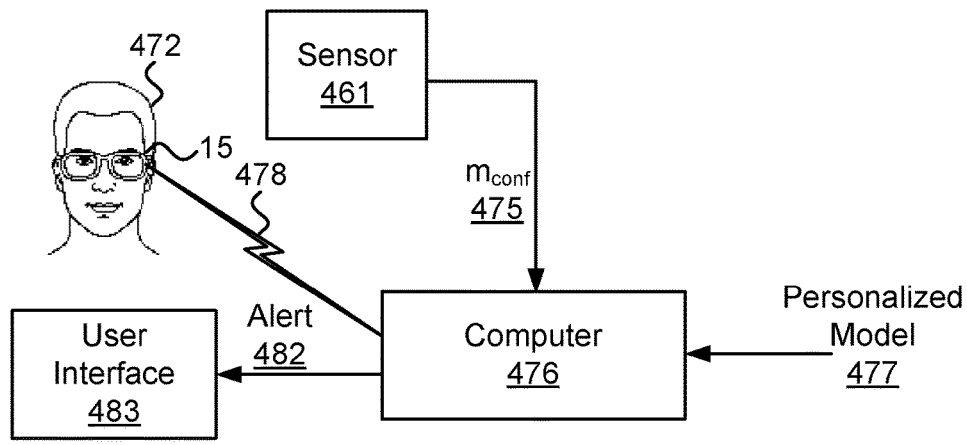
FIG. 38 illustrates an embodiment of a system configured to perform personalized detection of stress.

And in Step 484e, providing the model to be used by a system that detects stress based on $TH_{ROI1}$ and $TH_{ROI2}$, such as the system illustrated in FIG. 38.

In one embodiment, generating the samples in Step 484c may optionally involve receiving additional measurements of the user and generating at least one of the feature values of a sample from among the samples based on the additional measurements. Optionally, the additional measurements are indicative of one or more of the following signals: a heart rate of the user, heart rate variability of the user, brainwave activity of the user, galvanic skin response of the user, muscle activity of the user, and an extent of movement of the user.

In another embodiment, generating the samples in Step 484c may optionally involve receiving values comprising measurements of the environment in which the user was in while $TH_{ROI1}$ and $TH_{ROI2}$ of the user were taken and generating at least one of the feature values of a sample from among the samples based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In one embodiment, the method may optionally include a step of receiving descriptions of events corresponding to when at least some of $TH_{ROI1}$ and $TH_{ROI2}$ were taken, and generating one or more of the indications received in Step 484b based on analysis the descriptions. Optionally, the descriptions may include various forms of information. In one example, the descriptions include content of a communication of the user, and the method optionally includes a step of utilizing semantic analysis in order to determine whether the communication is indicative a stressful event for the user. In another example, the method optionally includes a step involving receiving images of an event, such as images taken by a visible-light camera coupled to the frame worn by the user and pointed away from the user. In this example, image analysis techniques may be utilized to determine whether the event corresponds to a stressful event.

In one embodiment the method may optionally include steps comprising: taking measurements of the user (denoted $m_{conf}$) with a sensor, which are indicative of at least one of the following: a skin inflammation on the face of the user, touching the face of the user, a magnitude of thermal radiation directed at the face of the user, and a magnitude of direct airflow on the face of the user, and generating one or more of the samples also based on $m_{conf}$ (by generating at least one feature value belonging the one or more samples based on $m_{conf}$).

In another embodiment, the method may optionally involve additional thermal measurements of additional thermal cameras and utilizing the additional thermal measurements to generate one or more feature values of the samples used to generate the model. In one example, the method optionally includes steps comprising: taking thermal measurements of portions of the right and left cheeks utilizing third and fourth thermal cameras, respectively, and generating the samples also based on the thermal measurements of the cheeks. Optionally, the third and fourth thermal cameras each: weighs below 5 g, is physically coupled to the frame, and is located less than 15 cm away from the user's face. Additionally, in this example, the third and fourth thermal cameras are located to the right and left of the vertical symmetry axis, respectively. In another example, the method optionally includes steps comprising: taking thermal measurements of portions of the forehead and nose utilizing third and fourth thermal cameras, respectively, and generating the samples also based on the thermal measurements of the forehead and nose. Optionally, the third and fourth thermal cameras each: weighs below 5 g, is physically coupled to the frame, and is located less than 15 cm away from the user's face.

Once the model 477 is generated, it may be utilized to detect stress of the user 472 based on other $TH_{ROI1}$ and $TH_{ROI2}$ of the user 472, which are not among $TH_{ROI1}$ and $TH_{ROI2}$ 471 that were used for generating the model 477. Such utilization of the model 477 is illustrated in FIG. 38, which illustrates an embodiment of a system configured to perform personalized detection of stress based on thermal measurements of the face. One embodiment of the illustrated system includes a frame (e.g., the frame 15), first and second thermal cameras, and a computer 476.

The frame and thermal cameras may belong to an HMS from among the HMSs described in this disclosure, such as HMSs illustrated in FIG. 29, FIG. 6, and FIG. 8a. Optionally, the frame and first and second thermal cameras are the same frame and thermal cameras utilized to take $TH_{ROI1}$ and $TH_{ROI2}$ 471. However, in this embodiment, the frame and first and second thermal cameras take $TH_{ROI1}$ and $TH_{ROI2}$ 478, which are thermal measurements of the periorbital regions region of the right and left eyes of the user 472, which are taken over a certain period. Optionally, the certain period is as at least one second, at least ten seconds, at least one minute, at least five minutes, at least twenty minutes, at least one hour, or at least three hours.

It is to be noted $TH_{ROI1}$ and $TH_{ROI2}$ 478 are similar in their nature to $TH_{ROI1}$ and $TH_{ROI2}$ 471; $TH_{ROI1}$ and $TH_{ROI2}$ 478 are taken using the same hardware setup as $TH_{ROI1}$ and $TH_{ROI2}$ 471. However, $TH_{ROI1}$ and $TH_{ROI2}$ 478 are taken after $TH_{ROI1}$ and $TH_{ROI2}$ 471 were taken, and after the model was generated. Thus, in this embodiment, $TH_{ROI1}$ and $TH_{ROI2}$ 478 were not utilized to generate the model 477.

In one embodiment, the computer 476 is configured to: generate feature values based on $TH_{ROI1}$ and $TH_{ROI2}$ 478 and utilize the model 477 to calculate, based on the feature values, a value indicative of the stress level the user 472. Optionally, the model is generated based on previous $TH_{ROI1}$ and $TH_{ROI2}$ of the user 472 (e.g., $TH_{ROI1}$ and $TH_{ROI2}$ 471), which were taken over more than a week.

The feature values generated based on $TH_{ROI1}$ and $TH_{ROI2}$ 478 are similar in their nature to the feature values generated based on $TH_{ROI1}$ and $TH_{ROI2}$ 471, which were discussed in more detail above. Some examples of feature values that may be generated based on $TH_{ROI1}$ and $TH_{ROI2}$ 478 include: (i) values comprised in $TH_{ROI1}$ and $TH_{ROI2}$ 478 (optionally these values may undergo various forms of filtering and/or normalization), (ii) values of one or more respiratory parameters calculated based on thermal measurements of the face, (iii) values generated based on additional measurements of the user 472 (e.g., measurements of heart rate, heart rate variability, brainwave activity, galvanic skin response, muscle activity, and an extent of movement), and (iv) measurements of the environment in which the user 472 was in while $TH_{ROI1}$ and $TH_{ROI2}$ 478 were taken.

In one embodiment, the computer 476 is configure to utilize the model 477 to calculate, based on the feature values, a value indicative of the stress level of the user 472. In one example, the value is a binary value (e.g., indicating whether the user is in stress/not in stress). In another example, the value is a categorial value (e.g., indicating no stress/low stress/medium stress/or high stress). In still another example, the value is a numerical value (e.g., a value on a scale of 0 to 10). Optionally, responsive to the value indicating that the stress level reaches a threshold, the computer 476 generates an alert 482 that is presented to the user 472 via a user interface 483.

The model 477 may include different types of parameters, in different embodiments. Following are some examples of various possibilities for the model 477 and the type of calculations that are accordingly performed by the computer 476.

In one embodiment, the model 477 comprises parameters of a decision tree. Optionally, in this embodiment, in order to calculate the value indicative of the stress level, the computer 476 simulates a traversal along a path in the decision tree, determining which branches to take based on the feature values. Optionally, the value indicative of the stress level is obtained from a leaf node of the tree that is reached at the end of the path. Additionally or alternatively, the value indicative of the stress level may be calculated based on values of nodes of the tree that are on the traversed path.

In another embodiment, the model 477 comprises parameters of a regression model (e.g., regression coefficients in a linear regression model or a logistic regression model). Optionally, in this embodiment, in order to calculate the value indicative of the stress level, the computer 476 multiplies the feature values (which may be considered a regressor) with the parameters of the regression model.

In yet another embodiment, the model 477 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, in this embodiment, in order to calculate the value indicative of the stress level, the computer 476 provides the feature values as inputs to the neural network, computes the values of the various activation functions and propagates values between layers, and obtains an output from the network, which is the value indicative of the stress level.

In one embodiment, the user interface 483 is configured to present the user 472 with the alert 482 responsive to an indication that the stress level of the user 472 reaches a threshold. In one embodiment, the user interface 483 may comprise a screen on which the alert 482 may be presented (e.g., in the form of text, an image, or video). Optionally, the screen may be part of a display coupled to a frame worn by the user 472 (e.g., a screen of an augmented reality or a virtual reality headset). Additionally or alternatively, the screen may be a display of a device of the user, such as a display of a smartphone or smartwatch. In another embodiment, the alert 482 may involve and audio notification that is generated via the user interface 483. For example, the user interface 483 may include a speaker, earphones, and/or an earbud through which an audio signal is provided to the user 472 in order to make the user 472 aware of the stress level. In still another embodiment, the user interface 483 may be part of a frame worn on the head of the user 472 and the alert 482 involves the frame and/or another device physically and/or communicatively coupled to the frame making noises (e.g., beeping sounds), making a visual indication (e.g., lighting of lights on the frame), and/or providing a tactile indication (e.g., by vibrating).

It is to be noted that some embodiments of the system configured to perform a personalized detection of a stress level of a user include multiple thermal cameras. Optionally, thermal measurements of the multiple thermal cameras may be utilized to generate feature values similarly to how $TH_{ROI1}$ are $TH_{ROI2}$ 478 are utilized, as described above.

In one example, the system configured to perform personalized detection of a stress level may include third and fourth thermal cameras, which are physically coupled to the frame and configured to take thermal measurements of third and fourth ROIs (denoted $TH_{ROI3}$ and $TH_{ROI4}$, respectively). Optionally, the third region of interest (ROI$_3$) covers a portion of the user's forehead and the fourth region of interest (ROI$_4$) covers a portion of the user's nose. Optionally, the computer 476 is further configured to generate one or more feature values based on $TH_{ROI3}$ and $TH_{ROI4}$, which are utilized to calculate the value indicative of the stress level of the user 472.

In another example, the system configured to perform personalized detection of a stress level may include a third thermal camera that is physically coupled to the frame and configured to take thermal measurements of a third region of interest ($TH_{ROI3}$). Optionally, the third region of interest (ROI$_3$) covers an area below the nostrils. Optionally, $TH_{ROI3}$ may be utilized to determine a value of respiratory parameter of the user as discussed in more detail in Section 5.

Optionally, the computer 476 is further configured to generate one or more feature values based on $TH_{ROI3}$, which are utilized to calculate the value indicative of the stress level of the user 472.

In one embodiment, the computer 476 is further configured to receive measurements ($m_{conf}$475), which are indicative of at least one of the following confounding factors: a skin inflammation on the face of the user, touching the face of the user, a magnitude of thermal radiation directed at the face of the user, and a magnitude of direct airflow on the face of the user. Optionally, $m_{conf}$475 are measured utilizing the sensor 461. In one example, the sensor 461 is physically coupled to the frame worn on the user's head. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. In one embodiment, the computer 476 generates at least some of feature values based on $m_{conf}$475 and utilizes the at least some feature values to calculate the value indicative of the extent of the stress level. For example, at least some of the feature values may include values of measurements from among $m_{conf}$475, which were taken during the certain period during which $TH_{ROI1}$ and $TH_{ROI2}$ 478 were taken.

It is to be noted that since the model 477 is personalized for the user 472, when such a model is generated for different users, it may lead to different detections of stress, even when provided with similar $TH_{ROI1}$ and $TH_{ROI2}$ of the users. In one example, first and second models generated based on previous $TH_{ROI1}$ and $TH_{ROI2}$ of first and second different users, respectively. Responsive to utilizing the first model, a first value is calculated based on first feature values generated based on $TH_{ROI1}$ and $TH_{ROI2}$ of the first user, which is indicative of a first stress level. Responsive to utilizing the second model, a second value is calculated based on second feature values generated based on $TH_{ROI1}$ and $TH_{ROI2}$ of the second user, which is indicative of a second stress level. In this example, $TH_{ROI1}$ and $TH_{ROI2}$ of the first user indicate a greater temperature change at the periorbital regions of the first user compared to the change at the periorbital regions of the second user indicated by $TH_{ROI1}$ and $TH_{ROI2}$ of the second user. However, in this example, the first stress level is lower than the second stress level.

Figure 39:
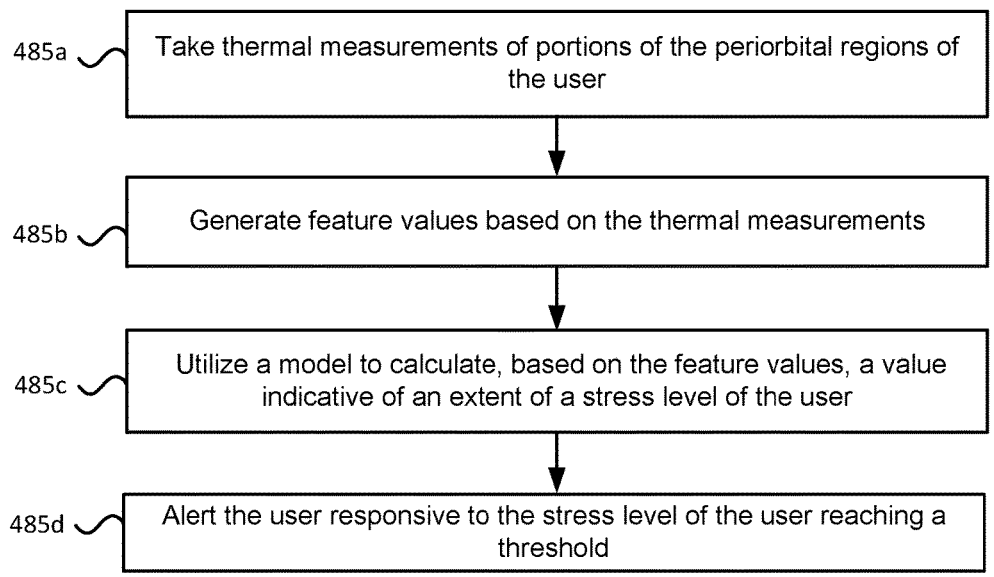
FIG. 39 illustrates an embodiment of a method for performing a personalized detection of stress.

FIG. 39 illustrates steps that may be performed in one embodiment of a method for performing a personalized detection of stress. The steps described below may be, in some embodiments, part of the steps performed by an embodiment of a system described above, which is illustrated in FIG. 38. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a or FIG. 72b. Optionally, different steps of the method may be performed utilizing different systems comprising a processor and memory.

In one embodiment, a method for performing a personalized detection of stress includes at least the following steps:

In Step 485a, thermal measurements of a first region of interest ($TH_{ROI1}$), where the first regions of interest ($ROI_1$) covers a portion of the periorbital region of the right eye of the user, and thermal measurements of a second region of interest ($TH_{ROI2}$), where the second region of interest ($ROI_2$) covers a portion of the periorbital region of the left eye of the user. Optionally, $TH_{ROI1}$ and $TH_{ROI2}$ are taken utilizing first and second thermal cameras that are physically coupled to a frame worn by the user. Optionally, each of the first and second thermal cameras is located less than 10 cm away from the user's face. Optionally, the first and second thermal cameras are located at least 0.5 cm to the right and to the left of the vertical symmetry axis that divides the face, respectively. Optionally, each of the first and second thermal cameras weighs below 5 g.

In Step 485b, generating feature values based on $TH_{ROI1}$ and $TH_{ROI2}$, of the user.

And in Step 485c, utilizing a model to calculate, based on the feature values, a value indicative of the stress level the user. The model used in this step is generated based on previous $TH_{ROI1}$ and $TH_{ROI2}$ of the user. Optionally, the model is the model 477.

In one embodiment, the method described above may optionally include Step 485d, involving alerting the user responsive to the stress level of the user, which is calculated in Step 485c, reaching a threshold.

Generating the feature values in Step 485bc may involve, in some embodiments, additional sources of information, which may be utilized in addition to $TH_{ROI1}$ and $TH_{ROI2}$ of the user. Additional discussion regarding various sources of information which may be utilized to detect a physiological response in general, which are applicable to detecting stress, are provided in Section 4.

In one embodiment, Step 485b optionally involves receiving additional measurements of the user taken during the same period $TH_{ROI1}$ and $TH_{ROI2}$ of the user were taken and generating at least one of the feature values based on the additional measurements. Optionally the additional measurements are indicative of one or more of the following signals: a heart rate of the user, heart rate variability of the user, brainwave activity of the user, galvanic skin response of the user, muscle activity of the user, and an extent of movement of the user.

In another embodiment, Step 485b optionally involves receiving measurements of the environment in which the user was in while $TH_{ROI1}$ and $TH_{ROI2}$ of the user were taken and generating at least one of the feature values based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In one embodiment the method may optionally include steps comprising: taking measurements of the user (denoted $m_{conf}$) with a sensor, which are indicative of at least one of the following: a skin inflammation on the face of the user, touching the face of the user, a magnitude of thermal radiation directed at the face of the user, and a magnitude of direct airflow on the face of the user, generating one or more feature values based on $m_{conf}$ and utilizing the one or more feature values to calculate the value indicative of the stress level of the user.

In another embodiment, the method may optionally involve taking additional thermal measurements of additional thermal cameras and utilizing the additional thermal measurements to generate one or more feature values of used to calculate the value indicative of the stress level of the user. In one example, the method optionally includes steps comprising: taking thermal measurements of portions of the right and left cheeks utilizing third and fourth thermal cameras, respectively, and generating the samples also based on the thermal measurements of the cheeks. Optionally, the third and fourth thermal cameras each: weighs below 5 g, is physically coupled to the frame, and is located less than 15 cm away from the user's face. Additionally, in this example, the third and fourth thermal cameras are located to the right and left of the vertical symmetry axis, respectively. In another example, the method optionally includes steps comprising: taking thermal measurements of portions of the forehead and nose utilizing third and fourth thermal cameras, respectively, and generating the samples also based on the thermal measurements of the forehead and nose. Optionally, the third and fourth thermal cameras each: weighs below 5 g, is physically coupled to the frame, and is located less than 15 cm away from the user's face.

Some aspects of this disclosure involve monitoring a user overtime with a Head-Mounted System (HMS) that includes one or more thermal cameras that are pointed to one or more Regions Of Interest (ROIs) on the user's face. One application for which the thermal measurements of the one or more ROIs may be useful is to detect the stress level of the user. Analysis of these detections combined with information regarding factors that affected the user at different times can reveal what factors may be stressor that may increase the stress level of the user.

Some examples of factors that may be considered stressors for certain users include being in certain locations, interacting with certain entities, partaking in certain activities, or being exposed to certain content. Having knowledge of which factors are likely stressors can help the user avoid the stressors and/or take early measures to alleviate the effects of stress.

Figure 40:
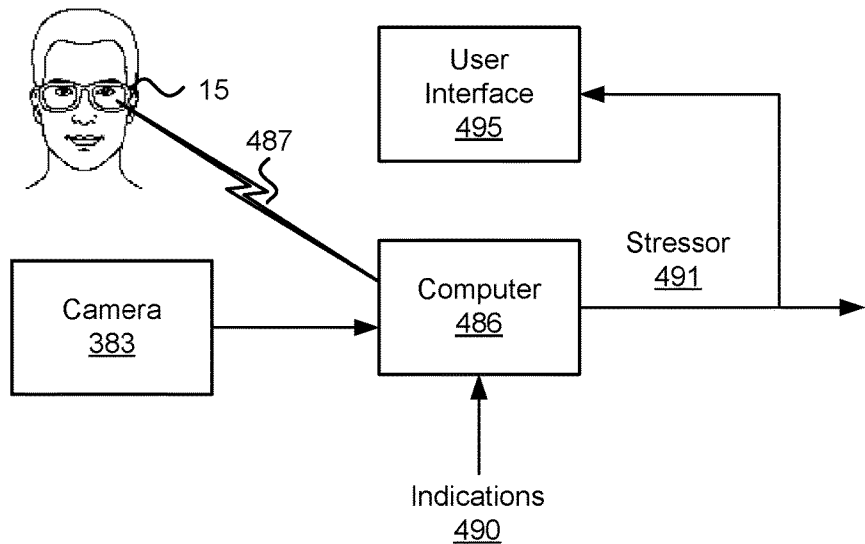
FIG. 40 illustrates an embodiment of a system configured to select a stressor.

FIG. 40 illustrates an embodiment of a system configured to select a stressor for a user. The system includes at least first and second thermal cameras and a computer 486. The system may optionally include a frame that is worn on the user's head, a camera 383, and/or a user interface 495.

The frame is configured to be worn on the user's head. Optionally, the frame may be any of the frames of a Head-Mounted System (HMS) described in this disclosure, such as a frame of eyeglasses (e.g., frame 15 illustrated in FIG. 29 or frame 90 illustrated in FIG. 6), or a frame of some other HMS, such as a hat, a helmet, and/or part of a system comprising a head-mounted display (e.g., an augmented reality system, a virtual reality system, or a mixed reality system). Various properties of the frame (and other system components) are described in more detail in Section 2.

Each of the first and second thermal cameras is physically coupled to the frame, and is located less than 10 cm away from the user's face. Optionally, the first and second thermal cameras are located at least 0.5 cm to the right and to the left of the vertical symmetry axis that divides the face, respectively. Optionally, each of the first and second thermal cameras weighs below 5 g. Optionally, each of the first and second thermal cameras is located less than 3 cm away from the face and weighs below 1 g. Optionally, at least one of the first and second thermal cameras is based on at least one of the following uncooled sensors: a thermopile, a microbolometer, and a pyroelectric sensor. Optionally, at least one of the first and second thermal cameras is a focal-plane array (FPA) thermal camera. In one example, the first and second thermal cameras are cameras 30 and 32 in FIG. 29, respectively. In another example, the first and second thermal cameras are cameras 94 and 93 in FIG. 6, respectively.

The first thermal camera is configured to take thermal measurements of a first region of interest ($TH_{ROI1}$), where the first region of interest ($ROI_1$) covers a portion of the periorbital region of the right eye. The second thermal camera is configured to take thermal measurements of a second region of interest ($TH_{ROI2}$), where the second region of interest ($ROI_2$) covers a portion of the periorbital region of the left eye. $TH_{ROI1}$ and $TH_{ROI2}$ of the user are denoted in the figure with the reference numeral 487 and referred to herein as "$TH_{ROI1}$ and $TH_{ROI2}$ 487". $TH_{ROI1}$ and $TH_{ROI2}$ 487 may include values that are indicative of the temperature at the $ROI_1$ and $ROI_2$, respectively. Additionally or alternatively, $TH_{ROI1}$ and $TH_{ROI2}$ 487 may include values that are indicative of the change to temperature at the $ROI_1$ and $ROI_2$, respectively. In one embodiment, the first thermal camera does not occlude $ROI_1$ and/or the second thermal camera does not occlude $ROI_2$. In one example, $ROI_1$ is the region denoted by the reference numeral 31 in FIG. 29 and $ROI_2$ is the region denoted by the reference numeral 33 in that figure. In another example, $ROI_1$ is the region denoted by the reference numeral 100 in FIG. 6 and $ROI_2$ is the region denoted by the reference numeral 99 in that figure.

$TH_{ROI1}$ and $TH_{ROI2}$ 487 are provided, in one embodiment, to the computer 486, which is configured to calculate, based on $TH_{ROI1}$ and $TH_{ROI2}$ 487, values that are indicative of stress levels of the user at different times. Optionally, $TH_{ROI1}$ and $TH_{ROI2}$ 487 comprise thermal measurements taken while the user had at least two different stress levels according to a predetermined stress scale. $TH_{ROI1}$ and $TH_{ROI2}$ 487 comprise thermal measurements taken over at least a week.

In order to calculate the values indicative of the stress levels of the user, the computer 486 may implement one or more of the various approaches for detecting stress described in this disclosure. In one embodiment, the computer 486 may execute operations described in this disclosure that may be used to detect a stress level based on $TH_{ROI1}$ and $TH_{ROI2}$ For example, in one embodiment, the computer 486 implements operations described above, which are attributed to the computer 476. Additionally or alternatively, the computer 486 may implement one or more of the various approaches to detecting a physiological response (of which stress is a specific type), which are described in Section 4.

Depending on the embodiment, values that are indicative of stress levels of the user at different times may expresses stress levels using different types of values. In one example, the values include binary values (e.g., indicating whether the user was stressed or not). In another example, the values may include categorial values (e.g., indicating whether the extent of stress falls into one of the following categories: no stress/low stress/medium stress/or high stress). In yet another example, the values include numerical values (e.g., values on a scale of 0 to 10, with 10 corresponding to the highest stress level).

In some embodiments, the system configured to select a stressor may include additional thermal cameras besides the first and second thermal cameras described above. Optionally, measurements taken by the additional thermal cameras may be utilized by the computer 486 to calculate the values that are indicative of stress levels of the user at different times. In one example, the system includes third and fourth thermal cameras that are physically coupled to the frame and configured to take thermal measurements of a portion of the user's forehead and thermal measurements of a portion of the user's nose. In another example, the system includes a thermal camera that is physically coupled to the frame and configured to take thermal measurements of a portion of the area below the user's nostrils ($TH_{ROI3}$)

The computer 486 is further configured, in one embodiment, to receive indications 490 of factors that affected the user at various times. Optionally, each of the indications 490 is indicative of a time during which a certain factor, from among the factors, affected the user. Additionally, the computer 486 is further configured to select a stressor 491, from among the factors, based on the indications 490 and the values that are indicative of stress levels of the user at different times.

In one embodiment, the indications 490 include a list of periods of time during which various factors affected the user. Optionally, the indications 490 are provided via a data structure and/or a queryable system that provides information for different points in time about which of the factors affected the user at the points in time. There are various types of factors that may be indicated by the indications 490. The following are some examples of types of factors that may be analyzed in some embodiments.

In one embodiment, one or more of the factors may relate to various locations the user was at (e.g., work, school, doctor's office, in-laws house, etc.) and/or to various activities the user partakes in (e.g., driving, public speaking, operating machinery, caring for children, choosing clothes to wear, etc.)

In another embodiment, one or more of the factors may relate to entities with which the user interacts. For example, an entity may be a certain person, a person with a certain role (e.g., a teacher, a police officer, a doctor, etc.), a certain software agent, and/or an avatar (representing a person or a software agent).

In yet another embodiment, one or more of the factors may relate to situations in which the user is in, which can increase stress. For example, a situation may be being unemployed, having financial difficulties, being separated after being in a relationship with another person, being alone, or awaiting an important event (e.g., an exam, a job interview, or results of an important medical test). In another example, a situation may relate to a physical condition of the user, such as being sick or suffering from a certain chronic disease. Optionally, when the situations described above are applicable to another person who the user cares about (e.g., a spouse, child, parent, or close friend), then those situations, which relate to the other person, may be considered factors that can lead to stress in the user.

In still another embodiment, one or more of the factors may relate to the user's behavior (e.g., each of the factors may correspond to a certain behavioral characteristic). For example, at a certain time, the user's behavior may be considered argumentative, manipulative, deceptive, and/or untruthful; for some users, behaving in a way that may be characterized as having one or more of the traits mentioned above may increase the stress level.

Herein, stating that a factor affected the user at a certain time does not imply a certain minimal extent to which the factor affected user. Rather, the term "affected" in this context should be interpreted as having the potential to have an effect on the user. In practice, many factors may not cause a noticeable or measurable effect on the user (with respect to the stress level). Stating that a certain factor affected a user at a certain time implies that the factor is relevant to a certain time. For example, if the user visited a doctor's office at a certain time then that factor may be considered to affect the user. However, if the user did not visit a doctor's office that day, then visiting the doctor's office is not a factor that affected the user that certain time.

When a user is affected by one or more factors, in some embodiments, the stress level of the user may depend on quantitative aspects of the factors. In some examples, the extent a factor effects the user's stress level may depend on the amount of time the factor affected the user (e.g., the duration the user spent at a certain location) and/or the magnitude of the factor (e.g., the extent to which an argument was heated which may be expressed by the level of noise in peoples shouting). In other examples, the number of times the user was affected by a factor may influence the effect of the factor on the stress level of the user. In some case, being affected by a factor multiple times may greatly increase stress (e.g., after multiple failures in exams). In other cases, being affected multiple times may decrease the effect of the factor on the stress level because of habituation.

In some embodiments, the indications 490 include values that quantify how much at least some of factors affected the user. For example, these values may corresponds to durations the factors affected the user, the number of times the factors affected the user, and/or intensity of factors. Optionally, the indications 490 are indicative of whether certain factors reach a threshold. For example, if a factor reaches the threshold it is considered to affect the user (e.g., if the user spends at least a certain amount of time in a location), and if it does not reach the threshold it is not considered to affect the user (e.g., when the user spent less than the certain amount of time at the location).

The stressor 491 is a factor that is correlated with an increase in the stress level of the user. Additionally, in some embodiments, the stressor 491 may be a factor that may be considered a direct cause of the increase in the stress level of the user. When considering how being affected by factors relates to the stress level of the user, an effect of the stressor 491 is higher than effects of most of the factors.

The effect of a factor may be considered a measure of how much the factor influences the stress level the user. This can range from no influence on the stress level of the user to a profound influence on the stress level. More specifically, in one embodiment, the effect of a factor is a value indicative of the average extent of change to the stress level of the user at a time t+Δ after being affected by the factor at time t. Here, Δ corresponds to the typical time it may take the stress to manifest itself after being affected by the factor. This time may range from a short period e.g., several seconds or minutes, to several hours, or even twelve hours or more. In one example, Ms at least one minute. In another example, Δ is at most twelve hours.

In some embodiments, the effect of the stressor 491 is not lower than the effect of any of the other factors. And in some embodiments, the effect of the stressor 491 is higher than the effect when the stressor 491 does not affect the user. For example, based on the values indicative of the stress levels of the user and indications 490, an average stress level of the user at a time t+Δ when the user was affected by the stressor 491 at some time during [t, t+Δ], is greater than an average stress level of the user at a time t+Δ when the user was not affected by the stressor at any time during [t, t+Δ].

There are various ways in which the computer 486 may select, based on the indications 490 and the values indicative of the stress levels of the user, the stressor 491 from among the multiple factors being considered. The following are some examples of approaches the computer 486 may employ in order to analyze the indications 490 and the values indicative of the stress levels of the user and select, based on the analysis, the stressor 491.

In some embodiments, the computer 486 performs a direct analysis of the effect of each of the factors in order to identify factors that have a large Optionally, the effect of each factor is indicative of the extent to which it increases the stress level of the user. Optionally, the effect of each factor is calculated by determining, based on the indications 490, times at which the user was affected by each factor, and observing the stress level of the user at one or more times that are up to a certain period Δ later (where Δ may be a period of time up to 12 hours long or shorter, e.g., several seconds or minutes). In one example, Δ is ten seconds, thirty seconds, or one minute. In another example, Δ is one minute, ten minutes, or one hour.

In one embodiment, a stress level (or change to the stress level) following being affected by a factor is the maximum stress level that is detected from the time t the user was affected by a factor until the time t+Δ. In another example, the stress level (or change to the stress level) following being affected by a factor is the extent of the stress level and/or change to the stress level that is detected at a time t+Δ (when the user was affected by a factor at time t). Optionally, the extent may be normalized based on a quantitative value representing how much the user was affected by the factor. Optionally, the stress level may be normalized with respect to a stress level detected prior to being affected by the factor. Optionally, the effect of each factor from among the factors is calculated based on the stress levels (or changes to the stress levels) following being affected by the factor, as described above. In one example, the effect may be an average of the observed extents. In another example, the effect may be a value indicative of the proportion of the observed extents that reach a threshold (which may signify that the user is stressed at those times).

Following a calculation of the effects of the factors, in one embodiment, the computer 486 selects a factor from among the factors as the stressor 491. Optionally, the stressor 491 is a factor from among the factors that has a maximal effect (i.e., there is no other factor from among the factors that has a higher effect). Optionally, the stressor 491 is a factor from among the factors that has an effect that reaches a threshold, while the effect of most of the factors does not reach the threshold.

In one embodiment, in order to increase confidence in the selection of the stressor, the stressor 491 is selected based on at least a certain number of times in which the user was affected by the stressor 491. For example, the certain number may be at least 3, at least 5, or at least 10 different times. Thus, in this embodiment, factors that did not affect the user at least the certain number of times are not considered stressors.

In some embodiments, the computer 486 is configured to generate a machine learning-based model based on the indications 490 and the values indicative of the stress levels of the user, and to select the stressor 491 based on an analysis of the model. Optionally, the computer 486 generates samples used to train the model.

In one embodiment, the samples used to train the model may correspond to different times, with each samples corresponding to a time t+Δ including feature values and a label (target value) indicative of the stress level of the user at the time t+Δ (where depending on the embodiment Δ may have a value between several seconds, to minutes, and even several hours). Optionally, the label of each sample is determined based on one or more of the values that are indicative of the stress level at the time t+Δ. Optionally, the feature values are based on indications, from among the indications 490, which are indicative of the extent various factors affected the user during a period [t, t+Δ]. Optionally, some of the feature values are indicative of the extent to which the factors affected the user (e.g., durations and/or numbers of times) and/or how long before t+Δ the factors affected the user.

Each of the samples described above may be considered to represent a snapshot of factors that affected the user during a certain period and a label that is indicative of the stress level of the user following being affected by those factors. Given multiple such samples, a machine learning training algorithm can be utilized to generate a model for a predictor module that can predict the stress level at a certain time based on feature values that describe the factors that affected the user during a certain period of time leading up to a certain time. For example, if the model is a regression model, the predictor module may perform a dot product multiplication between a vector of regression coefficients (from the model) and a vector of the feature values in order to calculate a value corresponding to the predicted stress level of the user at the certain time.

When such a predictor module is capable of predicting stress level of the user based on the feature values described above, this may mean that the model captures, at least to some extent, the effects of at least some of the factors on the stress level of the user. Thus, extracting this information about the effects of the factors can help to select a factor that has a large effect on the user.

Generating the model based on the samples described above may involve utilizing one or more of various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

In some embodiments, the predictor module may be provided multiple inputs representing the factors that affected the user at different points of time. For example, the predictor module may be provided with a series of vectors of feature values, each representing the factors that affect the user during a period (e.g., during a minute, five minutes, thirty minutes, an hour, or six hours). In these embodiments, the predictor module may have a capability to store state information of previous inputs corresponding to earlier times when it comes to predict the stress level of the user at a certain time. One example of a predictor module with such a capability is a predictor module that is based on a recurrent neural network Once the model is generated, in some embodiments, it is analyzed by the computer 486 in order to determine the effects of one or more of the factors on the stress level of the user. Depending on the type of model that was generated, this analysis may be performed in different ways.

In one embodiment, the computer 486 is further configured to perform the analysis of the model by evaluating parameters of the model that correspond to the factors. Optionally, the computer 486 selects as the stressor 491 a certain factor that has a corresponding parameter that is indicative of an effect that reaches a threshold while effects indicated in parameters corresponding to most of the factors do not reach the threshold. In one example, the model may be a linear regression model in which each factor correspond to a regression variable. In this example, a magnitude of a value of a regression coefficient may be indicative of the extent of the effect of its corresponding factor. In another example, the model may be a nave Bayes model in which various classes correspond to stress levels (e.g., a binary classification model that is used to classify a vector of feature values to classes corresponding to "stressed" vs. "not stressed"). In this example, each feature value may correspond to a factor, and the class conditional probabilities in the model are indicative of the effect of each of the factors on the user.

In another embodiment, the computer 486 is further configured to perform an analysis of the model, which may be characterized as "black box" analysis. In this approach, the predictor module is provided with various inputs that correspond to different factors that affect the user and calculates, based on the inputs and the model, various predicted stress levels of the user. The various inputs can be used to independently and individually increase the extent to which each of the factors affects the user. This type of the model probing can help identify certain factors that display an increase in the predicted stress level, which corresponds to an increase in the extent to which the factors affect the user (according to the model). Optionally, the stressor 491 is a factor for which a positive correlation is observed between increasing the extent to which the factor affects that user, and the predicted stress level of the user. Optionally, the stressor 491 is selected from among the factors, responsive to identifying that that: (i) based on a first subset of the various predicted stress levels of the user, the effect of the stressor reaches a threshold, and (ii) based on a second subset of the various predicted stress levels of the user, the effects of most of the factors does not reach the threshold.

The indications 490 may be received from various sources. In one embodiment, the user may provide at least some of the indications 490 (e.g., by inputting data via an app and/or providing vocal annotations that are interpreted by a speech analysis software). In other embodiments, at least some of the indications 490 are provided by analysis of one or more sources of data. Optionally, the computer 486 generates one or more of the indications 490 based on the analysis of data obtained from the one or more sources. The following are some examples of sources of data that may be utilized to identify factors that affected the user at different times.

In one embodiment, the system configured to select a stressor may optionally include the camera 383 that is configured to capture images of the surroundings of the user. Optionally, the camera 383 may be coupled to a frame worn on the user's head. Optionally, the camera 383 may belong to a device of the user (e.g., a smartphone). Optionally, the camera 383 is not coupled to the user (e.g., a webcam or a camera that is part of CCTV system). There are various ways in which the camera 383 may be utilized to identify factors that affect the user. In one example, camera-based systems such as OrCam (http://www.orcam.com/) may be utilized to identify various objects, products, faces, and/or recognize text.

Other sensors may be used, in some embodiments, to identify factors that affect the user, in addition to, or instead of, the camera 383. Examples of such sensors include microphones, accelerometers, thermometers, pressure sensors, and/or barometers, which may be used to identify factors that may affect the user, such as identifying what the user is doing (e.g., by analyzing movement patterns) and/or under what conditions (e.g., by analyzing ambient noise, temperature, and/or pressure).

Measurements of the environment that user is in are another source of information for determining what factors affect the user at a certain time. Optionally, at least some of the measurements of the environment are performed using a device of the user that contains one or more sensors that are used to measure or record the environment. Optionally, the measurements are received from a third party (e.g., a website that provides environmental information for various locations). Optionally, these measurements may be indicative of one or more of the following: temperature, pressure, humidity, and/or particle counts for various types of chemicals or compounds (e.g. pollutants and/or allergens).

Some examples of additional sources of information that may be utilized by the computer 486 to identify factors that affect the user at different times include various IoT (Internet of Things) devices. For example, such devices may provide information when they are moved and/or utilized. Additionally or alternatively, communications of the user (e.g., email, text messages, voice conversations, and/or video conversations) may also be analyzed, in some embodiments, to provide context and/or to identify factors that affect the user. Similarly, the user's calendar and/or schedule, as well as billing information, may provide information that may be used in some embodiments to identify factors that affect the user.

There are various approaches known in the art for identifying, indexing, and/or searching for factors that may affect the user, which may be utilized in embodiments described herein. In one example, identifying factors that affect the user may be done according to the teachings described in U.S. Pat. No. 9,087,058 titled "Method and apparatus for enabling a searchable history of real-world user experiences", which describes a searchable history of real-world user experiences of a user utilizing data captured by a mobile computing device. In another example, identifying factors that affect the user may be done according to the teachings described in U.S. Pat. No. 8,762,102 titled "Methods and systems for generation and rendering interactive events having combined activity and location information", which describes identification of events based on sensor data of mobile devices.

In some embodiments, identifying factors that affect the user is done, at least in part, by a software agent operating on behalf of the user (e.g., the computer 486 may run the software agent). Optionally, a software agent operating on behalf of a user may participate in the process of selecting which factors are relevant to an event and/or assigning weights to the factors. For example, the software agent may narrow down a list of possible factors provided by another program and select certain ones that best represent factors that are relevant to stress.

Knowledge of the stressor 491 may be utilized for various purposes. Optionally, the knowledge of the stressor 491 is utilized by a software agent operating on behalf of the user in order to better serve the user. In some embodiments, information about the stressor 491 is provided to the user via a user interface 495. Optionally, the user interface 495 comprises a display of a device of the user, such as a smartphone or a head-mounted display coupled to a frame worn by the user (e.g., the frame 15). Optionally, the user interface 495 comprises speakers (e.g., a speaker of earbuds or headphones worn by the user).

The user interface 495 may be utilized on a day-to-day basis to warn the user when the stressor 491 is detected. For example, the computer 486 may provide real-time indications of factors that affect the user. Upon detecting that those factors include the stressor 491, the user interface 495 notifies the user about the stressor 491 in order for the user to take action. Optionally, taking action involves reducing the exposure to of the stressor 491 (e.g., by leaving a certain location or ceasing a certain activity). Optionally, taking action involves performing actions aimed at reducing stress such as breathing exercises.

In one embodiment, a software agent may identify that the user is going to be affected by the stressor 491 in the future (e.g., by analyzing the user's calendar schedule and/or communications). Responsive to such an identification the software agent may suggest to the user, via the user interface 495, to perform various exercises (e.g., breathing exercises) and/or remind the user to prepare for the stressor 491 in order to reduce its effect on the user.

Figure 41:
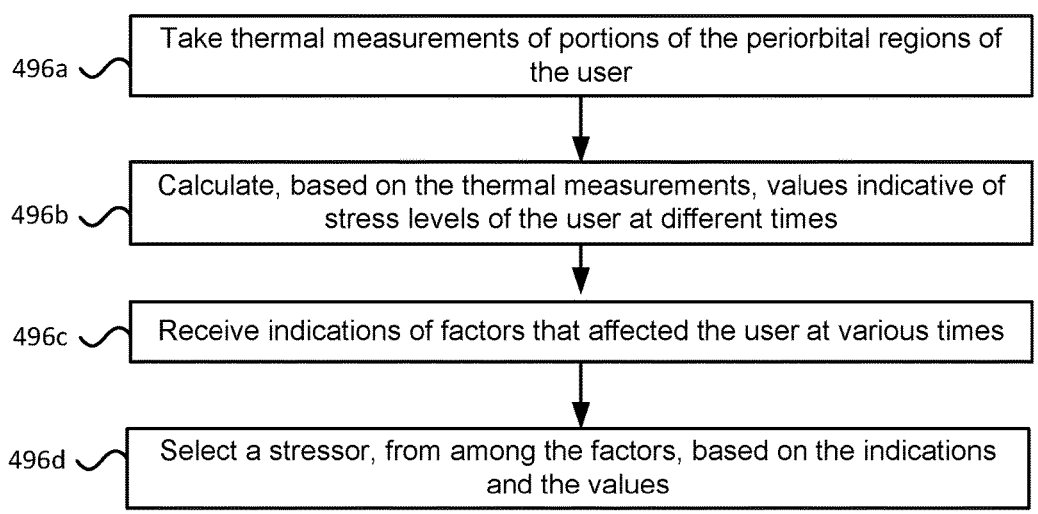
FIG. 41 illustrates an embodiment of a method for selecting a stressor.

FIG. 41 illustrates steps that may be performed in one embodiment of a method for selecting a stressor. In some embodiments, the steps described below may be part of the steps performed by an embodiment of a system described above, which is illustrated in FIG. 40. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a. Optionally, different steps of the method may be performed utilizing different systems comprising a processor and memory.

In one embodiment, a method for selecting a stressor includes at least the following steps:

In Step 496a, taking, utilizing a first thermal camera thermal measurements of a first region of interest ($TH_{ROI1}$), and taking, utilizing a second thermal camera thermal measurements of a second region of interest ($TH_{ROI2}$) Where the first region of interest ($ROI_1$) covers a portion of the periorbital region of the right eye of a user, and the second region of interest ($ROI_2$) covers a portion of the periorbital region of the left eye of the user. Optionally, each of the first and second thermal cameras is physically coupled to the frame, and is located less than 10 cm away from the user's face. Optionally, the first and second thermal cameras are located at least 0.5 cm to the right and to the left of the vertical symmetry axis that divides the face, respectively. Optionally, each of the first and second thermal cameras weighs below 5 g.

In Step 496b, calculating, based on $TH_{ROI1}$ and $TH_{ROI2}$ of the user, values indicative of stress levels of the user at different times.

In Step 496c, receiving indications of factors that affected the user at various times. Optionally, each indication is indicative of a time during which a certain factor, from among the factors, affected the user. Optionally, the indications received in this step are the indications 490.

And in Step 496d, selecting the stressor, from among the factors, based on the indications received in Step 496d and the values calculated in Step 496b. Optionally, the stressor has a higher effect than most of the factors, where the effect of a factor is the average stress level of the user at a time t+Δ after being affected by the factor at time t. Optionally, Δ is at most twelve hours. In one example, Δ is ten seconds, thirty seconds, or one minute. In another example, Δ is one minute, ten minutes, or one hour.

In one embodiment, the method optionally includes a step that involves taking images of the surroundings of the user and generating at least some of the indications based on analysis of the images. Optionally, the images are taken with the camera 383 and/or the indications are generated by the computer 486.

Selecting the stressor in Step 496d may involve various calculation in different embodiments. Optionally, the various calculations are performed by the computer 486. In one embodiment, Step 496d involves calculating, based on the indications received in Step 496d and the values calculated in Step 496b, an effect of each of the factors, and selecting as the stressor a factor with a maximal calculated effect. In another embodiment, Step 496d involves generating a machine learning based model based on the indications and values, and selecting the stressor based on an analysis of the model. Optionally, the model may include parameters of one or more of the following: a regression model (e.g., a regression model), a nave Bayes model, a Bayes network, a support vector machine for regression, a decision tree, and a neural network model.

In one example, the analysis of the model involves evaluating parameters of the model that correspond to the factors and selecting as the stressor a certain factor that has a corresponding parameter that is indicative of an effect that reaches a threshold while effects indicated in parameters corresponding to most of the factors do not reach the threshold.

In another example, the analysis of the model involves: (i) providing a predictor module with various inputs that correspond to different factors that affect the user, (ii) calculating, based on the inputs and the model, various predicted stress levels of the user; and (iii) determining, based on the various predicted stress levels of the user, effects of the factors (i.e., the extent to which the factors contribute to the user's stress); and (iv) selecting the stressor based on the effects. The stressor is selected such that the effect of the stressor reaches a threshold, while the effect of most of the factors does not reach the threshold.

In one embodiment, the method may optionally involve taking additional thermal measurements of additional thermal cameras and utilizing the additional thermal measurements to calculate the values indicative of the stress levels of the user. In one example, the method optionally includes steps comprising: taking thermal measurements of portions of the right and left cheeks utilizing third and fourth thermal cameras, respectively, and generating the samples also based on the thermal measurements of the cheeks. Optionally, the third and fourth thermal cameras each: weighs below 5 g, is physically coupled to the frame, and is located less than 15 cm away from the user's face. Additionally, in this example, the third and fourth thermal cameras are located to the right and left of the vertical symmetry axis, respectively. In another example, the method optionally includes steps comprising: taking thermal measurements of portions of the forehead and nose utilizing third and fourth thermal cameras, respectively, and generating the samples also based on the thermal measurements of the forehead and nose. Optionally, the third and fourth thermal cameras each: weighs below 5 g, is physically coupled to the frame, and is located less than 15 cm away from the user's face.

It is to be noted that with little modifications, the system illustrated in FIG. 40 and the method illustrated in FIG. 41 may be utilized, in some embodiments, to detect a calming factor that reduces the user's stress, rather than one that increases it. In particular, instead of selecting a stressor that has a large effect (or maximal effect) on the user, a factor that has a large negative effect on the stress level may be selected. Optionally, in the event that a high stress level of the user is detected, the calming factor may be suggested to the user (in order to reduce the user's stress level).

Alertness, anxiety, and even fear are often experienced by people perpetrating illegal activities during their illicit actions. Since those symptoms are produced by the sympathetic system, they usually cannot be totally controlled, and thus constitute a powerful biometric that is difficult to conceal. This biometric can provide valuable clues to security systems monitoring access to critical and/or sensitive data about potential suspects who are often not typically detected with identification biometrics, such as first time offenders.

When a user experiences elevated feelings of alertness, anxiety, or fear, increased levels of adrenaline regulate blood flow. Redistribution of blood flow in superficial blood vessels causes changes in local skin temperature that is apparent in the user's face, where the layer of flesh is very thin. The human face and body emit radiation both in the mid-infrared (3-5 μm) and far-infrared (8-12 μm) bands, thus mid-infrared and far-infrared thermal sensors can sense temperature variations in the face and trigger a process for detecting illegal activity. Such phenomena can be utilized to offer secure access to sensitive data in a way that can detect misuse, and/or intentions of misuse, of the sensitive data.

In some embodiments, a user is permitted to access sensitive data through an HMD equipped with a thermal camera that measures temperature variations on the user's face while he/she access the sensitive data. Optionally, access through the HMD is the only permitted access to the sensitive data. This way the user is under surveillance each time he/she accesses the sensitive data, and optionally there is no way for the user to access the sensitive data without being monitored by the system. Thus, if the user has an irregular physiological response while being exposed to the sensitive data, this event can be detected by the system.

In one embodiment, a system configured to detect an irregular physiological response of a user while the user is exposed to sensitive data includes at least a head-mounted display (HMD), a thermal camera, and a computer. Optionally, the thermal camera is coupled to a frame worn on the user's head. Optionally, the HMD is coupled to the frame. In one embodiment, the system further includes a repository (e.g., a database), which is configured to store records comprising sensitive data to which the user may be exposed.

The HMD is configured to expose sensitive data to a user who wears the HMD. For example, the HMD may display text, images, and/or video. Optionally, the HMD may be a virtual reality display, an augmented reality display, or a mixed-reality display. Optionally, the HMD is designed such that only a user who wears the HMD can view the sensitive data displayed on the HMD.

The thermal camera is configured to take thermal measurements of a region of interest ($TH_{ROI}$) on the user's face while the user is exposed to the sensitive data. The thermal camera weighs below 10 g, is physically coupled to the HMD, and is located less than 15 cm away from the face. In some embodiments, the system may include additional thermal cameras, which are coupled to the frame, and take thermal measurements of additional ROIs on the user's face. In some embodiments, the thermal camera may weigh below 5 g and/or is located less than 5 cm away from the user's face.

The computer is configured to calculate, based on certain $TH_{ROI}$ taken while the user is exposed to a certain sensitive data, an indication indicating whether the user experienced the irregular physiological response while being exposed to the certain sensitive data. In one example, the indication comprises one or more values that describe the physiological response (e.g., the temperature at the ROI and/or the change in temperature at the ROI). In another example, the indication comprises one or more values that describe a probability and/or extent to which $TH_{ROI}$ are to be considered irregular.

In some embodiments, the computer may be the computer 400 or the computer 410, illustrated in FIG. 72*a* and FIG. 72*b*, respectively. In one embodiment, the processor may be physically coupled to the frame. In another embodiment, the processor may be apart from the frame. For example, the processor may belong to a server.

In one embodiment, the certain $TH_{ROI}$ are taken during a certain window of time that depends on the type of irregular physiological response (e.g., a certain stress level and/or a certain emotional response). Optionally, the window is at least five seconds long, at least thirty seconds long, at least two minutes long, at least five minutes long, at least fifteen minutes long, at least one hour long, or is some other window that is longer than one second. Optionally, during the time the user is exposed to sensitive data, $TH_{ROI}$ from multiple windows may be evaluated (e.g., using a sliding window approach), which include a window that contains a period during which the certain $TH_{ROI}$ were taken.

In some embodiments, detecting the irregular physiological response is done based on additional inputs such as thermal measurements taken by additional cameras (which may cover additional ROIs), and/or values of physiological signals and/or behavioral cues of the user such as heart rate, respiration rate, galvanic skin response, movements, facial expressions, and/or brainwave activity. Optionally, the values of physiological signals and/or behavioral cues are obtained utilizing sensors that are not thermal cameras.

What corresponds to an "irregular physiological response" may vary between different embodiments. The following are some examples of criteria and/or ways of determining whether a physiological response is considered an "irregular physiological response".

In one example, the irregular physiological response involves the user experiencing stress that reaches a certain threshold. Optionally, for most of the time the user wears the HMD, the stress level detected for the user does not reach the certain threshold. In another example, the irregular physiological response involves the user experiencing at least a certain level of one or more of the following emotions: anxiety, fear, and anger. Optionally, for most of the time the user wears the HMD, the extent to which the user experiences the one or more emotions does not reach the certain level. In yet another example, an irregular physiological response corresponds the atypical measurement values. For example, if a probability density function is generated based on observed measurements of the user, measurements with a low probability, such as a probability value that is lower than the probability of 97% of the observed measurements, may be considered atypical.

In order to detect the irregular physiological response, the processor may utilize $TH_{ROI}$ in various ways, as described below. Optionally, detection of the irregular physiological response is done while taking into account various factors that may influence the user's measured physiological responses, such as the user's emotional state (e.g., whether the user is anxious, distraught, or calm), the environmental conditions (e.g., the temperature, humidity level, and/or level of oxygen in the air), and/or the type of sensitive data that the user accesses.

In one embodiment, the processor is configured to compare one or more values derived from $TH_{ROI}$ to a certain threshold, and determine whether the threshold is reached (which is indicative of an occurrence of the irregular physiological response). Optionally, the threshold is determined based on thermal measurements of the user (e.g., taken when the user had an irregular physiological response). Optionally, the threshold is determined based on baseline thermal measurements of the user, and the threshold represents a difference of a certain magnitude relative to the baseline measurements. Optionally, different thresholds may be utilized to detect different types of irregular physiological responses, to detect irregular physiological responses to different types of sensitive data, and/or to detect irregular physiological responses when the user is in a certain emotional state and/or under certain environmental conditions.

In one embodiment, the processor is further configured to receive values that characterize the user's emotional state while being exposed to the certain sensitive data, and to calculate a value indicative of whether the user experienced the irregular physiological response based on analyzing the certain $TH_{ROI}$ relative to previous $TH_{ROI}$ taken while the user was in a similar or same emotional state. Optionally, the values indicative of the emotional state are obtained utilizing one or more sensors that are not a thermal camera. Optionally, the one or more sensors measure at least one of the following signals related to the user: a heart rate, heart rate variability, galvanic skin response, a respiration rate, facial expressions, and body language. In one example, the certain emotional state may be considered exhibiting at least a certain extent of excitement. In another example, the certain emotional state may be considered being in an emotional state that falls within a certain region in a multidimensional representation of emotions (e.g., a certain region in the valance/arousal plane, or some other multidimensional space).

In another embodiment, the processor is further configured to receive values describing the environment the user is in while being exposed to the certain sensitive data, and to determine whether the user experienced the irregular physiological response based on analyzing the certain $TH_{ROI}$ relative to previous $TH_{ROI}$ taken while the user was in an environment characterized by similar properties. In one example, the certain threshold is determined based on the values of the previous $TH_{ROI}$.

Various environmental parameters may be utilized to characterize an environment (and determine whether environments may be considered similar environments). In one example, the difference in ambient temperatures of similar environments is less than one of the following values: 2° C., 3° C., or 5° C. In another example, the difference in humidity of similar environments is less than 5%, 10%, or 20%. In still another example, the difference in oxygen percentage in the air of similar environments is less than 1%, 2%, 3%, 4%, or 5%.

In yet another embodiment, the processor is further configured to receive values describing the type of the certain sensitive data, and to determine whether the user experienced the irregular physiological response based on analyzing the certain $TH_{ROI}$ relative to previous $TH_{ROI}$ taken while the user was exposed to sensitive data of the same type as the certain sensitive data. In one example, the certain threshold is determined based on the values of the previous $TH_{ROI}$.

Determining what constitutes a certain type of data may be done according to various criteria. In one example, different types of sensitive data involve data with different content (e.g., intelligence reports vs. billing statements). In another example, different types of sensitive data involve data with different levels of sensitivity (e.g., involve different levels of security clearance). In yet another example, different types of sensitive data come from different sources. In another example, different types of sensitive data involve different types of media (e.g., text information vs. video). In still another example, different types of sensitive data may correspond to the relationship of the sensitive data to the user (e.g., data that involves someone close to the user vs. data that involves a stranger).

In another embodiment, the processor may be configured to determine a similarity between a reference time series corresponding to the irregular physiological response and $TH_{ROI}$ (or a time series derived from $TH_{ROI}$). Optionally, when a sufficiently high similarity is detected, the processor may interpret that as an indication of an occurrence of the irregular physiological response. Optionally, the reference time series is generated based on thermal measurements of the user (taken when the user had an irregular physiological response). Optionally, the reference time series is generated based on thermal measurements of other users. Optionally, different reference time series may be based on different sets of thermal measurements (e.g., collected under different conditions). The different reference time series may be utilized to detect different types of irregular physiological responses, to detect irregular physiological responses to different types of sensitive data, and/or to detect irregular physiological responses when the user is in a certain emotional state and/or under certain environmental conditions.

In yet another embodiment, the processor may generate feature values based on $TH_{ROI}$, and utilize a machine learning-based model to calculate, based on the feature values, a value indicative of whether the irregular physiological response occurred. Optionally, the value is indicative of the extent to which the physiological response is to be considered "irregular", such as a value indicative of how similar the feature values are to other feature values generated when a user had an irregular physiological response. Optionally, at least one of the feature values may be generated based on the sensitive data, e.g., the at least one of the feature values may describe properties of the sensitive data. In one example, the model may be generated based on thermal measurements of the user (e.g., a personalized model). In another example, the model may be generated based on thermal measurements of other users (e.g., a general model).

The emotional state of the user while accessing the certain sensitive data may influence the user's physiological response, and thus may play a role in determining whether the user had an irregular physiological response. Similarly, the environmental conditions that prevail when the user accesses the certain sensitive data and also the type of sensitive data being accessed may influence the user's physiological response and thus may have a bearing on whether the user's physiological response should be considered irregular or not. Addressing these factors may be done in different ways.

In one embodiment, multiple machine learning based models may be generated utilizing different training sets of data. For example, different models may be created to detect different types of irregular physiological responses, to detect irregular physiological responses to different types of sensitive data, and/or to detect irregular physiological responses when the user is in a certain emotional state and/or under certain environmental conditions.

In another embodiment, the feature values generated by the processor may include feature values that describe one or more of the following factors: an emotional state of the user while accessing the certain sensitive data, a condition of the environment in which the user accessed the certain sensitive data, and the type of the certain sensitive data. Thus, the factors mentioned above may be considered when the determination is made regarding whether the user experienced an irregular physiological response.

The following is a more detailed description of how the system may utilize information about the type of sensitive data the user is exposed to in order to improve the detection of an irregular physiological response during exposure to that data. In one example, certain sensitive data is associated with a first type of sensitive data, and the processor is configured to indicate that the user experienced the irregular physiological response while being exposed to the certain sensitive data when the certain $TH_{ROI}$ reach a first threshold. Optionally, the first threshold is calculated based on other $TH_{ROI}$ taken while the user was exposed to sensitive data associated with the first type of sensitive data. Additionally, the user is exposed to second certain sensitive data, which is associated with a second type of sensitive data. The processor is further configured to indicate that the user experienced the irregular physiological response while being exposed to the second certain sensitive data when second certain $TH_{ROI}$ reach a second threshold. The second certain $TH_{ROI}$ are taken while the user is exposed to the second certain sensitive data, the second threshold is calculated based on other $TH_{ROI}$ taken while the user was exposed to sensitive data associated with the second type of sensitive data, and the second threshold is different from the first threshold.

In one embodiment, the sensitive data is associated with a type of data that belongs to a set comprising at least first and second types of sensitive data. In this embodiment, the processor is further configured to utilize $TH_{ROI}$ to generate feature values and to utilize a model to calculate, based on the feature values, a value indicative of the extent of the irregular physiological response. Optionally, at least one of the feature values are indicative of the type of sensitive data to which the user was exposed. Optionally, the model is generated based on previous $TH_{ROI}$ of one or more users and indications of the type of sensitive data to which each of the one or more users was exposed. Optionally, the previous $TH_{ROI}$ comprise at least some measurements taken while the one or more users were exposed to the first type of sensitive data and at least some measurements taken while the one or more users were exposed to the second type of sensitive data.

Detecting the irregular physiological response may involve utilization of one or more baselines. Optionally, a baseline may be indicative of typical values for the user, such as typical values of thermal measurements when exposed to sensitive data, the extent to which a user is typically stressed when exposed to sensitive data, and/or the extent the user typically expresses one or more of the following emotions when exposed to sensitive data: anxiety, fear, and anger. Optionally, a baseline may correspond to the user, i.e., it may represent expected values of the user. Additionally or alternatively, a baseline may correspond to multiple users, and represent expected values of other users (e.g., a general response).

In some embodiments, a baseline may be determined based on previous thermal measurements. In one example, the previous thermal measurements comprise thermal measurements of the user. In another example, the previous thermal measurements comprise thermal measurements of other users. Optionally, the previous thermal measurements are taken while being exposed to baseline sensitive data. Optionally, the baseline sensitive data may be of the same type as the certain sensitive data. Optionally, the previous thermal measurements are taken with essentially the same system as the certain $TH_{ROI}$ (e.g., the same headset or a headset with a similar positioning of the thermal camera).

In some embodiments, multiple baselines may be generated, corresponding to different types of sensitive data, different environmental conditions, and/or different emotional states of the user. Optionally, the multiple baselines are each generated based on corresponding thermal measurements, such as thermal measurements taken while the person being measured (e.g., the user or some other user) was exposed to a certain type of sensitive data, in a certain type of environment, and/or in a certain emotional state.

In some cases, it may be useful to generate a baseline based on measurements taken in temporal proximity to when the user is exposed to the certain sensitive data. Comparing close events may be beneficial because the shorter the time between being exposed to baseline sensitive data and being exposed to the certain sensitive data, the smaller the effect of environmental changes and/or normal physiological changes may be. In one example, the user is exposed to the certain sensitive data immediately before and/or after being exposed to the baseline sensitive data. In another example, the user is exposed to the certain sensitive data within less than 5 minutes before and/or after being exposed to the baseline sensitive data. In still another example, the user exposed to the certain sensitive data within less than 15 minutes before or after being exposed to the baseline sensitive data.

In some embodiments, a baseline may be calculated utilizing a predictor, which receives input comprising feature values describing various values such as characteristics of user (e.g., age, gender, weight, occupation), the sensitive data, the environment in which the user is in, and/or the emotional state of the user. The predictor utilizes a machine learning-based model to calculate, based on the feature values, the baseline which may be, for example, a value of thermal measurements, a stress level, or an extent of expressing a certain emotion. Optionally, the model is generated based on measurements of the user (e.g., a personalized model). Optionally, the model is generated based on measurements of other users (e.g., a general model).

Baseline values may be utilized by the processor in various ways. For example, values of thermal measurements may be normalized with respect to a baseline in order to help identify when the values of the thermal measurements deviate from the expected values (which may be indicative of the irregular physiological response). In another example, a threshold to which the processor compares the certain $TH_{ROI}$ may be a value that is defined relative to the baseline. In yet another example, a reference time series may be selected based on a corresponding baseline (i.e., a reference time series may correspond to an irregular physiological response that occurs when the user is in a certain baseline state). In still another example, one or more feature values utilized to calculate a value indicative of a physiological response may be generated based on a baseline value (i.e., the baseline may be one of the inputs for predicting a physiological response based on thermal measurements).

In one embodiment, $TH_{ROI}$ express temperature at the ROI, and the baseline expresses ordinary temperature at the ROI while the user is exposed to sensitive data. In another embodiment, $TH_{ROI}$ express temperature change at the ROI, and the baseline expresses ordinary temperature changes at the ROI around the time of switching from being exposed to non-sensitive data to being exposed to sensitive data. In still another embodiment, $TH_{ROI}$ express temperature change at the ROI, and the baseline expresses ordinary temperature changes at the ROI around the time of switching from being exposed to sensitive data to being exposed to non-sensitive data.

It is noted that when calculating based on a threshold, it is expected that the difference between $TH_{ROI}$ and the baseline that corresponds to the sensitive data does not reach the threshold for most of the time in which the user is exposed to sensitive data. Additionally, it is noted that when the user is exposed to data over a period of time, in some embodiments, each segment of data (e.g., data watched during a certain span of a few minutes) may serve both as a baseline sensitive data and/or as the certain sensitive data.

In one embodiment, the certain sensitive data is associated with a first type of sensitive data, and the processor is configured to indicate that the user experienced the irregular physiological response while being exposed to the certain sensitive data when a difference between the certain $TH_{ROI}$ and a first baseline reaches a first threshold. Optionally, the first baseline is calculated based on other $TH_{ROI}$ taken while the user was exposed to sensitive data associated with the first type of sensitive data. Additionally, the user is exposed to a second certain sensitive data that is associated with a second type of sensitive data, and the processor is further configured to indicate that the user experienced the irregular physiological response while being exposed to the second certain sensitive data when a difference between second certain $TH_{ROI}$ and a second baseline reaches a second threshold. Here, the second certain $TH_{ROI}$ are taken while the user is exposed to the second certain sensitive data, the second baseline is calculated based on other $TH_{ROI}$ taken while the user was exposed to sensitive data associated with the second type of sensitive data. In this embodiment, the second threshold is different from the first threshold. Optionally, the system is further configured to utilize the indication to estimate job burnout; the greater differences between $TH_{ROI}$ and their associated baselines, the worse is the job burnout.

In different embodiments of the system configured to detect an irregular physiological response of a user while the user is exposed to sensitive data, the ROI may comprise different regions of the face and/or the system may involve various hardware configurations (e.g., certain types of thermal cameras and/or additional thermal cameras).

In one embodiment, the ROI covers a portion of periorbital region of the user's face and the thermal camera comprises an uncooled thermal sensor. Optionally, the ROI covers a portion of the periorbital region of the right eye, and the system further comprises a second thermal camera that weighs below 10 g, is physically coupled to the frame, is located less than 15 cm away from the face, and is configured to take thermal measurements of a second ROI ($TH_{ROI2}$). Here, $ROI_2$ covers a portion of the periorbital region of the left eye. Optionally, each of the thermal camera and the second thermal camera comprises an uncooled thermal sensor. Optionally, the processor is configured, in this embodiment, to calculate a value indicative of whether the user experienced an irregular physiological response based on analyzing the certain $TH_{ROI}$ relative to previous $TH_{ROI}$, and analyzing certain $TH_{ROI2}$, taken while the user is exposed to the certain sensitive data, relative to previous $TH_{ROI2}$ In another embodiment, the ROI covers a portion of the user's nose. Optionally, the ROI covers a portion of the right side of the user's nose and the system further comprises a second thermal camera that weighs below 10 g, is physically coupled to the frame, is located less than 15 cm away from the face, and is configured to take thermal measurements of a second ROI ($TH_{ROI2}$). Here $ROI_2$ covers a portion of the left side of the nose. Optionally, each of the thermal camera and the second thermal camera comprises an uncooled thermal sensor. Optionally, the processor is configured, in this embodiment, to calculate a value indicative whether the user experienced an irregular physiological response based on analyzing the certain $TH_{ROI}$ relative to previous $TH_{ROI}$, and analyzing certain $TH_{ROI2}$, taken while the user is exposed to the certain sensitive data, relative to previous $TH_{ROI2}$.

In yet another embodiment, the ROI covers a portion of the user's forehead. Optionally, the ROI covers a portion of the right side of the user's forehead, and the system further comprises a second thermal camera that weighs below 10 g, is physically coupled to the frame, is located less than 15 cm away from the face, and is configured to take thermal measurements of a second ROI ($TH_{ROI2}$). Here, $ROI_2$ covers a portion of the left side of the forehead. Optionally, each of the thermal camera and the second thermal camera comprises an uncooled thermal sensor. Optionally, the processor is configured, in this embodiment, to calculate a value indicative of whether the user experienced an irregular physiological response based on analyzing the certain $TH_{ROI}$ relative to previous $TH_{ROI}$, and analyzing certain $TH_{ROI2}$, taken while the user is exposed to the certain sensitive data, relative to previous $TH_{ROI2}$.

In still another embodiment, the ROI covers a portion of at least one of the user's right and left cheeks. Optionally, the ROI covers a portion of the user' right cheek, and the system further comprises a second thermal camera that weighs below 5 g, is physically coupled to the frame, is located less than 10 cm away from the user's face, and is configured to take thermal measurements of a second ROI ($TH_{ROI2}$). Here, $ROI_2$ covers a portion of the user's left cheek Optionally, the processor is further configured, in this embodiment, to calculate a stress level of the user based on the thermal measurements of the cheeks.

Figure 42:
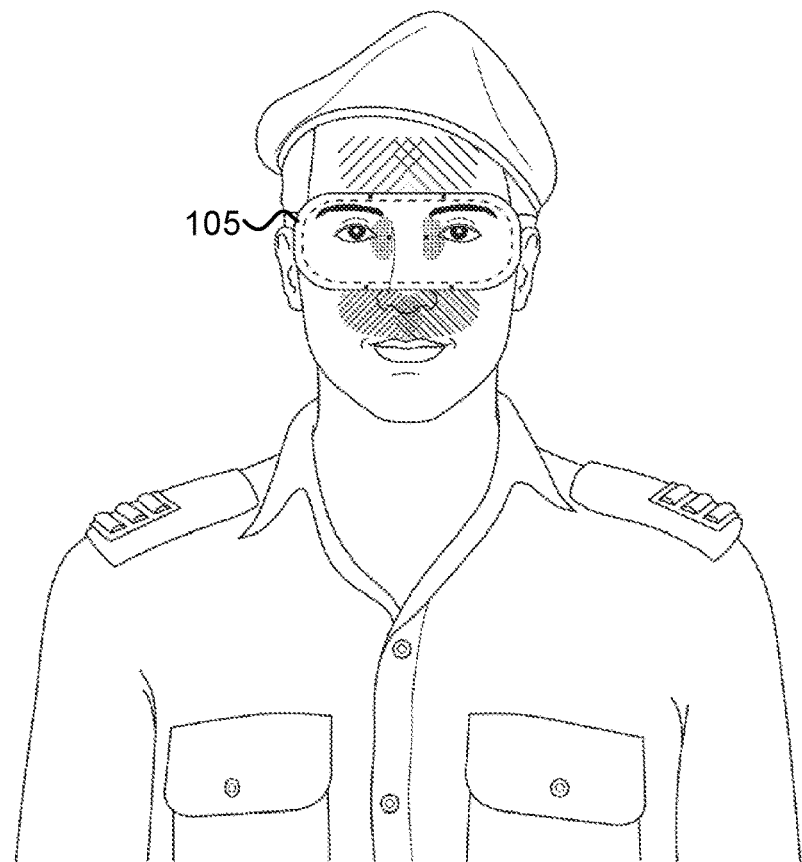
FIG. 42 illustrates one embodiment of a system configured to detect an irregular physiological response of a user while the user is exposed to sensitive data.

FIG. 42 illustrates one embodiment of a system configured to detect an irregular physiological response of a user while the user is exposed to sensitive data. The system includes head-mounted system HMS 105, which includes a head-mounted display (HMD) for exposing the user to sensitive data (not depicted in the figure) and six thermal cameras coupled to the frame of the HMS 105 (illustrated as small black boxes: 2 on the bottom of the frame, 2 near the nose, and 2 on the top of the frame). The thermal cameras take thermal measurements of various regions on the face, which here illustrated as shaded areas (e.g., regions comprising portions of the upper lip and nose, portions of the periorbital legions, and portions of the forehead). It is to be noted that though the user's eyes are visible in the figure, the front of the HMS may in fact be opaque as common in virtual reality headsets.

Figure 43:
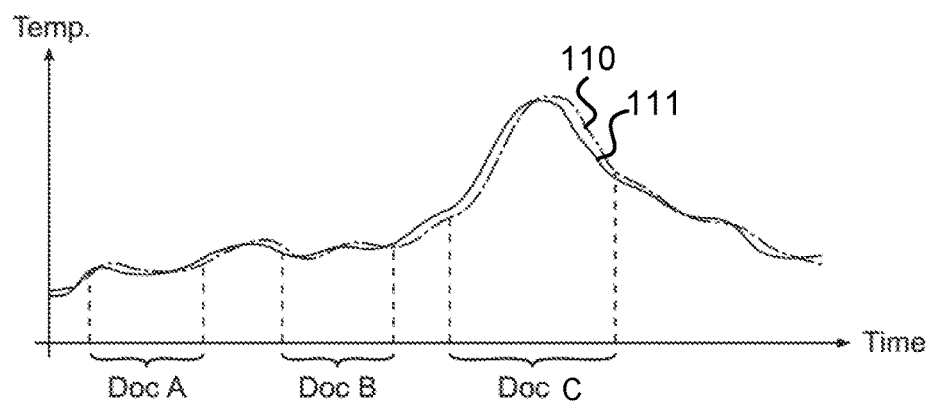
FIG. 43 illustrates detection of an irregular physiological response.

FIG. 43 illustrates detection of an irregular physiological response. The figure depicts a graph displaying temperatures at the left and right periorbital regions (lines 110 and 111 in the figure). The user is exposed to three documents via a HMD, "doc A", "doc B", and "doc C". With the first two documents ("doc A" and "doc B"), the temperatures remain low, but when the user is exposed to "doc C" the temperature rises dramatically, which in this exemplary figure may constitute an irregular physiological response.

Figure 44:
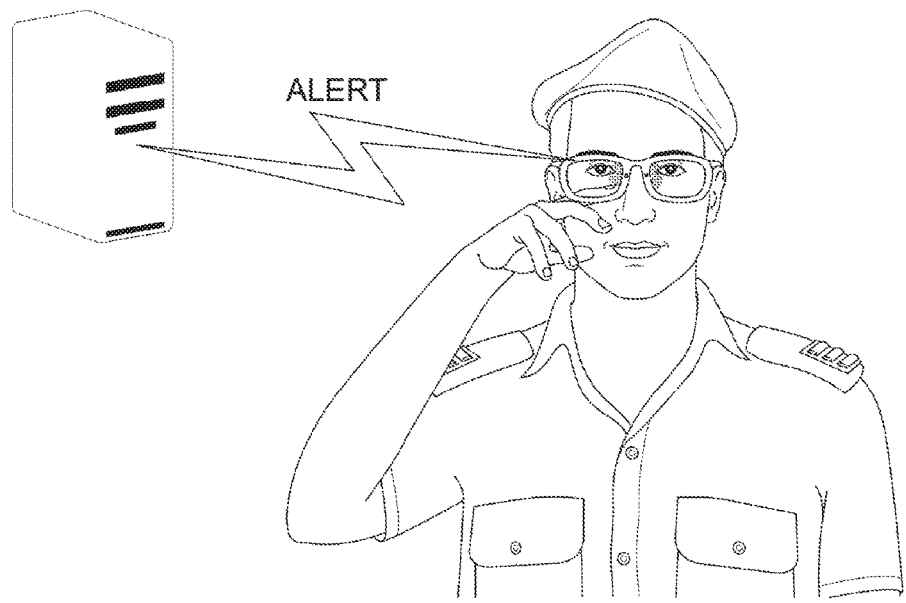
FIG. 44 illustrates touching of a thermal camera which triggers an alert.

In order to avoid detection of an irregular physiological response, a user exposed to sensitive data via the HMD may attempt to take evasive measures such as touching the face or moving the HMD (e.g., in order to disrupt sensor measurements). An example of such behavior is illustrated in FIG. 44 in which the user moves the HMD a bit and touches a thermal camera of the system, which triggers an alert.

In one embodiment, the system may detect whether the user moves the HMD relative to the face while being exposed to the certain sensitive data, based on at least one of the following sensors: an optical sensor physically coupled to the HMD, an optical sensor that captures the user's face without being physically coupled to the HMD, a non-optical sensor physically coupled to the HMD, and a non-optical sensor physically coupled to the user's body. Optionally, the processor is further configured to perform at least one of the following security measures responsive to detecting that the user moved the HMD relative to the face while being exposed to the certain sensitive data: storing in a database an indication that the user moved the HMD relative to the face while being exposed to the certain sensitive data at a certain point in time, ceasing from exposing the user to the certain sensitive data, not allowing the user to perform a certain transaction related to the certain sensitive data, blocking the user's access to the certain sensitive data, issuing an alert, marking as suspicious the relationship between the user and the certain sensitive data, tightening the security restrictions for the user for accessing sensitive data on the system, providing the user a canary trap, and providing the user a barium meal test.

Herein, a "canary trap" refers to a practice of providing the user with a version of the sensitive data that contains certain indicators (e.g., small variations) that are unique to the version provided to the user. Thus, if the sensitive data is leaked, the user may be identified as the source based on detecting the small variations in the leaked data. A "barium meal test" refers to a practice of including in the sensitive data certain information; when the certain information reaches an entity it causes the entity to take a certain action (e.g., visit a certain website it would not ordinarily visit). Thus, detecting the certain action is indicative of the sensitive data (to which the user was exposed) being passed on to the entity.

It is noted that sentences such as "while being exposed to the certain sensitive data" does not include removing the HMD off the face, because after removing the HMD off the face the user is not exposed to the certain sensitive data. In one example, moving the HMD relative to the face refers to a relative movement above a minimum threshold (e.g., moving the frame to a distance that is greater than 1 cm). In another example, making facial expressions does not cause the system to detect that the user is moving the HMD relative to the face. In one embodiment, the system identifies moving the HMD relative to the face based on analyzing images taken by at least one of the following sensors: (i) an optical sensor physically coupled to the HMD, such as a thermal camera coupled to the HMD, an active near-IR camera coupled to the HMD, and/or a visible-light camera coupled to the HMD, (ii) an optical sensor that captures the user's face without being physically coupled to the HMD, such as a 2D or a 3D camera located in a position that faces the user or located on a smartwatch or a smart-shirt, (iii) a non-optical sensor physically coupled to the HMD, such as a movement sensor, a miniature radar operating in the Extremely High Frequency (FI-1F) band, an acoustic sensor, an electroencephalogram sensor, an electromyogram sensor, a piezoelectric sensor, and/or strain gauges, as mentioned for example in the reference Li, Hao, et at "Facial performance sensing head-mounted display" ACM Transactions on Graphics 2015, and (iv) a non-optical sensor physically coupled to the user's body, such as a movement sensor embedded in a wrist band or embedded in a smart-shirt.

In one embodiment, the processor is further configured to tighten security restrictions for the user responsive to detecting multiple occurrences where the user moved the HMD relative to the face while being exposed to sensitive data that is of the same type as the certain sensitive data. Optionally, moving the HMD relative to the face may include one or more of changing the position of the HMD relative to the face, and removing the HMD off the face. Optionally, tightening security restrictions for the user involves restricting the user from performing a certain transaction related to the sensitive data. In one example, the certain transaction comprises at least one of the following transactions: copying, reading, and modifying the certain sensitive data. In another example, the certain sensitive data relates to money, and the certain transaction comprises an electronic funds transfer from one person or entity to another person or entity.

In another embodiment, the system includes a sensor configured to provide measurements indicative of times at which the user touches the ROI. Optionally, touching the ROI is expected to influence $TH_{ROI}$ and/or disrupt the ability to detect the irregular physiological response. The user may touch the ROI using at least one of the following: a finger of the user, a palm of the user, a tissue or a towel held by the user, a makeup-related item held by the user, a material that is expected to cool the ROI (such as a metal that is colder than the skin), and/or a material that is transparent in the visible spectrum (such as a transparent glass that is colder than the skin). In this embodiment, the system is further configured to perform at least one of the following security measures responsive to detecting that the user touched the ROI while being exposed to the certain sensitive data: storing in a database an indication that the user touched the ROI while being exposed to the certain sensitive data at a certain point in time, ceasing from exposing the user to the certain sensitive data, not allowing the user to perform a certain transaction related to the certain sensitive data, blocking the user's access to the certain sensitive data, issuing an alert, marking as suspicious the relationship between the user and the certain sensitive data, tightening the security restrictions for the user for accessing sensitive data on the system, providing the user a canary trap, and providing the user a barium meal test. Optionally, the processor is further configured to tighten security restrictions for the user responsive to detecting multiple occurrences where the user touched the ROI while being exposed to sensitive data that is of the same type as the certain sensitive data.

In yet another embodiment, the system is further configured to detect occlusion of the thermal camera based on at least one of the following steps: identifying a sudden change of more than 3° C. in $TH_{ROI}$, and utilizing a sensor configured to generate a signal indicative of whether a solid object is located between the thermal camera and the ROI. Optionally, the system is further configured to perform at least one of the following security measures responsive to detecting that the user occludes the thermal camera while being exposed to the certain sensitive data: storing in a database an indication that the user occluded the thermal camera while being exposed to the certain sensitive data at a certain point in time, ceasing from exposing the user to the certain sensitive data, not allowing the user to perform a certain transaction related to the certain sensitive data, block the user's access to the certain sensitive data, issuing an alert, marking as suspicious the relationship between the user and the certain sensitive data, tightening the security restrictions for the user for accessing sensitive data on the system, providing the user a canary trap, and providing the user a barium meal test.

Some embodiments of the system configured to detect an irregular physiological response of a user while the user is exposed to sensitive data include added security measures such as encryption of the sensitive data to which the user is exposed via the HMD. Optionally, the system receives the certain sensitive data in an encrypted form, and the processor is further configured to decrypt the certain sensitive data in order to expose the user to the certain sensitive data in an understandable form (e.g., a decrypted form). Optionally, the decryption involves hardware based decryption, which includes an element that comprises data required for the decryption (e.g., a decryption key), and the element is implemented in the hardware of the system. Optionally, the user provides data required to decrypt the information via a user interface. Optionally, the system obtains data required for the decryption by measuring the user with a sensor (e.g., an iris scan, taking an image of the user, and/or measuring brainwave patterns of the user).

Another security measure that may be included in some embodiments of the system involves biometric identification of the user. In these embodiments, the system may include a biometric identification device, which is physically coupled to the HMD, and is configured to identify the user while the user wears the HMD. Optionally, the processor is further configured to expose the user to the sensitive data responsive to receiving an indication that confirms the user's identity. Optionally, the biometric identification device performs one or more of the following operations: an iris scan, detection of brainwave patterns, detection of a cardiac activity pattern, and detection of thermal patterns on the user's face.

In some embodiments, an indication that the user had an irregular physiological response may prompt the system to initiate a process to detect an illegal activity responsive to the indication. Optionally, the time that elapses between initiation of the detection of the illegal activity and the time of detecting the irregular physiological response is less than two minutes. Optionally, the sensitive data belongs to an organization, the user is an employee of the organization, and the system helps in preventing illegal activities of employees related to sensitive data.

Heightened alertness, anxiety, and fear are often experienced by people perpetrating illegal activities during their illicit acts. A person's agitation, e.g., when viewing something that makes a person uncomfortable, can cause an increase in the stress felt by the user in addition to an atypical gaze (e.g., fixation on an agitating item or averting the ones eyes from it). These symptoms are difficult to conceal, and often cannot be totally controlled. Thus, they may serve as a powerful biometric that can provide valuable clues when monitoring human behavior.

When a user experiences elevated feelings of alertness, anxiety, or fear, increased levels of adrenaline regulate blood flow. Redistribution of blood flow in superficial blood vessels causes changes in local skin temperature that is apparent in the user's face, where the layer of flesh is very thin. The human face and body emit radiation both in the mid-infrared (3-5 µm) and far-infrared (8-12 µm) bands, thus mid-infrared and far-infrared thermal sensors can sense temperature variations in the face that are indicative of the aforementioned stress-related emotions. Additionally, when a person is confronted with images that include certain items that make him or her uncomfortable (e.g., because they are related to illicit activity of the person), the person may instinctively avert the gaze from the certain items and/or fixate on the certain items. This type of behavior can be detected using eye tracking. The combination of detecting stress and atypical gaze patterns can be utilized in order to identify when a person is viewing agitating images. This capability may have various security-related applications.

Some aspects of this disclosure include a system that is configured to identify agitation from viewing a video. In some embodiments, the system includes a frame that is configured to be worn on a user's head, an eye tracking module that is coupled to the frame, a thermal camera that is coupled to the frame, and a processor. The eye tracking module is configured to track the user's gaze while watching a video depicting items, where each item may be an object, a person, an animal, etc. The eye tracking module generates data that is indicative of attention the user paid to each item. The thermal camera weights below 5 g, is physically coupled to the frame, is pointed at a region of interest (ROI) on the user's face, and is configured to take thermal measurements of the ROI ($TH_{ROI}$). In one example, the ROI covers a portion of a periorbital region of the face. In another example, the ROI covers a portion of the user's nose or forehead. The processor is configured to calculate a stress level based on $TH_{ROI}$ and to calculate an extent of discordance between the attention the user paid to the items and expected attention levels in the items.

In one example, the expected attention levels are generated based on a model generated based on previous eye tracking data of the user. In another example, the expected attention levels are calculated using a saliency mapping algorithm. The processor is further configured to calculate, based on the stress level and the extent of discordance, a value indicative of a probability that the items include an item that agitates the user.

In one embodiment, a system configured to identify agitation from viewing a video includes at least a frame that is configured to be worn on a user's head, an eye tracking module that is coupled to the frame, a thermal camera that is coupled to the frame, and a processor. Optionally, the system also includes a head-mounted display (HMD), which is configured to display the video to the user.

The eye tracking module coupled to the frame and configured to track the user's gaze while watching a video depicting items. Optionally, the user's gaze is indicative of attention the user paid to each item. Optionally, the eye tracking module includes a camera that takes images of at least one of the user's eyes. Some examples of implementations of an eye tracking module that may be utilized in some embodiments include systems described in U.S. Pat. No. 9,535,251 ("HMD apparatus with adjustable eye tracking device"), systems described in US patent application 2014/0361957 ("Compact eye-tracked head-mounted display"), and U.S. Pat. No. 7,542,210 ("Eye tracking head mounted display"), to name a few examples of the many implementations of eye tracking modules known in the art. In some embodiments, the eye tracking module may be physically coupled to the frame, and include an eye tracker module that is part of an HMD such as in the one used in the FOVE VR display (https://www.getfove.com/). In other embodiments, the eye tracking module may include a camera that is remote of the user (e.g., more than 15 cm away from the face), as described in US patent application ("Visual attention and emotional response detection and display system").

The data generated by the eye tracking module describes the gaze of the user. For example, the data may be indicative of the coordinates, on a display displaying the video, at which the user focused during various times while watching the video. Optionally, the coordinates represent certain pixels and/or sets of pixels. This information may be analyzed along with information that describes the boundaries (e.g., coordinates) of the items in the video at different times during its presentation, in order to determine when the user focused on each item. Optionally, determining which items were presented in the video may involve utilizing various image processing algorithms, which can identify items (e.g., objects and/or people) in the video and/or define the boundaries of the items in the video at various times. Thus, using the data generated by the eye tracking module, attention levels of the user in each item can be determined (e.g., by the processor). In one example, an attention level of the user in an item is indicative of the amount of time the user spent focusing on the item. In another example, the attention level of the user in an item is indicative of the number of times the user's sight was focused on the item (e.g., before moving to some other item in the video). In still another example, the attention level of the user in an item is indicative of a relative value, which indicates whether the user paid more attention or less attention to the item compared to the other items in the video.

The thermal camera, which weights below 5 g (herein "g" denotes grams), is physically coupled to the frame. Additionally, is pointed at a region of interest (ROI) on the user's face, and is configured to take thermal measurements of the ROI ($TH_{ROI}$). Optionally, the thermal camera is located less than 15 cm away from the face (herein "g" denotes centimeters). Optionally, the thermal camera is located less than 5 cm away from the face. In some embodiments, the system may include additional thermal cameras, which are coupled to the frame, and take thermal measurements of additional ROIs on the user's face.

The ROI may cover various regions of the user's face. Optionally, the regions are known to exhibit a change in cutaneous temperature when a person experiences stress. In one embodiment, the ROI covers a portion of a periorbital region of the face (e.g., the periorbital region around the right or left eyes). In another embodiment, the ROI covers a portion of the user's nose. And in still another embodiment, the ROI covers a portion the user's forehead.

In one embodiment, $TH_{ROI}$ are taken during a window of time that lasts between a seconds to a few minutes. Optionally, the window is at least five seconds long, at least thirty seconds long, at least two minutes long, at least five minutes long, at least fifteen minutes long, at least one hour long, or is some other window that is longer than one second. Optionally, during the time the user is exposed to the video, $TH_{ROI}$ from multiple windows may be evaluated (e.g., using a sliding window approach).

The processor is configured, in some embodiments, to calculate, based on $TH_{ROI}$ taken while the user views the video a value describing a stress level of the user. Additionally, the processor is configured to calculate an extent of discordance between the attention the user paid to the items and expected attention levels in the items. These two values (the stress level and extent of discordance) are utilized by the processor to calculate a value indicative of a probability that the items include an item that agitates the user.

In some embodiments, the processor may be the processor 401 or the processor 411, illustrated in FIG. 72*a* and FIG. 72*b*, which are schematic illustrations of possible embodiments for computers 400 and 410, respectively. In one embodiment, the processor may be physically coupled to the frame. In another embodiment, the processor may be apart from the frame. For example, the processor may belong to a server.

The probability mentioned above is, in some embodiments, a value that is proportional to the product of the stress level and the extent of the discordance. That is, in most scenarios, the larger one or both of these values (the stress level and the extent of the discordance), the larger probability that the items include an item that agitates the user. In one example, probability is indicative of negative feelings related to at least one of an item and a situation presented in the video (the larger the probability to likelier is the case that the user harbors such negative feelings). In another example, probability is indicative of an extent to which it is likely that the user is concealing something related to the content of the video.

In one embodiment, agitation due to the item may be manifested by an increase of at least a certain level in the stress of the user and/or by the user having an atypical gaze pattern in which the user pays significantly less attention or significantly more attention to the item than expected. In one example, "significantly more attention" refers to staring at the item at least double the expected time, and "significantly less attention" refers to staring at the item less than half the expected time.

The expected attention levels in the items may be based, in some embodiments, on tracking gazes during previous viewings of the video and/or previous viewings of similar videos in order to determine attention in the items. In one embodiment, the attention levels in the items are based on attention levels detected when the same video was viewed by other people. For example, the attention levels may represent the average attention paid by the other users to each item. In another embodiment, the attention levels in the items are based on attention levels of the user to items in similar videos. For example, if the video depicts a scene (e.g., a person filling out a loan application), then a similar video may include the same scene, possibly with slightly different items (e.g., a different person filling out a loan application).

In some embodiments, determining the expected attention levels in the items may involve utilizing a model Optionally, the model is generated based previous tracking of the user's gaze when observing other videos. Additionally or alternatively, the model is generated based on tracking of other users' gaze when observing other videos. Optionally, the model may be generated using one or more of the various attention modelling algorithms known in the art (such algorithms may also be referred to as saliency mapping algorithms). Some of the many algorithms that may be utilized are surveyed in A. Borji, L. Itti, "State-of-the-Art in Visual Attention Modeling", IEEE Transactions on Pattern Analysis & Machine Intelligence vol. 35(1), p. 185-207, 2013.

In one embodiment, a model for attention in visual items may be generated by creating a training set of samples. Where each sample corresponds to an item in a video and includes features values and a label describing the extent of attention in the item. Various feature values may be included in each sample. For example, some feature values may be generated using various image processing techniques and represent various low-level image properties. Some examples of such features may include features derived using Gabor filters, local binary patterns and their derivatives, features derived using algorithms such as SIFT, SURF, and/or ORB, and features derived using PCA or LDA. In another example, at least some feature values may include higher-level description of the items (e.g., after identification of the items and/or actions depicted in the video). In yet another example, some feature values may describe the user viewing the video (e.g., demographic information about the user and/or data related to the user's physiological state). A collection of samples, such as the ones described above, may be provided to a machine learning based training algorithm in order to generate the model. Some examples of the types of models that may be generated include support vector machines (SVMs) and neural networks.

Obtaining the expected attention levels may be done in various ways. In one embodiment, values of the attention levels are determined based on tracking the gaze of the user (and/or other users) in previous viewing the video and/or similar videos; the attention levels determined in this tracking may be used as the expected attention levels in the items displayed in the video while $TH_{ROI}$ are taken. In another embodiment, feature values are generated based on the video and/or a description of the user, and the expected attention values are calculated based on the feature values utilizing a model for attention in visual items, as described above.

In one embodiment, the expected attention levels comprise values of attention in two or more of the items. Additionally, the attention the user paid to the two or more items is determined based on the gaze of the user. These two sets of values may be compared in order to calculate the extent of the discordance between the attention the user paid to the items and expected attention levels in the items. In one example, a divergence metric, such as the Kullback-Leibler divergence may be used to calculate the discordance between the two sets of values. In another example, a distance metric, such as a vector dot product may be used to calculate the discordance between the two sets of values.

In another embodiment, the expected attention levels comprise an indication of a subset comprising one or more of the items to which the user is expected to pay at least a certain amount of attention or one or more of the items to which the user is expected to pay at most a certain amount of attention. Additionally, a subset of the items to which the user paid at least the certain amount of attention (or at most the certain amount of attention), is determined based on the gaze of the user. In this embodiment, a comparison between the subset of items selected based on expected attention levels and the subset selected based on the gaze of the user may be done in order to calculate the extent of the discordance between the attention the user paid to the items and expected attention levels in the items. In one example, the extent of the discordance is proportional to the size of the symmetric difference between the two subsets.

There are various ways in which the processor may calculate the stress level based on $TH_{ROI}$. Optionally, the stress level is a value that is indicative of whether the user felt at least a certain amount of stress, at most a certain amount of stress, and/or whether the user felt stress that falls between a certain range of values (e.g., on a scale between 1 to 10, with ten being a high stress level). Optionally, the processor is further configured to calculate, based on $TH_{ROI}$, stress levels corresponding to different times, and to utilize tracking of the user's gaze to assign stress levels to the different items.

In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on thermal measurements of the user (e.g., thermal measurements taken when the user was stressed). Optionally, the certain threshold is determined based on baseline thermal measurements of the user, and the certain threshold represents a difference of a certain magnitude relative to the baseline measurements. Optionally, different thresholds may be utilized to calculate different levels of stress and/or to calculate the stress level when the user is in a certain emotional state and/or is in an environment characterized by certain environmental conditions.

In another embodiment, the stress level is calculated by determining a similarity between a reference time series corresponding to a certain stress level and $TH_{ROI}$ (or a time series derived from $TH_{ROI}$). Optionally, when a sufficiently high similarity is detected, the processor may interpret that as an indication that the user experienced the certain stress level. Optionally, the reference time series is generated based on thermal measurements of the user (e.g., thermal measurements taken when the user experienced stress at the certain stress level). Optionally, the reference time series is generated based on thermal measurements of other users. Optionally, different reference time series may be based on different sets of thermal measurements (e.g., sets collected under different conditions). The different reference time series may be utilized to detect different levels of stress and/or to detect a stress level when the user is in a certain emotional state and/or is in an environment characterized by certain environmental conditions.

In yet another embodiment, the stress level is calculated by generating feature values based on $TH_{ROI}$ and utilizing a machine learning-based model to calculate, based on the feature values, a value indicative of a stress level experienced by the user. Optionally, at least one of the feature values are generated based on the video, e.g., the at least one of the feature values describe properties of the items depicted in the video. In one example, the model is generated based on thermal measurements of the user (e.g., the model is a personalized model). In another example, the model is generated based on thermal measurements of other users (e.g., the model is a general model). Optionally, at least one of the feature values describe the emotional state of the user and/or environmental conditions corresponding to when $TH_{ROI}$ were taken. Optionally, at least one of the feature values are generated based on previous $TH_{ROI}$ taken before the user viewed the video (e.g., up to 15 minutes before); thus, when determining the extent of stress the user experienced, the processor can account for the user's baseline stress level.

There are various ways in which the processor may calculate, based on the stress level and the extent of discordance, a value indicative of a probability that the items include an item that agitates the user. Optionally, the calculated value is indicative of the probability reaching at least a certain threshold. For example, the calculated value may indicate whether the probability is at least 5%, at least 10%, at least 25%, at least 50%, at least 75%, at least 90%, or at least some other threshold value greater than 1%. Additionally or alternatively, the calculated value may be the probability itself and/or a value that may be mapped to a range of probabilities. Optionally, the processor is further configured to identify that an item from among the items is a suspicious item based on the stress level reaching a first threshold and a difference between the attention the user paid to the item and the expected attention to the item reaching a second threshold.

In one embodiment, the value indicative of the probability is calculated by comparing the stress level and the extent of discordance to corresponding thresholds. For example, when the stress level reaches at least a certain level and the discordance is at least a certain extent, that is indicative that there is at least a certain probability that that the items include an item that agitates the user. Optionally, calculating the probability involves utilizing a table that includes probability values for different combinations of thresholds (i.e., for different combinations of minimal stress levels and extents of discordance). Optionally, the table is generated based on observations of events in which the extent of stress of users was measured along with the extent of discordance based on their gaze, along with indications of whether the events involved a video that includes an item that agitated the viewer.

In another embodiment, the processor is configured to generate feature values based on the stress level and the extent of discordance and to utilize a machine learning based model to calculate, based on the feature values, a value indicative of the probability that the items include an item that agitates the user. It is to be noted that this machine learning-based model is a different model than the one used in the embodiment described further above to calculate the stress level. Optionally, the feature values include at least some features values indicative of the value of the stress level and/or the extent of discordance. Optionally, the feature values include at least one feature value indicative of a difference between the stress level and a baseline stress level of the user. Optionally, the feature values include at least one feature value that describes the video. For example, the at least one feature values may be indicative of what types of items are presented in the video. Optionally, the feature values include at least one feature value describing the user (e.g., the at least one feature value may be indicative of values such as the user's, the user's gender, the user's occupation, etc.) Optionally, the machine learning-based model is trained based on samples generated from previous events in which the extent of stress of users was measured along with the extent of discordance based on their gaze, along with indications of whether the events involved a video that includes an item that agitated the viewer.

When utilizing feature values along with a machine learning-based model, such as the model used to calculate the stress level or the model used to calculate the probability that the items in the video include an item that agitates the user, in some embodiments, the feature values may include values based on additional inputs (beyond $TH_{ROI}$). In one example, the processor is further configured to: (i) receive one or more values indicative of at least one of the following parameters of the user: heart rate, heart rate variability, galvanic skin response, respiratory rate, and respiratory rate variability, and (ii) to generate one or more of the feature values based on the one or more values. In another example, the processor is further configured to: (i) receive one or more values measured by at least one of the following sensors coupled to the user: a photoplethysmogram (PPG) sensor, an electrocardiogram (ECG) sensor, an electroencephalography (EEG) sensor, a galvanic skin response (GSR) sensor, and a thermistor, and (ii) to generate one or more of the feature values based on the one or more values. In yet another example, the processor is further configured to: (i) receive one or more values indicative of at least one of the following: whether the user touched at least one of the eyes, whether the user is engaged in physical activity, and an environmental parameter, and (ii) to generate one or more of the feature values based on the one or more values. In still another example, the processor is further configured to: (i) receive one or more values measured by at least one of the following sensors: an accelerometer, a pedometer, a humidity sensor, a miniature radar, a miniature Lidar, an anemometer, an acoustic sensor, and a light meter, and (ii) to generate one or more of the feature values based on the one or more values. And in another example, the processor is further configured to: (i) receive values indicative of at least one of the following properties describing the user: age, gender, weight, height, health problems, mental health problems, occupation, education level, marital status, and (ii) to generate one or more of the feature values based on the one or more values.

Figure 45:
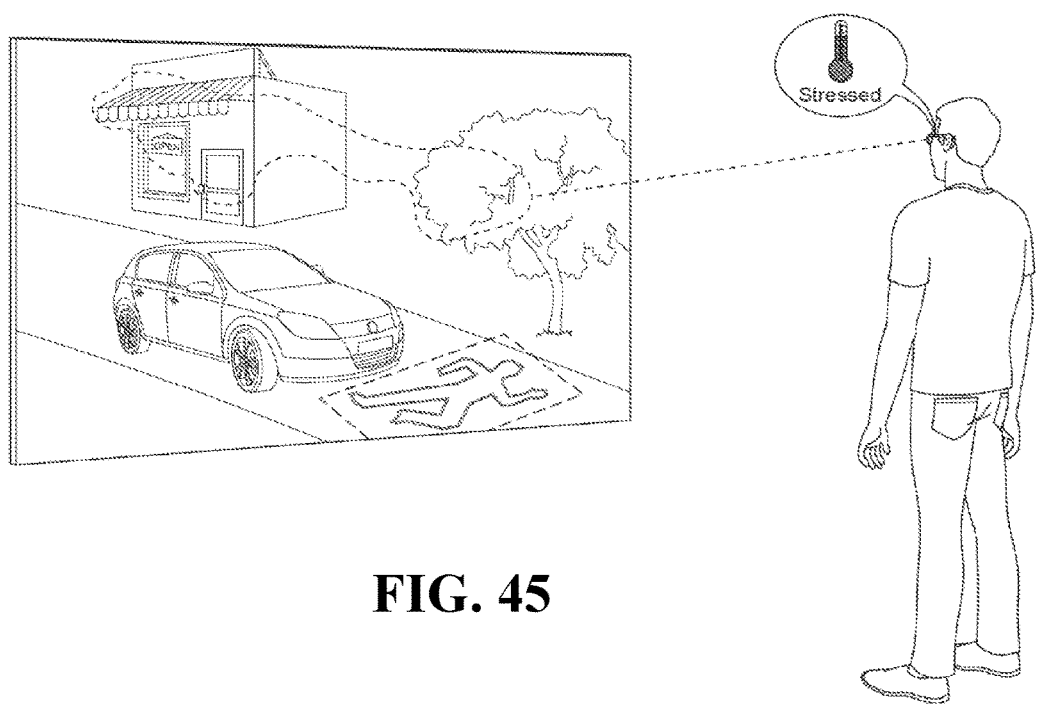
FIG. 45 illustrates a scenario in which it is identified that a user is agitated (stressed) from viewing a video.

FIG. 45 illustrates a scenario in which an embodiment of a system described above is utilized to identify that a user is agitated (stressed) from viewing a video. In this scenario, a user is measured with thermal cameras coupled to a frame worn on the user's head while viewing an image of an accident scene. Eye tracking reveals that the user is avoiding a region that corresponds to the accident and the thermal measurements indicate an elevated stress level. Thus, the system may indicate that there is a high probability that the scene includes something that particularly agitates the user.

People performing routine activities often tend to exhibit a certain physiological response that characterizes their performance of the activity. However, when something is very different about the activity, such as when it involves something illegal or dishonest, they may experience heightened alertness, anxiety, and fear that are often difficult to control or conceal. Thus, when a person knows that he or she are doing something wrong, even if it concerns a seemingly routine action for them, their physiological response may be a telltale.

Some aspects of this disclosure involve identifying when a user has an atypical physiological response. When a user experiences elevated feelings of alertness, anxiety, or fear, increased levels of adrenaline regulate blood flow. Redistribution of blood flow in superficial blood vessels causes changes in local skin temperature that is apparent in the user's face, where the layer of flesh is very thin. The human face and body emit radiation both in the mid-infrared (3-5 μm) and far-infrared (8-12 μm) bands, thus mid-infrared and far-infrared thermal sensors can sense temperature variations in the face that are indicative of the aforementioned stress-related emotions. Additionally, when a person is confronted with images that include certain items that make him or her uncomfortable (e.g., because they are related to illicit activity of the person), the person may instinctively avert the gaze from the certain items and/or fixate on the certain items. This type of behavior can be detected using eye tracking. The combination of detecting stress and atypical gaze patterns can be utilized in order to identify when a person has an atypical physiological response. This capability may have various security-related applications.

Some aspects of this disclosure include a system that is configured to identify atypical behavior. In some embodiments, the system includes a frame that is configured to be worn on a user's head, an eye tracking module that is coupled to the frame, a thermal camera that is coupled to the frame, and a processor. The eye tracking module is coupled to the frame and is configured to track the user's gaze while viewing one or more items, where each item may be an object, a person, an animal, etc. The eye tracking module generates data that is indicative of attention the user paid to each item. The thermal camera weights below 5 g, is physically coupled to the frame, is pointed at a region of interest (ROI) on the user's face, and is configured to take thermal measurements of the ROI ($TH_{ROI}$). In one example, the ROI covers a portion of a periorbital region of the face. In another example, the ROI covers a portion of the user's nose or forehead. The processor is configured to generate features and to utilize a model to calculate a value indicative of whether the user's behavior while viewing the one or more items was atypical. Optionally, the feature values include at least one feature generated based on $TH_{ROI}$ and at least one feature value indicative of the attention of the user in the one or more items. The model is generated based on previous tracking of the user's gaze while viewing other items and previous $TH_{ROI}$ taken during the viewing of the other items.

Some aspects of this disclosure involve monitoring a user while performing his or her job in order to create a model of the user's typical behavior. This monitoring may involve determining the typical stress level of the user and gaze pattern (e.g., what the user typically pays attention too when performing the usual activities on the job). When the user exhibits atypical behavior, when performing a job, this may be an indication that something illicit and/or illegal is being performed. For example, a bank loan officer knowingly approving a faulty loan may exhibit higher stress levels while evaluating the loan forms and may also have a significantly different gaze pattern compared to when working on a regular loan application. In another example, a doctor examining a patient in order to assist in a faulty insurance claim may also be more stressed and/or have a different gaze pattern. In yet another example, a customs official "looking the other way" when an accomplice smuggles contraband is also expected to have elevated stress levels and a different gaze pattern than ordinarily observed on the job. When atypical behavior is detected, it can be noted in order to have the event to which it corresponds inspected more thoroughly by other parties (e.g., a supervisor).

Figure 46A:
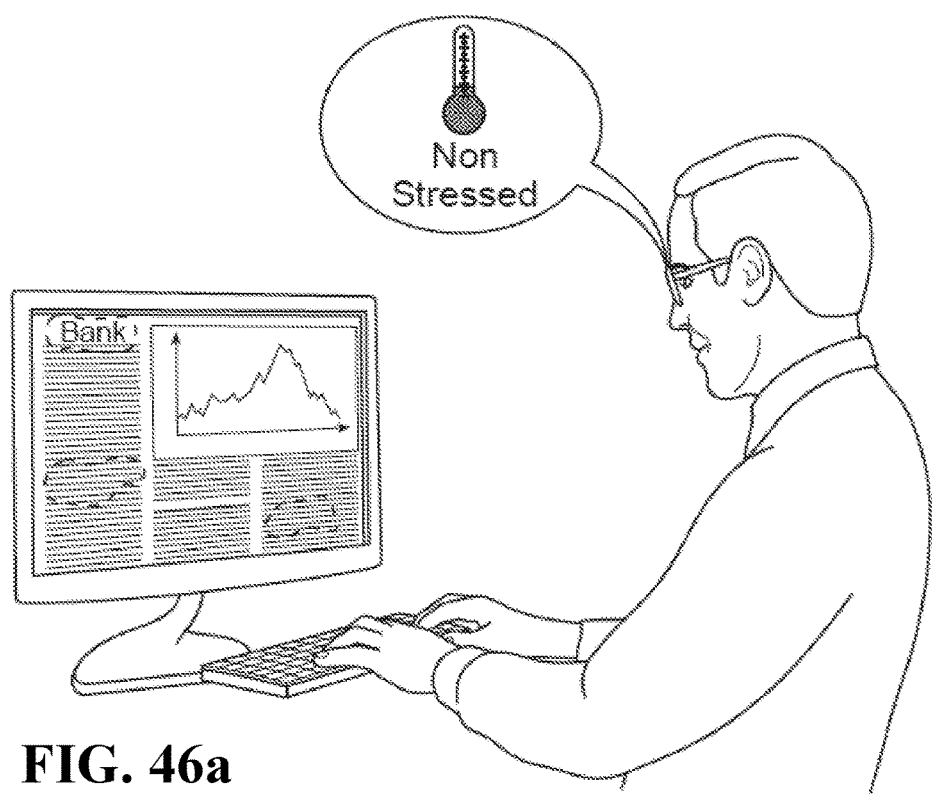
FIG. 46a and FIG. 46b illustrate a scenario in which stress levels and gaze patterns may be utilized do detect atypical user behavior.
Figure 46B:
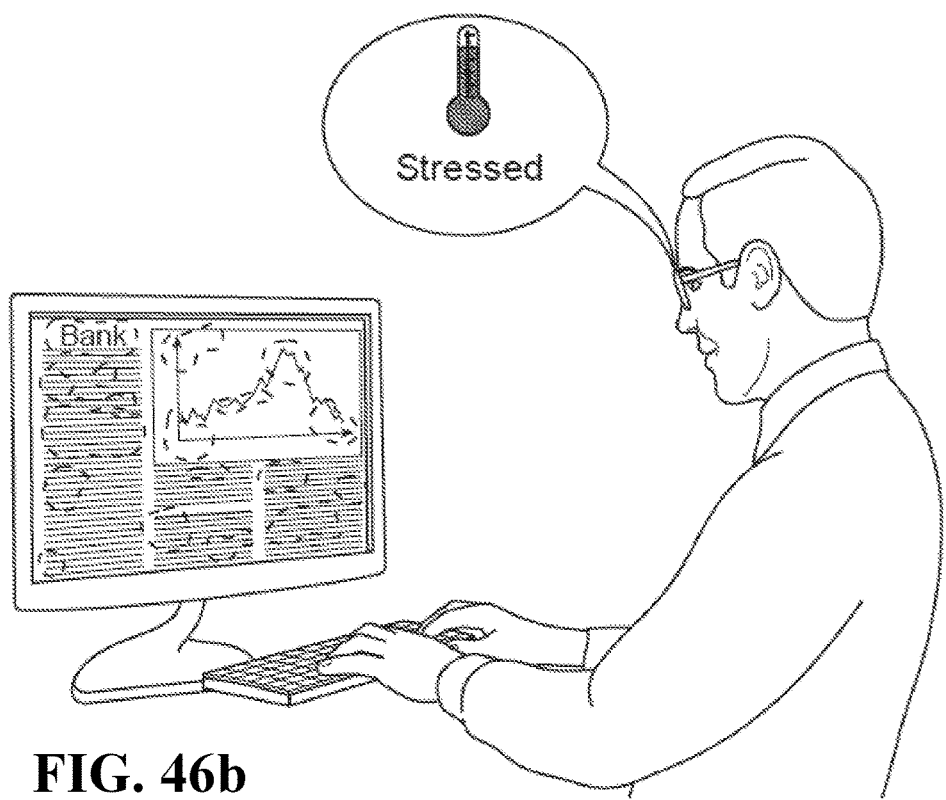

FIG. 46a and FIG. 46b illustrate a scenario in which stress levels and gaze patterns may be utilized do detect atypical user behavior. FIG. 46a illustrates a typical gaze pattern of the user (obtained using eye tracking), while the user performs his job at a computer terminal. Thermal measurements of the user indicate that the user is not stressed. FIG. 46b illustrates an instance in which the user has an atypical gaze pattern and in addition, the user is stressed. Embodiments of the system described below can identify the atypical gaze pattern and the user elevated stress level and generate an indication that the user is behaving atypically.

In one embodiment, a system configured to identify atypical behavior of a user includes at least a frame that is configured to be worn on a user's head, an eye tracking module that is coupled to the frame, a thermal camera that is coupled to the frame, and a processor. Optionally, the system also includes a head-mounted display (HMD), which is configured to display video to the user.

The eye tracking module coupled to the frame and configured to track the user's gaze while viewing one or more items. Optionally, the user's gaze is tracked while the user performs some work related task, such as performing office work (e.g., if the user is a clerk) or examining a patient (e.g., if the user is a doctor). Optionally, the user's gaze is tracked while the user views video related to the task the user is performing. In one example, the video is presented via the HMD, which may be a virtual reality display, a mixed reality display, and/or an augmented reality display. Optionally, the user's gaze is indicative of attention the user paid to each of the one or more items.

In one embodiment, the eye tracking module includes a camera that takes images of at least one of the user's eyes. Some examples of implementations of an eye tracking module that may be utilized in some embodiments include systems described in U.S. Pat. No. 9,535,251 ("HMD apparatus with adjustable eye tracking device"), systems described in US patent application 2014/0361957 ("Compact eye-tracked head-mounted display"), and U.S. Pat. No. 7,542,210 ("Eye tracking head mounted display"), to name a few examples of the many implementations of eye tracking modules known in the art. In some embodiments, the eye tracking module may be physically coupled to the frame, and include an eye tracker module that is part of an HMD such as in the one used in the FOVE VR display (https://www.getfove.com/). In other embodiments, the eye tracking module may include a camera that is remote of the user (e.g., more than 15 cm away from the face), as described in US patent application ("Visual attention and emotional response detection and display system").

The data generated by the eye tracking module describes the gaze of the user. For example, the data may be indicative of the coordinates, on a display displaying a video, at which the user focused during various times while watching the video. Optionally, the coordinates represent certain pixels and/or sets of pixels. This information may be analyzed along with information that describes the boundaries (e.g., coordinates) of one or more the items in the display at different times during its presentation, in order to determine when the user focused on each item. Optionally, determining which items were viewed by the user may involve utilizing various image processing algorithms, which can identify items (e.g., objects and/or people) and/or define the boundaries of the items at various times. Thus, using the data generated by the eye tracking module, attention levels of the user in each item can be determined (e.g., by the processor). In one example, an attention level of the user in an item is indicative of the amount of time the user spent focusing on the item. In another example, the attention level of the user in an item is indicative of the number of times the user's sight was focused on the item (e.g., before moving to some other item). In still another example, the attention level of the user in an item is indicative of a relative value, which indicates whether the user paid more attention or less attention to the item compared to the other items in the video.

The thermal camera, which weights below 5 g (herein "g" denotes grams), is physically coupled to the frame. Additionally, is pointed at a region of interest (ROI) on the user's face, and is configured to take thermal measurements of the ROI ($TH_{ROI}$). Optionally, the thermal camera is located less than 15 cm away from the face (herein "g" denotes centimeters). Optionally, the thermal camera is located less than 5 cm away from the face. In some embodiments, the system may include additional thermal cameras, which are coupled to the frame, and take thermal measurements of additional ROIs on the user's face. Some examples of systems comprising frames and thermal cameras that may be utilized to implement the system configured to identify atypical behavior of the user are illustrated in FIG. 29 and FIG. 6.

The ROI may cover various regions of the user's face. Optionally, the regions are known to exhibit a change in cutaneous temperature when a person experiences stress. In one embodiment, the ROI covers a portion of a periorbital region of the face (e.g., the periorbital region around the right or left eyes). In another embodiment, the ROI covers a portion of the user's nose. And in still another embodiment, the ROI covers a portion the user's forehead.

In one embodiment, $TH_{ROI}$ are taken during a window of time that lasts between a seconds to a few minutes. Optionally, the window is at least five seconds long, at least thirty seconds long, at least two minutes long, at least five minutes long, at least fifteen minutes long, at least one hour long, or is some other window that is longer than one second. Optionally, during the time the user is exposed to the video, $TH_{ROI}$ from multiple windows may be evaluated (e.g., using a sliding window approach).

The processor is configured, in some embodiments, to generate features and to utilize a model to calculate, based on the feature values, a value indicative of whether the user's behavior while viewing the one or more items was atypical. Optionally, the feature values include at least one feature generated based on $TH_{ROI}$ and at least one feature value indicative of the attention of the user in the one or more items.

In some embodiments, the processor may be the processor 401 or the processor 411, illustrated in FIG. 72a and FIG. 72b, which are schematic illustrations of possible embodiments for computers 400 and 410, respectively. In one embodiment, the processor may be physically coupled to the frame. In another embodiment, the processor may be apart from the frame. For example, the processor may belong to a server.

The model used to calculate the value indicative of whether the user's behavior was atypical is generated based on previous tracking of the user's gaze while viewing other items and previous $TH_{ROI}$ taken during the viewing of the other items. Optionally, the user's behavior during most of the viewing of the other items was typical (i.e., it was not considered atypical). Optionally, the viewing of the previous items was done while the user was performing a similar activity to one performed by the user while $TH_{ROI}$. Optionally, the model is generated based on training samples, with each training sample corresponding to an event in which the user was monitored with the eye tracking module and the thermal camera, and each training sample comprising feature values generated based on a tracking of the user's gaze and $TH_{ROI}$ taken during the event.

In one embodiment, the model is indicative of a probability density function of values derived from $TH_{ROI}$ and/or values derived from tracking the gaze of the user. For example, the model may be a regression model (e.g., a maximum entropy model) generated based on the training samples described above. Optionally, if the value calculated by the processor represents a probability that is below a threshold, the behavior of the user is considered atypical.

In another embodiment, the model describes one or more thresholds derived from $TH_{ROI}$ and/or values derived from tracking the gaze of the user. For example, the model may include typical ranges for $TH_{ROI}$, which are indicative of typical stress levels, and/or typical gaze patterns of the user, which are indicative of how much attention the user pays to different items. Optionally, if the user exhibits behavior that does not correspond to values in the ranges that appear in the model, that is indicative that the user's behavior while viewing the one or more items was atypical.

The processor is configured, in some embodiments, to calculate, based on $TH_{ROI}$ a value describing a stress level of the user. Additionally or alternatively, the processor may be configured to calculate an extent of discordance between the attention the user paid to the one or more items and expected attention levels in the one or more items. Optionally, the stress level and/or the extent of discordance are utilized by the processor to calculate the value indicative of whether the user's behavior while viewing the one or more items was atypical. For example, one or more of the feature values may be generated based on the stress level and/or one or more of the feature values may be generated based on the extent of the discordance.

In some embodiments, when the value calculated by the processor based on the feature values indicates the user's behavior while viewing the one or more items was atypical, that is indicative that a stress level of the user during the viewing, which is calculated based on $TH_{ROI}$, reaches a threshold. The stress levels of the user during most of the time spent viewing the other items, as calculated based on the previous $TH_{ROI}$, do not reach the threshold.

There are various ways in which the processor may calculate the stress level based on $TH_{ROI}$. Optionally, the stress level is a value that is indicative of whether the user felt at least a certain amount of stress, at most a certain amount of stress, and/or whether the user felt stress that falls between a certain range of values (e.g., on a scale between 1 to 10, with ten being a high stress level). Optionally, the processor is further configured to calculate, based on $TH_{ROI}$, stress levels corresponding to different times, and to utilize tracking of the user's gaze to assign stress levels to different items.

In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on thermal measurements of the user (e.g., thermal measurements taken when the user was stressed). Optionally, the certain threshold is determined based on baseline thermal measurements of the user, and the certain threshold represents a difference of a certain magnitude relative to the baseline measurements. Optionally, different thresholds may b e utilized to calculate different levels of stress and/or to calculate the stress level when the user is in a certain emotional state and/or is in an environment characterized by certain environmental conditions.

In another embodiment, the stress level is calculated by determining a similarity between a reference time series corresponding to a certain stress level and $TH_{ROI}$ (or a time series derived from $TH_{ROI}$). Optionally, when a sufficiently high similarity is detected, the processor may interpret that as an indication that the user experienced the certain stress level. Optionally, the reference time series is generated based on thermal measurements of the user (e.g., thermal measurements taken when the user experienced stress at the certain stress level). Optionally, the reference time series is generated based on thermal measurements of other users. Optionally, different reference time series is based on different sets of thermal measurements (e.g., sets collected under different conditions). The different reference time series may be utilized to detect different levels of stress and/or to detect a stress level when the user is in a certain emotional state and/or is in an environment characterized by certain environmental conditions.

In yet another embodiment, the stress level is calculated by generating certain feature values based on $TH_{ROI}$ and utilizing a machine learning based model to calculate, based on the certain feature values, a value indicative of a stress level experienced by the user. Optionally, at least some of the certain feature values are generated based on video, e.g., the at least some of the certain feature values describe properties of the items depicted in the video. In one example, the machine learning-based model is generated based on thermal measurements of the user (e.g., the model is a personalized model). In another example, the machine learning-based model is generated based on thermal measurements of other users (e.g., the model is a general model). Optionally, at least some of the certain feature values describe the emotional state of the user and/or environmental conditions corresponding to when $TH_{ROI}$ were taken. Optionally, at least some of the certain feature values are generated based on previous $TH_{ROI}$ taken before the user viewed the video (e.g., up to 15 minutes before); thus, when determining the extent of stress the user experienced, the processor can account for the user's baseline stress level.

In some embodiments, when the value calculated by the processor based on the feature values indicates the user's behavior while viewing the one or more items was atypical, a divergence between the attention of the user in the one or more items and expected attention of the user in the one or more items is above a certain value. During most of the time spent viewing of the other items, divergences between the attention of the user in the other items and expected attention of the user in the other items were below the threshold.

Expected attention levels in items may be based, in some embodiments, on tracking gazes during the previous viewings of the other items. For example, the attention levels may represent the average attention paid by the other user to each item during the previous viewings.

In some embodiments, determining the expected attention levels in items may involve utilizing a model. Optionally, the model is generated based previous tracking of the user's gaze when observing various videos. Optionally, the model may be generated using one or more of the various attention modelling algorithms known in the art (such algorithms may also be referred to as saliency mapping algorithms). Some of the many algorithms that may be utilized are surveyed in A. Borji, L. Itti, "State-of-the-Art in Visual Attention Modeling", IEEE Transactions on Pattern Analysis & Machine Intelligence vol. 35(1), p. 185-207, 2013.

In one embodiment, a model for attention in visual items may be generated by creating a training set of samples. Where each sample corresponds to an item in a video and includes features values and a label describing the extent of attention in the item. Various feature values may be included in each sample. For example, some feature values may be generated using various image processing techniques and represent various low-level image properties. Some examples of such features may include features derived using Gabor filters, local binary patterns and their derivatives, features derived using algorithms such as SIFT, SURF, and/or ORB, and features derived using PCA or LDA. In another example, at least some feature values may include higher-level description of the items (e.g., after identification of the items and/or actions depicted in the video). In yet another example, some feature values may describe the user viewing the video (e.g., demographic information about the user and/or data related to the user's physiological state). A collection of samples, such as the ones described above, may be provided to a machine learning based training algorithm in order to generate the model. Some examples of the types of models that may be generated include support vector machines (SVMs) and neural networks.

In one embodiment, the expected attention levels comprise values of attention in two or more items. Additionally, the attention the user paid to the two or more items is determined based on the gaze of the user. These two sets of values may be compared in order to calculate the extent of the discordance between the attention the user paid to the items and expected attention levels in the items. In one example, a divergence metric, such as the Kullback-Leibler divergence may be used to calculate the discordance between the two sets of values. In another example, a distance metric, such as a vector dot product may be used to calculate the discordance between the two sets of values.

In another embodiment, the expected attention levels comprise an indication of a subset comprising one or more items to which the user is expected to pay at least a certain amount of attention or one or more items to which the user is expected to pay at most a certain amount of attention. Additionally, a subset of the items to which the user paid at least the certain amount of attention (or at most the certain amount of attention), is determined based on the gaze of the user. In this embodiment, a comparison between the subset of items selected based on expected attention levels and the subset selected based on the gaze of the user may be done in order to calculate the extent of the discordance between the attention the user paid to the items and expected attention levels in the items. In one example, the extent of the discordance is proportional to the size of the symmetric difference between the two subsets.

When utilizing feature values along with a model, such as the model used to calculate the stress level or the model used to calculate the value indicative of whether the user's behavior was atypical, in some embodiments, the feature values may include values based on additional inputs (beyond $TH_{ROI}$). In one example, the processor is further configured to: (i) receive one or more values indicative of at least one of the following parameters of the user: heart rate, heart rate variability, galvanic skin response, respiratory rate, and respiratory rate variability, and (ii) to generate one or more of the feature values based on the one or more values. In another example, the processor is further configured to: (i) receive one or more values measured by at least one of the following sensors coupled to the user: a photoplethysmogram (PPG) sensor, an electrocardiogram (ECG) sensor, an electroencephalography (EEG) sensor, a galvanic skin response (GSR) sensor, and a thermistor, and (ii) to generate one or more of the feature values based on the one or more values. In yet another example, the processor is further configured to: (i) receive one or more values indicative of at least one of the following: whether the user touched at least one of the eyes, whether the user is engaged in physical activity, and an environmental parameter, and (ii) to generate one or more of the feature values based on the one or more values. In still another example, the processor is further configured to: (i) receive one or more values measured by at least one of the following sensors: an accelerometer, a pedometer, a humidity sensor, a miniature radar, a miniature Lidar, an anemometer, an acoustic sensor, and a light meter, and (ii) to generate one or more of the feature values based on the one or more values. And in another example, the processor is further configured to: (i) receive values indicative of at least one of the following properties describing the user: age, gender, weight, height, health problems, mental health problems, occupation, education level, marital status, and (ii) to generate one or more of the feature values based on the one or more values.

Various respiration parameters, such as the breathing rate and breathing type (e.g., nasal vs. mouth breathing) can be important indicators for both stress and the physical condition in general. Though there are times when people tend to breathe through the mouth, such as during exertion, breathing through the mouth on a regular basis can cause health problems. With children, these problems can affect the development of the face, with implications on dental and facial growth. However, generally, predominantly breathing through the mouth can disrupt natural body mechanics, which can lead to various symptoms such as headaches, gingivitis, gum disease, sore throat, bad breath, dental problems, poor sleep, and digestive problems.

People who breathe through the mouth are often not aware when they are doing so. Thus, they cannot take steps to rectify their breathing habits and breathe more through the nose. There is a need for a way to monitor people's breathing during day-to-day activities, in order to determine their breathing rate and extent of mouth breathing, and be able to alert when it is practiced.

Some aspects of this disclosure involve a system that can be utilized to monitor a user's respiration in order to determine the user's breathing rate and/or whether the user's breathing may be characterized as mouth breathing. This information may be utilized to help the user improve his/her breathing habits by encouraging the user to breathe slowly and/or to breathe more through the nose.

Various embodiments described in this disclosure involve systems that can be utilized to collect thermal measurements of Regions Of Interest (ROIs) on a user's face. These thermal measurements can be utilized to calculate values of one or more parameters related to the user's respiration (which are referred to herein as "respiration parameters" and are elaborated on further below). Some examples of respiration parameters include the breathing rate (e.g., the number of breaths per minute), and a type of breathing (e.g., whether the breathing is considered "mouth breathing" or "nasal breathing").

In one embodiment, a system configured to collect thermal measurements related to respiration comprises a frame configured to be worn on a user's head and at least one thermal camera. Each thermal camera from among the at least one thermal camera is physically coupled to the frame and is located less than 15 cm away from the user's face (herein "g" refers to centimeters). Optionally, each thermal camera from among the at least one thermal camera weighs below 5 g (herein "g" refers to grams).

Additionally, the at least one thermal camera is configured to take thermal measurements of first, second, and third regions of interest ($TH_{ROI1}$, $TH_{ROI2}$, $TH_{ROI3}$) on the user's face. Optionally, $ROI_1$ covers a portion of the right side of the upper lip, $ROI_2$ covers a portion of the left side of the upper lip, $ROI_3$ covers a portion of the user's mouth, the center of $ROI_1$ is to the right of the center of $ROI_2$, and the center of $ROI_3$ is below the centers of $ROI_1$ and $ROI_2$. Optionally, each camera, from among the at least one thermal camera, is located less than 8 cm away from the face and above the tip of the nose, and does not occlude $ROI_1$, $ROI_2$, and $ROI_3$. Optionally, $TH_{ROI1}$, $TH_{ROI2}$, and $TH_{ROI3}$ are indicative of the breathing rate of the user. In one example, $ROI_1$ covers more than 60% of a 2×2 cm square adjacent to the right side of the vertical symmetry axis that divides the face and below the right nostril, $ROI_2$ covers more than 60% of a 2×2 cm square adjacent to the left side of the vertical symmetry axis and below the left nostril, and $ROI_3$ covers more than 60% of a 2×5 cm ellipse centered over the vertical symmetry axis and below the nostrils.

It is to be noted that when the at least one thermal camera comprise multiple thermal cameras, then each of the multiple thermal cameras may be used to take thermal measurement of one or more of $ROI_1$, $ROI_2$, and $ROI_3$, but necessarily of all three ROIs. As described in the examples below.

In one embodiment, the at least one thermal camera comprises a narrow band-pass optical filter configured to filter wavelengths around absorption wavelength of $CO_2$. In one example, the center wavelength of the filter is around 4269 nm, and using the filter makes it easier to differentiate between the inhalation and exhalation phases since the concentration of $CO_2$ in exhaled air is typically higher than the concentration of $CO_2$ in inhaled air.

A different number of thermal cameras may be utilized in different embodiments in order to take $TH_{ROI1}$, $TH_{ROI2}$, and $TH_{ROI1}$.

In one embodiment, the at least one thermal camera is one thermal camera, located above the tip of the nose, which comprises microbolometer sensing elements or thermopile sensing elements. For example, camera 115 illustrated in FIG. 47 may be such a camera in one embodiment.

In another embodiment, the at least one thermal camera comprises at least first and second thermal cameras, located at least 0.5 cm to the right and to the left of the vertical symmetry axis that divides the face, respectively, and above the tip of the nose; the first thermal camera is configured to take $TH_{ROI1}$, and the second thermal camera is configured to take $TH_{ROI2}$. Optionally, at least one of the first and second thermal cameras is configured to take $TH_{ROI3}$. Optionally, the at least one thermal camera further comprises a third thermal camera, located above the tip of the nose, and configured to take $TH_{ROI4}$.

Figure 48:
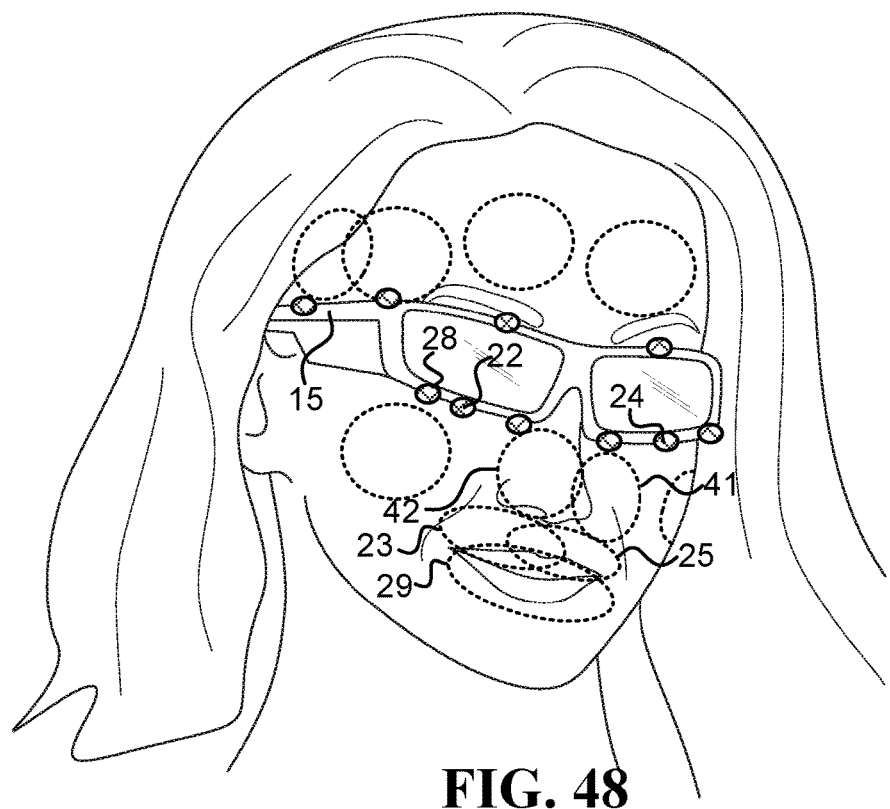
FIG. 48 illustrates another embodiment of the system configured to collect thermal measurements related to respiration.

The following is an example of one embodiment of a system configured to collect thermal measurements related to respiration that includes a frame configured to be worn on a user's head, and first, second, and third thermal cameras. Each of the first, second, and third thermal cameras is physically coupled to the frame, is located less than 15 cm away from the user's face, and does not occlude any of the user's mouth and nostrils. Optionally, each of the thermal cameras weighs below 5 g. The first thermal camera, which is located to the right of the vertical symmetry axis that divides the face, is configured to take thermal measurements of a first region of interest ($TH_{ROI1}$), where $ROI_1$ covers a portion of the right side of the upper lip. The second thermal camera, which is located to the left of the vertical symmetry axis, is configured to take thermal measurements of a second region of interest ($TH_{ROI2}$), where $ROI_2$ covers a portion of the left side of the upper lip. The third thermal camera is configured to take thermal measurements of a third region of interest ($TH_{ROI3}$), where $ROI_3$ covers a portion of the mouth and the center of $ROI_3$ is below the centers of $ROI_1$ and $ROI_2$. Optionally, the first, second, and third thermal cameras are located outside the exhale streams of the mouth and nostrils. Optionally, the first, second, and third thermal cameras are located less than 5 cm away from the face and above the tip of the nose, and the system does not occlude $ROI_1$, $ROI_2$, and $ROI_3$. In another embodiment, the first, second, and third thermal cameras are located less than 5 cm away from the face, and the system occludes $ROI_1$, $ROI_2$, and $ROI_3$. In yet another embodiment, the first and second thermal cameras are located less than 5 cm away from the face. In addition, the first and second thermal cameras may be located at least 0.5 cm to the right and to the left of the vertical symmetry axis that divides the face, respectively. FIG. 48 illustrates one embodiment of the system configured to collect thermal measurements related to respiration in which the first thermal camera 22 measures $ROI_1$ 23, the second thermal camera 24 measures $ROI_2$ 25, and the third thermal camera 28 measures $ROI_3$ 29. These thermal cameras are physically coupled to a frame 15. The figure illustrates additional thermal cameras (illustrated as ovals coupled to the frame 15) and additional ROIs (e.g., ellipses on the cheeks or forehead).

Figure 47:
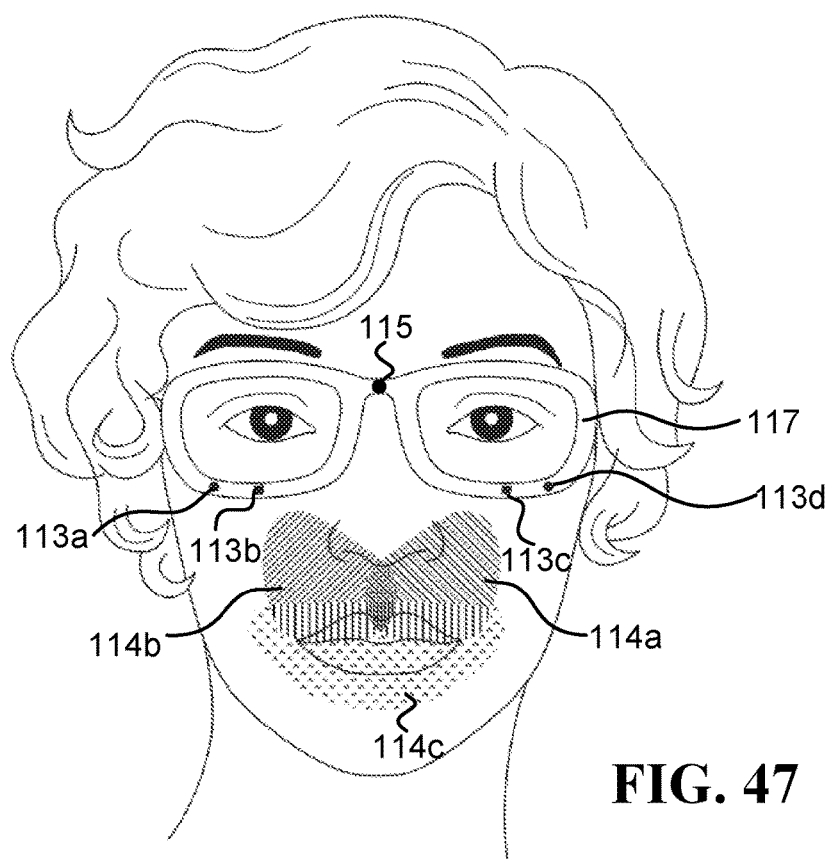
FIG. 47 illustrates an embodiment of a system configured to collect thermal measurements related to respiration.

FIG. 47 illustrates an embodiment of a system configured to collect thermal measurements related to respiration in which four thermal cameras (denoted 113*a* to 113*d*) are coupled to the bottom of a frame 117, which belongs to a pair of eyeglasses. The four thermal cameras are used to take thermal measurements of three ROIs: ROI 114*a* (left nostril area), ROI 114*b* (right nostril area), and ROI 114*c* (mouth area). It is to be noted that the four thermal cameras are located outside of the exhale streams of the nostrils and mouth. Additionally, as illustrated in the figure, at least some portions of the ROIs overlap (illustrated as vertical lines in the region of the upper lip).

Figure 49:
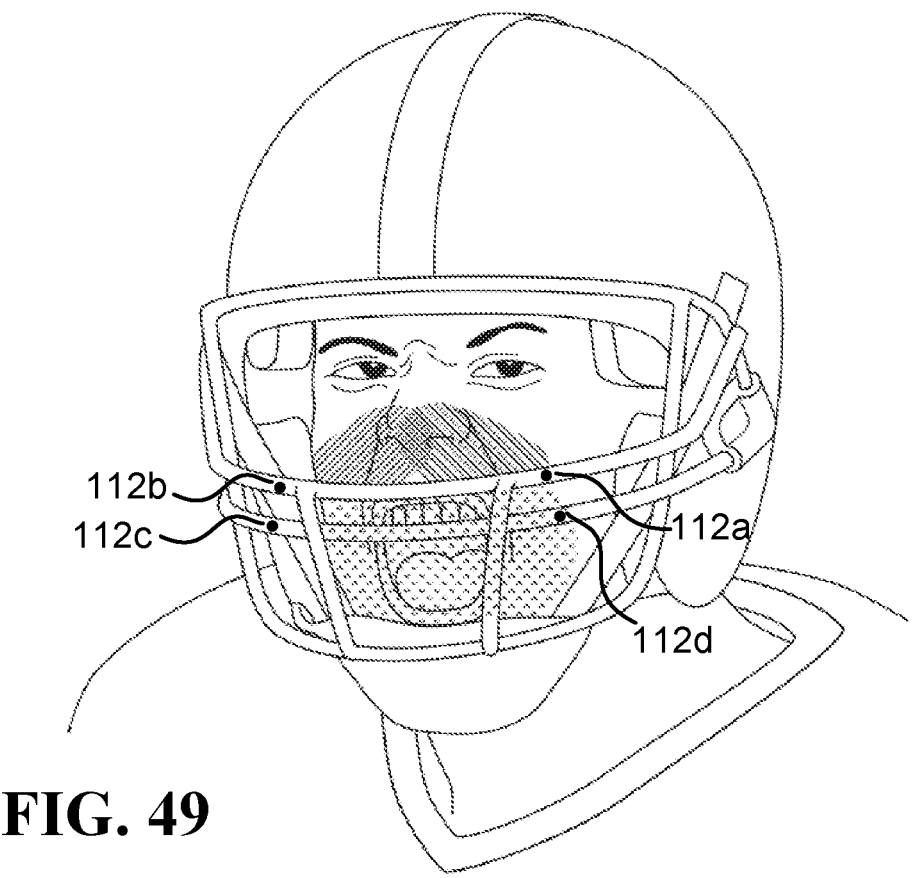
FIG. 49 illustrates one embodiment in which four thermal cameras are coupled to a football helmet.

FIG. 49 illustrates another embodiment of a system configured to collect thermal measurements related to respiration in which four thermal cameras (denoted 112*a* to 112*d*) are coupled to a football helmet, and take thermal measurements of three ROIs: the right and left sides of the nose and the mouth (appear as shaded regions on the users face). In the figure, the thermal cameras are outside of the exhale streams of the mouth and nostrils in order to maintain good measurement accuracy also when using thermal sensors such as thermopiles.

In one embodiment, the at least one thermal camera is based on microbolometer sensing elements or thermopile sensing elements, and comprises a focal plane array (FPA) thermal camera that is used to take at least $TH_{ROI1}$ and $TH_{ROI2}$. In still another embodiment, the at least one thermal camera is based on discrete microbolometer sensing elements or discrete thermopile sensing elements, and comprises at least first second and third thermal cameras configured to provide $TH_{ROI1}$, $TH_{ROI2}$ and $TH_{ROI3}$, respectively.

It is noted that, herein, an "FPA thermal camera" refers to a sensor that includes multiple non-contact temperature sensing elements. In this case, "at least one thermal camera, which is based on discrete microbolometer sensing elements or discrete thermopile sensing elements" refers herein to a combination of at least two sensors, each includes one non-contact temperature sensing element.

As a result of being physically coupled to the frame, each of the at least one thermal cameras remain pointed at their corresponding ROIs when the user's head makes angular movements. In one example, the angular movements include movements of more than 45°. In another example, the locations of the first and second cameras relative to the user's head do not change even when the user's head performs wide angular and lateral movements, where wide angular and lateral movements include angular movements of more than 60° and lateral movements of more than 1 meter.

A more detailed discussion regarding the various types of thermal cameras that may be used in embodiments described in this disclosure, including properties of thermal measurements, is provided in Section 1.

Herein, "mouth breathing" refers to breathing that involves inhaling most of the breathed air through the mouth, and "nasal breathing" refers to breathing that involves inhaling most of the breathed air through the nose. Thus, during a period of time in which the user's breathing is characterized as being mouth breathing, a larger volume of the breathed air enters the body through the mouth, compared to the volume of air that enters the body through the nose. Similarly, during a period of time in which the user's breathing is characterized as being nasal breathing, a larger volume of air enters the body through the nose, compared to the volume of air that enters the body through the mouth.

Figure 51:
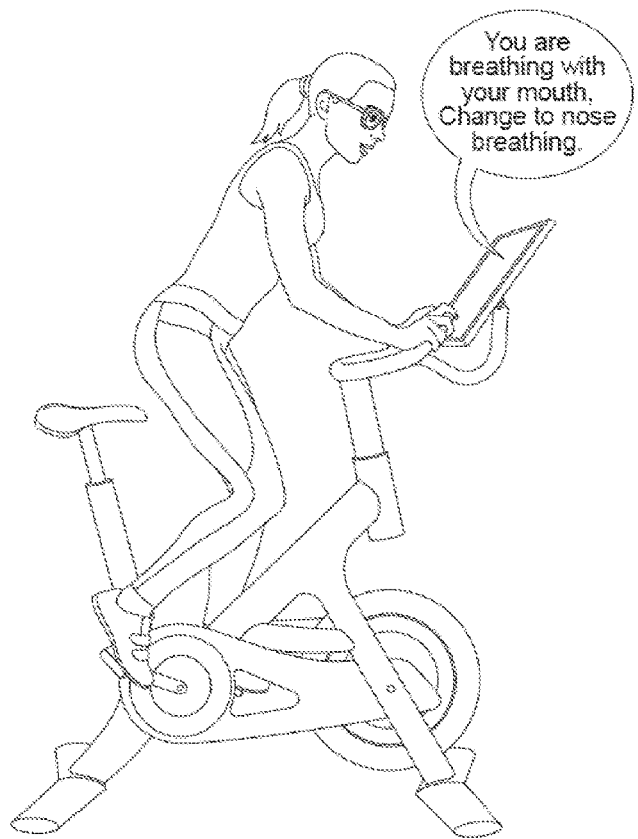
FIG. 51 illustrates an example in which a computer may alert a user who is exercising about the need to breathe through the nose.

The system configured to collect thermal measurements related to respiration may include, in some embodiments, a computer configured to calculate, based on $TH_{ROI1}$, $TH_{ROI2}$, and $TH_{ROI3}$, one or more respiration parameters (which are discussed in more detail further below). Optionally, the computer calculates, based on $TH_{ROI1}$, $TH_{ROI2}$, and $TH_{ROI3}$, a value indicative of the user's breathing rate. Optionally, the computer is configured to calculate, based on $TH_{ROI1}$, $TH_{ROI2}$, and $TH_{ROI3}$, a value indicative of at least one of the following values: an extent to which the breathing was done through the mouth, and an extent to which the breathing was done through the nostrils. For example, the computer may calculate a value that is indicative of an extent to which the user's breathing is characterized as mouth breathing or nasal breathing. Optionally, the computer is further configured to calculate a ratio between the extent to which the user was mouth breathing and the extent to which the user was nasal breathing based on $TH_{ROI1}$, $TH_{ROI2}$, and $TH_{ROI3}$. Optionally, the system is configured to help the user to prefer nasal breathing to mouth breathing by notifying the user when the ratio between mouth breathing and nasal breathing reaches a predetermined threshold. FIG. 51 illustrates an example in which a computer may alert a user who is exercising about the need to breathe through the mouth.

The processor described above may be, in some embodiments, the computer 400 or the computer 410, illustrated in FIG. 72a and FIG. 72b, respectively. Optionally, the computer is not carried by the user, and the system configured to collect thermal measurements related to respiration further includes a communication device that is coupled to the frame and is configured to send $TH_{ROI1}$, $TH_{ROI2}$, and $TH_{ROI3}$ to the computer. For example, the communication device may include a transmitter (which may transmit data wirelessly and/or via a wired connection).

Differentiating between mouth breathing and nasal breathing may involve slightly different objectives, in different embodiments. In one embodiment, differentiating between mouth breathing and nasal breathing corresponds to identifying periods of time during which the user's breathing may be characterized as being predominantly nasal breathing or predominantly mouth breathing. In another embodiment, differentiating between mouth breathing and nasal breathing involves estimating the proportion of air that the user breathed during a certain period of time that passed through the left nostril, the right nostril, and/or the mouth.

In some embodiments, $TH_{ROI1}$, $TH_{ROI2}$, and $TH_{ROI3}$ reflect changes in temperatures around the user's nose and/or mouth due to respiration. For example, the thermal measurements are indicative to temperature changes due to activity involving inhalation of air from the environment and/or exhalation of, typically warmer, air from the body. The frequency at which these changes occur is indicative of the respiration rate. Additionally, the extent at which the temperature changes occur at different ROIs can be indicative of the type of breathing, such as determining whether the breathing is characterized as being mouth breathing or nasal breathing, and/or determining whether the left nostril is dominant or the right nostril is dominant. For example, strong temperature changes measured at the mouth region compared to mild temperature changes measured at the nasal region may be indicative of mouth breathing. In another example, more extreme temperature changes measured at the left nostril compared to the right nostril are indicative of the left nostril being dominant.

Usually, when the temperature of exhaled air is warmer than the environment, the exhaled air (also referred to herein as "exhale") warms up the skin around the nostrils and the inhale cools the skin around the nostrils. This enables the system to identify an inhale, for example based on measuring a decrease stronger than a first rate and/or a first value in the temperature of the skin around the nostrils; identify times of no breathing through the nostrils, for example based on measuring a decrease weaker than the first rate and/or the first value in the temperature of the skin around the nostrils; and identify an exhale, for example based on measuring an increase in the rate and/or value in the temperature of the skin around the nostrils.

In some embodiments, it may be complicated to differentiate between the inhale duration and the no breathing duration (such as the post-exhale pause) based on the thermal measurements. In this case, the system configured to collect thermal measurements related to respiration may implement one or more of the following approaches: (i) combine the inhale duration and the post-exhale pause and treat them as a single event, (ii) extract the inhale duration based on measurements of both skin regions and non-skin regions (e.g., measuring temperature at locations corresponding to exhale stream in front of the user's face and not only temperature at regions on the face), (iii) extract the inhale duration from a non thermal camera sensor, such as (a) a microphone/acoustic sensors configured to detect acoustic vibrations indicative of inhaling; examples of possible locations for the microphone include locating the microphone close to the respiratory airways, over the throat, on the neck, nearby the mouth, and/or in the ear, (b) using an anemometer located inside the inhale breathing stream, such as anemometers located inside the nostrils, and/or (c) a movement sensors coupled to the abdomen, chest and/or neck, (iv) extract the inhale duration from electrocardiogram (ECG), and (v) extract the inhale duration from images of one or more visible-light cameras that are physically coupled to the frame, and are configured to take images of at least part of the nose; the computer identifies the inhale duration based on image analysis of the images of the nose by identifying movements of the nose, especially at the edges of the nostrils, indicative of breathing. The following are some more detailed examples of a couple of the approaches mentioned above.

In some embodiments, the system configured to collect thermal measurements related to respiration comprises at least one visible-light camera that is physically coupled to the frame, and is configured to take images of at least part of the nose. Optionally, images of the nose may be utilized in the process of calculating a value of a respiration parameter of the user (e.g., a breathing rate or a post-inhale pause). In one example, the camera 115 (illustrated in FIG. 47) is such a visible light camera that may be utilized to take images of the nose.

In one embodiment, one or more feature values may be generated based on images of the nose taken utilizing the one or more visible-light cameras. Examples of the various types of feature values that may be generated based on the images are described in Section 6. The one or more feature values may be utilized in the calculation of the respiration parameter in addition to feature values generated based on $TH_{ROI1}$, $TH_{ROI2}$, and/or $T_{ROI3}$. In another embodiment, a computer is configured to identify an inhale based on image analysis of the images of the nose. Optionally, the image analysis identifies movements of the nose, especially at the edges of the nostrils, which are indicative of inhaling. Optionally, the computer is further configured to calculate the ratio between the extent to which the user performed mouth breathing and the extent to which the user performed nasal breathing based on $TH_{ROI1}$, $TH_{ROI2}$, $TH_{ROI3}$, and results of the image analysis, and the system is configured to help the user to prefer nasal breathing over mouth breathing by notifying the user when the ratio between mouth breathing and nasal breathing reaches a predetermined threshold. In yet another embodiment, a computer is configured to differentiate between an inhale and a breathing pause that follows the inhale based on image analysis of the images of the nose. Optionally, the image analysis identifies movements of the nose, especially at the edges of the nostrils, which are indicative of the inhale versus the breathing pause.

In some embodiments, the system configured to collect thermal measurements related to respiration further comprises an in-the-ear earbud comprising a microphone that is configured to measure sounds inside the ear canal. Optionally, these sounds may include breathing sounds. Optionally, a computer is configured to identify an inhale based on audio signal analysis of the recordings from the earbud. Optionally, the inhale sound measured by the earbud is stronger when the dominant nostril is the nostril closer to the ear in which the earbud is plugged in, compared to the inhale sound measured by the earbud when the other nostril is the dominant nostril. Optionally, the computer is further configured to calculate a ratio between mouth breathing and nasal breathing based on $TH_{ROI1}$, $TH_{ROI2}$, $TH_{ROI3}$, (as discussed in more detail below) and results of the audio signal analysis, and the system is configured to help the user to prefer nasal breathing over mouth breathing by notifying the user when the ratio between mouth breathing and nasal breathing reaches a predetermined threshold.

In order to increase the user's awareness to periods in which the user is practicing mouth breathing, some embodiments may include a graphical user interface (GUI) for the user. Optionally, colors and/or other aspects of images displayed on the GUI are determined by a theme. Optionally, the system is configured to help the user to develop awareness towards the type of breathing being conducted by: utilizing a first theme when the user's breathing is characterized as nasal breathing, and utilizing a second theme when the user's breathing is characterized as mouth breathing. Optionally, the first and second themes differ with respect to at least one of the following properties: color selection for various objects, brightness level, and way of organizing data to be presented to the user.

When breathing through the nostrils, the air does not typically flow uniformly through both nostrils. Often one of the nostrils is dominant, and most of the air that is breathed through the nose flows through it. Knowing which nostril is dominant may have various applications as discussed elsewhere in this disclosure.

In one embodiment, a computer is further configured to calculate, based on $TH_{ROI1}$ and $TH_{ROI2}$, a ratio between an extent the user breathed through the right nostril and an extent the user breathed through the left nostril. Optionally, the extent to which a user breathed through a nostril is proportional to the volume of air breathed through the nostril. Optionally, the system is further configured to help the user to develop awareness to the dominant nostril by performing at least one of the following steps: notifying the user the ratio between the extent the user breathed through the right and left nostrils is balanced, notifying the user when the ratio reaches a predetermined threshold, notifying the user when a trend in values of the ratio changes direction, notifying the user when the right nostril is the dominant nostril, and notifying the user when the left nostril is the dominant nostril.

Figure 52:
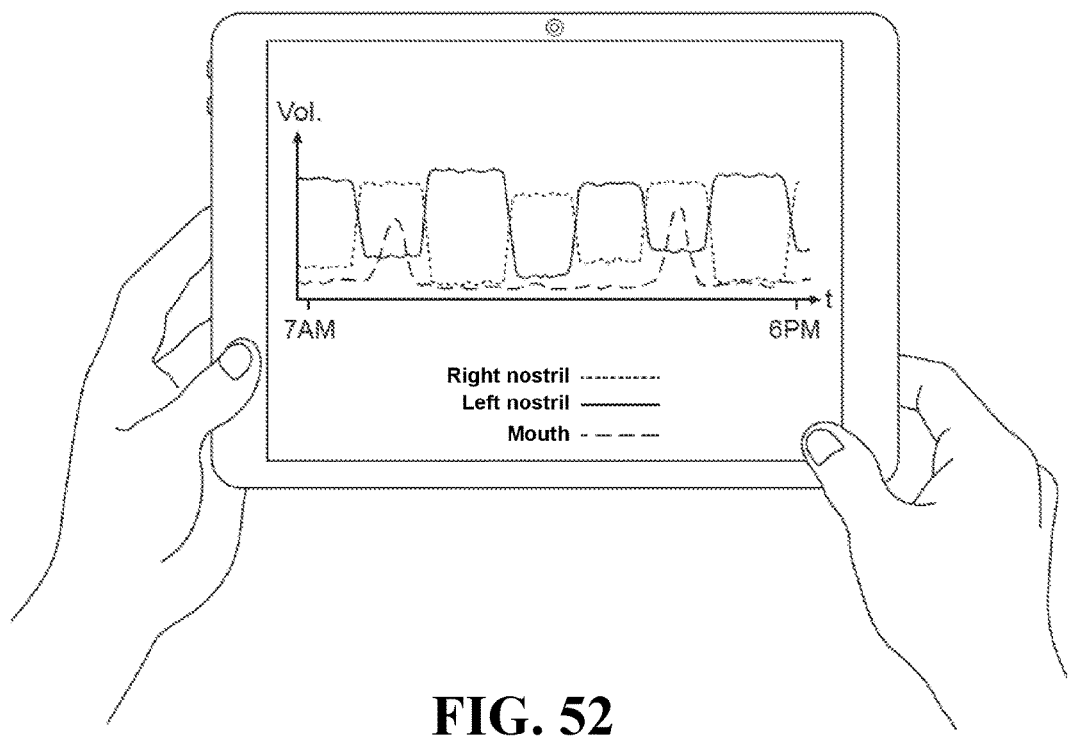
FIG. 52 illustrates one example of an interface that provides a graphical display of the extent of air breathed through each of the nostrils and the mouth.

In one example, when the ratio between the extent the user breathed through the right nostril and an extent the user breathed through the left nostril is balanced, it means that the amount of air going through the left nostril is at least 80%, and at most 125%, of the amount of air going through the right nostril. In another example, the ratio is considered balanced when the amount of air going through the left nostril is at least 67%, and at most 150%, of the amount of air going through the right nostril. It is to be noted that the dominant nostril of a normal healthy person changes every 90-120 minutes on average. Thus, over the course of a day, the trend in the values of the ratio typically changes direction several times. FIG. 52 illustrates one example of an interface that provides a graphical display of the extent of air breathed through each of the nostrils and the mouth over the course of a day from 7 AM to 6 PM. Reviewing such a graph can help make a user more self-aware of the type of how the user breaths throughout the day.

Another approach to increase the user's awareness to the dominant nostril (and of mouth breathing vs. nasal breathing), which may be utilized in some embodiments, involves a graphical user interface (GUI) that may present information for the user in different ways. Optionally, colors and/or other aspects of images displayed on the GUI are determined by a theme. Optionally, the system is configured to help the user develop awareness towards the dominant nostril by: utilizing a first theme when the right nostril is dominant, using a second theme when the left nostril is dominant, and utilizing a third theme breathing through the nose is balanced. Optionally, the first, second, and third themes differ with respect to at least one of the following properties: color selection for various objects, brightness level, and way of organizing data to be presented to the user.

The duration of exhaling an inhaling (denoted herein $t_{exhale}$ and $t_{inhale}$, respectively) can have various physiological effects. For example, for some users, breathing with prolonged inhales (relative to the exhales) can increase the possibility of suffering an asthma attack. In particular, keeping the duration of exhaling longer than the duration of inhaling (i.e., $t_{exhale}/t_{inhale}>1$, and preferably $t_{exhale}/t_{inhale}\approx 2$) may provide many benefits, such as having a calming effect and relieving asthma symptoms. In one embodiment, the computer is further configured to calculate, based on $TH_{ROI1}$, $TH_{ROI2}$ and $TH_{ROI3}$, the ratio between exhale and inhale durations ($t_{exhale}/t_{inhale}$).

Many people are not aware of their breathing most of the time. These people can benefit from a system that is able to calculate $t_{exhale}/t_{inhale}$ and provide them with feedback when it is beneficial to increase the ratio (i.e., increase the duration of exhaling and/or reduce the duration of inhaling) when it falls below a threshold. In one embodiment, the computer is further configured to alert the user, via a user interface (UI), and instruct the user to increase $t_{exhale}/t_{inhale}$ when it falls below the threshold. Optionally, the computer is further configured to update occasionally the calculation of $t_{exhale}/t_{inhale}$, and to suggest to the user, via the UI, to progressively increase $t_{exhale}/t_{inhale}$ at least until reaching a ratio of 1.5. Optionally, the computer is further configured not to suggest to the user, via the UI, to increase $t_{exhale}/t_{inhale}$ responsive to identifying that $t_{exhale}/t_{inhale} \geq 2$.

Figure 50:
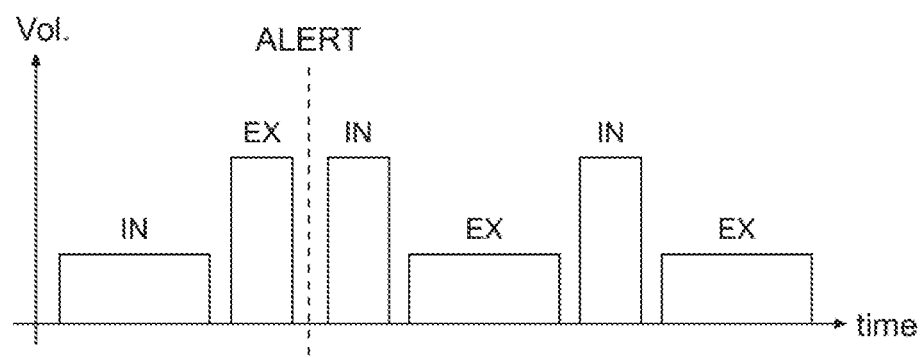
FIG. 50 illustrates a situation in which an alert is issued to a user when it is detected that the ratio $t_{exhale}/t_{inhale}$ is too low.
Figure 53:
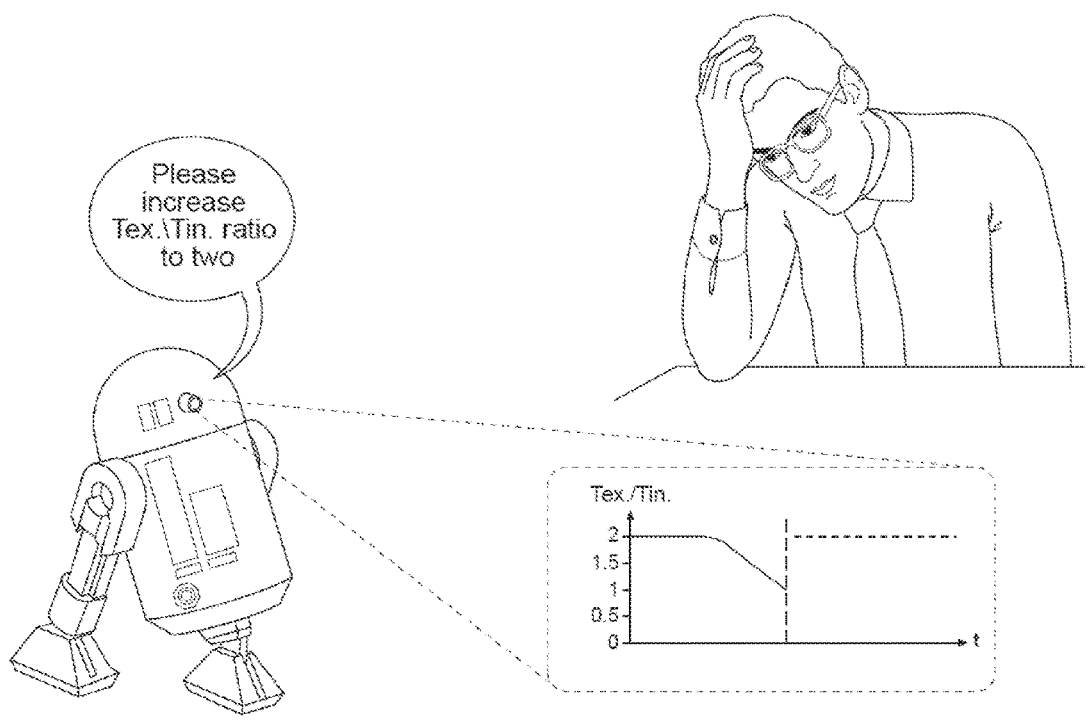
FIG. 53 illustrates a virtual robot that urges a user to increase the ratio between the duration of the user's exhales and inhales in order to alleviate stress that builds up.

FIG. 50 illustrates a situation in which an alert is issued to a user when it is detected that the ratio $t_{exhale}/t_{inhale}$ is too low. Another scenario in which such an alert may be issued to a user is illustrated in FIG. 53, which shows a virtual robot that the user sees via augmented reality (AR). The robot urges the user to increase the ratio between the duration of the user's exhales and inhales in order to alleviate the stress that builds up. Monitoring of respiratory parameters, and in particular, the ratio $t_{exhale}/t_{inhale}$ can help a user address a variety of respiratory-related symptoms, as described in the following examples.

Asthma attacks are a physiological response that is closely related to a person's breathing. In particular, certain changes in a person's respiratory behavior can indicate an imminent asthma attack. Herein, an asthma attack may be considered imminent if it is likely to occur within seconds or several minutes. In some embodiments, the system configured to collect thermal measurements related to respiration includes a computer that is configured to alert the user, via a UI, about an imminent asthma attack responsive to identifying an increase in the user's breathing rate above a predetermined threshold. Optionally, the computer receives, prior to alerting the user, an indication that the user suffers from asthma (e.g., an indication that asthma is a preexisting condition and optionally an indication of the severity of the condition).

Figure 54:
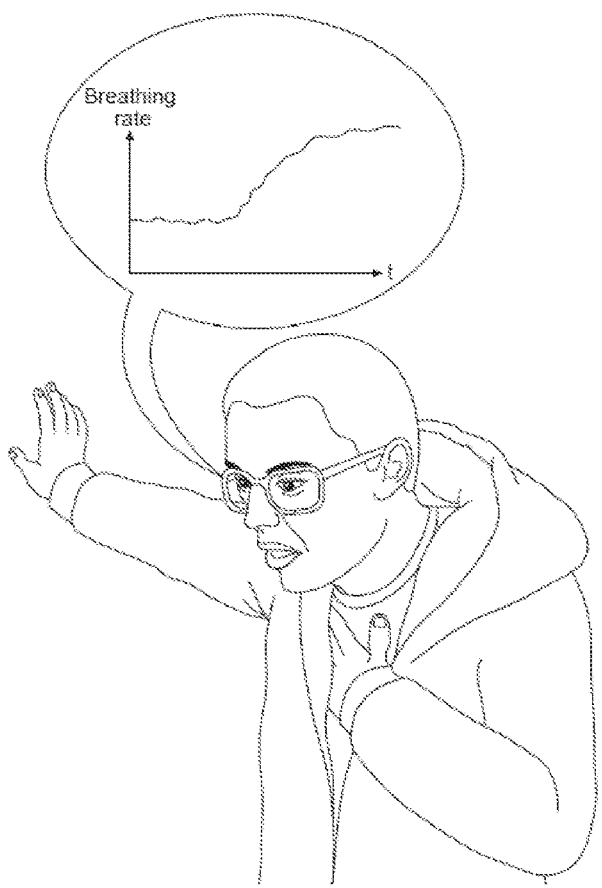
FIG. 54 illustrates an asthmatic patient that receives an alert that his breathing rate increased to an extent that often precedes an asthma attack.

FIG. 54 illustrates an asthmatic patient that receives an alert (e.g., via an augmented reality display) that his breathing rate increased to an extent that often precedes an asthma attack. It is noted that in addition to the breathing rate, the computer may base its determination that an asthma attack is imminent on additional factors, as described in the following examples.

In one embodiment, the computer may receive recordings of the user obtained with a microphone. Such recordings may include sounds that can indicate that an asthma attack is imminent; these sounds may include: asthmatic breathing sounds, asthma wheezing, and coughing. Optionally, the computer analyzes the recordings to identify occurrences of one or more of the above sounds. Optionally, taking into account the recordings of the user can affect how the computer issues alerts regarding an imminent asthma attack. For example, a first alert provided to the user in response to identifying the increase in the user's breathing rate above the predetermined threshold without identifying at least one of the body sounds is less intense than a second alert provided to the user in response to identifying both the increase in the user's breathing rate above the predetermined threshold and at least one of the body sounds. Optionally, in the example above, the first alert may not be issued to the user at all.

In another embodiment, the computer may receive measurements obtained from a movement sensor worn by the user and configured to measure user movements. Some movements that may be measured and may be related to an asthma attack include: spasms, shivering, and sagittal plane movements indicative of one or more of asthma wheezing, coughing, and chest tightness. Optionally, the computer analyzes the measurements of the movement sensor to identify occurrences of one or more of the above movements. Optionally, taking into account measurements of the movement sensor can affect how the computer issues alerts regarding an imminent asthma attack. For example, a first alert provided to the user in response to identifying the increase in the user's breathing rate above the predetermined threshold without the sensor measurements reflecting at least one of the movements mentioned above is less intense than a second alert provided to the user in response to identifying the increase in the user's breathing rate above the predetermined threshold and the sensor measurements reflecting at least one of the movements mentioned above.

Upon determining that an asthma attack is imminent, in some embodiments, a user interface (UI) may be used to alert the user regarding the imminent asthma attack and/or provide suggestions that may alleviate it or even stave it off at that time. Optionally, responsive to a determination that an asthma attack imminent, the UI suggests the user to take a precaution, such as increasing $t_{exhale}/t_{inhale}$, preforming various breathing exercises (e.g., exercises that involve holding the breath), taking medication (e.g., medication administered using an inhaler), and/or performing a shoulder stand (sarvāṅgāsana), in order to prevent or decrease the severity of the asthma attack Optionally, detecting of the signs of an imminent asthma attack comprises identifying an increase in the breathing rate above a predetermined threshold.

Stress is also a physiological response that is closely related to a person's breathing. In embodiment, the system includes a computer that is configured to: receive a first indication that the user's stress level reaches a threshold, receive at least one of the following second indications: (i) that the ratio between exhaling and inhaling durations is below 1.5 ($t_{exhale}/t_{inhale}<1.5$), and (ii) that the user's breathing rate reached a predetermined threshold, and command a UI to suggest the user to increase $t_{exhale}/t_{inhale}$ to at least 1.5. Optionally, the computer is further configured to: receive the first indication from a wearable device, calculate $t_{exhale}/t_{inhale}$ based on $TH_{ROI1}$, $TH_{ROI2}$, and $TH_{ROI3}$ and command the UI to provide the user with an auditory and/or visual feedback indicative of the change in $t_{exhale}/t_{inhale}$ in response to the suggestion to increase the ratio. Optionally, the computer is further configured to command the UI to: update the user about changes in the stress level in response to increasing $t_{exhale}/t_{inhale}$, and provide positive reinforcement to help the user to maintain the required ratio at least until a certain improvement in the stress level is achieved.

Various events may be the cause of stress and/or other phenomena whose symptoms may involve a user's breathing. In one embodiment, the system includes a computer that is configured to receive a first indication that the user is about to have an imminent event, and at least one of the following second indications: (i) that the ratio between exhaling and inhaling durations is below 1.5 ($t_{exhale}/t_{inhale}<1.5$), and (ii) that the user's breathing rate reached a predetermined threshold. The computer is further configured to command a UI to suggest the user to increase $t_{exhale}/t_{inhale}$ responsive to receiving such first and second indications. Optionally, the imminent event comprises at least one of the following events: entering a social interaction, entering a meeting, entering one's home, entering a pleasant or unpleasant situation, entering a place with unpleasant temperature, taking a test, starting a game session, making a speech, making a phone call, responding to a request to make a decision, reading something that is expected to affect the user's emotions above a predetermined threshold, and reaching a traffic jam. Optionally, the first indication is received from at least one of the following sources of information: a virtual assistant (e.g., a software agent), a calendar, a to-do list application, a reminder application, a project management application, a navigation application, a messaging application with semantic analysis and emotional response predictor, and an interactive computer program. Optionally, the computer is further configured not to command the UI to suggest the user to increase $t_{exhale}/t_{inhale}$ responsive to identifying that $t_{exhale}/t_{inhale} \geq 1.5$.

Some elderly and/or unfit people can find it difficult to stand up and/or make other physical efforts because many of them do not exhale while making the effort, and/or do not synchronize the physical effort with their breathing. These people can benefit from a system that is able to remind them to exhale while making the effort, and/or help them synchronize the physical effort with their breathing, instead of trying to synchronize their breathing with the physical effort.

In one embodiment, the system configured to collect thermal measurements related to respiration includes a computer that is configured to: receive a first indication that the user is going to make a physical effort, command a UI to suggest the user to exhale while making the physical effort, determine based on $TH_{ROI1}$, $TH_{ROI2}$, and $TH_{ROI3}$ whether the user exhaled while making the physical effort, and command the UI to play a positive feedback in response to determining that the user managed to exhale while making the physical effort. Optionally, in response to determining that the user did not exhale while making the physical effort, the computer commands the UI to play an explanation why the user should try next time to exhale while making the physical effort. Optionally, the computer is further configured to: receive the first indication from a wearable device, calculate the second indication based on $TH_{ROI1}$, $TH_{ROI2}$, and $TH_{ROI3}$ and command the UI to provide the user with an auditory and/or visual feedback indicative of the change in $t_{exhale}/t_{inhale}$ in response to the suggestion to increase the ratio. Optionally, the computer is further configured to command the UI to: update the user about changes in the stress level in response to increasing $t_{exhale}/t_{inhale}$, and provide positive reinforcement to help the user to maintain the required ratio at least until a certain improvement in the stress level is achieved. Optionally, the physical effort includes at least one of the following activities: standing up, sitting down, manipulating with the hands an item that requires applying a significant force, defecating, dressing, leaning over, and lifting an item.

Figure 55A:
FIG. 55a and FIG. 55b illustrate training a user to exhale while exerting an effort.
Figure 55B:

FIG. 55a and FIG. 55b illustrate how an embodiment of a system described above may help train a user to exhale while exerting an effort. In FIG. 55a the system identifies that the user inhaled rather than exhaled, while getting up from a sitting position in a chair; the system alerts the user to this fact and suggests that next time the user should exhale while getting up. In FIG. 55b, the system identifies that the user exhaled at the correct time and commends the user on doing so.

In various embodiments described herein, one or more thermal cameras coupled to a frame worn by a user, e.g., as illustrated in FIG. 47 and/or FIG. 48, may be utilized to take thermal measurements of one or more ROIs that cover at least a portion of at least one of the following regions: the user's upper lip, the user's mouth, the space where the exhale stream form the user's nose flows, and/or the space where the exhale stream from the user's mouth flows (these thermal measurements are denoted $TH_{NM}$). In one example, $TH_{NM}$ include $TH_{ROI1}$, $TH_{ROI2}$, and $TH_{ROI3}$, which are mentioned above in the discussion regarding embodiments illustrated in FIG. 47 and/or FIG. 48. Optionally, the value of one or more of the following respiration parameters is calculated by a processor belonging to an embodiment described in this disclosure of a system configured to collect thermal measurements related to respiration.

In other embodiments, one or more of the respiratory parameters may be calculated by generating feature values based on $TH_{NM}$ and utilizing a model to calculate, based on the feature values, the value of a certain respiratory parameter from among the parameters mentioned above. A detailed discussion regarding how such a model may be generated and utilized is given in the description below of embodiments illustrated in FIG. 56 and FIG. 58.

Figure 56:
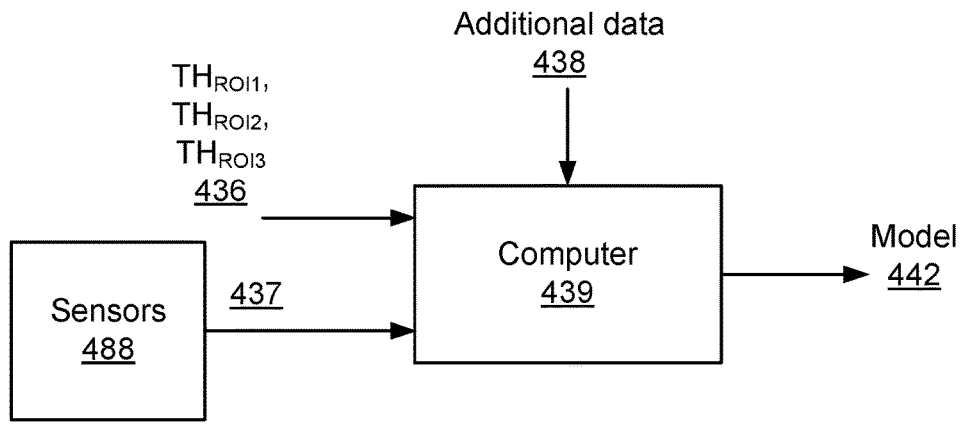
FIG. 56 illustrates an embodiment of a system configured to generate a model for detecting a physiological response based on thermal measurements of the face.

FIG. 56 illustrates an embodiment of a system configured to generate a model for estimating values of a respiratory parameter based on thermal measurements of the face. The system includes head-mounted systems (HMSs) configured to be worn by users, sensors 488, and a computer 439.

Each HMS may be one of the HMSs described in this disclosure, such as HMSs illustrated in FIG. 47 or FIG. 48, FIG. 49, or FIG. 8a. In one embodiment, each HMS comprises a frame and one or more thermal cameras that are physically coupled to the frame and configured to take: thermal measurements of a portion of the right side of the upper lip ($TH_{ROI1}$), thermal measurements of a portion of the left side of the upper lip ($TH_{ROI2}$), and thermal measurements of a portion of the mouth ($TH_{ROI3}$) of the user who wears the HMS. In one embodiment, the first region of interest ($ROI_1$) covers a portion of the right side of the upper lip, the second region of interest ($ROI_2$) covers a portion of the left side of the upper lip, and the third region of interest ($ROI_3$) covers a portion of the user's mouth, the center of $ROI_1$ is to the right of the center of $ROI_2$, and the center of $ROI_3$ is below the centers of $ROI_1$ and $ROI_2$. Additionally, $TH_{ROI1}$, $TH_{ROI2}$, and $TH_{ROI3}$ are taken from a distance of less than 15 cm from the user's face (e.g., by one or more thermal cameras physically coupled to a frame worn by the user). Optionally, $TH_{ROI1}$, $TH_{ROI2}$, and $TH_{ROI3}$ are taken by an embodiment of a system configured to collect thermal measurements related to respiration, which is described above (e.g., see FIG. 47 and FIG. 48). In FIG. 56 $TH_{ROI1}$, $TH_{ROI2}$, and $TH_{ROI3}$ of the one or more users are denoted with reference numeral 436 and the values of the respiratory parameter, which correspond to $TH_{ROI1}$, $TH_{ROI2}$, and $TH_{ROI3}$ 436, are denoted with the reference numeral 437. Optionally, each thermal camera weighs below 5 g and is located less than 15 cm away from the user's face. Examples of the various types of thermal cameras that may be utilized to obtain $TH_{ROI1}$, $TH_{ROI2}$, and $TH_{ROI3}$ 436 are given at least in Section 1.

In one embodiment, the sensors 488 are configured to measure values 437 of respiratory parameters of the users. Optionally, a value of the respiratory parameter is indicative of at least one of the following values: a respiration rate, respiration volume, an extent of mouth breathing, an extent of nasal breathing, exhale (inhale) duration, post-exhale (post-inhale) breathing pause, a dominant nostril, an exhale stream shape, exhale stream smoothness, and an exhale stream temperature. Some examples of the sensors 488 are discussed further below.

The computer 439 is configured, in one embodiment, to generate samples based on data pertaining to one or more users. The data pertaining to each user, from among the one or more users, includes: (i) $TH_{ROI1}$, $TH_{ROI2}$, and $TH_{ROI3}$ of the user (from among $TH_{ROI1}$, $TH_{ROI2}$, and $TH_{ROI3}$ 436), and (ii) one or more values of the respiratory parameter of the user (from among the values 437). The computer 439 is further configured to generate a model 442 based on the samples, and to provide the model 442 to be used by a system that estimates the values of the respiratory parameter based on $TH_{ROI1}$, $TH_{ROI2}$, and $TH_{ROI3}$ such as a system illustrated in FIG. 58. Optionally, each sample comprises feature values based on $TH_{ROI1}$, $TH_{ROI2}$, and $TH_{ROI3}$ of a user, from among the one or more users, taken during a certain period, and a label indicative of a value of a respiratory parameter of the user during the certain period. In some embodiments, feature values in a sample from among the samples may include feature values that are based on other sources of information. For example, at least one of the feature values in the sample may be generated based on physiological measurements of the user, which are not among $TH_{ROI1}$, $TH_{ROI2}$, and $TH_{ROI2}$ of the user, and/or measurements of the environment in which the user was in during the certain period.

It is to be noted that references to "the computer 439" should be interpreted as one or more computers. In some embodiments, multiple computers, possibly in different sites, may be employed in order to implement the functionality attributed herein to the computer 439. In one example, samples generated based on data of different users may be generated by different computers (e.g., computers belonging to devices of the users), while generating the model 442 may be done by a computer that is a server (which does not belong to any of the users).

In one embodiment, at least some of the values 437 corresponding to $TH_{ROI1}$, $TH_{ROI2}$, and $TH_{ROI3}$ of a user, from among the one or more users, are determined based on analysis of measurements of the user, which are taken using a sensor from among the sensors 488. Optionally, the sensor is different from the one or more thermal cameras used to take $TH_{ROI1}$, $TH_{ROI2}$, and $TH_{ROI3}$. Optionally, the sensor is not physically coupled to the frame worn by the user. Measurements obtained by the one or more devices may be analyzed by a human expert and/or a software program in order to generate the at least some of the values 437. In one example, the sensor is part of a smart shirt and/or chest band that measures various respiratory (and other) parameters. One example of a smart shirt is the Hexoskin smart shirt that can measure Breathing Rate (RPM), Minute Ventilation (L/min), and various other parameters related to a user's respiration, heart rate, and physical activity. In another example, the sensor comprises devices that may be used to measure respiratory volume such as a balloon or a spirometer. In yet another example, the sensor may include a thermal imaging camera that takes images of the user's face and surroundings (e.g., in order to receive images of the exhale stream). In this example, the thermal camera may be detached from the user (i.e., not physically coupled to the user).

In addition to the sensors 488, and/or instead of the sensors 488, in some embodiments, the values 437 may be obtained from other sources. In one embodiment, at least some of the values 437 corresponding to $TH_{ROI1}$, $TH_{ROI2}$, and $TH_{ROI3}$ of a user, from among the one or more users, are generated by an external source such as an entity that observes the user, which may be a human observer or a software program. Optionally, the software program is a software agent operating on behalf of the user. In one example, the entity may determine the smoothness of the user's exhaling. In another example, the entity may determine whether the user's breathing is mouth breathing or nasal breathing.

In another embodiment, at least some of the values 437 corresponding to $TH_{ROI1}$, $TH_{ROI2}$, and $TH_{ROI3}$ of a user, from among the users, may be generated by the user. For example, the user may provide indications indicating whether he/she is breathing through the mouth or nose and/or which nostril is dominant Optionally, the indications are provided via a mobile "app" (e.g., by pressing a certain button on a screen of a smartphone). Optionally, indications may be provided by making comments that are interpreted by a software agent and/or a program with speech analysis capabilities.

The certain period of time during which $TH_{ROI1}$, $TH_{ROI2}$, and $TH_{ROI3}$ used to generate each sample may be different in different embodiments. In some embodiments, each of the samples represents a short snapshot of temperatures and/or changes to temperatures at the corresponding ROIs due to respiratory activity; thus, the certain period in these embodiments may be less than five seconds, less than ten seconds, or less than thirty seconds. In some embodiments, each of the samples may be based on $TH_{ROI1}$, $TH_{ROI2}$, and $TH_{ROI3}$ taken during a period of time sufficiently long to include multiple measurements of temperatures and/or temperature changes at each of the ROIs. Optionally, the certain period during which each $TH_{ROI1}$, $TH_{ROI2}$, and $TH_{ROI3}$ for each of the samples were taken is at least one second, at least five seconds, at least ten seconds, at least one minute, at least five minutes, at least one hour, or at least one day.

When the certain period is sufficiently long to include successive thermal measurements at the same corresponding ROIs (i.e., $ROI_1$, $ROI_2$, and $ROI_3$ mentioned above) the feature values generated based on $TH_{ROI2}$ $TH_{ROI2}$, and $T_{ROI3}$ taken during the certain period may include various types of features. In one embodiment, some of the feature values may represent statistics of the successive thermal measurements at the corresponding ROIs (e.g., the average at an ROI during the certain period). In another embodiment, the feature values may include multiple values based on the successive measurements. In yet another embodiment, the features value may include a feature value that represents a trend of $TH_{ROI1}$, $TH_{ROI2}$, and $TH_{ROI3}$ during a portion of the certain period. For example, the feature values may include a feature value indicative of the extent the temperature at a certain ROI, from among $ROI_1$, $ROI_2$, and $ROI_3$, changed throughout the portion of the certain period and/or a feature value indicative of the extent the average temperature at multiple ROIs changed during the portion of the certain period.

The computer 439 is configured, in some embodiments, generate feature values for each of the samples based on $TH_{ROI1}$, $TH_{ROI2}$, and $TH_{ROI3}$ of a user taken during a certain period and possibly other information sources pertaining to the user and/or the environment the user was is, as mentioned below.

The term "feature values" is typically used herein to represent data comprising values on which calculations may be performed. In one exemplary embodiment, feature values may be provided to a machine learning based estimator (which may also be called a "predictor") in order to perform calculations on the data utilizing a model (e.g., in order to perform inference). In one example, feature values are data that may be represented as a vector of numerical values (e.g., integer and/or real values), with each position in the vector corresponding to a certain feature. In some examples, in vectors representing feature values of different samples, each position (dimension) in the vectors corresponds to the same feature. Thus, in these examples, different samples may be considered to include data representing the same features, but include different feature values. For example, the vectors may include measurements of temperatures at ROIs, but each sample may include different values of temperatures (at the ROIs). In another example, feature values are stored in a data structure having a predetermined section that identifies the type of data stored in the data structure. For example, the feature values may be stored in the payload of a packet, and a predefined data structure in the packet's header identifies the one or more types of data stored in the payload. Alternatively or additionally, a predefined data structure in the packet's tail may identify the one or more types of data stored in the packet's payload.

In some embodiments, at least one of the feature values generated based on $TH_{ROI1}$, $TH_{ROI2}$, and $TH_{ROI3}$ of a user, from among the users, taken during a certain period include values measured by the one or more thermal cameras during the certain period. Optionally, the values measured by the one or more thermal cameras may undergo various forms of filtering and/or normalization. In one example, some feature values may be average values of certain sensors (pixels) of the one or more thermal cameras during the certain period and/or some feature values may be values measured at certain times during the certain period by the certain sensors. In another example, the feature values generated based on $TH_{ROI2}$, $TH_{ROI2}$, and $TH_{ROI3}$ of the user taken during the certain period may include time series data comprising values measured by the one or more sensors during the certain period.

In addition to $TH_{ROI1}$, $TH_{ROI2}$, and $TH_{ROI3}$ of a user taken during a certain period, in some embodiments, additional sources of information may be utilized to generate one or more of the feature values. Optionally, these additional sources of information pertain to the user. Additionally or alternatively, the additional sources of information may pertain to the environment the user is in. The following are some examples of additional sources of information that may be utilized to generate feature values. Additional discussion regarding the additional sources of information and their utilization may be found in Section 4.

In one embodiment, the computer 439 may be further configured to receive additional measurements of the user and to generate at least one of the feature values based on the additional measurements. Optionally, the additional measurements are indicative of one or more of the following signals of the user: a heart rate, heart rate variability, brainwave activity, galvanic skin response, muscle activity, and an extent of movement. Optionally, the additional measurements may be obtained utilizing one or more of the various sensors that are described in Section 4, which are not thermal cameras.

Some of the additional sources of information may relate to the environment a user was in when $TH_{ROI1}$, $TH_{ROI2}$, and $TH_{ROI3}$ of the user were taken. In one embodiment, the computer 439 may be further configured to receive measurements of the environment and to generate at least one feature value based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In some embodiments, additional data pertaining to a user, which may be used to generate one or more of the feature values, involves indications of various factors that may be considered confounding factors that may hamper accurate calculation of a value of a respiratory parameter. Some examples of such confounding factors include: touching the face of the user, thermal radiation directed at the face of the user, occlusion of a region of the face by at least one of hair and a foreign object, and direct airflow on at the face of the user. In one example, one or more of the indications may be provided in "raw" form, for example, as feature values that represent input from one or more sensors (e.g., a visible-light camera or an anemometer). In another example, one or more of the indications may be provided utilizing algorithms that process input from the one or more sensors mentioned above (e.g., an image analysis algorithm that detects presence of a finger touching the face, hair on the face, etc.)

The samples used to generate the model 442 include, in some embodiments, samples corresponding to different values of the respiratory parameter. In particular, the samples may comprise at least first and second samples, with the first sample having a label indicative of a first value of the respiratory parameter and a second sample having a second label indicative of a second value of the respiratory parameter. Optionally, in this example, the first and second samples are generated based on $TH_{non}$, $TH_{ROI2}$, and $TH_{ROI3}$ of the same user. Herein, a sample is considered generated based on $TH_{ROI1}$, $TH_{ROI2}$, and $TH_{ROI3}$ of a user if the sample includes one or more feature values generated based on $TH_{ROI1}$, $TH_{ROI2}$, and $TH_{ROI3}$ of the user.

In some embodiments, the samples include samples generated based on $TH_{ROI1}$, $TH_{ROI2}$, and $TH_{ROI3}$ taken at different times of the day, while the users were at different locations, and/or while the users were conducting different activities. In one example, the samples include one or more samples taken in the morning and one or more samples taken in the evening. In another example, the samples include one or more samples generated based on $TH_{ROI1}$, $TH_{ROI2}$, and $TH_{ROI3}$ taken indoors, and one or more samples generated based on $TH_{ROI1}$, $TH_{ROI2}$, and $TH_{ROI3}$ taken outdoors. In yet another example, the samples include one or more samples generated based on $TH_{ROI1}$, $TH_{ROI2}$, and $TH_{ROI3}$ taken while a user was sitting down, and one or more samples generated based on $TH_{ROI1}$, $TH_{ROI2}$, and $TH_{ROI3}$ taken while a user was walking, conning, and/or engaging in physical exercise (e.g., dancing, biking, etc.).

In some embodiments, the samples include samples generated based on $TH_{ROI1}$, $TH_{ROI2}$, and $TH_{ROI3}$ taken while various environmental conditions persisted. For example, the samples include first and second samples generated based on $TH_{ROI1}$, $TH_{ROI2}$, and $TH_{ROI3}$ taken while the environment had first and second temperatures, respectively (with the first temperature being at least 10° C. warmer than the second temperature). In another example, the samples may include samples taken while there were different extents of direct sunlight and/or different extents of wind blowing.

Additionally or alternatively, the samples utilized to generate the model 442 may be based on measurements ($TH_{ROI1}$, $TH_{ROI2}$, and, $TH_{ROI3}$) taken over a long period of time, such as more than a day, more than a week, more than a month, or more than a year. Herein, samples may be considered to be generated based on measurements taken over more than a certain period (e.g., a week) if the samples include at least first and second samples, generated based on measurements taken during first and second periods of time, respectively, such that the difference between when the first period and the second period start is at least as long as the certain period. That is, the starting times first and second periods are at least the certain period apart.

In some embodiments, the samples include samples generated based on $TH_{ROI1}$, $TH_{ROI2}$, and $TH_{ROI3}$ taken while different confounding factors occurred. For example, the samples include some samples taken while a user touched the face, talked, ate, drank, had hair fall on the face, etc. Optionally, including samples taken while confounding factors occurred can help generate a model that may be more robust to occurrences of the confounding factors (than a model that is not trained on such samples). In other embodiments, samples that are generated based on $TH_{ROI1}$, $TH_{ROI2}$, and $TH_{ROI3}$ taken while certain confounding factors occurred may be filtered out. In one example, the samples do not include samples that are generated based on $TH_{ROI1}$, $TH_{ROI2}$, and $TH_{ROI3}$ taken during times in which it is known that the user being measured conducted in certain activities (e.g., eating).

The computer 439 may employ various computational approaches to generate the model 442 based on the samples. In one example, generating the model 442 may involve selecting, based on the samples, a threshold. Optionally, if certain feature value reaches the threshold then a certain respiratory condition is detected (e.g., unsmooth breathing).

Optionally, the model 442 includes a value describing the threshold. In another example, the computer 439 is configured to utilize a machine learning-based training algorithm to generate the model 442 based on the samples. Optionally, the model comprises parameters of at least one of the following models: a regression model, a neural network, a nearest neighbor model, a support vector machine, a support vector machine for regression, a naïve Bayes model, a Bayes network, and a decision tree.

In some embodiments, the computer 439 may utilize deep learning algorithms to generate the model 442. In one example, the model 442 may include parameters describing multiple hidden layers of a neural network. In one embodiment, when $TH_{ROI1}$, $TH_{ROI2}$, and $TH_{ROI3}$ include measurements of multiple pixels, such as when the one or more thermal camera include a focal-plane array (FPA), the model 442 may include a convolution neural network (CNN). In one example, a CNN may be utilized to identify certain patterns in the thermal images, such as patterns of temperatures in the region of the exhale stream that may be indicative a respiratory parameter involving aspects such as the location, direction, size, and/or shape of an exhale stream from the nose and/or mouth. In another example, estimating a value of a respiratory parameter, such as the breathing rate, may be done based on multiple, possibly successive, thermal measurements. Optionally, estimating values of a respiratory parameter based on thermal measurements may involve retaining state information that is based on previous measurements. Optionally, the model 442 may include parameters that describe an architecture that supports such a capability. In one example, the model 442 may include parameters of a recurrent neural network (RNN), which is a connectionist model that captures the dynamics of sequences of samples via cycles in the network of nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

Depending on the composition of the samples, the model 442 may be considered, in some embodiments, either a general model or a personalized model. In one embodiment, the samples comprise samples generated based on $TH_{ROI1}$, $TH_{ROI2}$, and $TH_{ROI3}$ of multiple users. In this case, the model 442 may be considered a general model that can be used to estimate the value of the respiratory parameter with a variety of users who may have different manifestations of physiological responses (as it is reflected in $TH_{ROI1}$, $TH_{ROI2}$, and $TH_{ROI3}$ and/or other sensor measurements).

In other embodiments, the samples used to generate the model 442 comprise samples generated based on $TH_{ROI1}$, $TH_{ROI2}$, and $TH_{ROI3}$ of a certain user, or a certain proportion of the samples are generated based on $TH_{ROI1}$, $TH_{ROI2}$, and $TH_{ROI3}$ of a certain user. For example, at least 20% of the samples are generated based on $TH_{ROI1}$, $TH_{ROI2}$, and $TH_{ROI3}$ of the certain user, which is larger than a proportion of the samples that are generated based on $TH_{ROI1}$, $TH_{ROI2}$, and $TH_{ROI3}$ of any other user. In this embodiment, the model 442 may be considered personalized for the certain user, and as such, in some cases, may be more accurate at estimating the value of the respiratory parameter when the certain user is measured, compared to its accuracy when other users are measured.

Generating a model that is personalized for the certain user may require collecting a sufficient number of training samples that are generated based on $TH_{ROI1}$, $TH_{ROI2}$, and $TH_{ROI3}$ of the certain user. Thus, initially estimation of the value of the respiratory parameter when the certain user is measured may be done utilizing a general model, which may be replaced by a personalized model for the certain user as a sufficiently large number of samples are generated based on $TH_{ROI1}$, $TH_{ROI2}$, and $TH_{ROI3}$ of the certain user. Another approach involves gradually modifying a general model based on samples of the certain user. To this end, in one embodiment, generating the model 442 involves altering parameters of another model, which is generated based on $TH_{ROI1}$, $TH_{ROI2}$, and $TH_{ROI3}$ of other users. For example, the computer 439 may utilize the other model as an initial model. As the samples are acquired from measurements of the certain user, the computer 439 may update parameters of an initial model based on the samples. Thus, this process may be considered personalizing a general model according to measurements of the certain user.

Providing a model to be used by a system that estimates values of a respiratory parameter, such as when the computer 439 provides the model 442, may involve performing different operations, in different embodiments. In one embodiment, providing the model to the system involves forwarding the model to the system via a computer network and/or a shared computer storage medium (e.g., writing the model to a memory that may be accessed by the system that estimates values of the respiratory parameter). In another embodiment, providing the model to the system involves storing the model in a location from which the system can retrieve the model. For example, the model may be stored on a database and/or cloud-based storage (e.g., an "app" store) from which the system may retrieve the model. In still another embodiment, providing the model for use by the system involves notifying the system regarding the existence of the model and/or regarding an update to the model. Optionally, this notification includes information needed in order for the system to obtain the model.

Figure 57:
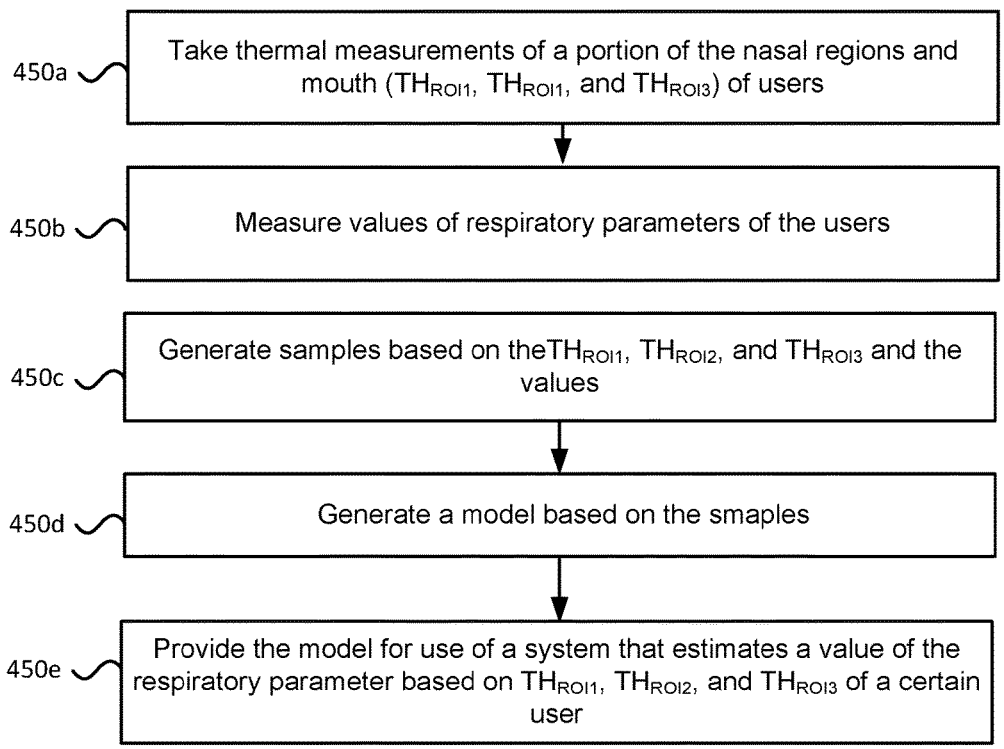
FIG. 57 illustrates an embodiment of a method for generating a model for detecting a physiological response based on thermal measurements.

FIG. 57 illustrates steps that may be performed in one embodiment of a method for generating a model for estimating values of a respiratory parameter based on thermal measurements of the face. The steps described below may be, in some embodiments, part of the steps performed by an embodiment of a system described above, which is illustrated in FIG. 56. In some embodiments, instructions for implementing an embodiment of the method described below may be stored on a computer-readable medium, which may optionally be a non transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a. Optionally, different steps of the method may be performed utilizing different systems comprising a processor and memory.

In one embodiment, a method for generating a model for estimating values of a respiratory parameter based on thermal measurements of the face includes at least the following steps:

In Step 450a, taking thermal measurements of users using head-mounted systems (HMSs) worn by the users; each HMS comprises a frame and one or more thermal cameras that are physically coupled to the frame. Taking thermal measurements of each user comprises taking thermal measurements of: a portion of the right side of the user's upper lip ($TH_{ROI1}$), a portion of the left side of the user's upper lip ($TH_{ROI2}$), and a portion of the user's mouth ($TH_{ROI3}$).

Optionally, each thermal camera weighs below 5 g. Optionally, each thermal camera is located less than 15 cm away from the user's face. FIG. 47 and FIG. 48 illustrate examples of systems that include thermal cameras that may be utilized to take $TH_{ROI1}$, $TH_{ROI2}$, and $TH_{ROI3}$ of the user in this step.

In Step 450b, measuring, using sensors, values of the respiratory parameter of the users corresponding to when $TH_{ROI1}$, $TH_{ROI2}$, and $TH_{ROI3}$ were taken.

In Step 450c, generating samples based on the data obtained in Step 450a and Step 450b. Optionally, each sample comprises feature values generated based on $TH_{ROI1}$, $TH_{ROI2}$, and $TH_{ROI3}$ of a user taken during a certain period and a label indicative of a value of the respiratory parameter during the certain period.

In Step 450d, generating a model based on the samples generated in Step 450c. Optionally, the model generated in this step is the model 442. Optionally, generating the model based on the samples involves utilizing a machine learning-based training algorithm. Optionally, generating the model involves personalizing the model for a certain user by updating parameters of an initial model based on samples generated based on $TH_{ROI1}$, $TH_{ROI2}$, and $TH_{ROI3}$ of the certain user, where the initial model is generated based on samples generated from $TH_{ROI1}$, $TH_{ROI2}$, and $TH_{ROI3}$ of other users.

Figure 58:
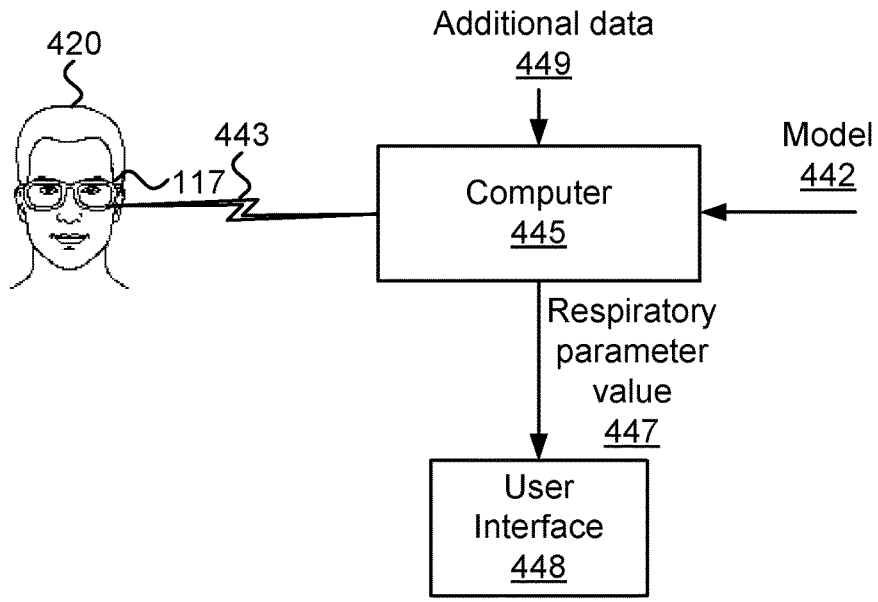
FIG. 58 illustrates an embodiment of a system configured detect a physiological response based on thermal measurements of the face.

And in Step 450e, providing the model to be used by a system that estimates values of the respiratory parameter based on $TH_{ROI1}$, $TH_{ROI2}$, and $TH_{ROI3}$, such as the system illustrated in FIG. 58.

In one embodiment, generating the samples in Step 450c may optionally involve receiving additional data pertaining to a user from among the users and generating one or more feature values belonging to at least one of the samples based on the additional data. Optionally, the additional data pertaining to the user comprises additional measurements of the user that are indicative of one or more of the following signals: a heart rate of the user, heart rate variability of the user, brainwave activity of the user, galvanic skin response of the user, muscle activity of the user, and an extent of movement of the user.

In another embodiment, generating the samples in Step 450c may optionally involve receiving additional data pertaining to a user from among the users and generating one or more feature values belonging to at least one of the samples based on the additional data. Optionally, the data pertaining to the user comprises measurements of the environment in which the user was in while $TH_{ROI1}$, $TH_{ROI2}$, and $TH_{ROI3}$ of the user were taken. Optionally, each measurement of the environment is indicative of one or more of the following values at a certain time: a temperature of the environment, a humidity level of the environment, a noise level of the environment, air quality in the environment, a wind speed in the environment, an extent of precipitation in the environment, and an infrared radiation level in the environment.

Once the model 442 is generated, it may be utilized to calculate a value of a respiratory parameter of a user 420 based on $TH_{ROI1}$, $TH_{ROI2}$, and $TH_{ROI3}$ of the user 420, which are not among $TH_{ROI1}$, $TH_{ROI2}$, and $TH_{ROI3}$ 436 that were used for generating the model 442. FIG. 58 illustrates an embodiment of a system configured to detect a physiological response based on thermal measurements of the face. One embodiment of the illustrated system includes a frame (e.g., the frame 117), one or more thermal cameras, and a computer 445.

The frame and the one or more thermal cameras may belong to an HMS from among the HMSs described in this disclosure, such as HMSs illustrated in FIG. 47, FIG. 48, FIG. 49, or FIG. 8a Optionally, the frame and the one or more thermal cameras are the same frame and thermal cameras utilized to take $TH_{ROI1}$, $TH_{ROI2}$, and $TH_{ROI3}$ 436. However, in this embodiment, the frame and the one or more thermal cameras take $TH_{ROI1}$, $TH_{ROI2}$, and $TH_{ROI3}$ 443, which are thermal measurements of regions of the upper lip and mouth of the user 420 that are taken over a certain period. Optionally, the certain period is as at least one second, at least ten seconds, at least one minute, at least five minutes, at least twenty minutes, at least one hour, or at least three hours.

The computer 445 is configured, in one embodiment, to generate feature values based on $TH_{ROI1}$, $TH_{ROI2}$, and $TH_{ROI3}$ 443 and to utilize the model 442 to calculate, based on the feature values, a value 447 of the respiratory parameter of the user 420. Optionally, the model 442 is generated based on previous $TH_{ROI1}$, $TH_{ROI2}$, and $TH_{ROI3}$ of users (e.g., $TH_{ROI1}$, $TH_{ROI2}$, and $TH_{ROI3}$ 436) taken over more than a week Optionally, the user 420 is not among the users whose measurements are among $TH_{ROI1}$, $TH_{ROI2}$, and $TH_{ROI3}$ 436.

As discussed in more detail above (in the discussion regarding feature values generated by the computer 439), feature values generated by the computer 445 based on $TH_{ROI1}$, $TH_{ROI2}$, and $TH_{ROI3}$ 443 may include: (i) values comprised in $TH_{ROI1}$, $TH_{ROI2}$, and $TH_{ROI3}$ 443 (optionally these values may undergo various forms of filtering and/or normalization), (ii) values generated based on additional measurements of the user 420 (e.g., measurements of heart rate, heart rate variability, brainwave activity, galvanic skin response, muscle activity, and an extent of movement), (iii) measurements of the environment in which the user 420 was in while $TH_{ROI1}$, $TH_{ROI2}$, and $TH_{ROI3}$ 443 were taken, and (iv) indications of various occurrences which may be considered confounding factors (e.g., touching the face, thermal radiation directed at the face, or airflow directed at the face).

The computer 445 is further configured, in one embodiment, to utilize the model 442 to calculate, based on the feature values generated based on $TH_{ROI2}$ $TH_{ROI4}$, and $TH_{ROI3}$ 443, a value 447 of a respiratory parameter of the user 420 corresponding to when $TH_{ROI1}$, $TH_{ROI2}$ and $TH_{ROI3}$ 443 were taken. Optionally, the value 447 is a value of a respiratory parameter that is indicative of at least one of the following values: a respiration rate, respiration volume, an extent of mouth breathing, an extent of nasal breathing, exhale (inhale) duration, post-exhale (post-inhale) breathing pause, a dominant nostril, an exhale stream shape, exhale stream smoothness, and an exhale stream temperature.

In one embodiment, the value 447 is presented to the user 420 via a user interface 448. Optionally, responsive to the value 447 reaching a threshold, an alert is presented to the user 420 via the user interface 448. Optionally, the value 447 is stored (e.g., for life-logging purposes) and/or forwarded to a software agent operating on behalf of the user 420 (e.g., in order for the software agent to make a decision regarding the user 420).

The model 442 is generated based on $TH_{ROI1}$, $TH_{ROI2}$, and $TH_{ROI3}$ 436 of users, which were taken prior to $TH_{ROI1}$, $TH_{ROI2}$ and $TH_{ROI3}$ 443. In one embodiment, the users comprise the user 420. Optionally, at least a certain portion (e.g., at least 20%) of the data used to generate the model 442 relates to the user 420. Optionally, the model 442 is a model personalized for the user 420. Optionally, the users include only the user 420. In another embodiment, the user 420 is not among the users whose measurements are comprised in $TH_{ROI1}$, $TH_{ROI2}$, and $TH_{ROI3}$ 436, which were utilized to generate the model 442.

The model 442 may include different types of parameters, in different embodiments. Following are some examples of various possibilities for the model 442 and the type of calculations that are accordingly performed by the computer 445 to generate the value 447.

In one embodiment, the model 442 comprises parameters of a decision tree. Optionally, in this embodiment, in order to calculate the value 447 the computer 445 simulates a traversal along a path in the decision tree, determining which branches to take based on the feature values. Optionally, the value 447 is obtained from a leaf node of the tree that is reached at the end of the path. Optionally, the value 447 is calculated based on values of nodes of the tree that are on the traversed path.

In another embodiment, the model 442 comprises parameters of a regression model (e.g., regression coefficients in a linear regression model or a logistic regression model). Optionally, in this embodiment, in order to calculate the value 447 the computer 445 multiplies the feature values (which may be considered a regressor) with the parameters of the regression model.

In yet another embodiment, the model 442 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, in this embodiment, in order to calculate the value 447, the computer 445 provides the feature values as inputs to the neural network, computes the values of the various activation functions and propagates values between layers, and obtains an output from the network, which is the value 447.

The user interface 448 may be utilized, in some embodiments, to present the user 420 the value 447 of the respiratory parameter. Additionally or alternatively, in some embodiments, the user interface 448 may be utilized to present to the user 420 an alert responsive to an indication that the value 447 reaches a threshold. For example, the user 420 may be alerted when the breathing rate exceeds a certain value and/or when the user 420 spends at least a certain period of time mouth breathing instead nasal breathing. In one embodiment, the user interface 448 may comprise a screen on which the value 447 and/or the alert may be presented (e.g., in the form of text, an image, or video). Optionally, the screen may be part of a display coupled to a frame worn by the user 420 (e.g., a screen of an augmented reality headset, a mixed reality headset, or a virtual reality headset). Additionally or alternatively, the screen may be a display of a device of the user, such as a display of a smartphone or smartwatch. In another embodiment, presenting the value 447 and/or the alert may involve an audio notification that is generated via the user interface 448. For example, the user interface 448 may include a speaker, earphones, or an earbud through which an audio signal is provided to the user 420 in order to make the user 420 aware of the magnitude of the value 447 and/or that the alert has been generated. In still another embodiment, the user interface 448 may be part of a frame worn by the user 420; presenting the user 420 with the value 447 and/or the alert may involve the frame and/or another device physically and/or communicatively coupled to the frame making noises (e.g., beeping sounds), making a visual indication (e.g., lighting of lights on the frame), and/or providing a tactile indication (e.g., by vibrating).

Figure 59:
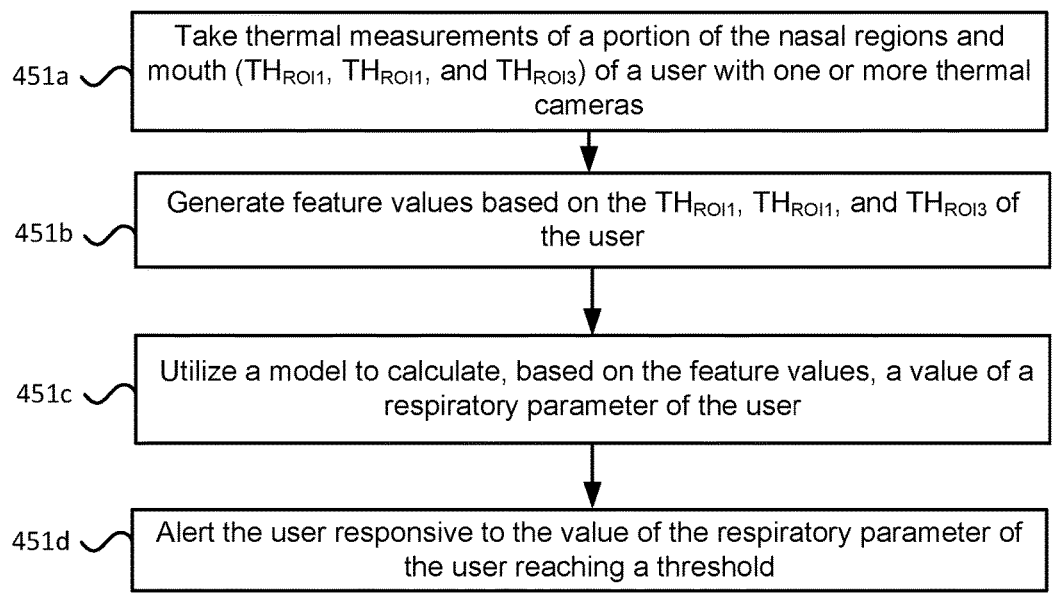
FIG. 59 illustrates an embodiment of a method for detecting a physiological response based on thermal measurements of the face.

FIG. 59 illustrates steps that may be performed in one embodiment of a method for estimating a respiratory parameter of a user based on thermal measurements of the user's face. The steps described below may be, in some embodiments, part of the steps performed by an embodiment of a system described above, which is illustrated in FIG. 58. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a or FIG. 72b. Optionally, different steps of the method may be performed utilizing different systems comprising a processor and memory.

In one embodiment, a method for estimating a respiratory parameter of a user based on thermal measurements of the user's face includes at least the following steps:

In Step 451a, taking, using at least one head-mounted thermal camera, thermal measurements of: a portion of the right side of the user's upper lip ($TH_{ROI1}$), a portion of the left side of the user's upper lip ($TH_{ROI2}$), and a portion of the user's mouth ($TH_{ROI3}$). Optionally, each thermal camera is physically coupled to the frame and is located less than 15 cm away from the face.

In Step 451b, generating feature values based on $TH_{ROI1}$, $TH_{ROI2}$, and $TH_{ROI3}$ of the user.

And in Step 451c, utilizing a model to calculate, based on the feature values, a value of the respiratory parameter of the user. The model used in this step is generated based on previous $TH_{ROI1}$, $TH_{ROI2}$, and $TH_{ROI3}$ of users taken over a period of a week. Optionally, the model used in this step is the model 442. Optionally, the value calculated in this step is indicative of at least one of the following values: a respiration rate, respiration volume, an extent of mouth breathing, an extent of nasal breathing, exhale (inhale) duration, post-exhale (post-inhale) breathing pause, a dominant nostril, an exhale stream shape, exhale stream smoothness, and an exhale stream temperature.

In one embodiment, the method described above may optionally include a step involving presenting the user with the value calculated in Step 451c. For example, the value may be presented via a user interface, such as the user interface 448 mentioned above. In another embodiment, the method described above may optionally include a step involving alerting the user responsive to the value calculated in Step 451c reaching a threshold.

Generating the feature values in Step 451b may involve, in some embodiments, utilization of additional sources of information, which may be utilized in addition to $TH_{ROI1}$, $TH_{ROI2}$, and $TH_{ROI3}$ of the user. In one embodiment, Step 451b optionally involves receiving additional measurements of the user taken during the same period $TH_{ROI1}$, $TH_{ROI2}$, and $TH_{ROI3}$ of the user 420 were taken and generating at least one of the feature values in Step 451b based on the additional measurements. Optionally the additional measurements are indicative of one or more of the following signals: a heart rate of the user, heart rate variability of the user, brainwave activity of the user, galvanic skin response of the user, muscle activity of the user, and an extent of movement of the user.

In another embodiment, Step 451b optionally involves receiving measurements of the environment in which the user was in while $TH_{ROI1}$, $TH_{ROI2}$, and $TH_{ROI3}$ of the user were taken and generating at least one of the feature values in Step 451b based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In another embodiment, Step 451b optionally involves receiving an additional indication and generating, based on the additional indication, at least one of the feature values in Step 451b. Optionally, the additional indication is indicative of an extent of one or more of the following: touching the face of the user, occlusion of a region of the face by at least one of hair and a foreign object, thermal radiation directed at the face of the user, and direct airflow on the face of the user.

Figure 60:
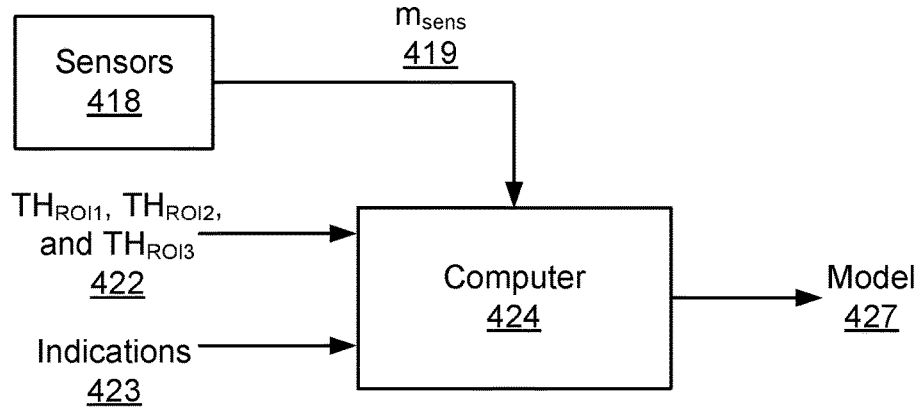
FIG. 60 illustrates an embodiment of a system configured to generate a model for detecting an imminent respiratory-related attack based on thermal measurements.

FIG. 60 illustrates an embodiment of a system configured to generate a model for detecting an imminent respiratory-related attack based on thermal measurements. The system includes head-mounted systems (HMSs) configured to be worn by users, sensors 418, and a computer 424.

Herein, a respiratory-related attack refers to a physiological response whose manifestation typically involves a change to a user's respiration (e.g., increased breathing rate and/or shortened exhales). Optionally, the change to the user's respiration is associated with being in a physical and/or emotional state of distress. Some examples of phenomena that may be considered a respiratory-related attack include an asthma attack, an epileptic attack, an anxiety attack, a panic attack, and a tantrum. Additionally, references to a user "having an attack" refer to the user experiencing one or more of the respiratory-related attacks mentioned above.

Each HMS may be one of the HMSs described in this disclosure, such as HMSs illustrated in FIG. 47 or FIG. 48, FIG. 49, or FIG. 8a. In one embodiment, each HMS comprises a frame and one or more thermal cameras that are physically coupled to the frame and configured to take: thermal measurements of a portion of the right side of the upper lip ($TH_{ROI1}$), thermal measurements of a portion of the left side of the upper lip ($TH_{ROI2}$), and thermal measurements of a portion of the mouth ($TH_{ROI3}$) of the user who wears the HMS. In one embodiment, the first region of interest ($ROI_1$) covers a portion of the right side of the upper lip, the second region of interest ($ROI_2$) covers a portion of the left side of the upper lip, and the third region of interest ($ROI_3$) covers a portion of the user's mouth, the center of $ROI_1$ is to the right of the center of $ROI_2$, and the center of $ROI_3$ is below the centers of $ROI_1$ and $ROI_2$. Additionally, $TH_{ROI1}$, $TH_{ROI2}$, and $TH_{ROI3}$ are taken from a distance of less than 15 cm from the user's face (e.g., by one or more thermal cameras physically coupled to a frame worn by the user). Optionally, $TH_{ROI1}$, $TH_{ROI2}$, and $TH_{ROI3}$ are taken by an embodiment of a system configured to collect thermal measurements related to respiration, which is described above (e.g., see FIG. 47 and FIG. 48). In FIG. 60 $TH_{ROI1}$, $TH_{ROI2}$, and $TH_{ROI3}$ of the one or more users are denoted with reference numeral 422. Optionally, each thermal camera weighs below 5 g and is located less than 15 cm away from the user's face. Examples of the various types of thermal cameras that may be utilized to obtain $TH_{ROI1}$, $TH_{ROI2}$, and $TH_{ROI3}$ 422 are given at least in Section 1.

The sensors 418 are configured to take measurements indicative of movements ($m_{sens}$ 419) of the users, which correspond to when $TH_{ROI1}$, $TH_{ROI2}$, and $TH_{ROI3}$ 422 were taken. In one example, the sensors 418 may include a gyroscope and/or an accelerometer. In another example, the sensors 418 may include LiDar and/or Radar based sensors. In another example, the sensors 418 may be configured to receive wireless signals in order to perform triangulation of the location of the users (in order to deduce movement of users), such as GPS receivers.

The computer 424 is configured, in one embodiment, to generate samples based on data pertaining to one or more users. The data pertaining to each user, from among the one or more users, includes: (i) $TH_{ROI1}$, $TH_{ROI2}$, and $TH_{ROI3}$ of the user (from among $TH_{ROI1}$, $TH_{ROI2}$, and $TH_{ROI3}$ 422), (ii) $m_{sens}$ of the user (from among $m_{sens}$ 419), and (iii) indications corresponding to different times, from among indications 423, which are indicative of whether the user had an attack at the different times. Optionally, each sample comprises feature values that are generated based on $TH_{ROI1}$, $TH_{ROI2}$, and $TH_{ROI3}$ of a user and $m_{sens}$ of the user, which were taken during a certain period, and a label that is generated based on an indication that is indicative of whether the user had an attack at a time that is within temporal proximity of the certain period.

"Temporal proximity" may involve different durations in different embodiments. In one example, an attack is considered in temporal proximity of a certain period during which $TH_{ROI1}$, $TH_{ROI2}$, and $TH_{ROI3}$ of a user were taken if the attack occurred during the certain period and/or at most three hours after the certain period ended. In another example, the attack is considered in temporal proximity of the certain period if the attack occurred during the certain period and/or at most one hour after the certain period ended. In yet another example, the attack is considered in temporal proximity of the certain period if the attack occurred at most fifteen minutes after the certain period ended. In still another example, the attack is considered in temporal proximity of the certain period if the attack occurred during the certain period and/or at most one minute after the certain period ended.

Herein, a respiratory-related attack is considered "imminent" at a certain time (e.g., the end of a certain period during which $TH_{ROI1}$, $TH_{ROI2}$, and $TH_{ROI3}$ of a user are taken) if the attack's symptoms occur at a future time that is in temporal proximity of the certain time. Optionally, the attack is considered "imminent" if the user is to become aware of the attack by the future time.

The indications 423 may be generated in different ways, in different embodiments. In one embodiment, at least some of the indications 423 corresponding to $TH_{ROI1}$, $TH_{ROI2}$, and $TH_{ROI3}$ of a user, from among the users, are generated by an external source such as an entity that observes the user, which may be a human observer or a software program. Optionally, the software program is a software agent operating on behalf of the user. In one example, the entity may determine the whether the user's behavior corresponds to an attack of one or more of the types mentioned above (an asthma attack, an epileptic attack, an anxiety attack, a panic attack, and a tantrum).

In another embodiment, at least some of the indications 423 corresponding to $TH_{ROI1}$, $TH_{ROI2}$, and $TH_{ROI3}$ of a user, from among the users, are determined based on analysis of measurements of the user, which are taken using one or more devices. Optionally, the one or more devices are different from the one or more thermal cameras used to take $TH_{ROI1}$, $TH_{ROI2}$, and $TH_{ROI3}$. Optionally, the one or more devices are not physically coupled to the frame worn by the user. Measurements obtained by the one or more devices may be analyzed by a human expert and/or a software program in order to generate the at least some of the indications 423. In one example, the one or more devices are part of a smart shirt and/or chest band that measures various respiratory (and other) parameters. One example of a smart shirt is the Hexoskin smart shirt that can measure Breathing Rate (RPM), Minute Ventilation (L/min), and various other parameters related to a user's respiration, heart rate, and physical activity. In another example, the one or more devices comprise devices that measure movement (e.g., to detect spasms) and/or a microphone (e.g., to detect sounds that are characteristic of the attack).

In yet another embodiment, at least some of the indications 423 corresponding to $TH_{ROI1}$, $T_{ROI2}$, and $TH_{ROI3}$ of a user, from among the users, may be generated by the user. For example, the user may provide indications indicating whether he/she had an attack (e.g., the user may provide information about the time of the attack, its duration, and/or its severity). Optionally, the indications are provided via a mobile "app" (e.g., by pressing a certain button on a screen of a smartphone). Optionally, indications may be provided by making comments that are interpreted by a software agent and/or a program with speech analysis capabilities.

The certain period of time, during which $TH_{ROI1}$, $TH_{ROI2}$, $T_{ROI3}$, and $m_{sens}$ used to generate each sample were taken, may be different in different embodiments. In some embodiments, each of the samples may be based on $TH_{ROI1}$, $TH_{ROI2}$, and $TH_{ROI3}$ taken during a period of time sufficiently long to include multiple measurements of temperatures and/or temperature changes at each of the ROIs. Optionally, the certain period is at least five seconds, at least ten seconds, at least one minute, at least five minutes, at least one hour, or at least one day.

In some embodiments, at least one of the feature values generated based on $TH_{ROI1}$, $TH_{ROI2}$, and $TH_{ROI3}$ of a user, from among the users, taken during a certain period include values measured by the one or more thermal cameras during the certain period. Optionally, the values measured by the one or more thermal cameras may undergo various forms of filtering and/or normalization. In one example, some feature values may be average values of certain sensors (pixels) of the one or more thermal cameras during the certain period and/or some feature values may be values measured at certain times during the certain period by the certain sensors. In another example, the feature values generated based on $TH_{ROI1}$, $TH_{ROI2}$, and $TH_{ROI3}$ of the user taken during the certain period may include time series data comprising values measured by the one or more sensors during the certain period. In yet another example, the feature values generated based on $TH_{ROI1}$, $TH_{ROI2}$, and $TH_{ROI3}$ of the user taken during the certain period may include a feature value indicative of a value of a respiratory parameter of the user during the certain period. Optionally, the respiratory parameter is indicative of at least one of the following values: a respiration rate, respiration volume, an extent of mouth breathing, an extent of nasal breathing, exhale (inhale) duration, post-exhale (post-inhale) breathing pause, a dominant nostril, an exhale stream shape, exhale stream smoothness, and an exhale stream temperature.

In addition to $TH_{ROI1}$, $TH_{ROI2}$, and $TH_{ROI3}$ of a user taken during a certain period, in some embodiments, additional sources of information may be utilized to generate one or more of the feature values. Optionally, these additional sources of information pertain to the user. Additionally or alternatively, the additional sources of information may pertain to the environment the user is in. The following are some examples of additional sources of information that may be utilized by the computer 424. Additional discussion regarding the additional sources of information and their utilization may be found in Section 4.

In one embodiment, the computer 424 may be further configured to receive additional measurements of the user and to generate at least one of the feature values based on the additional measurements. Optionally, the additional measurements are indicative of one or more of the following signals of the user: a heart rate, heart rate variability, brainwave activity, galvanic skin response, muscle activity, and an extent of movement. Optionally, the additional measurements may be obtained utilizing one or more of the various sensors that are described in Section 4, which are not thermal cameras. Optionally, the additional measurements comprise $m_{sens}$ of the user.

Some of the additional sources of information may relate to the environment a user was in while $TH_{ROI1}$, $TH_{ROI2}$, and $TH_{ROI3}$ of the user were taken. In one embodiment, the computer 424 may be further configured to receive measurements of the environment and to generate at least one feature value based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In some embodiments, additional data pertaining to a user, which may be used by the computer 424 to generate one or more of the feature values of a sample, involves indications of various factors that may be considered confounding factors. Some examples of such confounding factors include: touching the face of the user, thermal radiation directed at the face of the user, occlusion of a region of the face by at least one of hair and a foreign object, and direct airflow on at the face of the user. In one example, one or more of the indications may be provided in "raw" form, for example, as feature values that represent input from one or more sensors (e.g., a visible-light camera or an anemometer). In another example, one or more of the indications may be provided utilizing algorithms that process input from the one or more sensors mentioned above (e.g., an image analysis algorithm that detects presence of a finger touching the face, hair on the face, etc.)

In other embodiments, the computer 424 may be further configured to receive one or more values indicative of a situation of a user while $TH_{ROI1}$, $TH_{ROI2}$, and $TH_{ROI3}$ of the user were taken. Optionally, the one or more values may be utilized to generate at least one of the feature values of samples. Optionally, the one or more values comprise a value that is indicative of one or more of the following: consumption of a certain drug, consumption of a certain food item, a location of the user, a time of day, an identify of a person who is with the user, a type of activity the user is conducting, and a type of activity the user is about to conduct within thirty minutes (e.g., take an exam, speak in front of a crowd, or perform some other activity that may be stressful for the user).

The samples used to generate the model 427 may include, in some embodiments, samples corresponding to different states of the user, which correspond to whether or not the user had an attack in temporal proximity to when the thermal measurements used to generate the samples were taken. In particular, in these embodiments, the samples comprise at least first and second samples, with the first sample having a label indicative of a user having an attack in temporal proximity to when $TH_{ROI1}$, $TH_{ROI2}$, and $TH_{ROI3}$ of the user, which used to generate the first sample, were taken; the second sample has a label indicative of a user not having an attack in temporal proximity to when $TH_{ROI1}$, $TH_{ROI2}$, and $TH_{ROI3}$ of the user, which used to generate the second sample, were taken. Optionally, in this example, the first and second samples are generated based on $TH_{ROI1}$, $TH_{ROI2}$, and $TH_{ROI3}$ of the same user. Herein, a sample is considered generated based on $TH_{ROI1}$, $TH_{ROI2}$, and $TH_{ROI3}$ of a user if the sample includes one or more feature values generated based on $TH_{ROI1}$, $TH_{ROI2}$, and $TH_{ROI3}$ of the user.

In some embodiments, the samples used to generate the model 427 include samples generated based on $TH_{ROI1}$, $TH_{ROI2}$, and $TH_{ROI3}$ taken at different times of the day, while the users were at different locations, and/or while the users were conducting different activities. In one example, the samples include one or more samples taken in the morning and one or more samples taken in the evening. In another example, the samples include one or more samples generated based on $TH_{ROI1}$, $TH_{ROI2}$, and $TH_{ROI3}$ taken indoors, and one or more samples generated based on $TH_{ROI1}$, $TH_{ROI2}$, and $TH_{ROI3}$ taken outdoors. In yet another example, the samples include one or more samples generated based on $TH_{ROI1}$, $TH_{ROI2}$, and $TH_{ROI3}$ taken while a user was sitting down, and one or more samples generated based on $TH_{ROI1}$, $TH_{ROI2}$, and $TH_{ROI3}$ taken while a user was walking, running, and/or engaging in physical exercise (e.g., dancing, biking, etc.).

In some embodiments, the samples include samples generated based on $TH_{ROI1}$, $TH_{ROI2}$, and $TH_{ROI3}$ taken while various environmental conditions persisted. For example, the samples include first and second samples generated based on $TH_{ROI1}$, $TH_{ROI2}$, and $TH_{ROI3}$ taken while the environment had first and second temperatures, respectively (with the first temperature being at least 10° C. warmer than the second temperature). In another example, the samples may include samples taken while there were different extents of direct sunlight and/or different extents of wind blowing.

In some embodiments, the samples include samples generated based on $TH_{ROI1}$, $TH_{ROI2}$, and $TH_{ROI3}$ taken while different confounding factors occurred. For example, the samples include some samples taken while a user touched the face, talked, ate, drank, had hair fall on the face, etc. Optionally, including samples taken while confounding factors occurred can help generate a model that may be more robust to occurrences of the confounding factors (than a model that is not trained on such samples). In other embodiments, samples that are generated based on $TH_{ROI1}$, $TH_{ROI2}$, and $TH_{ROI3}$ taken while certain confounding factors occurred may be filtered out. In one example, the samples do not include samples that are generated based on $TH_{ROI1}$, $TH_{ROI2}$, and $TH_{ROI3}$ taken during times in which it is known that the user being measured conducted in certain activities (e.g., eating).

Additionally or alternatively, the samples utilized to generate the model 427 may be based on $TH_{ROI1}$, $TH_{ROI2}$, and $TH_{ROI3}$ taken over a long period of time, such as more than a day, more than a week, more than a month, or more than a year. Herein, samples may be considered to be generated based on measurements taken over more than a certain period (e.g., a week) if the samples include at least first and second samples, generated based on measurements taken during first and second periods of time, respectively, such that the difference between when the first period and the second period start is at least as long as the certain period. That is, the starting times first and second periods are at least the certain period apart.

Generating the model 427 may involve various computational approaches. In one example, generating the model 427 may involve selecting, based on the samples, a threshold. Optionally, if certain feature value reaches the threshold then an attack is considered to have occurred and/or is considered imminent (e.g., the attack is considered likely to occur in within a short while that is considered to be in "temporal proximity"). Optionally, the model 427 includes a value describing the threshold. In another example, the computer 424 is configured to utilize a machine learning based training algorithm to generate the model 427 based on the samples. Optionally, the model comprises parameters of at least one of the following models: a regression model, a neural network, a nearest neighbor model, a support vector machine, a support vector machine for regression, a naïve Bayes model, a Bayes network, and a decision tree.

In some embodiments, the computer 424 may utilize deep learning algorithms to generate the model 427. In one example, the model 427 may include parameters describing multiple hidden layers of a neural network. In one embodiment, when $TH_{ROI1}$, $TH_{ROI2}$, and $TH_{ROI3}$ include measurements of multiple pixels, such as when the one or more thermal camera include a focal-plane array (FPA), the model 427 may include a convolution neural network (CNN). In one example, a CNN may be utilized to identify certain patterns in the thermal images, such as patterns of temperatures in the region of the exhale stream that may be indicative a respiratory parameter involving aspects such as the location, direction, size, and/or shape of an exhale stream from the nose and/or mouth. In another example, estimating values based on thermal measurements, such as a respiratory parameter and/or values indicative of physiological changes related to an attack, may be done based on multiple, possibly successive, measurements. Optionally, estimating these values may involve retaining state information that is based on previous measurements. Optionally, the model 427 may include parameters that describe an architecture that supports such a capability. In one example, the model 427 may include parameters of a recurrent neural network (RNN), which is a connectionist model that captures the dynamics of sequences of samples via cycles in the network of nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

Depending on the composition of the samples, the model 427 may be considered, in some embodiments, either a general model or a personalized model. In one embodiment, the samples comprise samples generated based on $TH_{ROI1}$, $TH_{ROI2}$, and $TH_{ROI3}$ of multiple users. In this case, the model 427 may be considered a general model that can be used to detect an imminent respiratory-related attack with a variety of users who may have different manifestations of physiological responses the lead up to, and/or are involved in, the attack (as it is reflected in $TH_{ROI1}$, $TH_{ROI2}$, and $TH_{ROI3}$ and/or other sensor measurements).

In other embodiments, the samples used to generate the model 427 comprise samples generated based on $TH_{ROI1}$, $TH_{ROI2}$, and $TH_{ROI3}$ of a certain user, or a certain proportion of the samples used to generate the model 427 are generated based on $TH_{ROI1}$, $TH_{ROI2}$, and $TH_{ROI3}$ of a certain user. For example, at least 20% of the samples are generated based on $TH_{ROI1}$, $TH_{ROI2}$, and $TH_{ROI3}$ of the certain user, which is larger than a proportion of the samples used to generate the model 427 that are generated based on $TH_{ROI1}$, $TH_{ROI2}$, and $TH_{ROI3}$ of any other user. In this embodiment, the model 427 may be considered personalized for the certain user, and as such, in some cases, may be more accurate at detecting an imminent respiratory-related attack based on thermal measurements of the certain user, compared to its accuracy when other users are measured.

Generating a model that is personalized for the certain user may require collecting a sufficient number of training samples that are generated based on $TH_{ROI1}$, $TH_{ROI2}$, and $TH_{ROI3}$ of the certain user. Thus, initially detecting an imminent respiratory-related attack based on thermal measurements of the certain user may be done utilizing a general model, which may be replaced by a personalized model for the certain user as a sufficiently large number of samples are generated based on $TH_{ROI1}$, $TH_{ROI2}$, and $TH_{ROI3}$ of the certain user. Another approach involves gradually modifying a general model based on samples of the certain user. To this end, in one embodiment, generating the model 427 involves altering parameters of another model, which is generated based on $TH_{ROI1}$, $TH_{ROI2}$, and $TH_{ROI3}$ of other users. For example, the computer 424 may utilize the other model as an initial model. As the samples are acquired from measurements of the certain user, the computer 424 may update parameters of an initial model based on the samples. Thus, this process may be considered personalizing a general model according to measurements of the certain user.

Providing a model to be used by a system that detects an imminent respiratory-related attack, such as when the computer 424 provides the model 427, may involve performing different operations, in different embodiments. In one embodiment, providing the model to the system involves forwarding the model to the system via a computer network and/or a shared computer storage medium (e.g., writing the model to a memory that may be accessed by the system that detects an imminent respiratory-related attack). In another embodiment, providing the model to the system involves storing the model in a location from which the system can retrieve the model. For example, the model may be stored on a database and/or cloud-based storage (e.g., an "app" store) from which the system may retrieve the model. In still another embodiment, providing the model for use by the system involves notifying the system regarding the existence of the model and/or regarding an update to the model. Optionally, this notification includes information needed in order for the system to obtain the model.

In one embodiment, the samples used to generate the model 427 include feature values that are generated based on additional thermal measurements. In one example, the computer 424 is further configured to generate the samples based on thermal measurements of a fourth region ($TH_{ROI4}$) that covers a portion of the user's forehead. Optionally, $TH_{ROI4}$ are obtained using at least one additional thermal camera that is physically coupled to the frame (worn by the user being measured), is located less than 15 cm away from the user's face, and is configured to take $TH_{ROI4}$.

Figure 61:
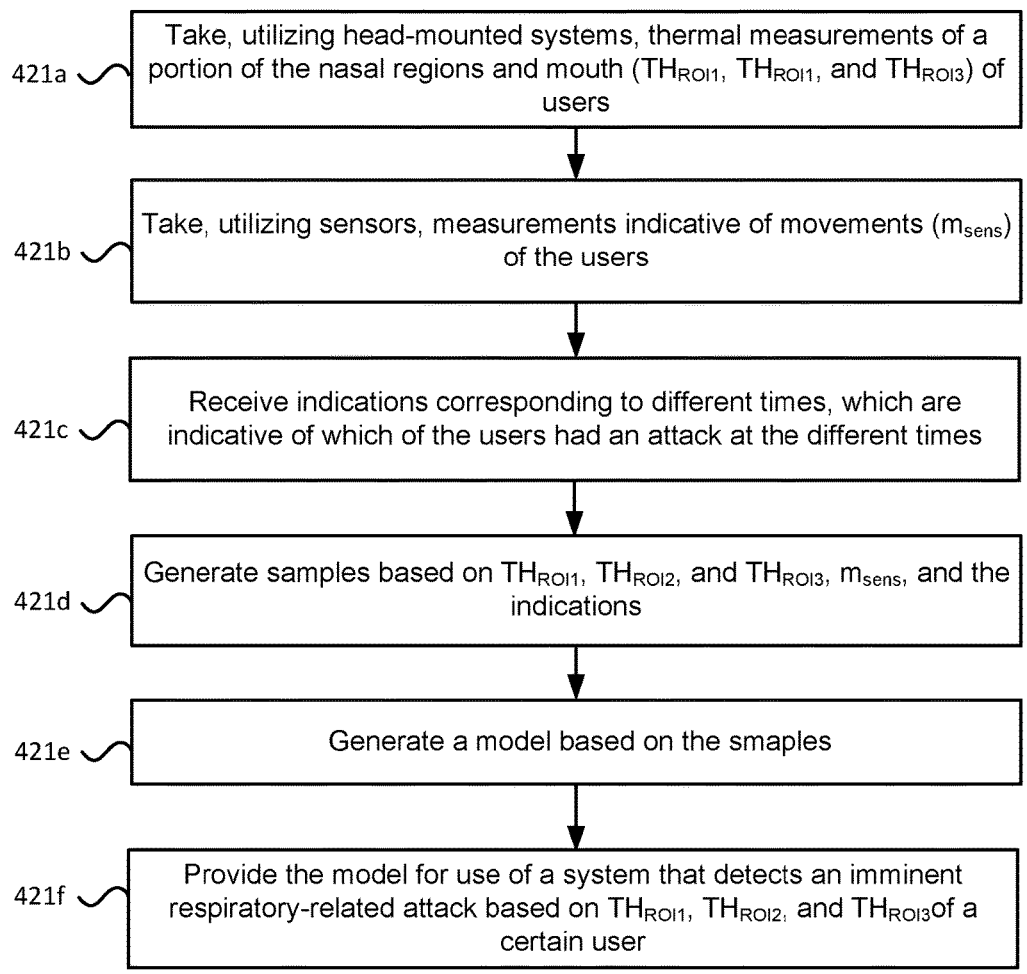
FIG. 61 illustrates an embodiment of a method for generating a model for detecting an imminent respiratory-related attack based on thermal measurements.

FIG. 61 illustrates steps that may be performed in one embodiment of a method for generating a model for detecting an imminent respiratory-related attack based on thermal measurements of the face. The steps described below may be, in some embodiments, part of the steps performed by an embodiment of a system described above, which is illustrated in FIG. 60. In some embodiments, instructions for implementing an embodiment of the method described below may be stored on a computer-readable medium, which may optionally be a non transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a. Optionally, different steps of the method may be performed utilizing different systems comprising a processor and memory.

In one embodiment, a method for generating a model for detecting an imminent respiratory-related attack based on thermal measurements of the face includes at least the following steps:

In Step 421a, taking $TH_{ROI1}$, $TH_{ROI2}$, and $TH_{ROI3}$ of users utilizing HMSs, with each HMS comprising one or more thermal cameras physically coupled to a frame that is configured to be worn on a user's head. Optionally, each thermal camera weighs below 5 g. Optionally, each thermal camera is located less than 15 cm away from the user's face. FIG. 47 and FIG. 48 illustrate examples of systems that include thermal cameras that may be utilized to take $TH_{ROI1}$, $TH_{ROI2}$, and $TH_{ROI3}$ of the user in this step.

In Step 421b, taking, utilizing sensors, measurements indicative of movements ($m_{sens}$) of the users.

In Step 421c, receiving indications corresponding to different times, which are indicative of which of the users had an attack at the different times. Optionally, the attack involves a user experiencing at least one of the following: an asthma attack, an epileptic attack, an anxiety attack, a panic attack, and a tantrum.

In Step 421d, generating samples based on the data received in Steps 421a-421c. Optionally, each sample comprises feature values generated based on $TH_{ROI1}$, $TH_{ROI2}$, $TH_{ROI3}$, and $m_{sens}$ of a user taken during a certain period and a label indicative of whether the user had an attack at a time that is in temporal proximity to the certain period. For example, in some embodiments, labels may be indicative of whether the user had an attack at most an hour after the certain period ends.

In Step 421e, generating a model based on the samples generated in Step 421d. Optionally, the model generated this step is the model 427. Optionally, generating the model based on the samples involves utilizing a machine learning-based training algorithm. Optionally, generating the model involves personalizing the model for a certain user by updating parameters of an initial model based on samples generated based on $TH_{ROI1}$, $TH_{ROI2}$, and $TH_{ROI3}$ of the certain user, where the initial model is generated based on samples generated from $TH_{ROI1}$, $TH_{ROI2}$, and $T_{ROI3}$ of other users.

Figure 62:
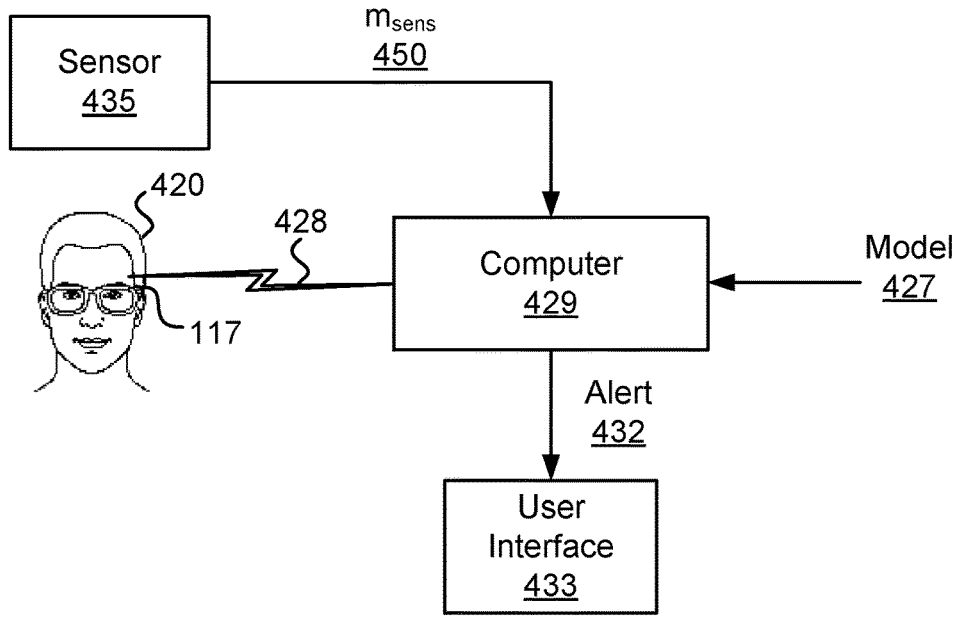
FIG. 62 illustrates an embodiment of a system that is configured to detect an imminent respiratory-related attack.

And in Step 421f, providing the model to be used by a system that detects an imminent respiratory-related attack based on thermal measurements, such as the system illustrated in FIG. 62.

In one embodiment, generating the samples in Step 421d may optionally involve receiving additional data pertaining to a user from among the users and generating one or more feature values belonging to at least one of the samples based on the additional data. Optionally, the additional data pertaining to the user comprises additional measurements of the user that are indicative of one or more of the following signals: a heart rate of the user, heart rate variability of the user, brainwave activity of the user, galvanic skin response of the user, muscle activity of the user, and an extent of movement of the user.

In another embodiment, generating the samples in Step 421d may optionally involve receiving additional data pertaining to a user from among the users and generating one or more feature values belonging to at least one of the samples based on the additional data. Optionally, the data pertaining to the user comprises measurements of the environment in which the user was in while $TH_{ROI1}$, $TH_{ROI2}$, and $TH_{ROI3}$ of the user were taken. Optionally, each measurement of the environment is indicative of one or more of the following values at a certain time: a temperature of the environment, a humidity level of the environment, a noise level of the environment, air quality in the environment, a wind speed in the environment, an extent of precipitation in the environment, and an infrared radiation level in the environment.

In yet another embodiment, generating the samples in Step 421d may optionally involve receiving one or more values indicative of the situation of the user while at least some of $TH_{ROI1}$, $TH_{ROI2}$, and $TH_{ROI3}$ were taken, and generating one or more feature values belonging to at least one of the samples based on the one or more values. Optionally, the one or more values comprise a value that is indicative of one or more of the following: consumption of a certain drug, consumption of a certain food item, a location of the user, a time of day, an identity of a person who is with the user, a type of activity the user is conducting, and a type of activity the user is about to conduct within thirty minutes.

Once the model 427 is generated, it may be utilized detect an imminent respiratory-related attack on $TH_{ROI1}$, $TH_{ROI2}$, and $TH_{ROI3}$ of the user 420, which are not among $TH_{ROI1}$, $TH_{ROI2}$, and $TH_{ROI3}$ 422 that were used for generating the model 427. FIG. 62 illustrates an embodiment of such a system that is configured to detect an imminent respiratory-related attack One embodiment of the illustrated system includes a frame (e.g., the frame 117), one or more thermal cameras, a sensor 435, and a computer 429.

The frame and the one or more thermal cameras may belong to an HMS from among the HMSs described in this disclosure, such as HMSs illustrated in FIG. 47, FIG. 48, FIG. 49, or FIG. 8a. Optionally, the frame and the one or more thermal cameras are the same frame and thermal cameras utilized to take $TH_{ROI1}$, $TH_{ROI2}$, and $TH_{ROI3}$ 422. However, in this embodiment, the frame and the one or more thermal cameras take $TH_{ROI1}$, $TH_{ROI2}$, and $TH_{ROI3}$ 428, which are thermal measurements of regions of the upper lip and mouth of the user 420 that are taken over a certain period. Optionally, the certain period is as at least one second, at least ten seconds, at least one minute, at least five minutes, at least twenty minutes, at least one hour, or at least three hours.

The sensor 435 is configured to take measurements indicative of movements ($m_{sens}$ 450) of the user 420, which correspond to when $TH_{ROI1}$, $TH_{ROI2}$, and $TH_{ROI3}$ 428 were taken. In one example, the sensor 435 may include a gyroscope and/or an accelerometer. In another example, the sensor 435 may include LiDar and/or a Radar based sensor. In another example, the sensor 435 may be configured to receive wireless signals in order to perform triangulation of the location of the user 420 (in order to deduce movement of user 420), such as a GPS receiver. Optionally, the sensor 435 is physically coupled to the frame. Optionally, the sensor 435 belongs to a device carried by the user 420.

The computer 429 is configured, in one embodiment, to generate feature values based on $m_{sens}$ 450 and $TH_{ROI1}$, $TH_{ROI2}$, and $TH_{ROI3}$ 428 and to utilize the model 427 to calculate, based on the feature values, a value indicative of the extent of an imminent attack. Optionally, the attack involves the user experiencing at least one of the following: an asthma attack, an epileptic attack, an anxiety attack, a panic attack, and a tantrum. Optionally, the model is generated based on previous $TH_{ROI1}$, $TH_{ROI2}$, and $TH_{ROI3}$ (e.g., $TH_{ROI1}$, $TH_{ROI2}$, and $TH_{ROI3}$ 422), which were taken over more than a week.

As discussed in more detail above (e.g., in the description of the computer 424), feature values generated based on $TH_{ROI1}$, $TH_{ROI2}$, and $TH_{ROI3}$ may include various types of values. Some examples of feature values include: (i) values comprised in $TH_{ROI1}$, $TH_{ROI2}$, and $TH_{ROI3}$ 428 (optionally these values may undergo various forms of filtering and/or normalization), (ii) values of respiratory parameters of the user 420, which are generated based on $TH_{ROI1}$, $TH_{ROI2}$, and $TH_{ROI3}$ 428 (iii) values generated based on additional measurements of the user 420 (e.g., measurements of heart rate, heart rate variability, brainwave activity, galvanic skin response, muscle activity, and an extent of movement), (iv) measurements of the environment in which the user 420 was in while $TH_{ROI1}$, $TH_{ROI2}$, and $TH_{ROI3}$ 428 were taken, (v) indications of various occurrences which may be considered confounding factors (e.g., touching the face, thermal radiation directed at the face, or airflow directed at the face), and (vi) values indicative of movement of the user (based on $m_{sens}$ 450).

The computer 429 is configured, in one embodiment, to utilize the model 427 to calculate, based on the feature values, a value indicative of whether a respiratory-related attack is imminent. For example, the value may be indicative of the extent to which the user suffers at the time and/or is about to suffer from one or more of the following: an asthma attack, an epileptic attack, an anxiety attack, a panic attack, and a tantrum. Optionally, by "imminent" it is meant that the attack is expected to occur within a certain period of time, where the certain period of time is shorter than one or more of the following durations: three hours, one hour, thirty minutes, five minutes, one minute, fifteen seconds, and five seconds.

The model 427 is generated based on $TH_{ROI1}$, $TH_{ROI2}$, and $TH_{ROI3}$ 422 of users, which were taken prior to $TH_{ROI1}$, $TH_{ROI2}$, and $TH_{ROI3}$ 428. In one embodiment, the users comprise the user 420. Optionally, at least a certain portion (e.g., at least 20%) of the data used to generate the model 427 relates to the user 420. Optionally, the model 427 is a model personalized for the user 420. Optionally, the users include only the user 420. In another embodiment, the user 420 is not among the users whose measurements are comprised in $TH_{ROI1}$, $TH_{ROI2}$, and $TH_{ROI3}$ 422, which were utilized to generate the model 427.

The model 427 may include different types of parameters, in different embodiments. Following are some examples of various possibilities for the model 427 and the type of calculations that are accordingly performed by the computer to generate the value indicative of whether a respiratory-related attack is imminent.

In one embodiment, the model 427 comprises parameters of a decision tree. Optionally, in this embodiment, in order to calculate the value indicative of whether a respiratory-related attack is imminent, the computer 429 traverses along a path in the decision tree, determining which branches to take based on the feature values 430. Optionally, the value indicative of whether a respiratory-related attack is imminent is obtained from a leaf node of the tree that is reached at the end of the path. Optionally, the value is calculated based on values of nodes of the tree that are on the traversed path.

In another embodiment, the model 427 comprises parameters of a regression model (e.g., regression coefficients in a linear regression model or a logistic regression model). Optionally, in this embodiment, in order to calculate the value indicative of whether a respiratory-related attack is imminent the computer 429 multiplies the feature values (which may be considered a regressor) with the parameters of the regression model.

In yet another embodiment, the model 427 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, in this embodiment, in order to calculate the value indicative of whether a respiratory-related attack is imminent, the computer 429 provides the feature values as inputs to the neural network, computes the values of the various activation functions and propagates values between layers, and obtains an output from the network, which is the value indicative of whether a respiratory-related attack is imminent.

The user interface 433 may be utilized, in some embodiments, to present the user 420 the value indicative of whether a respiratory-related attack is imminent. Additionally or alternatively, in some embodiments, the user interface 433 may be utilized to present to the user 420 an alert 432 responsive to an indication that the value indicative of whether a respiratory-related attack is imminent reaches a threshold. For example, the user 420 may be alerted when the breathing rate exceeds a certain value and/or when the user 420 spends at least a certain period of time mouth breathing instead nasal breathing. In one embodiment, the user interface 433 may comprise a screen on which the value and/or the alert 432 may be presented (e.g., in the form of text, an image, or video). Optionally, the screen may be part of a display coupled to a frame worn by the user 420 (e.g., a screen of an augmented reality headset, a mixed reality headset, or a virtual reality headset). Additionally or alternatively, the screen may be a display of a device of the user, such as a display of a smartphone or smartwatch. In another embodiment, presenting the value and/or the alert 432 may involve an audio notification that is generated via the user interface 433. For example, the user interface 433 may include a speaker, earphones, or an earbud through which an audio signal is provided to the user 420 in order to make the user 420 aware of the magnitude of the value and/or that the alert 432 has been generated. In still another embodiment, the user interface 433 may be part of a frame worn by the user 420; presenting the user 420 with the value and/or the alert 432 may involve the frame and/or another device physically and/or communicatively coupled to the frame making noises (e.g., beeping sounds), making a visual indication (e.g., lighting of lights on the frame), and/or providing a tactile indication (e.g., by vibrating).

Figure 63:
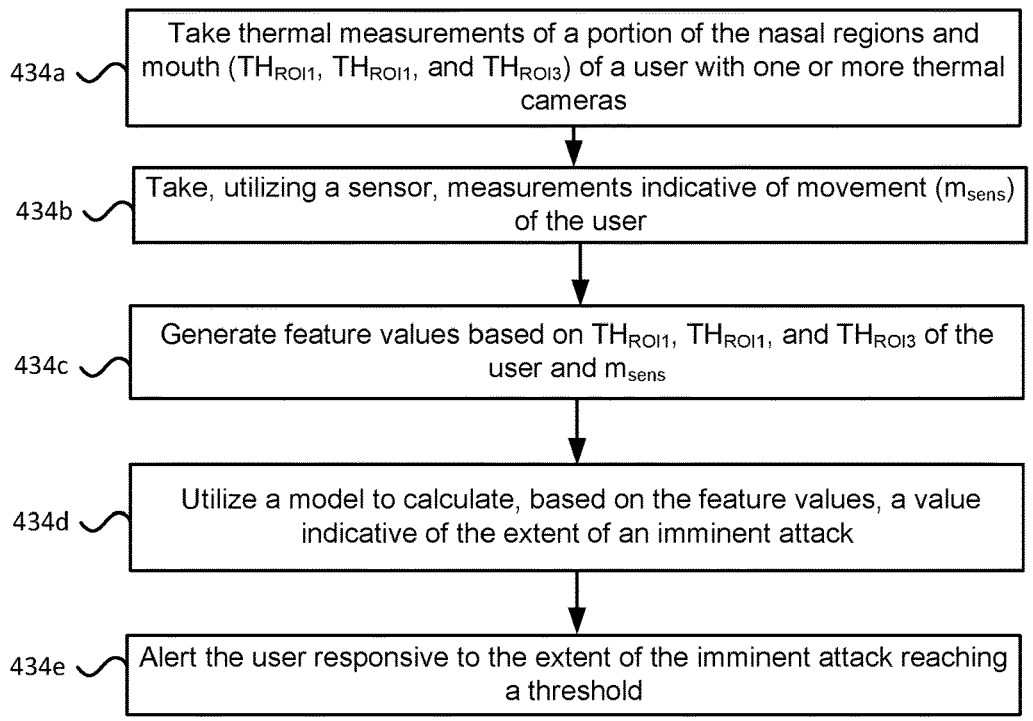
FIG. 63 illustrates an embodiment of a method for detecting an imminent respiratory-related attack.

FIG. 63 illustrates steps that may be performed in one embodiment of a method for detecting an imminent respiratory-related attack. The steps described below may be, in some embodiments, part of the steps performed by an embodiment of a system described above, which is illustrated in FIG. 62. In some embodiments, instructions for implementing an embodiment of the method described below may be stored on a computer-readable medium, which may optionally be a non-transitory computer-readable medium. In response to execution by a system that includes a processor and memory, the instructions cause the system to perform operations that are part of the embodiment of the method. Optionally, embodiments of the method described below may be executed on a system comprising a processor and memory, such as the computer illustrated in FIG. 72a or FIG. 72b. Optionally, different steps of the method may be performed utilizing different systems comprising a processor and memory.

In one embodiment, a method for estimating a respiratory parameter of a user based on thermal measurements of the user's face includes at least the following steps:

In Step 451a, taking $TH_{ROI1}$, $TH_{ROI2}$, and $TH_{ROI3}$ of the user utilizing one or more thermal cameras physically coupled to a frame that is configured to be worn on the user's head. Optionally, each thermal camera weighs below 5 g. Optionally, each thermal camera is located less than 15 cm away from the face.

In Step 451b, taking measurements indicative of movement ($m_{sens}$) of the user utilizing a sensor In Step 451c, generating feature values based on $m_{sens}$ and $TH_{ROI1}$, $TH_{ROI2}$, and $TH_{ROI3}$ of the user.

And in Step 451d, utilizing a model to calculate, based on the feature values, a value of whether an attack is imminent. The model used in this step is generated based on previous $m_{sens}$ and $TH_{ROI1}$, $TH_{ROI2}$, and $TH_{ROI3}$ of one or more users. Optionally, the model used in this step is the model 427.

In one embodiment, the method further involves alerting the user, via a user interface, responsive to the extent of the imminent attack reaching a threshold.

In one embodiment, the method further involves determining, based on $TH_{ROI1}$, $TH_{ROI2}$, and $TH_{ROI3}$ of the user, an extent to which the user's breathing is smooth; and responsive to smoothness of the breathing being below a second threshold, providing a feedback to the user to increase the user's awareness to the lack of sufficient smoothness in the user's breathing.

In one embodiment, the method further involves providing the user with feedback by at least one of the following: (i) providing an audio cue that is indicative of the smoothness of breathing (ii) providing a visual cue that is indicative of the smoothness of breathing; and (iii) providing haptic feedback indicative of the extent of the smoothness of the breathing.

Generating the feature values in Step 451c may involve, in some embodiments, utilization of additional sources of information, which may be utilized in addition to data received in Step 451a and Step 451b. In one embodiment, Step 451c optionally involves receiving additional measurements of the user taken during the same period $TH_{ROI1}$, $TH_{ROI2}$, and $TH_{ROI3}$ of the user 420 were taken and generating at least one of the feature values in Step 451c based on the additional measurements. Optionally the additional measurements are indicative of one or more of the following signals: a heart rate of the user, heart rate variability of the user, brainwave activity of the user, galvanic skin response of the user, muscle activity of the user, and an extent of movement of the user.

In another embodiment, Step 451c optionally involves receiving measurements of the environment in which the user was in while $TH_{ROI1}$, $TH_{ROI2}$, and $TH_{ROI3}$ of the user were taken and generating at least one of the feature values in Step 451c based on the measurements of the environment. Optionally, each measurement of the environment is indicative of one or more of the following values: a temperature of the environment, a humidity level of the environment, a noise level of the environment, air quality in the environment, a wind speed in the environment, an extent of precipitation in the environment, and an infrared radiation level in the environment. Optionally, the measurements of the environment relate to a certain time during the certain period and/or the measurements may be an average value representing the state of the environment throughout the certain period.

In another embodiment, Step 451c optionally involves receiving an additional indication and generating, based on the additional indication, at least one of the feature values in Step 451c. Optionally, the additional indication is indicative of an extent of one or more of the following: touching the face of the user, occlusion of a region of the face by at least one of hair and a foreign object, thermal radiation directed at the face of the user, and direct airflow on the face of the user.

When a person breathes primarily through the nose (nasal breathing), one of the nostrils may be more dominant than the other nostril, with most of the exhaled air flowing through it. The left and right nostrils may switch roles as dominant nostril several times a day, and sometimes the breathing may essentially be the same through them both. Research has shown that brain activity, and in particular, which hemisphere is relatively more effective, is correlated with the dominant nostril. When the left nostril is dominant, the right hemisphere ("right brain") is typically more effective at performing certain activities associated with it, and when the right nostril is dominant, the left hemisphere ("left brain") is more effective at performing certain activities associated with it.

Since each side of the brain plays a dominant role if different types of activities, it has long been believed (e.g., by practitioners of yoga), and to some extent confirmed in research, that it is better to conduct certain activities when "their" side of the brain is more effective. For example, exercising, eating, digesting, and taking care of the body—like using the bathroom or showering, are best done when the left brain is more effective. Various forms of mental activity, such as planning, memorizing, writing, thinking, etc. are best done when the right brain is effective.

Achieving awareness of which side of the brain is more effective at a given time is not easy or even possible for many people. Thus, due to the correlation between the dominant nostril and effective hemisphere, knowing which nostril is dominant at a certain time can be a good indicator for which side of the brain is more effective. However, keeping track of which nostril is dominant is also not an easy task for most people. Thus, there is a need for a way to automatically keep track of the dominant nostril and utilize this information in order to organize activities to coincide with periods in which "their" side of the brain is more effective.

Some aspects of this disclosure include a system that ranks a user's activities based on the nostril dominance. The system includes at least one sensor configured to take measurements of the user, which are indicative of which of the user's nostrils is dominant at the time the measurements were taken. The system also includes a computer that is configured to rank activities for the user to have at a given time based on which of the user's nostrils are dominant at that time and/or whether the user's nasal breathing is balanced. Typically, having a first activity at a certain time is ranked higher than having a second activity at the certain time if it is deemed more appropriate the first activity is deemed to be preferred, e.g., because it may be performed more effectively than the second activity, at the certain time.

Figure 64:
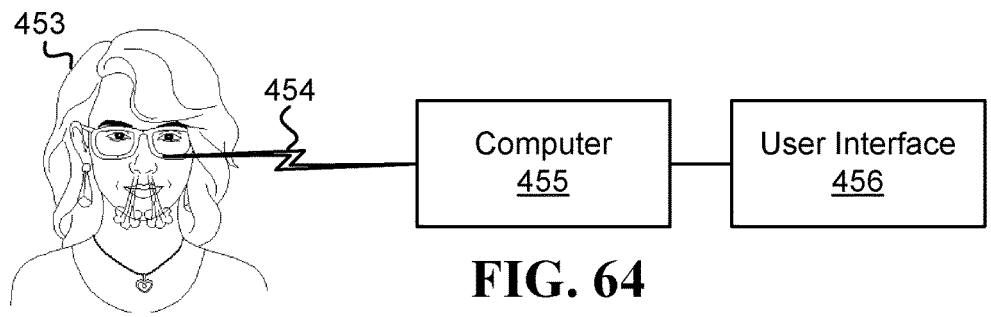
FIG. 64 illustrates one embodiment of a system configured to rank activities according to nostril dominance.

In some embodiments, the system ranks activities based on the premise that the dominant nostril is indicative of which of the user's brain hemispheres is more effective at performing activities that are associated with it. In one example, the left side of the user's brain is expected to be more effective at performing tasks when the right nostril is dominant compared to when the left nostril is dominant Thus, it is better to perform a first activity, which is considered associated with activity in the left side of the brain more than it associated with activity in the right side of the brain, when the right nostril is dominant. Similarly, in another example, the right side of the user's brain is expected to be more effective at performing other tasks when the left nostril is dominant compared to when the right nostril is dominant Thus, it is better to perform a second activity, which is considered associated with activity in right side of the brain more than it associated with activity in the left side of the brain, when the left nostril is dominant FIG. 64 illustrates one embodiment of a system configured to rank activities according to nostril dominance. The system includes at least one sensor configured to take measurements 454 of a user 453, which are indicative of which of the user's nostrils is dominant at the time the measurements 454 were taken. In the illustrated embodiment, the one or more sensors used to take the measurements 454 may be one or more thermal cameras (e.g., one or more of the thermal sensors illustrated in FIG. 47). However, as discussed below, in other embodiments, other types of sensors may be utilized to take the measurements 454.

Figure 65A:
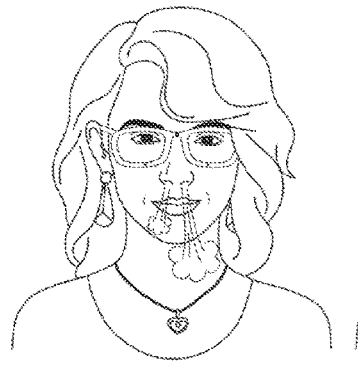
FIG. 65a is a schematic illustration of a left dominant nostril.
Figure 65B:
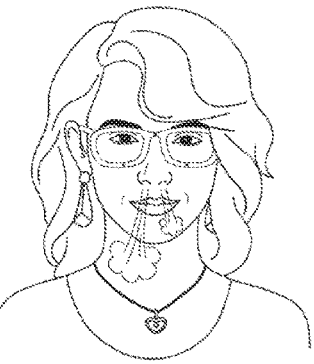
FIG. 65b is a schematic illustration of a right dominant nostril.
Figure 65C:
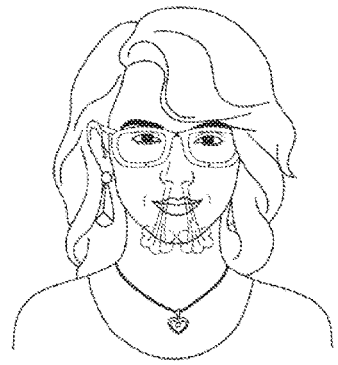
FIG. 65c is a schematic illustration balanced nasal breathing.

In one embodiment, the dominant nostril at a given time is the nostril through which most of the air that is exhaled through the nose, is exhaled. Optionally, the dominant nostril is the nostril through which at least 66% of the air exhaled through the nose is exhaled. Optionally, the measurements 454 may be utilized to determine whether the user's nasal breathing is considered balanced (as defined further below). These different types of breathing are illustrated in FIG. 65a to FIG. 65c. FIG. 65a is a schematic illustration of a left dominant nostril (note the significantly larger exhale stream from the left nostril). FIG. 65b is a schematic illustration of a right dominant nostril. And FIG. 65c is a schematic illustration balanced nasal breathing.

In some embodiments, values of the measurements 454 taken by the at least one sensor include changes in temperatures around the user's nose and/or mouth due to respiration. For example, the measurements 454 may be indicative of temperature changes due to activity involving inhalation of air from the environment and/or exhalation of, typically warmer, air from the body. The frequency at which these changes occur is indicative of the respiration rate. Additionally, the extent at which the temperature changes occur at different ROIs can be indicative of the type of breathing, such as determining whether the left nostril is dominant or the right nostril is dominant, and/or determining whether the breathing is characterized as being mouth breathing or nasal breathing. For example, more extreme temperature changes measured at the left nostril compared to the right nostril are indicative of the left nostril being dominant. In another example, strong temperature changes measured at the mouth region compared to mild temperature changes measured around the nostrils may be indicative of mouth breathing.

The system illustrated in FIG. 64 includes a computer 455 that is configured, in one embodiment, to identify, based on the measurements 454, which of the user's nostrils is dominant, and to rank, based on the dominant nostril, first and second activities for the user 453. Optionally, the first activity requires more verbal-analytic skills and less spatial skills relative to the second activity, and the computer 455 is configured to rank the first activity higher than the second activity at times in which the right nostril is dominant, and to rank the first activity lower than the second activity at times in which the left nostril is dominant The computer 455 may be one of the various computers described in this disclosure that include a processor and memory. In particular, it may be an embodiment of the computer system 400 illustrated in FIG. 72a or it may be an embodiment of the computer system 410 illustrated in FIG. 72b.

In one embodiment, the computer 455 may be part of a device carried by the user (e.g., a smartphone or a wearable device). In another embodiment, the computer 455 is remote of the user, such as processor of a cloud-based server on which a program utilized to implement a software agent runs. In some embodiments, the software agent may provide the functionality of at least one of the following programs: a virtual assistant, a calendar management program, a priority management program, a project management program, a "to do" list program, a work schedule program, and a self-learning program. Optionally, the software agent provides an interface to at least one of the programs mentioned above.

In one embodiment, the system includes a user interface (UI) 456 that is configured to notify the user 453 about his/her dominant nostril, and to suggest the user 453 to prefer having the first activity at times in which the right nostril is dominant, and to prefer having the second activity at times in which the left nostril is dominant. Optionally, the UI includes a display such as a display of a device carried by the user 453 (e.g., a smartphone or a smartwatch). Optionally, the UI includes a display of an augmented reality system, a virtual reality system, and/or a mixed reality system. Optionally, the UI includes a speaker that provides the user 453 with audio such as a speaker of an earbud or an earphone worn by the user 453.

In various embodiments, activities may be ranked by the computer 455 based on the measurements 454. The results of this action are referred to as a "ranking of the activities". A ranking is an ordering of at least some of the activities, which is indicative of a preference towards performing the activities. For example, the higher the rank of an activity, the more it is recommended for the user 453 to perform the activity.

Herein, when a first activity is ranked higher than a second activity, it typically means that the first activity is to be preferred over the second activity. In one embodiment, this may mean that given a choice to perform either activities, it is recommended that the first activity be performed first and/or that only the first activity is recommended and not the second. In another embodiment, when the first activity is ranked higher than the second activity it means that the probability that the first activity is recommended is higher than the second activity. Thus, one average, given multiple instances in which the first activity is ranked higher than the second activity, the number of times the first activity is recommended over the second activity is higher than the number of times the second activity is recommend over the first activity. In still another embodiment, when the first activity is ranked higher than the second activity it means that the first activity is given a stronger recommendation than the second activity. For example, a stronger recommendation may involve the first activity may be suggested by displaying it first on a list of suggested activities. In another example, a stronger recommendation may involve suggesting the first activity with a larger image, a more prominent visual effect, and/or a more noticeable auditory signal than the one used to recommend the second activity.

In some embodiments, determining the ranking of activities for during a certain time is determined based on the dominant nostril at the certain time (or the predicted dominant nostril, if the certain time is in the future). As explained above, the dominant nostril can be indicative of which side of the brain is more effective at a given time at performing activities that are associated with it. Therefore, generally, a higher rank is given to a certain activity to be performed at a certain time when the dominant nostril indicates that, at the certain time, the side of the brain that is more adept to performing the certain activity is more effective than the other side of the brain. Similarly, a lower rank may be given to the certain activity if the dominant nostril at the certain time corresponds to the side of the brain that is less adept to performing the certain activity. Following are some examples in which rankings of activities may be done according to the dominant nostril.

The left side of the user's brain is expected to be more effective when the right nostril is dominant compared to when the left nostril is dominant. In one example, when performing a first activity, the user 453 utilizes the left side of the brain more than the user 453 utilizes the right side of the brain. In this example, ranking of activities by the computer 455 will give, on average, a higher rank to the first activity at times in which the right nostril is dominant compared to the rank given to the first activity by the computer 455 at times in which the left nostril is dominant The first activity may be any one of several activities that are recommended to be performed when the left brain is more effective at performing tasks associated with it. In one embodiment, the first activity is eating, and the computer 455 is configured to assist the user 453 to spend more time eating when the right nostril is dominant Optionally, the computer 455 further assists the user to spend less time eating when the left nostril is dominant. For example, the computer 455 may arrange the user's schedule such that at least 60% of the occurrences of lunch and/or dinner are planned to a time when the right nostril is dominant Optionally, the computer 455 recommends to the user to go on a meal break while the left nostril is dominant. In another example, the first activity is defecating, and the computer 455 is configured to assist the user to increase the time spent at the toilet when the right nostril is dominant Optionally, the computer 455 recommends to the user to spend less time at the toilet while the left nostril is dominant. For example, the computer 455 may recommend to the user to go on a bathroom break when the right nostril is dominant The right side of the user's brain is expected to be more effective when the left nostril is dominant compared to when the right nostril is dominant. In one example, when performing a second activity, the user 453 utilizes the right side of the brain more than the user 453 utilizes the left side of the brain. In this example, ranking of activities by the computer 455 will give, on average, a higher rank to the second activity at times in which the left nostril is dominant compared to the rank given to the second activity by the computer 455 at times in which the right nostril is dominant It is recommended to perform some activities when the breathing through the nose is balanced. Such activities typically involve a heightened state of self-awareness, e.g., meditation. Optionally, the breathing through the nose is considered balanced if the amount of air that flows through each of the nostrils is at least a certain percent of the total amount of air breathed through the nose. Optionally, the certain percent may be at least 25%, 30%, 35%, 45%, or more (but not greater than 50%).

In one embodiment, the computer 455 is further configured to rank a third activity that requires higher than the usual self-awareness. In this example, ranking of activities by the computer 455 will give, on average, a higher rank to the third activity at times in which the breathing is balanced compared to the rank given to the third activity by the computer 455 at times in which the breathing is not balanced.

In another embodiment, the computer 455 is configured to rank, on average, a first set of activities higher than a second set of activities when the right nostril is dominant, and to rank, on average, the first set of activities lower than the second set of activities when the left nostril is dominant Optionally, the first set of activities is more related to a certain aspect, compared to the second set of activities, and the certain aspect involves one or more of the following: solving language based problems of a literary, logical, social skills, and ability to listen and recall spoken information, and less related to navigating a route, creativity, imagination, and feelings.

It is to be noted that part of the reason activities may be more suitable to perform when one nostril is dominant and not the other may be based on the different functionality associated with each side of the brain. The right side of the brain is usually believed to be better at expressive and creative tasks. Some of the abilities associated with the right side of the brain include recognizing faces, expressing emotions, music, reading emotions, color, images, intuition, and creativity. The left side of the brain is usually believed to be adept to tasks that involve logic, language, and analytical thinking. The left side of the brain is usually described as being better at language, logic, critical thinking, numbers, and reasoning. However, many abilities in subjects such as math are strongest when both halves of the brain work together, which may be when the breathing is equal on both nostrils.

There are various hardware configurations may be utilized in different embodiments of the system in order to take the measurements 454 of the user 453.

In one embodiment, the system further comprises a frame configured to be worn on the user's head, and the at least one sensor comprises a thermal camera that weighs below 5 g, is physically coupled to the frame, and is configured to measure the nostrils. In this embodiment, the dominant nostril and/or whether the breathing is balanced may be identified based on signal processing of the measurements.

In another embodiment, the system further comprises a frame configured to be worn on the user's head, and the at least one sensor is configured to operate in at least one of the visible-light spectrum and near-infrared spectrum, is physically coupled to the frame, and is configured to take images of the nostrils. In this embodiment, the dominant nostril and/or whether the breathing is balanced may be identified based on analysis of hemoglobin concentration changes (HCC) determined based on analysis of the images.

In yet another embodiment, the at least one sensor comprises thermistors that are in contact with the nostrils and/or the upper lip in order to take the measurements. In this embodiment, the dominant nostril and/or whether the breathing is balanced may be identified based on signal processing of the measurements.

In still another embodiment, the at least one sensor comprises anemometers located inside the breathing streams of the nostrils in order to take the measurements. In this embodiment, the dominant nostril and/or whether the breathing is balanced may be identified based on signal processing of the measurements.

In yet another embodiment, the at least one sensor comprises a non-wearable IR (infrared) camera pointed to the area around the nostrils in order to take the measurements. In this embodiment, the dominant nostril and/or whether the breathing is balanced may be identified based on image processing of the measurements.

And in still another embodiment, the at least one sensor comprises implanted sensors located around the area of the nostrils. In this embodiment, the dominant nostril and/or whether the breathing is balanced may be identified based on signal processing of the measurements.

Ranking activities based on the dominant nostril by the computer 455 may be done in different ways in different embodiments. Optionally, the ranking is done based on values assigned for having activities at different times (when different sides of the brain are considered more effective). Optionally, a suitability level for the activity for having an activity at a certain time is a value indicative of an extent to which it is recommended for the user to have the activity at the certain time. Optionally, the higher the suitability level for having the activity at the certain time, the more it is recommended that the user have the activity at the certain time, and similarly, the lower the suitability level for having the activity at the certain time, the less it is recommended that the user have the activity at the certain time. Optionally, for at least some activities not all times have equal valued suitability levels.

Determining the suitability values may be done in various ways in different embodiments. The following are some examples of how the suitability values may be determined.

In some embodiments, the computer 455 has access to a predetermined list that indicate the suitability level of having various activities when the breathing is characterized as being one or more of the following types: left nostril dominant, right nostril dominant, balanced breathing, or imbalanced breathing. Where imbalanced breathing is breathing that is not considered balanced breathing. Thus, given a certain a certain activity the computer 455 may consult the list in order to performing a ranking of activities, and assign higher ranks to activities appropriate for the type of breathing the user 452 is conducting at the time. Optionally, the list includes suitability values for various activities and types of breathing. Additionally or alternatively, the suitability values may be deduced by presence or absence from the list (e.g., the list may include only activities that are recommended to have when the breathing is of a certain type).

In one embodiment, the list mentioned above includes numerical values indicating suitability levels (e.g., a higher numerical value corresponds to a higher suitability of an activity to be performed when breathing is of a certain type). The numerical values may be determined in various ways.

In one example, the numerical values are determined based on self-reported scores (of the user 453 and/or other users). In one example, self-reported scores are provided for having activities at different times for which the breathing type is known (e.g., using the above one or more sensors). This information can then be tallied in order to provide a table that includes suitability levels (e.g., averages of the values) for having different activities at times in which the breathing is characterized as being of one or more of the types (e.g., left nostril, right nostril, balance, or imbalanced).

In another example, the user 453 (and/or other users), may be measured by one or more additional sensors in order to take measurements of affective response while having activities at different times for which the breathing type is known (e.g., using the above one or more sensors). Optionally, the one or more additional sensors take measurements of one or more physiological signals and/or behavioral cues. For example, the one or more additional sensors may provide measurements of one or more of the following signals: heart rate, galvanic skin response, brainwave activity, and/or facial expressions. Optionally, the measurements of affective response are indicative of an extent to which one or more of the following emotions were felt while having the activities: anger, disgust, fear, happiness, sadness, and surprise. This affective response information can then be tallied in order to provide a table that includes suitability levels (e.g., averages of the affective responses) for having different activities at times in which the breathing is characterized as being of one or more of the types (e.g., left nostril, right nostril, balance, or imbalanced).

The computer 455 may utilize, in some embodiments, a predictor to calculate a value indicative of the suitability level of having a certain activity when the breathing is of a certain type. These predicted values can then be utilized to rank different activities. Optionally, the certain type may correspond to a category, e.g., left nostril dominant, right nostril dominant, balanced breathing, or imbalanced breathing. Optionally, the certain type may correspond to certain parametric values characterizing the breathing at a certain time (e.g., values indicating a percentage and/or volume of air breathed through each of the mouth, left nostril, and right nostril). Optionally, the predictor receives feature values comprising one or more feature values describing the certain activity (e.g., type of activity, its duration, location, and/or other properties) and/or one or more feature values describing the type of breathing. Additionally, the feature values may include one or more feature values describing the user (e.g., demographic statistics), the environment, and/or the situation the user is in (e.g., emotional state). The predictor then utilizes a machine learning based model to calculate, based on the feature values, a value indicative of the suitability level of having the certain activity when the breathing is of the certain type.

In one embodiment, the machine learning-based model described above is generated based on training data comprising samples, each sample corresponding to an instance involving having an activity while the breathing is characterized as being of a certain type. Each of the samples includes feature values corresponding to the instance (of the same structure of feature value described above), and a label indicative of the suitability level of having the activity while the breathing type of the certain type. Optionally, label is self-reported by the person having the activity. Additionally or alternatively, the label may be determined based on measurements of affective response taken with one or more additional sensors, as described above.

Given the training data described above, various machine learning-based training algorithms can be utilized to generate the model. Optionally, the model may include one or more of the following parameters: parameters of a regression model, parameters of a graphical model, parameters of a neural network, parameters of a support vector machine, and parameters of a decision tree.

It is to be noted that, in some embodiments, when the data used to determine the suitability levels (e.g., the list or machine learning based model) is based on data collected from multiple users, then the suitability levels may be considered general (e.g., determined based on a general model). Additionally, if the data used to determine the suitability levels is based to a large extent on data corresponding to the user 453 (e.g., based on training data corresponding to activities the user 453 had), then the model may be considered personalized for the user 453. Optionally, a new user may start with a general model, but as more data of the user is collected, then a personalized model can be created for the user (by modifying the general model or training a new model from the user's data). This bootstrapping approach may enable a new user to utilize the system from day one, and obtain personalized behavior of the system when sufficient data is available to do so.

The computer 455 may utilize, in some embodiments, predictions indicative of which nostril is expected to be dominant at a future time, and/or of whether the breathing is expected to be balanced at the certain time. Optionally, the predictions may be utilized in order to plan an itinerary for the user in which an activity may be slotted for a future time based on the expected breathing type at that time (and the corresponding suitability level for having the activity with the expected breathing type).

In one embodiment, the predictions described above may be obtained utilizing a predictor module that is configured to receive feature values corresponding to a future time and utilize a machine learning-based model to calculate a value indicative of an expected breathing type at the future time (e.g., the value may be indicative of whether the breathing at the future time may be expected to be left nostril dominant, right nostril dominant and/or balanced). Optionally, the feature values comprise one or more feature values describing aspects the future time such as the time of day to which it corresponds, the location the user is expected to be at the future time, and/or an activity the user is expected to partake in during the future time. Optionally, the feature values may include one or more features values corresponding to a state of the user at an earlier time that precedes the future time, such as the user's breathing type (e.g., determined using the one or more sensors), an activity the user has during the earlier time, and/or values of one or more physiological signals of the user at the earlier time.

In one embodiment, the machine learning-based model for predicting a breathing type at a future time is generated based on samples, each corresponding to a certain time. Each sample corresponding to a certain time comprises feature values, as described above, corresponding to a certain earlier time (that before the certain time), and a label indicative of the breathing type at the certain time. Optionally, the breathing type at the certain time is determined utilizing the one or more sensors. Optionally, the samples comprise samples of the user. Optionally, the model is generated using a machine learning based training algorithm.

Typically, the dominant nostril switches throughout the day, with the duration elapsing between each switch varying, depending on the individual and various other factors. Each cycle usually lasts from thirty minutes to several hours. Disruption of the nasal cycle may be indicative of physiological imbalance and/or sickness (e.g., slower switching of the dominant nostril may be a precursor for some diseases).

In one embodiment, the system includes another sensor configured to take measurements indicative of whether one or more of the user's nostrils is clogged. Examples of sensors that can be used to take measurements indicative of whether one or more of the user's nostrils is clogged include (i) a visible-light camera that provides images to an image processing unit able to identify the clogging, (ii) active sensors that penetrates the skin, such as ultrasound, which provide returned signals to a signal processing unit able to identify the clogging, and (iii) a sensor implanted in the user's head. In this embodiment, the computer 455 is further configured to alert the user 453 when identifying irregularity in the dominant nostril cycle, which does not result from one or more of the nostrils being clogged, and not alert the user 453 when identifying irregularity in the dominant nostril cycle, which does result from one or more of the nostrils being clogged. In one example, the irregularity involves a switching of the dominant nostril within a period of time that is shorter than a certain amount of time, such as shorter than twenty minutes, shorter than ten minutes, or shorter than five minutes. In another example, the irregularity involves a lack of switching of the dominant nostril for a period that is certain than a certain period, which is at least three hours, at least five hours, or at least eight hours. In yet another example, the dominant nostril may be described as a time series (e.g., stating for each minute a value indicative of the dominant nostril). In this example, the computer 455 may have record of previous time series of the user 453, acquired when the user 453 was healthy, and the computer 455 may compare the time series to one or more of the previous time series in order to determine whether a sufficiently similar match is found. A lack of such a similar match may be indicative of the irregularity.

In another embodiment, the system includes another sensor configured to take measurements indicative of a stress level of the user 453. Examples of sensors configured to take measurements indicative of the stress level include (i) thermal cameras operating according to embodiments disclosed herein, and (ii) a heart rate sensor that provide its measurements to a heart rate variability calculator able to identify stress. In this embodiment, the computer 455 is further configured to alert the user 453 when identifying irregularity in the dominant nostril cycle, which does not result from stress.

Some embodiments of the system may involve notification of the user about which of the nostrils is dominant at a given time (e.g., vi the UI 456). Optionally, the notification involves providing a user with an indication (e.g., via sound and/or an image) when the dominant nostril changes and/or every certain period of time (e.g., every hour). Additionally or alternatively, notifying the user 453 about which of the nostrils is dominant may involve utilizing different themes for the UI 456. In one example, a first theme for the UI 456 is utilized when the right nostril is the dominant nostril, and a second theme for the UI 456 is utilized when the left nostril is the dominant nostril. Optionally, the first theme is more logical than the second theme (e.g., presenting data and/or suggestions involves providing more facts and/or detailed explanations), and the second theme is more emotional than the first theme (e.g., presenting data and/or suggestions includes more emotional phrases, images, and/or less factual information).

In one embodiment, the computer 455 is programmed to talk to the user 453 according to at least first and second modes. The first mode is perceived by the user 453 as more logical than the second mode, and the second mode is perceived by the user 453 as more emotional than the first mode. The computer 455 is configured to use, on average, the first mode more frequently than the second mode when the right nostril is the dominant nostril, and to use, on average, the second mode more frequently than the first mode when the left nostril is the dominant nostril. Examples of logical speech include sentences built around numbers and facts, while emotional speech includes sentences built around emotions and intuition.

Examples of alternative devices that may be used to identify the dominant nostril include contact and non-contact devices. Contact devices may use sensors such as thermistors, respiratory gauge transducers, MEMS sensor-based anemometer, and/or acoustic sensors, which are placed in or around one of the nostrils or both nostrils. Contact devices are well known in the art and can provide accurate identification of the dominant nostril. Non-contact devices may use sensors such as infrared video cameras, radar, and/or Doppler modalities. For example, FIG. 3 in Lewis, Gregory F., Rodolfo G. Gatto, and Stephen W. Porges, "A novel method for extracting respiration rate and relative tidal volume from infrared thermography" Psychophysiology 48.7 (2011): 877-887, illustrates measurements of thermal changes from the right nostril and the left nostril. Electromagnetic and ultrasound devices may be adapted to identify the dominant nostril by transmitting from two adjacent transmitters, located in one example 1 to 5 cm from each other; the dominant nostril can be identified based on comparing the difference between the returning waves from the adjacent transmitters. For example, the reference Arlotto, Philippe, et at "An ultrasonic contactless sensor for breathing monitoring" Sensors 14.8 (2014): 15371-15386 may be adapted to identifying the dominant nostril by transmitting alternately from two adjacent ultrasound transmitters.

In some embodiments the computer 455 runs a software agent (and/or is utilized to perform operations involved in running a software agent). As used herein, "software agent" may refer to one or more computer programs that operate on behalf of an entity. For example, an entity may be a person, a group of people, an institution, a computer, and/or computer program (e.g., an artificial intelligence). Software agents may be sometimes referred to by terms including the words "virtual" and/or "digital", such as "virtual agents", "virtual helpers", "digital assistants", and the like. Optionally, a software agent acting on behalf of an entity is implemented, at least in part, via a computer program that is executed with the approval of the entity and/or in order to achieve at least one of the following: advance a goal of the entity, protect an interest of the entity, and/or benefit the entity.

In some embodiments, a software agent, and/or one or more of the programs it may comprise, may simultaneously operate on behalf of multiple entities. In one example, a single process running on a CPU or even a single execution thread, may execute commands that represent actions done on behalf of multiple entities. In another example, a certain running program, such as a server that responds to queries, may be considered comprised in multiple software agents operating on behalf of multiple entities.

In some embodiments, a single service, which in itself may involve multiple programs running on multiple servers, may be considered a software agent that operates on behalf of a user or multiple users. Optionally, a software agent may be considered a service that is offered as part of an operating system. Following are some examples of services that may be considered software agents or may be considered to include a software agent. In one example, a service simply called "Google", "Google Now", or some other variant such as "Google Agent" may be services that implement software agents on behalf of users who have accounts with Google™. Similarly, Siri® or "Proactive Assistant" may be considered software agents offered by Apple™. In another example, "Cortana" may be considered a software agent offered by Microsoft™. In yet another example, "Viv" may be considered a software agent from Viv Labs. And in another example, "Watson" may be considered a software agent developed and/or offered by IBM™.

Implementation of a software agent may involve executing one or more programs on a processor that belongs to a device of a user, such as a processor of a smartphone of the user or a processor of a wearable and/or implanted device of the user. Additionally or alternatively, the implementation of a software agent may involve execution of at least one or more programs on a processor that is remote of a user, such as a processor belonging to a cloud-based server.

Thermal measurements of a user's face can be useful for various applications such as detection of physiological responses that may manifest through temperature changes to various regions of the face. Some examples include certain emotional responses (e.g., fear and anxiety) or physiological signals (e.g., heart rate, respiration rate, and brain activity). However, detecting physiological responses based on thermal measurements of regions of the face can be influenced by various facial movements, such as making a facial expression, talking, eating, drinking, sneezing, and coughing. These facial movements can introduce artifacts and change values of the thermal measurements, which can lead to errors in the detection of the physiological responses.

Facial movements are often not easily identified with thermal measurements. Thus, there is a need to incorporate identification of facial movements into the process of detection of physiological responses based on thermal measurements.

Some aspects of this disclosure involve a system that can be utilized to detect a physiological response based on both thermal and visible measurements of a user's face. The system includes at least two types of cameras: a thermal camera, and a visible-light camera. Both cameras take images of similar regions of the user's face. The system can utilize images of the visible-light camera to improve detection of the physiological response based on thermal measurements taken by the thermal camera in various ways that may involve identifying disruptive facial movements, determining movement of facial landmarks, and/or utilizing the images of the visible-light camera as additional feature values used to detect the physiological response with a machine learning based model.

In one embodiment, a system configured to detect a physiological response based on both thermal and visible measurements includes, a frame configured to be worn on a user's head, a thermal camera, a visible-light camera, and a processor.

The thermal camera weighs below 5 g, is physically coupled to the frame, is located less than 15 cm away from the user's face, and is configured to take thermal measurements of a first region of interest ($TH_{ROI1}$) on the face. Optionally, the thermal camera utilizes at least one of the following sensing elements: a microbolometer, and a thermopile, and the thermal camera weighs below at least one of the following weights: 10 g, 5 g, 2 g, 1 g, 0.5 g, and 0.3 g. Optionally, the thermal camera comprises focal-plane array (FPA) and at least one lens that is tilted relative to the sensor according to the Scheimpflug principle in order to achieve a sharper image of $ROI_1$ than it would be without the tilt.

The visible-light camera weighs below 5 g, is physically coupled to the frame, is located less than 15 cm away from the face, and is configured to take images of a second ROI ($IM_{ROI2}$) on the face. Additionally, $ROI_2$ covers at least half of $ROI_1$. Optionally, the visible-light camera comprises at least one lens tilted relative to the sensor according to the Scheimpflug principle in order to achieve an extended depth of field (DOF) that provides a sharper image of $ROI_2$ than it would be without the tilt. Additional discussion of application of the Scheimpflug principle appears given elsewhere in this disclosure.

Due to their physical coupling to the frame, in some embodiments, the thermal camera and/or the visible-light camera remain pointed at their respective ROIs when the user's head makes angular movements. For example, the thermal camera and/or the visible-light camera may remain pointed at their respective ROIs when the user's head makes angular movements that exceed 0.1 rad/sec, 0.5 rad/sec, and/or 2 rad/sec.

It is to be noted that the in some embodiments the system may be constructed in a way that none of the system components (including the frame and cameras) occludes $ROI_1$ and/or $ROI_2$. In other embodiments, the system may be constructed in a way that at least some of the system components (e.g., the frame and/or thermal cameras) may occlude $ROI_1$ and/or $ROI_2$.

The processor is configured, in one embodiment, to detect the physiological response based on $TH_{ROI1}$ and $IM_{ROI2}$. Optionally, $T_{ROI2}$ is utilized to identify, and/or account for, various facial expressions and facial movements, which can introduce artifacts that alter the values of $TH_{ROI1}$ (without the alterations being direct related to the physiological response). Thus, on average, detections of the physiological responses based on $TH_{ROI1}$ and $IM_{ROI2}$ are more accurate than detections of the physiological responses based on $TH_{ROI1}$ without $IM_{ROI2}$.

In one example, the physiological response is indicative of an occurrence of at least one of the following emotional states of the user: fear, anxiety, guilt, pain, and sexual arousal. In another example, the physiological response is indicative of an occurrence of one or more of the following: stress, mental workload, an allergic reaction, a migraine, dehydration, intoxication, and a stroke.

The physiological response may be a physiological signal of the user. In one example, the physiological response is a heart rate of the user, and in this example, $ROI_1$ covers a portion of the skin above at least one of the superficial temporal artery and the frontal superficial temporal artery. In another example, the physiological response is frontal lobe brain activity of the user, and in this example, $ROI_1$ covers a portion of the forehead. In still another example, the physiological is a respiratory rate of the user, and $ROI_1$ covers a portion of the nasal area.

The processor may utilize $TH_{ROI1}$ in various ways in order to detect the physiological response. In one example, the processor may be configured to compare one or more values derived from $TH_{ROI1}$ to a certain threshold, and determine whether the threshold is reached (which is indicative of an occurrence of the physiological response). In another example, the processor may be configured to determine a similarity between a reference time series corresponding to the physiological response and $TH_{ROI1}$ (or a time series derived from $TH_{ROI1}$). Optionally, when a sufficiently high similarity is detected, the processor may interpret that as an indication of an occurrence of the physiological response. In another example, the processor may generate feature values based on $TH_{ROI2}$ and utilize a machine learning-based model to calculate, based on the feature values, a value indicative of whether the physiological response occurred (and/or the extent of the physiological response). Optionally, the feature values comprise at least some feature values generated based on $IM_{ROI2}$.

Figure 66A:
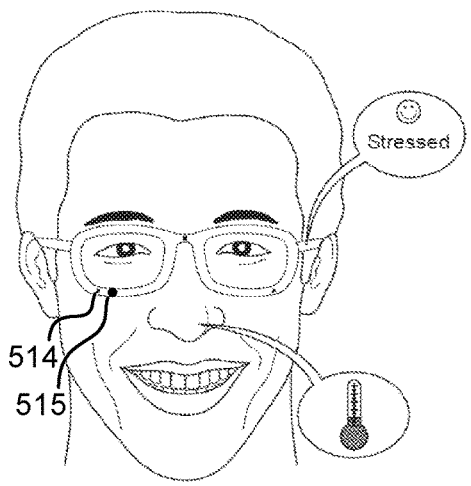
FIG. 66a illustrates a case in which a user smiles but is in fact stressed.
Figure 66B:
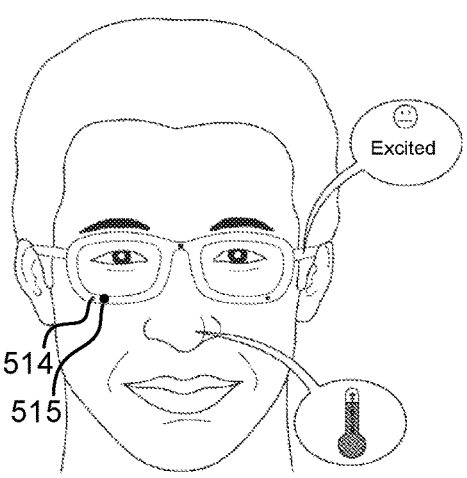
FIG. 66b illustrates a case in which a facial expression indicates that a user is in a neutral state when in fact the user is excited.

Examples of how it may be useful to utilize $IM_{ROI2}$ in addition to $TH_{ROI1}$ to detect a physiological response is given in FIG. 66a and FIG. 66b, which illustrate a scenario in which the processor implements an emotional state analyzer. Relying only on facial expressions that are based on images received from a visible-light camera 511 may not give accurate results at all times. In some cases, receiving thermal measurements, e.g., from a thermal camera 510, can help determine the user's true emotional state. For example, FIG. 66a illustrates a case in which the user's smiling face may be mistaken for happiness; however, the cold nose indicates that the user is in fact stressed. FIG. 66b illustrates a case in which the facial expression indicates that the user is in a neutral state; however, the warm nose indicates that the user is excited.

In one embodiment, the processor is further configured to calculate, based on $IM_{ROI2}$, hemoglobin concentration changes (HCC), and to detect an emotional state of the user based on the HCC. On average, detections of the physiological responses based on both $TH_{ROI1}$ and HCC are more accurate than detections of the physiological responses based on either $TH_{ROI1}$ or HCC.

In another embodiment, the processor is further configured to: calculate hemoglobin concentration changes (HCC) based on $IM_{ROI2}$, generate feature values, and utilize a model to calculate an extent of the physiological response based on the feature values. Optionally, at least one of the feature values are generated based on $TH_{ROI1}$ and the HCC. Optionally, the model is generated based on samples, each sample comprising corresponding feature values generated based on corresponding measurements of the user and a label indicative of an extent of the physiological response of the user while the corresponding measurements were taken.

Throughout day-to-day activities, a user may make various facial movements that can affect the temperature on the face causing warming or cooling of certain regions of the face. Some examples of such facial movements include making a certain facial expression (e.g., smiling or frowning), talking, eating, drinking, sneezing, and coughing. Since these movements may affect the temperature at various regions of the face, but are often not directly related to the physiological response being detected, these movements may be considered disruptive facial movements (DFMs). Occurrence of FDMs while thermal measurements are taken (and/or slightly before they are taken) can lead to artifacts which may be incorrectly interpreted as being caused due to the physiological response. There, in some embodiments, ignoring DFMs may lead to less accurate detection of the physiological response. To address this issue, as explained in more detail below, in some embodiments, the processor may be further configured to identify, based on $IM_{ROI2}$, whether there were occurrences of one or more DFMs, and to utilize identifications of DFMs in order to more accurately detect the physiological response.

Identifying DFMs may be done utilizing a machine learning-based approach, in which the processor utilizes a machine learning-based model to calculate, based on feature values, one or more values indicative of whether the user made at least one of the DFMs.

In one embodiment, the processor generates at least one of the feature values based on $IM_{ROI2}$. Optionally, at least one of the feature values are generated based on $IM_{ROI2}$ taken during a certain period. For example, the certain period may be 1 second, 5 seconds, 10 seconds, 30 seconds, or some other period greater than 0.1 seconds. Optionally, $IM_{ROI2}$ includes a sequence of images such as video taken during the certain period. The at least some of feature values may include values of various image and/or facial features described in this disclosure. For example, the at least one of the feature values may include high-level facial-related feature values and their derivatives, such as location and dimensions of facial features and/or landmarks, identification of action units (AUs) in sequences of images, and/or blendshape weights. Other examples of features include various low-level features such as features derived using Gabor filters, local binary patterns (LBP) and their derivatives, HOG descriptors, features derived using algorithms such as SIFT, SURF, and/or ORB, image keypoints, and features derived using PCA or LDA. Additional examples of features may also include features derived from multiple images taken at different times, such as volume local binary patterns (VLBP), optical strain-based features, and/or cuboids that are described in this disclosure.

In addition to the at least one of the feature values generated based on $IM_{ROI2}$, in some embodiments, the processor may generate some of the feature values based on other data. In one example, these additional feature values include feature values generated based on $TH_{ROI1}$. In another example, the additional feature values may include feature values generated based on other sensors such as a microphone that detects noises that may be associated with some of the DFMs, and/or one or more movement sensors (e.g., an accelerometer). In still another example, the additional feature values may include feature values representing environmental parameters (e.g., temperature, humidity, noise level, etc.) And in yet another example, the additional feature values may include feature values that describe the user (e.g., age, gender, facial features) and/or a situation of the user (e.g., the user's mood or an activity the user is doing at the time).

The processor may utilize a machine learning based model to calculate, based on the feature values generated based on $IM_{ROI2}$ (and possibly other data described above), a value indicative of whether the user made at least one of the DFMs. It is to be noted that this typically is not the same model as a machine learning-based model utilized to detect the physiological response.

In one embodiment, the model utilized to identify the at least one of the DFMs corresponds to a specific type DFM (e.g., the model may be used to identify talking). Optionally, the processor may utilize multiple models each corresponding to a certain one or more types of DFMs (e.g., one model for talking, another for eating, and still another for various facial expressions). Additionally or alternatively, the model may correspond to multiple types of DFMs. For example, the model may be used to classify $IM_{ROI2}$ into classes (e.g., where each class corresponds to a certain type of DFM or to not making any of the DFMs). In another example, the processor may calculate, utilizing the model, multiple values each indicative the extent the user made of the DFMS.

Generation of the machine learning based model described above typically requires a training set that includes multiple samples corresponding to examples of the DFMs and also, optionally, samples that correspond to none of the DFMs (e.g., samples corresponding to neutral facial expressions). Each sample mentioned above includes feature values generated based on $IM_{ROI2}$ taken during a certain time (and optionally, other feature values as described above). In addition to the feature values, for training, the samples need to be assigned with labels describing the whether they correspond to a DFM and/or the extent of the DFM to which they correspond. Optionally, the extent may be indicative of a distance from a neutral expression the face and/or a duration of the DFM (e.g., a brief cough or a coughing fit). Labels may be provided in different embodiments in various ways. Some examples are given below.

In one embodiment, labels for samples may be created by an expert. For example, the expert may be a human that views images taken by a camera coupled to a frame of an HMS at a certain location and/or orientation and indicates what DFMs (if any) occurred at that time. Additionally or alternatively, the expert may examine other images of the user taken at the same time by a camera that is not coupled to the frame. Optionally, the expert is a software agent. In another embodiment, a user may annotate images of him/her, e.g., using an application (e.g., a smartphone application) and/or via issuing verbal comments which are processed by a software agent who performs the annotation. In yet another embodiment, labels may be assigned by analyzing data from addition al sensors, such as a microphone and/or movement sensors that can identify certain sound and/or movement patterns that are characteristic of certain DFMs.

In another embodiment, at least some labeled samples for training the model may be collected by prompting a user to perform DFMs (e.g. talking, coughing, and/or making certain facial expressions). Thus, the system may collect samples for which it is known both to what DFMs they correspond, and during which durations they occurred.

Various types of machine learning-based training algorithms may be utilized, in embodiments described herein, to generate the machine learning-based model described above, which is used to identify occurrences at least one of the DFMs. Thus, depending on the training algorithm or algorithms that are used, the model may include various types of parameters, such as one or more of the following: a regression model, a support vector machine, a neural network, a graphical model, a decision tree, a random forest, and other models of other types of machine learning classification and/or prediction approaches.

It is to be noted that when the samples used to generate the machine learning-based model comprise samples corresponding to multiple users (i.e., samples generated based on $IM_{ROI2}$ of multiple users), then the model may be considered a general model. When the samples used to generate the machine learning-based model comprise samples that primarily correspond to a certain user, then the generated model may be considered a personalized model for the certain user. Personalized models have an advantage that given sufficient training data, they may give more accurate results when used with the certain user(s) for whom they were personalized, compared to using a general model; a personalized model can better account for a user's specific facial characteristics and mannerisms.

In some embodiments, a new user may initially utilize a general model and/or a model personalized for some other user or set of users. However, as the new user uses the system, it is possible to accumulate more and more samples corresponding to the user and thus generate a personalized model for the (not so) new user. Thus, this bootstrapping approach enables the system to be utilized by new users from day one.

There are various ways in which a processor may account for DFMs which it detects (e.g., as described above) and/or receives an indication of (e.g., from an external source).

In one embodiment, detection of the physiological response is done based on $TH_{ROI1}$ taken at different times (e.g., during a certain window in time). In this embodiment, thermal measurements taken at different times may be weighted in order to determine to what extent they are to be relied on. Optionally, the processor is further configured to reduce, for the purpose of detecting the physiological response, weight of $TH_{ROI1}$ taken at times coinciding with the DFMs, compared to weight of $TH_{ROI1}$ taken at times that do not coincide with the DFMs. Thus, example, when detecting stress, the processor may rely more on $TH_{ROI1}$ taken during times in which the user did not make many DFMs compared to times in which the user made many DFMs (e.g., talked a lot or sneezed a lot). Optionally, the reduction in weights is proportional to the extent of the DFMs, such that the more DFMs a user makes during a certain period, the less the processor relies on $TH_{ROI1}$ taken during the certain period for detecting the physiological response. Optionally, if the extent of DFMs during a certain period reaches a threshold, the processor does not utilize $TH_{ROI1}$ taken during the certain period to detect the physiological response.

In another embodiment, detection of the physiological response is done based on $TH_{ROI1}$ taken during a certain window. In this embodiment, the processor is calculates a value indicative of an occurrence of the physiological response at a certain time based on $TH_{ROI1}$ taken during a window corresponding to the certain time. For example, a physiological signal, such as respiration rate at a given time may be done based on $TH_{ROI1}$ taken during a window of 30 seconds ending at the given time (or in temporal proximity to the given time). The size of the window used by the processor may depend on the detection of DFMs, such that with more DFMs a larger window may be used (in order to reduce the effect of $TH_{ROI1}$ taken during elevated DFMs). In one example, responsive to identifying during a certain period preceding the certain time, DFMs that reach a threshold, the processor selects a first duration for the window (e.g., an "extended" window 60 seconds to calculate respiration rate). However, responsive to not identifying during the certain period preceding the certain time, DFMs that reach the threshold, the processor selects a second duration for the window, which is shorter than the first duration (e.g., a "regular" window of 30 seconds to calculate respiration rate). It is to be noted the extending the size of the window may be done in conjunction with decreasing weights of $TH_{ROI1}$ taken during periods in which the user made DFMs.

In yet another embodiment, the processor may utilize a machine learning-based model to calculate, based on feature values, a value indicative of an occurrence of the physiological response. In this embodiment, identifications of DFMs may be utilized to generate one or more of the feature values.

Contraction and relaxation of various facial muscles can cause facial tissue to slightly change its position and/or shape. Thus, facial movements can involve certain movements to ROIs. With thermal cameras that have multiple sensing elements (pixels), this can cause the ROI to move and be covered by various subsets of pixels as the user's face moves (e.g., due to talking/or making facial expressions). For example, smiling can cause the user's cheeks to move upwards. This can cause a thermal camera that covers a cheek to capture an ROI located on a cheek with a first set of pixels (from among the camera's pixels) when the user has a neutral expression, and to capture images of the ROI with a second set of pixels, when the user is smiling. In this example, on average, the pixels in the second set are likely to be located higher in the images than the pixels in the first set.

To account for the possible movement of ROIs due to DFMs, in some embodiments, the processor is further configured to track locations of one or more facial landmarks in a series of $IM_{ROI2}$ and to utilize the locations to adjust $TH_{ROI1}$. Facial landmarks are usually the most salient facial points on the face, and typically include at least some of the following points: the edges and centers of the eyes, the ears, the nose and edges of the nostrils, the edges and center of the mouth, and the center of the chin. Additional details regarding facial landmarks and how they can be detected based on $IM_{ROI2}$ are given elsewhere in this disclosure.

In one embodiment in which the thermal camera comprises multiple sensing elements, which correspond to values of multiple pixels in $TH_{ROI1}$, the processor is further configured to assign weights to the multiple pixels based on the locations of the one or more facial landmarks. The locations of the landmarks are determined based on $IM_{ROI2}$ taken essentially at the same time as $TH_{ROI1}$ (e.g., typically within 0.2 seconds of each other). In this embodiment, the processor is further configured to calculate a value indicative of an occurrence of the physiological response based on $TH_{ROI1}$ and the weights.

Assigning weights to pixels based on their location with respect to a facial landmark can be considered a form of selection of the pixels that cover the ROI based on the location of the landmark. In one example, the weights are assigned based on a function that takes into account the distance of each pixel from the locations of one or more facial landmarks and/or the relative position of each pixel with respect to the locations.

In another embodiment, the processor may generate certain feature values based on locations of one or more landmarks, which are determined based on analysis of $IM_{ROI2}$. These certain feature values may be utilized in conjunction with other feature values (e.g., feature values generated based on $TH_{ROI1}$) to detect the physiological response using a machine learning-based model.

The following are some specific examples how utilization of $IM_{ROI2}$ may be utilized to help make detections of a physiological response more accurate. In one example, $ROI_1$ and $ROI_2$ cover portions of the mouth and $IM_{ROI2}$ are indicative of a change in a facial expression, during a certain period, which involves a transition from a facial expression in which the lips are in contact to a facial expression with an open mouth. Optionally, by utilizing $IM_{ROI2}$ to detect the physiological response based on $TH_{ROI1}$ taken during the certain period, the processor may be able attribute a change in $TH_{ROI1}$ to opening the mouth rather than a change in the temperature of the lips.

In another example, $ROI_1$ and $ROI_2$ cover portions of the nose and upper lip and $IM_{ROI2}$ are indicative of a change in a facial expression, during a certain period, which involves a transition from a neutral facial expression to a facial expression of disgust. Optionally, by utilizing $IM_{ROI2}$ to detect the physiological response based on $TH_{ROI1}$ taken during the certain period, the processor may be able attribute a change in $TH_{ROI1}$ to a raised upper lip and wrinkled nose instead of a change in the temperature of the nose and upper lip.

In yet another example, $ROI_1$ and $ROI_2$ cover portions of the user's forehead located about 1 cm above at least one of the user's eyebrows and $IM_{ROI2}$ are indicative of a change in a facial expression, during a certain period, which involves a transition from a neutral expression to a facial expression involving raised eyebrows. Optionally, by utilizing $IM_{ROI1}$ to detect the physiological response based on $TH_{ROI1}$ taken during the certain period, the processor may be able attribute a change in $TH_{ROI1}$ to raising the eyebrows instead of a change in the temperature of forehead.

In one embodiment, the system configured to detect a physiological response based on both thermal and visible measurements includes a second thermal camera that weighs below 5 g, is physically coupled to the frame, and is configured to take thermal measurements of a third region of interest ($TH_{ROI3}$) on the face; the center of $ROI_1$ is to the right of the center of $ROI_3$, and the symmetric overlapping between $ROI_1$ and $ROI_3$ is above 30%. Optionally, temperature changes at $ROI_1$ and $ROI_3$, in response to the physiological response, are asymmetric. In this embodiment, the processor is further configured to account for the asymmetry when detecting the physiological response. Optionally, accounting for the asymmetry comprises utilizing at least one of the following calculations for calculating the physiological response based on $TH_{ROI1}$ and $TH_{ROI3}$: utilizing different thresholds to which $TH_{ROI1}$ and $TH_{ROI3}$ are compared when determining whether the physiological response occurs; utilizing different reference time series to which $TH_{ROI1}$ and $TH_{ROI3}$ are compared in order to determine whether the user is experiencing the physiological response; utilizing a machine learning-based model that provides different results for first and second events that involve the same average change in $TH_{ROI1}$ and $TH_{ROI3}$ with different extents of asymmetry in $TH_{ROI1}$ and $TH_{ROI3}$; and utilizing the asymmetry for differentiating between (i) temperature changes in $TH_{ROI1}$ and $TH_{ROI3}$ that are related to the physiological response and (b) temperature changes in $TH_{ROI1}$ and $TH_{ROI3}$ that are unrelated to the physiological response.

In another embodiment, the system configured to detect a physiological response based on both thermal and visible measurements includes a second visible-light camera that is physically coupled to the frame and is configured to take images of a third ROI ($IM_{ROI3}$) on the face. Optionally, the visible-light camera and the second visible-light camera are located less than 5 cm away from the face, and the visible-light camera and the second visible-light camera are located at least 0.5 cm to the right and to the left of the vertical symmetry axis that divides the face, respectively. Optionally, the processor is further configured to detect the physiological response also based on $IM_{ROI3}$ At times, a user's facial expressions may not reflect the user's true emotions. For example, the user may be embarrassed or stressed from the presence of other people and therefore make a certain facial expression, while in fact the user may have a completely different feeling. This difference between facial expressions and true emotions can make it difficult to understand how the user truly feels. For example, a software agent tasked with learning the user's preferences (e.g., in order to make recommendations of the user), may make inaccurate models of the user if it cannot determine when the user's facial expression does not correspond to the user's true emotions. Thus, there is a need for a way to make a more accurate determination of a user's emotional response and be able to tell when a user's facial expressions do not match the user's true feelings.

Some aspects of this disclosure involve head-mounted systems that include thermal cameras that take thermal measurements of regions of the face and one or more visible-light cameras that take images of the face.

In some cases, thermal imaging and visible-light imaging provide different indications about the user's emotional response. For example, a review of research on thermal IR imaging in psychophysiology and in the assessment of affective states can be found in the publication Merla, A. (2014), "Thermal expression of intersubjectivity offers new possibilities to human-machine and technologically mediated interactions", Frontiers in Psychology, 5, 802. The reference Ioannou, S., Gallese, V., & Merla, A. (2014), "Thermal infrared imaging in psychophysiology: potentialities and limits", Psychophysiology, 51(10), 951-963, provides in Table 1 a useful overview of the direction of temperature variation in various ROIs across emotions, and a useful summary regarding temporal latency of cutaneous temperature change.

In some embodiments, both types of data (thermal imaging and visible-light imaging) are utilized to determine a user's emotional response. Using both types of data enables the system, in some cases, to determine more accurately emotional responses of the user compared to determination of emotional response based on visible-light imaging alone.

In one embodiment, a system configured to estimate emotional response includes a frame configured to be worn on a user's head, first and second thermal cameras, a visible-light camera, and a processor.

The first and second thermal cameras are physically coupled to the frame, and are configured to take thermal measurements of first and second regions of interest ($TH_{ROI1}$, $TH_{ROI2}$) on the user's face, respectively. Optionally, the first and second thermal cameras are located less than 15 cm away from the face, and utilize at least one of the following sensing elements: a microbolometer, and a thermopile. Optionally, each of the first and second thermal cameras weighs below at least one of the following weights: 10 g, 5 g, 2 g, 1 g, 0.5 g, and 0.3 g. Optionally, each of the first and second thermal cameras is located less than 5 cm away from the face. Optionally, the first thermal camera comprises a focal-plane array (FPA) and at least one lens that is tilted relative to the sensor according to the Scheimpflug principle in order to achieve a sharper image of $ROI_1$ than it would be without the tilt. Optionally, the second thermal camera may comprise an FPA and at least one lens that is tilted relative to the sensor according to the Scheimpflug principle in order to achieve a sharper image of $ROI_2$ than it would be without the tilt.

The visible-light camera is physically coupled to the frame, and is configured to take images of a third region of interest ($IM_{ROI3}$) on the face. Optionally, the visible-light camera weighs less than 5 g. Optionally, the visible-light camera is located less than 15 cm from the user's face. Optionally, the visible-light camera is located less than 5 cm from the user's face. Optionally, the visible-light camera comprises at least one lens tilted relative to the sensor according to the Scheimpflug principle in order to achieve an extended depth of field (DOF) that provides a sharper image of $ROI_3$ than it would be without the tilt. Additional discussion of application of the Scheimpflug principle appears given elsewhere in this disclosure.

Due to their physical coupling to the frame, in some embodiments, the thermal cameras and/or the visible-light camera remain pointed at their respective ROIs when the user's head makes angular movements. For example, the thermal cameras and/or the visible-light camera may remain pointed at their respective ROIs when the user's head makes angular movements that exceed 0.1 rad/sec, 0.5 rad/sec, and/or 2 rad/sec.

It is to be noted that the in some embodiments the system may be constructed in a way that none of the system components (including the frame and cameras) occludes $ROI_1$, $ROI_2$ and/or $ROI_3$. In other embodiments, the system may be constructed in a way that at least some of the system components (e.g., the frame and/or thermal cameras) may occlude $ROI_1$, $ROI_2$ and/or $ROI_3$.

The processor is configured to calculate a value indicative of an emotional response of the user based on $TH_{ROI1}$, $TH_{ROI2}$, and $IM_{ROI3}$. Optionally, $TH_{ROI1}$ and/or $TH_{ROI2}$ may be indicative of times at which the facial expression of the user, which may be identified based on $IM_{ROI2}$ does not accurately reflect the user's physiological response (as reflected in $TH_{ROI1}$ and/or $TH_{ROI2}$). Thus, utilizing $TH_{ROI1}$ and/or $TH_{ROI2}$ can at times help estimations of the emotional response of the user to be more accurate. Therefore, in some embodiments, on average, calculations of the value indicative of the emotional response based on $TH_{ROI1}$, $TH_{ROI2}$ and $IM_{ROI3}$ are more accurate than calculations of the value indicative of the emotional response based on $IM_{ROI3}$ without $TH_{ROI1}$ and $TH_{ROI2}$.

There are different ways in which the processor may utilize $TH_{ROI1}$, $TH_{ROI2}$, and $IM_{ROI3}$ to estimate the user's emotional response. In some embodiments, the processor may estimate emotional response based on the user's facial expressions as detected in the visible images ($IM_{ROI3}$). This emotional response may be referred to as an "image-based emotional response". Additionally, the processor may detect a physiological response based on $TH_{ROI1}$ and $TH_{ROI2}$ and compare it to a threshold in order to determine how set the emotional response of the user. Optionally, responsive to $TH_{ROI1}$ and $TH_{ROI2}$ being indicative of a physiological response that reaches a threshold, the processor assigns to the value indicative of the emotional response of the user a value indicative of the image-based emotional response. Optionally, responsive to $TH_{ROI1}$ and $TH_{ROI2}$ being indicative of a physiological response that does not reach the threshold, the processor as signs to the value indicative of the emotional response of the user a value indicative of an emotional response that is different from the image-based emotional response. Additionally or alternatively, the processor may determine that there is a discordance between physiological response based on the thermal imaging ($TH_{ROI1}$ and/or $TH_{ROI2}$) and the image-based emotional response, in which case, the processor may take several actions, such as change the estimation of the emotional response or refrain from making an estimation of the emotional response. For example, if the user smiles, but the thermal cameras capture indications of severe stress, then the system may refrain from reporting the user is happy; it may report that the user is stressed or in an ambiguous state, or not report an emotional state at all.

There are various algorithmic approaches for estimating an emotional response based on images of the face. For example, the reference Zeng, Zhihong, et at "A survey of affect recognition methods: Audio, visual, and spontaneous expressions." *IEEE transactions on pattern analysis and machine intelligence* 31.1 (2009): 39-58, describes some of the algorithmic approaches known in the art. As discussed in more detail in this disclosure regarding identification of high-level facial features, many approaches known in the art can be easily adapted to work with images obtained by visible-cameras coupled to the frame worn by the user, since for these images to the various low-level image features and high-level facial features described herein can be extracted and used similarly to how features from full face frontal images are used.

In some embodiments, the processor calculates the value indicative of the emotional response of the user utilizing a machine learning based model. Optionally, the model is generated based on training data that comprises labeled samples. Optionally, each labeled sample is generated based on one or more images in which a user made a facial expression, and includes feature values generated based on the one or more images (which may be from among the various low-level image features and high-level facial features described herein). Additionally, the sample has a label describing the emotional response of the user, which may be provided from analysis of the images (e.g., by an expert), from analysis of other images taken at the time (e.g., frontal images of the user), and/or reported by the user. In some embodiments, the model described above may be a general model (i.e., the model is trained based on samples corresponding to facial expressions of multiple users). In other embodiments, the model may be personalized for a certain user (i.e., the model is trained based on samples corresponding to facial expressions of the certain user). It is to be noted that generation and utilization of the model described above is similar to how a model for detecting a physiological response may be generated and/or utilized (which are described in more detail in this disclosure).

Estimation of an emotional response may be considered a detection of a certain type of physiological response; in the example above, the feature values are generated based on visible-light images instead of thermal images that are typically used in this disclosure. Various options and variations described in this disclosure with respect to a model detection of a physiological response may be applied mutatis mutandis to the model used for estimating the emotional response described above.

Another way in which the processor may utilize $TH_{ROI1}$, $TH_{ROI2}$ and $IM_{ROI3}$ to estimate the user's emotional response involves direct estimation the emotional response from $TH_{ROI1}$, $TH_{ROI2}$, and $IM_{ROI3}$. In some embodiments, the processor may generate feature values based on $TH_{ROI1}$, $TH_{ROI2}$, and $IM_{ROI3}$ and utilize a machine learning based model to calculate, based on the feature values, the value indicative of the emotional response of the user (and thus utilize both the visible and IR images to make its estimation). Estimating emotional response this way may be done similarly to how it is described above with the addition that instead of the feature values being based on $IM_{ROI3}$ (and not on thermal measurements), the feature values in this case include additional feature values based on $TH_{ROI1}$ and $TH_{ROI2}$. These additional feature values may be any of the various types of feature values generated based on thermal measurements that are described in this disclosure.

In one embodiment, the center of $ROI_1$ is to the right of the center of $ROI_2$, the symmetric overlapping between $ROI_1$ and $ROI_2$ is above 30%, and the temperature changes at $ROI_1$ and $ROI_2$ are asymmetric in response to the emotional response. In this embodiment, the processor is further configured to account for the asymmetry when detecting the emotional response. Optionally, accounting for the asymmetry comprises utilizing at least one of the following calculations for calculating the emotional response based on $TH_{ROI1}$ and $TH_{ROI4}$: utilizing different thresholds to which $TH_{ROI1}$ and $TH_{ROI2}$ are compared when determining whether the emotional response occurs; utilizing different reference time series to which $TH_{ROI1}$ and $TH_{ROI2}$ are compared in order to determine whether the user is experiencing the emotional response; utilizing a machine learning-based model that provides different results for first and second events that involve the same average change in $TH_{ROI1}$ and $TH_{ROI2}$ with different extents of asymmetry in $TH_{ROI1}$ and $TH_{ROI2}$; and utilizing the asymmetry for differentiating between (i) temperature changes in $TH_{ROI1}$ and $TH_{ROI2}$ that are related to the emotional response and (b) temperature changes in $TH_{ROI1}$ and $TH_{ROI2}$ that are unrelated to the emotional response.

One outcome of relying on both visible-light imaging and thermal imaging for estimating the emotional response is that, in some instances, the system may output different estimations of emotional response even when the user makes the same facial expressions. In these instances, different $IM_{ROI3}$ may correspond to the same facial expression. For example, the different $IM_{ROI3}$ may belong to the same cluster of images and/or be identified by an algorithm as corresponding to the same type of facial expression. However, while the different $IM_{ROI3}$ may be similar, their corresponding thermal measurements taken at the same time may tell a completely different story, as the following example demonstrates.

In one example, responsive to receiving a first set of $TH_{ROI1}$, $TH_{ROI2}$, and $IM_{ROI3}$ taken during a first period in which the user expressed a certain facial expression, the processor calculates a first value indicative of a certain emotional response of the user. Additionally, responsive to receiving a second set of $TH_{ROI1}$, $TH_{ROI2}$, and $IM_{ROI1}$ taken during a second period in which the user expressed again the certain facial expression, the processor calculates a second value indicative of a different emotional response of the user, which is not the same as the certain emotional response. In this example, $TH_{ROI1}$ and $TH_{ROI2}$ of the first set are indicative of a first physiological response that reaches a threshold (e.g., the thermal measurements indicate that the user felt at least a certain level of stress). However, $TH_{ROI1}$ and $TH_{ROI2}$ of the second set are indicative of a second physiological response that does not reach the threshold (e.g., these thermal measurements indicate that the user felt a low level of stress). Therefore, in this example, assuming the certain facial expression is smiling, the processor may output for the first set a value indicative of stress, discomfort, and/or or an ambiguous feeling, while for the second set the processor may output a value indicative of happiness.

The following are additional examples of first and second sets of measurements in which different thermal measurements can lead to different emotional responses even when the user makes similar facial expressions. In another example, the first set comprises $IM_{ROI3}$ indicative of a facial expression that is a neutral expression, $TH_{ROI1}$ and $TH_{ROI2}$ are indicative of a physiological response that corresponds to stress below a certain threshold, and the emotional response corresponding to the first set is comfort. The second set in this example comprises $IM_{ROI3}$ indicative of a facial expression that is neutral, $TH_{ROI1}$ and $TH_{ROI2}$, are indicative of a physiological response that corresponds to stress above the certain threshold, and the emotional response corresponding to the second set is concealment. In yet another, the first set comprises $IM_{ROI3}$ indicative of a facial expression that is an angry expression, $TH_{ROI1}$ and $TH_{ROI2}$ are indicative of a physiological response that corresponds to stress above a certain threshold, and the emotional response corresponding to the first set is anger. The second set in this example comprises $IM_{ROI3}$ indicative of a facial expression that is an angry expression, $TH_{ROI1}$ and $TH_{ROI2}$ are indicative of a physiological response that corresponds to stress below the certain threshold, and the emotional response corresponding to the second set describes pretending to be angry.

It is to be noted that in some instances, when the thermal measurements in different sets of measurements are similar and the user makes similar facial expressions, the processor may assign the same emotional response to the different sets of measurements. For example, responsive to receiving a third set of $TH_{ROI1}$, $TH_{ROI2}$, and $IM_{ROI1}$ taken during a third period in which the user expressed the certain facial expression, the processor calculates a third value indicative of the certain emotional response of the user. Additionally, responsive to receiving a fourth set of $TH_{ROI1}$, $TH_{ROI2}$ and $IM_{ROI1}$ taken during a fourth period in which the user expressed the again certain facial expression, the processor calculates a fourth value indicative of the certain emotional response of the user. In this example, $TH_{ROI1}$ and $TH_{ROI2}$ of the third set are indicative of a third physiological response that reaches the threshold (mentioned above), and additionally $TH_{ROI1}$ and $TH_{ROI2}$ of the fourth set are indicative of a fourth physiological response that also reaches the threshold.

Various types of values indicative of emotional responses may be used in different embodiments described herein. The various types of values correspond to various ways in which emotion is represented in the different embodiments. In one embodiment, emotions are represented using discrete categories. For example, the categories may include three emotional states: negatively excited, positively excited, and neutral. In another example, the categories may include emotions such as happiness, surprise, anger, fear, disgust, and sadness. In still another example, the emotions may selected from the following set that includes basic emotions, including a range of positive and negative emotions such as amusement, contempt, contentment, embarrassment, excitement, guilt, pride in achievement, relief, satisfaction, sensory pleasure, and shame, as described by Ekman P (1999), "Basic Emotions", in Dalgleish Power, *Handbook of Cognition and Emotion*, Chichester, UK: Wiley. In another embodiment, emotions are represented using a multidimensional representation, which typically characterizes the emotion in terms of a small number of dimensions. In one example, emotional states are represented as points in a two dimensional space of Arousal and Valence. Arousal describes the physical activation and valence the pleasantness or hedonic value. Each detectable experienced emotion is assumed to fall in a specified region in that two-dimensional space. Other dimensions that are typically used to represent emotions include potency/control (refers to the individual's sense of power or control over the eliciting event), expectation (the degree of anticipating or being taken unaware), and intensity (how far a person is away from a state of pure, cool rationality). In yet another embodiment, emotions are represented using a numerical value that represents the intensity of the emotional state with respect to a specific emotion. For example, a numerical value stating how much the user is enthusiastic, interested, and/or happy. Optionally, the numeric value for the emotional state may be derived from a multidimensional space representation of emotion; for instance, by projecting the multidimensional representation of emotion to the nearest point on a line in the multidimensional space.

In one embodiment, the processor is further configured to calculate, based on $IM_{ROI3}$, hemoglobin concentration changes (HCC), and to detect an emotional state of the user based on the HCC. On average, detections of the emotional response based on both $TH_{ROI1}$, $TH_{ROI2}$, and HCC are more accurate than detections of the physiological response based on $TH_{ROI1}$, $TH_{ROI2}$, and $IM_{ROI3}$ without calculating the HCC.

In another embodiment, the processor is further configured to: calculate hemoglobin concentration changes (HCC) based on $IM_{ROI1}$, generate feature values, and utilize a model to calculate an extent of the emotional response based on the feature values. Optionally, at least one of the feature values is generated based on $TH_{ROI1}$ and the HCC. Optionally, the model is generated based on samples, each sample comprising corresponding feature values generated based on corresponding measurements of the user and a label indicative of an extent of the emotional response of the user while the corresponding measurements were taken.

Thermal measurements of the face can be utilized for various applications, which include detection of various health problems. However, when taken in uncontrolled real-life scenarios, thermal measurements can be influenced by various external factors such as contact with the face (e.g., touching it with a finger), air-conditioning, or direct sunlight. Thus, there is a need for systems that utilize thermal measurements collected in real-life scenarios to account for various external factors that may alter the values of the thermal measurements, which affects the thermal measurements utility for various applications.

There are various ways in which heat can be transferred to a Region Of Interest (ROI) on a user's face, which can influence the values of thermal measurements of the ROI. For example, heat can be transferred to the ROI by thermal conduction (e.g., touching the ROI with the finger), thermal convection (e.g., through the surrounding air), and/or thermal radiation (e.g., direct sunlight or thermal radiation from a radiating heater). A thermal sensor located on the face can detect thermal radiation more accurately than a similar thermal sensor, which is located near the user, but not on the face. Therefore, in some embodiments, the system includes at least one outward facing thermal camera that is physically coupled to the frame and directed towards the environment in order to take thermal measurements of the environment ($TH_{ENV}$) from a location on the face. This enables the system to mitigate measurement errors resulting from thermal radiation, such as sunlight or a radiating heater that may heat the face more than other parts of the body, and/or may heat a first facial ROI more than a second facial ROI.

The following is a description of a system that utilizes measurements of an outward-facing thermal camera that measures the environment in order to utilize more accurately measurements of an inward-facing thermal camera pointed at the face to detect a physiological response. In one embodiment, the system includes at least a frame configured to be worn on a user's head, the outward-facing thermal camera, the inward-facing thermal camera, and a processor.

Each of the inward-facing and outward-facing thermal cameras weighs below 5 g, is physically coupled to the frame, and is located less than 15 cm away from the user's face. Optionally, the angle between the optical axes of the inward-facing and outward-facing thermal cameras is at least one of the following angles: 45°, 90°, 130°, 170°, and 180°. Optionally, the inward-facing thermal camera remains pointed at the ROI even when the head makes angular movements that involve an angular velocity above 0.1 rad/sec. Optionally, the inward-facing thermal camera includes at least twice the sensing elements the outward-facing thermal camera includes.

The inward facing thermal camera is configured to take thermal measurements of a region of interest ($TH_{ROI}$) on the face, does not occlude the ROI, and has a first field of view ($FOV_1$). The outward-facing thermal camera is configured to take thermal measurements of the environment ($TH_{ENV}$), and has a second FOV ($FOV_2$) that is larger than $FOV_1$ (i.e., $FOV_2$ may be considered to have a wider angle than $FOV_1$). In one example, $FOV_1<60°$ and $FOV_2>120°$. In another example, $FOV_1<30°$ and $FOV_2>90°$.

In one embodiment, the inward-facing and outward-facing thermal cameras are based on thermal sensors of the same type, which have similar operating parameters. For example, both the inward-facing thermal camera and the outward facing thermal camera may be based on a Texas Instruments TMP006B infrared thermopile sensor, while the FOV of the inward-facing thermal camera is limited to below 30° and the FOV of the outward facing thermal camera may reach up to 180°. Alternatively, the inward facing and outward facing thermal cameras may be based on different types of thermal sensors, which have different operating parameters. For example, the inward-facing thermal camera may be based on a microbolometer FPA and the outward facing thermal camera may be based on a thermopile.

In one embodiment, the accuracy of the inward facing and outward-facing thermal cameras, when providing values of temperature changes, are significantly greater than their accuracy when measuring temperatures. Optionally, the processor is configured to detect the physiological response based on $\Delta T$ determined based on measurements of the inward facing and outward-facing thermal cameras. In one example, the inward facing and outward facing thermal cameras measure temperature with accuracies above $\pm 1.0°$ C. and provide values of temperature change ($\Delta T$) with accuracies below $\pm 0.10°$ C. In another example, the inward facing and outward facing thermal cameras measure temperature with accuracies above $\pm 0.20°$ C. and provide values of temperature changes ($\Delta T$) with accuracies below $\pm 0.050°$ C. The processor is configured to detect the physiological response based on $\Delta T$ measured by the inward facing and outward facing thermal cameras.

Figure 67A:
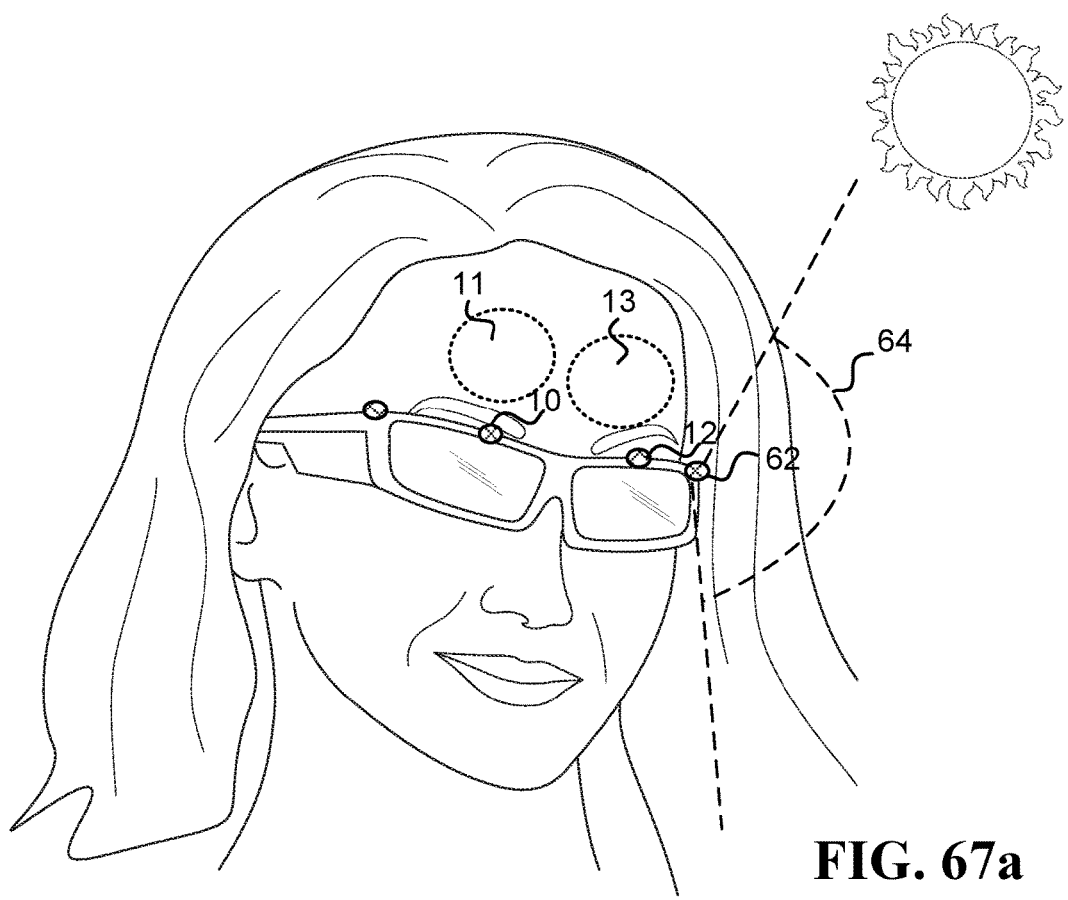
FIG. 67a illustrates one embodiment of the system that includes inward facing cameras and outward-facing cameras on both sides of the head.

FIG. 67a illustrates one embodiment of the system that includes inward facing cameras and outward-facing cameras on both sides of the head. The (inward facing) thermal camera 10 and the second (inward-facing) thermal camera 12 are configured to take measurements of the temperature at the user's forehead (ROI 11 and ROI 13, respectively). In addition to the illustrated inward facing thermal cameras, the system includes first and second outward facing thermal cameras (61 and 62, respectively), which are configured to take thermal measurements of the environment. Arc 64 illustrates the larger FOV of the outward-facing thermal camera 62, compared to the FOV of the inward-facing camera that covers the ROI 13.

Figure 67B:
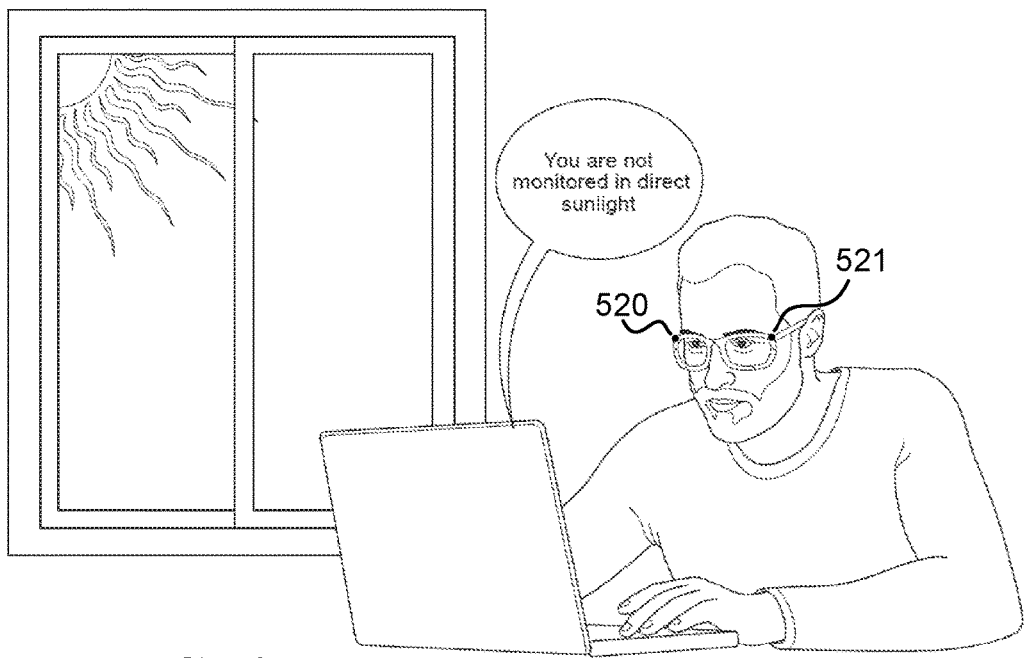
FIG. 67b illustrates receiving an indication on a GUI (laptop) that the user is not monitored in direct sunlight.

FIG. 67b illustrates receiving an indication on a GUI (laptop) that the user is not monitored in direct sunlight. Camera 520 and camera 521 are the outward-facing thermal cameras.

The processor is configured to detect a physiological response based on $TH_{ROI}$ and $TH_{ENV}$. Optionally, $TH_{ENV}$ are utilized to account for at least some of the effect of heat transferred to the ROI from the environment (and not due to the user's physiological activity). Thus, on average, the detections of the physiological response based on $TH_{ROI}$ and $TH_{ENV}$ are more accurate than detections of the physiological response based on $TH_{ROI}$ without $TH_{ENV}$. In one example, the physiological response is indicative of stress felt by the user. In another example, the physiological response is indicative of an allergic reaction of the user. In still another example, the physiological response is indicative of a level of pain felt by the user. And in yet another example, the physiological response is indicative of an occurrence of at least one of the following emotional states of the user: fear, anxiety, guilt, pain, and sexual arousal.

As described in more detail elsewhere in this disclosure, the processor may utilize $TH_{ROI}$ in various ways in order to detect the physiological response. In one example, the processor may be configured to compare one or more values derived from $TH_{ROI}$ to a certain threshold, and determine whether the threshold is reached (which is indicative of an occurrence of the physiological response). In another example, the processor may be configured to determine a similarity between a reference time series corresponding to the physiological response and $TH_{ROI}$ (and/or a time series derived from $TH_{ROI}$). Optionally, when a sufficiently high similarity is detected, the processor may interpret that as an indication of an occurrence of the physiological response. In another example, the processor may generate feature values based on $TH_{ROI}$, and utilize a machine learning-based model to calculate, based on the feature values, a value indicative of whether the physiological response occurred (and/or the extent of the physiological response).

There are various way in which the processor may utilize $TH_{ENV}$ to make the various detection approaches listed above produce more accurate results. Some examples or ways in which $TH_{ENV}$ may be utilized to this end are given below.

In one embodiment, responsive to determining that $TH_{ENV}$ represent an extreme temperature (e.g., lower than 5° C., higher than 35° C., or some other ranges deemed inappropriate), the processor may refrain from performing detection of the physiological response. This way, the processor can avoid making a prediction that is at high risk of being wrong due to the influence of extreme environmental temperatures. In a similar manner, instead of determining that $TH_{ENV}$ represent an extreme temperature, the processor may determine that the difference between $TH_{ROI}$ and $TH_{ENV}$ are not in an acceptable range (e.g., there is a difference of more than 15° C. between the two), and refrain from making a detection of the physiological response in that event.

In another embodiment, the processor may normalize $TH_{ROI}$ based on $TH_{ENV}$. In one example, the normalization may involve subtracting a value proportional to $TH_{ENV}$ from $TH_{ROI}$, such that the value of the temperature at the ROI is adjusted based on the temperature of the environment at that time and/or in temporal proximity to that time (e.g., using an average of the environment temperature during the preceding minute). Additionally or alternatively, the processor may adjust weights associated with at least some $TH_{ROI}$ based on $TH_{ENV}$, such that the weight of measurements from among $TH_{ROI}$ that were taken during times the measurements of the environment indicated extreme environmental temperatures is reduced. Optionally, the weight in such cases is reduced to zero, such that $TH_{ROI}$ taken in times of extreme environmental temperatures are essentially not utilized in the detection of the physiological response. Optionally, times of extreme environmental temperatures are times during which $TH_{ENV}$ are outside of a specific range. Optionally, most of the time the user wears the frame, $TH_{ENV}$ are within the specific range.

In yet another embodiment, the processor may utilize $TH_{ENV}$ for the selection of values that are appropriate for the detection of the physiological response. In one example, the processor may select a threshold to which one or more values derived from $TH_{ROI}$ are compared to determine whether the threshold is reached (which is indicative of an occurrence of the physiological response). In this example, different values of $TH_{ENV}$ may cause the processor to use different thresholds. Optionally, the different thresholds are determined based on $TH_{ROI}$ taken while the user (and/or other users) had the physiological response while in environments in which different $TH_{ENV}$ were measured. In another example, the processor may utilize $TH_{ENV}$ to select an appropriate reference time series to which $TH_{ROI}$ may be compared to detect the physiological response. Optionally, the appropriate reference times series is selected from among multiple reference time series generated from $TH_{ROI}$ taken while the user (and/or other users) had the physiological response while in environments in which different $TH_{ENV}$ were measured. In yet another example, the processor may utilize $TH_{ENV}$ to select an appropriate model to utilize to calculate, based on the feature values generated based on $TH_{ROI}$, a value indicative of whether the physiological response occurred. Optionally, the appropriate model is selected from among multiple models generated from $TH_{ROI}$ taken while the user (and/or other users) had the physiological response while in environments in which different $TH_{ENV}$ were measured. Thus, by being generated based on $TH_{ROI}$ taken in different environmental conditions, each model may be able to account for the effect of the specific environmental conditions to which it corresponds.

In still another embodiment, $TH_{ENV}$ may be utilized to generate at least some feature values that are utilized to calculate a value indicative of the physiological response using a machine learning-based model. Optionally, the model is trained based on data comprising $TH_{ROI}$ and $TH_{ENV}$ collected while the user (and/or other users) had the physiological response while in different environments characterized by different values of $TH_{ENV}$. Thus, the model can account, in its parameters, for various effects that the values of $TH_{ENV}$ may have on $TH_{ROI}$ in order to more accurately detect the physiological response.

In one embodiment, the processor is further configured to learn the effect of $TH_{ENV}$ on $TH_{ROI}$ based on sets comprising the $TH_{ROI}$ and $TH_{ENV}$, taken at first and second occasions, during which the user is estimated to be in the same physiological state. Optionally, during the first occasion $TH_{ENV}$ is below a threshold and thus is not supposed to affect $TH_{ROI}$, and during the second occasion $TH_{ENV}$ is above the threshold and thus is supposed to affect $TH_{ROI}$.

Following is a more detailed discussion of various embodiments in which the processor may utilize $TH_{ENV}$ to detect the physiological response based on $TH_{ROI}$ more accurately.

In one embodiment, the processor is configured to detect the physiological response based on a difference between $TH_{ROI}$ and $TH_{ENV}$. Optionally, detecting the physiological response based on the difference enables the system to operate well in an uncontrolled environment that does not maintain environmental temperature in a range below ±1° C. and does not maintain humidity in a range below ±3%.

In another embodiment, the processor is configured to detect the physiological response as follows: calculate a temperature difference between $TH_{ROI}$ and $TH_{ENV}$ taken at time x ($\Delta T_x$), calculate a temperature difference between $TH_{ROI}$ and $TH_{ENV}$ taken at time y ($\Delta T_y$), and detect the physiological response based on a difference between $\Delta T_x$ and $\Delta T_y$. Optionally, detecting the physiological response is based on the difference between $\Delta T_x$ and $\Delta T_y$ reaching a predetermined threshold. Optionally, the predestined threshold is selected from at least one of the following thresholds: threshold in the time domain, threshold in the frequency domain, an upper threshold where reaching the threshold means equal or above the threshold, and a lower threshold where reaching the threshold means equal or below the threshold. Optionally, the magnitude of the difference between $\Delta T_x$ and $\Delta T_y$ is indicative of an extent of the physiological response.

It is noted that sentences such as "calculate a difference between M and N" are to be interpreted as "calculate a value indicative of a difference between M and N", which means that said calculation covers any function that is proportional to the difference between M and N.

Because the FOV of the outward facing thermal camera is limited, e.g., often it is below 180°, and the responsivity decreases when drawing away from the optical axis, it may be beneficial, in some embodiments, to utilize two or more outward-facing thermal cameras pointed at different angles.

In one embodiment, the system includes a second outward-facing thermal camera, physically coupled to the frame, and configured to take thermal measurements of the environment ($TH_{ENV2}$). Optionally, there is an angle of at least 10° between the optical axes of the outward-facing thermal camera and the second outward facing thermal camera. The processor is further configured to utilize $TH_{ENV2}$ to detect the physiological response. In one example, responsive to receiving a first set of measurements in which $TH_{ROI}$ reach a first threshold while the difference between $TH_{ENV}$ and $TH_{ENV}$ does not reach a second threshold, the processor detects the physiological response. However, responsive to receiving a second set of measurements in which $TH_{ROI}$ reach the first threshold while the difference between $TH_{ENV}$ and $TH_{ENV2}$ reaches the second threshold, the processor does not detect the physiological response. In another example, the processor is configured to detect the physiological response based on a difference between $TH_{ROI}$, $TH_{ENV}$, and $TH_{ENV2}$, while taking into account (i) the angle between the optical axes of the outward-facing thermal camera and the second outward-facing thermal camera, and (ii) the decrease in responsivity that occurs when drawing away from the optical axes of the outward-facing thermal camera and the second outward-facing thermal camera.

The skin in a thermodynamic equilibrium emits radiation in all directions into a hemisphere. This radiation is affected by the skin's emissivity, which depends on the temperature and superficial characteristics such as moisture level, roughness, and fat. Although the skin radiance in the long-wave IR (LWIR) is similar to a Lambertian radiator, the skin reflectance is not completely Lambertian and has a specular behavior. As a result, $TH_{ROI}$ of a non-occluded skin may be affected by mirrored radiation from the environment (i.e. IR radiation reflected from the ROI, which corresponds to the environment instead of the physiological response of interest). In one embodiment, the system utilizes multiple non-coplanar outward-facing thermal cameras, which take thermal measurements of the environment, to improve the accuracy of calculating the physiological response by accounting for the mirrored radiation from an interfering thermal radiating source (ITRS) in the environment.

In one example, the following method is utilized to improve the accuracy of calculating the physiological response: In step 1, calculating the position of an ITRS (such as a heater or the sun) relative to the frame based on (i) the known fixed positions of the outward-facing thermal cameras relative to the frame, and (ii) the differences in thermal measurements of the outward-facing thermal cameras, which result from the different positions of the outward facing thermal cameras relative to the ITRS, while taking into account the known decrease in responsivity as the distance between the optical axes of the outward-facing thermal cameras increases. In step 2, calculating the position of the ITRS relative to the ROI, based on (i) the position of the ITRS relative to the frame, and (ii) the known position of the ROI relative to the frame (optionally using a model of the shape of the specific user, or using a general model for the shape of the user's face). In step 3, calculating the mirrored radiation from the ITRS based on (i) the position of the ITRS relative to the ROI, and (ii) the angle between the ROI and the optical axis of the thermal camera that measures $TH_{ROI}$. In step 4, calculating the amount of radiation from the environment (including the ITRS), which is absorbed by the ROI and then emitted in a Lambertian manner (i.e., according to Lambert's cosine law), based on the thermal measurements of the outward-facing thermal cameras. And in step 5, calculating the physiological response by deducting the emitted and mirrored interfering thermal radiation from the measured $TH_{ROI}$.

In another example, the accuracy of calculating the physiological response is improved based on a lookup table derived from empiric measurements of the effect of an ITRS located in different positions relative to the ROI.

In still another example, the effect of the mirrored interfering thermal radiation can be reduced by modifying the emissivity value of the skin based on the differences in thermal measurements of the outward facing thermal cameras.

Optionally, the outward-facing thermal camera and the second outward facing thermal camera are based on thermal sensors of the same type, having similar operating parameters, and the second outward-facing thermal camera has a third FOV ($FOV_3$), where $FOV_2 \approx FOV_3$.

Detection of some physiological responses and/or medical conditions may be improved when multiple thermal cameras are utilized to take thermal measurements of ROIs on the face. This detection may benefit from additional thermal measurements of the environment. In one embodiment, the system further comprises: (i) a second inward facing thermal camera, physically coupled to the frame, and configured to take thermal measurements of a second ROI ($TH_{ROI2}$) on the face, where $ROI_2$ is to the left of ROI and/or below ROI, and (ii) a second outward-facing thermal camera, configured to take thermal measurements of the environment ($TH_{ENV2}$), physically coupled to the frame such that there is an angle of at least 10° between the optical axes of the outward-facing thermal camera and the second outward-facing thermal camera. Additionally, in this embodiment the processor is further configured to detect the physiological response also based on $TH_{ROI2}$ and $TH_{ENV2}$.

In one example, ROI and $ROI_2$ cover symmetric regions on the face, and a difference between $TH_{ROI}$ and $TH_{ROI2}$ is indicative of an extent of thermal asymmetry on the face; the optical axis of the outward-facing thermal camera is to the right of the optical axis of the second outward facing thermal camera, and a difference between $TH_{ENV}$ and $TH_{ENV2}$ is indicative of the energy received from an interfering thermal radiating source (e.g., a radiating heater or sunlight) and an angular location of the interfering thermal radiating source relative to the outfacing thermal cameras.

In another example, ROI covers an area above $ROI_2$, the optical axis of the outward-facing thermal camera is above the optical axis of the second outward facing thermal camera, and a difference between $TH_{ENV}$ and $TH_{ENV2}$ is indicative of the power received from an interfering thermal radiating source and angular location of the interfering thermal radiating source relative to the outfacing thermal cameras.

The processor may utilize $TH_{ROI}$ and $TH_{ROI2}$ to detect the physiological response in various ways. In one example, the processor is further configured to (i) utilize $TH_{ROI}$ and $TH_{ROI2}$ to detect the physiological response when the difference between $TH_{ROI}$ and $TH_{ROI2}$ reaches a first threshold while the difference between $TH_{ENV}$ and $TH_{ENV2}$ does not reach a second threshold, and (ii) not utilize $TH_{ROI}$ and $TH_{ROI2}$ to detect the physiological response when the difference between $TH_{ROI}$ and $TH_{ROI2}$ reaches the first threshold while the difference between $TH_{ENV}$ and $TH_{ENV2}$ reaches the second threshold. In another example, the processor is further configured to perform at least one of the following calculations: (i) when the difference between $TH_{ENV}$ and $TH_{ENV2}$ reaches a threshold, the processor is configured to normalize $TH_{ROI}$ and $TH_{ROI2}$ differently against thermal interference from the environment, and (ii) when $TH_{ENV}$ does not reach a predetermined threshold for thermal environmental interference while $TH_{ENV2}$ reaches the predetermined threshold, the processor is configured to assign $TH_{ROI}$ a higher weight than $TH_{ROI2}$ for detecting the physiological response.

It is noted that sentences in the form of "difference between X and Y" (e.g., "the difference between $TH_{ROI1}$ and $TH_{ROI2}$", or "the difference between $TH_{ENV}$ and $TH_{ENV2}$") may be interpreted as referring to normalized differences. A normalized difference means that when the compared measurements are received from essentially the same cameras (e.g., cameras using the same type of sensor with the same FOV), then the normalized difference is the difference between the measurements; however, when the compared measurements are received from different cameras (e.g., cameras using different types of sensors with different FOVs), then the normalized difference compensates for the differences between the cameras (e.g., equalize the compared measurements when measuring the same object from the same position with the same conditions.

In some embodiments, $TH_{ENV}$ and $TH_{ENV2}$ may influence the detection of physiological response, such that based on similar values of $TH_{ROI}$ and $TH_{ROI2}$ at different times, the physiological response may or may not be detected based on the values of $TH_{ENV}$ and $TH_{ENV2}$. In one example, responsive to receiving a first set of measurements in which the difference between $TH_{ROI}$ and $TH_{ROI2}$ reaches a first threshold while the difference between $TH_{ENV}$ and $TH_{ENV2}$ does not reach a second threshold, the processor detects the physiological response. However, when a second set of measurements is received, in which the difference between $TH_{ROI}$ and $TH_{ROI2}$ reaches the first threshold but the difference between $TH_{ENV}$ and $TH_{ENV2}$ reaches the second threshold, the processor does not detect the physiological response.

The following is a description of a system in which measurements of a thermal camera pointed at the face are utilized to detect a physiological response. To improve the accuracy of detections of the physiological response, the system utilizes measurements of a sensor, which are indicative of the distance between the thermal camera and the face. In one embodiment, the system includes at least a frame configured to be worn on a user's head, the thermal camera, the sensor, and a processor.

The thermal camera is physically coupled to the frame, is located less than 15 cm away from the user's face, and is configured to take thermal measurements of a region of interest ($TH_{ROI}$) on a user's face. Optionally, the thermal camera weighs less than 5 g. Optionally, the thermal camera remains pointed at the ROI even when the head makes angular movements that involve an angular velocity that is above 0.1 rad/sec.

The sensor is configured to take measurements indicative of distance between the thermal camera and the ROI, while the frame is still worn on the head. The measurements enable detection of changes in the distance that are smaller than 1 cm. Optionally, at least some of the changes are expected to influence $TH_{ROI}$. For example, moving the thermal sensor may change the value of $TH_{ROI}$ due to changing the distance between the sensing elements of the thermal camera and the primary heat source they are measuring (the user's face).

In one embodiment, the sensor comprises at least one of the following components: a visible-light camera configured to take images that are indicative of the distance, and a range finder that provides data indicative of the distance based on transmitting electromagnetic waves and measuring the roundtrip delay from the transmission to receiving the reflections.

In some embodiments, because the thermal camera is physically coupled to the frame, the measurements indicative of distance between the thermal camera and the ROI can be taken from various locations, as long as the sensor is physically coupled to the frame, and the transformation from the pair [location of sensor, location of measured area on the head] to the pair [location of thermal camera, location of ROI] is known. Optionally, the location of the sensor is selected such as to enable the sensor to measure distance to a stationary point on the head, such as the root of the nose, the glabella, the frontal bone, or the tragus. In one example, measuring distance to the stationary point is expected not to cause the sensor to measure a change in the distance greater than a predetermined threshold as a result of the user making normal facial expressions; however, moving the frame relative to the head, such as to increase the distance between the sensor and the stationary point by more than 1 cm, does cause the sensor to measure a change in the distance greater than the predetermined threshold.

The processor is configured to detect a physiological response based on $TH_{ROI}$ and the distance. Optionally, the distance is utilized to account for at least some of the effect of the movement of the thermal camera. Thus, on average, detections of the physiological response based on $TH_{ROI}$ and the distance are more accurate compared to detections of the physiological response based on $TH_{ROI}$ without accounting for the distance, while the frame is still worn on the head. In one example, the physiological response is indicative of stress felt by the user. In another example, the physiological response is indicative of an allergic reaction of the user. In still another example, the physiological response is indicative of a level of pain felt by the user. And in yet another example, the physiological response is indicative of an occurrence of at least one of the following emotional states of the user: fear, anxiety, guilt, pain, and sexual arousal.

Figure 68A:
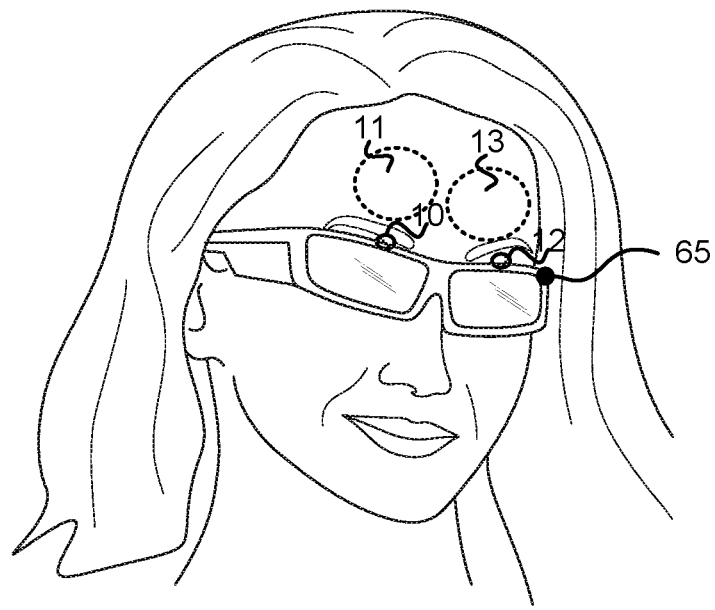
FIG. 68a and FIG. 68b illustrate how movement of a frame can impact thermal measurements of the face taken by a thermal camera coupled to the frame.
Figure 68B:
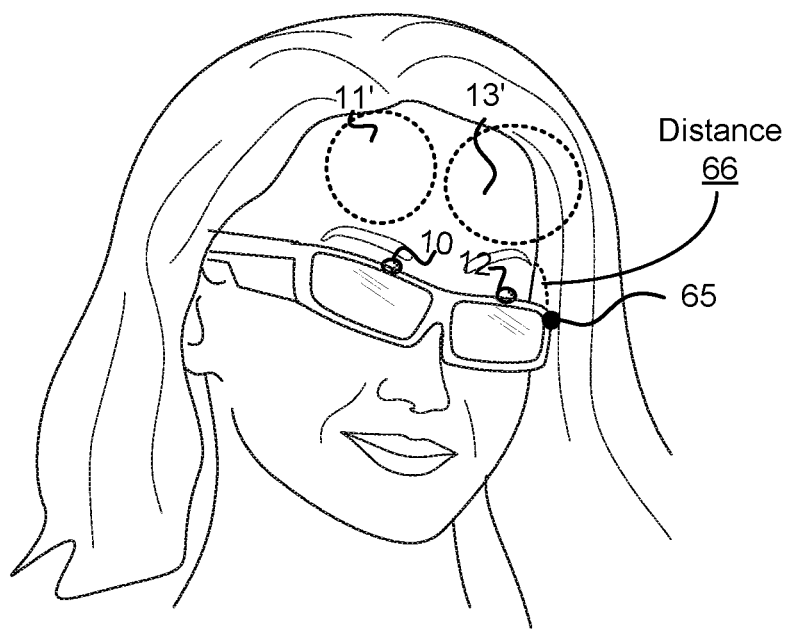

FIG. 68a and FIG. 68b illustrate an embodiment of the system described above. The sensor 65 is coupled to a frame (eyeglasses in this example), and the thermal camera 12 takes measurements $TH_{ROI}$ of ROI 13. In FIG. 68a, the frame is positioned at an appropriate distance from the face. FIG. 68b illustrates how movement of the frame causes a distance 66 to emerge between the frame and the face, which is detected by the sensor 65 that may be, for example, a visible-light camera or a range finder. Responsive to detecting the distance 66, the processor may take various actions (e.g., refrain from detecting the physiological response or take other steps described below). FIG. 68b also demonstrates how movement of the glasses may influence $TH_{ROI}$, since before the thermal cameras 10 and 12 measured at ROIs 11 and 13, respectively, and after the movement (which caused a change in the location and orientation of the thermal cameras relative to the face), they measure regions 11' and 13' on the face, which are not identical to ROIs 11 and 13.

As described in more detail elsewhere in this disclosure, the processor may utilize $TH_{ROI}$ in various ways in order to detect the physiological response. In one example, the processor may be configured to compare one or more values derived from $TH_{ROI}$ to a certain threshold, and determine whether the threshold is reached (which is indicative of an occurrence of the physiological response). In another example, the processor may be configured to determine a similarity between a reference time series corresponding to the physiological response and $TH_{ROI}$ (or a time series derived from $TH_{ROI}$). Optionally, when a sufficiently high similarity is detected, the processor may interpret that as an indication of an occurrence of the physiological response. In another example, the processor may generate feature values based on $TH_{ROI}$, and utilize a machine learning-based model to calculate, based on the feature values, a value indicative of whether the physiological response occurred (and/or the extent of the physiological response).

There are various way in which the processor may utilize the distance (and/or indications of changes to the distance) to make the various detection approaches listed above produce more accurate results. Some examples or ways in which the distance may be utilized to this end are given below.

In one embodiment, responsive to determining that the distance falls within an inappropriate range, which places the thermal camera too close to the ROI or too far from the ROI, the processor may refrain from performing detection of the physiological response. This way, the processor can avoid making a prediction that is at high risk of being wrong due to the influence of the irregular distance on $TH_{ROI}$. In one example, the processor is configured to: (i) utilize $TH_{ROI}$, taken at times in which the measurements of the sensor do not indicate a change in the distance above a predetermined threshold, to detect the physiological response, and (ii) not utilize $TH_{ROI}$, taken at times in which the measurements indicate a change in the distance above the predetermined threshold, to detect the physiological response. Optionally, the threshold in this example conforms to at least one of the following distance changes: 1-2 cm, 0.5-1 cm, and 0.2-0.5 cm. Optionally, the processor refrains from detecting the physiological response based on $TH_{ROI}$ obtained when the system experiences movement that is angular movement above a certain threshold. For example, the processor may be configured to utilize $TH_{ROI}$ taken while the angular movement was below 0.2 rad/sec, and not utilize $TH_{ROI}$ taken while the angular movement was above 2 rad/sec.

In another embodiment, the processor may normalize $TH_{ROI}$ based on the distance. In one example, the normalization may involve subtracting (or adding) a value proportional to the distance from $TH_{ROI}$, such that the value of the temperature at the ROI is adjusted based on the distance. In another example, the normalization may involve a non-linear adjustment to $TH_{ROI}$. Optionally, parameters used to perform the normalization are determined based on controlled calibration experiments in which $TH_{ROI}$ are measured when placing the thermal camera at different distances from the ROI. Additionally or alternatively, the processor may weight at least some $TH_{ROI}$ based on the distance, such that the weight of measurements from among $TH_{ROI}$ that were taken during times the distance was outside of an accepted range is reduced. Optionally, the weight in such cases is reduced to zero, such that $TH_{ROI}$ taken in times in which the distance is not in the specific range are essentially not utilized in the detection of the physiological response. Optionally, most of the time the user wears the frame, the distance is within the specific range.

In yet another embodiment, the processor may utilize the distance to select appropriate values to use in the detection of the physiological response. In one example, the processor may select a threshold to which one or more values derived from $TH_{ROI}$ are compared to determine whether the threshold is reached (which is indicative of an occurrence of the physiological response). In this example, different values of the distance may cause the processor to use different thresholds. Optionally, the different thresholds are determined based on multiple instances of $TH_{ROI}$ taken with the thermal camera being at different distances from the ROI in the multiple instances. In another example, the processor may utilize the distance to select an appropriate reference time series to which $TH_{ROI}$ may be compared to detect the physiological response. Optionally, the appropriate reference time series is selected from among multiple reference time series generated from $TH_{ROI}$ taken with the thermal camera at different distances from the ROI. In yet another example, the processor may utilize the distance to select an appropriate model to utilize to calculate, based on the feature values generated based on $TH_{ROI}$, a value indicative of whether the physiological response occurred. Optionally, the appropriate model is selected from among multiple models generated based on multiple instances of $TH_{ROI}$ taken with the thermal camera being at different distances from the ROI in the multiple instances.

In still another embodiment, the distance may be utilized to generate at least some feature values that are utilized to calculate a value indicative of the physiological response using a machine learning-based model. Optionally, the model is trained based on data comprising $TH_{ROI}$ collected while the thermal camera was at different distances from the ROI. Thus, the model can account, in its parameters, for various effects that the distance may have on $TH_{RO}$ in order to more accurately detect the physiological response.

Utilization of the distance by the processor can cause different behavior with respect to detection of the physiological response by the processor, even when given similar $TH_{ROI}$ as input. In one example, responsive to receiving a first set of measurements in which the change in the distance does not reach a first threshold and a change in $TH_{ROI}$ reaches a second threshold, the processor detects the physiological response. However, responsive to receiving a second set of measurements in which the change in the distance reaches the first threshold and a change in $TH_{ROI}$ reaches the second threshold, the processor does not detect the physiological response.

The following is additional discussion regarding how the distance between the thermal camera and the ROI may be determined. In one embodiment, in order to identify the change in the distance, the system includes a distance module configured to identify changes in the distance between the system (e.g., represented by the frame and/or the thermal camera) and the face. Optionally, the sensor is part of the distance module. Alternatively, the distance module may be an additional component that does not include the sensor.

Examples of possible configurations for the distance module include: (i) An inward-facing camera coupled to the frame. The camera may capture the face or any other part of the skull. The camera produces a video stream that is fed to a video analyzer configured to estimate the distance between the camera and the face and/or to identify a relative movement between the camera and the face. Optionally, the video analyzer utilizes correlation between the images in order to estimate the distance. (ii) A transducer of electromagnetic waves and/or a transducer of sound waves (e.g., ultrasound) that estimates the distance based on reflections of the waves it transmits. (iii) A mechanical probe that touches the face and identifies a change in the distance based on deformation of or pressure on the mechanical probe. (iv) A touch sensor configured to touch the face while the frame is properly mounted on the face, and not touch the face while the frame is not properly mounted on the face.

In one embodiment, the distance module points at an area on the head that usually does not move relative to the frame, such as the forehead, the ears, and short hair on the scalp. In another embodiment, the distance module points at an area on the face that is expected to move from time to time in relation to the frame (referred to as expected movements of the area). Examples of areas that are expected to move when the system is still properly mounted on the face include: the nose, the mouth, a brow, and/or a cheek. In this case, the expected movements of the area may be taken into account in order to differentiate between the following movements: (a) a measured movement of the area that does not cause a significant movement between the HMS and the face, and (b) a measured movement of the area that does cause a significant movement between the HMS and the face 1—Thermal Cameras and Thermal Measurements "Thermal camera" refers herein to a non-contact device, which means that in a nominal operating condition there should be a space of at least 1 millimeter (mm) between the thermal camera (including its optional optics) and the user's skin. The thermal camera does not touch its Region Of Interest (ROI) directly in a manner similar to a thermistor that requires physical contact with the ROI. The thermal camera utilizes a thermal sensor designed to measure electromagnetic radiation having wavelengths longer than 2500 nanometer (nm). Although the thermal camera may also measure electromagnetic radiation in wavelengths shorter than 2500 nm, a camera that measures near-IR (such as electromagnetic radiation with wavelengths of 700-1200 nm), and is not typically considered useful for measuring electromagnetic radiation with wavelengths longer than 2500 nm, is referred to herein as a near-IR camera and is not considered herein a thermal camera.

Various thermal cameras mentioned in this disclosure may include one or more sensing elements (that are also referred to herein as "sensing pixels" or simply "pixels"). Texas Instruments' TMP006B Infrared Thermopile Sensor is an example of a thermal camera that includes just one thermopile sensing element. Some thermal cameras with multiple sensing pixels may be referred to as a focal-plane array (FPA) thermal cameras. An FPA thermal camera refers to a sensor that includes multiple non-contact temperature sensing elements. The Melexis MLX90621 16×4 thermopile array is an example of a thermal camera with multiple sensing elements, it is a thermopile based focal-plane array (FPA) that may be utilized by some of the disclosed embodiments, optionally with suitable optics. Another example of a thermal camera with multiple sensing elements is FUR Lepton® long-wave infrared camera module with an 80,450 microbolometer sensor array, which weighs 0.55 g, and may be utilized by some of the disclosed embodiments optionally with suitable optics.

In some embodiments, the thermal camera is based on an uncooled thermal sensor, such as a thermopile, a microbolometer sensor, a pyroelectric sensor, or a ferroelectric sensor. It is noted that the term microbolometer refers to any type of bolometer sensors and their equivalents. An uncooled thermal sensor refers herein to a sensor useful for measuring electromagnetic radiation with wavelengths longer than 2500 nm, which (i) operates at ambient temperature, or (ii) is stabilized at a temperature that is no more than ±20° C. from the ambient temperature. Additionally or alternatively, one or more of the thermal cameras utilized herein may be based on a cooled thermal sensor.

Examples of thermopile sensors that may be useful for at least some of the embodiments herein, optionally with some adaptations, include Texas Instruments TMP006B Infrared Thermopile Sensor, Melexis MLX90614 Infra-Red Thermometer, HL-Planartechnik GmbH TS118-3 thermopile sensor, Dexter Research Center, Inc. DX-0875 detector, and/or Dexter Research Center, Inc. Temperature Sensor Module (TSM) with ST60 thermopile and onboard ASIC for amplification, digitizing, temperature compensation and calibration. When it is assumed that the sensor keeps measuring the same area on an object, these examples of thermopile sensors can provide readings of ΔT (the change to the temperature), where often the measurement error of ΔT is much smaller than the measurement error of T (the temperature). Therefore, maintaining the thermal camera pointed at an ROI when the user's head makes angular movements enables at least some of the embodiments to utilize the more accurate ΔT measurements to identify physiological responses that may not be identified based on image processing of temperature measurements (T) received from a camera that is not continuously pointed at the ROI (assuming sensors with same characteristics are used in both scenarios). It is noted that each of the above-mentioned thermal cameras weighs below 1 g.

In some embodiments, a thermal camera may operate at a frequency that may be considered relatively low. For example, one or more of the thermal cameras in one or more of the disclosed embodiments may be based on a thermopile sensor configured to provide temperature measurements at a rate below at least one of the following rates: 15 Hz, 10 Hz, 5 Hz, and 1 Hz.

In some embodiments, the field of view of a thermal camera is limited by a field limiter. For example, the thermal camera may be based on a Texas Instruments TMP006B IR thermopile utilizing a field limiter made of thin polished metal, or based on Melexis MLX90614 IR thermometers in a TO-39 package.

Herein, a direction of the optical axis of a camera having focusing optics is usually determined by the focusing optics, while the direction of the optical axis of a camera without focusing optics (such as a single pixel thermopile) is usually determined by the angle of maximum responsivity of its sensor, which is usually perpendicular to the sensor.

When optics are utilized to take measurements with a thermal camera, then the term "thermal camera" may optionally include the optics (e.g., one or more lenses). In some embodiments, the optics of a thermal camera may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the optics may include one or more diffractive optical elements, and/or or a combination of one or more diffractive optical elements and one or more refractive optical elements.

When an optical limiter that limits the angle of view is utilized to take measurements with a thermal camera (such as in a pinhole camera, or a thermopile sensor inside a standard TO-5, TO-18, or TO-39 package with a window, or a thermopile sensor with a polished metal field limiter), then the term "thermal camera" may also refer to the optical limiter. "Optical limiter" may also be referred to herein as a "field limited" or "field of view limiter". Optionally, the field limiter may be made of a material with low emissivity and small thermal mass, such as Nickel-Silver and/or Aluminum foil. The term "thermal camera" may also refer to a readout circuit adjacent to the thermal sensor, and/or the housing that holds the thermal sensor.

It is noted that the elliptic and other shapes of the ROIs in some of the drawings are just for illustration purposes, and the actual shapes of the ROIs are usually not as illustrate. It is possible to calculate the accurate shape of an ROI using various methods, such as a computerized simulation using a 3D model of the face and a model of an HMS to which a thermal camera is coupled, or by placing a LED instead of the sensor (while maintaining the same field of view) and observing the illumination pattern on the face. Furthermore, unless indicated to the contrary, the cameras may include one or more sensing elements (pixels); when a camera includes multiple sensing elements then the illustrated ROI usually refers to the total ROI captured by the camera, which is made of multiple regions that are respectively captured by the different sensing elements.

Some embodiments described herein include a thermal camera that measures temperature changes. For example, the thermal camera may be a pyroelectric sensor. Examples of pyroelectric sensors that may be useful for at least some of the embodiments, optionally with some adaptations, include: (i) Excelitas Technologies analog pyroelectric non-contact sensor series, having one, two, four, or more elements; (ii) Excelitas Technologies DigiPyro® digital pyroelectric non-contact sensor series, having two, four, or more elements; and (iii) Murata Manufacturing Co., Ltd. dual type pyroelectric infrared sensor series, or Parallel Quad Type Pyroelectric Infrared Sensor Series.

In some embodiments, some of the various cameras described herein may be coated with a water-repellant (hydrophobic) coating and/or an oil-repellant (oleophobic) coating, and are therefore less susceptible to be smudged due to secretions from the skin, such as oils and other substances, and particles from the environment. Examples of such coatings include nanotechnology hydrophobic coatings, nanotechnology superhydrophobic coatings, and/or nanotechnology oleophobic coatings. In addition, some of the various cameras described herein may be treated to have antistatic properties. For example, antistatic agents for plastic lenses may have among the molecules composing them both hydrophobic and hydrophilic radicals, where the hydrophobic radicals turn to the plastic, while the hydrophilic radicals turn to the air attracting the moisture in the atmosphere. The antistatic agents may be internal antistatic agents designed to be mixed directly into the material of a component of a camera, or external antistatic agents applied to the surface of a component of the camera.

The term "thermal measurements of the ROI" (usually denoted $TH_{ROI}$ or some variant thereof) refers to at least one of: (i) temperature measurements of the ROI, and (ii) temperature change measurements of the ROI. "Temperature measurements of the ROI" (usually denoted $T_{ROI}$) can be taken, for example, with a thermopile sensor or a microbolometer sensor, which measure the temperature at the ROI. "Temperature change measurements of the ROI" (usually denoted $\Delta T_{ROI}$) can be taken, for example, with a pyroelectric sensor that measures the temperature change at the ROI, or derived from temperature measurements taken at different times by a thermopile sensor or a microbolometer sensor.

Terms such as "change in $TH_{ROI}$" denote change to temperature of the ROI. It is noted that "change in $TH_{ROI}$" still denotes a change to temperature of the ROI when $TH_{ROI}$ denotes a temperature change.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence such as "calculating based on $TH_{ROI}$" may be interpreted as "calculating based on the values of $TH_{ROI}$", and a sentence such as "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (denoted $TH_{ROI}$ or using some similar notation) may include various types of data. In some embodiments, the thermal measurements comprise data that may be characterized as time series data, which may include temperatures at the ROI (or changes to the temperature at the ROI) at different points in time. Depending on the type of thermal camera and application, the sampling frequency may vary from multiple times a second, to taking measurements every few seconds (or at an even lower frequency), or may be performed at irregular intervals. In some embodiments, thermal measurements may include various statistics of the temperature measurements (or change to temperature measurements), such as minimum, maximum, and/or average values. Thermal measurements may be raw and/or processed values, as described in more detail below. When a thermal camera has multiple pixels, the thermal measurements may include values corresponding to each of the pixels, and/or include values representing processing of the values of the pixels, as discussed further below.

In some embodiments, the thermal measurements may be normalized in one or more ways. In one example, the thermal measurements are normalized with respect to a baseline (e.g., based on typical measurement values from when the physiological response in question is not experienced). In another example, the normalization may account for effects that correspond to the time of day (e.g., in order to account for the circadian rhythm), the day in the month (to account of a lunar rhythm), the type of activity being conducted by the user (e.g., resting, working, exercising), and/or various environmental parameters (e.g., the environment's temperature, humidity, radiation level, etc.)

Since ROIs measured by thermal cameras mounted to a frame worn on the head are typically in direct contact with the environment, the environmental temperature has a direct and often profound influence on the temperature measurements at the ROIs. Therefore, in some embodiments, thermal measurements may be normalized with respect to the temperature measured in the environment at the time. For example, a temperature t that is measured at a certain ROI, while the in the environment was $t_{env}$ may be corrected according to a function $t'=f(t, t_{env})$. In one example, the formula may be a linear correction of the form $t'=t+a \cdot t_{env}+b$ where a and b are certain constants. It is to be noted that since different ROIs are typically more susceptible than others to environmental temperatures, the function used to adjust the measured temperatures may be different for different ROIs. For example, often, a change to the temperature of nose due to the environment is greater than the change to the temperature forehead.

In some embodiments, a device, such as a thermal camera, may be positioned such that it occludes an ROI (e.g., an area on a user's face), while in other embodiments, the device may be positioned such that it does not occlude the ROI. Herein, sentences of the form of "the system/camera does not occlude the ROI" indicate that more than 90% of the ROI can be observed by a third person standing near the user and looking at the ROI from a point of view that is essentially perpendicular to the ROI. Sentences in the form of "the system/camera occludes the ROI" indicate that more than 50% of the ROI cannot be observed by that third person.

Although the disclosed embodiments can use occluding thermal cameras successfully, in certain scenarios, such as using an HMS on a daily basis and/or in a normal day-to-day setting, utilization of thermal cameras that do not occlude their ROIs on the face may have several advantages. These advantages may be related to esthetics, such as offering a less obstructed view of the face and improved comfort and usability. For example, non-occluding thermal cameras offer better ventilation of the face than thermal cameras that are in close proximity to the face and occlude the ROI. In another example, utilizing non-occluding thermal cameras reduces the weight of the HMS compared to utilizing mechanical structures for bringing the occluding thermal cameras in front of the ROI. Often, an HMS with non-occluding thermal cameras is simpler to wear than an HMS with occluding thermal cameras because of its smaller physical dimensions and/or its lack of additional elements that may require placing or adjusting. Another possible advantage of utilizing non-occluding thermal cameras is that they may be placed farther away from the skin compared to occluding thermal cameras, and therefore are less susceptible to be tarnished due to secretions from the skin, such as oils and other substances, especially when measuring regions of the nose and the mouth.

Some embodiments may involve visible-light cameras. Herein, a "Visible-light camera" refers to a camera designed to detect at least some of the visible spectrum. Examples of visible-light sensors include active pixel sensors in complementary metal-oxide-semiconductor (CMOS), and semiconductor charge-coupled devices (CCD).

Many of the thermal cameras and/or visible-light cameras utilized in embodiments described herein are lightweight cameras, weighing less than 5 g and even less than 1 g each.

2—Hardware Components

Various embodiments described herein involve a Head-Mounted System (HMS) that includes a frame that is worn by a user. Herein, sentences of the form "a frame configured to be worn on a user's head" refer to a mechanical structure that loads more than 50% of its weight on the user's head. For example, the frames in Oculus Rift and HTC Vive include the foam placed on the user's face and the straps; the frame in Microsoft HoloLens includes the adjustment wheel in the headband placed on the user's head. In another example, the frame may be similar to an eyeglasses frame, which holds prescription and/or UV-protective lenses. A frame similar to an eyeglasses frame may have extending side arms (i.e., eyeglasses temples) that extend behind the ears to secure the HMS. In embodiments, a frame may secure the HMS to the user by extending around a rear portion of the user's head. Additionally or alternatively, the frame may connect to, be affixed within, or integrated with, a helmet (e.g., sports, motorcycle, bicycle, and/or combat helmets) and/or a brainwave-measuring headset.

Some embodiments may include a helmet that is coupled to the frame (or the helmet may form the frame itself), where the helmet is configured to protect a user's scalp and/or other regions of the head (e.g., the temples). Optionally, the helmet may be at least one of the following: a sports helmet, a motorcycle helmet, a bicycle helmet, and a combat helmet. Phrases of the form of "a helmet coupled to the frame" are to be interpreted in the context of one or more of the following configurations: (i) a frame that is worn and/or taken off together with the helmet such that when the user wears/takes off the helmet he/she also wears/takes off the HMS, (ii) a frame integrated with the helmet and/or the helmet itself forms the frame; optionally the HMS is sold together with the helmet, and/or (iii) the HMS and the helmet share at least one electronic element, such as an inertial measurement sensor, a circuit, a processor, a memory, a battery, an image sensor, and/or a communication unit for communicating with a computer that is not head-mounted.

Other embodiments may include a brainwave-measuring headset that is coupled to the frame and is configured to collect brainwave signals of the user. Phrases in the form of "a brainwave-measuring headset coupled to the frame" are to be interpreted in the context of one or more of the following configurations: (i) a frame that is worn and/or taken off together with the brainwave-measuring headset such that when the user wears/takes off the brainwave-measuring headset he/she also wears/takes off the HMS, (ii) a frame integrated with the brainwave-measuring headset and/or the brainwave-measuring headset itself forms the frame; optionally the HMS is sold together with the brainwave-measuring headset, and/or (iii) the HMS and the brainwave-measuring headset share at least one electronic element, such as an inertial measurement sensor, a circuit, a processor, a memory, a battery, and/or a communication unit.

In some embodiments, an HMS worn on a user's head is connected, via a wire and/or wirelessly, with a device carried by the user. For example, the HMS may be connected to a device carried by the user (e.g., in a pocket of the user's clothes or in a backpack carried by the user) and/or a device embedded in the user's clothing (e.g., the HMS may be connected to "smart" clothes). In one example, the device may include batteries and/or provide components of the HMS with power (e.g., via a power cord and/or wireless transmission of power). In another example, the device may include a processor that is used to process thermal measurements and/or other data, e.g., in order to detect whether the user has a certain physiological response. In yet another example, the device may include a transmitter that is configured to transmit data collected by components of the HMS (e.g., thermal measurements collected utilizing thermal cameras). And in still another example, the device may include a receiver that is configured to receive data provided to the HMS (e.g., data that is to be presented to the user via a display coupled to the HMS).

Unless otherwise indicated, as a result of the thermal camera being physically coupled to the frame, the thermal camera remains pointed at the ROI when the user's head makes angular movements. Sentences such as "the thermal camera is physically coupled to the frame" refer to both direct physical coupling to the frame, which means that the thermal camera is fixed to (or integrated into) the frame, and indirect physical coupling to the frame, which means that the thermal camera is fixed to (or integrated into) an element that is physically coupled to the frame. In both embodiments (direct and indirect physical coupling), the thermal camera remains pointed at the ROI when the user's head makes angular movements. In some examples, the rate of angular movement referred to in sentences such as "when the head makes angular movements" is above 0.02 rad/sec, 0.1 rad/sec, 0.5 rad/sec, or above 1 rad/sec. In some embodiments, the thermal camera is physically coupled to the frame in a fixed position. Alternatively, the system may be able to control, to some extent, the spatial position of a camera relative to the frame using a small motor, such as a step motor or a piezoelectric motor.

In various embodiments, thermal cameras are located close to a user's face, such as at most 2 cm, 5 cm, 10 cm, 15 cm, or 20 cm from the face. The distance from the face in sentences such as "a thermal camera that is located less than 15 cm away from the face" refers to the shortest possible distance between the thermal camera and the face. For example, the shortest distance between sensor 10 and the face in FIG. 1a is from sensor 10 to the lower part of the right eyebrow, and not from sensor 10 to ROI 11.

This disclosure includes various figures that illustrate exemplary embodiments of various systems that include thermal cameras and/or visible-light cameras. It is to be noted that positions of the cameras in the figures are just for illustration, and the cameras may be placed at other positions on the HMS. Moreover, one or more of the cameras may be configured to capture images at various resolutions and/or at different frame rates. Multiple visible-light cameras with a small form-factor, such as cameras used in cell phones, may be incorporated into some of the embodiments. Furthermore, illustrations and discussions of a camera represent one or more cameras, where each camera may be configured to capture the same field of view (FOV), and/or to capture different FOVs (i.e., the cameras may have essentially the same or different FOVs). Additionally, each illustrated camera may include one or more sensing elements (even if multiple sensing elements do not explicitly appear in the illustration).

In one embodiment, because facial structures may differ from user to user, the HMS may support calibrating the direction, position, algorithms, and/or characteristics of one or more of the cameras and/or light sources based on the facial structure of the user. In one example, a portion of the HMS is manufactured to suit a certain feature on the face of a certain user, in order to position a thermal camera properly for the certain user. In another example, the HMS includes a motor configured to change the positioning of a camera relative to the frame in order to adapt itself to a certain facial structure. In yet another example, the HMS includes a non-motorized mechanical device (e.g., latches, straps, or levers) that enable a manual change of the positioning of a camera relative to the frame in order to adapt itself to a certain facial structure.

Processors utilized in embodiments described herein may include one or more of the various types of processors mentioned in this disclosure, such as an electronic circuit, a differential amplifier, an analog device, a digital processor, an ASIC, or an FPGA. Some examples of processors include the processor 401 and the processor 411, which are illustrated in FIG. 72a and FIG. 72b, respectively.

In some embodiments, the processor may be physically coupled to the frame and/or to an HMS of which the frame is a part, such as the computer 16 described in FIG. 1a. In other embodiments, the processor may belong to a device carried by the user (e.g., a processor of a smartwatch or a smartphone). In still other embodiments, the processor may be remote from the user, such as a processor in a server accessed via a communication network, and/or a processor in a cloud computer accessed via the Internet. Optionally, the processor is configured to receive values comprising thermal measurements and possibly values obtained utilizing other sensors coupled to the HMS, and to use the values in order to detect a physiological response of the user. It is to be noted that the use of the singular form "processor" or "computer" in this disclosure is not intended to be limiting to the case of a single processor/computer, but should be interpreted as "one or more" processors/computers, which may perform different aspects of the functionality attributed to the processor in the description. Thus, for example, when it is stated that a computer is configured to detect a physiological response, more than one computer may participate in calculations involved in the detection of the physiological response.

Some embodiments described herein involve forwarding thermal measurements to a processor in order to perform calculations, such as calculations used to detect whether a user had a physiological response. Optionally, these embodiments may involve additional elements such as memory configured to store the thermal measurements (and possibly other data) and/or a transmitter that is used to transmit the thermal measurements (and possibly other data) to the processor. In one example, the memory may include one or more of the following memory components: CPU cache, main memory, read-only memory (ROM), dynamic random access memory (DRAM) such as synchronous DRAM (SDRAM), flash memory, static random access memory (SRAM), and/or a data storage device. Optionally, the transmitter may be configured to transmit data via a wired connection and/or be configured to transmit data wirelessly such as via Bluetooth, ZigBee, Wi-Fi, and/or a cellular phone network.

Thermal measurements that are forwarded to a processor/computer may include "raw" values that are essentially the same as the values measured by thermal cameras, and/or processed values that are the result of applying some form of preprocessing and/or analysis to the raw values. There are various methods that may be used to process the raw values, such as analog signal processing, digital signal processing, and various forms of normalization, noise cancellation, and/or feature extraction. In one example, processing of thermal measurements may include harmonic analysis, such as a Fast Fourier Transform, to the temperature signal and/or temperature change signal of each pixel, or pixel clusters, over time in a sliding window, which may be followed by a non-linear filter. In cases where some pixels may be less informative than others, a clustering procedure may be implemented to remove the outliers. Then the frequency peaks in the set of pixels of interest may be used to vote for the dominant frequency component, and the bin with the most votes is selected as the dominant frequency. In this example, estimation of a physiological response based on thermal measurements may involve a calculation that utilizes the median filtered results of the dominant frequency components in a small sliding window.

In some embodiments, after receiving thermal measurements, the processor performs some forms of the above-mentioned processing on the thermal measurements in order to obtain processed values on which it performs its calculations (e.g., detection of a physiological response).

Systems described herein that include one or more thermal cameras coupled to a frame may also include one or more batteries to power the one or more thermal cameras and/or other system components (e.g., a processor, various types of sensors, and/or a display). Additionally or alternatively, such systems may include one or more wireless power receivers configured to power the thermal cameras and/or other system components via inductive charging. Additionally or alternatively, some systems may be powered via a wired connection. For example, an HMS may be connected via one or more wires that conduct electricity to a power source embedded in clothing worn by the user or in a device carried by the user.

Various systems described in this disclosure may include a display that is coupled to a frame worn on the user's head, e.g., a frame of an HMS. The display may be any device that provides a user with visual images (e.g., text, pictures, and/or video). The images provided by the display may be two-dimensional or three-dimensional images. Some examples of display technologies that may be used in embodiments described in this disclosure include: liquid-crystal display (LCD), organic light-emitting diode (OLED), virtual retinal display (VRD), light-field based display, and bionic contact lens. In some embodiments, the display coupled to the frame is configured to present digital content, which includes any type of content that can be stored in a computer and presented by the computer to a user. Phrases of the form "a display coupled to the frame" are to be interpreted in the context of one or more of the following configurations: (i) a display that is worn and/or taken off together with the frame, such that when the user wears/takes off the HMS he/she also wears/takes off the display, (ii) a display integrated with the frame; optionally the display is sold together with the HMS, and/or (iii) the HMS and the display share at least one head-mounted electronic element, such as a circuit, a processor, a memory, a battery, an optical element, and/or a communication unit for communicating with a computer that is not head-mounted. Examples of commercial head-mounted displays that can be adapted to use one or more of the disclosed embodiments include Microsoft HoloLens, Oculus rift, HTC Vive, Sony Play Station VR, Samsung GearVR (with a connected smartphone), and Magic Leap mixed reality.

Systems described herein, which include one or more thermal cameras coupled to a frame, may also include other types of sensing devices for measuring the user and/or the environment, such as a gyroscope, an accelerometer, a visible-light camera, and/or a proximity sensor.

3—Face Terminology

Various embodiments described herein involve taking thermal measurements of one or more Regions of Interest (ROIs) on a user's face. The following is a discussion regarding facial anatomy and nomenclature that may be used to define the various facial regions covered by the one or more ROIs and/or locations of thermal cameras, in embodiments described herein.

Figure 70:
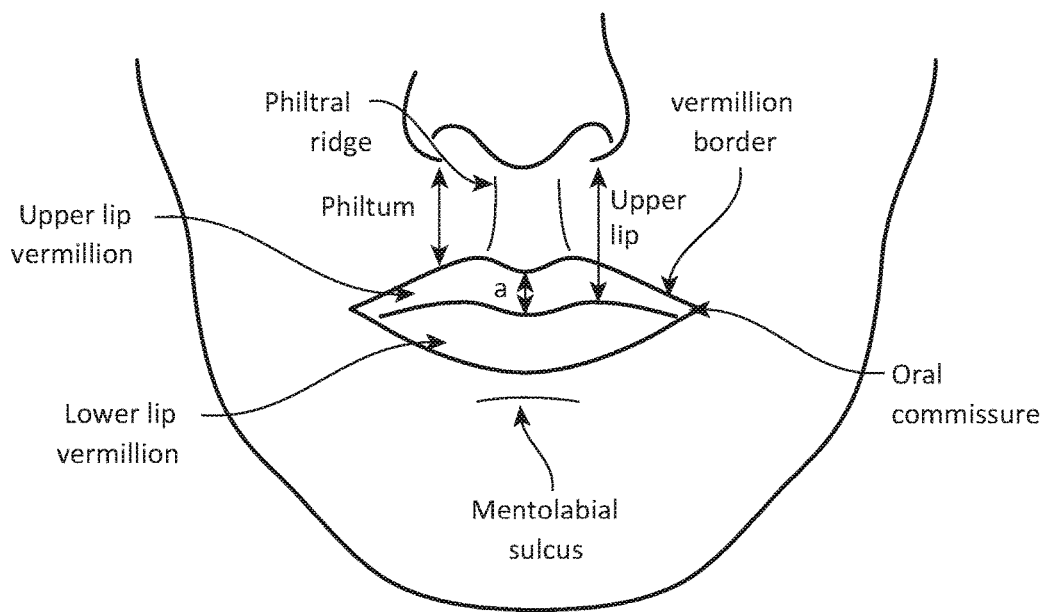

FIG. 69 illustrates the Frankfort horizontal plane and anterior facial plane as these terms are used herein. A line from the superior aspect of the external auditory canal to the most inferior point of the orbital rim creates the Frankfort horizontal plane (known also as the Frankfurt horizontal plane or Frankfort plane). A line from the glabella to the pogonion creates the anterior facial plane. FIG. 70 illustrates the upper lip, upper lip vermillion, lower lip vermillion, and the oral commissure, which is the place where the lateral aspects of the vermilion of the upper and lower lips join. FIG. 71 illustrates the horizontal facial thirds. The upper horizontal facial third extends from the hairline to the glabella, the middle horizontal facial third extends from the glabella to the subnasale, and the lower horizontal facial third extends from the subnasale to the menton. The lower horizontal facial third is further divided into thirds: the lower-upper horizontal facial third extends from the subnasale to the stomion (which defines the upper lip), the lower-middle horizontal facial third extends from the stomion to the labiomental crease (which defines the lower lip), and the lower-lower horizontal facial third extends from the labiomental crease to the menton (which defines the chin). It is noted that the thirds are usually not equal. Vertical symmetry axis 444 divides the face to the right and left sides.

It is noted that all measurements, notations, planes, angles, distances, horizontal facial thirds, and/or elements of the user's face (such as eyes, nose, lips, eyebrows, hairline) herein refer to a normal, 20 year old, aesthetic human, such as described in Chapter 2, Facial Proportions, by Peter M. Prendergast, in the book "Advanced Surgical Facial Rejuvenation, Art and Clinical Practice", Editors: Erian, Anthony, Shiffman, Melvin A., Publisher: Springer-Verlag Berlin Heidelberg, 2012. It is further noted that the appearance of the face varies with facial movement, thus, when appropriate according to the context, the positions of the elements of the user's face (such as eyes, nose, lips, eyebrows, hairline), and the distances between various cameras/sensors and the user's face, are usually assessed herein when the user has a relaxed (neutral) face: the eyes are open, the lips make gentle contact, and the teeth are slightly separated. The neck, jaw, and facial muscles are not stretched nor contracted, and the face is positioned using the Frankfort horizontal plane.

In some embodiments, an ROI may include the area around a user's nose. Herein, sentences such as "the area around the user's nose" may refer to the area of the nose and up to 3 cm from the nose, where the exact area depends on the application and the physiological response to be measured. One example of the ROI around the user's nose includes the area around the nostrils, as described in the reference Shastri, D., Papadakis, M., Tsiamyrtzis, P., Bass, B., & Pavlidis, I. (2012), "Perinasal imaging of physiological stress and its affective potential", Affective Computing, IEEE Transactions on, 3(3), 366-378. Sentences such as "the area around the right nostril" may refer to the area of the right nostril and up to 4 cm to the right up to and 2 cm to the left, where the exact area depends on the application, the locations of other ROIs, and the physiological response that is to be detected.

In the case of a thermal camera based on a thermal sensor such as a thermopile, the thermopile's reference junctions may compensate for changes in the temperature of the ROI. If the reference junction temperature is fixed, for example by placing the reference junctions over a heat sink and/or insulating them, then exhale streams from the nostrils and/or mouth may not affect the temperature difference between the ROI and the sensing junctions. However, when the reference junction temperature is not fixed, then the breath passing over the sensor may change the measured value of the thermopile merely because the temperature of the exhale stream is close to body temperature. In order to avoid such an error, in one embodiment, a non-well isolated thermal camera is located outside the exhale streams, which means that the thermal camera is not placed in front of the nostrils and/or in front of the mouth, but to the side, above, below, and/or in any other possible location that is away from the nostrils and the mouth. Herein, sentences such as "located outside the exhale streams of the mouth and nostrils" means located outside most of the normally expected exhale stream of the mouth and located outside most of the normally expected exhale streams from the nostrils. The normally expected exhale streams are determined according to a normal human who breathes normally. In one example, thermal cameras are considered to be located outside the exhale streams from the nostrils when they are located to the right of the right nostril and to the left of the left nostril and outside a 3D rectangle that extends from below the tip of the nose to the lower part of the chin with a minimum size of 4×4 cm. In another example, a thermal camera is considered to be located outside the exhale stream of the mouth when it is located outside a horizontal cylinder having height of 10-20 cm and diameter of 4-10 cm, where the top of the cylinder touches the base of the nose. In some embodiments, another thermal camera may be located inside the exhale streams from at least one of the mouth and the nostrils.

4—Detecting a Physiological Response

Herein, a physiological response (of a user) may refer to phenomena that cause a change to the physiological state of the user. Some examples of physiological responses described in this disclosure include an allergic reaction, an asthma attack, stress, a stroke, dehydration, intoxication, and a migraine. Additionally, a physiological response may refer to a manifestation of an emotional response, such as fear, startle, sexual arousal, anxiety, joy, pain and guilt. When a physiological response refers to a persistent state of the user, it may be referred to herein as a "medical disorder". Some examples of medical disorders that may be detected based on thermal measurements of ROIs on the face include a stroke, nerve damage, sinusitis, a migraine, and Bell's palsy. Additionally, when the physiological response refers to vital signs such as the pulse or the breathing rate, they may be referred to herein as "physiological signals". Thus, sentences in the form of "detect a physiological response" may be interpreted as "detect a medical disorder" and/or "detect a physiological signal", depending on the context. Additionally, sentences of the form of "detect a physiological response" are to be interpreted herein as "detect an occurrence of a physiological response".

Some physiological responses typically cause various changes to the temperature at various ROIs on the face. For example, the reference Ioannou, S., Gallese, V., & Merla, A. (2014), "Thermal infrared imaging in psychophysiology: potentialities and limits", Psychophysiology, 51(10), 951-963, provides in Table 1 a useful overview of the direction of temperature variation in various ROIs across emotions, and a useful summary regarding temporal latency of cutaneous temperature changes. Some of the disclosed embodiments can calculate, based on measurements of head mounted thermal cameras, a cardiac pulse, a respiration rate, a cutaneous blood perfusion rate, and/or a sudomotor response, optionally using signal processing similar to the methods reviewed in the reference Cardone, Daniela, Paola Pinti, and Arcangelo Merla, "Thermal infrared imaging based computational psychophysiology for psychometrics", Computational and mathematical methods in medicine (2015).

Detecting a physiological response of a user based on thermal measurements of ROIs on the user's face may often involve determining whether, at the time the thermal measurements were taken, the user experienced the physiological response. With some physiological responses, the time leading up to the full manifestation of the physiological response may be characterized by changes to the temperature at various ROIs on the user's face. Thus, in some embodiments, detecting the physiological response may involve determining whether an onset of the physiological response is imminent. In some embodiments, detecting a physiological response may involve calculating a value that is indicative of the extent to which the user is experiencing the physiological response. For example, detecting the physiological response may involve calculating a value indicative of the severity of a stress, the severity of a migraine, or the severity of an allergic reaction. In yet other embodiments, detecting a physiological response of the user may involve calculating the value of a physiological signal of the user (e.g., the breathing rate or pulse) based on the thermal measurements of the user.

Various embodiments described herein involve detection of a physiological response based on thermal measurements and possibly other types of input values. Optionally, the detection of the physiological response is done by a processor that receives data comprising the thermal measurements (in a "raw" and/or processed form), and optionally the other types of inputs, and detects the physiological response. Examples of processors that may be utilized to detect the physiological response are the processor 401 and the processor 411 illustrated in FIG. 72a and FIG. 72b, respectively. The following is a discussion of various ways in which the thermal measurements may be utilized by the processor to detect the physiological response.

One approach for detecting a physiological response, which may be utilized in some embodiments, involves comparing thermal measurements to a threshold. In these embodiments, the processor is configured to detect the physiological response by comparing the thermal measurements, and/or values derived therefrom (e.g., a statistic of the measurements and/or a function of the measurements), to the threshold. Optionally, when the thermal measurements reach the threshold, this is indicative of an occurrence of the physiological response. The threshold may include at least one of the following thresholds: a threshold in the time domain, a threshold in the frequency domain, an upper threshold where reaching the threshold means equal or above the threshold (e.g., "X reaches a threshold Y" means X≥Y), and a lower threshold (e.g., X≤Y). For example, when the threshold equals 0.5, then both $\Delta T_{ROI}$=0.5 and $\Delta T_{ROI}$=0.7 are considered values of $\Delta T_{ROI}$ that reach the threshold, while $\Delta T_{ROI}$=0.3 is not considered a value that reaches the threshold. It is to be noted that when a threshold involves a certain change to temperature, the certain change may be positive (corresponding to at least a certain degree of increase in temperature) or the certain change may be negative (corresponding to at least a certain degree of decrease in temperature). Different physiological responses described herein may involve different types of thresholds, which may be positive or negative; for example, each of the physiological responses may involve at least a certain degree of heating, or at least a certain degree cooling, at an ROI on the face.

In some embodiments, a threshold may be compared with values that are a function of multiple measurements, such as measurements of different ROIs and/or measurements taken during a certain window of time. For example, a threshold may be compared to an average temperature over a period of time, such as an average temperature at an ROI over a period of five minutes. Thus, in one example, a threshold (e.g., $\Delta T_{ROI}$=0.5° C.) may be considered reached by certain measurements if the certain measurements include a certain portion (e.g., measurements that fall within a window of five minutes), for which the average change at the ROI, which is computed by comparing measurements taken during the certain portion with previous measurements, reaches the value of the threshold.

In other embodiments, a threshold may relate to a certain difference in temperature between different ROIs and/or at different times. For example, in one embodiment, first and second thermal cameras provide to a processor multiple measurements of temperatures at first and second ROIs ($ROI_1$ and $ROI_2$), which are denoted $T_{ROI1}$ and $T_{ROI2}$, respectively. A change-to-temperature-at-$ROI_1$ ($\Delta T_{ROI1}$) may be calculated based on $T_{ROI1}$, and a change-to-temperature-at-$ROI_2$ ($\Delta T_{ROI2}$) may be calculated based on $T_{ROI2}$. In this embodiment, detection of the physiological response may be done based on $\Delta T_{ROI1}$ and/or $\Delta T_{ROI2}$. For example, the $\Delta T_{ROI1}$ and/or $\Delta T_{ROI2}$ may be compared to a threshold in order to detect the physiological response (e.g., $\Delta T_{ROI1}$ and/or $\Delta T_{ROI2}$ reaching the threshold is indicative of the occurrence of the physiological response). In another embodiment, a difference between $T_{ROI1}$ and $T_{ROI2}$ is calculated for different times. The difference between $T_{ROI1}$ and $T_{ROI2}$, at time m (denoted $\Delta T_m$), and the difference between $T_{ROI1}$ and $T_{ROI2}$, at time n (denoted $\Delta T_n$), may be utilized in order to determine a temporal difference. For example, when the difference between $\Delta T_m$ and $\Delta T_n$ reaches a threshold (e.g., indicating heating or cooling), that may be indicative of an occurrence of the physiological response.

A threshold used to detect a physiological response may be considered, in some embodiments, a general threshold, which is suitable for multiple users and/or conditions. In other embodiments, a threshold used to detect a physiological response may be considered a personalized threshold, which is suitable for a certain user. Optionally, different users may have different thresholds that are used to detect the same physiological responses (based on thermal measurements of the same ROIs). The different thresholds may correspond to the different physiological dynamics that may be observed with different users. Optionally, a personalized threshold for a user is set based on observations of the user (e.g., based on observing thermal measurements of the user when the user had the physiological response).

In some embodiments, different thresholds may be selected for detecting the same physiological response based on different conditions related to the taking of the thermal measurements. For example, different thresholds may be utilized for different activity levels of the user, different weather conditions, and/or different configurations and/or positions of the HMS relative to the face. Optionally, determining the values of the different thresholds is done based on values of the thermal measurements observed when the physiological response occurred while the different conditions prevailed.

Another approach for detecting a physiological response, which may be utilized in some embodiments, may be applicable when the thermal measurements are treated as time series data. For example, the thermal measurements may include data indicative of temperatures at one or more ROIs at different points of time during a certain period, based on measurements taken with one or more thermal cameras. In different embodiments, these measurements may be taken at different intervals, such as a few times a second, once a second, every few seconds, once a minute, and/or every few minutes. Additionally or alternatively, the time series data may contain measurements taken at different times that do not correspond to regular intervals. As used herein, the term "time series" may involve data with a time dimension, and optionally additional dimensions. Additionally, a time series may represent data obtained from multiple thermal cameras and/or data representing measurements at multiple ROIs.

In some embodiments, a processor is configured to compare thermal measurements of a user (represented as a time series) to one or more reference time series that correspond to periods of time in which the physiological response occurred. Additionally or alternatively, the processor may compare the thermal measurements of the user to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user experienced the physiological response. Optionally, if the similarity between the thermal measurements and a reference time series that does not correspond to a physiological response reaches another threshold, this is indicative of the fact that the thermal measurements correspond to a period of time in which the user did not experience the physiological response. In some embodiments, different reference time series may correspond to different extents of the physiological response (e.g., different series corresponding to no allergic reaction, a mild allergic reaction, or a severe allergic reaction), which can be used to determine the extent of the physiological response represented by the thermal measurements.

Some of the reference time series mentioned above may be time series generated from previous thermal measurements of the user taken with the one or more thermal cameras (e.g., some reference time series were taken during periods of time in which the user experienced the physiological response and others were taken during periods of time in which the user did not experience the physiological response). Additionally or alternatively, some of the reference time series mentioned above might be time series generated from previous thermal measurements of other users, taken with a similar HMS to the one used to measure the user. In one example, a reference time series may include values generated from thermal measurements of a single user. In another example, a reference time series may include values generated from thermal measurements of multiple users (e.g., an average of patterns of multiple users).

When multiple reference time series are available, one or more reference time series may be selected for a certain user, in order to be utilized by a processor to detect whether the user had the physiological response. In some embodiments, this selection is done based on a profile similarity between the certain user and users whose thermal measurements were utilized to generate the reference time series. Optionally, each profile (of the certain user and the users) may include various information such as demographic statistics, physiological values (e.g., weight, height, activity level), baseline measurement values (e.g., typical time series data), and more. The profile similarity may be utilized to find among the users, one or more users that are most similar to the certain user, and then select their time series data as references used by the processor to detect whether the certain user had the physiological response. This approach may be beneficial when there are no (or not enough) reference time series for the certain user. For example, there may be no reference series of measurements taken at times leading up to, and during, an allergic reaction of the certain user, so reference time series of other users may be used instead. Optionally, as reference time series of the certain user become available, they are used by the processor to detect further occurrences of the physiological response.

Time series analysis may involve various forms of processing for segmenting data, aligning data, clustering, time warping, and various functions for determining similarity between sequences of time series data. It is to be noted that time warping may be useful to detect the physiological response when the manifestation of the physiological response does not occur each time on the same exact time scale. Some of the techniques that may be utilized in various embodiments are described in Ding, Hui, et al "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Yet another approach for detecting a physiological response based on thermal measurements may involve utilization of machine learning methods. In these embodiments, a processor is configured to detect the physiological response by generating feature values based on the thermal measurements (and possibly other values), and/or based on values derived therefrom (e.g., statistics of the measurements). The processor then utilizes a machine learning-based model to calculate, based on the feature values, a value that is indicative of whether, and/or to what extent, the user is experiencing the physiological response (or is about to experience, such as in the case of an onset of an allergic reaction). Optionally, the value calculated by the processor is indicative of the probability that the user had the physiological response. Herein, for brevity's sake, a "machine learning based model" may simply be called a "model". Referring to a model as being "machine learning-based" is intended to indicate that typically (but not necessarily) such a model is generated using machine learning methods which are based on learning from examples (e.g., using one or more approaches that may be considered supervised, semi-supervised, and/or unsupervised methods).

Various types of feature values may be generated in embodiments described herein based on thermal measurements. Some feature values may be indicative of temperatures at certain ROIs, while other feature values may represent a temperature difference at the certain ROIs. In one example, the difference may be with respect to a certain time (e.g., the change to the temperature at an ROI compared to the temperature at the ROI five minutes before). In another example, the difference may be with respect to a different ROI (e.g., the temperature difference between the forehead and the nose). In order to better detect physiological responses that take some time to manifest, some feature values may describe temperatures (or temperature differences) at a certain ROI at different points of time, such as at time t, t−1 minute, t−2 minutes, . . . , t−n minutes. In some embodiments, feature values may include various functions and/or statistics of the thermal measurements such as minimum/maximum measurement values and/or average values during certain windows of time.

The terms "feature" and "feature value" may be used interchangeably in this disclosure when the context of their use is clear. However, a "feature" typically refers to a certain type of value, and represents a property, while "feature value" is the value of the property with a certain instance (sample). For example, a feature may be "heart rate". A feature value for that feature may be 86 beats per minute. In another example, a feature may be the temperature at a certain ROI, while the feature value corresponding to that feature may be 36.9° C. with one instance (e.g., corresponding to a measurement taken at 10 AM), and 37.3° C. with another instance (e.g., corresponding to a measurement taken at 11 AM). Optionally, when referring to feature values as vectors of feature values, each position in the vector (each dimension) represents a feature; the content of each position in the vector is a feature value (of the feature that corresponds to the position).

In some embodiments, the machine-learning based model is generated based on labeled training data that includes samples, each of which includes feature values derived from values of the thermal measurements (and possibly other inputs) and labels indicative of a physiological response. Optionally, the labels may be indicative of whether the physiological response occurred and/or the extent of the physiological response. Additionally or alternatively, the labels may be indicative of how long the physiological response has occurred. Optionally, each sample corresponds to a time t (e.g., it includes measurements that end at the time t) and the label is related to the physiological response corresponding to time t. Examples of such values include whether the user is experiencing the physiological response at time t, the extent of the physiological response at time t, how long the user experienced the physiological response at time t, and/or how much time remains to experience the physiological response after the time t. The labels may be generated using various approaches, such as self-report by users, annotation by experts that analyze the training data, and/or utilizing additional sensors (e.g., an independent apparatus that does not involve thermal measurements of ROIs at the face may be utilized to determine labels indicative of a user's breathing rate).

Various types of machine learning-based training algorithms may be utilized, in embodiments described herein, to generate the machine learning-based model. Thus, depending on the algorithm or algorithms that are used, the model may include various types of parameters, such as parameters belonging to one or more of the following: a regression model, a support vector machine, a neural network, a graphical model, a decision tree, a random forest, and other models of other types of machine learning classification and/or prediction approaches.

Various embodiments described herein may include references to utilization of the machine learning-based model to calculate a value. For example, the embodiments may be described as including a processor that utilizes the model to calculate, based on feature values, a value indicative of a physiological response (or an emotional response). In such cases, the feature values may be considered an input to a module that utilizes parameters of the model to perform the calculation of the value (such a module may be referred to herein as a "predictor", a "classifier", and/or an "estimator"). In one example, in which the model comprises regression coefficients, utilizing the model to calculate the value based on the feature values involves calculating a dot product between the regression coefficients and a vector of the feature values. In another example, in which the model comprises parameters of a decision tree, utilizing the model to calculate the value based on the feature values may involve tracing a path in the decision tree based on the feature values relevant to certain nodes and using the leaf node for the calculated value.

It is to be noted that when the samples used to generate the machine learning-based model comprise samples corresponding to multiple users (i.e., samples generated based on thermal measurements of multiple users), then the model may be considered a general model. When the samples used to generate the machine learning-based model comprise samples that primarily correspond to a certain user, then the generated model may be considered a personalized model for the certain user. Personalized models have the advantage that given sufficient training data, they may give more accurate results when used with the certain user(s) for whom they were personalized, compared to using a general model.

In some embodiments, a new user may initially utilize a general model and/or a model personalized for some other user or set of users. However, as the new user uses the system, it is possible to accumulate more and more samples corresponding to the user, and thus generate a personalized model for the (by then not so) new user. Thus, this bootstrapping approach can enable some embodiments of systems in this disclosure to be utilized by new users from day one.

In some embodiments, there may be various models available to be utilized for a certain user (e.g., various general models and/or various models personalized for various users). In such a case, one or more of the various models may be selected and utilized to detect whether the certain user had the physiological response. In some embodiments, this selection is done based on a profile similarity between the certain user and users whose thermal measurements were utilized to generate the various models. Optionally, each profile (of the certain user and the users) may include various information such as demographic statistics, physiological values (e.g., weight, height, body build, and activity level), baseline measurement values, and more. The profile similarity may be utilized to find among the various users, one or more users that are most similar to the certain user, and then select their models to be used to detect physiological responses based on thermal measurements of the certain user.

The machine learning based model used to detect a physiological response may be generated, in some embodiments, based on data collected in day-to-day, real world scenarios. As such, the data may be collected at different times of the day, while users perform various activities, and in various environmental conditions (e.g., different temperatures, humidity levels, IR levels, etc.) Utilizing such diverse training data may enable a generated model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may be considered an artifact that can reduce the accuracy of the detection of the physiological response.

Some examples of confounding factors include disruptive facial movements (DFMs), which may include things such as making a facial expression (e.g., smiling or frowning), talking, eating, drinking, sneezing, and coughing. Other examples of confounding factors may include things that are on the user's face, which are not typically there (or do not characterize the faces of most users), which may include things like skin blemishes, piercings, stubble or other forms of facial hair, acne, inflammation, and/or presence of various matter on the face such as makeup, body paint, snot or food leftovers. Still other examples of confounding factors include movements that may affect the heart rate, blood circulation, and/or blood distribution, such as conning, jumping, and/or bending over (which can cause the face to warm). And in yet other examples, environmental phenomena such as direct sunlight, air conditioning, and/or wind may be considered confounding factors that may affect the detection of the physiological response.

Occurrences of confounding factors may not always be easily identified in thermal measurements. Thus, in some embodiments, systems may incorporate measures designed to accommodate for the confounding factors, in order to improve the detection of the physiological response when confounding factors are present. These measures may involve generating feature values that are based on additional sensors other than thermal cameras, as elaborated on below.

In one embodiment, feature values of samples may include one or more feature values that are based on a movement sensor. For example, the sensor may be an accelerometer physically coupled to a frame worn on the user's head, an accelerometer in a device carried by the user (e.g., a smartwatch or smartphone), or embedded in clothing worn by the user. In another embodiment, one or more feature values may be generated based on a sensor that measures the environment. In one example, the sensor may measure the magnitude of visible light directed at the face. In another example, the sensor may be an anemometer that measures the strength and/or direction of wind blowing on the user's face.

One source that may be useful for identifying confounding factors involves images of portions of the face taken with visible-light cameras (e.g., one or more visible-light cameras that are coupled to a frame worn by a user, at a distance of less than 15 cm from the user's face). In one embodiment, feature values utilized to detect a physiological response include one or more feature values generated based on images taken by the one or more visible-light cameras mentioned above. These feature values may correspond to various low-level features and/or high-level facial features described in this disclosure. For example, the one or more feature values may include feature values derived using Gabor filters, local binary patterns and their derivatives, features derived using algorithms such as SIFT, SURF, and/or ORB, image keypoints, HOG descriptors and features derived using PCA or LDA. Other examples of features may include features derived from sequences of images taken at different times, such as volume local binary patterns (VLBP), cuboids, and/or optical strain-based features. Additionally or alternatively, the one or more feature values may include feature values indicative of locations and/or dimensions of facial features and/or facial landmarks, identification of action units (AUs) in sequences of images, and/or blendshape weights. Additional details regarding various image processing approaches that may be used and facial feature values that may be generated is given in Section 6.

Training data used to generate a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user bends over or touches the face) can lead to generation of a model that is less susceptible to wrongfully detect the physiological response (which may be considered an occurrence of a false positive) in real world situations. For example, including in the samples of the training data at least one of the feature values mentioned above (i.e., the low-level features and/or the high-level facial features) and/or one or more feature values generated based on other factors (e.g., movement sensors and/or environmental sensors), may enable a model generated based on the samples to be able to accommodate (i.e., compensate), at least to certain extent, for the effects of the confounding factors. Thus, for example, a model trained on data in which visible-light cameras are used to generate feature values indicative of facial movements may be more accurate at detecting the physiological response than a model that does not involve such features. This is because a system utilizing the former model is less likely to be confused by user actions like eating or talking than a system utilizing the latter model.

In other embodiments, feature values utilized to detect a physiological response include one or more feature values generated based on indications indicative of occurrences of one or more confounding factors. Optionally, the indications are generated utilizing various approaches for identifying confounding factors from images and/or other sources, which are described in this disclosure. Optionally, the indications are generated based on input from a microphone (e.g., in order to identify talking, coughing, sneezing, and/or eating), a visible-light camera (e.g., in order to identify touching the ROI), movement sensors, and/or other sensors that measure the environment and/or the body of the user.

In one embodiment, a model may be generated to identify occurrences in which a user performs a certain action such as bending over, touching the face, or eating. Optionally, the model is generated based training data that includes samples of one or more users corresponding to times in which the one or more users performed the certain action and other samples of one or more users (possibly the same one or more users above) corresponding to times in which the one or more users did not perform the certain action. Optionally, each sample comprises feature values generated based on measurements of a user and a label indicative of whether (and/or to what extent) the user performed the certain action. In one example, the label may be indicative of the duration the user performed the certain action (e.g., how long the user touched the face). The measurements used to generate at least some of the feature values of each of the samples described above may be obtained utilizing one or more of various sensors mentioned above such as a movement sensor, a microphone, and a visible-light camera. Optionally, the measurements may include values obtained utilizing one or more thermal cameras (e.g., thermal cameras of an HMS described in this disclosure). Once the model is generated, it may be utilized to generate a feature value that is indicative of whether a user performed the certain action, based on measurements of the user taken with the one or more various sensors. This feature value may then be utilized in the detection of the physiological response in order to better accommodate for a confounding factor that corresponds to the certain action.

Referring back to the model for detecting the physiological response, in some embodiments, detection of a physiological response based on thermal measurements is done by evaluating measurements that fall within a certain window of time that characterizes the physiological response. For example, depending on the physiological response, in some embodiments, the window may be thirty seconds long, two minutes long, five minutes long, fifteen minutes long, or one hour long. In some embodiments, detecting a physiological response and/or a medical condition may involve analysis of data comprising thermal measurements taken during multiple of the above-described windows, such as measurements taken during different days. In some embodiments, a processor may receive a stream of thermal measurements, taken while the user wears an HMS during the day, and periodically evaluate measurements that fall within a sliding window of a certain size. For example, at various times t during the day, the processor may analyze a window of thermal measurements taken between t−1 minute and t, in order to detect the physiological response.

When detecting a physiological response based on thermal measurements, in some embodiments, additional inputs other than the thermal measurements may be utilized. Optionally, the additional inputs may be utilized to improve the detection of the physiological response by providing information that is not provided in the thermal measurements of the user. In some embodiments, at least some of the values of the additional inputs may come from sensors belonging to a device of a user, which are not thermal cameras. In some cases, these sensors may be physically coupled to a frame worn by the user, to which the thermal cameras are coupled. In some embodiments, at least some of the values of the additional inputs may come from at least one of the following sources: an external source that is not physically coupled to the frame, a module physically coupled to the frame, and a device carried by the user. In some embodiments, at least some of the additional inputs may be generated utilizing additional cameras coupled to the frame, such as a visible-light camera. The following are some non-limiting examples of additional inputs.

In one embodiment, the additional inputs may comprise values of one or more environmental parameters corresponding to the state of the environment in which the thermal measurements were taken. Optionally, the one or more environmental parameters describe at least one of the following: a temperature of the environment, a level of precipitation in the environment, a level of illumination in the environment (e.g., as measured in lux), wind speed in the environment, a noise level in the environment, an extent at which the environment is overcast. Optionally, the values of the one or more environmental parameters are obtained utilizing various sensors such as a thermometer (e.g., to measure the environmental temperature), a light meter, an anemometer, and an acoustic sensor.

In another embodiment, the additional inputs may include values indicative of user activity such as the pace a user traveled, a distance the user traveled, and indications of various types of movements and their extent, which were performed by the user. Optionally, the values indicative of user activity are obtained utilizing at least one of the following sensors: an accelerometer, a pedometer, a miniature radar, a miniature Lidar, and an acoustic sensor.

In still another embodiment, the additional inputs may include temperatures of the user's body and/or cutaneous temperatures of other regions on the user's face and/or body (e.g., the forehead when referring to allergy). Optionally, these temperatures may serve for the purpose of a baseline and/or in order to normalize thermal measurements of various ROIs on the face.

In yet another embodiment, the additional inputs may include various values that describe the user. Optionally, these values may be data from a profile of the user. In one example, the one or more values may include values indicative of the age of the user, the user's gender, the user's marital status, the user's occupation, and/or the user's education level. In another example, the one or more values may include information indicative of the user's health, such as indications of health conditions (e.g., high blood pressure) and/or mental health issues that the user may have.

In still another embodiment, the additional inputs may be indicative of consumption of certain products and/or substances by the user, such as taking medication, smoking, alcohol, drugs, drinking cold liquids, eating a hot soup, and/or eating spicy food. Optionally, identifying the consumption of the certain products and/or substances is done utilizing image analysis of video taken with a visible-light camera coupled to a frame worn by the user. In one example, camera based systems such as OrCam (http://www.orcam.com/) may be utilized to identify various objects, products, and/or text. In another example, photos of meals consumed by the user may be utilized to generate estimates of food intake and meal composition, such as the approach described in Noronha, et al., "Platemate: crowdsourcing nutritional analysis from food photographs", Proceedings of the 24th annual ACM symposium on User interface software and technology, ACM, 2011.

And in yet another embodiment, the additional inputs may include various physiological signals of the user. Optionally, some of the physiological signals are obtained utilizing one or more sensors that are not thermal cameras. Optionally, some of the physiological signals are obtained utilizing one or more thermal cameras (e.g., respiratory parameters that are generated based on thermal measurements). Some examples of physiological signals that the one or more values may represent include a heart rate, heart rate variability, galvanic skin response, and various respiratory parameters that are described further below (e.g., respiratory rate, respiratory volume, and more). Optionally, the one or more values are obtained utilizing at least one of the following sensors: a photoplethysmogram (PPG) sensor, an electrocardiogram (ECG) sensor, an electroencephalography (EEG) sensor, a galvanic skin response (GSR) sensor, and a thermistor. Optionally, the one or more values include values that are an output of at least one of the sensors mentioned above. Additionally or alternatively, the one or more values include values obtained by processing values generated by at least one of the sensors mentioned above.

The various inputs described above may be utilized, in some embodiments, by a processor to improve the accuracy of values calculated based on thermal measurements, which are indicative of a physiological response. For example, these inputs may be utilized in order to rule out false positives in which ROIs may exhibit an increase in temperature that is not due to the physiological response (e.g., not due to an allergic reaction), such as temperature increases due to the environment (e.g., when a user is exposed to the sun or a heater) and/or temperature increases due to the user's activity (e.g., due to running or exercising). Additionally or alternatively, measurements of temperatures of other regions of the user's body may serve to normalize the values measured at the ROI. For example, if there is a change to the temperature at the forehead that is similar to the change in the nasal area, then in some cases, this may indicate that the user is not having an allergic reaction (even if the change is significant, such as exceeding 1° C.).

The following are examples indications that may be received and utilized by a system in order to improve detection of a physiological response. The indications are indicative of times at which the user touches certain ROIs (which may change the skin temperature) and/or moves the frame relative to the head (which may change temperature readings of various thermal cameras). For example, these indications may be generated based on detecting a movement in a video received from an inward facing head-mounted visible-light camera. These indications may be utilized in various ways to increase the accuracy of the detection of the physiological response (and avoid false positives that are due, for example, to the touching and/or moving of the frame). In one example, when an indication of touching a certain ROI is received, the system refrains from detecting the physiological response based on thermal measurements of the certain ROI, and/or refrains from alerting about the physiological response, for a certain period until the skin temperature at the certain ROI is no longer significantly influenced by the touching. Optionally, the duration of the certain period is determined based on the amount of time the user touched the certain ROI, such that the longer the contact with the certain ROI, the longer the hiatus in detection of the physiological response. In another example, an indication may be received that the HMS, frame, and/or a thermal camera has moved with respect to the ROI, such as a movement that is greater than a threshold, which may be between one millimeter and a few centimeters, depending on the thermal camera and its location. In such a case, the system may refrain from detecting the physiological response and/or refrain from alerting about it until receiving an indication that the HMS, frame, and/or thermal camera have returned to their original position.

In various embodiments, detecting a physiological response involves determining the extent of the physiological response (that the user is experiencing). An extent of a physiological response, such as extent of an allergic reaction, may be expressed in various ways. In one embodiment, the extent is treated as a binary value indicative of whether the user experienced, and/or is experiencing, the physiological response (e.g., is the user having an allergic reaction or not) and/or as a numerical value indicative of the magnitude of the physiological response (e.g., on a scale from 1 to 10). In another embodiment, the extent is a categorial value indicative of the severity/extent of the physiological response (e.g., the categories may correspond to no allergic reaction, a low-level allergic reaction, a medium allergic reaction, or an extreme allergic reaction). In yet another embodiment, the extent of the physiological response is expressed as an expected change in temperature or as a temporal value. For example, when the physiological response is an allergic reaction, the extent of the physiological response may be expressed as the maximum change that is measured for the temperature at the nasal area. In another example, the extent of the allergic reaction may be expressed as a temporal value, such as the time it took an increase to the temperature in the nasal area to reach a certain threshold, or the expected time until the temperature at the nasal area will return to normal. In still another embodiment, the extent of the physiological response is determined based on the rate of change in temperature, such that the larger the increase for a given period of time (e.g., five minutes), the more severe the physiological response is considered. And in still another embodiment, the extent of a physiological response is a value that is indicative of the area under the curve of the temperature change at an ROI overtime. For example, a stronger allergic reaction may correspond to a larger area under the curve than the area under the curve of a mild allergic reaction (in this example the curve may represent the change in temperature at an ROI that covers a portion of the nasal area). In some embodiments, the processor provides, based on an input that comprises thermal measurements from one or more ROIs, one or more of the values mentioned above as an output indicative of the extent of the physiological response.

When the physiological response corresponds to a physiological signal (e.g., a heart rate, a respiration rate, and an extent of frontal lobe brain activity), detection of the physiological response may be interpreted as determining the value of the physiological signal (e.g., the value of the heart rate in beats per minute, or the value of the respiration rate in breaths per minute). Optionally, determining the value may involve calculating a value of a function whose input comprises values of the thermal measurements and/or values derived from the thermal measurements (and optionally one or more of the additional inputs mentioned above).

Following a determination that a user had a certain physiological response (e.g., an allergic reaction or stress that reaches a certain level), in some embodiments, an indication indicative of the extent of the physiological response may be provided to the user and/or to a third party. Optionally, the third party may be an entity related to the user (e.g., a person or a software agent operating on behalf of the user) or an entity that may provide medical assistance to the user. In one example, the indication may be indicative of the onset of an allergic reaction or an asthma attack and/or describe the extent of an allergic reaction or an asthma attack. In another example, the indication may be indicative of certain steps that the user should take in order to address the allergic reaction or asthma attack. For example, the indication may suggest the user take a certain dosage of medicine (e.g., an antihistamine or inhaled corticosteroids), that the user should leave the area (e.g., if outdoors), and/or that the user should seek medical assistance.

The indication indicative of an extent of a physiological response may be provided to the user via one or more forms of user interfaces. Optionally, the indication is given in the form of an alert that draws the user's attention to the fact he/she is experiencing the physiological response, the extent of the physiological response, and/or that the physiological response is imminent. In one embodiment, the user may be wearing a head-mounted system (HMS) that has a display, earphones, and/or other output means (such as blinking lights or vibrations), and the indication is provided by the HMS. In one example, the indication is given in the form of verbal instructions that explain how to react (e.g., instructions to control breathing when in stress or risk of an asthma attack). In another example, the indication is given in the form of images and/or video presented on a display of the HMS (e.g., images depicting values and/or icons representing an extent of the physiological response). In another embodiment, a processor, which generates the indication, forwards the indication (e.g., via wireless communication) to a device of the user such as a smartphone or a smartwatch, and the device provides the indication by alerting the user (e.g., via flashing lights, vibrations, and/or sound effects).

5—Respiratory Parameters

In various embodiments described herein, one or more thermal cameras coupled to a frame worn by a user, e.g., as illustrated in FIG. 1a, may be utilized to take thermal measurements of one or more ROIs that cover at least a portion of at least one of the following regions: the user's upper lip, the user's mouth, the space where the exhale stream form the user's nose flows, and/or the space where the exhale stream from the user's mouth flows (these thermal measurements denoted $TH_{NM}$).

The following are some examples of respiratory parameters that may be calculated based on $TH_{NM}$ of a user that are taken during a certain period of time. In some embodiments, the certain period of time during which $TH_{NM}$ are taken exceeds the time of a single breath or a small number of breaths. For example, the certain period during which $TH_{NM}$ of the user is taken, and according to which the respiratory parameters below are calculated, is longer than a threshold that may be at least 30 seconds, at least one minute, at least five minutes, at least ten minutes, or some other longer period. In other embodiments, the shape and/or the smoothness of the exhale stream may be calculated based on measurements of $TH_{NM}$ taken over a period that is shorter than the time of a single breath.

"Respiration rate (breathing rate)" may represent the number of breaths per minute the user took during the certain period. Optionally, the respiration rate may be expressed via some other value that is indicative of the number of breathes taken during the certain period, such as the average time between successive inhales, the average between successive exhales, etc.

"Respiration volume" may represent the volume of air breathed during a period of time (e.g., the number of Liters of air per minute), the volume of air breathed during a certain breath or an average breath during the certain period (e.g., "tidal volume"), and/or the ratio between two or more breaths. For example, a value of respiration parameter may indicate that a first breath was deeper than a second breath, or that breaths during a first minute were shallower than breaths during a second minute.

"Mouth breathing vs nasal breathing" is indicative of whether during the certain period the user breathed more through the mouth (a state characterized as "mouth breathing") or more through the nose (a state characterized as "nose breathing" or "nasal breathing"). Optionally, the parameter may be indicative of the percent of the air the user breathed through the nose or through the mouth. Optionally, the parameter may represent an extent to which the breathing was mouth breathing or nasal breathing (e.g., a proportion of the certain period during which the breathing was more mouth breathing). Optionally, determining whether breathing is mouth breathing or nasal breathing is done based on the relative volume of air that is exhaled from the nose and/or mouth.

"Exhale duration/Inhale duration" represents the duration of the user's exhale(s) during the certain period, the duration of the user's inhale(s) during the certain period, and/or a ratio of the two aforementioned durations. In one example, a parameter may represent the average duration of the user's exhales and/or inhales. In another example, a parameter may represent a maximum or minimum duration of exhales and/or inhales during the certain period. In yet another example, a parameter may represent a proportion of times in which the duration of the user's exhaling, and/or inhaling, reached a certain threshold.

"Post-exhale breathing pause" represents the time that elapses between when the user finishes exhaling and starts inhaling again.

"Post-inhale breathing pause" represents the time that elapses between when the user finishes inhaling and when the user starts exhaling after that.

The post exhale/inhale breathing pauses may be formulated as the average post exhale/inhale breathing pause during a certain period, a maximum or minimum duration of the user's post exhale/inhale breathing pause during the certain period, and/or a proportion of times in which the duration of the user's post exhale/inhale breathing pause reached a certain threshold.

"Dominant nostril" represents the nostril from which the user breathes more air. For example, during some times, the person may inhale and/or exhale more air through the left nostril, in which case the left nostril is considered the dominant nostril. During other times, the person may inhale and/or exhale more air through the right nostril, in which case the right nostril is considered the dominant nostril. In some embodiments, one or more parameters calculated based on $TH_{NM}$ of the user taken during a certain period may be indicative of whether the left (right) nostril was dominant during the certain period, the proportion of time during the certain period that the left (right) nostril was dominant, and/or the proportion of air that was breathed through the left (right) nostril relative to the total breathing volume. During other times, the breathing may be considered balanced, in which case the amount of air breathed through each nostril is similar. Optionally, breathing through the nostrils is considered balanced when the difference between the volume of air breathed through the right and left nostrils is below 30%, 20%, 10%, or 5%.

"Temperature of the exhale stream" may be measured based on thermal measurements of the stream that flows from one or both nostrils, and/or the heat pattern(s) on the upper lip that are caused by one or both exhale streams from the nose. In one example, it is not necessary to be able to measure the exact temperature of the exhale stream as long as it is able to differentiate between different temperatures of the exhale stream based on the differences between series of thermal measurements taken at different times. Optionally, the series of thermal measurements that are compared are temperature measurements received from the same pixel(s). Optionally, the temperature refers to a certain point (e.g., a center of the exhale stream) and/or multiple points. Optionally, the temperature refers to the maximum temperature or to an average over the duration of the exhaling during the certain period.

"Shape of the exhale stream" represents the three dimensional shape of the exhale stream. The shape of the exhale stream changes over the day and may reflect the mental, physiological, and/or energetic state of a user. Usually the temperature of the exhale stream is different from the temperature of the air in the environment; this enables a thermal camera, which captures a portion of the volume through which the exhale stream flows, to take a measurement indicative of the shape of the exhale stream, and/or to differentiate between different shapes of the exhale stream. Additionally, the temperature of the exhale stream is usually different from the temperature of the upper lip, which may change the resulting thermal pattern on the upper lip when the shape of the exhale stream changes; this can enable measurements of a thermal camera, which capture a portion of the upper lip, to be used to differentiate between different shapes of the exhale stream based on the properties of the thermal patterns generated on the upper lip by exhale streams having different shapes. In one embodiment, differences between values measured by adjacent thermal pixels, which measure the exhale stream and/or the upper lip over different time intervals, may correspond to different shapes of the exhale stream. In one example, it is not necessary to be able to measure the exact shape of the exhale stream as long as it is possible to differentiate between different shapes of the exhale stream based on the differences between the values of the adjacent thermal pixels. In another embodiment, differences between average values, measured by the same thermal pixel over different time intervals, may correspond to different shapes of the exhale stream. In one example, it is not necessary to be able to measure the exact shape of the exhale stream as long as it is possible to differentiate between different shapes of the exhale stream based on the differences between the values measured by the adjacent thermal pixels over different time intervals and/or based on the differences between the values measured by the same thermal pixel over different time intervals. In still another embodiment, the air that is within certain boundaries of a 3D shape, e.g., a cone or a pyramid protruding from the user's nose, which is warmer than the environment air by at least a certain temperature difference, as measured by one or more head-mounted thermal cameras, is considered to belong to the exhale stream. The certain temperature difference may have different values in different setups, such as being at least 0.25° C., at least at least 1° C., and/or at least 2° C. In one example, the shape of the exhale stream may be represented by at least one of the following parameters: the angle from which the exhale stream blows from a nostril, the width of the exhale stream, the length of the exhale stream, and other parameters that are indicative of the 3D shape of the exhale stream. Optionally, the shape of the exhale stream may be defined by the shape of a geometric body that confines it, such as a cone or a cylinder, protruding from the user's nose. For example, the shape of the exhale stream may be represented by parameters such as the altitude of the cone, the radius of the cone's base, and/or the angle between the cone's altitude axis and the nostril.

"Smoothness of the exhale stream" represents a level of continuity of the exhale stream from the nose and/or the mouth. In one embodiment, the smoothness of the exhale stream is a value that can be determined based on observing the smoothness of a graph indicative of thermal measurements that are indicative of the exhale stream (e.g., a time series of thermal measurements taken at different times from the areas of the nostrils and/or the mouth). Optionally, thermal measurements useful for calculating the smoothness of the exhale stream include one or more of the following: thermal measurements of the stream exhaled from the nose, thermal measurements of the stream exhaled from the mouth, and/or thermal measurements of the heat pattern generated on the upper lip by the exhale from the nose. Optionally, it is unnecessary for the system to measure the exact smoothness of the exhale stream as long as it is possible to differentiate between smoothness levels of thermal measurements (indicative of the exhale) taken at different times; moreover, the compared thermal measurements taken at different times may be measured by the same pixels or by different pixels.

There are well known mathematical methods to calculate the smoothness of a graph, such as Fourier transform analysis, polynomial fit, differentiability classes, multivariate differentiability classes, parametric continuity, and/or geometric continuity. In one example, the smoothness of the exhale stream is calculated based on a Fourier transform of a series of thermal measurements of the upper lip, the mouth, and/or the exhale stream. In the case of Fourier transform, the smaller the power of the high frequencies portion, the smoother the exhale is, and vice versa. Optionally, the threshold for differentiating between the high frequency and low-frequency portions may be different in different embodiments. For example, high frequencies may be considered frequencies that are above one or more of the following values: 2 times, 5 times, and 10 times the breathing rate. In another example, the smoothness of the exhale stream is calculated using a polynomial fit (with a bounded degree) of a series of thermal measurements of the upper lip, the mouth, and/or the exhale stream. Optionally, the degree of the polynomial used for the fit is proportional (e.g., linear) in the number of exhales in the time series. In the case of polynomial fit, the smoothness may be a measure of the goodness of fit between the thermal measurements and the polynomial (e.g., the squared error). For example, the lower the squared error, the smoother the graph is considered. In still another embodiment, the smoothness of the exhale stream may be calculated using a machine learning-based model trained with training data comprising reference time series of thermal measurements of the upper lip, the mouth, and/or the exhale stream for which the extent of smoothness is known (e.g., the training data may include controlled samples of smooth and unsmooth breathing).

As a rule of thumb, the smoother the exhale stream the lower the stress and the better the physical condition. For example, the exhale stream of a healthy young person is often smoother than the exhale stream of an elderly person, who may even experience short pauses in the act of exhaling. As another rule of thumb, the exhale stream usually becomes less smooth as the stress increases or due to intensive physical effort.

In an alternative embodiment, a microphone is used to measure the exhale sounds. The smoothness of the exhale stream may be a value that is proportional to the smoothness of the audio measurement time series taken by the microphone (e.g., as determined based on the power of the high-frequency portion obtained in a Fourier transform of the time series of the audio).

There are various approaches that may be employed in order to calculate values of one or more of the respiratory parameters mentioned above based on $TH_{NM}$ of a user, taken during a certain period. Optionally, calculating the values of one or more of the respiratory parameters may be based on additional inputs (besides $TH_{NM}$), which may include, for example, statistics about the user (e.g., age, gender, weight, height, and the like), indications about the user's activity level (e.g., input from a pedometer), and/or physiological signals of the user (e.g., heart rate and respiratory rate). Roughly speaking, some approaches may be considered analytical approaches while other approaches may involve utilization of a machine learning based model.

In some embodiments, one or more of the respiratory parameters mentioned above may be calculated based on $TH_{NM}$ of the user by observing differences in the values of pixels received from the one or more thermal cameras. In one embodiment, certain pixels that have alternating temperature changes may be identified as corresponding to exhale streams. In this embodiment, the breathing rate may be a calculated frequency of the alternating temperature changes at the certain pixels (e.g., a frequency having value between 0.05 Hz to 2 Hz). In another embodiment, the relative difference in magnitude of temperature changes at different ROIs, such as the alternating temperature changes that correspond to breathing activity, may be used to characterize different types of breathing. For example, if temperature changes at ROI near the nostrils reach a first threshold, while temperature changes at an ROI related to the mouth do not reach a second threshold, then the breathing may be considered nasal breathing; while if the opposite occurs, the breathing may be considered mouth breathing. In another example, if temperature changes at an ROI near the left nostril and/or on the left side of the upper lip are significantly higher than temperature changes at an ROI near the right nostril and/or on the right side of the upper lip, then the left nostril may be considered the dominant nostril at the time the measurements were taken. In still another example, the value of a respiratory parameter may be calculated as a function of one or more input values from among $TH_{NM}$ and/or one or more input values derived from $TH_{NM}$.

In other embodiments, one or more of the respiratory parameters may be calculated by generating feature values based on $TH_{NM}$ and utilizing a model to calculate, based on the feature values, the value of a certain respiratory parameter from among the parameters mentioned above. The model for a certain respiratory parameter is generated based on samples. Each sample comprises the feature values based on $TH_{NM}$ of a user, taken during a certain period of time, and a label indicative of the value of the certain respiratory parameter of the user during the certain period of time. For example, the feature values generated for a sample may include the values of pixels measured by the one or more cameras (e.g., thermal cameras and/or visible-light cameras), statistics of the values of the pixels, and/or functions of differences of values of pixels at different times. Additionally or alternatively, some of the feature values may include various low-level image analysis features, such as feature derived using Gabor filters, local binary patterns and their derivatives, features derived using algorithms such as SIFT, SURF, and/or ORB, image keypoints, HOG descriptors and features derived using PCA or LDA. The labels of the samples may be obtained through various ways. Some examples of approaches for generating the labels include manual reporting (e.g., a user notes the type of his/her breathing), manual analysis of images (e.g., an expert determines a shape of an exhale stream), and utilizing sensors (e.g., a chest strap that measures the breathing rate and volume).

Generating the model for the certain respiratory parameter based on the samples may involve utilizing one or more of the various machine learning-based training algorithms known in the art, such as a training algorithm for a decision tree, a regression model, or a neural network. Once the model is generated, it may be utilized to calculate the value of the certain respiratory parameter based on feature values generated based on $TH_{NM}$ taken during a certain period, for which the label (i.e., the value of the certain respiratory parameter) may not be known. It is to be noted that similarly to the case with other machine learning based models mentioned in this disclosure, when the model for a certain respiratory parameter is generated based on samples of multiple users, the model may be considered a general model. And when the samples used to generate the model include a significant proportion of samples of a certain user (e.g., at least 25%, at least 50%, or at least 75%), the model may be considered personalized for the certain user.

6—Image Processing and Facial Features

Some embodiments in this disclosure include one or more visible-light cameras that provide images of portions of a user's face. In some embodiments, these images may be utilized to detect various confounding factors that may influence values of thermal measurements of the face. Some confounding factors may be disruptive facial movements (DFMs), which may include things such as making a facial expression (e.g., smiling or frowning), talking, eating, drinking, sneezing, and coughing. Other confounding factors may include things that are on the user's face, which are not typically there (or do not characterize the faces of most users), which may include things like skin blemishes, piercings, stubble or other forms of facial hair, acne, inflammation, and/or presence of various matter on the face such as makeup, body paint, snot or food leftovers. In some embodiments, at least some of the confounding factors can lead to artifacts (e.g., warming and/or cooling of certain regions of the face). These artifacts are not directly related to an occurrence of the physiological response (or value of a physiological signal), and thus can, in some embodiments, lead to less accurate detections of the physiological response if not accounted for.

In order to identify occurrences of confounding factors and/or in order to account for confounding factors during detection of physiological responses, some embodiments described herein may employ various image processing and/or image detection techniques. Often this involves performing various operations such as image registrations and/or feature generation that involves representing images with feature values. Additionally or alternatively, detection of various facial features may also be part of the process. These aspects discussed in more detail below.

Registration is an initial step for many image processing tasks. When images include faces, the registration may also be referred to as facial registration. Facial registration typically involves identifying a face in an image and/or prominent facial features such as the corner of an eye, the tip of the nose, the edge of an eyebrow, the mouth, etc. Once facial registration is performed, the identified prominent features may be used to identify other points on the face. Additionally or alternatively, the identified features may be used to preprocess the image (e.g., move, rotate, and/or rescale) in order for the head and/or certain key points (e.g., the pupil) to be positioned in a certain place that is shared by multiple images being processed. For example, to ease feature extraction from frontal images of a face, after facial registration each image is transformed such that nose appears in the middle of the image and the height of the face is a certain number of pixels (e.g., occupying 90% of the height of the image).

While in may scenarios known in the art, facial registration may be a difficult task, due to the coupling of the cameras to the frame, which enable a stationary position and orientation relative to the face, in some embodiments, facial registration is a relatively simple step to perform, while in other embodiments, this step might not even be performed at all. Additionally, the coupling of cameras to the frame can help deal with complications caused by user movements, ROI alignment, a need for tracking based on hot spots or markers, and motion compensation which may be complex issues with other types of systems (which do not involve cameras coupled to a frame worn by the user), but are simplified, and maybe even eliminated in the embodiments described herein.

In some embodiments, registration involves identifying a certain facial landmark and/or facial feature in an image (various techniques for identifying landmarks and/or facial features are described further below). In one example, registration with images generated by an upward facing camera that is attached to a frame of a head-mounted system (HMS) may involve identifying the position of an eyebrow in the images (e.g., identifying the position of one or more edges of the eyebrow). In another example, registration with a downward facing camera attached to a frame of an HMS may involve identifying the position of an edge of the lip in the images. In still another example, registration with a camera attached to a frame of an HMS and oriented towards an eye may involve identifying the position of a pupil and/or an edge of an eye in the images. For the purpose of registration, various algorithms known in the art for identification of facial features can be used; examples of such algorithms are given below.

The process of converting one or more images to feature values may be referred to herein as "feature generation" (e.g., "generate feature values") and/or "feature extraction". Optionally, the feature values may be represented as one or more vectors of feature values. Stating that feature values may be represented as a vector does not imply that they necessary need to be stored in a data structure that is a vector. Rather, that the features may be referred to logically as being in a vector such that each different feature corresponds to a different position (dimension) in the vector.

In some embodiments, at least some feature values are based on a single image. For example, a feature value may be determined based on values of one or more pixels in a single image captured by a single camera. In other embodiments, images from multiple cameras (e.g., each covering different portions of the face) may be stitched together (e.g., by placing them one next to the other), and feature values may be generated based on multiple pixel values from multiple images. This can help generate feature that relate to properties on different sides of the face (e.g., the difference in height between both sides of the mouth) even if, due to the camera placement, there is no single image that covers the whole face. In still other embodiments, at least some features are generated based on multiple successive images (e.g., different video frames) from one or more cameras. Such features may be helpful in representing movement on the face (e.g., when a DFM takes place).

Cameras coupled to a frame worn by a user that are pointed to the user's face are typically very close to the user's face, with the distances between the camera to the face in some cases being less than 1 cm and usually no more than 15 cm. Thus, portions of the user's face typically occupy a large part of the images captured by the cameras, and even at times, portions of the user's face can occupy the entire images. This is in contrast with other scenarios in which images of the users face are captured by a front facing camera (e.g., a webcam, a camera embedded in a TV, etc.) in which the face may occupy a smaller portion of the image. Additionally, due to the coupling the orientation and position of the cameras relative to the face does not significantly change (or change at all) even when the user's head performs angular motions or other movements in space. This means that images captured by a camera capture the same facial region of the user over long periods. This is different from many scenarios in which frontal cameras that are farther from the user capture images of the user. In such cases, the position and orientation of the face in images may change significantly as the user moves.

Generally, the feature values may be divided in two types: low-level features, and high-level facial-related features. The low-level features are features that are typically used in image processing and vision-related applications; they do not necessarily involve human faces and they are typically used for various applications such as general object and/or motion recognition. The high-level features are typically related to specific properties of the face (e.g., parts of the face) and/or capture some aspect of facial expression. Optionally, deriving high-level features utilizes domain knowledge of the face.

There are various low-level and high-level features that are known in the art, which may be utilized in some of the embodiments described in this disclosure. Some examples of low-level features include: features derived using Gabor filters and/or local binary patterns (LBP) and their derivatives, HOG descriptors, features derived using algorithms such as SIFT, SURF, and/or ORB, image keypoints, and features derived using PCA or LDA. Some low-level features may be derived from multiple images, such as volume local binary patterns (VLBP), optical strain based features, and/or cuboids. Some examples of high-level features that may be utilized in some embodiments include location and dimensions of facial features and/or landmarks, identification of action units (AUs) in sequences of images, and/or blendshape weights.

7—Additional Considerations

FIG. 72a and FIG. 72b are schematic illustrations of possible embodiments for computers (400, 410) that are able to realize one or more of the embodiments discussed herein. The computer (400, 410) may be implemented in various ways, such as, but not limited to, a server, a client, a personal computer, a set-top box (STB), a network device, a handheld device (e.g., a smartphone), an HMS (such as a smart glasses, an augmented reality system, a virtual reality system, and/or a mixed reality system), a computing device embedded in a wearable device (e.g., a smartwatch or a computer embedded in clothing), a computing device implanted in the human body, and/or any other computer form capable of executing a set of computer instructions. Further, references to a computer include any collection of one or more computers that individually or jointly execute one or more sets of computer instructions to perform any one or more of the disclosed embodiments.

The computer 400 includes one or more of the following components: processor 401, memory 402, computer readable medium 403, user interface 404, communication interface 405, and bus 406. In one example, the processor 401 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 402 may include one or more of the following memory components: CPU cache, main memory, read-only memory (ROM), dynamic random access memory (DRAM) such as synchronous DRAM (SDRAM), flash memory, static random-dom access memory (SRAM), and/or a data storage device. The processor 401 and the one or more memory components may communicate with each other via a bus, such as bus 406.

The computer 410 includes one or more of the following components: processor 411, memory 412, and communication interface 413. In one example, the processor 411 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 412 may include one or more of the following memory components: CPU cache, main memory, read-only memory (ROM), dynamic random access memory (DRAM) such as synchronous DRAM (SDRAM), flash memory, static random access memory (SRAM), and/or a data storage device.

Still continuing the examples, the communication interface (405, 413) may include one or more components for connecting to one or more of the following: Bluetooth, ZigBee, Wi-Fi, LAN, Ethernet, intranet, the Internet, a fiber communication network, some other wired communication network, and/or some other wireless communication network. Optionally, the communication interface (405, 413) is used to connect with the network 408. Additionally or alternatively, the communication interface 405 may be used to connect to other networks and/or other communication interfaces. Still continuing the example, the user interface 404 may include one or more of the following components: (i) an image generation device, such as a video display, an augmented reality system, a virtual reality system, and/or a mixed reality system, (ii) an audio generation device, such as one or more speakers, (iii) an input device, such as a keyboard, a mouse, an electronic pen, a gesture based input device that may be active or passive, and/or a brain-computer interface, and (iv) a haptic feedback device.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium.

In one example, the computer-readable medium 403 may include one or more of the following: RAM, ROM, EEPROM, optical storage, magnetic storage, biologic storage, flash memory, or any other medium that can store computer readable data. Additionally, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, microwave, Bluetooth, ZigBee, Wi-Fi, and/or cellular, then the coaxial cable, fiber optic cable, twisted pair, DSL, or wireless technologies such as infrared, radio, microwave, Bluetooth, ZigBee, Wi-Fi, and/or cellular are included in the definition of a medium. It should be understood, however, that computer-readable medium does not include connections, carrier waves, signals, or other transient media, but are instead directed to non-transient, tangible storage media.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non transitory computer-readable medium. The non-transitory computer-readable medium may be implemented, for example, via one or more of a volatile computer memory, a non-volatile memory, a hard drive, a flash drive, a magnetic data storage, an optical data storage, and/or any other type of tangible computer memory to be invented that is not transitory signals per se. The computer program may be updated on the non-transitory computer-readable medium and/or downloaded to the non transitory computer-readable medium via a communication network such as the Internet. Optionally, the computer program may be downloaded from a central repository such as Apple App Store and/or Google Play. Optionally, the computer program may be downloaded from a repository such as an open source and/or community run repository (e.g., GitHub).

At least some of the methods described in this disclosure, which may also be referred to as "computer-implemented methods", are implemented on a computer, such as the computer (400, 410). When implementing a method from among the at least some of the methods, at least some of the steps belonging to the method are performed by the processor (401, 411) by executing instructions. Additionally, at least some of the instructions for running methods described in this disclosure and/or for implementing systems described in this disclosure may be stored on a non-transitory computer-readable medium.

Various embodiments herein may refer to a computer that is "configured to" perform certain operations. Configuring a computer to perform operation may be done in various ways. In some embodiments, one or more of the computer's processors may include logic gates that implement the certain operations (e.g., specifically designed chips and/or firmware). In some embodiments, instructions (e.g., computer code) for performing the operations may be stored in a memory that is accessed by one or more processor of the computer in order to perform the certain operations. Optionally, the instructions are read from a computer-readable medium and/or are received via a communication interface.

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Additionally, sentences in the form of "provide/receive an indication indicating whether X happened" refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). For example, most of an ROI refers to at least 51% of the ROI. A "portion" of something refers herein to 0.1% to 100% of the something (including 100% of the something). Sentences of the form "a portion of an area" refer herein to 0.1% to 100% of the area.

As used herein, the terms "comprises," "comprising," "includes," "including," "has," "having", or any other variation thereof, indicate an open claim language that does not exclude additional limitations. The "a" or is employed to describe one or more, and the singular also includes the plural unless it is obvious that it is meant otherwise.

While the methods disclosed herein may be described and shown with reference to particular steps performed in a particular order, it is understood that these steps may be combined, sub-divided, and/or reordered to form an equivalent method without departing from the teachings of some of the embodiments. Accordingly, unless specifically indicated herein, the order and grouping of the steps is not a limitation of the embodiments. Furthermore, methods and mechanisms of some of the embodiments will sometimes be described in singular form for clarity. However, some embodiments may include multiple iterations of a method or multiple instantiations of a mechanism unless noted otherwise. For example, when a processor is disclosed in one embodiment, the scope of the embodiment is intended to also cover the use of multiple processors. Certain features of some of the embodiments, which may have been, for clarity, described in the context of separate embodiments, may also be provided in various combinations in a single embodiment. Various features of some of the embodiments, which may have been, for brevity, described in the context of a single embodiment, may also be provided separately or in any suitable sub-combination.

Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the appended claims and their equivalents.

We claim:

1. A system configured to collect thermal measurements related to respiration, comprising:
a frame configured to be worn on a user's head; and
at least one thermal camera that is physically coupled to the frame; wherein the frame is configured to hold the at least one thermal camera less than 15 cm away from the user's face, such that the at least one thermal camera does not occlude any of the user's mouth and upper lip;
wherein the at least one thermal camera is configured to take thermal measurements of: a portion of the right side of the user's upper lip ($TH_{ROI1}$), a portion of the left side of the user's upper lip ($TH_{ROI2}$), and a portion of the user's mouth ($TH_{ROI3}$).

2. The system of claim 1, wherein the at least one thermal camera weighs below 5 g, and $TH_{ROI1}$, $TH_{ROI2}$, and $TH_{ROI3}$ are indicative of the breathing rate through at least one of the mouth and nostrils; and further comprising a computer configured to calculate the breathing rate based on $TH_{ROI1}$, $TH_{ROI2}$, and $TH_{ROI3}$.

3. The system of claim 1, further comprising a computer configured to calculate, based on $TH_{ROI1}$, $TH_{ROI2}$, and $TH_{ROI3}$, a value indicative of at least one of the following values: an extent to which the user's breathing was done through the mouth, and an extent to which the user's breathing was done through the nostrils.

4. The system of claim 1, wherein the at least one thermal camera is based on microbolometer sensing elements or thermopile sensing elements, and comprises a focal-plane array (FPA) sensor that provides at least $TH_{ROI1}$ and $TH_{ROI3}$.

5. The system of claim 1, wherein the at least one thermal camera comprises at least first and second thermal cameras, configured to be located at least 0.5 cm to the right and to the left of the vertical symmetry axis that divides the face, respectively, and above the tip of the user's nose; and wherein the first thermal camera is configured to take $TH_{ROI1}$, and the second thermal camera is configured to take $TH_{ROI2}$.

6. The system of claim 1, wherein $ROI_1$ covers more than 60% of a 2×2 cm area adjacent to the right side of the vertical symmetry axis that divides the face and below the right nostril of the user, $ROI_2$ covers more than 60% of a 2×2 cm area adjacent to the left side of the vertical symmetry axis and below the left nostril of the user, and $ROI_3$ covers more than 60% of a 2×5 cm area located over the vertical symmetry axis and below the nostrils of the user.

7. The system of claim 1, further comprising an in-the-ear earbud comprising a microphone, configured to measure breathing sounds inside the ear canal of the user; and further comprising a computer is configured to identify inhales based on audio signal analysis of the recordings from the earbud and $TH_{ROI1}$, $TH_{ROI2}$, and $TH_{ROI3}$.

8. The system of claim 7, wherein the computer is further configured to train a machine learning model to identify the inhales based on feature values generated based on data comprising $TH_{ROI1}$, $TH_{ROI2}$, $TH_{ROI3}$, and labels comprising identifications of the inhales that were calculated based on the audio signal analysis of the recordings from the earbud.

9. The system of claim 1, further comprising a computer configured to calculate a ratio between mouth breathing and nasal breathing based on $TH_{ROI1}$, $TH_{ROI2}$, and $TH_{ROI3}$; and the system is further configured to help the user to prefer nasal breathing over mouth breathing by notifying the user when the ratio between the mouth breathing and the nasal breathing reaches a predetermined threshold.

10. The system of claim 1, further comprising a computer configured to calculate, based on $TH_{ROI1}$ and $TH_{ROI2}$, a ratio between an extent the user breathed through the right nostril and an extent the user breathed through the left nostril.

11. The system of claim 10, wherein the system is further configured to help the user to develop awareness to the dominant nostril by at least one of the following: notifying the user when the ratio is balanced, notifying the user when the ratio reaches a predetermined threshold, notifying the user when a trend in values of the ratio changes direction, notifying the user when the right nostril is the dominant nostril, and notifying the user when the left nostril is the dominant nostril.

12. The system of claim 1, further comprising a computer configured to (i) receive an indication that the user suffers from asthma, (ii) identify, based on $TH_{ROI1}$, $TH_{ROI2}$, and $TH_{ROI3}$, an increase in the user's breathing rate above a predetermined threshold, and (iii) alert the user, via a user interface, about an imminent asthma attack.

13. The system of claim 12, further comprising a microphone configured to record the user; the computer is further configured to analyze the recording in order to identify at least one of the following body sounds: asthmatic breathing sounds, asthma wheezing, and coughing; wherein a first alert provided to the user in response to identifying the increase in the user's breathing rate above the predetermined threshold without identifying at least one of the body sounds is less intense than a second alert provided to the user in response to identifying both the increase in the user's breathing rate above the predetermined threshold and at least one of the body sounds.

14. The system of claim 1, further comprising a computer configured to calculate, based on $TH_{ROI1}$, $TH_{ROI2}$, and $TH_{ROI3}$, the ratio between exhale and inhale durations ($t_{exhale}/t_{inhale}$), and to alert the user, via a user interface, to increase the ratio responsive to detecting that $t_{exhale}/t_{inhale}$ is below a predetermined threshold.

15. The system of claim 1, further comprising a computer configured to: receive a first indication that the user's stress level reaches a threshold, detect at least one of the following two conditions based on $TH_{ROI1}$, $TH_{ROI2}$ and $TH_{ROI3}$: (i) that the ratio between exhaling and inhaling durations is below 1.5 ($t_{exhale}/t_{inhale}<1.5$), and (ii) that the user's breathing rate reached a predetermined threshold, and command a user interface to suggest the user to increase $t_{exhale}/t_{inhale}$ to at least 1.5.

16. The system of claim 15, wherein the computer is further configured to command the user interface to: update the user about changes in the stress level in response to increasing $t_{exhale}/t_{inhale}$, and provide positive reinforcement to help the user to maintain the required ratio at least until a certain improvement in the stress level is achieved.

17. The system of claim 1, further comprising a computer configured to: receive a first indication that the user is about to have an imminent event, detect at least one of the following two conditions based on $TH_{ROI1}$, $TH_{ROI2}$ and $TH_{ROI3}$: (i) that the ratio between exhaling and inhaling durations is below 1.5 ($t_{exhale}/t_{inhale}<1.5$), and (ii) that the user's breathing rate reached a predetermined threshold, and command a user interface to suggest the user to increase $t_{exhale}/t_{inhale}$.

18. The system of claim 17, wherein the imminent event comprises at least one of the following events: entering a social interaction, entering a meeting, entering one home, entering a pleasant or unpleasant situation, entering a place with unpleasant temperature, taking a test, starting a game session, making a speech, making a phone call, responding to a request to make a decision, reading something that is expected to affect the user's emotions above a predetermined threshold, and reaching a traffic jam.

19. The system of claim 1, further comprising a computer configured to: receive a first indication that the user is going to make a physical effort, command a user interface to suggest the user to exhale while making the physical effort, and determine based on $TH_{ROI1}$, $TH_{ROI2}$, and $TH_{ROI3}$ whether the user exhaled while making the physical effort.

20. The system of claim 19, wherein the computer is further configured to command the user interface to play a positive feedback in response to determining that the user managed to exhale while making the physical effort; wherein the physical effort includes at least one of the following activities: standing up, sitting down, manipulating with the hands an item that requires applying a significant force, defecating, dressing, leaning over, and lifting an item.

21. The system of claim 1, further comprising a computer configured to calculate, based on $TH_{ROI1}$, $TH_{ROI2}$, and $TH_{ROI3}$, at least one of: lung volumes, and tidal volume.

\* \* \* \* \*